US012678513B2

(12) United States Patent
Ackerman et al.

(10) Patent No.: US 12,678,513 B2
(45) **Date of Patent: *Jul. 14, 2026**

(54) ANTI-HER2 IMMUNOCONJUGATES, AND USES THEREOF

(71) Applicant: BOLT BIOTHERAPEUTICS, INC., Redwood City, CA (US)

(72) Inventors: Shelley Erin Ackerman, Redwood City, CA (US); Michael N. Alonso, Redwood City, CA (US); Romas Kudirka, Redwood City, CA (US); Arthur Lee, Redwood City, CA (US); Brian Safina, Redwood City, CA (US); Matthew Zhou, Redwood City, CA (US)

(73) Assignee: BOLT BIOTHERAPEUTICS, INC., Redwood City, CA (US)

( * ) Notice: Subject to any disclaimer, the term of this patent is extended or adjusted under 35 U.S.C. 154(b) by 518 days.

This patent is subject to a terminal disclaimer.

(21) Appl. No.: 18/038,812

(22) PCT Filed: Dec. 10, 2021

(86) PCT No.: PCT/US2021/062816

§ 371 (c)(1),
(2) Date: May 25, 2023

(87) PCT Pub. No.: WO2022/125904

PCT Pub. Date: Jun. 16, 2022

(65) Prior Publication Data

US 2024/0091370 A1 Mar. 21, 2024

Related U.S. Application Data

(60) Provisional application No. 63/124,367, filed on Dec. 11, 2020.

(51) Int. Cl.
*A61K 47/68* (2017.01)

(52) U.S. Cl.
CPC ...... *A61K 47/6855* (2017.08); *A61K 47/6803* (2017.08)

(58) Field of Classification Search
None
See application file for complete search history.

(56) References Cited

U.S. PATENT DOCUMENTS

| | | | | |
|---|---|---|---|---|
| 10,669,252 | B2 | 6/2020 | Gao et al. | |
| 2014/0088085 | A1 | 3/2014 | Burgess et al. | |
| 2016/0257653 | A1 | 9/2016 | Hoves et al. | |
| 2020/0206349 | A1 | 7/2020 | Sung et al. | |
| 2022/0195066 | A1 * | 6/2022 | Ackerman | A61K 47/6889 |
| 2025/0000995 | A1 * | 1/2025 | Ackerman | A61K 47/6849 |

FOREIGN PATENT DOCUMENTS

| | | | | |
|---|---|---|---|---|
| EP | 0825186 | A1 | 2/1998 | |
| EP | 3453707 | A1 | 3/2019 | |
| WO | 2007024612 | A2 | 3/2007 | |
| WO | 2010014913 | A1 | 2/2010 | |
| WO | 2010054215 | A1 | 5/2010 | |
| WO | 2011022508 | A2 | 2/2011 | |
| WO | 2011022509 | A2 | 2/2011 | |
| WO | 2012045090 | A2 | 4/2012 | |
| WO | 2012097177 | A2 | 7/2012 | |
| WO | 2016096778 | A1 | 6/2016 | |
| WO | 2016100302 | A2 | 6/2016 | |
| WO | 2017046112 | A1 | 3/2017 | |
| WO | 2017190669 | A1 | 11/2017 | |
| WO | 2017202703 | A1 | 11/2017 | |
| WO | 2017202704 | A1 | 11/2017 | |
| WO | 2017216054 | A1 | 12/2017 | |
| WO | 2018140831 | A2 | 8/2018 | |
| WO | 2018170179 | A1 | 9/2018 | |
| WO | 2019084060 | A1 | 5/2019 | |
| WO | 2019118884 | A1 | 6/2019 | |
| WO | 2019120258 | A1 | 6/2019 | |
| WO | 2020056008 | A1 | 3/2020 | |
| WO | 2020056194 | A1 | 3/2020 | |
| WO | 2020056198 | A2 | 3/2020 | |
| WO | 2020252254 | A1 | 12/2020 | |
| WO | 2020252294 | A1 | 12/2020 | |
| WO | 2021067242 | A1 | 4/2021 | |
| WO | 2021226440 | A1 | 11/2021 | |
| WO | 2022125891 | A2 | 6/2022 | |
| WO | 2022125908 | A1 | 6/2022 | |
| WO | 2022125915 | A1 | 6/2022 | |
| WO | WO-2022125884 | A1 * | 6/2022 | A61K 47/6803 |
| WO | WO-2023076599 | A1 * | 5/2023 | A61P 35/00 |

OTHER PUBLICATIONS

Ackerman, S , et al., "Immune-stimulating antibody conjugates elicit robust myeloid activation and durable antitumor immunity", Nature Cancer 2, 18-33, https://doi.org/10.1038/s43018-020-00136-x (2021).
Lu, H, et al., "VTX-2337 Is a Novel TLR8 Agonist That Activates NK Cells and Augments ADCC", Clin Cancer Res 18 (2), 499-509 (2011).
Patent Cooperation Treaty , International Search Report and Written Opinion for PCT/US2021/062816, 13 pages, dated Mar. 25, 2022.
CAPLUS, Accession No. 2020:2604323, 2 pages (2024).
CAPLUS, Accession No. 2020:2613372, 2 pages (2024).

* cited by examiner

*Primary Examiner* — Karl J Puttlitz
(74) *Attorney, Agent, or Firm* — Viksnins Harris Padys Malen LLP

(57) ABSTRACT

The invention provides immunoconjugates of Formula I comprising an anti-HER2 antibody linked by conjugation to one or more 8-Het-2-aminobenzazepine derivatives. The invention also provides 8-Het-2-aminobenzazepine derivative intermediate compositions comprising a reactive functional group. Such intermediate compositions are suitable substrates for formation of the immunoconjugates through a linker or linking moiety. The invention further provides methods of treating cancer with the immunoconjugates.

4 Claims, No Drawings

ANTI-HER2 IMMUNOCONJUGATES, AND USES THEREOF

CROSS REFERENCE TO RELATED APPLICATIONS

This application is a 35 U.S.C. § 371 of International Application Serial No. PCT/US2021/062816, filed 10 Dec. 2021; which claims the benefit of U.S. Provisional Application No. 63/124,367, filed 11 Dec. 2020. The entire content of the applications referenced above are hereby incorporated by reference herein.

FIELD OF THE INVENTION

The invention relates generally to an immunoconjugate comprising an anti-HER2 antibody conjugated to one or more 8-Het-2-aminobenzazepine molecules.

BACKGROUND OF THE INVENTION

New compositions and methods for the delivery of antibodies and immune adjuvants are needed in order to reach inaccessible tumors and/or to expand treatment options for cancer patients and other subjects. The invention provides such compositions and methods.

SUMMARY OF THE INVENTION

The invention is generally directed to immunoconjugates comprising an anti-HER2 antibody linked by conjugation to one or more 8-Het-2-aminobenzazepine derivatives. The invention is further directed to 8-Het-2-aminobenzazepine derivative intermediate compositions comprising a reactive functional group. Such intermediate compositions are suitable substrates for formation of immunoconjugates wherein an antibody may be covalently bound by a linker L to a 8-Het-2-aminobenzazepine (HxBz) moiety having the formula:

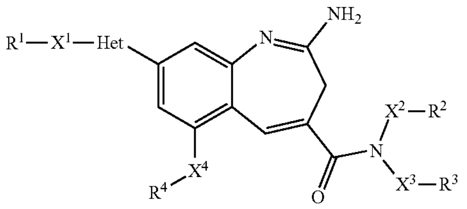

where Het is selected from heterocyclyldiyl and heteroaryldiyl; and one of $R^1$, $R^2$, $R^3$ and $R^4$ is attached to L. The $R^{1-4}$ and $X^{1-4}$ substituents are defined herein.

The invention is further directed to use of such an immunoconjugates in the treatment of an illness, in particular cancer.

An aspect of the invention is an immunoconjugate comprising an antibody covalently attached to a linker which is covalently attached to one or more 8-Het-2-aminobenzazepine moieties.

Another aspect of the invention is a 8-Het-2-aminobenzazepine-linker compound.

Another aspect of the invention is a method for treating cancer comprising administering a therapeutically effective amount of an immunoconjugate comprising an anti-HER2 antibody linked by conjugation to one or more 8-Het-2-aminobenzazepine moieties.

Another aspect of the invention is a use of an immunoconjugate comprising an anti-HER2 antibody linked by conjugation to one or more 8-Het-2-aminobenzazepine moieties for treating cancer.

Another aspect of the invention is a method of preparing an immunoconjugate by conjugation of one or more 8-Het-2-aminobenzazepine moieties with an anti-HER2 antibody.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the invention as defined by the claims.

One skilled in the art will recognize many methods and materials similar or equivalent to those described herein, which could be used in the practice of the present invention. The invention is in no way limited to the methods and materials described.

Definitions

The term "immunoconjugate" or "immune-stimulating antibody conjugate" refers to an antibody construct that is covalently bonded to an adjuvant moiety via a linker. the term "adjuvant" refers to a substance capable of eliciting an immune response in a subject exposed to the adjuvant.

"Adjuvant moiety" refers to an adjuvant that is covalently bonded to an antibody construct, e.g., through a linker, as described herein. The adjuvant moiety can elicit the immune response while bonded to the antibody construct or after cleavage (e.g., enzymatic cleavage) from the antibody construct following administration of an immunoconjugate to the subject.

"Adjuvant" refers to a substance capable of eliciting an immune response in a subject exposed to the adjuvant.

The terms "Toll-like receptor" and "TLR" refer to any member of a family of highly-conserved mammalian proteins which recognizes pathogen-associated molecular patterns and acts as key signaling elements in innate immunity. TLR polypeptides share a characteristic structure that includes an extracellular domain that has leucine-rich repeats, a transmembrane domain, and an intracellular domain that is involved in TLR signaling.

The terms "Toll-like receptor 7" and "TLR7" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ99026 for human TLR7 polypeptide, or GenBank accession number AAK62676 for murine TLR7 polypeptide.

The terms "Toll-like receptor 8" and "TLR8" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ95441 for human TLR8 polypeptide, or GenBank accession number AAK62677 for murine TLR8 polypeptide.

A "TLR agonist" is a substance that binds, directly or indirectly, to a TLR (e.g., TLR7 and/or TLR8) to induce TLR signaling. Any detectable difference in TLR signaling can indicate that an agonist stimulates or activates a TLR. Signaling differences can be manifested, for example, as changes in the expression of target genes, in the phosphorylation of signal transduction components, in the intracellular localization of downstream elements such as nuclear factor-κB (NF-κB), in the association of certain components (such as IL-1 receptor associated kinase (IRAK)) with other proteins or intracellular structures, or in the biochemical activity of components such as kinases (such as mitogen-activated protein kinase (MAPK)).

"Antibody" refers to a polypeptide comprising an antigen binding region (including the complementarity determining region (CDRs)) from an immunoglobulin gene or fragments thereof. The term "antibody" specifically encompasses monoclonal antibodies (including full length monoclonal antibodies), polyclonal antibodies, multispecific antibodies (e.g., bispecific antibodies), and antibody fragments that exhibit the desired biological activity. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa) connected by disulfide bonds. Each chain is composed of structural domains, which are referred to as immunoglobulin domains. These domains are classified into different categories by size and function, e.g., variable domains or regions on the light and heavy chains ($V_L$ and $V_H$, respectively) and constant domains or regions on the light and heavy chains ($C_L$ and $C_H$, respectively). The N-terminus of each chain defines a variable region of about 100 to 110 or more amino acids, referred to as the paratope, primarily responsible for antigen recognition, i.e., the antigen binding domain. Light chains are classified as either kappa or lambda. Heavy chains are classified as gamma, mu, alpha, delta, or epsilon, which in turn define the immunoglobulin classes, IgG, IgM, IgA, IgD and IgE, respectively.

IgG antibodies are large molecules of about 150 kDa composed of four peptide chains. IgG antibodies contain two identical class γ heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form the Y-like shape. Each end of the fork contains an identical antigen binding domain. There are four IgG subclasses (IgG1, IgG2, IgG3, and IgG4) in humans, named in order of their abundance in serum (i.e., IgG1 is the most abundant). Typically, the antigen binding domain of an antibody will be most critical in specificity and affinity of binding to cancer cells.

"Antibody construct" refers to an antibody or a fusion protein comprising (i) an antigen binding domain and (ii) an Fc domain.

In some embodiments, the binding agent is an antigen-binding antibody "fragment," which is a construct that comprises at least an antigen-binding region of an antibody, alone or with other components that together constitute the antigen-binding construct. Many different types of antibody "fragments" are known in the art, including, for instance, (i) a Fab fragment, which is a monovalent fragment consisting of the $V_L$, $V_H$, $C_L$, and $CH_1$ domains, (ii) a $F(ab')_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an $F(ab')_2$ fragment using mild reducing conditions, (v) a disulfide-stabilized Fv fragment (dsFv), and (vi) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain.

The antibody or antibody fragments can be part of a larger construct, for example, a conjugate or fusion construct of the antibody fragment to additional regions. For instance, in some embodiments, the antibody fragment can be fused to an Fc region as described herein. In other embodiments, the antibody fragment (e.g., a Fab or scFv) can be part of a chimeric antigen receptor or chimeric T-cell receptor, for instance, by fusing to a transmembrane domain (optionally with an intervening linker or "stalk" (e.g., hinge region)) and optional intercellular signaling domain.

"Epitope" means any antigenic determinant or epitopic determinant of an antigen to which an antigen binding domain binds (i.e., at the paratope of the antigen binding domain). Antigenic determinants usually consist of chemically active surface groupings of molecules, such as amino acids or sugar side chains, and usually have specific three dimensional structural characteristics, as well as specific charge characteristics.

The terms "Fc receptor" or "FcR" refer to a receptor that binds to the Fc region of an antibody. There are three main classes of Fc receptors: (1) FcγR which bind to IgG, (2) FcαR which binds to IgA, and (3) FcR which binds to IgE. The FcγR family includes several members, such as FcγI (CD64), FcγRIIA (CD32A), FcγRIIB (CD32B), FcγRIIIA (CD16A), and FcγRIIIB (CD16B). The Fcγ receptors differ in their affinity for IgG and also have different affinities for the IgG subclasses (e.g., IgG1, IgG2, IgG3, and IgG4).

Nucleic acid or amino acid sequence "identity," as referenced herein, can be determined by comparing a nucleic acid or amino acid sequence of interest to a reference nucleic acid or amino acid sequence. The percent identity is the number of nucleotides or amino acid residues that are the same (i.e., that are identical) as between the optimally aligned sequence of interest and the reference sequence divided by the length of the longest sequence (i.e., the length of either the sequence of interest or the reference sequence, whichever is longer). Alignment of sequences and calculation of percent identity can be performed using available software programs. Examples of such programs include CLUSTAL-W, T-Coffee, and ALIGN (for alignment of nucleic acid and amino acid sequences), BLAST programs (e.g., BLAST 2.1, BL2SEQ, BLASTp, BLASTn, and the like) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)). Percent (%) identity of sequences can be also calculated, for example, as $100\times[(\text{identical positions})/\min(TG_A, TG_B)]$, where $TG_A$ and $TG_B$ are the sum of the number of residues and internal gap positions in peptide sequences A and B in the alignment that minimizes $TG_A$ and $TG_B$. See, e.g., Russell et al., *J. Mol Biol.,* 244: 332-350 (1994).

The binding agent comprises Ig heavy and light chain variable region polypeptides that together form the antigen binding site. Each of the heavy and light chain variable regions are polypeptides comprising three complementarity determining regions (CDR1, CDR2, and CDR3) connected by framework regions. The binding agent can be any of a variety of types of binding agents known in the art that comprise Ig heavy and light chains. For instance, the binding agent can be an antibody, an antigen-binding antibody "fragment," or a T-cell receptor.

"Biosimilar" refers to an approved antibody construct that has active properties similar to, for example, a HER2-targeting antibody such as trastuzumab (HERCEPTIN™, Genentech, Inc.) or pertuzumab (PERJETA, Genentech, Inc.)

"Biobetter" refers to an approved antibody construct that is an improvement of a previously approved antibody construct, such as labetuzumab. The biobetter can have one or more modifications (e.g., an altered glycan profile, or a unique epitope) over the previously approved antibody construct. A biobetter is a recombinant protein drug from the same class as an existing biopharmaceutical but is not identical; and is superior to the original. A biobetter is not exclusively a new drug, neither a generic version of a drug. Biosimilars and biobetters are both variants of a biologic; with the former being close copies of the originator, while the latter ones have been improved in terms of efficacy, safety, and tolerability or dosing regimen.

"Amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid). The amino acids can be glycosylated (e.g., N-linked glycans, O-linked glycans, phosphoglycans, C-linked glycans, or glypication) or deglycosylated. Amino acids may be referred to herein by either the commonly known three letter symbols or by the one-letter symbols recommended by the IUPAC-IUB Biochemical Nomenclature Commission.

Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Naturally-occurring amino acids include those formed in proteins by post-translational modification, such as citrulline (Cit).

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

"Linker" refers to a functional group that covalently bonds two or more moieties in a compound or material. For example, the linking moiety can serve to covalently bond an adjuvant moiety to an antibody construct in an immunoconjugate.

"Linking moiety" refers to a functional group that covalently bonds two or more moieties in a compound or material. For example, the linking moiety can serve to covalently bond an adjuvant moiety to an antibody in an immunoconjugate. Useful bonds for connecting linking moieties to proteins and other materials include, but are not limited to, amides, amines, esters, carbamates, ureas, thioethers, thiocarbamates, thiocarbonates, and thioureas.

"Divalent" refers to a chemical moiety that contains two points of attachment for linking two functional groups; polyvalent linking moieties can have additional points of attachment for linking further functional groups. Divalent radicals may be denoted with the suffix "diyl". For example, divalent linking moieties include divalent polymer moieties such as divalent poly(ethylene glycol), divalent cycloalkyl, divalent heterocycloalkyl, divalent aryl, and divalent heteroaryl group. A "divalent cycloalkyl, heterocycloalkyl, aryl, or heteroaryl group" refers to a cycloalkyl, heterocycloalkyl, aryl, or heteroaryl group having two points of attachment for covalently linking two moieties in a molecule or material. Cycloalkyl, heterocycloalkyl, aryl, or heteroaryl groups can be substituted or unsubstituted. Cycloalkyl, heterocycloalkyl, aryl, or heteroaryl groups can be substituted with one or more groups selected from halo, hydroxy, amino, alkylamino, amido, acyl, nitro, cyano, and alkoxy.

A wavy line ("  ") represents a point of attachment of the specified chemical moiety. If the specified chemical moiety has two wavy lines present, it will be understood that the chemical moiety can be used bilaterally, i.e., as read from left to right or from right to left.

"Alkyl" refers to a straight (linear) or branched, saturated, aliphatic radical having the number of carbon atoms indicated. Alkyl can include any number of carbons, for example from one to twelve. Examples of alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, 1-heptyl, 1-octyl, and the like. Alkyl groups can be substituted or unsubstituted. "Substituted alkyl" groups can be substituted with one or more groups selected from halo, hydroxy, amino, oxo (=O), alkylamino, amido, acyl, nitro, cyano, and alkoxy.

The term "alkyldiyl" refers to a divalent alkyl radical. Examples of alkyldiyl groups include, but are not limited to, methylene ($—CH_2—$), ethylene ($—CH_2CH_2—$), propylene ($—CH_2CH_2CH_2—$), and the like. An alkyldiyl group may also be referred to as an "alkylene" group.

"Alkenyl" refers to a straight (linear) or branched, unsaturated, aliphatic radical having the number of carbon atoms indicated and at least one carbon-carbon double bond, sp2. Alkenyl can include from two to about 12 or more carbons atoms. Alkenyl groups are radicals having "cis" and "trans" orientations, or alternatively, "E" and "Z" orientations. Examples include, but are not limited to, ethylenyl or vinyl ($—CH=CH_2$), allyl ($—CH_2CH=CH_2$), butenyl, pentenyl, and isomers thereof. Alkenyl groups can be substituted or unsubstituted. "Substituted alkenyl" groups can be substituted with one or more groups selected from halo, hydroxy, amino, oxo (=O), alkylamino, amido, acyl, nitro, cyano, and alkoxy.

The terms "alkenylene" or "alkenyldiyl" refer to a linear or branched-chain divalent hydrocarbon radical. Examples include, but are not limited to, ethylenylene or vinylene ($—CH=CH—$), allyl ($—CH_2CH=CH—$), and the like.

"Alkynyl" refers to a straight (linear) or branched, unsaturated, aliphatic radical having the number of carbon atoms indicated and at least one carbon-carbon triple bond, sp. Alkynyl can include from two to about 12 or more carbons atoms. For example, $C_2$-$C_6$ alkynyl includes, but is not limited to ethynyl ($—C≡CH$), propynyl (propargyl, $—CH_2C≡CH$), butynyl, pentynyl, hexynyl, and isomers thereof. Alkynyl groups can be substituted or unsubstituted. "Substituted alkynyl" groups can be substituted with one or more groups selected from halo, hydroxy, amino, oxo (=O), alkylamino, amido, acyl, nitro, cyano, and alkoxy.

The term "alkynylene" or "alkynyldiyl" refer to a divalent alkynyl radical.

The terms "carbocycle", "carbocyclyl", "carbocyclic ring" and "cycloalkyl" refer to a saturated or partially unsaturated, monocyclic, fused bicyclic, or bridged polycyclic ring assembly containing from 3 to 12 ring atoms, or the number of atoms indicated. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbornane, [2.2.2] bicyclooctane, decahydronaphthalene and adamantane. Carbocyclic groups can also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

The term "cycloalkyldiyl" refers to a divalent cycloalkyl radical.

"Aryl" refers to a monovalent aromatic hydrocarbon radical of 6-20 carbon atoms ($C_6$-$C_{20}$) derived by the removal of one hydrogen atom from a single carbon atom of a parent aromatic ring system. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl.

The terms "arylene" or "aryldiyl" mean a divalent aromatic hydrocarbon radical of 6-20 carbon atoms ($C_6$-$C_{20}$) derived by the removal of two hydrogen atom from a two carbon atoms of a parent aromatic ring system. Some aryldiyl groups are represented in the exemplary structures as "Ar". Aryldiyl includes bicyclic radicals comprising an aromatic ring fused to a saturated, partially unsaturated ring, or aromatic carbocyclic ring. Typical aryldiyl groups include, but are not limited to, radicals derived from benzene (phenyldiyl), substituted benzenes, naphthalene, anthracene, biphenylene, indenylene, indanylene, 1,2-dihydronaphthalene, 1,2,3,4-tetrahydronaphthyl, and the like. Aryldiyl groups are also referred to as "arylene", and are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (═O) moieties are pyrimidinonyl and 1,1-dioxo-thiomorpholinyl. The heterocycle groups herein are optionally substituted independently with one or more substituents described herein.

The term "heterocyclyldiyl" refers to a divalent, saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents as described. Examples of 5-membered and 6-membered heterocyclyldiyls include morpholinyldiyl, piperidinyldiyl, piperazinyldiyl, pyrrolidinyldiyl, dioxanyldiyl, thiomorpholinyldiyl, and S-dioxothiomorpholinyldiyl.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroaryldiyl" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of 5-membered and 6-membered heteroaryldiyls include pyridyldiyl, imidazolyldiyl, pyrimidyldiyl, pyrazolyldiyl, triazolyldiyl, pyrazinyldiyl, tetrazolyldiyl, furyldiyl, thienyldiyl, isoxazolyldiyldiyl, thiazolyldiyl, oxadiazolyldiyl, oxazolyldiyl, isothiazolyldiyl, and pyrrolyldiyl.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "halo" and "halogen," by themselves or as part of another substituent, refer to a fluorine, chlorine, bromine, or iodine atom.

The term "carbonyl," by itself or as part of another substituent, refers to C(═O) or —C(═O)—, i.e., a carbon atom double-bonded to oxygen and bound to two other groups in the moiety having the carbonyl.

As used herein, the phrase "quaternary ammonium salt" refers to a tertiary amine that has been quaternized with an alkyl substituent (e.g., a $C_1$-$C_4$ alkyl such as methyl, ethyl, propyl, or butyl).

The terms "treat," "treatment," and "treating" refer to any indicia of success in the treatment or amelioration of an injury, pathology, condition (e.g., cancer), or symptom (e.g., cognitive impairment), including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., skin, lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

The phrases "effective amount" and "therapeutically effective amount" refer to a dose or amount of a substance such as an immunoconjugate that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics,* $11^{th}$ Edition (McGraw-Hill, 2006); and *Remington: The Science and Practice of Pharmacy,* $22^{nd}$ Edition, (Pharmaceutical Press, London, 2012)). In the case of cancer, the therapeutically effective amount of the immunoconjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the immunoconjugate may prevent growth and/or kill existing cancer cells, it may be cytostatic and/or cytotoxic. For cancer therapy, efficacy can, for example, be measured by assessing the time to disease progression (TTP) and/or determining the response rate (RR)

"Recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

The phrase "synergistic adjuvant" or "synergistic combination" in the context of this invention includes the combination of two immune modulators such as a receptor agonist, cytokine, and adjuvant polypeptide, that in combination elicit a synergistic effect on immunity relative to either administered alone. Particularly, the immunoconjugates disclosed herein comprise synergistic combinations of the claimed adjuvant and antibody construct. These synergistic combinations upon administration elicit a greater effect on immunity, e.g., relative to when the antibody construct or adjuvant is administered in the absence of the other moiety. Further, a decreased amount of the immunoconjugate may be administered (as measured by the total number of antibody constructs or the total number of adjuvants administered as part of the immunoconjugate) compared to when either the antibody construct or adjuvant is administered alone.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

The terms "about" and "around," as used herein to modify a numerical value, indicate a close range surrounding the numerical value. Thus, if "X" is the value, "about X" or "around X" indicates a value of from 0.9X to 1.1X, e.g., from 0.95X to 1.05X or from 0.99X to 1.01X. A reference to "about X" or "around X" specifically indicates at least the values X, 0.95X, 0.96X, 0.97X, 0.98X, 0.99X, 1.01X, 1.02X, 1.03X, 1.04X, and 1.05X. Accordingly, "about X" and "around X" are intended to teach and provide written description support for a claim limitation of, e.g., "0.98X."

HER2 Antibodies

Immunoconjugates of the invention comprise an antibody construct that comprises an antigen binding domain that specifically recognizes and binds HER2.

In certain embodiments, immunoconjugates of the invention comprise anti-HER2 antibodies. In one embodiment of the invention, an anti-HER2 antibody of an immunoconjugate of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337, which is specifically incorporated by reference herein. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN™ (Genentech, Inc.).

Trastuzumab (CAS 180288-69-1, HERCEPTIN®, huMAb4D5-8, rhuMAb HER2, Genentech) is a recombinant DNA-derived, IgG1 kappa, monoclonal antibody that is a humanized version of a murine anti-HER2 antibody (4D5) that selectively binds with high affinity in a cell-based assay (Kd=5 nM) to the extracellular domain of HER2 (U.S. Pat. Nos. 5,677,171; 5,821,337; 6,054,297; 6,165,464; 6,339,142; 6,407,213; 6,639,055; 6,719,971; 6,800,738; 7,074,404; Coussens et al (1985) *Science* 230:1132-9; Slamon et al (1989) *Science* 244:707-12; Slamon et al (2001) *New Engl. J. Med.* 344:783-792).

In an embodiment of the invention, the antibody construct or antigen binding domain comprises the CDR regions of trastuzumab. In an embodiment of the invention, the anti-HER2 antibody further comprises the framework regions of the trastuzumab. In an embodiment of the invention, the anti-HER2 antibody further comprises one or both variable regions of trastuzumab.

In another embodiment of the invention, an anti-HER2 antibody of an immunoconjugate of the invention comprises a humanized anti-HER2 antibody, e.g., humanized 2C4, as described in U.S. Pat. No. 7,862,817. An exemplary humanized 2C4 antibody is pertuzumab (CAS Reg. No. 380610-27-5), PERJETA™ (Genentech, Inc.). Pertuzumab is a HER dimerization inhibitor (HDI) and functions to inhibit the ability of HER2 to form active heterodimers or homodimers with other HER receptors (such as EGFR/HER1, HER2, HER3 and HER4). See, for example, Harari and Yarden, *Oncogene* 19:6102-14 (2000); Yarden and Sliwkowski. *Nat Rev Mol Cell Biol* 2:127-37 (2001); Sliwkowski *Nat Struct Biol* 10:158-9 (2003); Cho et al. *Nature* 421:756-60 (2003); and Malik et al. *Pro Am Soc Cancer Res* 44:176-7 (2003). PERJETA™ is approved for the treatment of breast cancer.

In an embodiment of the invention, the antibody construct or antigen binding domain comprises the CDR regions of pertuzumab. In an embodiment of the invention, the anti-HER2 antibody further comprises the framework regions of the pertuzumab. In an embodiment of the invention, the anti-HER2 antibody further comprises one or both variable regions of pertuzumab.

The immunoconjugate of the invention comprises an antibody which targets, binds, or recognizes HER2. Included in the scope of the embodiments of the invention are functional variants of the antibody constructs or antigen binding domain described herein. The term "functional variant" as used herein refers to an antibody construct having an antigen binding domain with substantial or significant sequence identity or similarity to a parent antibody construct or antigen binding domain, which functional variant retains the biological activity of the antibody construct or antigen binding domain of which it is a variant. Functional variants encompass, for example, those variants of the antibody constructs or antigen binding domain described herein (the parent antibody construct or antigen binding domain) that retain the ability to recognize target cells expressing HER2 to a similar extent, the same extent, or to a higher extent, as the parent antibody construct or antigen binding domain.

In reference to the antibody construct or antigen binding domain, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the antibody construct or antigen binding domain.

A functional variant can, for example, comprise the amino acid sequence of the parent antibody construct or antigen binding domain with at least one conservative amino acid substitution. Alternatively, or additionally, the functional variants can comprise the amino acid sequence of the parent antibody construct or antigen binding domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent antibody construct or antigen binding domain.

The antibodies comprising the immunoconjugates of the invention include Fc engineered variants. In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/I332E/A330L), GA (G236A), ALIE (A330L/I332E), GASDALIE (G236A/S239D/A330L/I332E), V9 (G237D/P238D/P271G/A330R), and V11 (G237D/P238D/H268D/P271G/A330R), and/or one or more mutations at the following amino acids: E345R, E233, G237, P238, H268, P271, L328 and A330. Additional Fc region modifications for modulating Fc receptor binding are described in, for example, U.S. Patent Application Publication 2016/0145350 and U.S. Pat. Nos. 7,416,726 and 5,624,821, which are hereby incorporated by reference in their entireties herein.

The antibodies comprising the immunoconjugates of the invention include glycan variants, such as afucosylation. In some embodiments, the Fc region of the binding agents are modified to have an altered glycosylation pattern of the Fc region compared to the native non-modified Fc region.

Amino acid substitutions of the inventive antibody constructs or antigen binding domains are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g., Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The antibody construct or antigen binding domain can consist essentially of the specified amino acid sequence or sequences described herein, such that other components, e.g., other amino acids, do not materially change the biological activity of the antibody construct or antigen binding domain functional variant.

In some embodiments, the antibodies in the immunoconjugates contain a modified Fc region, wherein the modification modulates the binding of the Fc region to one or more Fc receptors.

In some embodiments, the antibodies in the immunoconjugates (e.g., antibodies conjugated to at least two adjuvant moieties) contain one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to the native antibody lacking the mutation in the Fc region. In some embodiments, the antibodies in the immunoconjugates contain one or more modifications (e.g., amino acid insertion, deletion, and/or substitution) in the Fc region that reduce the binding of the Fc region of the antibody to FcγRIIB. In some embodiments, the antibodies in the immunoconjugates contain one or more modifications (e.g., amino acid insertion, deletion, and/or substitution) in the Fc region of the antibody that reduce the binding of the antibody to FcγRIIB while maintaining the same binding or having increased binding to FcγRI (CD64), FcγRIIA (CD32A), and/or FcRγIIIA (CD16a) as compared to the native antibody lacking the mutation in the Fc region. In some embodiments, the antibodies in the immunoconjugates contain one of more modifications in the Fc region that increase the binding of the Fc region of the antibody to FcγRIIB.

In some embodiments, the modulated binding is provided by mutations in the Fc region of the antibody relative to the native Fc region of the antibody. The mutations can be in a CH2 domain, a CH3 domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in the native antibody (e.g., cetuximab). Native sequence human Fc regions include a native sequence human IgG1 Fc region, native sequence human IgG2 Fc region, native sequence human IgG3 Fc region, and native sequence human IgG4 Fc region, as well as naturally occurring variants thereof. Native sequence Fc includes the various allotypes of Fcs (Jefferis et al., (2009) *mAbs,* 1(4):332-338).

In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/I332E/A330L), GA (G236A), ALIE (A330L/I332E), GASDALIE (G236A/S239D/A330L/I332E), V9 (G237D/P238D/P271G/A330R), and V11 (G237D/P238D/H268D/P271G/A330R), and/or one or more mutations at the following amino acids: E233, G237, P238, H268, P271, L328 and A330. Additional Fc region modifications for modulating Fc receptor binding are described in, for example, US 2016/0145350 and U.S. Pat. Nos. 7,416,726 and 5,624,821, which are hereby incorporated by reference in their entireties.

In some embodiments, the Fc region of the antibodies of the immunoconjugates are modified to have an altered glycosylation pattern of the Fc region compared to the native non-modified Fc region.

Human immunoglobulin is glycosylated at the Asn297 residue in the C72 domain of each heavy chain. This N-linked oligosaccharide is composed of a core heptasaccharide, N-acetylglucosamine4Mannose3 (GlcNAc4Man3). Removal of the heptasaccharide with endoglycosidase or PNGase F is known to lead to conformational changes in the antibody Fc region, which can significantly reduce antibody-binding affinity to activating FcγR and lead to decreased effector function. The core heptasaccharide is often decorated with galactose, bisecting GlcNAc, fucose, or sialic acid, which differentially impacts Fc binding to activating and inhibitory FcγR. Additionally, it has been demonstrated that α2,6-sialyation enhances anti-inflammatory activity in vivo, while defucosylation leads to improved FcγRIIIa binding and a 10-fold increase in antibody-dependent cellular cytotoxicity and antibody-dependent phagocytosis. Specific glycosylation patterns, therefore, can be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416,726 and U.S. Patent Application Publications 2007/0014795 and 2008/0286819, which are hereby incorporated by reference in their entireties.

In some embodiments, the antibodies of the immunoconjugates are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FcRγIIIa binding and effector function. In some embodiments, the antibodies of the immunoconjugates are engineered to be afucosylated.

In some embodiments, the entire Fc region of an antibody in the immunoconjugates is exchanged with a different Fc region, so that the Fab region of the antibody is conjugated to a non-native Fc region. In some embodiments, the Fc modified antibody with a non-native Fe domain also comprises one or more amino acid modification, such as the S228P mutation within the IgG4 Fe, that modulate the stability of the Fe domain described. In some embodiments, the Fc modified antibody with a non-native Fe domain also comprises one or more amino acid modifications described herein that modulate Fc binding to FcR.

In some embodiments, the modifications that modulate the binding of the Fc region to FcR do not alter the binding of the Fab region of the antibody to its antigen when compared to the native non-modified antibody. In other embodiments, the modifications that modulate the binding of the Fc region to FcR also increase the binding of the Fab region of the antibody to its antigen when compared to the native non-modified antibody.

In some embodiments, the antibodies in the immunoconjugates are glycosylated.

In some embodiments, the antibody in the immunoconjugates is a cysteine-engineered antibody which provides for site-specific conjugation of an adjuvant, label, or drug moiety to the antibody through cysteine substitutions at sites where the engineered cysteines are available for conjugation but do not perturb immunoglobulin folding and assembly or alter antigen binding and effector functions (Junutula, et al., 2008b *Nature Biotech.,* 26(8):925-932; Dornan et al. (2009) *Blood* 114(13):2721-2729; U.S. Pat. Nos. 7,521,541; 7,723,485; US 2012/0121615; WO 2009/052249). A "cysteine engineered antibody" or "cysteine engineered antibody variant" is an antibody in which one or more residues of an antibody are substituted with cysteine residues. Cysteine-engineered antibodies can be conjugated to the 8-Het-2-aminobenzazepine adjuvant moiety as an 8-Het-2-amino-benzazepine-linker compound with uniform stoichiometry (e.g., up to two 8-Het-2-aminobenzazepine moieties per antibody in an antibody that has a single engineered cysteine site).

In some embodiments, cysteine-engineered antibodies used to prepare the immunoconjugates of Table 3 have a cysteine residue introduced at the 149-lysine site of the light chain (LC K149C). In other embodiments, the cysteine-engineered antibodies have a cysteine residue introduced at the 118-alanine site (EU numbering) of the heavy chain (HC A118C). This site is alternatively numbered 121 by Sequential numbering or 114 by Kabat numbering. In other embodiments, the cysteine-engineered antibodies have a cysteine residue introduced in the light chain at G64C or R142C according to Kabat numbering, or in the heavy chain at D101C, V184C or T205C according to Kabat numbering.

8-Het-2-Aminobenzazepine Adjuvant Compounds

The immunoconjugate of the invention comprises an 8-Het-2-aminobenzazepine adjuvant moiety. The adjuvant moiety described herein is a compound that elicits an immune response (i.e., an immunostimulatory agent). Generally, the adjuvant moiety described herein is a TLR agonist. TLRs are type-I transmembrane proteins that are responsible for the initiation of innate immune responses in vertebrates. TLRs recognize a variety of pathogen-associated molecular patterns from bacteria, viruses, and fungi and act as a first line of defense against invading pathogens. TLRs elicit overlapping yet distinct biological responses due to differences in cellular expression and in the signaling pathways that they initiate. Once engaged (e.g., by a natural stimulus or a synthetic TLR agonist), TLRs initiate a signal transduction cascade leading to activation of nuclear factor-κB (NF-κB) via the adapter protein myeloid differentiation primary response gene 88 (MyD88) and recruitment of the IL-1 receptor associated kinase (IRAK). Phosphorylation of IRAK then leads to recruitment of TNF-receptor associated factor 6 (TRAF6), which results in the phosphorylation of the NF-κB inhibitor I-κB. As a result, NF-κB enters the cell nucleus and initiates transcription of genes whose promoters contain NF-κB binding sites, such as cytokines. Additional modes of regulation for TLR signaling include TIR-domain containing adapter-inducing interferon-β (TRIF)-dependent induction of TNF-receptor associated factor 6 (TRAF6) and activation of MyD88 independent pathways via TRIF and TRAF3, leading to the phosphorylation of interferon response factor three (IRF3). Similarly, the MyD88 dependent pathway also activates several IRF family members, including IRF5 and IRF7 whereas the TRIF dependent pathway also activates the NF-κB pathway.

Typically, the adjuvant moiety described herein is a TLR7 and/or TLR8 agonist. TLR7 and TLR8 are both expressed in monocytes and dendritic cells. In humans, TLR7 is also expressed in plasmacytoid dendritic cells (pDCs) and B cells. TLR8 is expressed mostly in cells of myeloid origin, i.e., monocytes, granulocytes, and myeloid dendritic cells. TLR7 and TLR8 are capable of detecting the presence of "foreign" single-stranded RNA within a cell, as a means to respond to viral invasion. Treatment of TLR8-expressing cells, with TLR8 agonists can result in production of high levels of IL-12, IFN-γ, IL-1, TNF-α, IL-6, and other inflammatory cytokines. Similarly, stimulation of TLR7-expressing cells, such as pDCs, with TLR7 agonists can result in production of high levels of IFN-α and other inflammatory cytokines. TLR7/TLR8 engagement and resulting cytokine production can activate dendritic cells and other antigen-presenting cells, driving diverse innate and acquired immune response mechanisms leading to tumor destruction.

Exemplary 8-Het-2-aminobenzazepine compounds (Hx) of the invention are shown in Table 1. Each compound was synthesized, purified, and characterized by mass spectrometry and shown to have the mass indicated. Additional experimental procedures are found in the Examples. Activity against HEK293 NFKB reporter cells expressing human TLR7 or human TLR8 was measured according to Example 202. The 8-Het-2-aminobenzazepine compounds of Table 1 demonstrate the surprising and unexpected property of TLR8 agonist selectivity which may predict useful therapeutic activity to treat cancer and other disorders.

TABLE 1

8-Het-2-aminobenzazepine compounds (HxBz)

| Hx No. | Structure | MW | HEK293 hTLR7 EC50 (nM) | HEK293 hTLR8 EC50 (nM) |
|---|---|---|---|---|
| HxBz-1 | 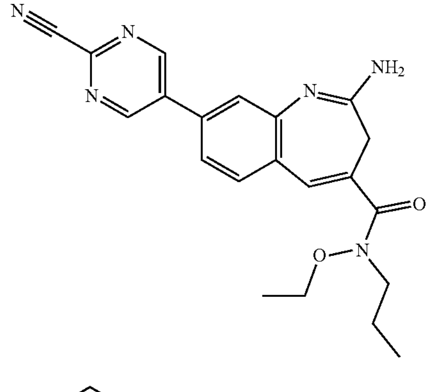 | 390.44 | 2536 | 163 |
| HxBz-2 | 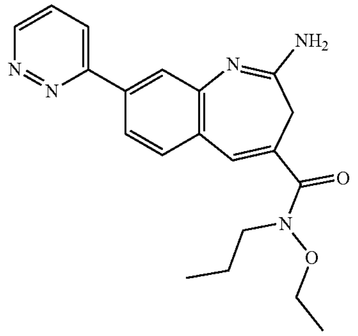 [SMILES: CCCN(OCC)C(=O)C1=Cc2ccc(-c3cccnn3)cc2N=C(N)C1] | 365.4 | 2238 | 276 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-3 | 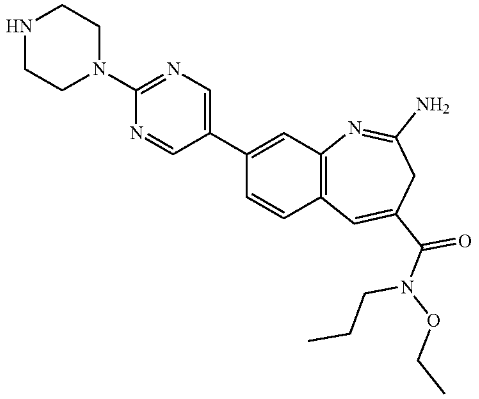 [SMILES: CCCN(OCC)C(=O)C1=Cc2ccc(-c3cnc(N4CCNCC4)nc3)cc2N=C(N)C1] | 449.6 | 562 | 43 |
| HxBz-4 | 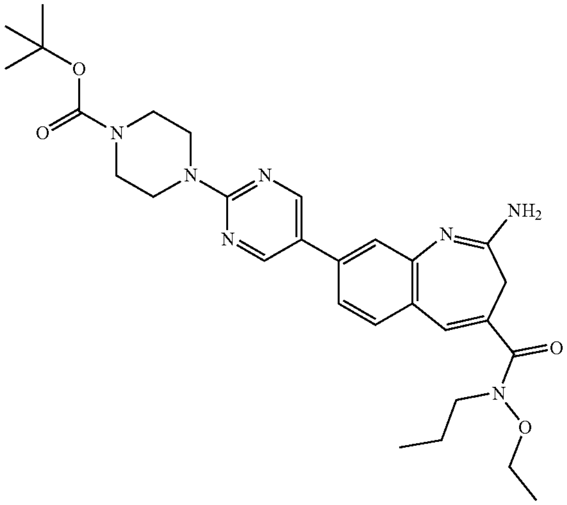 [SMILES: CCCN(OCC)C(=O)C1=Cc2ccc(-c3cnc(N4CCN(C(=O)OC(C)(C)C)CC4)nc3)cc2N=C(N)C1] | 549.7 | 3259 | 350 |
| HxBz-5 | 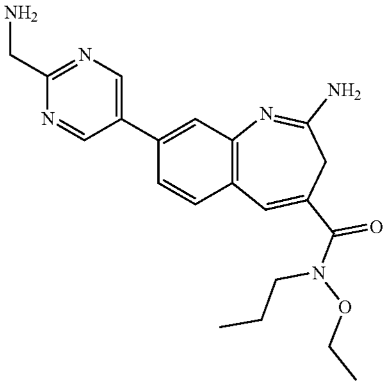 [SMILES: CCCN(OCC)C(=O)C1=Cc2ccc(-c3cnc(CN)nc3)cc2N=C(N)C1] | 394.5 | 525 | 17 |

TABLE 1-continued
8-Het-2-aminobenzazepine compounds (HxBz)
| Hx No. | Structure | MW | HEK293 hTLR7 EC50 (nM) | HEK293 hTLR8 EC50 (nM) |
|---|---|---|---|---|
| HxBz-6 | 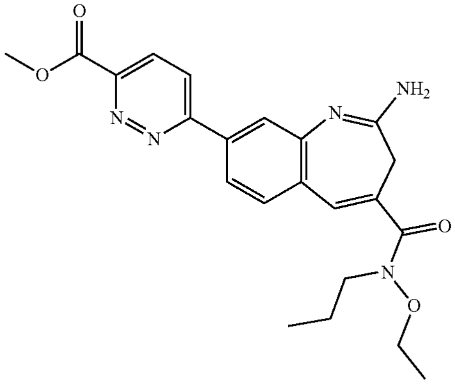 [SMILES: CCCN(OCC)C(=O)C1=Cc2ccc(-c3ccc(C(=O)OC)nn3)cc2N=C(N)C1] | 423.5 | 2659 | 339 |
| HxBz-7 | 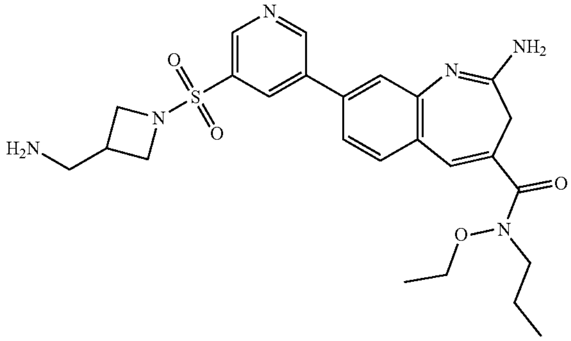 [SMILES: CCCN(OCC)C(=O)C1=Cc2ccc(-c3cncc(S(=O)(=O)N4CC(CN)C4)c3)cc2N=C(N)C1] | 512.6 | 3633 | 335 |
| HxBz-8 | 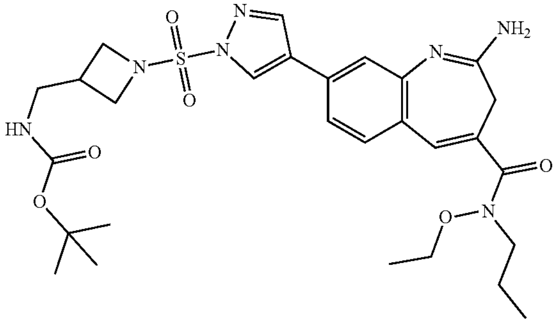 [SMILES: CCCN(OCC)C(=O)C1=Cc2ccc(-c3cnn(S(=O)(=O)N4CC(CNC(=O)OC(C)(C)C)C4)c3)cc2N=C(N)C1] | 601.7 | | |
| HxBz-9 | 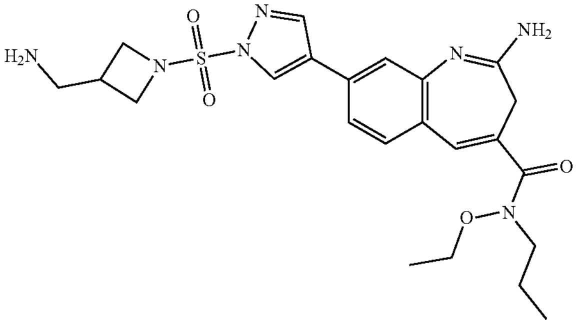 [SMILES: CCCN(OCC)C(=O)C1=Cc2ccc(-c3cnn(S(=O)(=O)N4CC(CN)C4)c3)cc2N=C(N)C1] | 501.6 | 8630 | 397 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-10 | 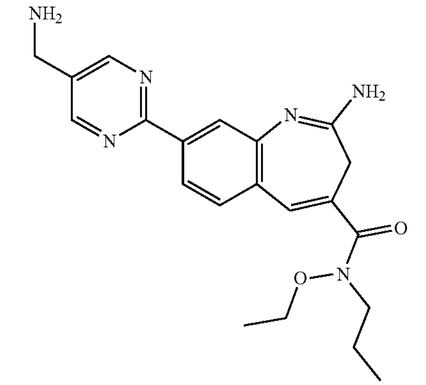 [SMILES: CCCN(OCC)C(=O)C1=Cc2ccc(-c3ncc(CN)cn3)cc2N=C(N)C1] | 394.5 | 9000 | 814 |
| HxBz-11 | 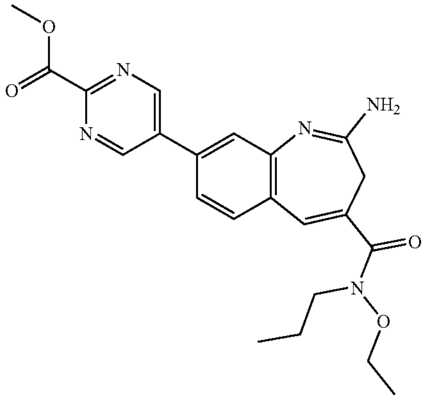 [SMILES: CCCN(OCC)C(=O)C1=Cc2ccc(-c3cnc(C(=O)OC)nc3)cc2N=C(N)C1] | 423.5 | 4070 | 161 |
| HxBz-12 | 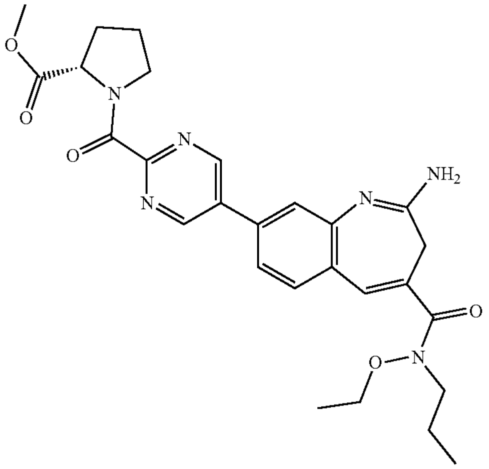 [SMILES: CCCN(OCC)C(=O)C1=Cc2ccc(-c3cnc(C(=O)N4CCC[C@H]4C(=O)OC)nc3)cc2N=C(N)C1] | 520.6 | 159 | 6 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-13 | 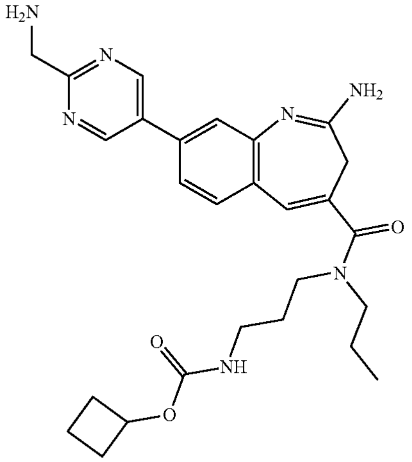 [SMILES: CCCN(CCCNC(=O)OC1CCC1)C(=O)C1=Cc2ccc(-c3cnc(CN)nc3)cc2N=C(N)C1] | 505.6 | 242 | 274 |
| HxBz-14 | 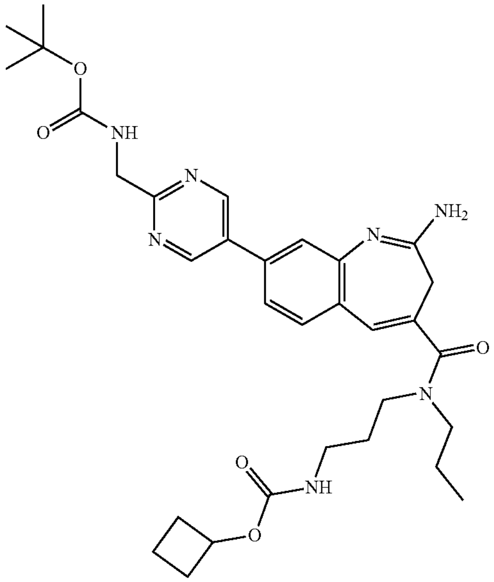 [SMILES: CCCN(CCCNC(=O)OC1CCC1)C(=O)C1=Cc2ccc(-c3cnc(CNC(=O)OC(C)(C)C)nc3)cc2N=C(N)C1] | 605.7 | | |
| HxBz-15 | 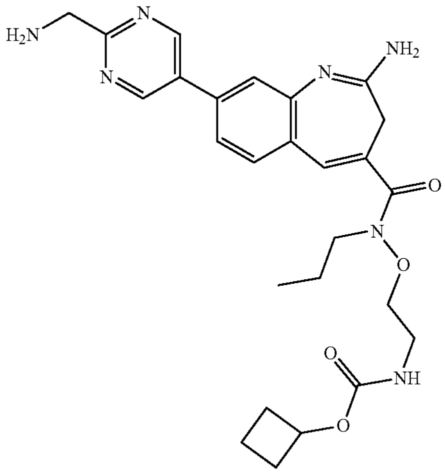 [SMILES: CCCN(OCCNC(=O)OC1CCC1)C(=O)C1=Cc2ccc(-c3cnc(CN)nc3)cc2N=C(N)C1] | 507.6 | 35 | 10 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-16 | 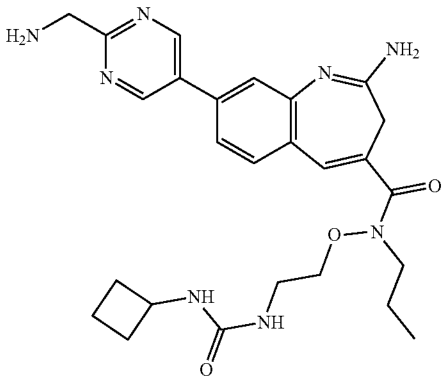 [SMILES: CCCN(OCCNC(=O)NC1CCC1)C(=O)C1=Cc2ccc(-c3cnc(CN)nc3)cc2N=C(N)C1] | 506.6 | 4602 | 399 |
| HxBz-17 | 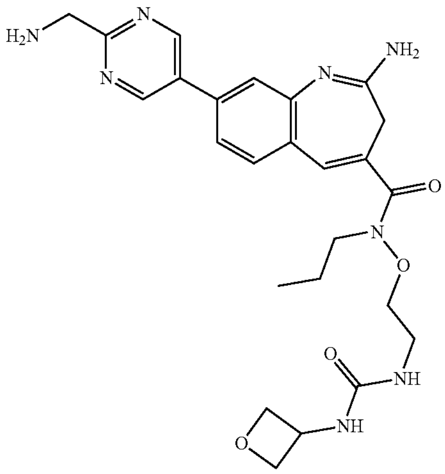 [SMILES: CCCN(OCCNC(=O)NC1COC1)C(=O)C1=Cc2ccc(-c3cnc(CN)nc3)cc2N=C(N)C1] | 508.6 | 9000 | 9000 |
| HxBz-18 | 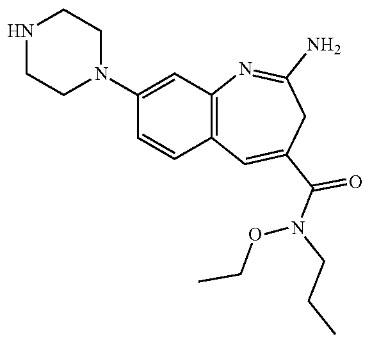 [SMILES: CCCN(OCC)C(=O)C1=Cc2ccc(N3CCNCC3)cc2N=C(N)C1] | 371.5 | 6310 | 281 |

TABLE 1-continued
8-Het-2-aminobenzazepine compounds (HxBz)
| Hx No. | Structure | MW | HEK293 hTLR7 EC50 (nM) | HEK293 hTLR8 EC50 (nM) |
|---|---|---|---|---|
| HxBz-19 | 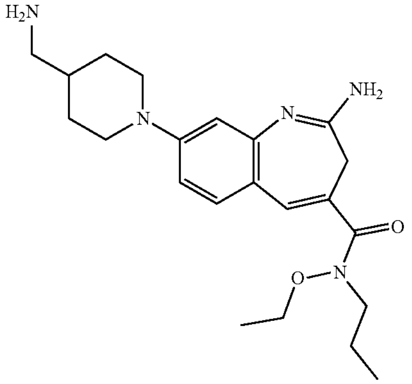 [SMILES: CCCN(OCC)C(=O)C1=Cc2ccc(N3CCC(CN)CC3)cc2N=C(N)C1] | 399.5 | | |
| HxBz-20 | 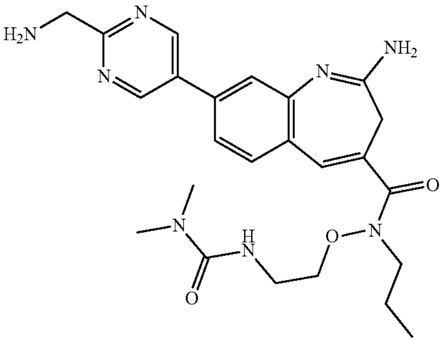 [SMILES: CCCN(OCCNC(=O)N(C)C)C(=O)C1=Cc2ccc(-c3cnc(CN)nc3)cc2N=C(N)C1] | 480.6 | 2943 | 3691 |
| HxBz-21 | 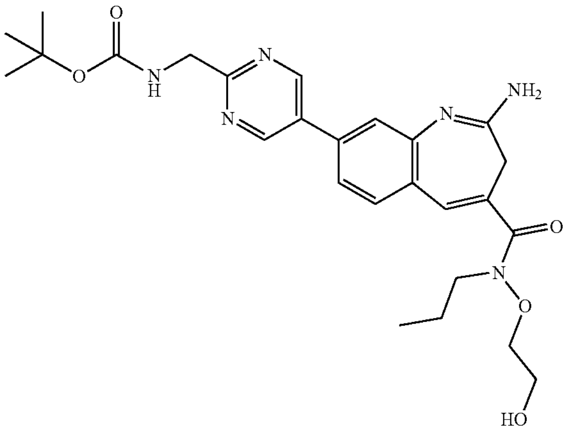 [SMILES: CCCN(OCCO)C(=O)C1=Cc2ccc(-c3cnc(CNC(=O)OC(C)(C)C)nc3)cc2N=C(N)C1] | 510.6 | | |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-22 | 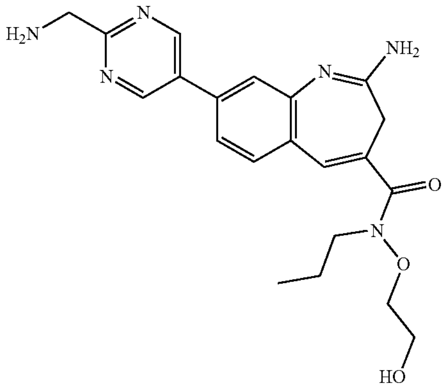 [SMILES: CCCN(OCCO)C(=O)C1=Cc2ccc(-c3cnc(CN)nc3)cc2N=C(N)C1] | 410.5 | 3916 | 1147 |
| HxBz-23 | 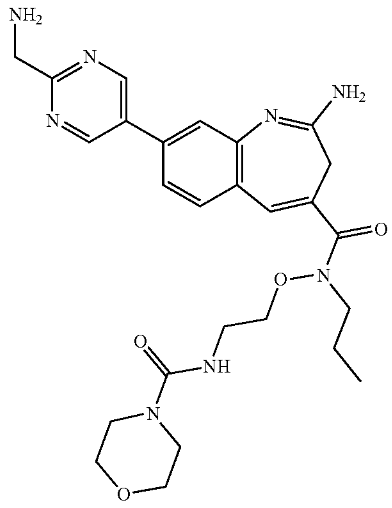 [SMILES: CCCN(OCCNC(=O)N1CCOCC1)C(=O)C1=Cc2ccc(-c3cnc(CN)nc3)cc2N=C(N)C1] | 522.6 | 6875 | 6176 |
| HxBz-24 | 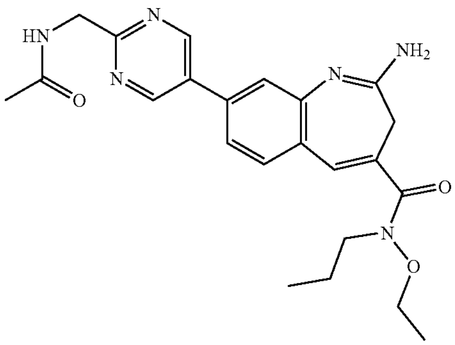 [SMILES: CCCN(OCC)C(=O)C1=Cc2ccc(-c3cnc(CNC(C)=O)nc3)cc2N=C(N)C1] | 436.5 | | |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-25 | 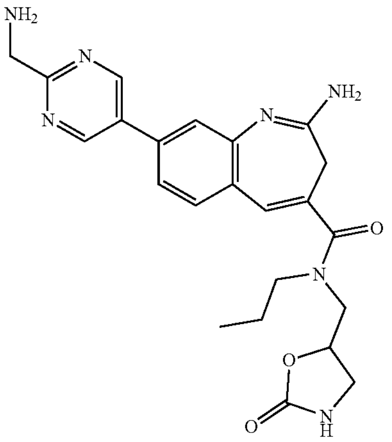 [SMILES: CCCN(CC1CNC(=O)O1)C(=O)C1=Cc2ccc(-c3cnc(CN)nc3)cc2N=C(N)C1] | 449.5 | 9000 | 3161 |
| HxBz-26 | 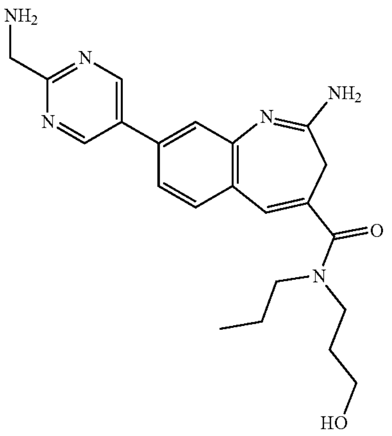 [SMILES: CCCN(CCCO)C(=O)C1=Cc2ccc(-c3cnc(CN)nc3)cc2N=C(N)C1] | 408.5 | 9000 | 9000 |
| HxBz-27 | 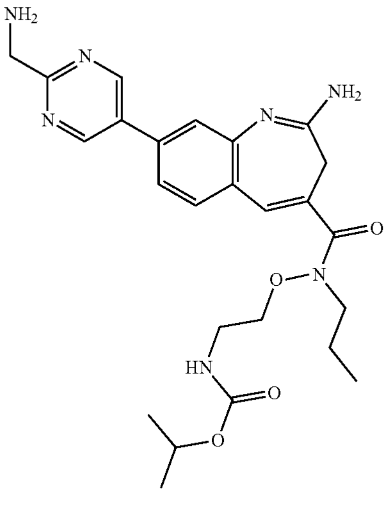 | 495.6 | 26 | 9 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-28 | 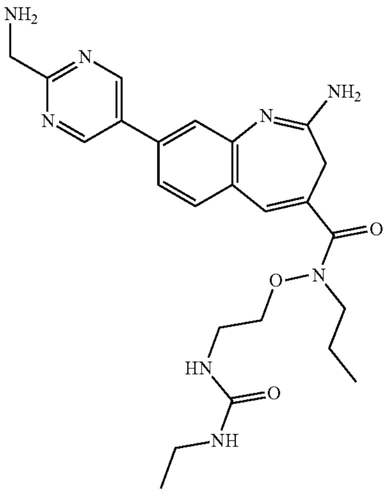 [SMILES: CCCN(OCCNC(=O)NCC)C(=O)C1=Cc2ccc(-c3cnc(CN)nc3)cc2N=C(N)C1] | 480.6 | 3771 | 2929 |
| HxBz-29 | 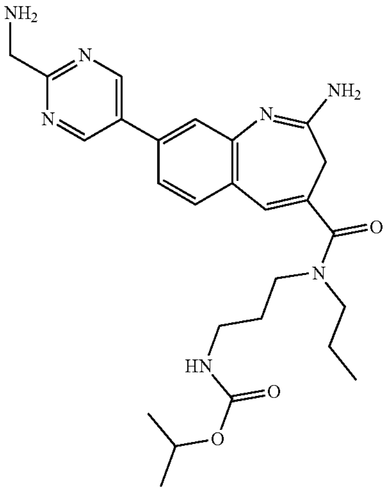 [SMILES: CCCN(CCCNC(=O)OC(C)C)C(=O)C1=Cc2ccc(-c3cnc(CN)nc3)cc2N=C(N)C1] | 493.6 | 134 | 296 |
| HxBz-30 | 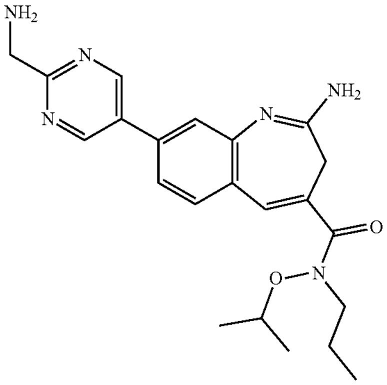 [SMILES: CCCN(OC(C)C)C(=O)C1=Cc2ccc(-c3cnc(CN)nc3)cc2N=C(N)C1] | 408.5 | 393 | 40 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-31 | 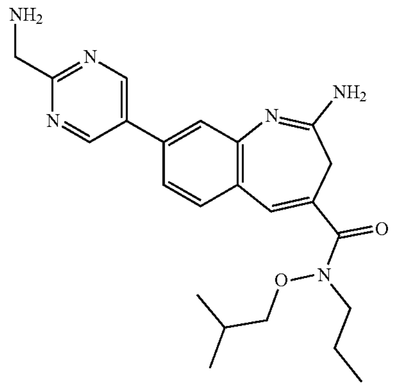 [SMILES: CCCN(OCC(C)C)C(=O)C1=Cc2ccc(-c3cnc(CN)nc3)cc2N=C(N)C1] | 422.5 | 763 | 358 |
| HxBz-32 | 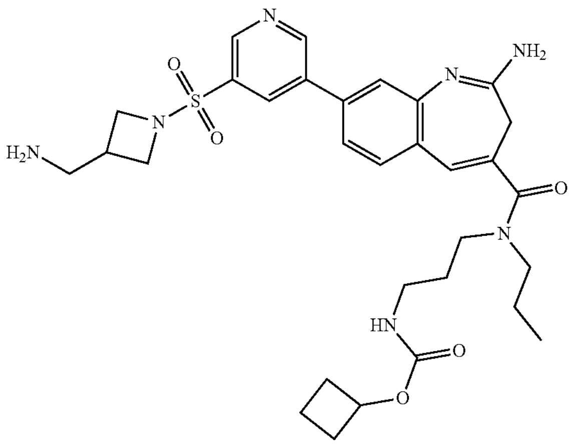 [SMILES: CCCN(CCCNC(=O)OC1CCC1)C(=O)C1=Cc2ccc(-c3cncc(S(=O)(=O)N4CC(CN)C4)c3)cc2N=C(N)C1] | 623.8 | 1280 | 1519 |
| HxBz-33 | 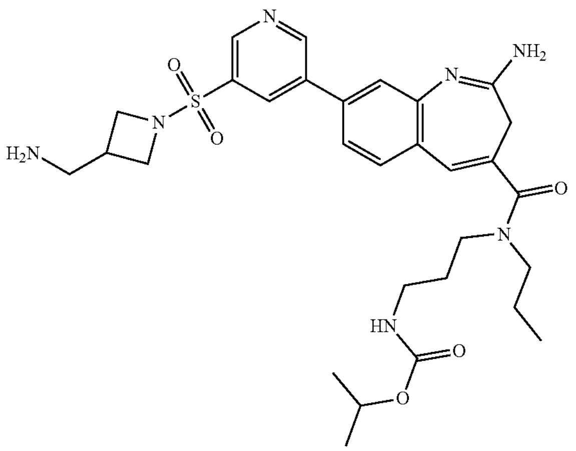 [SMILES: CCCN(CCCNC(=O)OC(C)C)C(=O)C1=Cc2ccc(-c3cncc(S(=O)(=O)N4CC(CN)C4)c3)cc2N=C(N)C1] | 611.8 | 7633 | 2876 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-34 | 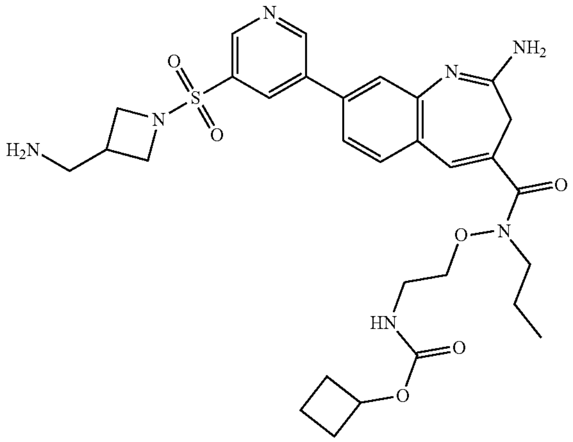 [SMILES: CCCN(OCCNC(=O)OC1CCC1)C(=O)C1=Cc2ccc(-c3cncc(S(=O)(=O)N4CC(CN)C4)c3)cc2N=C(N)C1] | 625.7 | 322 | 79 |
| HxBz-35 | 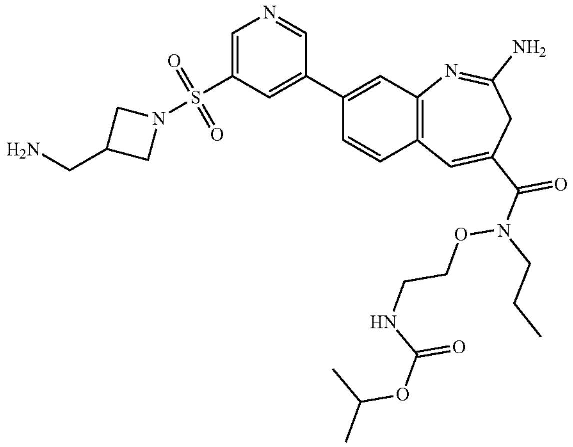 | 613.7 | 684 | 174 |
| HxBz-36 | 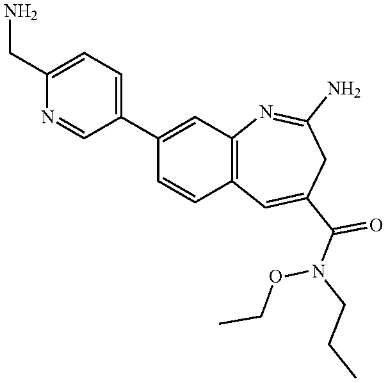 [SMILES: CCCN(OCC)C(=O)C1=Cc2ccc(-c3ccc(CN)nc3)cc2N=C(N)C1] | 393.5 | 439 | 54 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-37 | 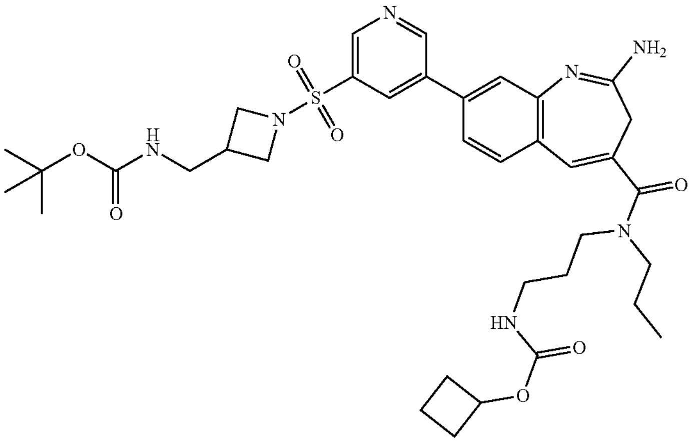 [SMILES: CCCN(CCCNC(=O)OC1CCC1)C(=O)C1=Cc2ccc(-c3cncc(S(=O)(=O)N4CC(CNC(=O)OC(C)(C)C)C4)c3)cc2N=C(N)C1] | 723.9 | | |
| HxBz-38 | 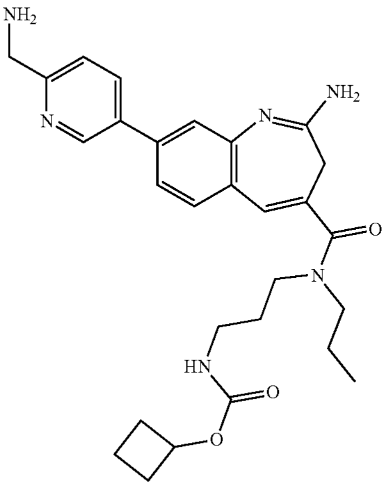 [SMILES: CCCN(CCCNC(=O)OC1CCC1)C(=O)C1=Cc2ccc(-c3ccc(CN)nc3)cc2N=C(N)C1] | 504.6 | 56 | 153 |
| HxBz-39 | 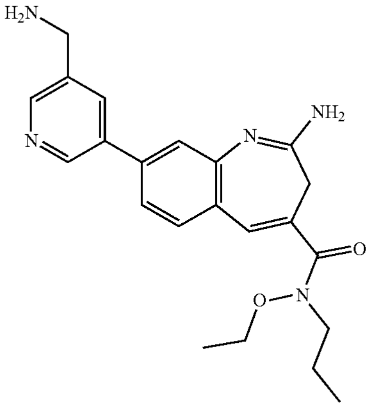 [SMILES: CCCN(OCC)C(=O)C1=Cc2ccc(-c3cncc(CN)c3)cc2N=C(N)C1] | 393.5 | 1780 | 65 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-40 | 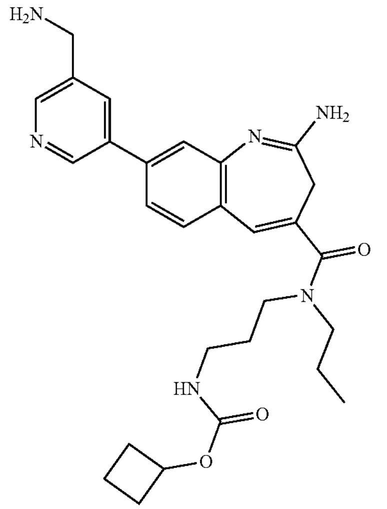 [SMILES: CCCN(CCCNC(=O)OC1CCC1)C(=O)C1=Cc2ccc(-c3cncc(CN)c3)cc2N=C(N)C1] | 504.6 | 357 | 755 |
| HxBz-41 | 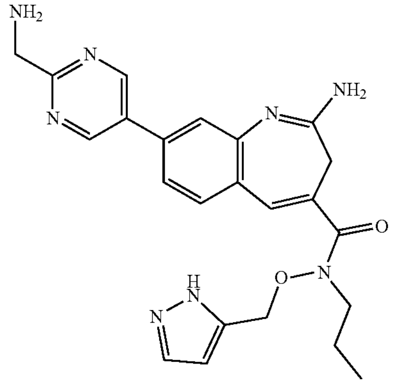 [SMILES: CCCN(OCc1ccn[nH]1)C(=O)C1=Cc2ccc(-c3cnc(CN)nc3)cc2N=C(N)C1] | 446.5 | 3926 | 128 |
| HxBz-42 | 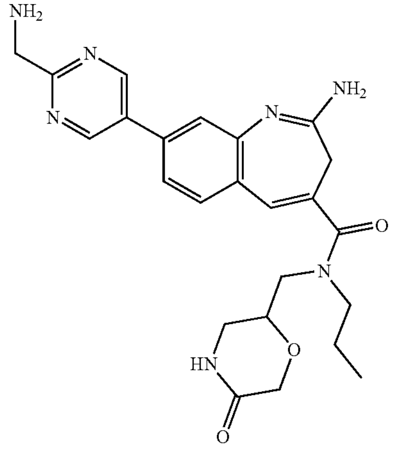 [SMILES: CCCN(CC1CNC(=O)CO1)C(=O)C1=Cc2ccc(-c3cnc(CN)nc3)cc2N=C(N)C1] | 463.5 | 9000 | 9000 |

TABLE 1-continued
| 8-Het-2-aminobenzazepine compounds (HxBz) | | | | |
|---|---|---|---|---|
| Hx No. | Structure | MW | HEK293 hTLR7 EC50 (nM) | HEK293 hTLR8 EC50 (nM) |
| HxBz-43 | 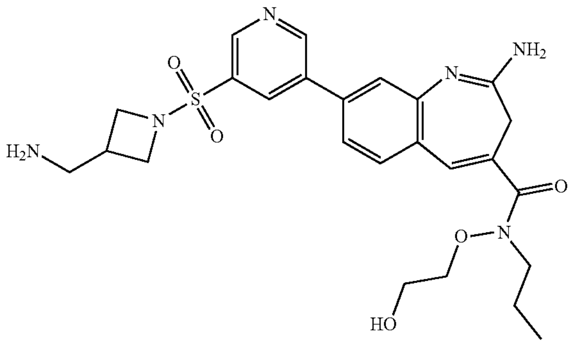 [SMILES: CCCN(OCCO)C(=O)C1=Cc2ccc(-c3cncc(S(=O)(=O)N4CC(CN)C4)c3)cc2N=C(N)C1] | 528.6 | 9000 | 6164 |
| HxBz-44 | 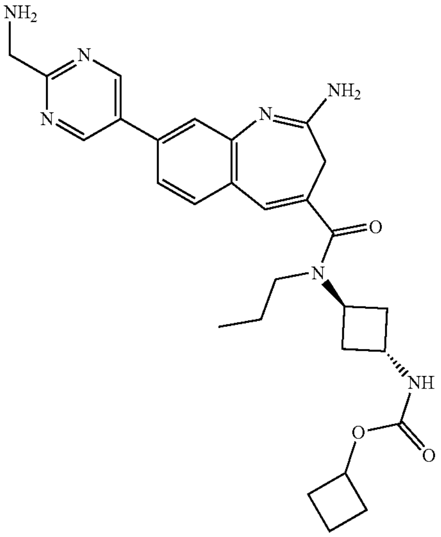 [SMILES: CCCN(C(=O)C1=Cc2ccc(-c3cnc(CN)nc3)cc2N=C(N)C1)[C@H]1C[C@H](NC(=O)OC2CCC2)C1] | 517.6 | 9000 | 6346 |
| HxBz-45 | 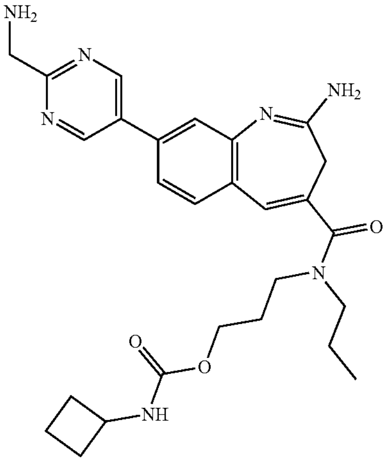 [SMILES: CCCN(CCCOC(=O)NC1CCC1)C(=O)C1=Cc2ccc(-c3cnc(CN)nc3)cc2N=C(N)C1] | 505.6 | 825 | 325 |

TABLE 1-continued

| Hx No. | Structure | MW | HEK293 hTLR7 EC50 (nM) | HEK293 hTLR8 EC50 (nM) |
|---|---|---|---|---|
| 8-Het-2-aminobenzazepine compounds (HxBz) | | | | |
| HxBz-46 | 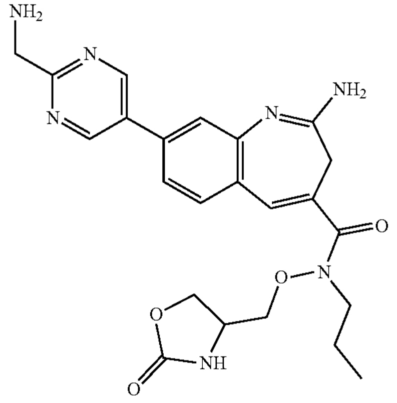 [SMILES: CCCN(OCC1COC(=O)N1)C(=O)C1=Cc2ccc(-c3cnc(CN)nc3)cc2N=C(N)C1] | 465.5 | 9000 | 3578 |
| HxBz-47 | 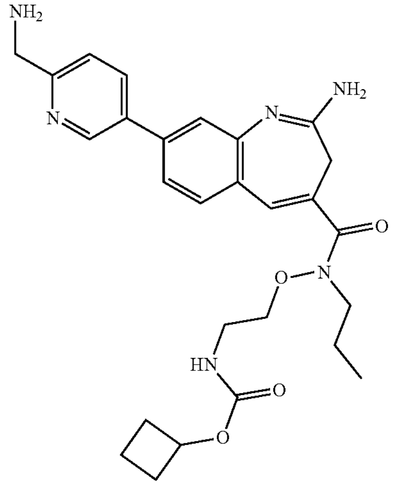 [SMILES: CCCN(OCCNC(=O)OC1CCC1)C(=O)C1=Cc2ccc(-c3ccc(CN)nc3)cc2N=C(N)C1] | 506.6 | 35 | 12 |
| HxBz-48 | 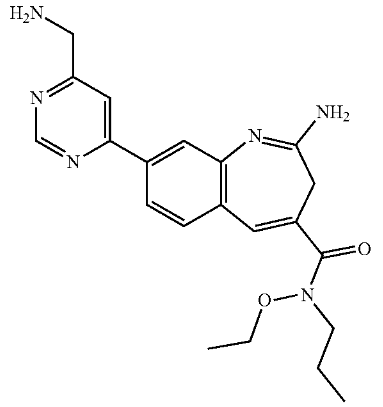 [SMILES: CCCN(OCC)C(=O)C1=Cc2ccc(-c3cc(CN)ncn3)cc2N=C(N)C1] | 394.5 | 9000 | 2164 |

8-Het-2-Aminobenzazepine-Linker Compounds

The immunoconjugates of the invention are prepared by conjugation of an anti-HER2 antibody with a 8-Het-2-aminobenzazepine-linker compound, HxBzL. The 8-Het-2-aminobenzazepine-linker compounds comprise a 8-Het-2-aminobenzazepine (Hx) moiety covalently attached to a linker unit. The linker units comprise functional groups and subunits which affect stability, permeability, solubility, and other pharmacokinetic, safety, and efficacy properties of the immunoconjugates. The linker unit includes a reactive functional group which reacts, i.e. conjugates, with a reactive functional group of the antibody. For example, a nucleophilic group such as a lysine side chain amino of the antibody reacts with an electrophilic reactive functional group of the Hx-linker compound to form the immunoconjugate. Also, for example, a cysteine thiol of the antibody reacts with a maleimide or bromoacetamide group of the Hx-linker compound to form the immunoconjugate.

Electrophilic reactive functional groups suitable for the Hx-linker compounds include, but are not limited to, N-hydroxysuccinimidyl (NHIS) esters and N-hydroxysulfosuccinimidyl (sulfo-NHIS) esters (amine reactive); carbodiimides (amine and carboxyl reactive); hydroxymethyl phosphines (amine reactive); maleimides (thiol reactive); halogenated acetamides such as N-iodoacetamides (thiol reactive); aryl azides (primary amine reactive); fluorinated aryl azides (reactive via carbon-hydrogen (C—H) insertion); pentafluorophenyl (PFP) esters (amine reactive); tetrafluorophenyl (TFP) esters (amine reactive); imidoesters (amine reactive); isocyanates (hydroxyl reactive); vinyl sulfones (thiol, amine, and hydroxyl reactive); pyridyl disulfides (thiol reactive); and benzophenone derivatives (reactive via C—H bond insertion). Further reagents include, but are not limited, to those described in Hermanson, *Bioconjugate Techniques* 2nd Edition, Academic Press, 2008.

The invention provides solutions to the limitations and challenges to the design, preparation and use of immunoconjugates. Some linkers may be labile in the blood stream, thereby releasing unacceptable amounts of the adjuvant/drug prior to internalization in a target cell (Khot, A. et al (2015) *Bioanalysis* 7(13):1633-1648). Other linkers may provide stability in the bloodstream, but intracellular release effectiveness may be negatively impacted. Linkers that provide for desired intracellular release typically have poor stability in the bloodstream. Alternatively stated, bloodstream stability and intracellular release are typically inversely related. In addition, in standard conjugation processes, the amount of adjuvant/drug moiety loaded on the antibody, i.e. drug loading, the amount of aggregate that is formed in the conjugation reaction, and the yield of final purified conjugate that can be obtained are interrelated. For example, aggregate formation is generally positively correlated to the number of equivalents of adjuvant/drug moiety and derivatives thereof conjugated to the antibody. Under high drug loading, formed aggregates must be removed for therapeutic applications. As a result, drug loading-mediated aggregate formation decreases immunoconjugate yield and can render process scale-up difficult.

Exemplary embodiments include a 8-Het-2-aminobenzazepine-linker compound of Formula II:

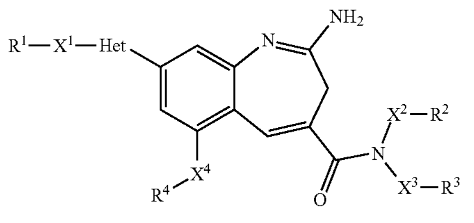

wherein Het is selected from heterocyclyldiyl and heteroaryldiyl;

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:

—($C_1$-$C_{12}$ alkyldiyl)-N($R^5$)—*;
—($C_1$-$C_{12}$ alkyldiyl)-N($R^5$)$_2$;
—($C_1$-$C_{12}$ alkyldiyl)-O$R^5$;
—($C_3$-$C_{12}$ carbocyclyl);
—($C_3$-$C_{12}$ carbocyclyl)-*;
—($C_3$-$C_{12}$ carbocyclyl)-($C_1$-$C_{12}$ alkyldiyl)-N$R^5$—*;
—($C_3$-$C_{12}$ carbocyclyl)-($C_1$-$C_{12}$ alkyldiyl)-N($R^5$)$_2$;
—($C_3$-$C_{12}$ carbocyclyl)-N$R^5$—C(═N$R^5$)N$R^5$—*;
—($C_6$-$C_{20}$ aryl);
—($C_6$-$C_{20}$ aryl)-*;
—($C_6$-$C_{20}$ aryldiyl)-N($R^5$)—*;
—($C_6$-$C_{20}$ aryldiyl)-($C_1$-$C_{12}$ alkyldiyl)-N($R^5$)—*;
—($C_6$-$C_{20}$ aryldiyl)-($C_1$-$C_{12}$ alkyldiyl)-($C_2$-$C_{20}$ heterocyclyldiyl)-*;
—($C_6$-$C_{20}$ aryldiyl)-($C_1$-$C_{12}$ alkyldiyl)-N($R^5$)$_2$;
—($C_6$-$C_{20}$ aryldiyl)-($C_1$-$C_{12}$ alkyldiyl)-N$R^5$—C(═N$R^{5a}$)N($R^5$)—*;
—($C_2$-$C_{20}$ heterocyclyl);
—($C_2$-$C_{20}$ heterocyclyl)-*;
—($C_2$-$C_9$ heterocyclyl)-($C_1$-$C_{12}$ alkyldiyl)-N$R^5$—*;
—($C_2$-$C_9$ heterocyclyl)-($C_1$-$C_{12}$ alkyldiyl)-N($R^5$)$_2$;
—($C_2$-$C_9$ heterocyclyl)-C(═O)—($C_1$-$C_{12}$ alkyldiyl)-N($R^5$)—*;
—($C_2$-$C_9$ heterocyclyl)-N$R^5$—C(═N$R^{5a}$)N$R^5$—*;
—($C_2$-$C_9$ heterocyclyl)-N$R^5$—($C_6$-$C_{20}$ aryldiyl)-($C_1$-$C_{12}$ alkyldiyl)-N($R^5$)—*;
—($C_2$-$C_9$ heterocyclyl)-($C_6$-$C_{20}$ aryldiyl)-*;
—($C_1$-$C_{20}$ heteroaryl);
—($C_1$-$C_{20}$ heteroaryl)-*;
—($C_1$-$C_{20}$ heteroaryl)-($C_1$-$C_{12}$ alkyldiyl)-N($R^5$)—*;
—($C_1$-$C_{20}$ heteroaryl)-($C_1$-$C_{12}$ alkyldiyl)-N($R^5$)$_2$;
—($C_1$-$C_{20}$ heteroaryl)-N$R^5$—C(═N$R^{5a}$)N($R^5$)—*;
—($C_1$-$C_{20}$ heteroaryl)-N($R^5$)C(═O)—($C_1$-$C_{12}$ alkyldiyl)-N($R^5$)—*;
—C(═O)—*;
—C(═O)—($C_1$-$C_{12}$ alkyldiyl)-N($R^5$)—*;
—C(═O)—($C_2$-$C_{20}$ heterocyclyldiyl)-*;
—C(═O)N($R^5$)$_2$;
—C(═O)N($R^5$)—*;
—C(═O)N($R^5$)—($C_1$-$C_{12}$ alkyldiyl)-N($R^5$)C(═O)R;
—C(═O)N($R^5$)—($C_1$-$C_{12}$ alkyldiyl)-N($R^5$)C(═O)N($R^5$)$_2$;
—C(═O)N$R^5$—($C_1$-$C_{12}$ alkyldiyl)-N($R^5$)$CO_2R^5$;
—C(═O)N$R^5$—($C_1$-$C_{12}$ alkyldiyl)-N($R^5$)C(═N$R^{5a}$)N($R^5$)$_2$;
—C(═O)N$R^5$—($C_1$-$C_{12}$ alkyldiyl)-N$R^5$C(═N$R^{5a}$)$R^5$;
—C(═O)N$R^5$—($C_1$-$C_8$ alkyldiyl)-N$R^5$($C_2$-$C_5$ heteroaryl);
—C(═O)N$R^5$—($C_1$-$C_{20}$ heteroaryldiyl)-N($R^5$)—*;
—C(═O)N$R^5$—($C_1$-$C_{20}$ heteroaryldiyl)-*;
—C(═O)N$R^5$—($C_1$-$C_{20}$ heteroaryldiyl)-($C_1$-$C_{12}$ alkyldiyl)-N($R^5$)$_2$;
—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-N$R^5$—*;
—N($R^5$)$_2$;
—N($R^5$)—*;
—N($R^5$)C(═O)$R^5$;
—N($R^5$)C(═O)—*;
—N($R^5$)C(═O)N($R^5$)$_2$;
—N($R^5$)C(═O)N($R^5$)—*;
—N($R^5$)$CO_2R^5$;
—N$R^5$C(═N$R^{5a}$)N($R^5$)$_2$;
—N$R^5$C(═N$R^{5a}$)N($R^5$)—*;
—N$R^5$C(═N$R^{5a}$)$R^5$;
—N($R^5$)C(═O)—($C_1$-$C_{12}$ alkyldiyl)-N($R^5$)—*;
—N($R^5$)—($C_2$-$C_5$ heteroaryl);
—N($R^5$)—S(═O)$_2$—($C_1$-$C_{12}$ alkyl);
—O—($C_1$-$C_{12}$ alkyl);
—O—($C_1$-$C_{12}$ alkyldiyl)-N($R^5$)$_2$;
—O—($C_1$-$C_{12}$ alkyldiyl)-N($R^5$)—*;

—O—C(═O)$N(R^5)_2$;

—O—C(═O)$N(R^5)$—*;

—$S(=O)_2$—($C_2$-$C_{20}$ heterocyclyldiyl)-*;

—$S(=O)_2$—($C_2$-$C_{20}$ heterocyclyldiyl)-($C_1$-$C_{12}$ alkyldiyl)-$N(R^5)_2$;

—$S(=O)_2$—($C_2$-$C_{20}$ heterocyclyldiyl)-($C_1$-$C_{12}$ alkyldiyl)-$NR^5$—*; and —$S(=O)_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(═O), C(═O)$N(R^5)$, O, $N(R^5)$, S, $S(O)_2$, and $S(O)_2N(R^5)$;

$R^5$ is independently selected from the group consisting of H, $C_6$-$C_{20}$ aryl, $C_3$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:

Q-C(═O)—PEG-;

Q-C(═O)—PEG-C(═O)$N(R^6)$—($C_1$-$C_{12}$ alkyldiyl)-C(═O)-Gluc-;

Q-C(═O)—PEG-O—;

Q-C(═O)—PEG-O—C(═O)—;

Q-C(═O)—PEG-C(═O)—;

Q-C(═O)—PEG-C(═O)—PEP-;

Q-C(═O)—PEG-$N(R^6)$—;

Q-C(═O)—PEG-$N(R^6)$—C(═O)—;

Q-C(═O)—PEG-$N(R^6)$—PEG-C(═O)—PEP-;

Q-C(═O)—PEG-$N^+(R^6)_2$-PEG-C(═O)—PEP-;

Q-C(═O)—PEG-C(═O)—PEP-$N(R^6)$—($C_1$-$C_{12}$ alkyldiyl)-;

Q-C(═O)—PEG-C(═O)—PEP-$N(R^6)$—($C_1$-$C_{12}$ alkyldiyl)$N(R^6)$C(═O)—($C_2$-$C_5$ monoheterocyclyldiyl)-;

Q-C(═O)—PEG-SS—($C_1$-$C_{12}$ alkyldiyl)-OC(═O)—;

Q-C(═O)—PEG-SS—($C_1$-$C_{12}$ alkyldiyl)-C(═O)—;

Q-C(═O)—($C_1$-$C_{12}$ alkyldiyl)-C(═O)—PEP-;

Q-C(═O)—($C_1$-$C_{12}$ alkyldiyl)-C(═O)—PEP-$N(R^6)$—($C_1$-$C_{12}$ alkyldiyl)-;

Q-C(═O)—($C_1$-$C_{12}$ alkyldiyl)-C(═O)—PEP-$N(R^6)$—($C_1$-$C_{12}$ alkyldiyl)-$N(R^5)$—C(═O);

Q-C(═O)—($C_1$-$C_{12}$ alkyldiyl)-C(═O)—PEP-$N(R^6)$—($C_1$-$C_{12}$ alkyldiyl)-$N(R^6)$C(═O)—($C_2$-$C_5$ monoheterocyclyldiyl)-;

Q-$(CH_2)_m$—C(═O)$N(R^6)$—PEG-;

Q-$(CH_2)_m$—C(═O)$N(R^6)$—PEG-C(═O)$N(R^6)$—($C_1$-$C_{12}$ alkyldiyl)-C(═O)-Gluc-;

Q-$(CH_2)_m$—C(═O)$N(R^6)$—PEG-O—;

Q-$(CH_2)_m$—C(═O)$N(R^6)$—PEG-O—C(═O)—;

Q-$(CH_2)_m$—C(═O)$N(R^6)$—PEG-C(═O)—;

Q-$(CH_2)_m$—C(═O)$N(R^6)$—PEG-$N(R^5)$—;

Q-$(CH_2)_m$—C(═O)$N(R^6)$—PEG-$N(R^5)$—C(═O)—;

Q-$(CH_2)_m$—C(═O)$N(R^6)$—PEG-C(═O)—PEP-;

Q-$(CH_2)_m$—C(═O)$N(R^6)$—PEG-SS—($C_1$-$C_{12}$ alkyldiyl)-OC(═O)—;

Q-$(CH_2)_m$—C(═O)—PEP-$N(R^6)$—($C_1$-$C_{12}$ alkyldiyl)-;

Q-$(CH_2)_m$—C(═O)—PEP-$N(R^6)$—($C_1$-$C_{12}$ alkyldiyl)$N(R^6)$C(═O)—; and

Q-$(CH_2)_m$—C(═O)—PEP-$N(R^6)$—($C_1$-$C_{12}$ alkyldiyl)$N(R^6)$C(═O)—($C_2$-$C_5$ monoheterocyclyldiyl)-;

$R^6$ is independently H or $C_1$-$C_6$ alkyl;

PEG has the formula: —$(CH_2CH_2O)_n$—$(CH_2)_m$—; m is an integer from 1 to 5, and n is an integer from 2 to 50;

Glue has the formula:

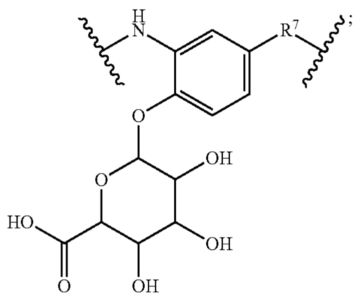

PEP has the formula:

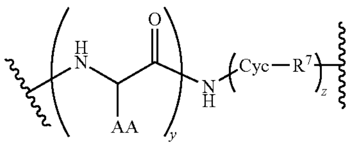

where AA is independently selected from a natural or unnatural amino acid side chain, or one or more of AA, and an adjacent nitrogen atom form a 5-membered ring proline amino acid, and the wavy line indicates a point of attachment;

Cyc is selected from $C_6$-$C_{20}$ aryldiyl and $C_1$-$C_{20}$ heteroaryldiyl, optionally substituted with one or more groups selected from F, Cl, $NO_2$, —OH, —$OCH_3$, and a glucuronic acid having the structure:

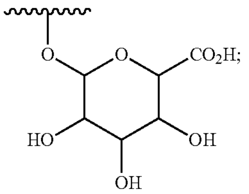 [SMILES: *OC1OC(C(=O)O)C(O)C(O)C1O]

$R^7$ is selected from the group consisting of —CH($R^8$)O—, —$CH_2$—, —$CH_2N(R^8)$—, and —CH($R^8$)O—C(═O)—, where $R^8$ is selected from H, $C_1$-$C_6$ alkyl, C(═O)—$C_1$-$C_6$ alkyl, and —C(═O)N$(R^9)_2$, where $R^9$ is independently selected from the group consisting of H, $C_1$-$C_{12}$ alkyl, and —$(CH_2CH_2O)_n$—$(CH_2)_m$—OH, where m is an integer from 1 to 5, and n is an integer from 2 to 50, or two $R^9$ groups together form a 5- or 6-membered heterocyclyl ring;

y is an integer from 2 to 12;

z is 0 or 1;

Q is selected from the group consisting of N-hydroxysuccinimidyl, N-hydroxysulfosuccinimidyl, maleimide, and phenoxy substituted with one or more groups independently selected from F, Cl, $NO_2$, and $SO_3^-$; and alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH═$CH_2$, —C≡CH, —C≡$CCH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —CH(OH)$CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH($CH_3$)CN, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —COCH(OH)$CH_3$, —$CONH_2$, —$CONHCH_3$, —CON$(CH_3)_2$, —$C(CH_3)_2CONH_2$, —$NH_2$, —$NHCH_3$, —$N(CH_3)_2$, —$NHCOCH_3$, —N($CH_3$)$COCH_3$, —NHS$(O)_2CH_3$, —N($CH_3$)$C(CH_3)_2CONH_2$, —N($CH_3$)$CH_2CH_2S(O)_2CH_3$, —NHC(═NH)H, —NHC(═NH)$CH_3$, —NHC(═NH)$NH_2$, —NHC(═O)$NH_2$, —$NO_2$, ═O, —OH, —$OCH_3$, —$OCH_2CH_3$, —$OCH_2CH_2OCH_3$, —$OCH_2CH_2OH$, —$OCH_2CH_2N(CH_3)_2$, —$O(CH_2CH_2O)_n$—$(CH_2)_mCO_2H$, —$O(CH_2CH_2O)_nH$, —$OCH_2F$, —$OCHF_2$, —$OCF_3$, —$OP(O)(OH)_2$, —$S(O)_2N(CH_3)_2$, —$SCH_3$, —$S(O)_2CH_3$, and —$S(O)_3H$.

An exemplary embodiment of the 8-Het-2-aminobenzazepine-linker compound of Formula II includes wherein Q is selected from:

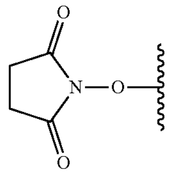
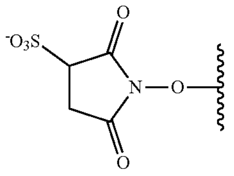

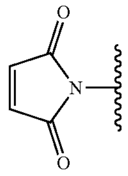
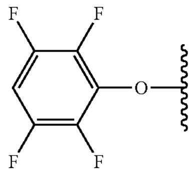

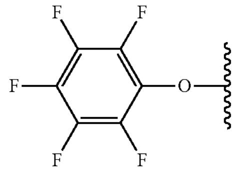
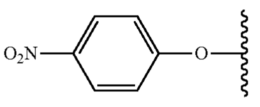

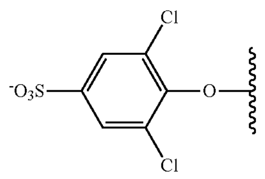
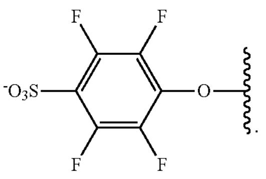

An exemplary embodiment of the 8-Het-2-aminobenzazepine-linker compound of Formula II includes wherein Q is phenoxy substituted with one or more F.

An exemplary embodiment of the 8-Het-2-aminobenzazepine-linker compound of Formula II includes wherein Q is 2,3,5,6-tetrafluorophenoxy.

An exemplary embodiment of the 8-Het-2-aminobenzazepine-linker (HxBzL) compound is selected from Tables 2a and 2b. Each compound was synthesized, purified, and characterized by mass spectrometry and shown to have the mass indicated. Additional experimental procedures are found in the Examples. The 8-Het-2-aminobenzazepine-linker compounds of Tables 2a and 2b demonstrate the surprising and unexpected property of TLR8 agonist selectivity which may predict useful therapeutic activity to treat cancer and other disorders. The 8-Het-2-aminobenzazepine-linker intermediate, Formula II compounds of Tables 2a and 2b are used in conjugation with antibodies by the methods of Example 201 to form the Immunoconjugates of Tables 3a and 3b.

TABLE 2a
| 8-Het-2-aminobenzazepine-linker intermediate, Formula II compounds (HxBzL) | | |
|---|---|---|
| HxBzL No. | Structure | MW |
| HxBzL-1 | 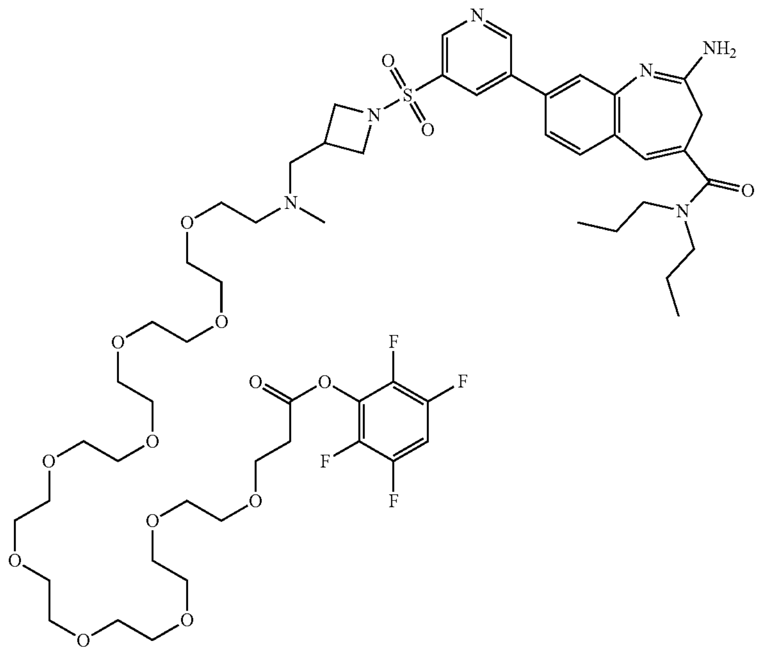 [SMILES: CCCN(CCC)C(=O)C1=Cc2ccc(-c3cncc(S(=O)(=O)N4CC(CN(C)CCOCCOCCOCCOCCOCCOCCOCCOCCOCCOCCC(=O)Oc5c(F)c(F)cc(F)c5F)C4)c3)cc2N=C(N)C1] | 1185.3 |
| HxBzL-2 | 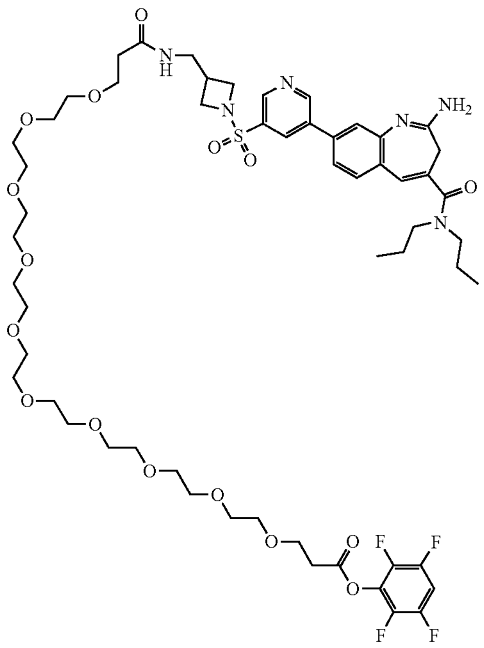 | 1199.3 |

TABLE 2a-continued
8-Het-2-aminobenzazepine-linker intermediate, Formula II compounds (HxBzL)
| HxBzL No. | Structure | MW |
|---|---|---|
| HxBzL-3 | 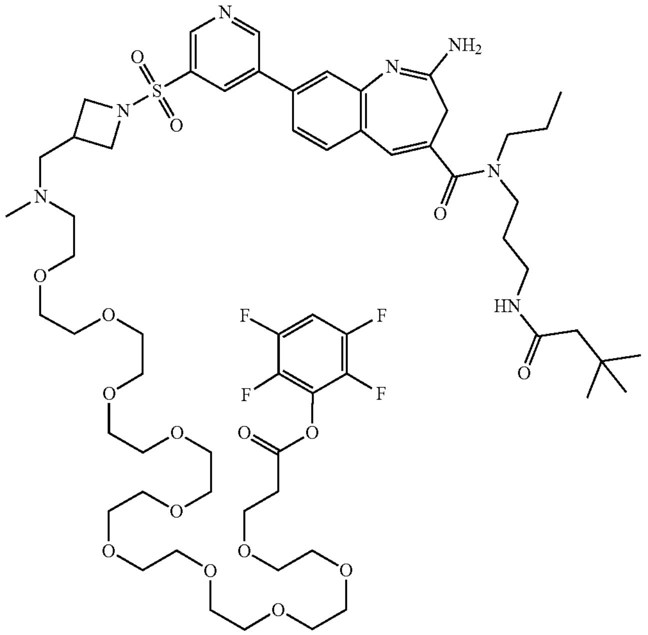 [SMILES: CCCN(CCCNC(=O)CC(C)(C)C)C(=O)C1=Cc2ccc(-c3cncc(S(=O)(=O)N4CC(CN(C)CCOCCOCCOCCOCCOCCOCCOCCOCCOCCOCCC(=O)Oc5c(F)c(F)cc(F)c5F)C4)c3)cc2N=C(N)C1] | 1298.5 |
| HxBzL-4 | 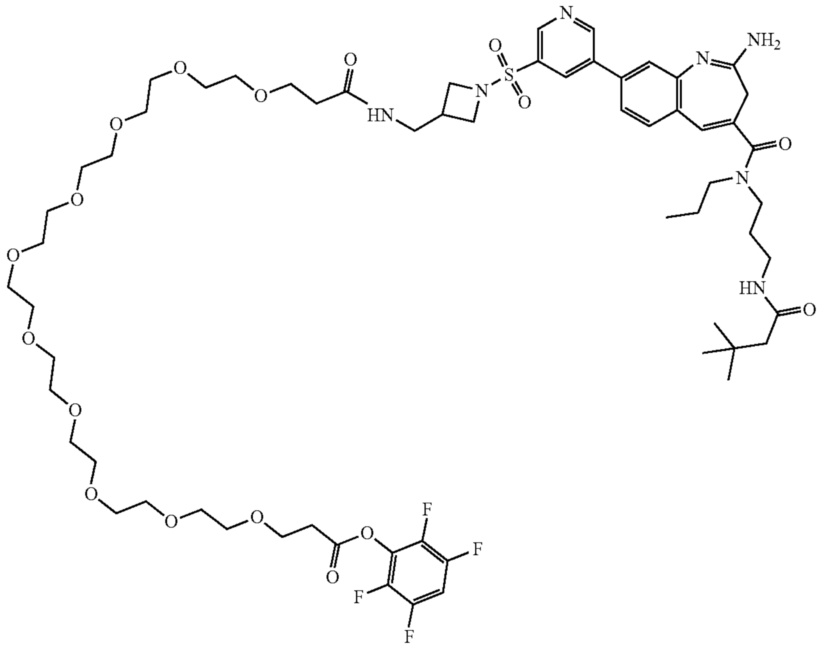 [SMILES: CCCN(CCCNC(=O)CC(C)(C)C)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1312.5 |

TABLE 2a-continued
| 8-Het-2-aminobenzazepine-linker intermediate, Formula II compounds (HxBzL) | | |
|---|---|---|
| HxBzL No. | Structure | MW |
| HxBzL-5 | 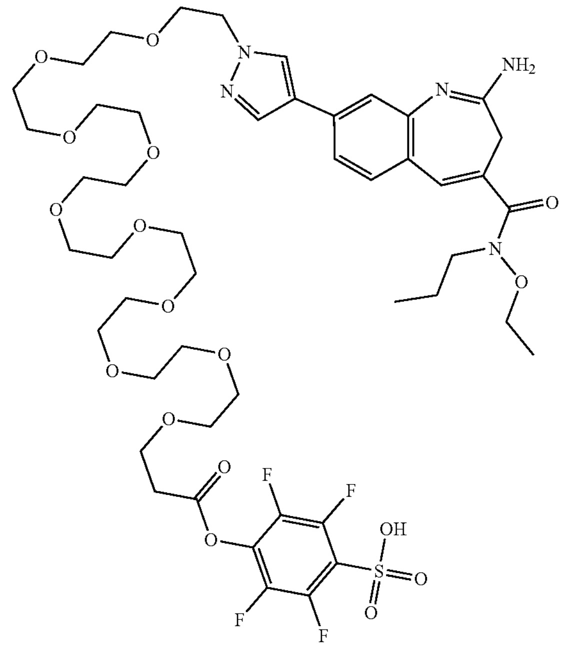 [SMILES: CCCN(OCC)C(=O)C1=Cc2ccc(-c3cnn(CCOCCOCCOCCOCCOCCOCCOCCOCCOCCOCCC(=O)Oc4c(F)c(F)c(S(=O)(=O)O)c(F)c4F)c3)cc2N=C(N)C1] | 1094.1 |
| HxBzL-6 | 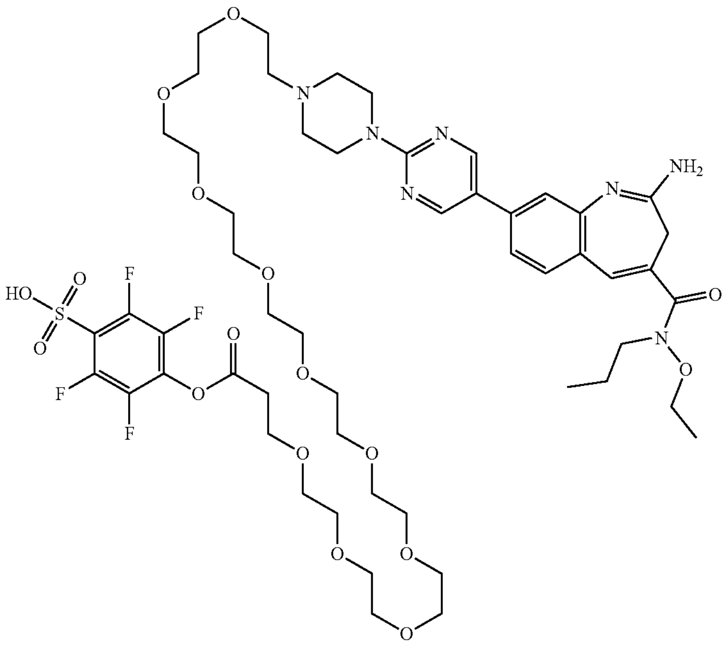 [SMILES: CCCN(OCC)C(=O)C1=Cc2ccc(-c3cnc(N4CCN(CCOCCOCCOCCOCCOCCOCCOCCOCCOCCOCCC(=O)Oc5c(F)c(F)c(S(=O)(=O)O)c(F)c5F)CC4)nc3)cc2N=C(N)C1] | 1190.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-7 | 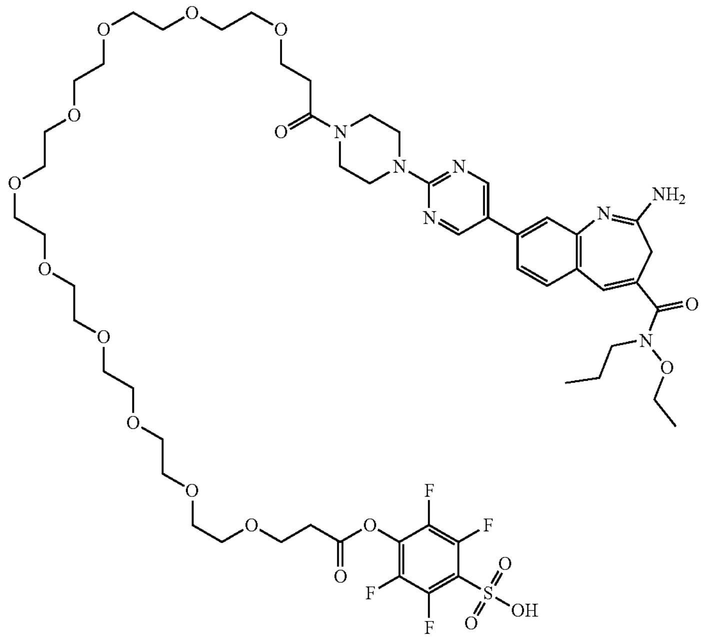 [SMILES: CCCN(OCC)C(=O)C1=Cc2ccc(-c3cnc(N4CCN(C(=O)CCOCCOCCOCCOCCOCCOCCOCCOCCOCCOCCC(=O)Oc5c(F)c(F)c(S(=O)(=O)O)c(F)c5F)CC4)nc3)cc2N=C(N)C1] | 1218.3 |
| HxBzL-8 | 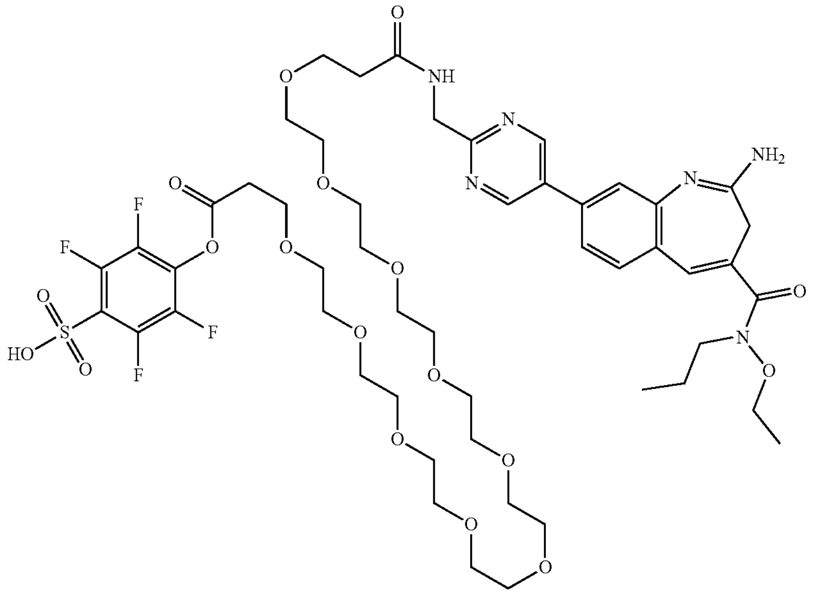 | 1163.2 |

TABLE 2a-continued
| 8-Het-2-aminobenzazepine-linker intermediate, Formula II compounds (HxBzL) | | |
|---|---|---|
| HxBzL No. | Structure | MW |
| HxBzL-9 | 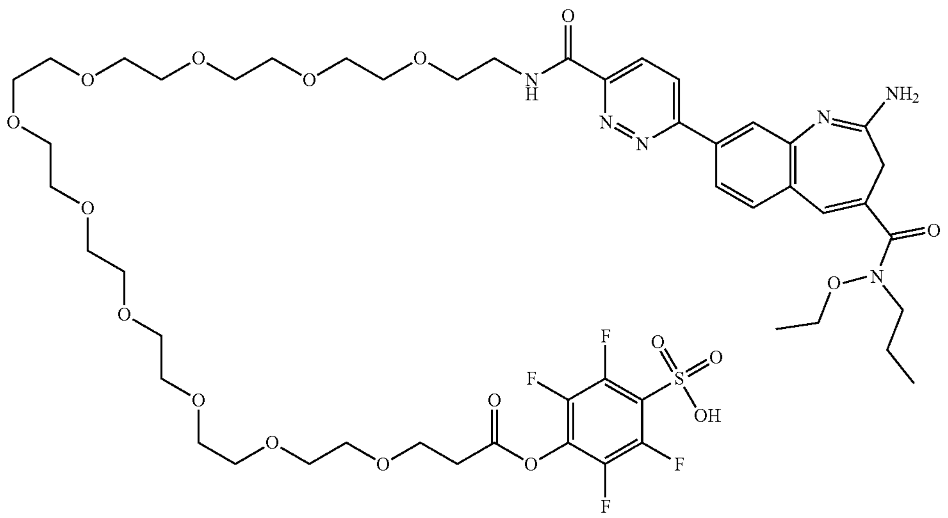 [SMILES: CCCN(OCC)C(=O)C1=Cc2ccc(-c3ccc(C(=O)NCCOCCOCCOCCOCCOCCOCCOCCOCCOCCOCCC(=O)Oc4c(F)c(F)c(S(=O)(=O)O)c(F)c4F)nn3)cc2N=C(N)C1] | 1149.2 |
| HxBzL-10 | 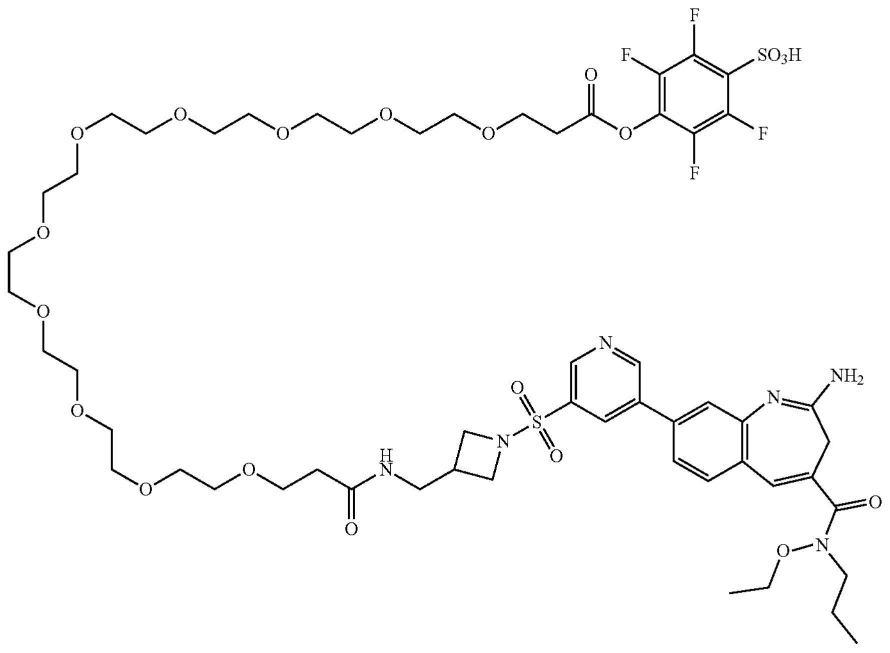 [SMILES: CCCN(OCC)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1281.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-11 | 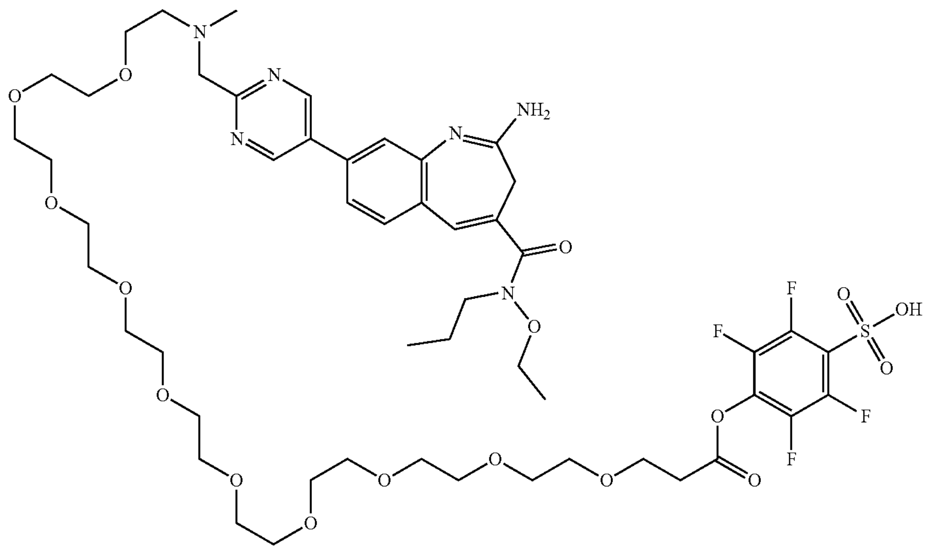 [SMILES: CCCN(OCC)C(=O)C1=Cc2ccc(-c3cnc(CN(C)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1149.2 |
| HxBzL-12 | 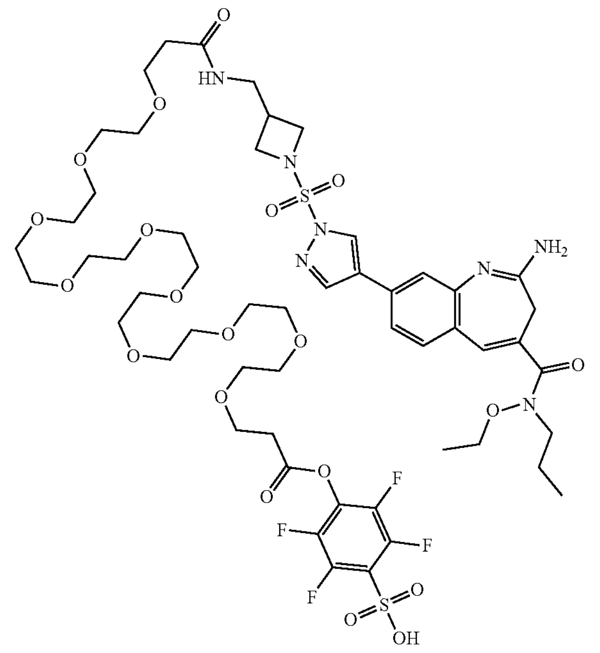 [SMILES: CCCN(OCC)C(=O)C1=Cc2ccc(-c3cnn(S(=O)(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1270.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-13 | 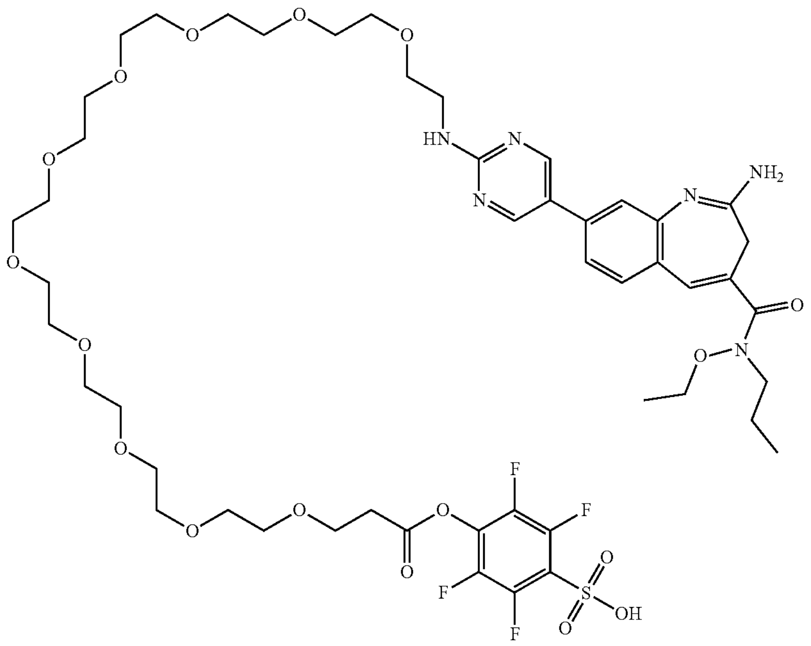 [SMILES: CCCN(OCC)C(=O)C1=Cc2ccc(-c3cnc(NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1121.2 |
| HxBzL-14 | 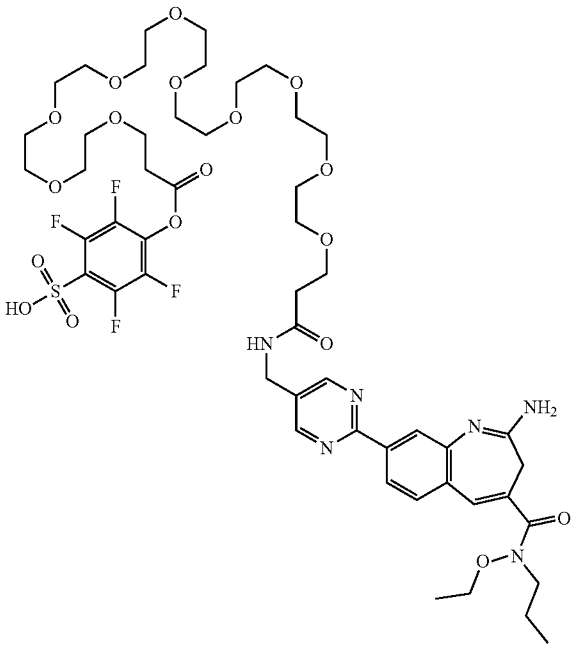 [SMILES: CCCN(OCC)C(=O)C1=Cc2ccc(-c3ncc(CNC(=O)CCOCCOCCOCCOCCOCCOCCOCCOCCOCCOCCC(=O)Oc4c(F)c(F)c(S(=O)(=O)O)c(F)c4F)cn3)cc2N=C(N)C1] | 1163.2 |

TABLE 2a-continued
| 8-Het-2-aminobenzazepine-linker intermediate, Formula II compounds (HxBzL) | | |
|---|---|---|
| HxBzL No. | Structure | MW |
| HxBzL-15 | 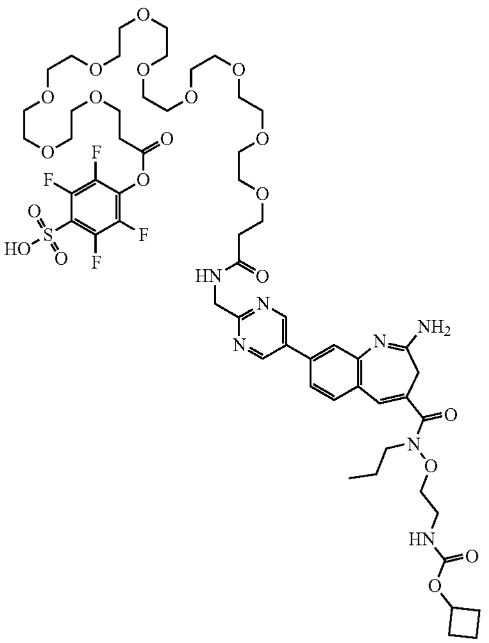 [SMILES: CCCN(OCCNC(=O)OC1CCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1276.3 |
| HxBzL-16 | 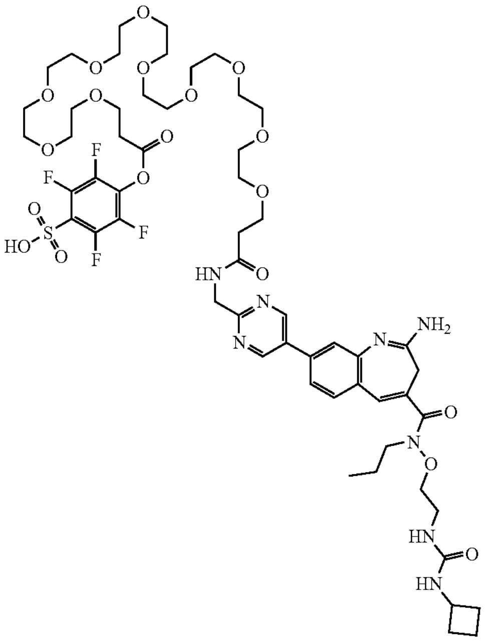 | 1275.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-17 | 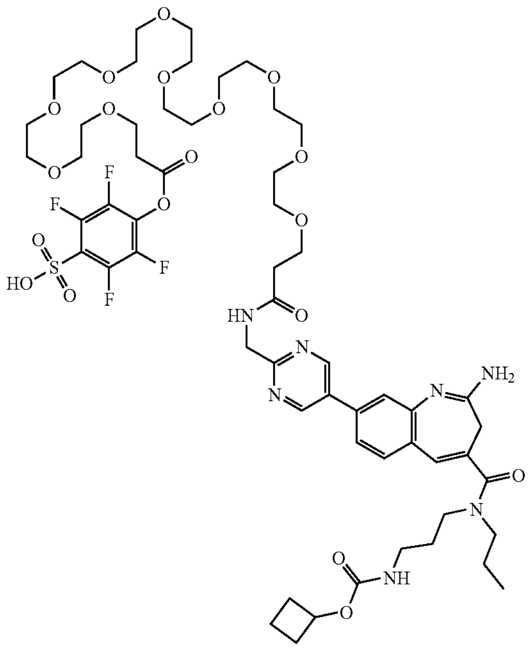 [SMILES: CCCN(CCCNC(=O)OC1CCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1274.3 |
| HxBzL-18 | 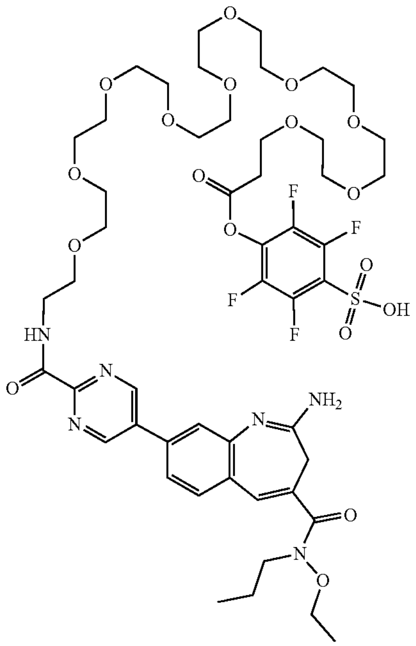 [SMILES: CCCN(OCC)C(=O)C1=Cc2ccc(-c3cnc(C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1135.1 |

TABLE 2a-continued
| 8-Het-2-aminobenzazepine-linker intermediate, Formula II compounds (HxBzL) | | |
|---|---|---|
| HxBzL No. | Structure | MW |
| HxBzL-19 | 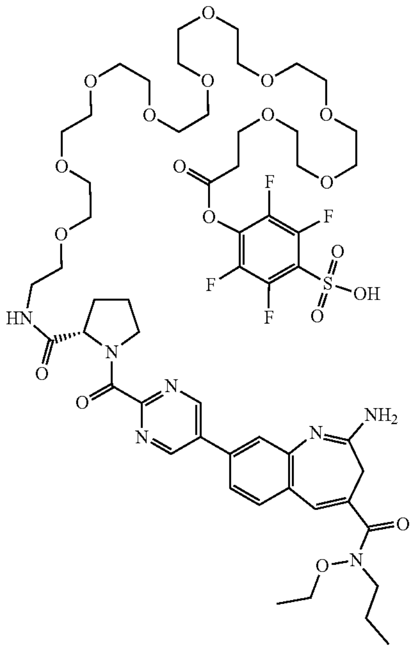 [SMILES: CCCN(OCC)C(=O)C1=Cc2ccc(-c3cnc(C(=O)N4CCC[C@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1232.3 |
| HxBzL-20 | 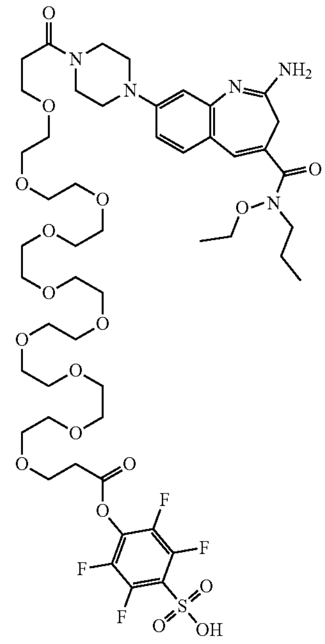 [SMILES: CCCN(OCC)C(=O)C1=Cc2ccc(N3CCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1140.2 |

TABLE 2a-continued
| 8-Het-2-aminobenzazepine-linker intermediate, Formula II compounds (HxBzL) | | |
|---|---|---|
| HxBzL No. | Structure | MW |
| HxBzL-21 | 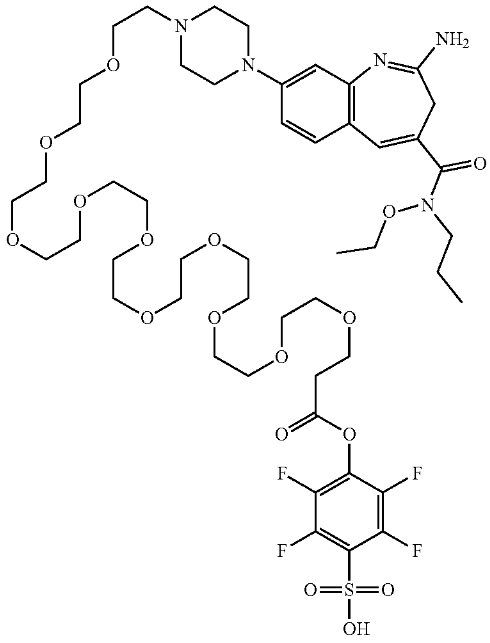 [SMILES: CCCN(OCC)C(=O)C1=Cc2ccc(N3CCN(CCOCCOCCOCCOCCOCCOCCOCCOCCOCCOCCC(=O)Oc4c(F)c(F)c(S(=O)(=O)O)c(F)c4F)CC3)cc2N=C(N)C1] | 1112.2 |
| HxBzL-22 | 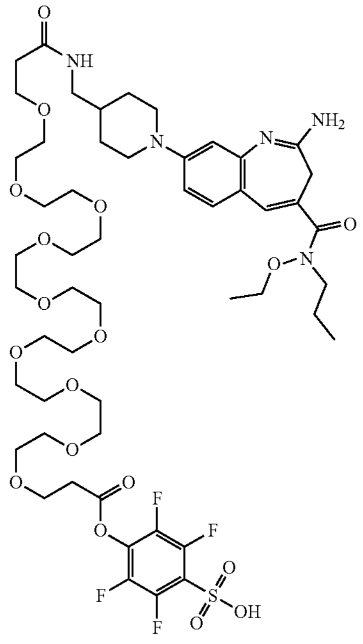 [SMILES: CCCN(OCC)C(=O)C1=Cc2ccc(N3CCC(CNC(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1168.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-23 | 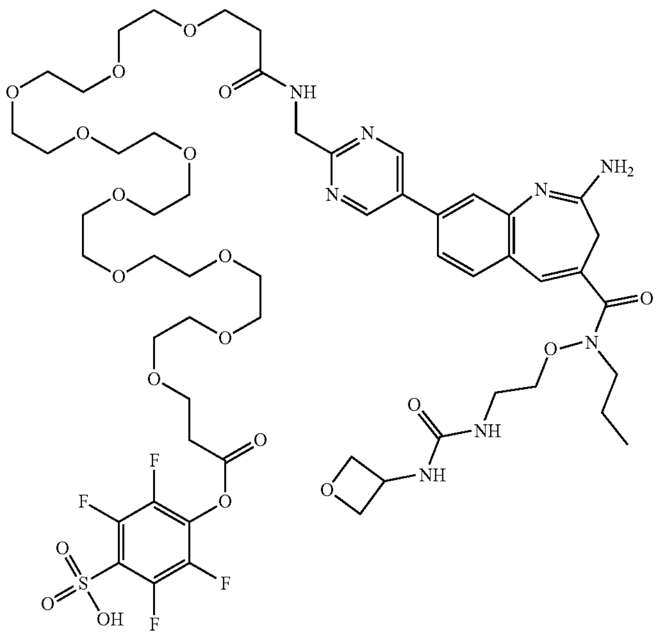 [SMILES: CCCN(OCCNC(=O)NC1COC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1277.3 |
| HxBzL-24 | 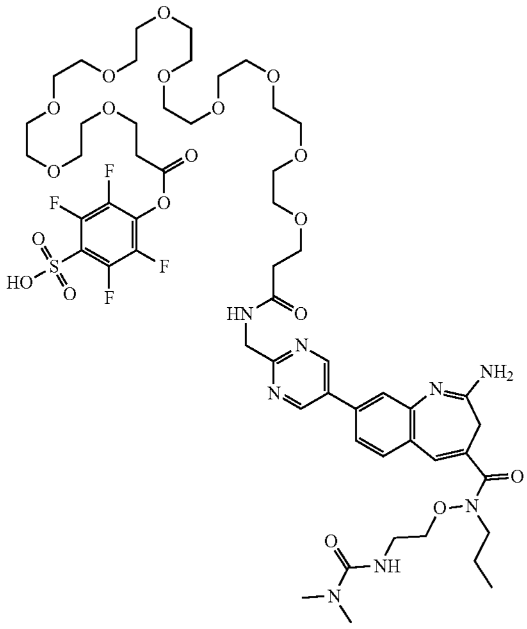 [SMILES: CCCN(OCCNC(=O)N(C)C)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1249.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-25 | 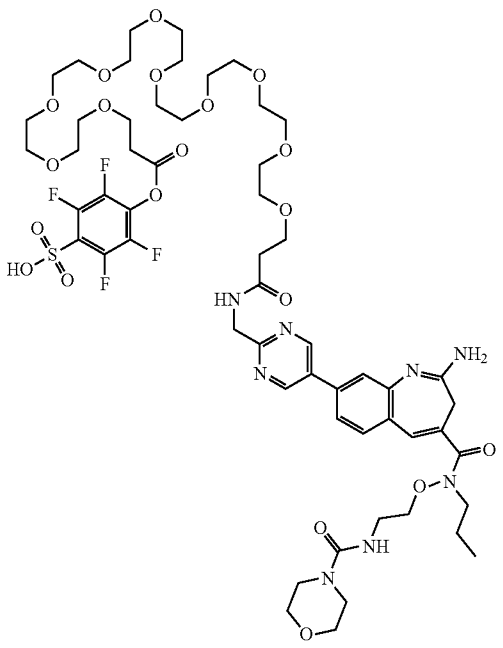 [SMILES: CCCN(OCCNC(=O)N1CCOCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1291.3 |
| HxBzL-26 | 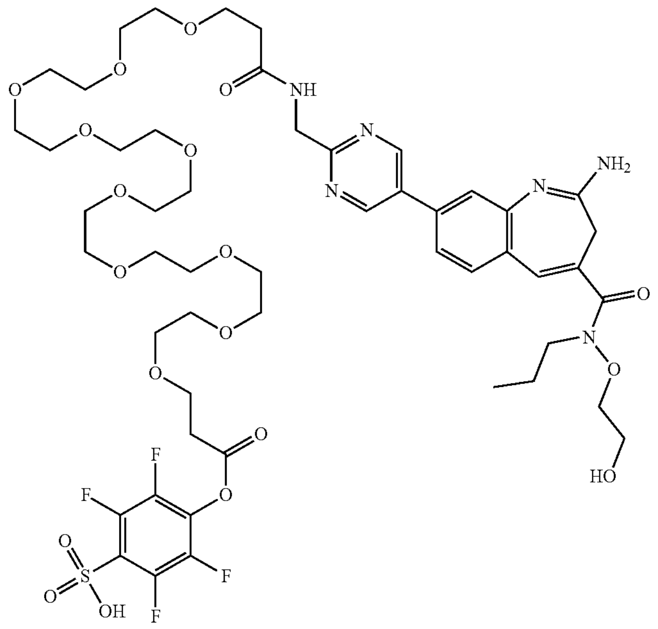 [SMILES: CCCN(OCCO)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1179.2 |

TABLE 2a-continued
| 8-Het-2-aminobenzazepine-linker intermediate, Formula II compounds (HxBzL) | | |
|---|---|---|
| HxBzL No. | Structure | MW |
| HxBzL-27 | 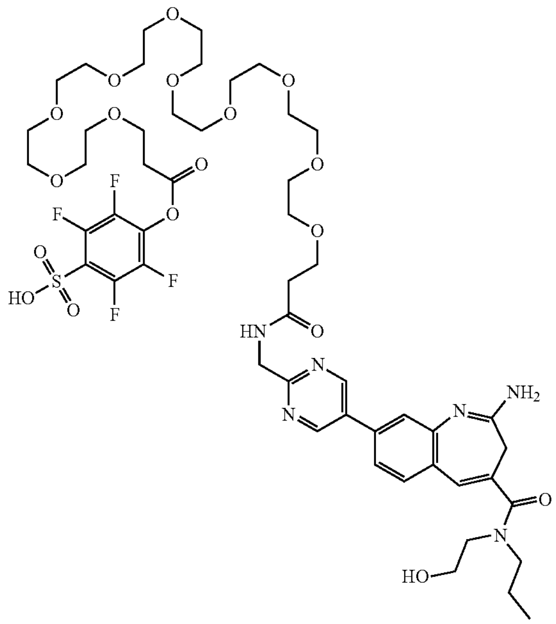 | 1163.2 |
| HxBzL-28 | 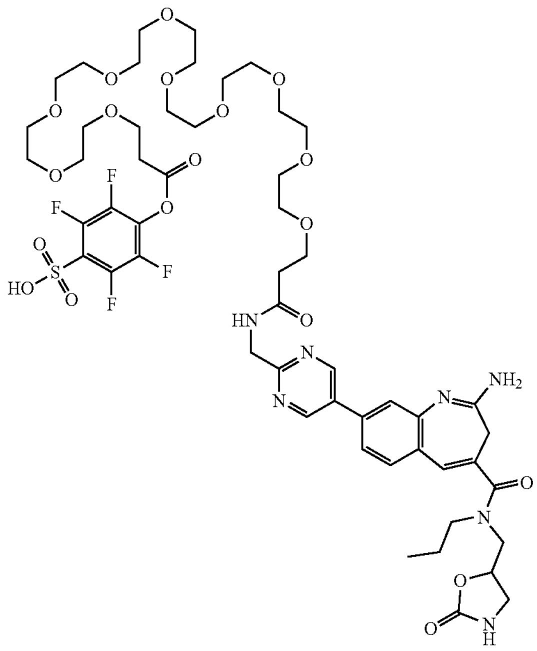 [SMILES: CCCN(CC1CNC(=O)O1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1218.2 |

TABLE 2a-continued
| 8-Het-2-aminobenzazepine-linker intermediate, Formula II compounds (HxBzL) | | |
|---|---|---|
| HxBzL No. | Structure | MW |
| HxBzL-29 | 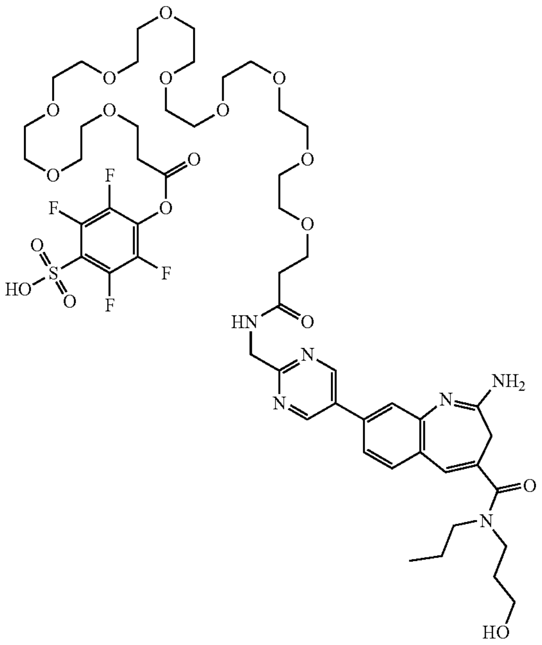 [SMILES: CCCN(CCCO)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1177.2 |
| HxBzL-30 | 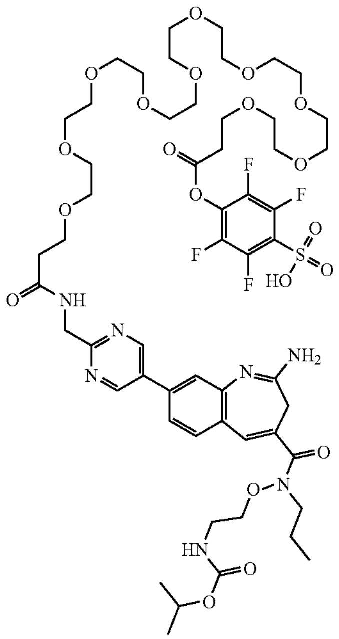 [SMILES: CCCN(OCCNC(=O)OC(C)C)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1264.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-31 | 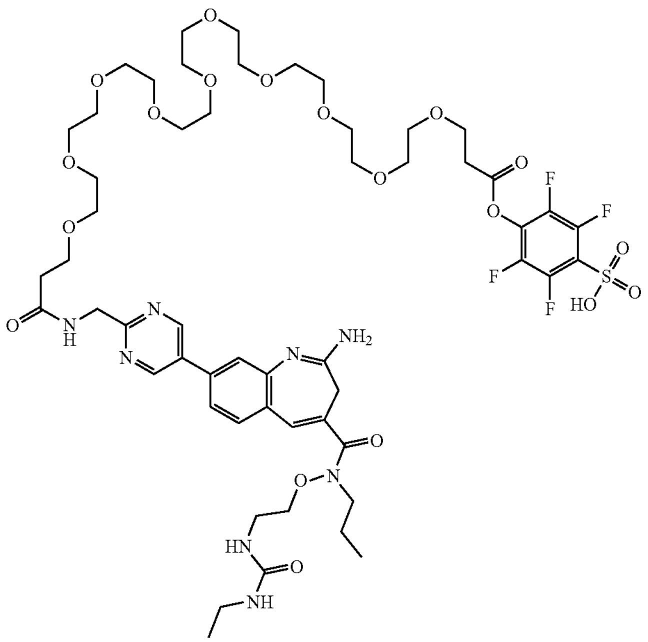 [SMILES: CCCN(OCCNC(=O)NCC)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1249.3 |
| HxBzL-32 | 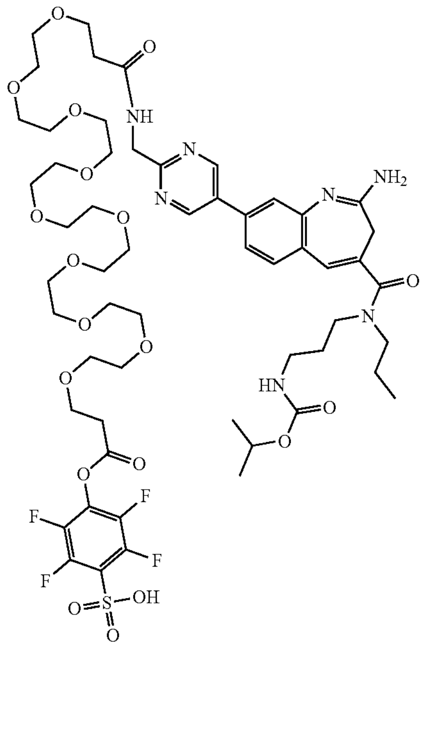 [SMILES: CCCN(CCCNC(=O)OC(C)C)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1262.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-33 | 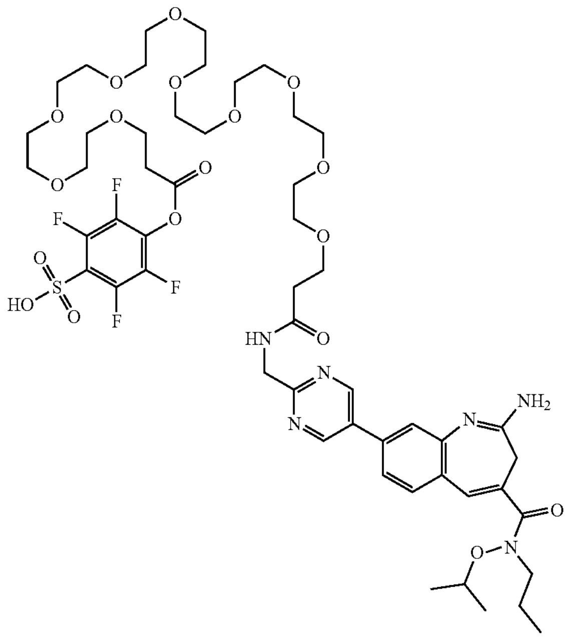 [SMILES: CCCN(OC(C)C)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1177.2 |
| HxBzL-34 | 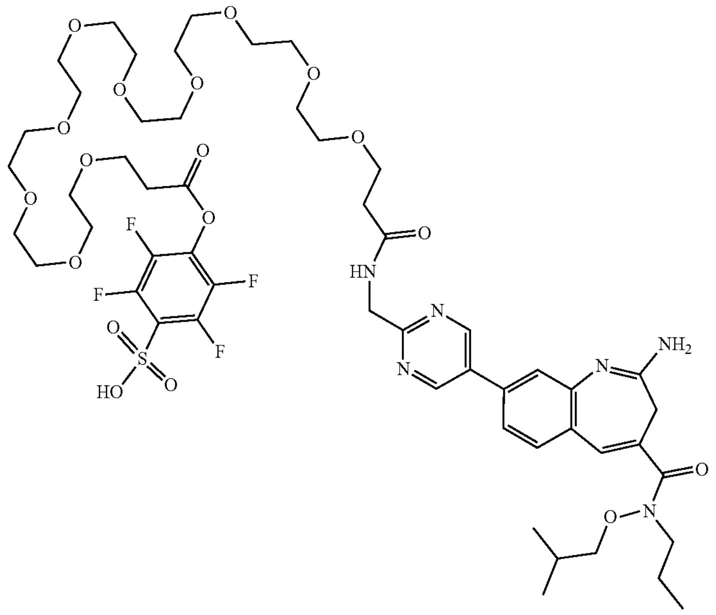 [SMILES: CCCN(OCC(C)C)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1191.2 |

TABLE 2a-continued
| 8-Het-2-aminobenzazepine-linker intermediate, Formula II compounds (HxBzL) | | |
|---|---|---|
| HxBzL No. | Structure | MW |
| HxBzL-35 | 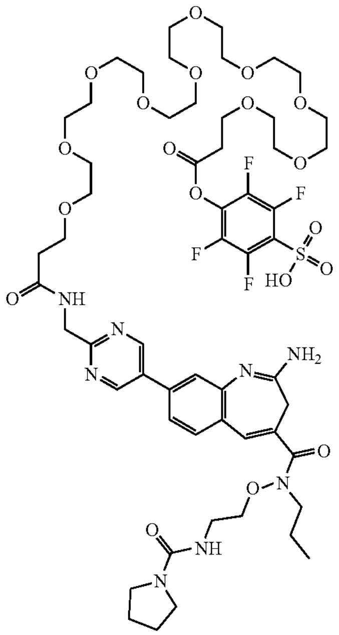 [SMILES: CCCN(OCCNC(=O)N1CCCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1275.3 |
| HxBzL-36 | 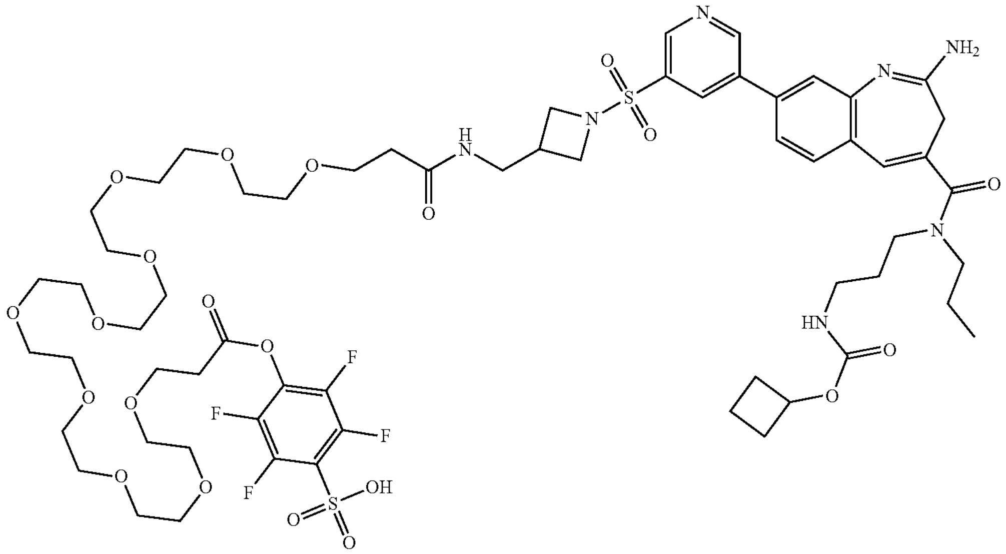 [SMILES: CCCN(CCCNC(=O)OC1CCC1)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1392.5 |

TABLE 2a-continued
| 8-Het-2-aminobenzazepine-linker intermediate, Formula II compounds (HxBzL) | | |
|---|---|---|
| HxBzL No. | Structure | MW |
| HxBzL-37 | 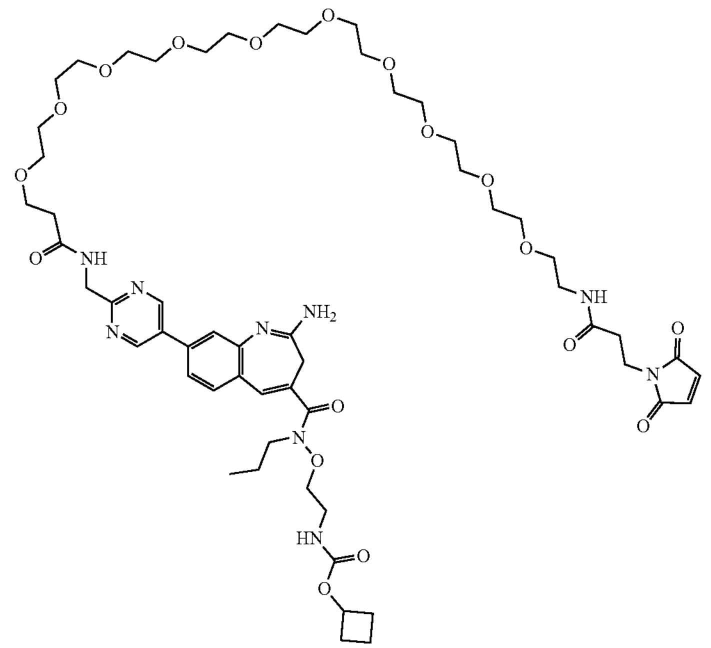 | 1170.3 |
| HxBzL-38 | 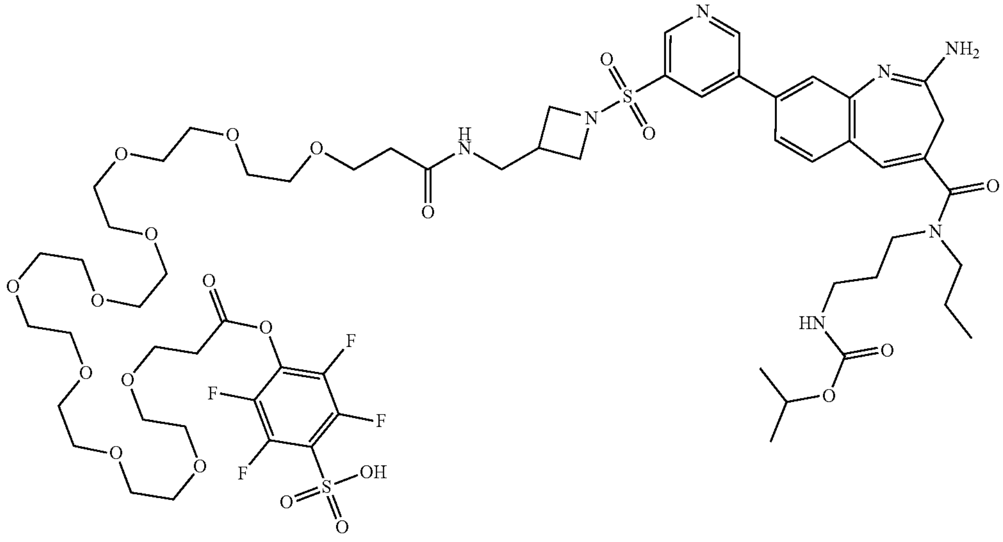 [SMILES: CCCN(CCCNC(=O)OC(C)C)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1380.5 |

TABLE 2a-continued
| 8-Het-2-aminobenzazepine-linker intermediate, Formula II compounds (HxBzL) | | |
|---|---|---|
| HxBzL No. | Structure | MW |
| HxBzL-39 | 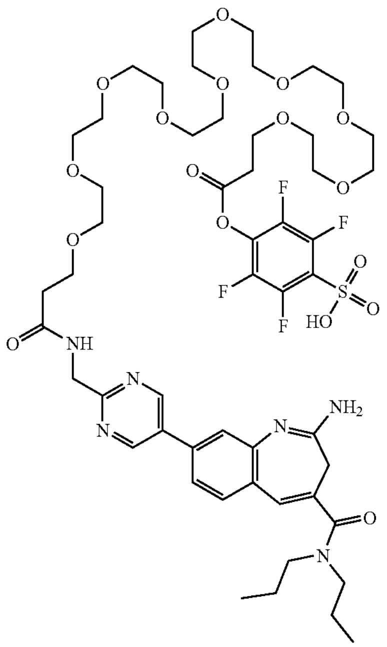 [SMILES: CCCN(CCC)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1161.2 |
| HxBzL-40 | 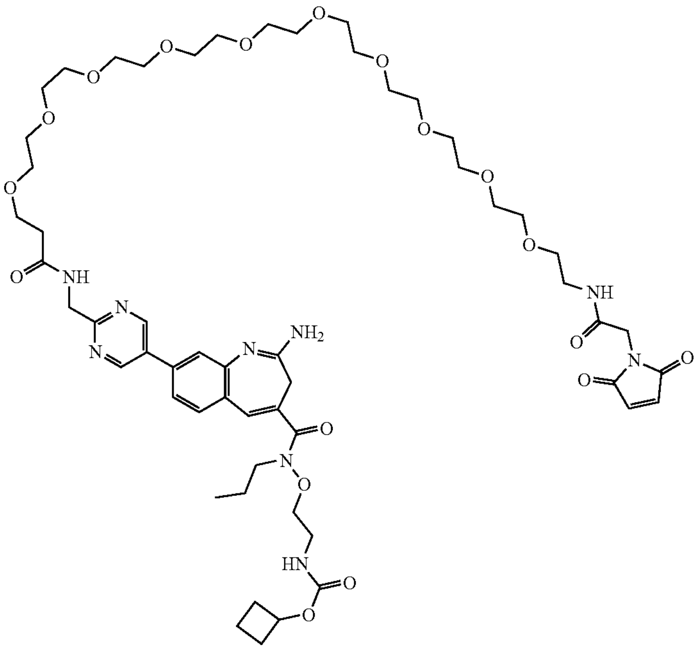 [SMILES: CCCN(OCCNC(=O)OC1CCC1)C(=O)C1=Cc2ccc(-c3cnc(CNC(=O)CCOCCOCCOCCOCCOCCOCCOCCOCCOCCOCCNC(=O)CN4C(=O)C=CC4=O)nc3)cc2N=C(N)C1] | 1156.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-41 | 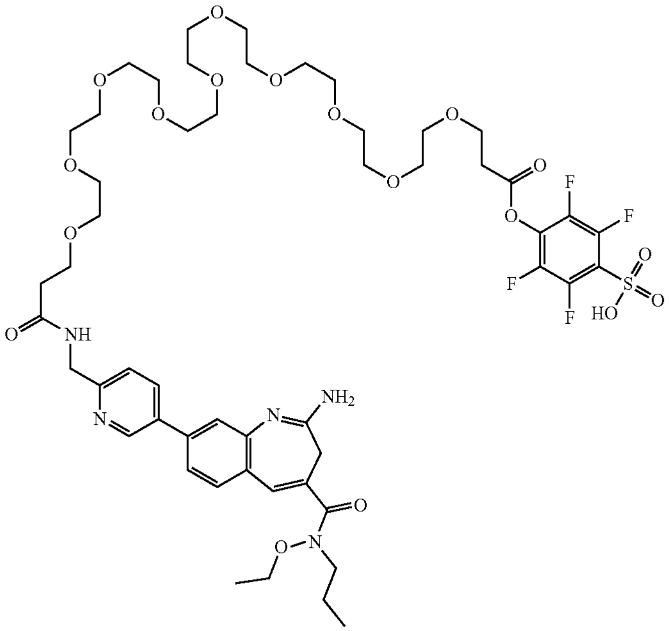 [SMILES: CCCN(OCC)C(=O)C1=Cc2ccc(-c3ccc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1162.2 |
| HxBzL-42 | 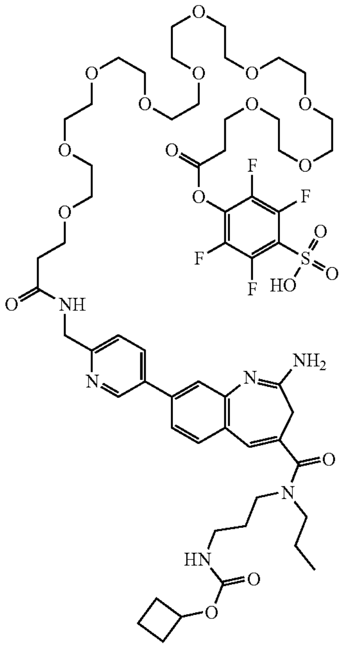 [SMILES: CCCN(CCCNC(=O)OC1CCC1)C(=O)C1=Cc2ccc(-c3ccc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1273.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-43 | 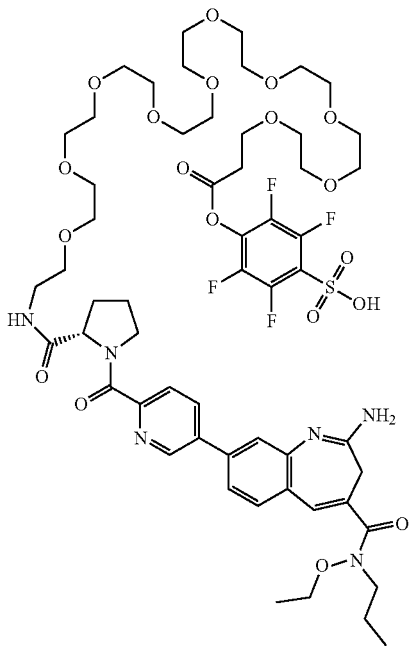 [SMILES: CCCN(OCC)C(=O)C1=Cc2ccc(-c3ccc(C(=O)N4CCC[C@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1245.3 |
| HxBzL-44 | 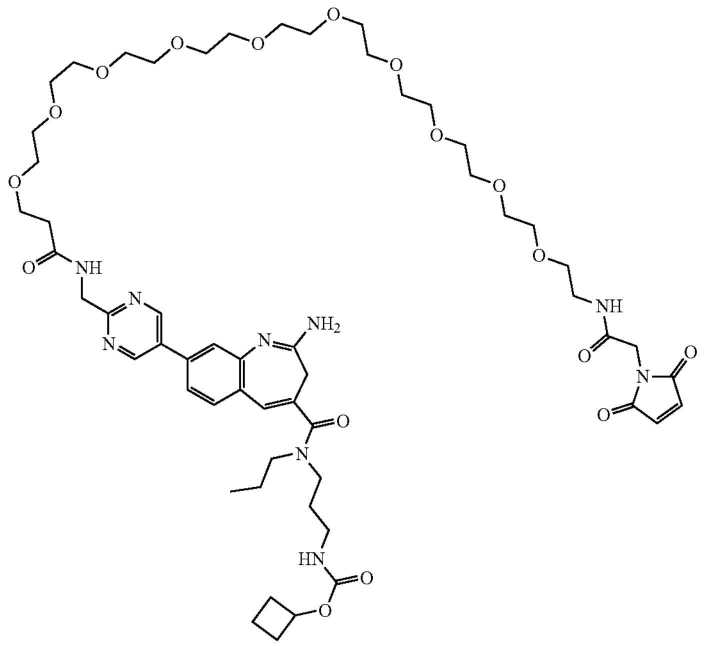 [SMILES: CCCN(CCCNC(=O)OC1CCC1)C(=O)C1=Cc2ccc(-c3cnc(CNC(=O)CCOCCOCCOCCOCCOCCOCCOCCOCCOCCOCCNC(=O)CN4C(=O)C=CC4=O)nc3)cc2N=C(N)C1] | 1154.3 |

TABLE 2a-continued
8-Het-2-aminobenzazepine-linker intermediate, Formula II compounds (HxBzL)
| HxBzL No. | Structure | MW |
| --- | --- | --- |
| HxBzL-45 | 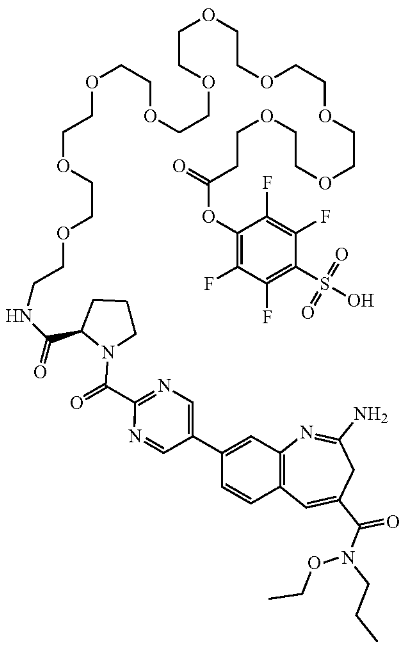 [SMILES: CCCN(OCC)C(=O)C1=Cc2ccc(-c3cnc(C(=O)N4CCC[C@@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1246.3 |
| HxBzL-46 | 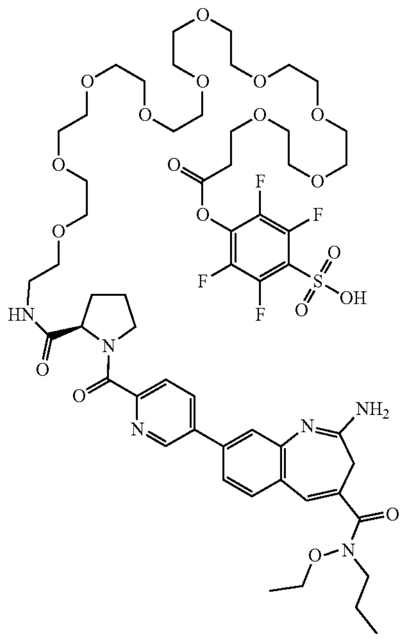 [SMILES: CCCN(OCC)C(=O)C1=Cc2ccc(-c3ccc(C(=O)N4CCC[C@@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1245.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-47 | 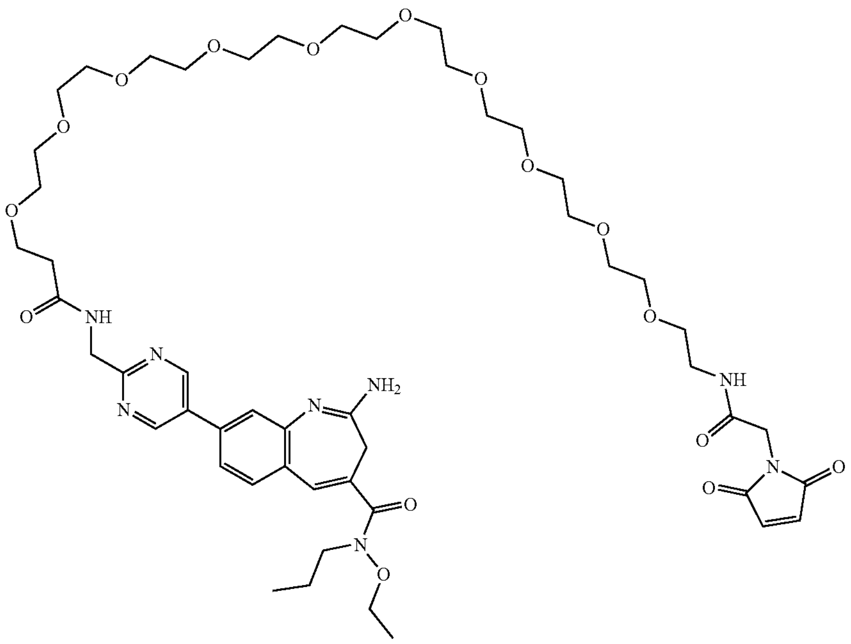 [SMILES: CCCN(OCC)C(=O)C1=Cc2ccc(-c3cnc(CNC(=O)CCOCCOCCOCCOCCOCCOCCOCCOCCOCCOCCNC(=O)CN4C(=O)C=CC4=O)nc3)cc2N=C(N)C1] | 1043.2 |
| HxBzL-48 | 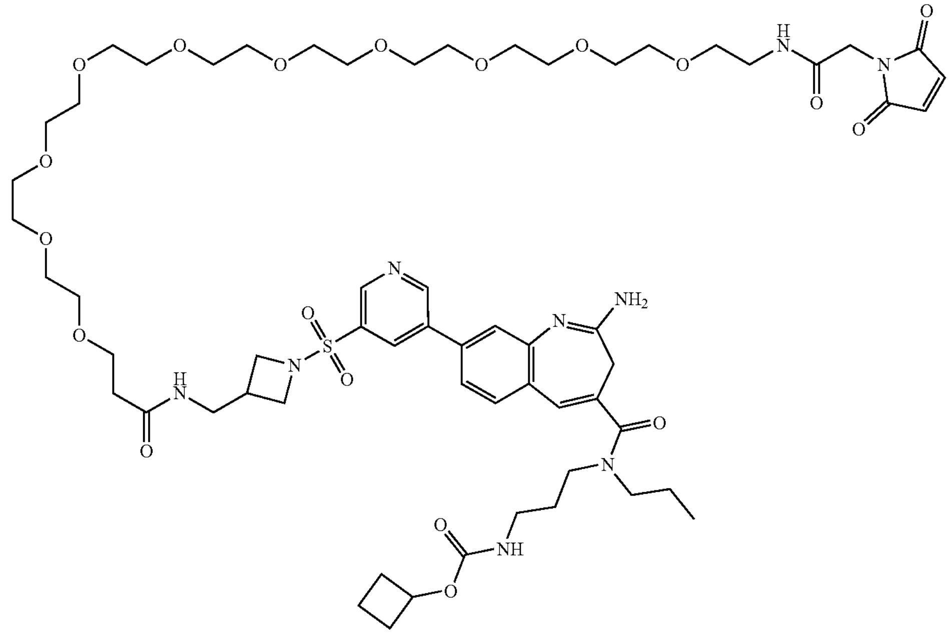 [SMILES: CCCN(CCCNC(=O)OC1CCC1)C(=O)C1=Cc2ccc(-c3cncc(S(=O)(=O)N4CC(CNC(=O)CCOCCOCCOCCOCCOCCOCCOCCOCCOCCOCCNC(=O)CN5C(=O)C=CC5=O)C4)c3)cc2N=C(N)C1] | 1272.5 |

TABLE 2a-continued
| 8-Het-2-aminobenzazepine-linker intermediate, Formula II compounds (HxBzL) | | |
|---|---|---|
| HxBzL No. | Structure | MW |
| HxBzL-49 | 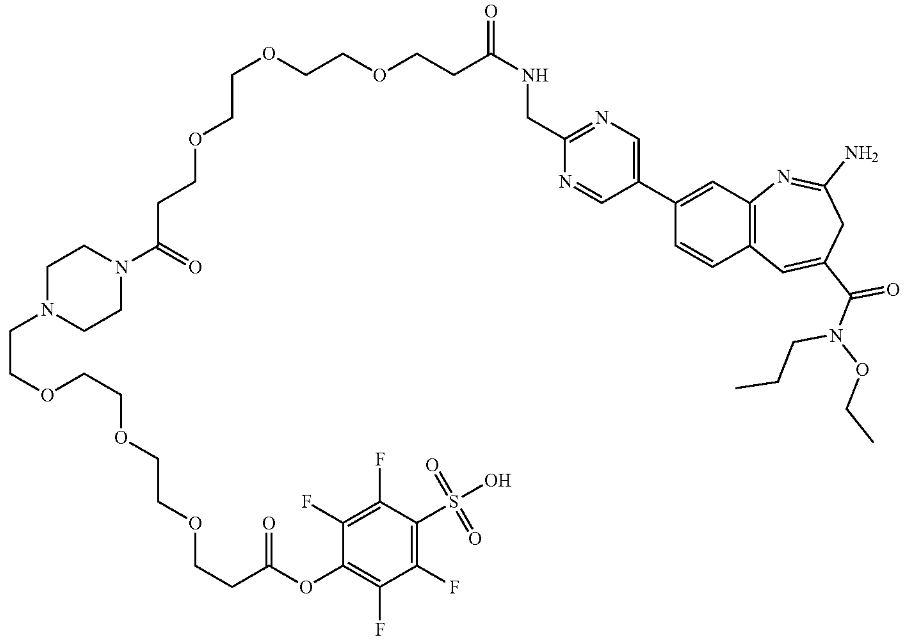 | 1127.2 |
| HxBzL-50 | 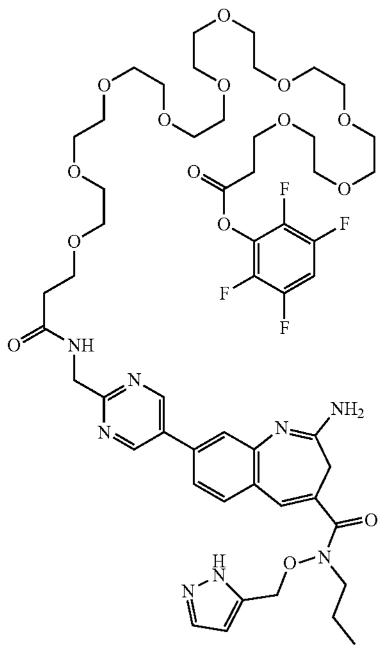 [SMILES: CCCN(OCc1ccn[nH]1)C(=O)C1=Cc2ccc(-c3cnc(CNC(=O)CCOCCOCCOCCOCCOCCOCCOCCOCCOCCOCCC(=O)Oc4c(F)c(F)cc(F)c4F)nc3)cc2N=C(N)C1] | 1135.2 |

TABLE 2a-continued
8-Het-2-aminobenzazepine-linker intermediate, Formula II compounds (HxBzL)
| HxBzL No. | Structure | MW |
|---|---|---|
| HxBzL-51 | 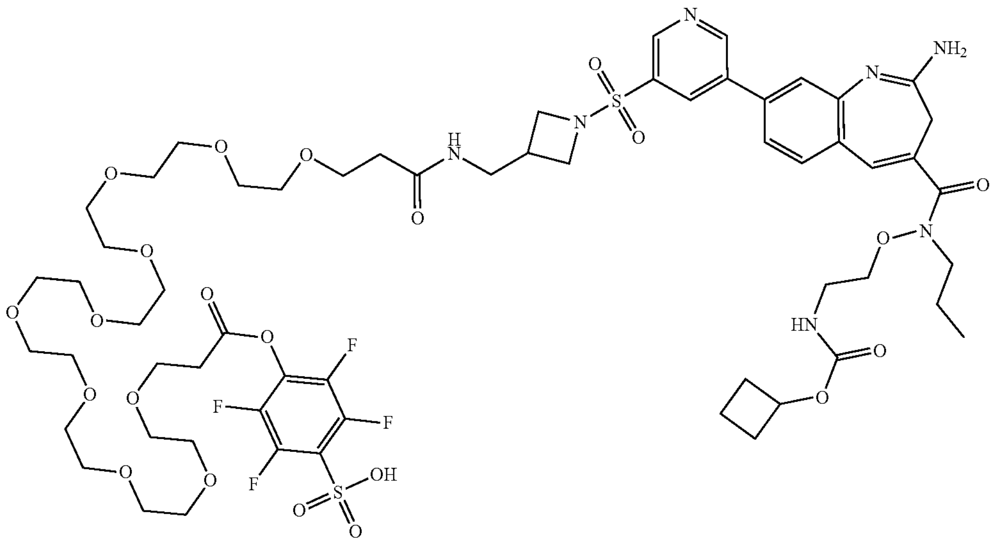 [SMILES: CCCN(OCCNC(=O)OC1CCC1)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1394.5 |
| HxBzL-52 | 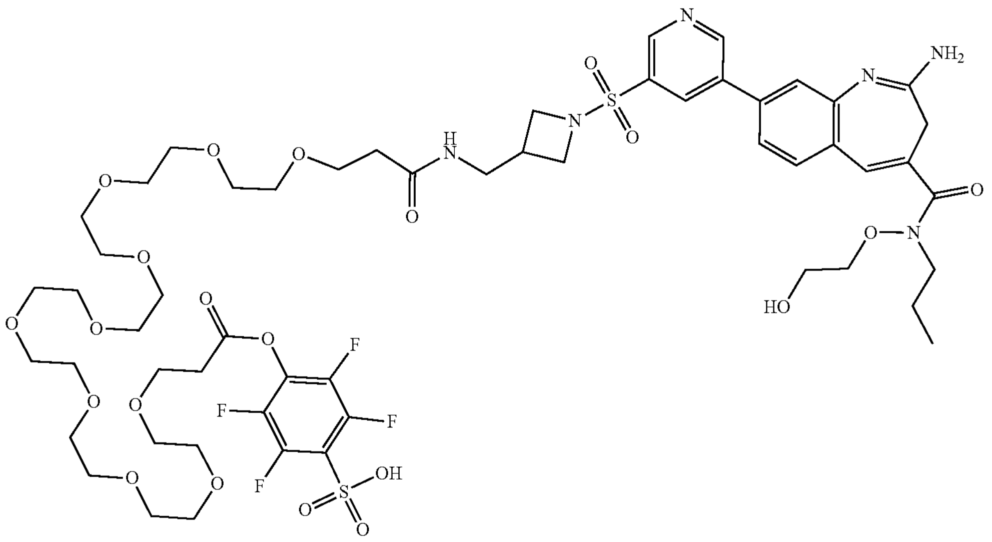 [SMILES: CCCN(OCCO)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1297.3 |

TABLE 2a-continued
| 8-Het-2-aminobenzazepine-linker intermediate, Formula II compounds (HxBzL) | | |
|---|---|---|
| HxBzL No. | Structure | MW |
| HxBzL-53 | 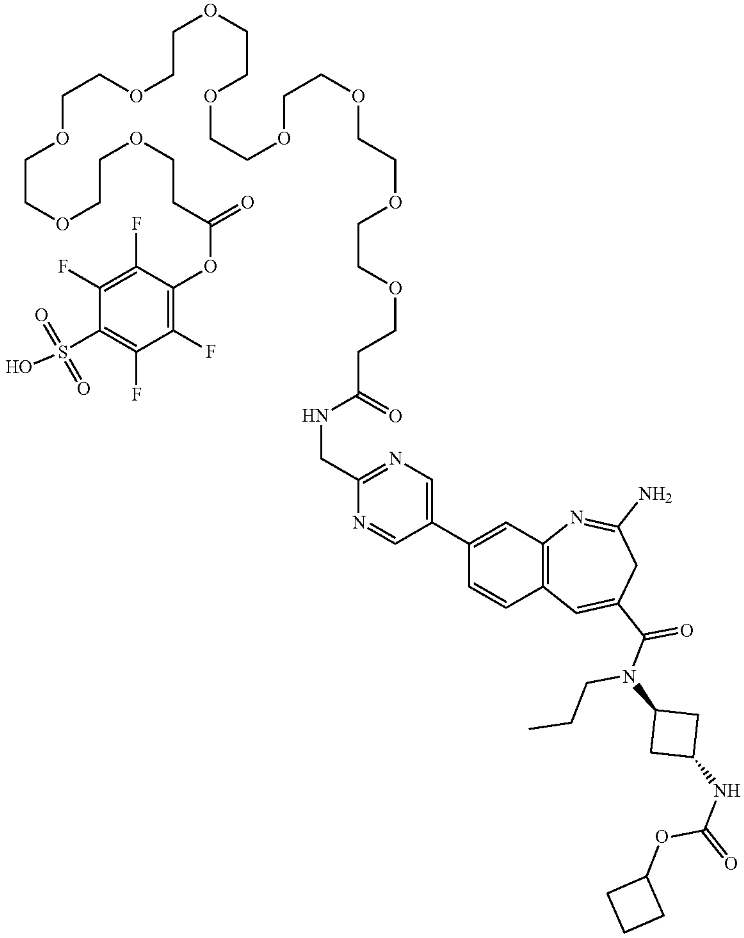 [SMILES: CCCN(C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1)[C@H]1C[C@H](NC(=O)OC2CCC2)C1] | 1286.3 |
| HxBzL-54 | 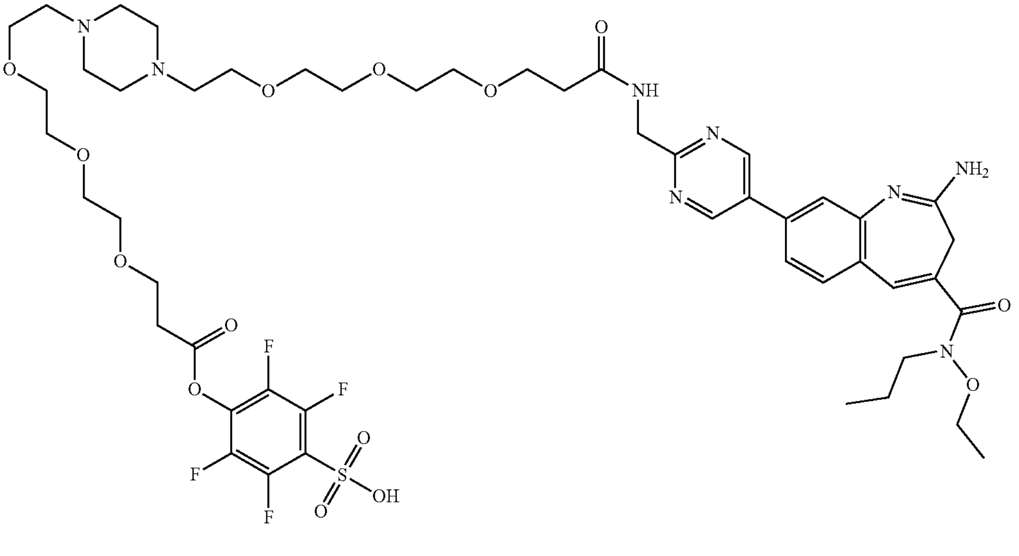 [SMILES: CCCN(OCC)C(=O)C1=Cc2ccc(-c3cnc(CNC(=O)CCOCCOCCOCCN4CCN(CCOCCOCCOCCC(=O)Oc5c(F)c(F)c(S(=O)(=O)O)c(F)c5F)CC4)nc3)cc2N=C(N)C1] | 1099.2 |

TABLE 2a-continued
| 8-Het-2-aminobenzazepine-linker intermediate, Formula II compounds (HxBzL) | | |
|---|---|---|
| HxBzL No. | Structure | MW |
| HxBzL-55 | 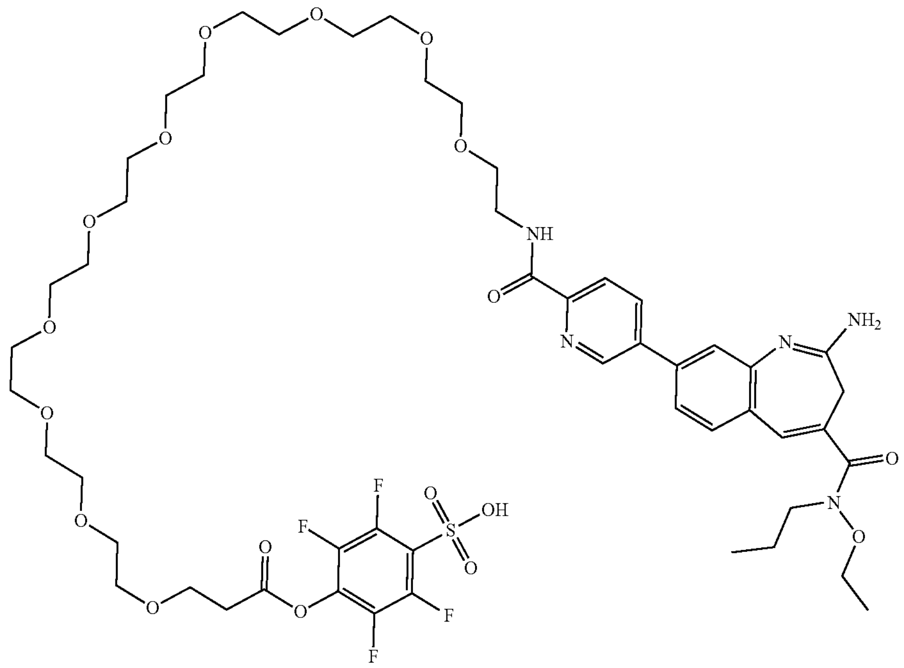 | 1148.2 |
TABLE 2b
| 8-Het-2-aminobenzazepine-linker intermediate, Formula II compounds (HxBzL) | | |
|---|---|---|
| HxBzL No. | Structure | MW |
| HxBzL-56 | 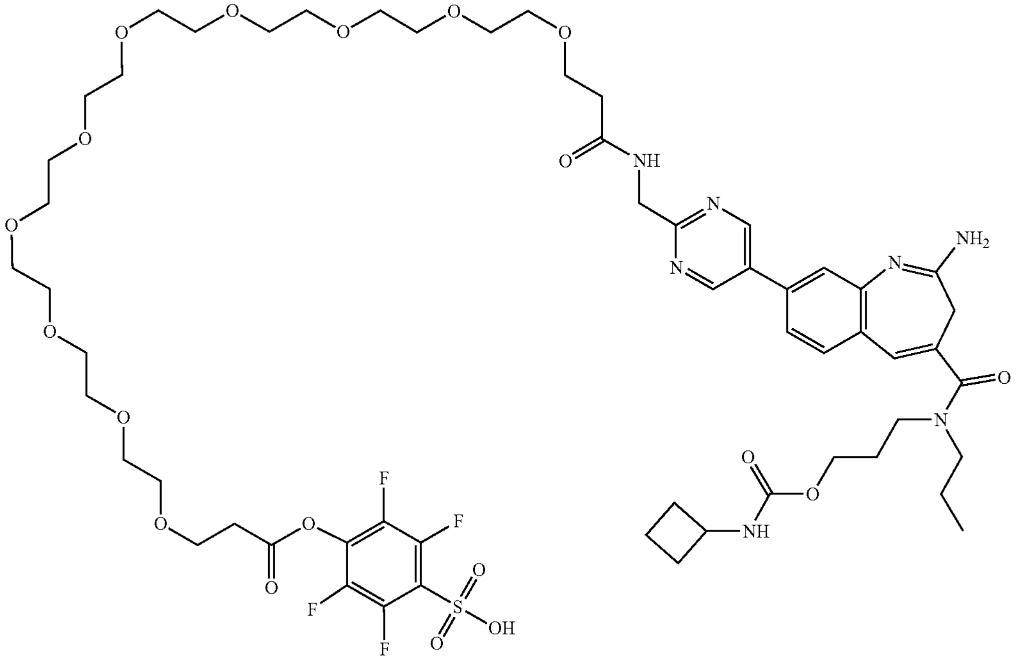 [SMILES: CCCN(CCCOC(=O)NC1CCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1274.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-57 | 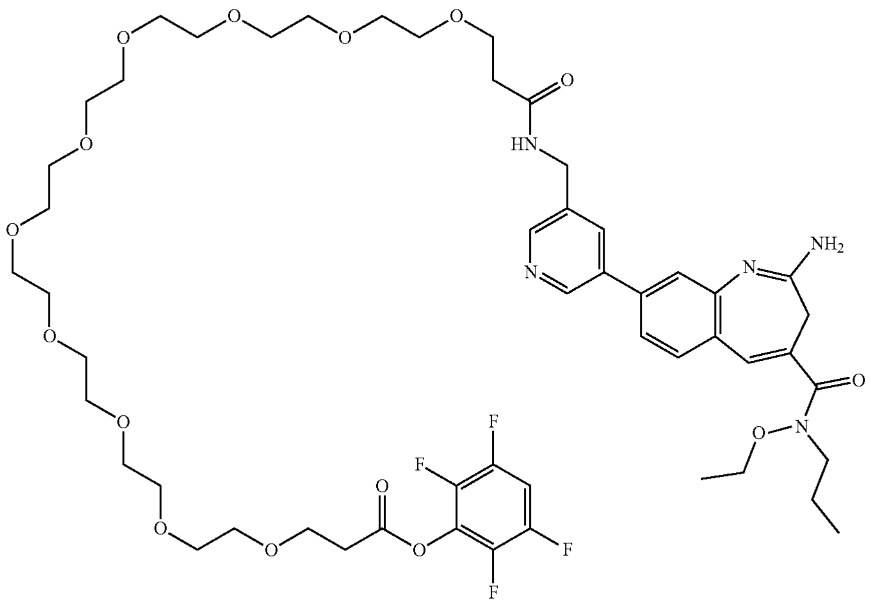 [SMILES: CCCN(OCC)C(=O)C1=Cc2ccc(-c3cncc(CNC(=O)CCOCCOCCOCCOCCOCCOCCOCCOCCOCCOCCC(=O)Oc4c(F)c(F)cc(F)c4F)c3)cc2N=C(N)C1] | 1082.2 |
| HxBzL-58 | 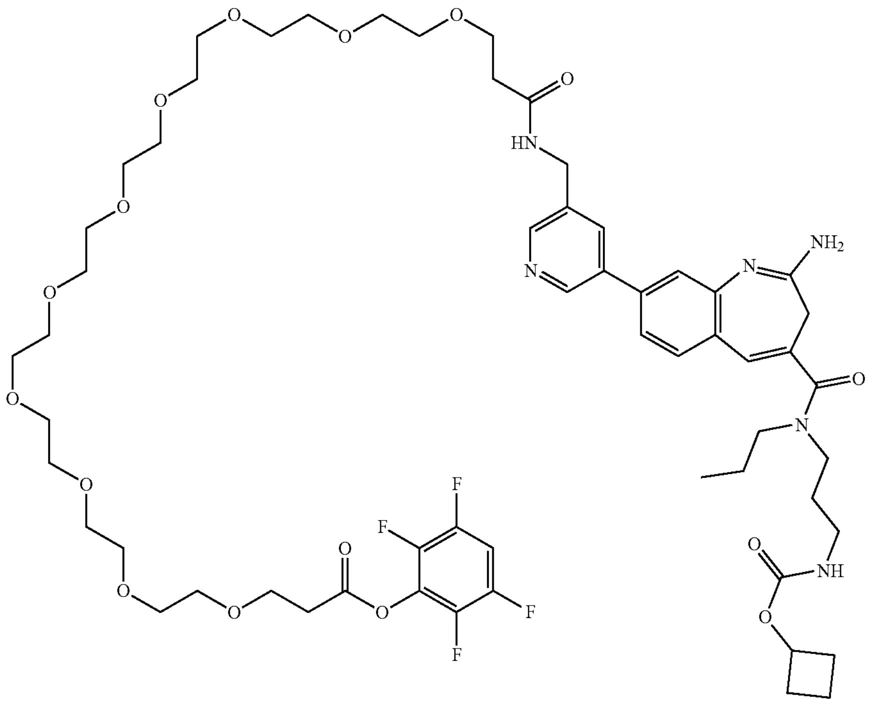 [SMILES: CCCN(CCCNC(=O)OC1CCC1)C(=O)C1=Cc2ccc(-c3cncc(CNC(=O)CCOCCOCCOCCOCCOCCOCCOCCOCCOCCOCCC(=O)Oc4c(F)c(F)cc(F)c4F)c3)cc2N=C(N)C1] | 1193.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-59 | 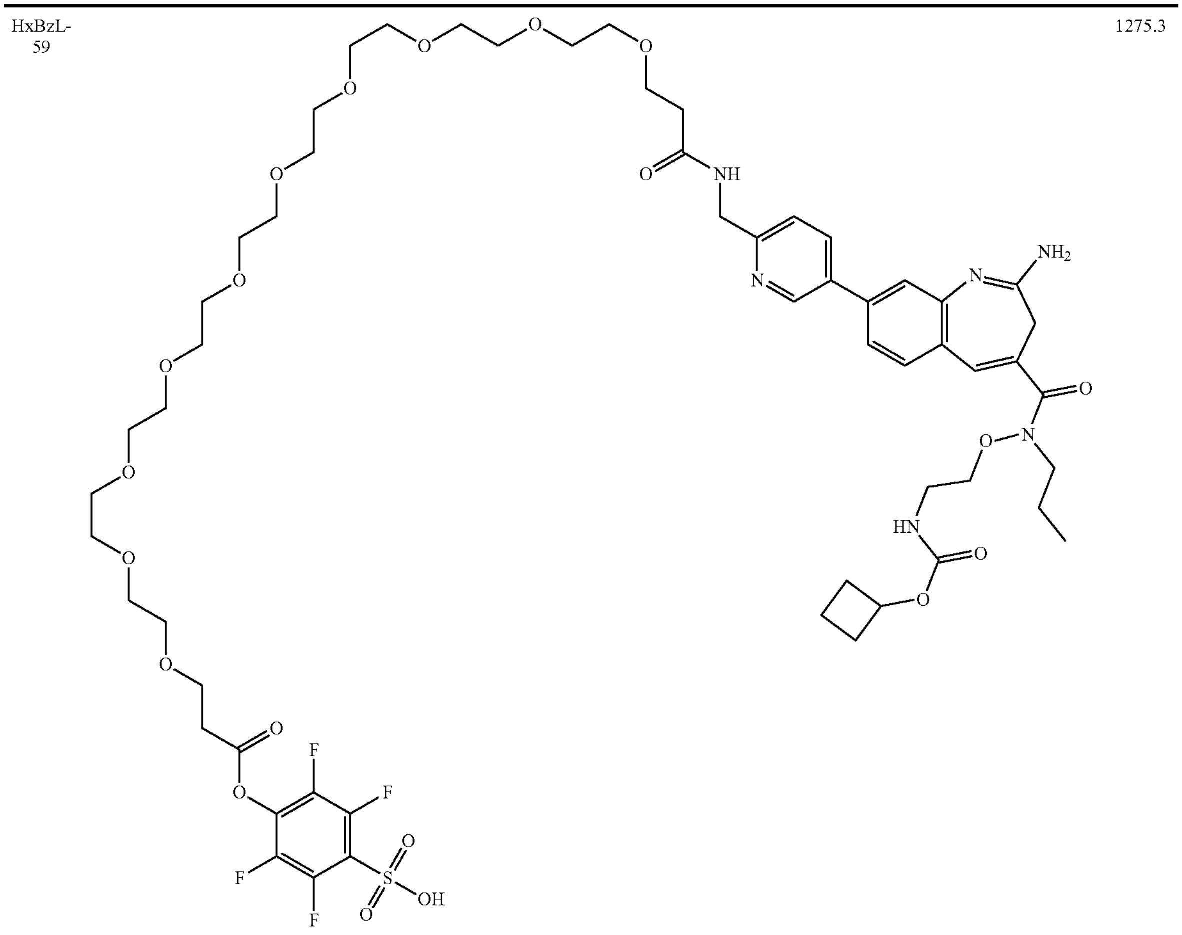 | 1275.3 |
| HxBzL-60 | 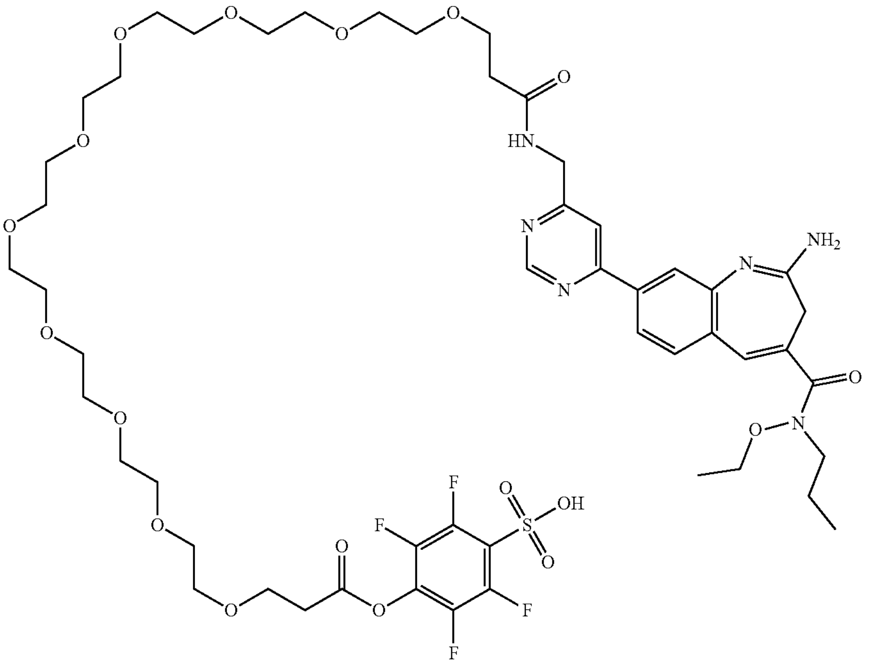 [SMILES: CCCN(OCC)C(=O)C1=Cc2ccc(-c3cc(CNC(=O)CCOCCOCCOCCOCCOCCOCCOCCOCCOCCOCCC(=O)Oc4c(F)c(F)c(S(=O)(=O)O)c(F)c4F)ncn3)cc2N=C(N)C1] | 1163.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-61 | 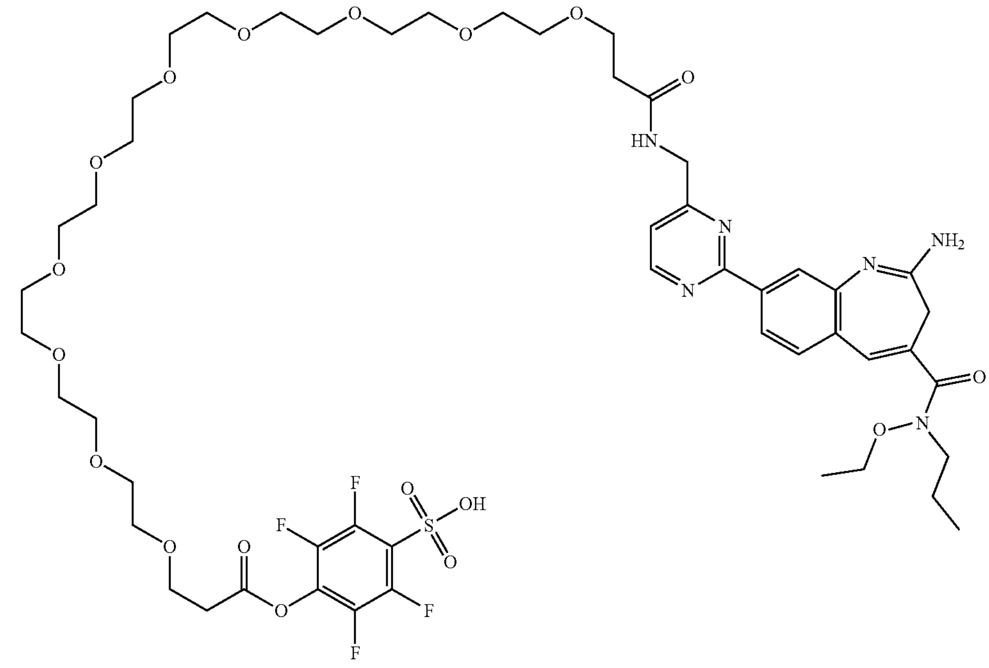 [SMILES: CCCN(OCC)C(=O)C1=Cc2ccc(-c3nccc(CNC(=O)CCOCCOCCOCCOCCOCCOCCOCCOCCOCCOCCC(=O)Oc4c(F)c(F)c(S(=O)(=O)O)c(F)c4F)n3)cc2N=C(N)C1] | 1163.2 |
| HxBzL-62 | 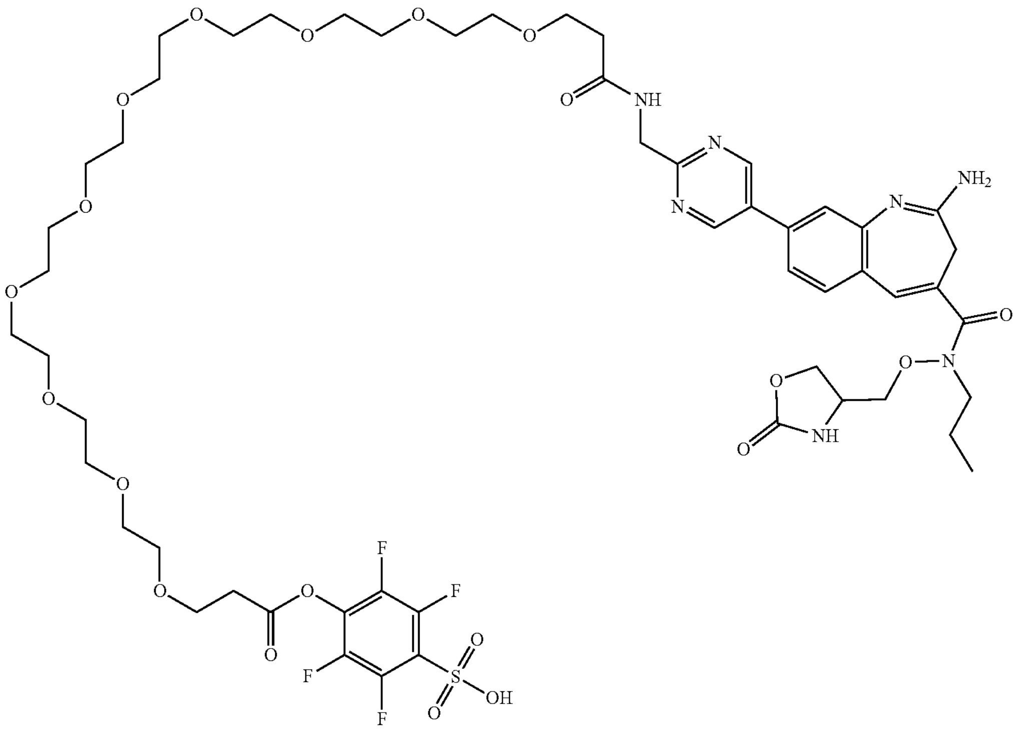 [SMILES: CCCN(OCC1COC(=O)N1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1234.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-63 | 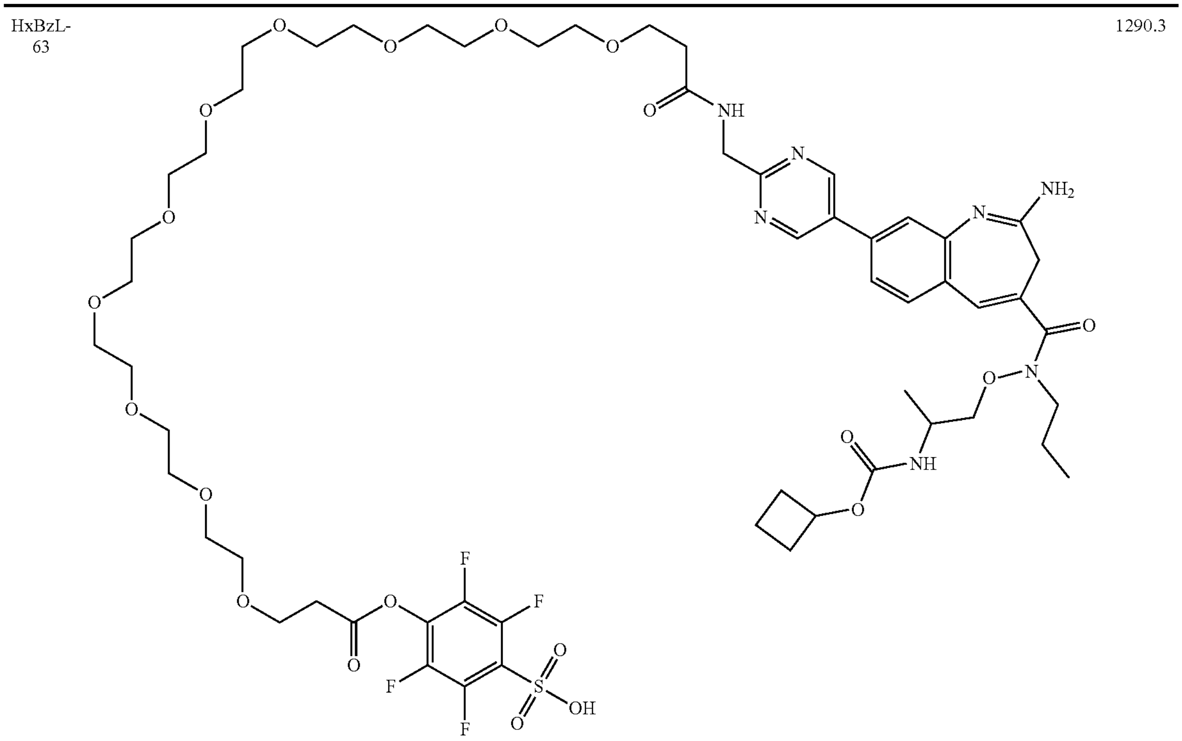 | 1290.3 |
| HxBzL-64 | 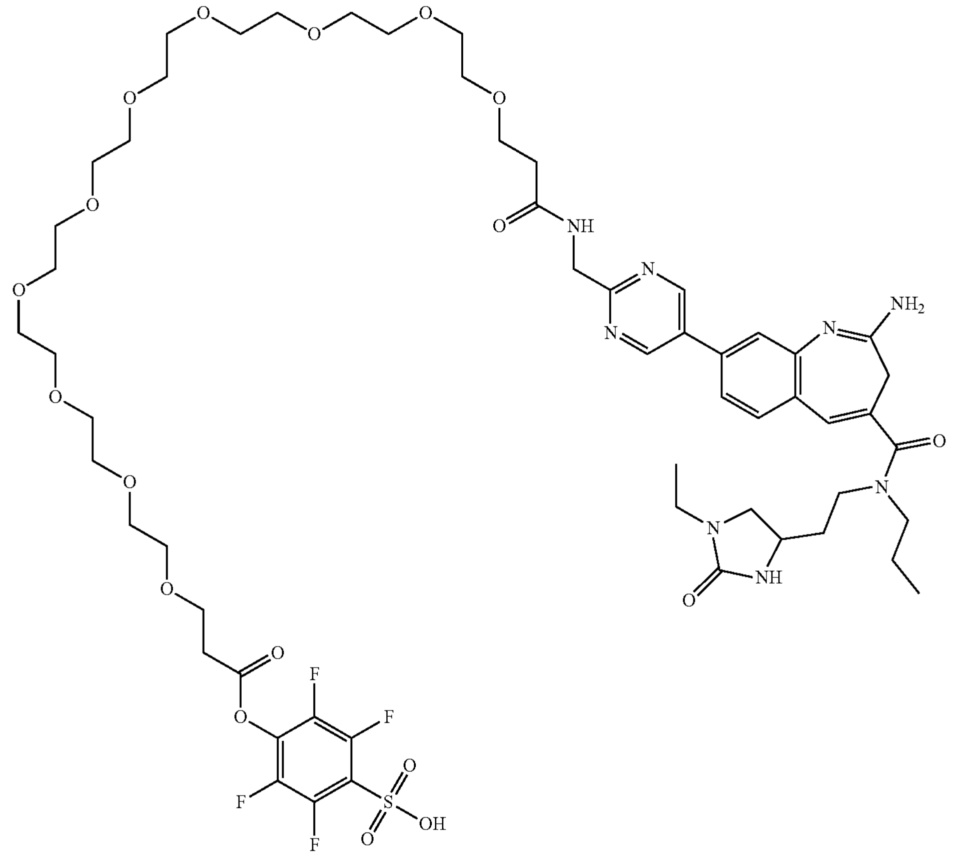 [SMILES: CCCN(CCC1CN(CC)C(=O)N1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1259.3 |

TABLE 2b-continued
| HxBzL No. | Structure | MW |
|---|---|---|
| 8-Het-2-aminobenzazepine-linker intermediate, Formula II compounds (HxBzL) | | |
| HxBzL-65 | 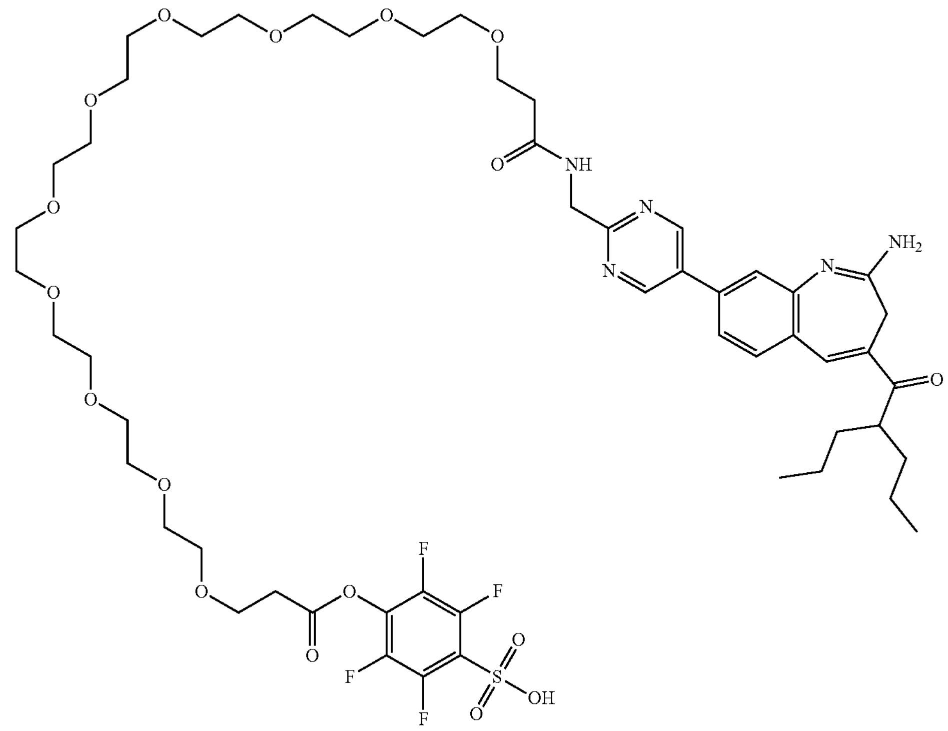 [SMILES: CCCC(CCC)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1160.2 |
| HxBzL-66 | 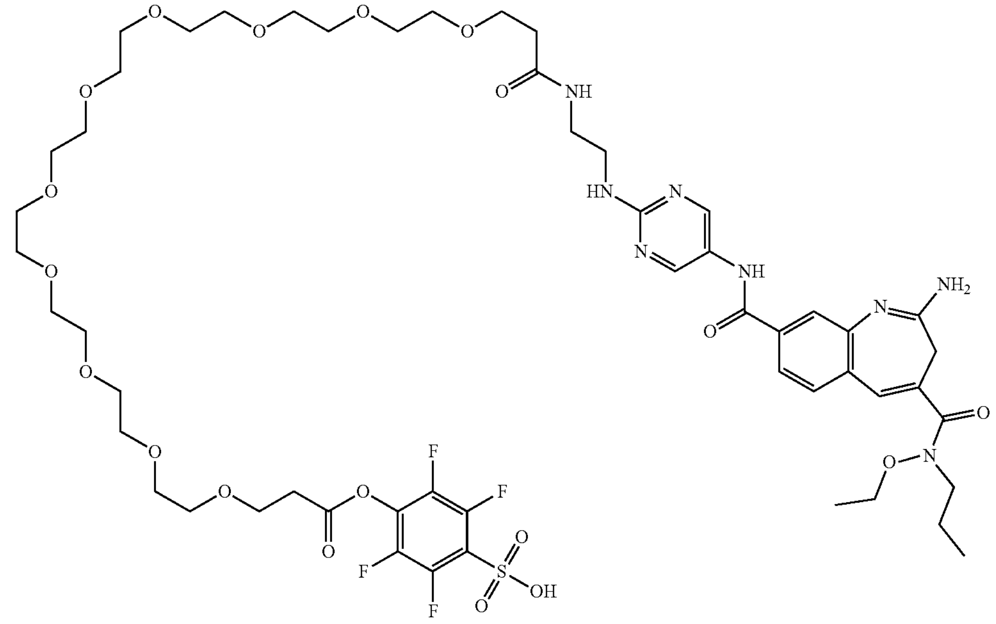 [SMILES: CCCN(OCC)C(=O)C1=Cc2ccc(C(=O)Nc3cnc(NCCNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1235.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-67 | 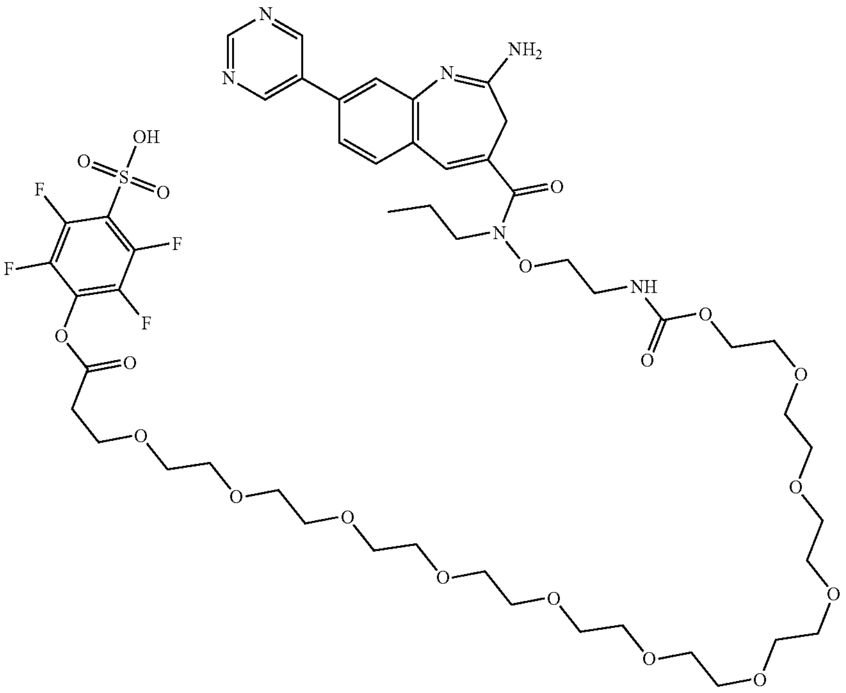 [SMILES: CCCN(OCCNC(=O)OCCOCCOCCOCCOCCOCCOCCOCCOCCOCCOCCC(=O)Oc1c(F)c(F)c(S(=O)(=O)O)c(F)c1F)C(=O)C1=Cc2ccc(-c3cncnc3)cc2N=C(N)C1] | 1165.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-68 | 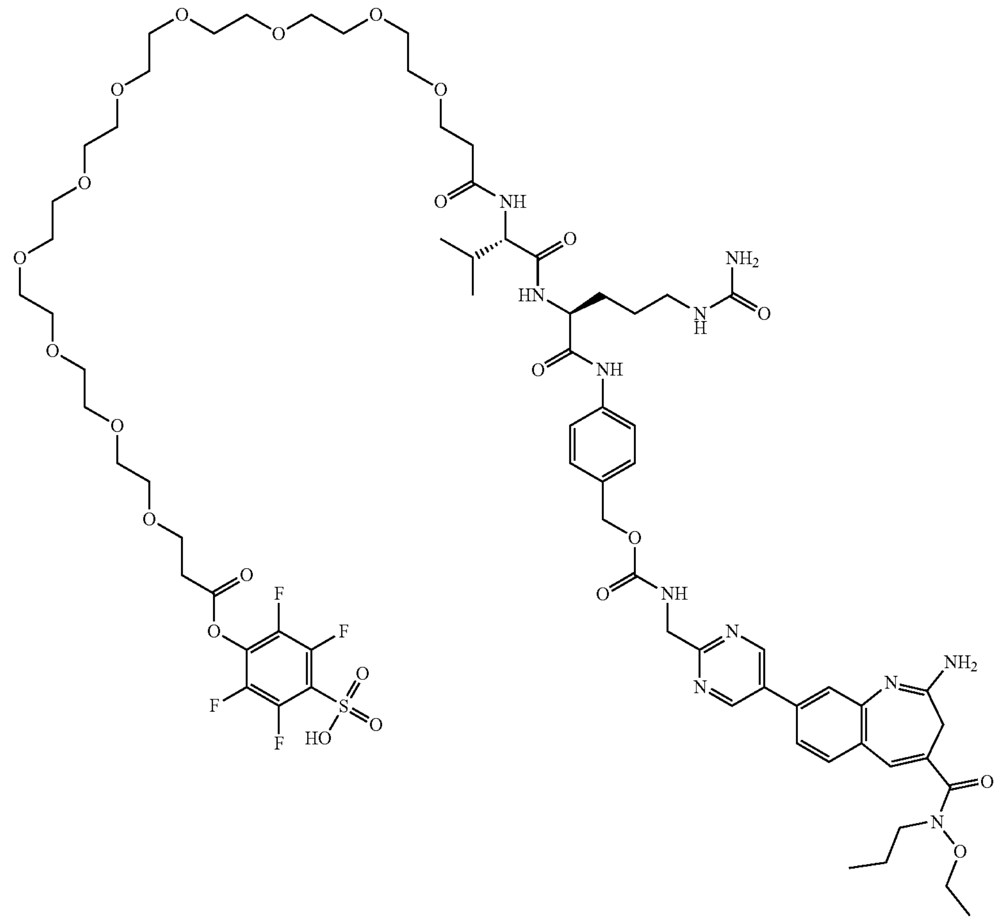 [SMILES: CCCN(OCC)C(=O)C1=Cc2ccc(-c3cnc(CNC(=O)OCc4ccc(NC(=O)[C@H](CCCNC(N)=O)NC(=O)[C@@H](NC(=O)CCOCCOCCOCCOCCOCCOCCOCCOCCOCCOCCC(=O)Oc5c(F)c(F)c(S(=O)(=O)O)c(F)c5F)C(C)C)cc4)nc3)cc2N=C(N)C1] | 1568.7 |

TABLE 2b-continued
| 8-Het-2-aminobenzazepine-linker intermediate, Formula II compounds (HxBzL) | | |
|---|---|---|
| HxBzL No. | Structure | MW |
| HxBzL-69 | 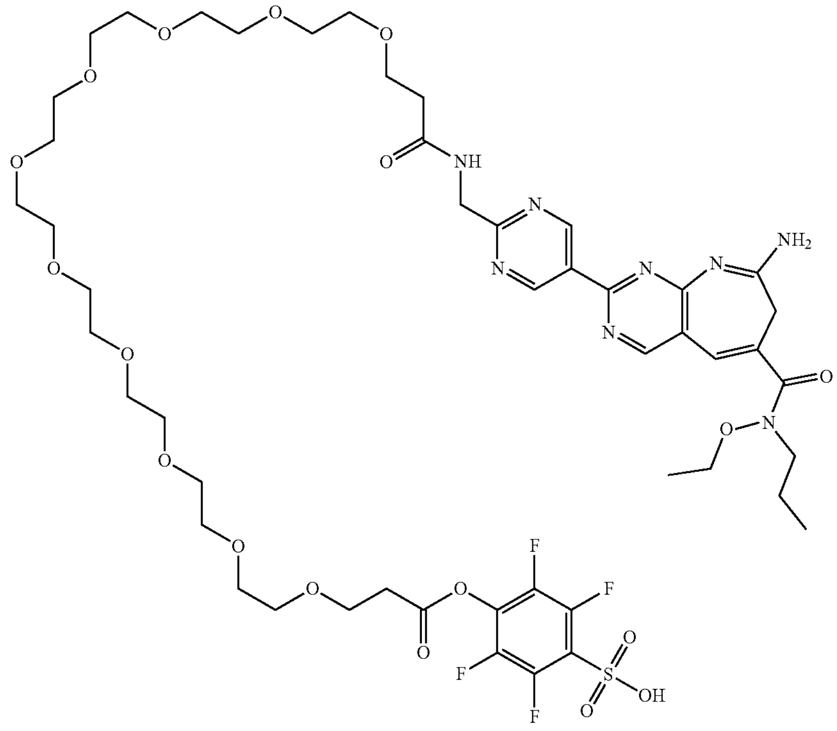 [SMILES: CCCN(OCC)C(=O)C1=Cc2cnc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)nc2N=C(N)C1] | 1165.2 |
| HxBzL-70 | 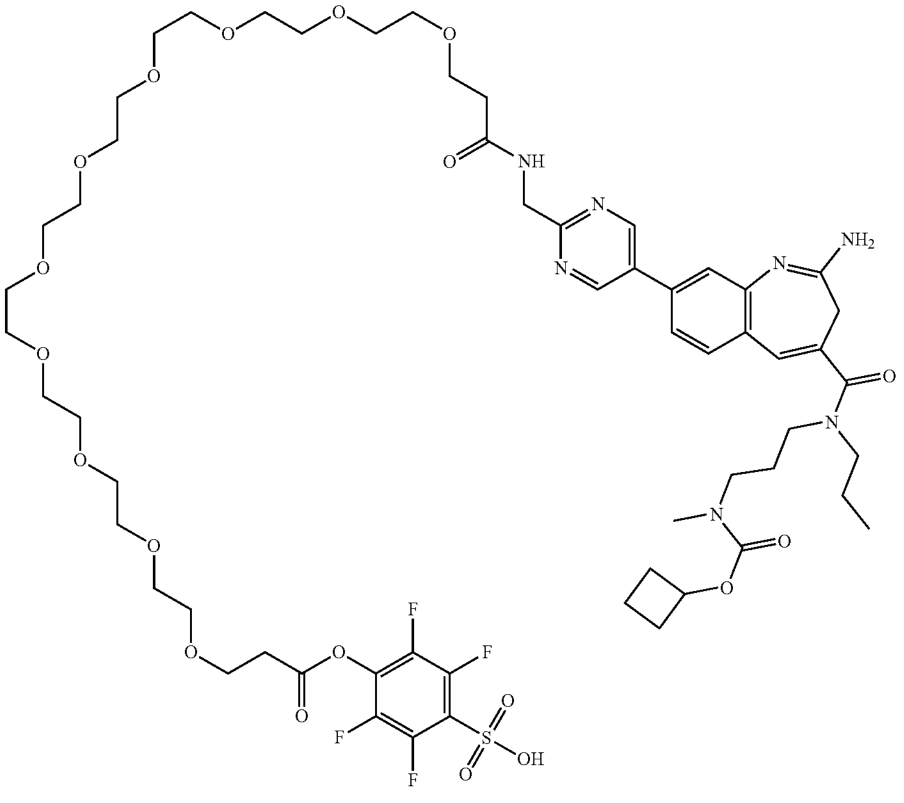 [SMILES: CCCN(CCCN(C)C(=O)OC1CCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1288.4 |

TABLE 2b-continued
8-Het-2-aminobenzazepine-linker intermediate, Formula II compounds (HxBzL)
| HxBzL No. | Structure | MW |
| --- | --- | --- |
| HxBzL-71 | 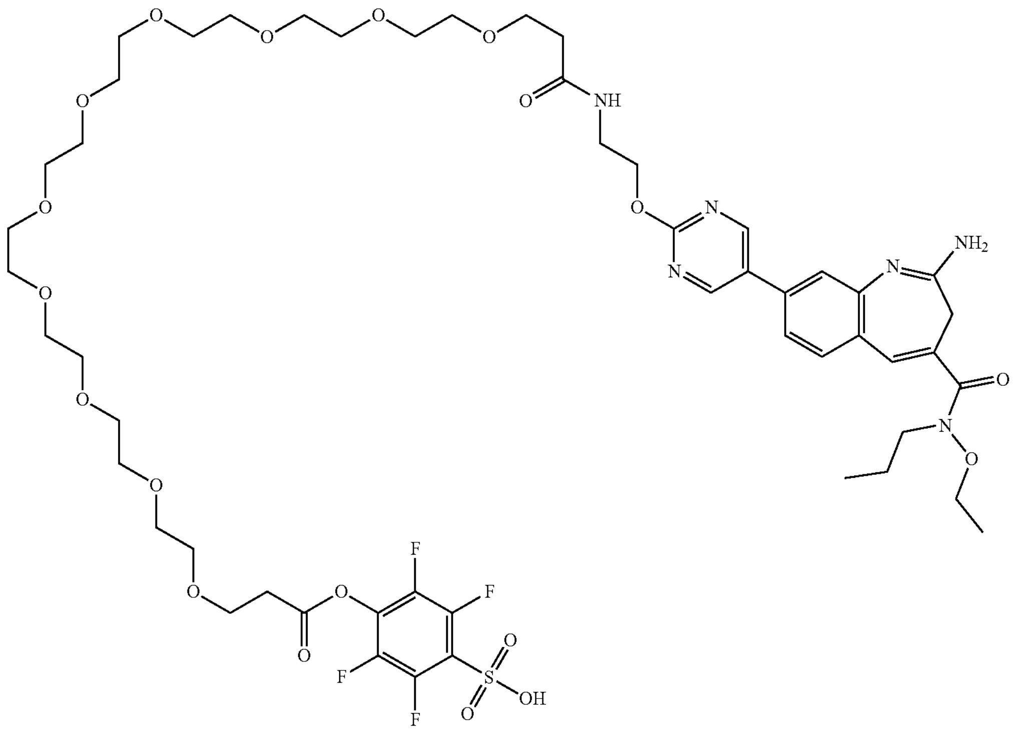 | 1193.2 |
| HxBzL-72 | 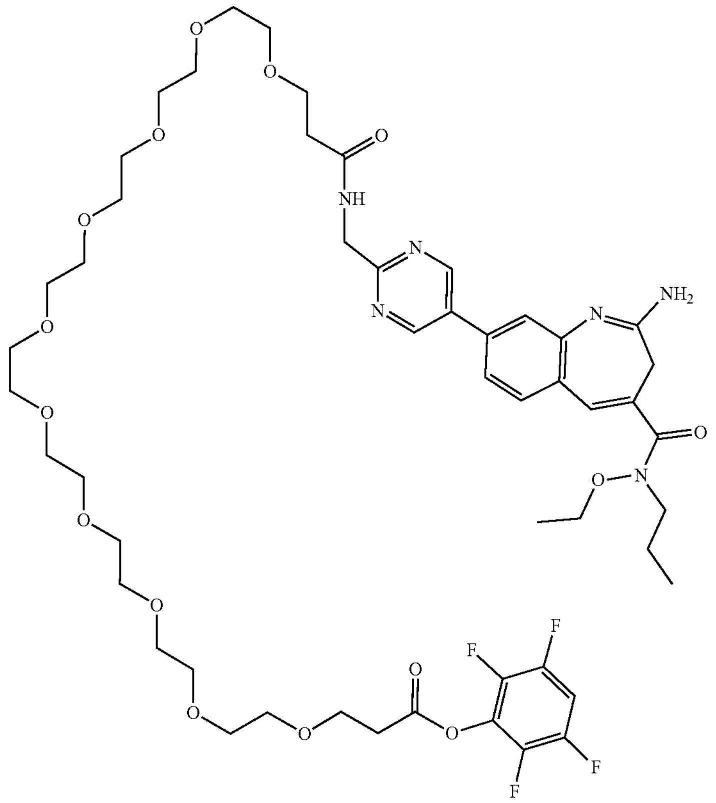 [SMILES: CCCN(OCC)C(=O)C1=Cc2ccc(-c3cnc(CNC(=O)CCOCCOCCOCCOCCOCCOCCOCCOCCOCCOCCC(=O)Oc4c(F)c(F)cc(F)c4F)nc3)cc2N=C(N)C1] | 1083.1 |

TABLE 2b-continued
| 8-Het-2-aminobenzazepine-linker intermediate, Formula II compounds (HxBzL) | | |
|---|---|---|
| HxBzL No. | Structure | MW |
| HxBzL-73 | 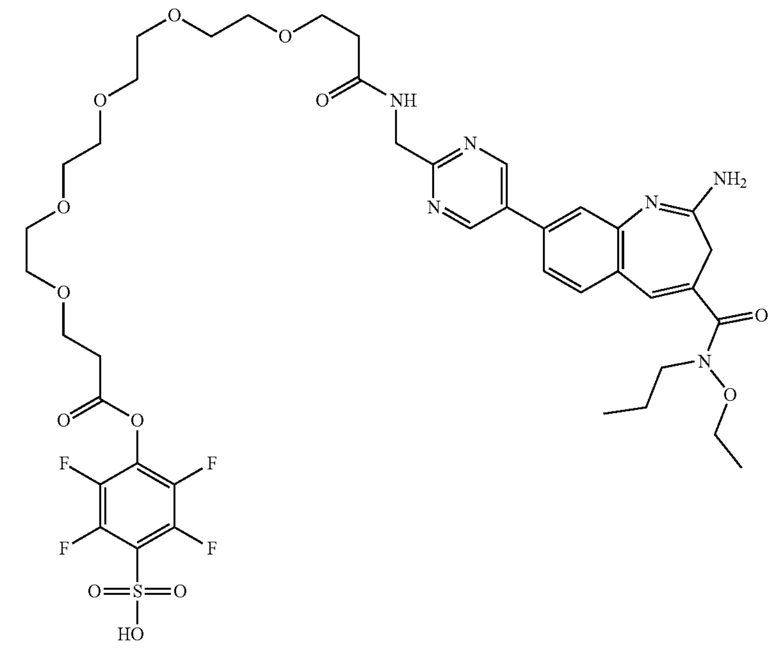 [SMILES: CCCN(OCC)C(=O)C1=Cc2ccc(-c3cnc(CNC(=O)CCOCCOCCOCCOCCOCCC(=O)Oc4c(F)c(F)c(S(=O)(=O)O)c(F)c4F)nc3)cc2N=C(N)C1] | 942.9 |
| HxBzL-74 | 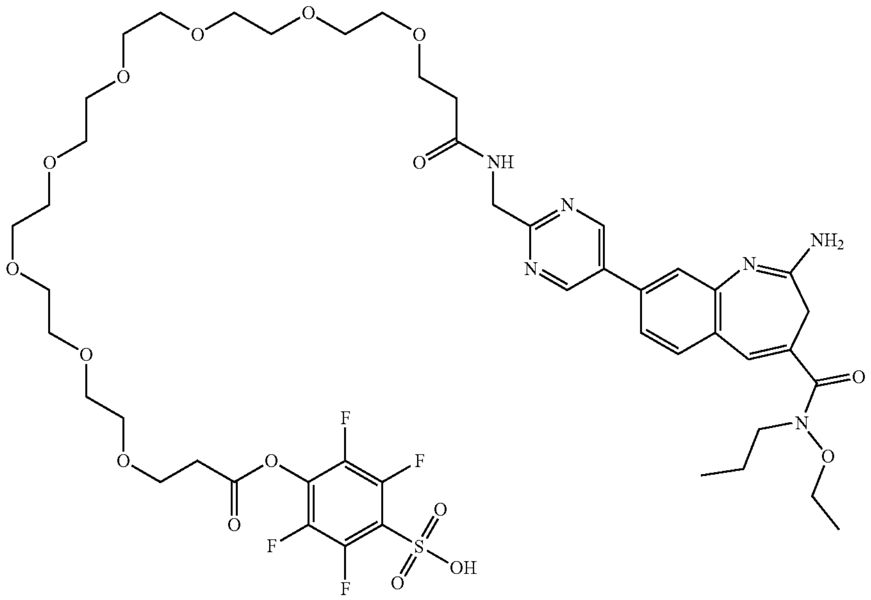 [SMILES: CCCN(OCC)C(=O)C1=Cc2ccc(-c3cnc(CNC(=O)CCOCCOCCOCCOCCOCCOCCOCCOCCC(=O)Oc4c(F)c(F)c(S(=O)(=O)O)c(F)c4F)nc3)cc2N=C(N)C1] | 1075.1 |

TABLE 2b-continued
| 8-Het-2-aminobenzazepine-linker intermediate, Formula II compounds (HxBzL) | | |
|---|---|---|
| HxBzL No. | Structure | MW |
| HxBzL-75 | 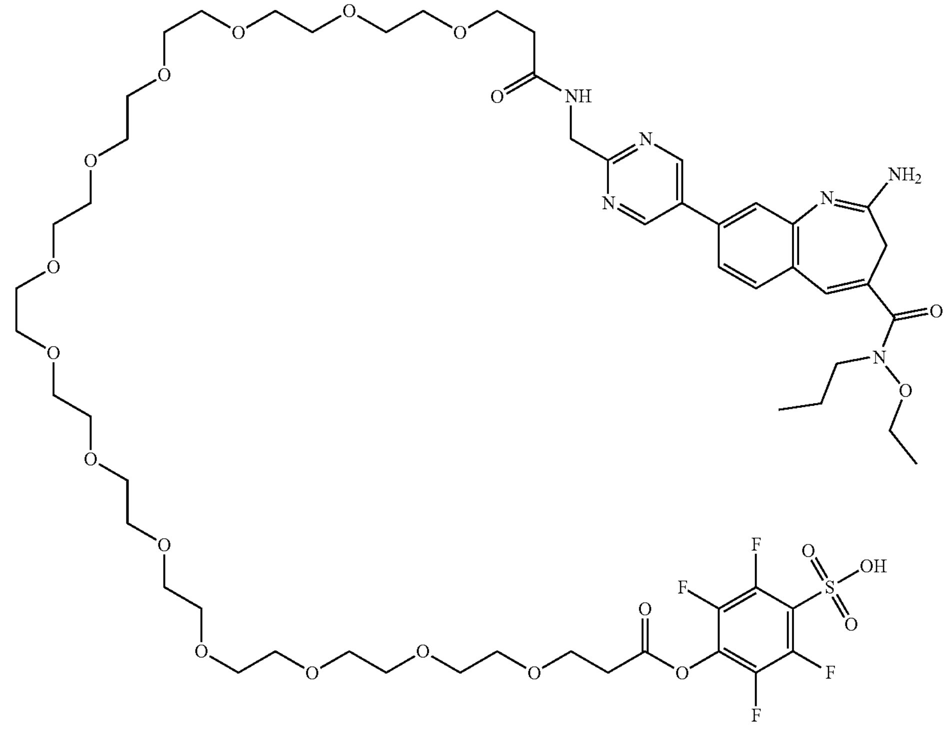 [SMILES: CCCN(OCC)C(=O)C1=Cc2ccc(-c3cnc(CNC(=O)CCOCCOCCOCCOCCOCCOCCOCCOCCOCCOCCOCCOCCOCCC(=O)Oc4c(F)c(F)c(S(=O)(=O)O)c(F)c4F)nc3)cc2N=C(N)C1] | 1295.4 |
| HxBzL-76 | 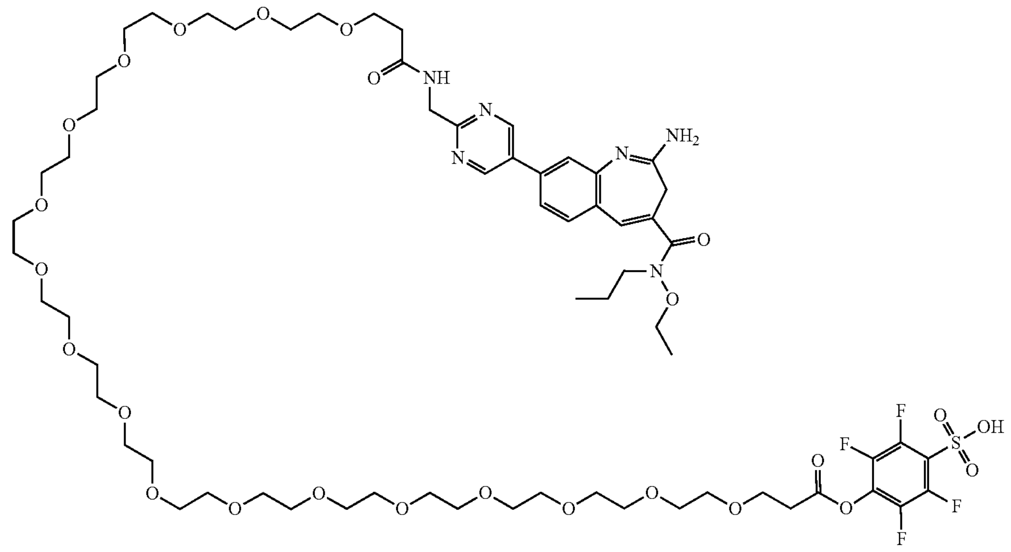 [SMILES: CCCN(OCC)C(=O)C1=Cc2ccc(-c3cnc(CNC(=O)CCOCCOCCOCCOCCOCCOCCOCCOCCOCCOCCOCCOCCOCCOCCOCCOCCOCCC(=O)Oc4c(F)c(F)c(S(=O)(=O)O)c(F)c4F)nc3)cc2N=C(N)C1] | 1471.6 |

TABLE 2b-continued
| 8-Het-2-aminobenzazepine-linker intermediate, Formula II compounds (HxBzL) | | |
|---|---|---|
| HxBzL No. | Structure | MW |
| HxBzL-77 | 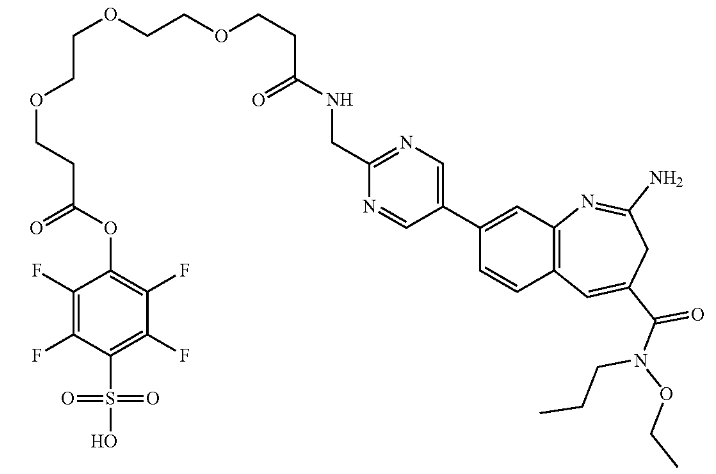 [SMILES: CCCN(OCC)C(=O)C1=Cc2ccc(-c3cnc(CNC(=O)CCOCCOCCOCCC(=O)Oc4c(F)c(F)c(S(=O)(=O)O)c(F)c4F)nc3)cc2N=C(N)C1] | 854.8 |
| HxBzL-78 | 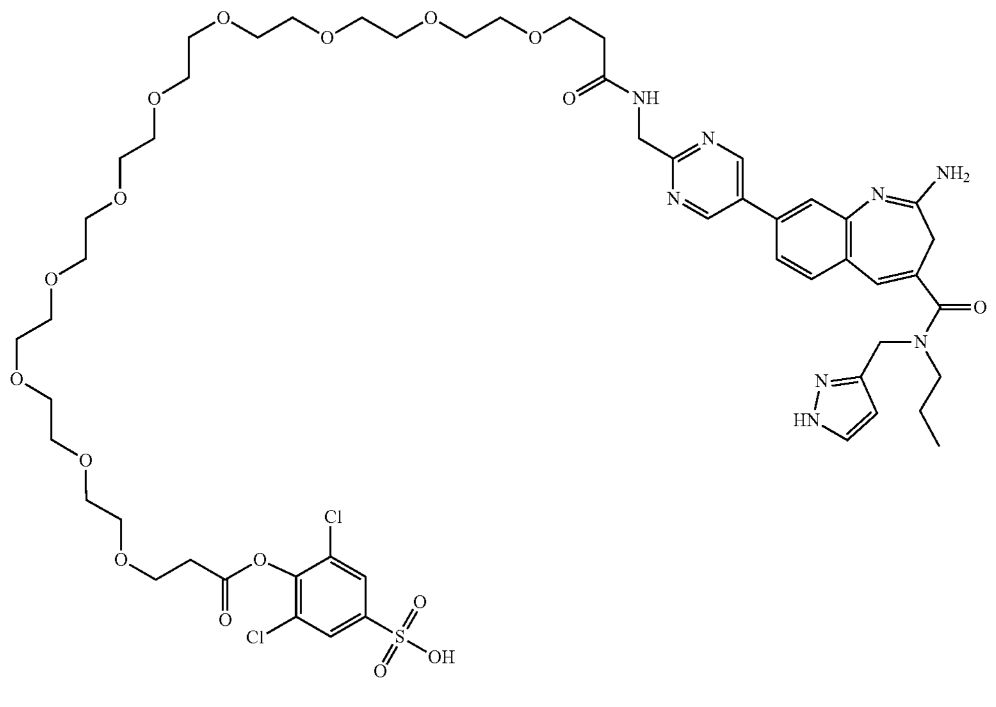 | 1196.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-79 | 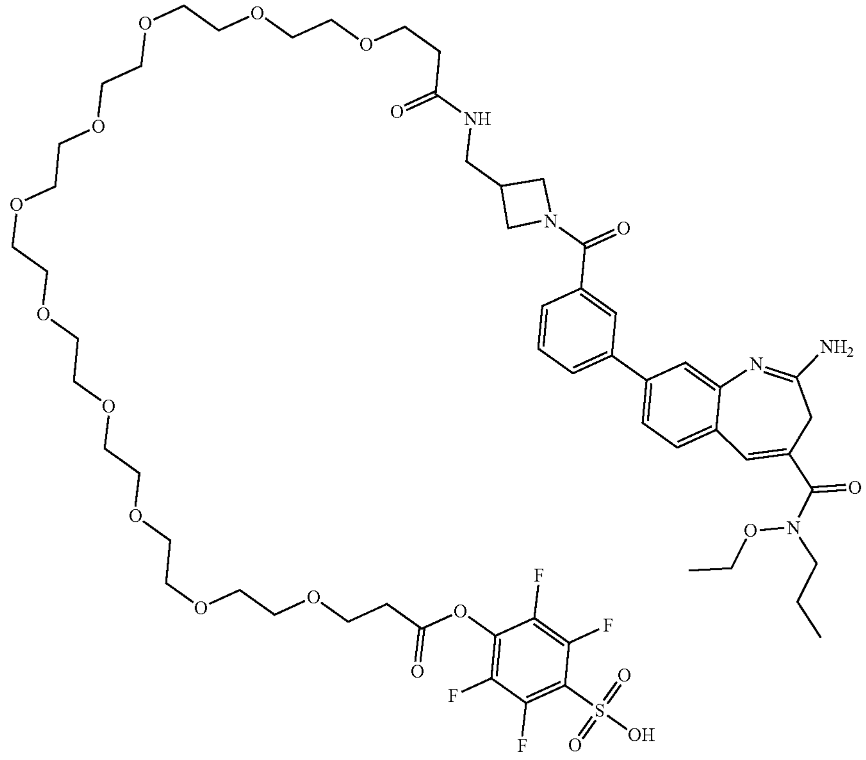 [SMILES: CCCN(OCC)C(=O)C1=Cc2ccc(-c3cccc(C(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1244.3 |
| HxBzL-80 | 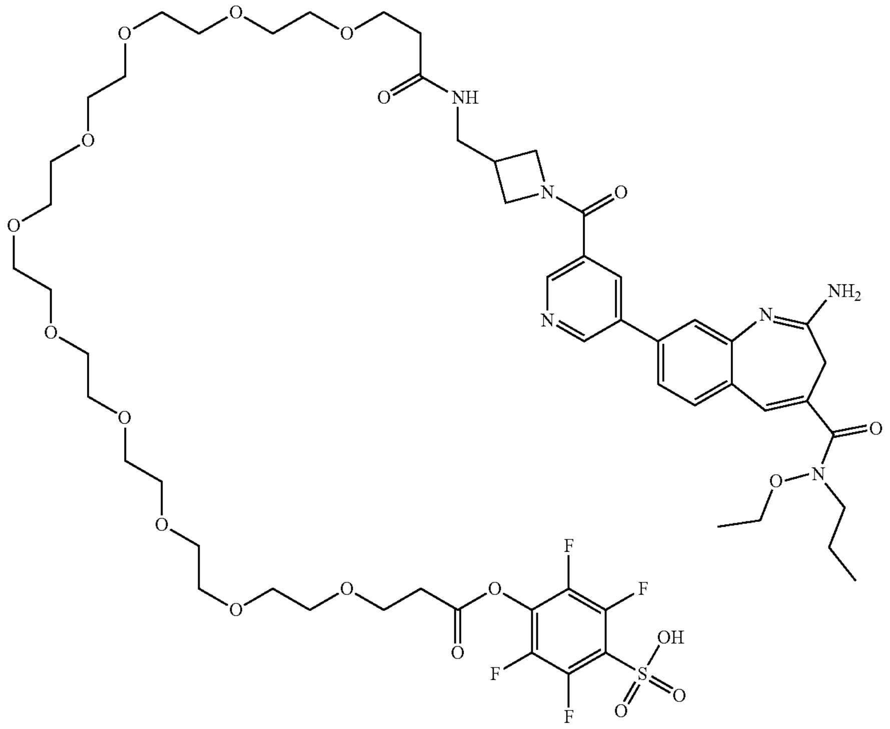 [SMILES: CCCN(OCC)C(=O)C1=Cc2ccc(-c3cncc(C(=O)N4CC(CNC(=O)CCOCCOCCOCCOCCOCCOCCOCCOCCOCCOCCC(=O)Oc5c(F)c(F)c(S(=O)(=O)O)c(F)c5F)C4)c3)cc2N=C(N)C1] | 1245.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-81 | 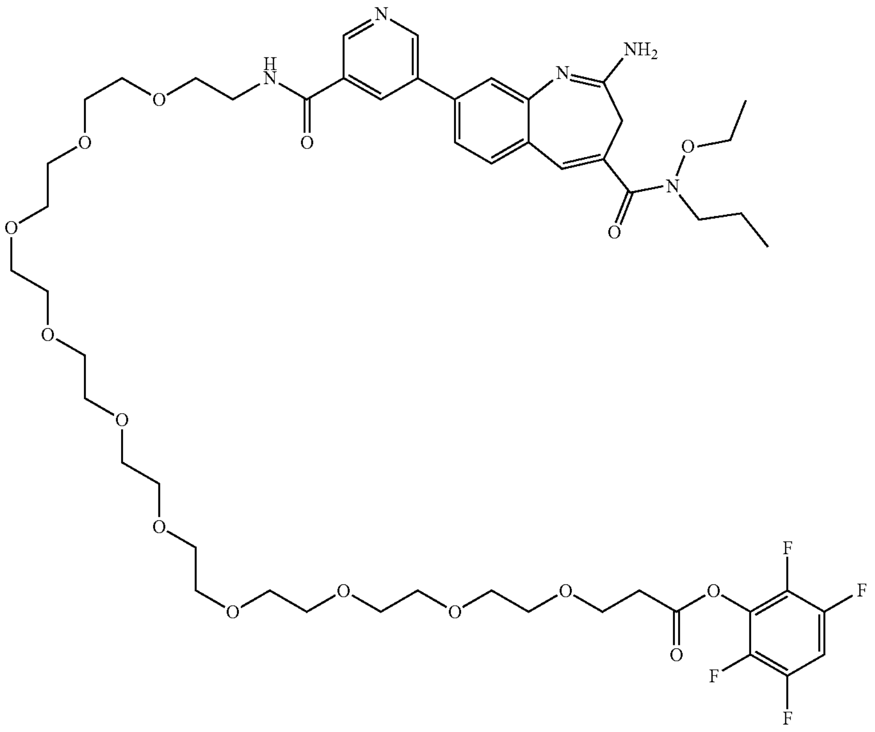 [SMILES: CCCN(OCC)C(=O)C1=Cc2ccc(-c3cncc(C(=O)NCCOCCOCCOCCOCCOCCOCCOCCOCCOCCOCCC(=O)Oc4c(F)c(F)cc(F)c4F)c3)cc2N=C(N)C1] | 1068.1 |
| HxBzL-82 | 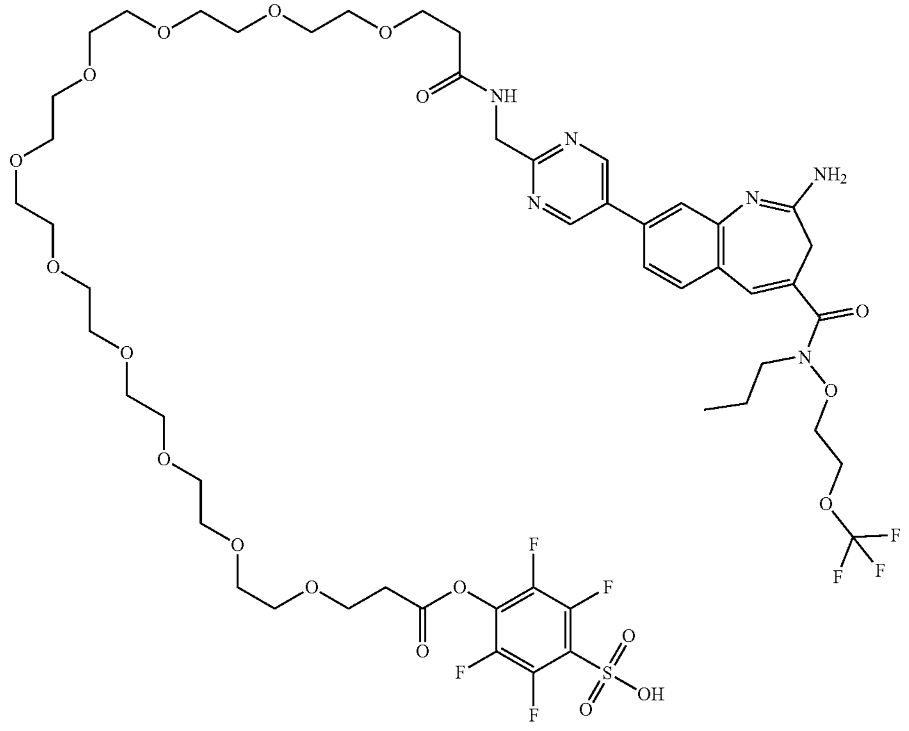 [SMILES: CCCN(OCCOC(F)(F)F)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1247.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-83 | 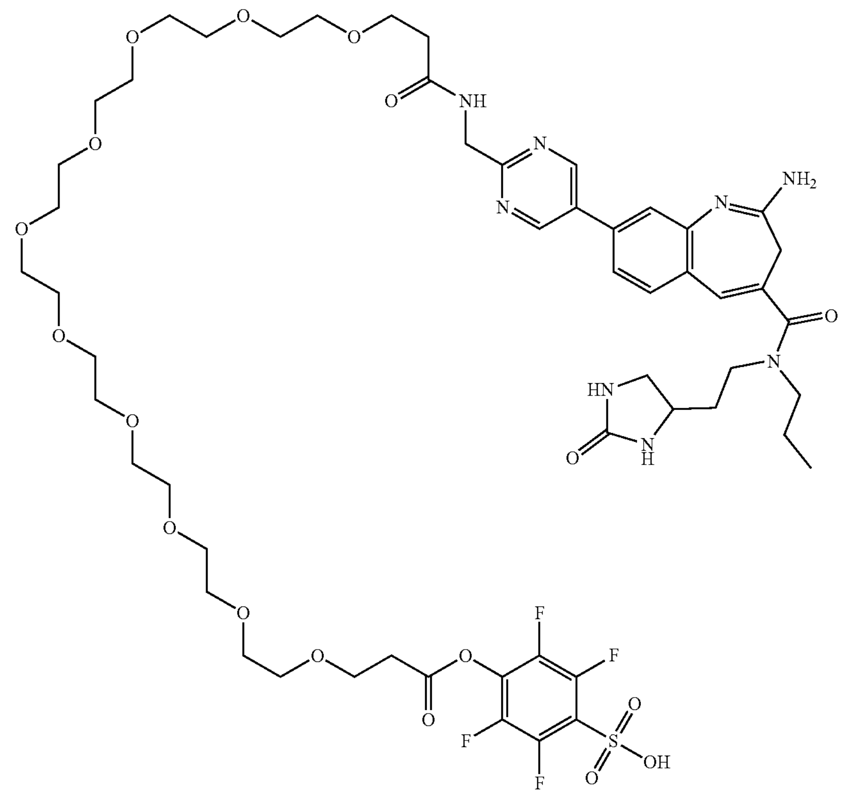 [SMILES: CCCN(CCC1CNC(=O)N1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1231.3 |
| HxBzL-84 | 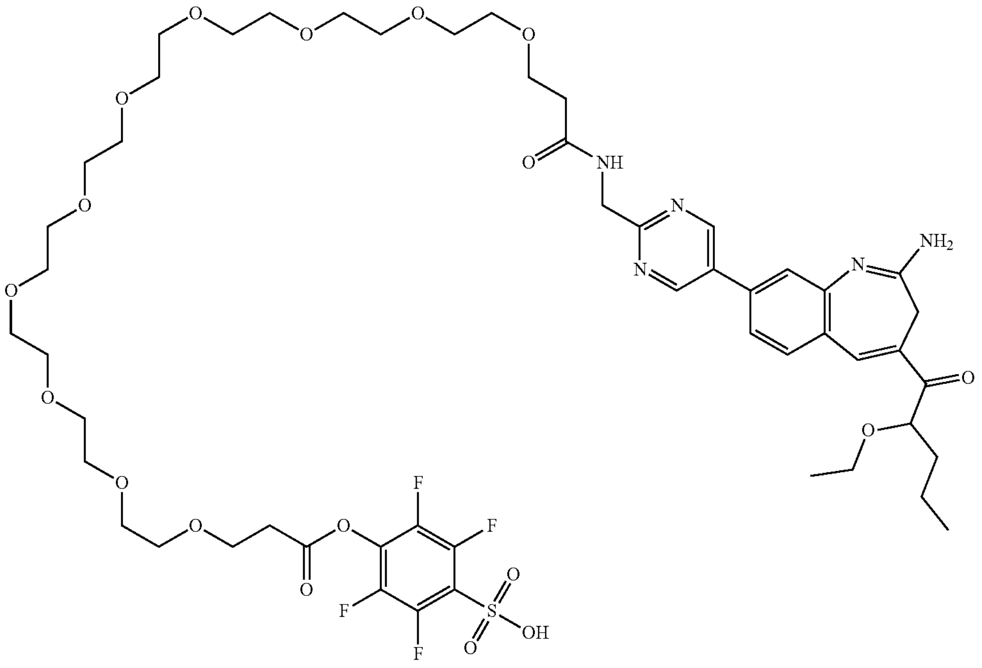 [SMILES: CCCC(OCC)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1162.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-85 | 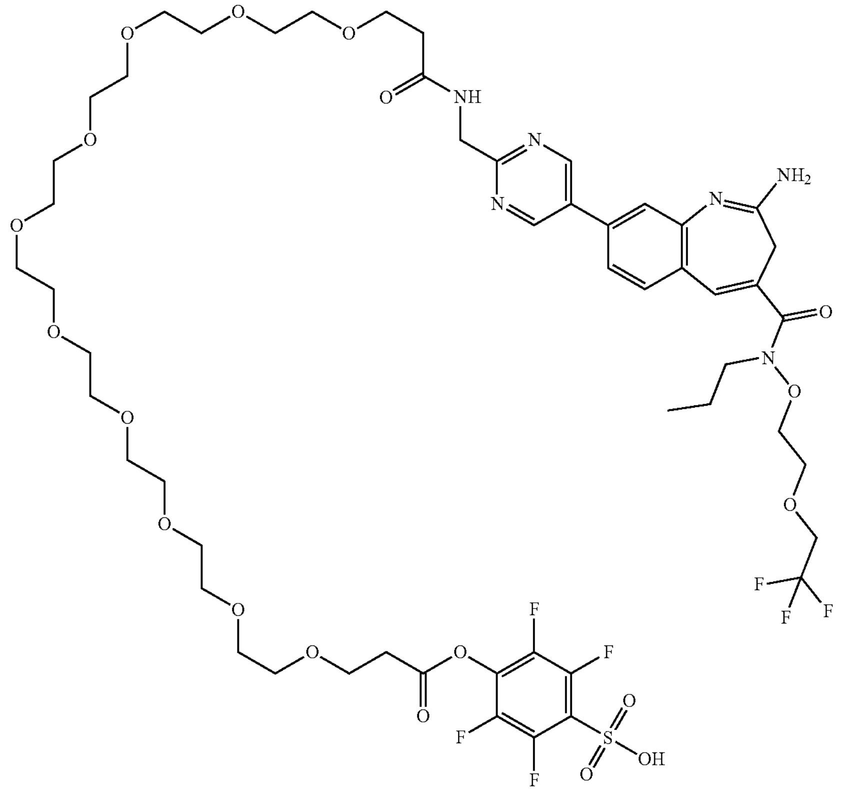 [SMILES: CCCN(OCCOCC(F)(F)F)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1261.2 |
| HxBzL-86 | 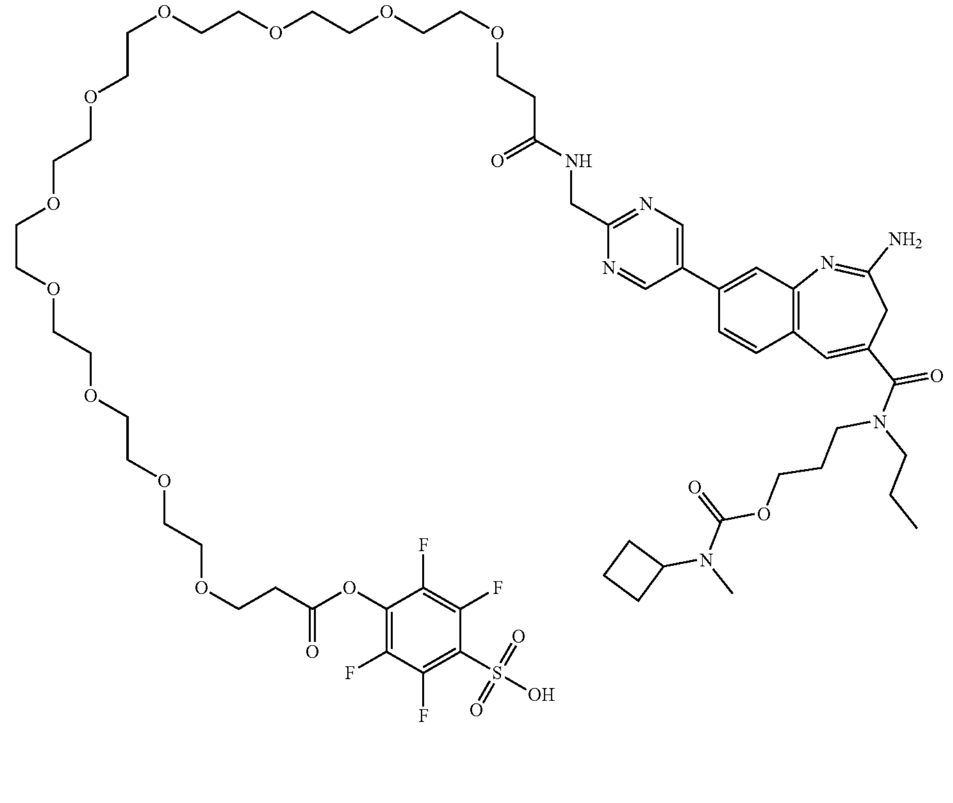 [SMILES: CCCN(CCCOC(=O)N(C)C1CCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1288.4 |

TABLE 2b-continued
| 8-Het-2-aminobenzazepine-linker intermediate, Formula II compounds (HxBzL) | | |
|---|---|---|
| HxBzL No. | Structure | MW |
| HxBzL-87 | 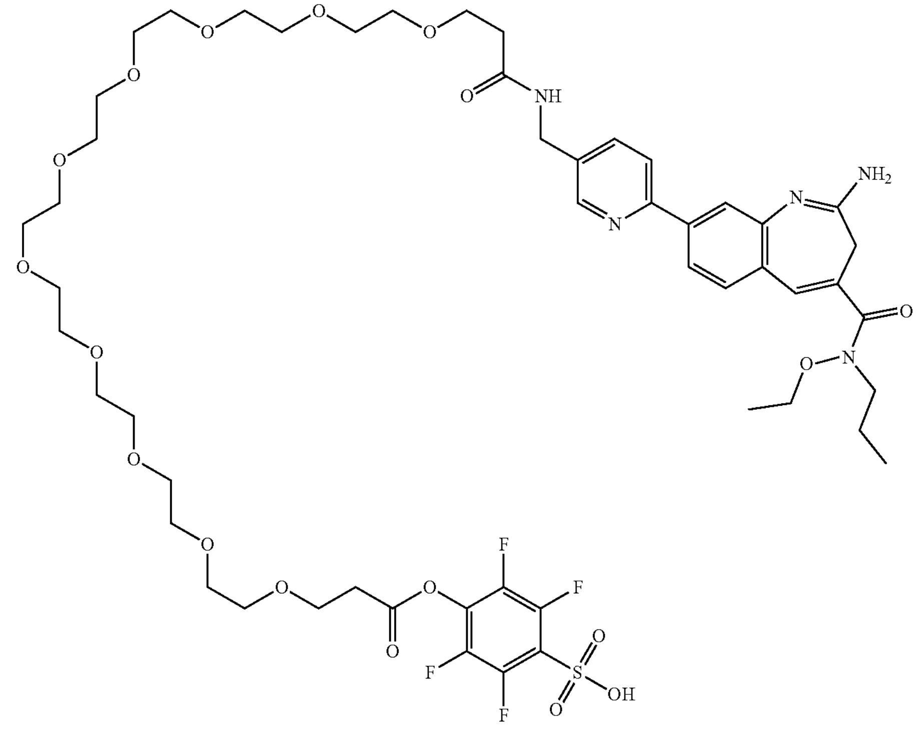 [SMILES: CCCN(OCC)C(=O)C1=Cc2ccc(-c3ccc(CNC(=O)CCOCCOCCOCCOCCOCCOCCOCCOCCOCCOCCC(=O)Oc4c(F)c(F)c(S(=O)(=O)O)c(F)c4F)cn3)cc2N=C(N)C1] | 1162.2 |
| HxBzL-88 | 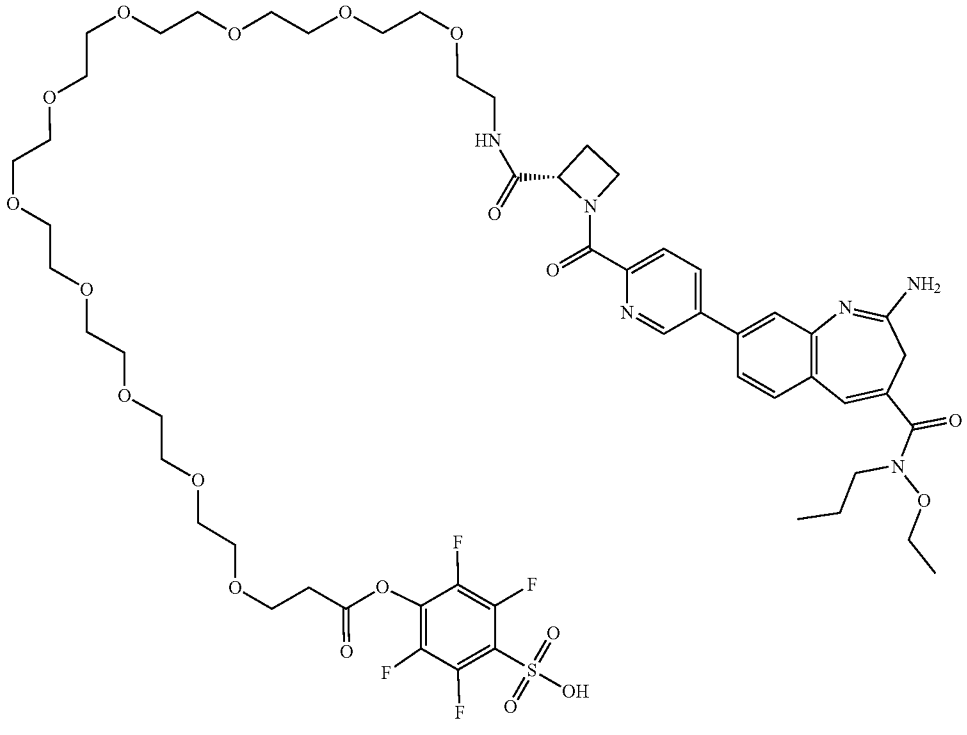 [SMILES: CCCN(OCC)C(=O)C1=Cc2ccc(-c3ccc(C(=O)N4CC[C@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1231.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-89 | 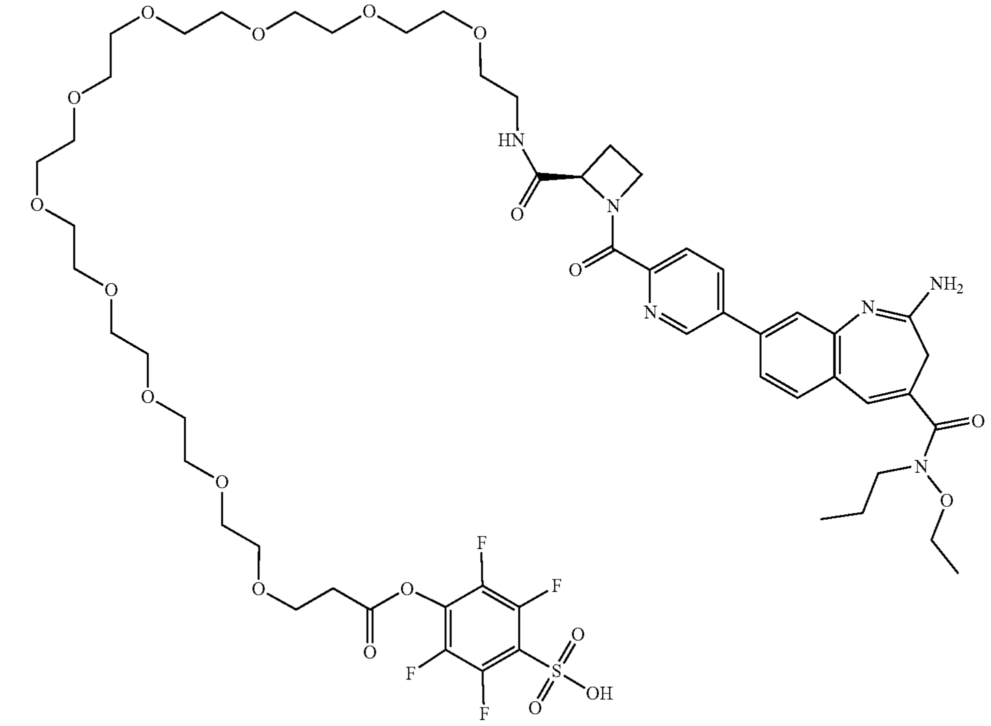 [SMILES: CCCN(OCC)C(=O)C1=Cc2ccc(-c3ccc(C(=O)N4CC[C@@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1231.3 |
| HxBzL-90 | 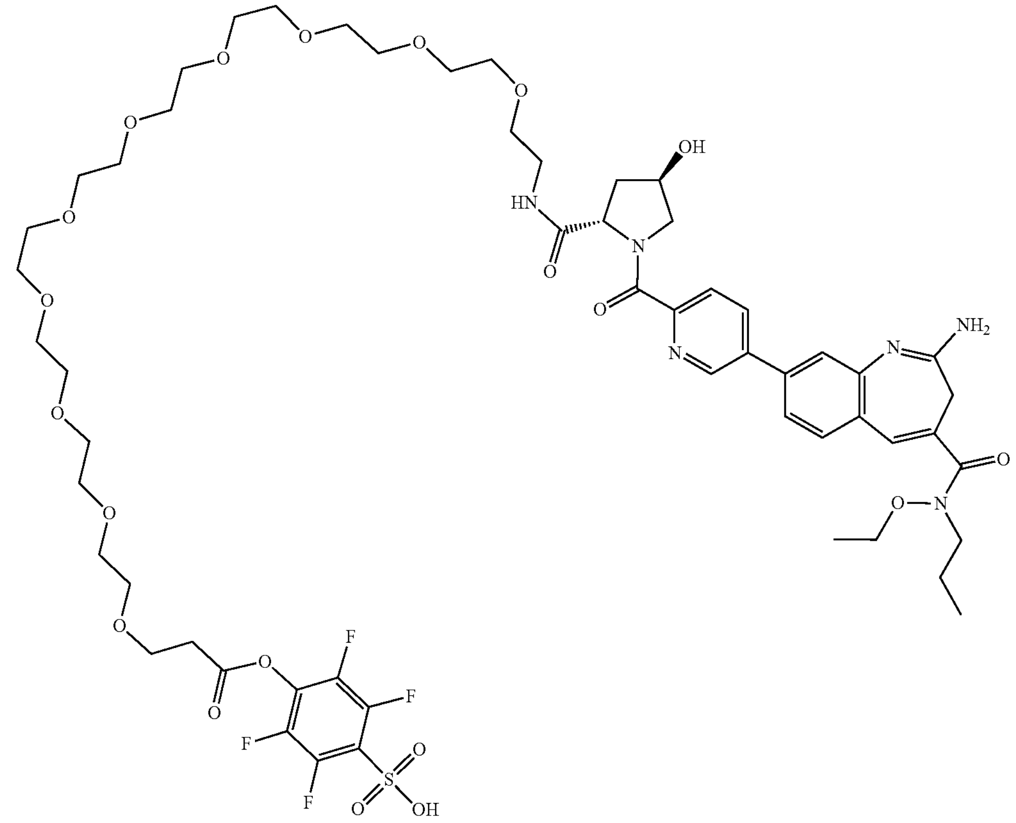 [SMILES: CCCN(OCC)C(=O)C1=Cc2ccc(-c3ccc(C(=O)N4C[C@H](O)C[C@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1261.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-91 | 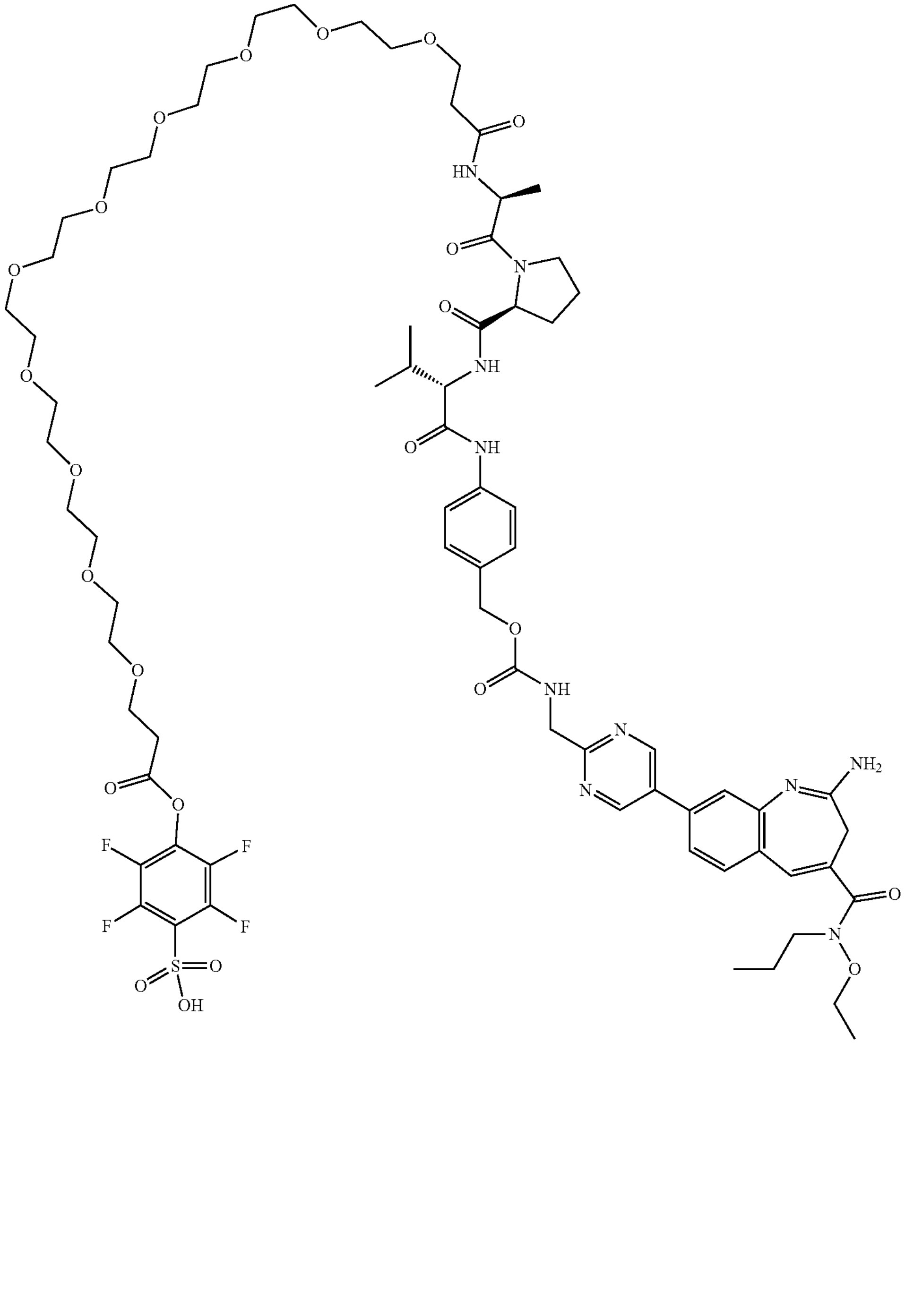 | 1579.7 |

TABLE 2b-continued
| 8-Het-2-aminobenzazepine-linker intermediate, Formula II compounds (HxBzL) | | |
|---|---|---|
| HxBzL No. | Structure | MW |
| HxBzL-92 | 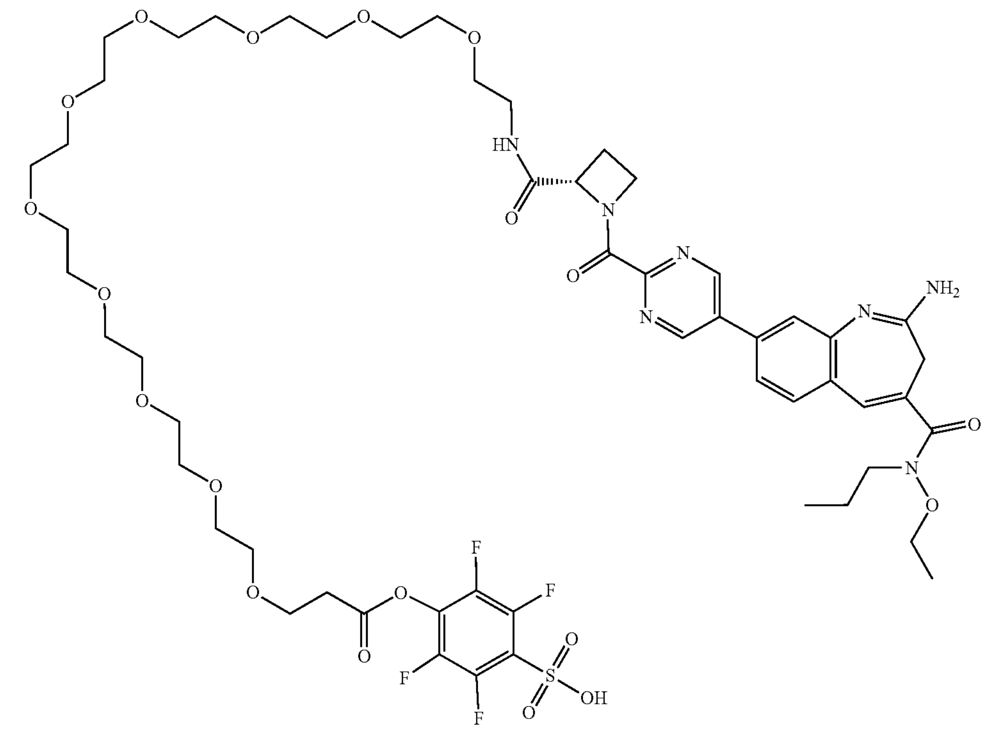 [SMILES: CCCN(OCC)C(=O)C1=Cc2ccc(-c3cnc(C(=O)N4CC[C@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1232.3 |
| HxBzL-93 | 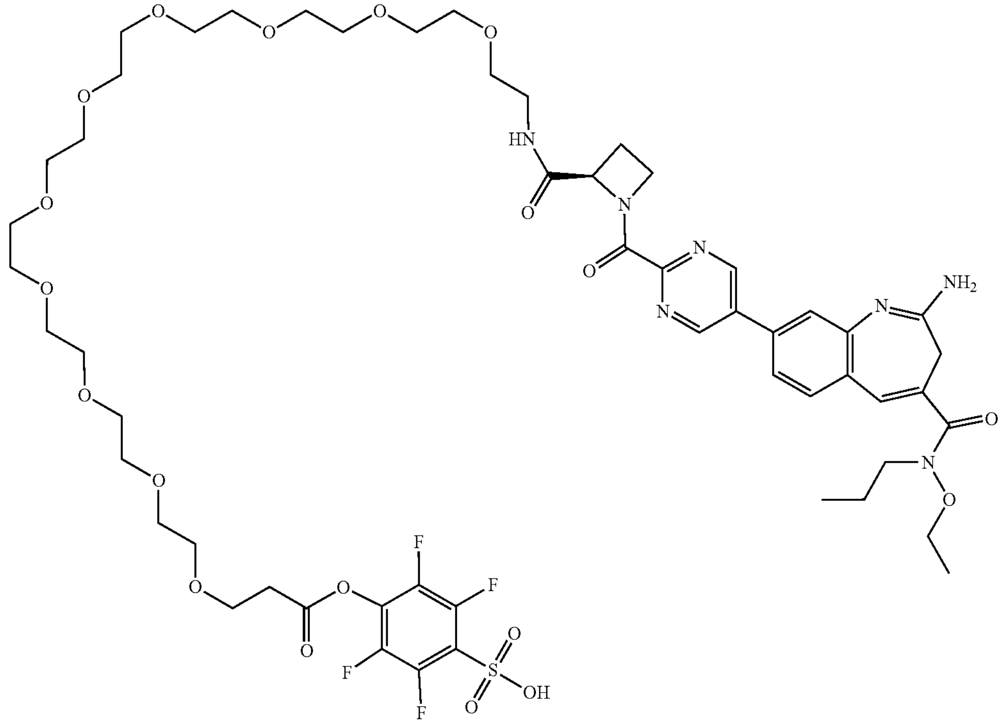 [SMILES: CCCN(OCC)C(=O)C1=Cc2ccc(-c3cnc(C(=O)N4CC[C@@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1232.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-94 | 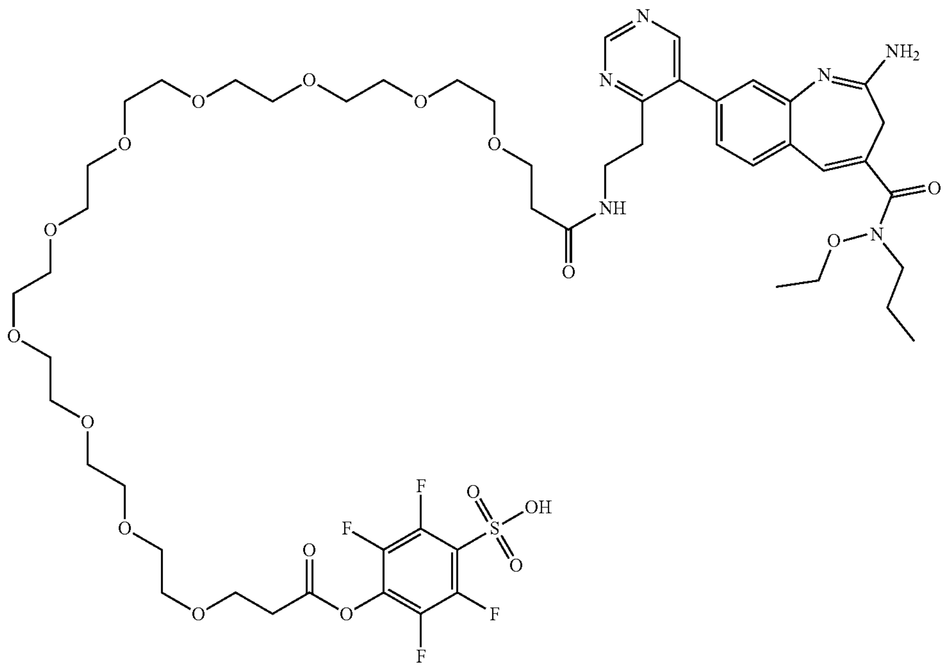 [SMILES: CCCN(OCC)C(=O)C1=Cc2ccc(-c3cncnc3CCNC(=O)CCOCCOCCOCCOCCOCCOCCOCCOCCOCCOCCC(=O)Oc3c(F)c(F)c(S(=O)(=O)O)c(F)c3F)cc2N=C(N)C1] | 1177.2 |
| HxBzL-95 | 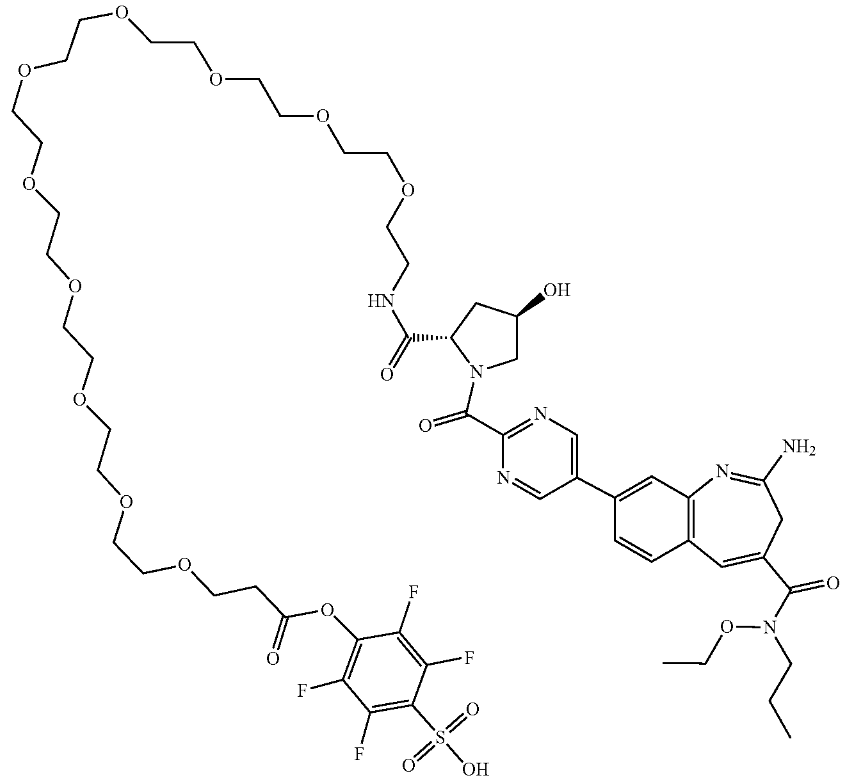 [SMILES: CCCN(OCC)C(=O)C1=Cc2ccc(-c3cnc(C(=O)N4C[C@H](O)C[C@H]4C(=O)NCCOCCOCCOCCOCCOCCOCCOCCOCCOCCOCCC(=O)Oc4c(F)c(F)c(S(=O)(=O)O)c(F)c4F)nc3)cc2N=C(N)C1] | 1262.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-96 | 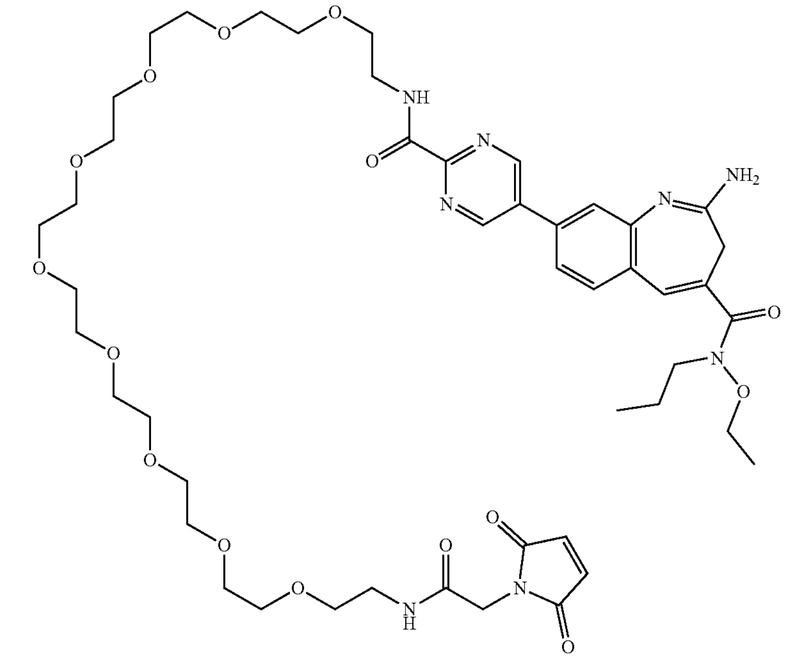 [SMILES: CCCN(OCC)C(=O)C1=Cc2ccc(-c3cnc(C(=O)NCCOCCOCCOCCOCCOCCOCCOCCOCCOCCNC(=O)CN4C(=O)C=CC4=O)nc3)cc2N=C(N)C1] | 985.1 |
| HxBzL-97 | 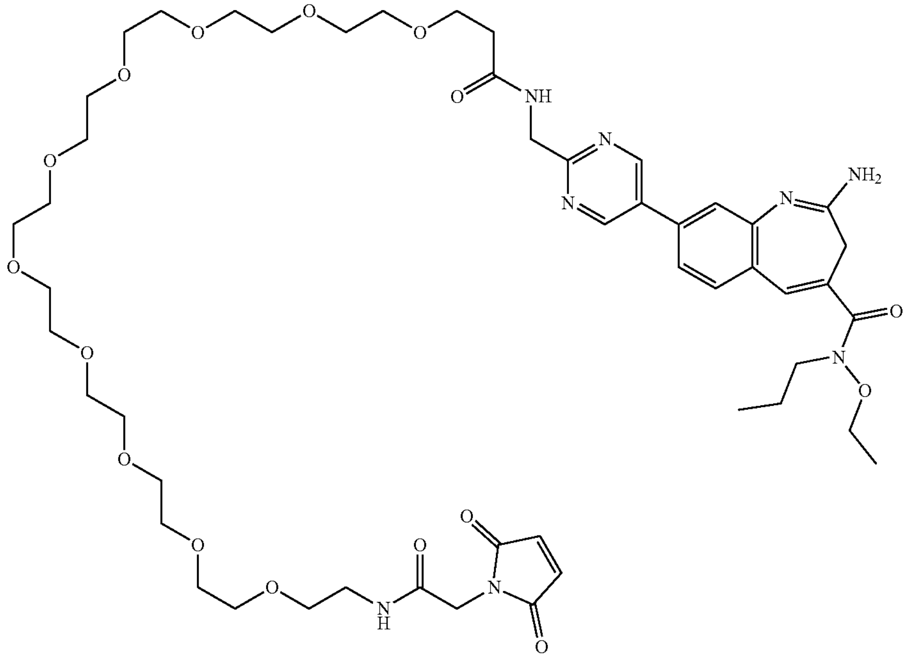 [SMILES: CCCN(OCC)C(=O)C1=Cc2ccc(-c3cnc(CNC(=O)CCOCCOCCOCCOCCOCCOCCOCCOCCOCCOCCNC(=O)CN4C(=O)C=CC4=O)nc3)cc2N=C(N)C1] | 1041.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-98 | 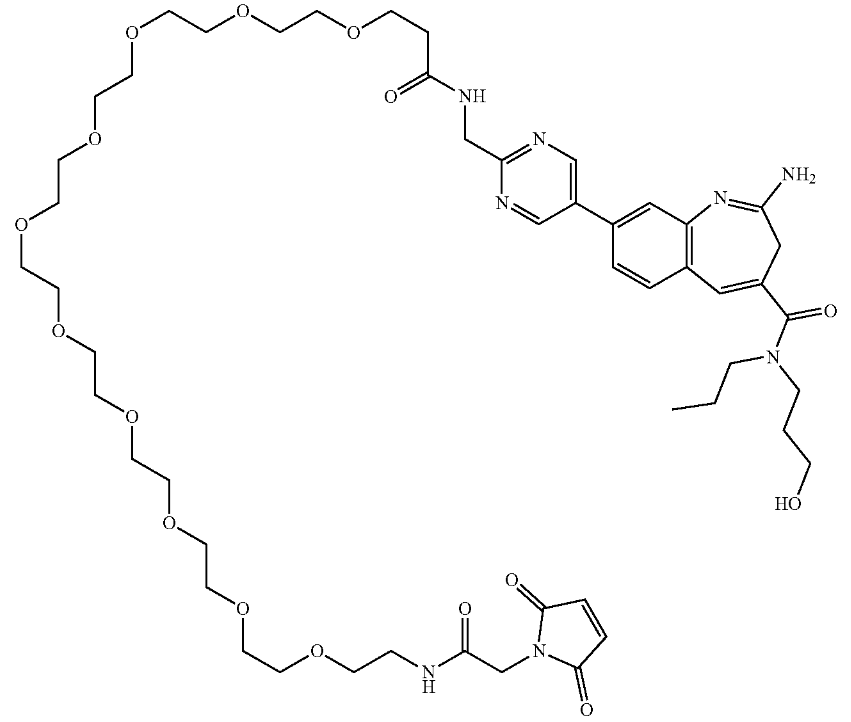 [SMILES: CCCN(CCCO)C(=O)C1=Cc2ccc(-c3cnc(CNC(=O)CCOCCOCCOCCOCCOCCOCCOCCOCCOCCOCCNC(=O)CN4C(=O)C=CC4=O)nc3)cc2N=C(N)C1] | 1057.2 |
| HxBzL-99 | 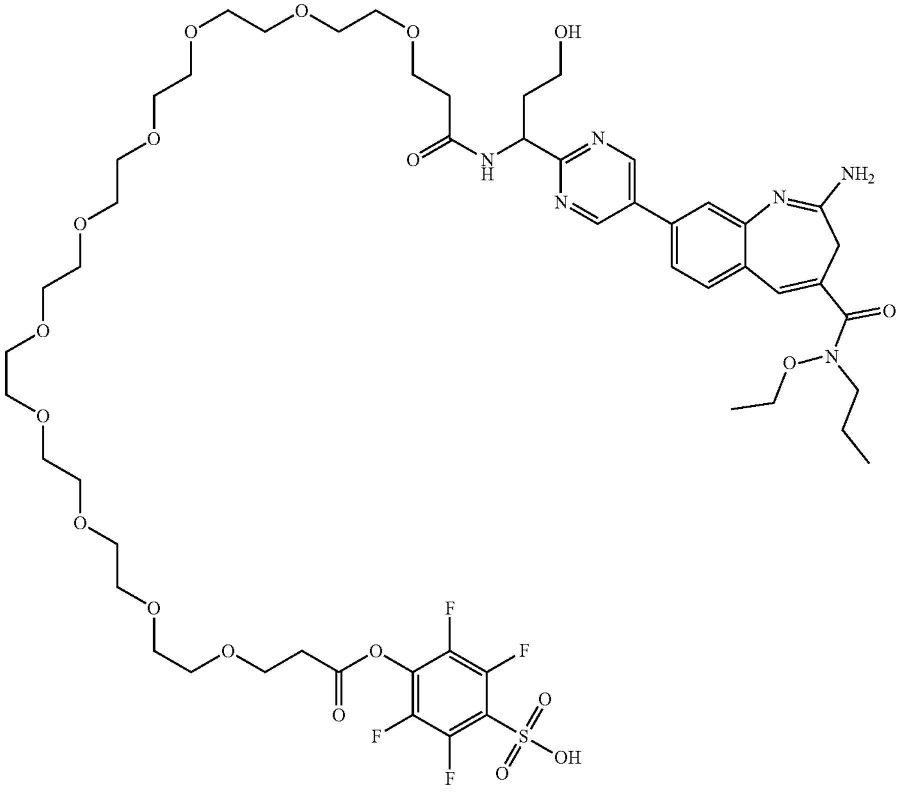 [SMILES: CCCN(OCC)C(=O)C1=Cc2ccc(-c3cnc(C(CCO)NC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1207.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-100 | 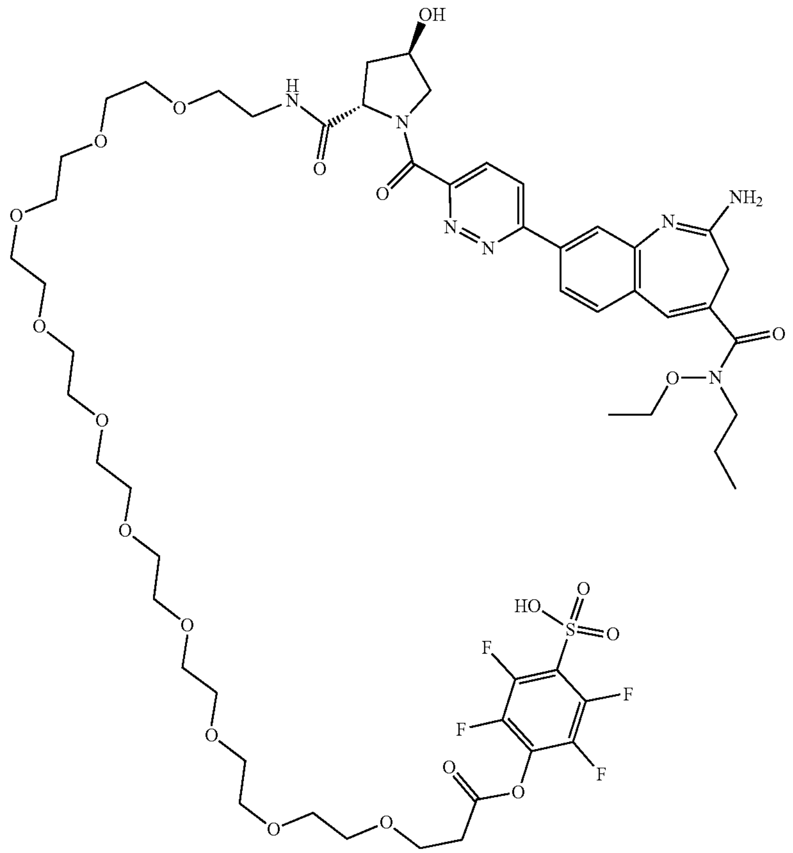 | 1262.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-101 | 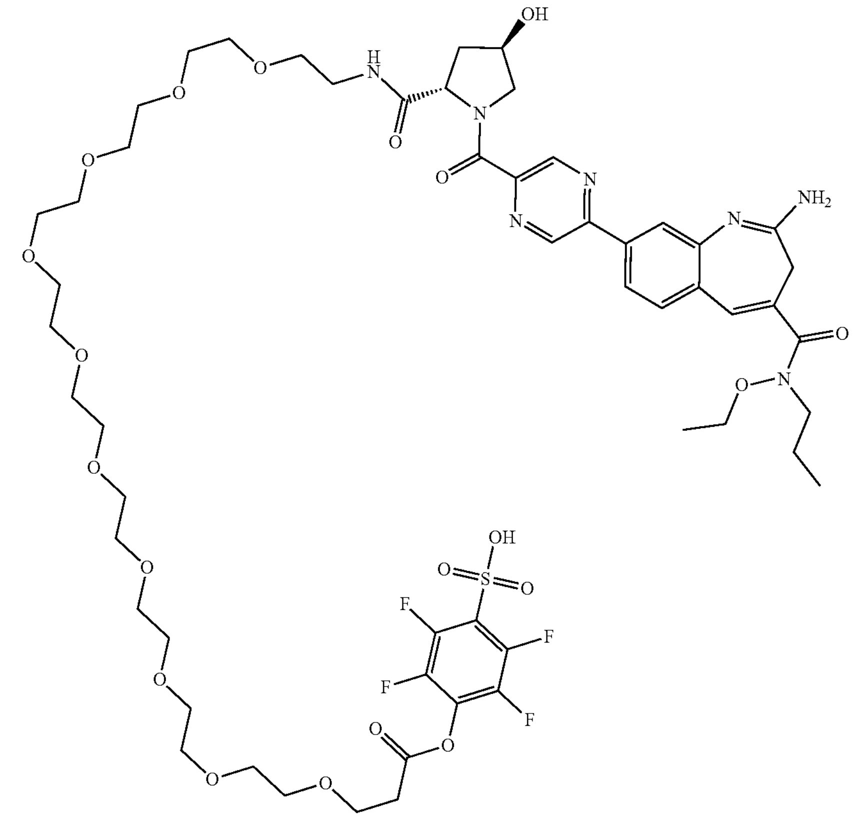 [SMILES: CCCN(OCC)C(=O)C1=Cc2ccc(-c3cnc(C(=O)N4C[C@H](O)C[C@H]4C(=O)NCCOCCOCCOCCOCCOCCOCCOCCOCCOCCOCCC(=O)Oc4c(F)c(F)c(S(=O)(=O)O)c(F)c4F)cn3)cc2N=C(N)C1] | 1262.3 |
| HxBzL-102 | 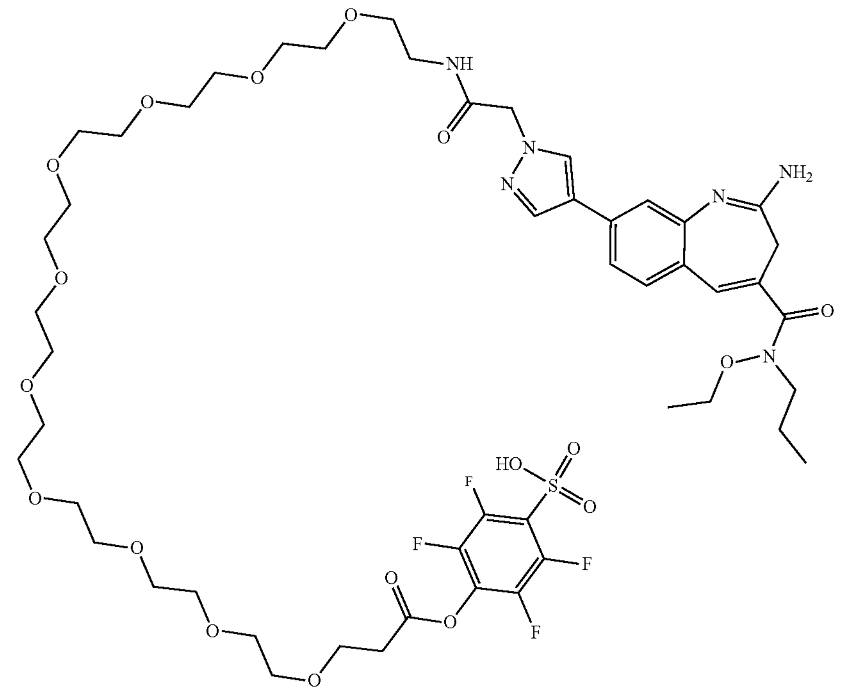 [SMILES: CCCN(OCC)C(=O)C1=Cc2ccc(-c3cnn(CC(=O)NCCOCCOCCOCCOCCOCCOCCOCCOCCOCCOCCC(=O)Oc4c(F)c(F)c(S(=O)(=O)O)c(F)c4F)c3)cc2N=C(N)C1] | 1151.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-103 | 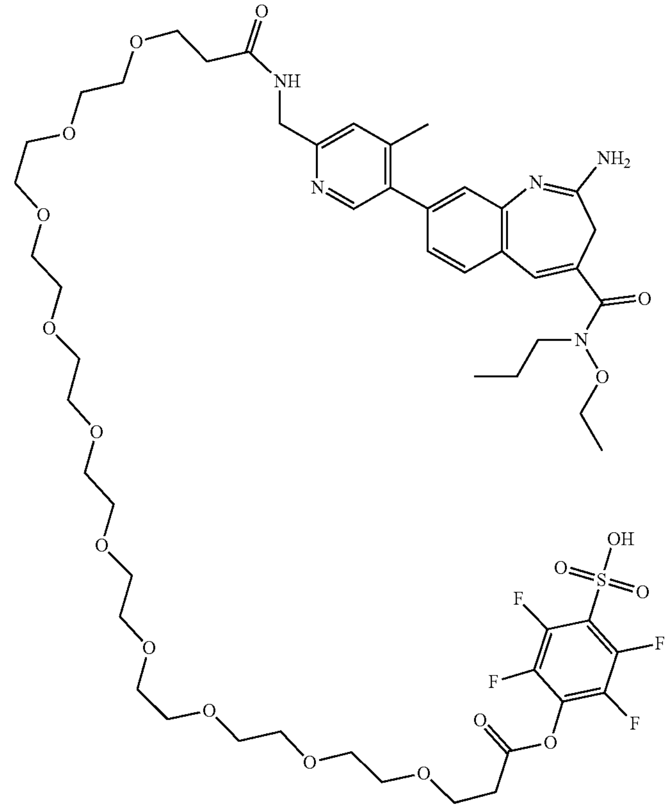 [SMILES: CCCN(OCC)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)cc3C)cc2N=C(N)C1] | 1176.2 |
| HxBzL-104 | 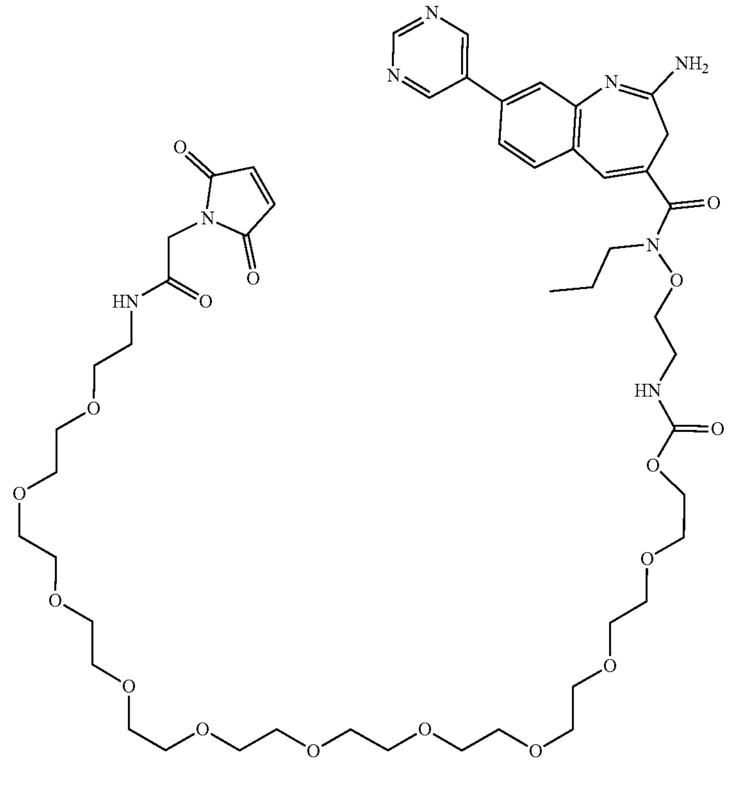 [SMILES: CCCN(OCCNC(=O)OCCOCCOCCOCCOCCOCCOCCOCCOCCOCCOCCNC(=O)CN1C(=O)C=CC1=O)C(=O)C1=Cc2ccc(-c3cncnc3)cc2N=C(N)C1] | 1045.2 |

TABLE 2b-continued
8-Het-2-aminobenzazepine-linker intermediate, Formula II compounds (HxBzL)
| HxBzL No. | Structure | MW |
| --- | --- | --- |
| HxBzL-105 | 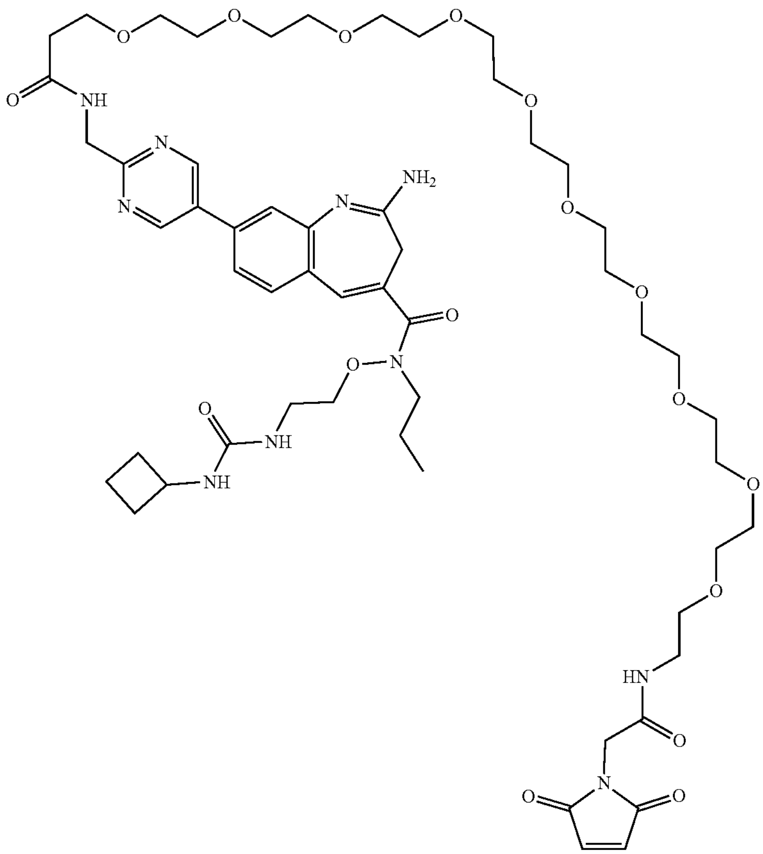 [SMILES: CCCN(OCCNC(=O)NC1CCC1)C(=O)C1=Cc2ccc(-c3cnc(CNC(=O)CCOCCOCCOCCOCCOCCOCCOCCOCCOCCOCCNC(=O)CN4C(=O)C=CC4=O)nc3)cc2N=C(N)C1] | 1155.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-106 | 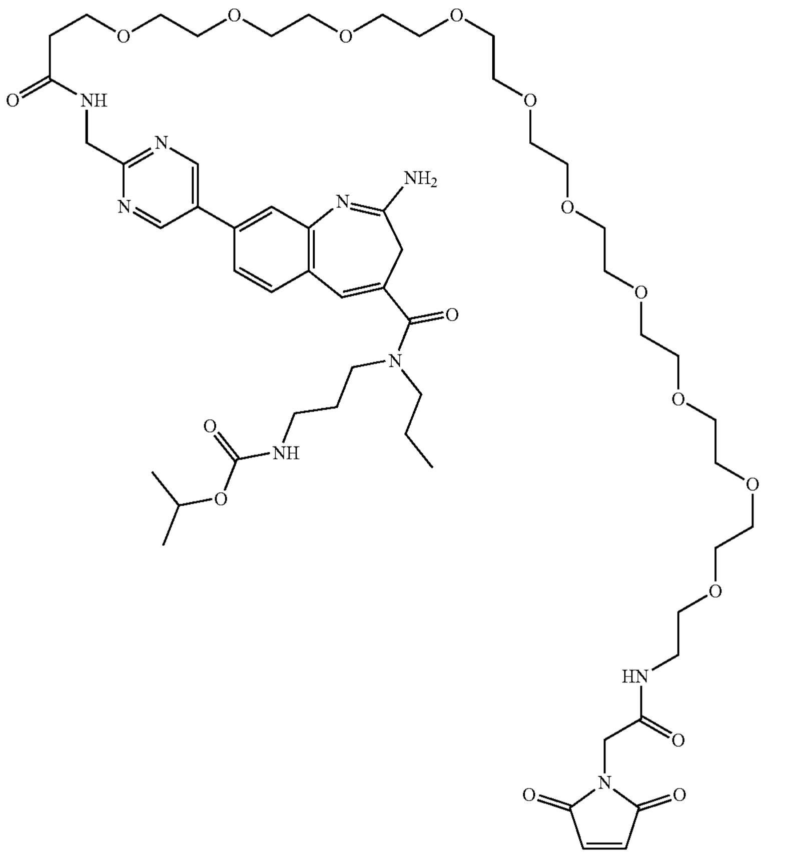 [SMILES: CCCN(CCCNC(=O)OC(C)C)C(=O)C1=Cc2ccc(-c3cnc(CNC(=O)CCOCCOCCOCCOCCOCCOCCOCCOCCOCCOCCNC(=O)CN4C(=O)C=CC4=O)nc3)cc2N=C(N)C1] | 1142.3 |
| HxBzL-107 | 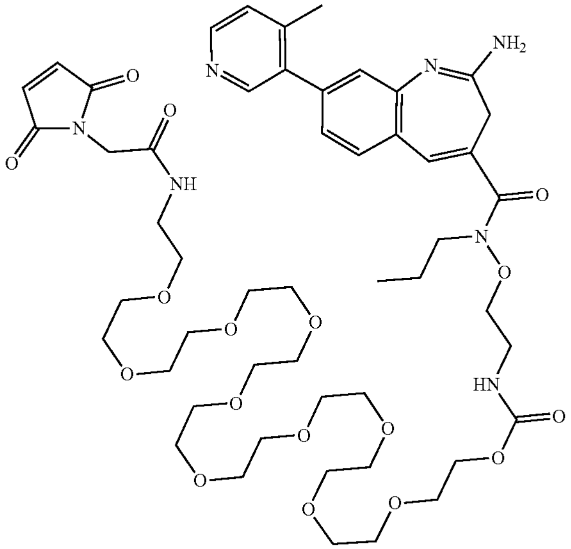 [SMILES: CCCN(OCCNC(=O)OCCOCCOCCOCCOCCOCCOCCOCCOCCOCCOCCNC(=O)CN1C(=O)C=CC1=O)C(=O)C1=Cc2ccc(-c3cnccc3C)cc2N=C(N)C1] | 1058.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-108 | 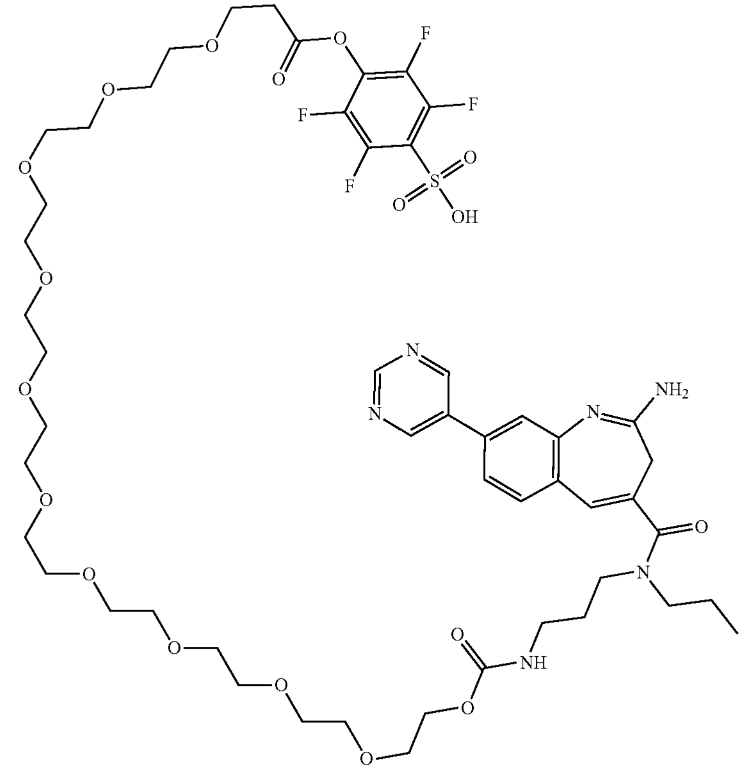 [SMILES: CCCN(CCCNC(=O)OCCOCCOCCOCCOCCOCCOCCOCCOCCOCCOCCC(=O)Oc1c(F)c(F)c(S(=O)(=O)O)c(F)c1F)C(=O)C1=Cc2ccc(-c3cncnc3)cc2N=C(N)C1] | 1163.2 |
| HxBzL-109 | 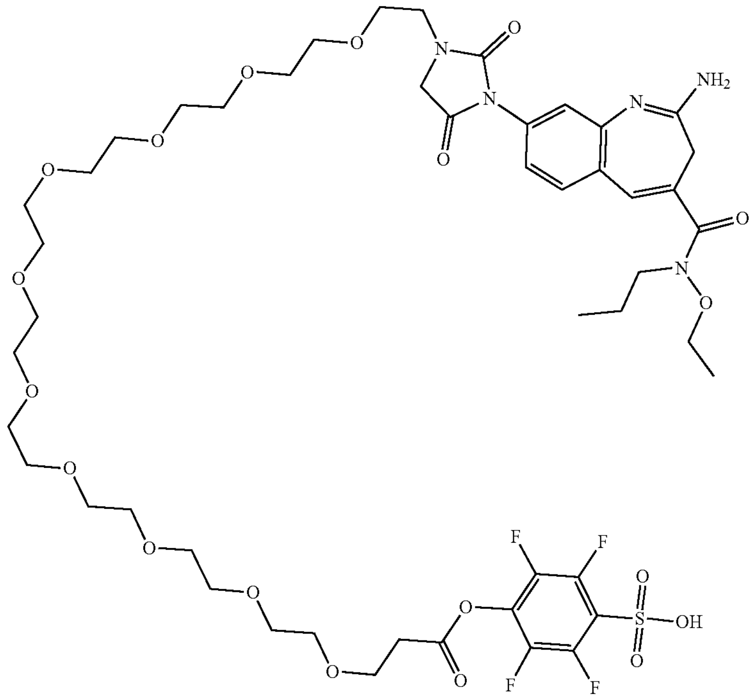 [SMILES: CCCN(OCC)C(=O)C1=Cc2ccc(N3C(=O)CN(CCOCCOCCOCCOCCOCCOCCOCCOCCOCCOCCC(=O)Oc4c(F)c(F)c(S(=O)(=O)O)c(F)c4F)C3=O)cc2N=C(N)C1] | 1126.1 |

TABLE 2b-continued
| 8-Het-2-aminobenzazepine-linker intermediate, Formula II compounds (HxBzL) | | |
|---|---|---|
| HxBzL No. | Structure | MW |
| HxBzL-110 | 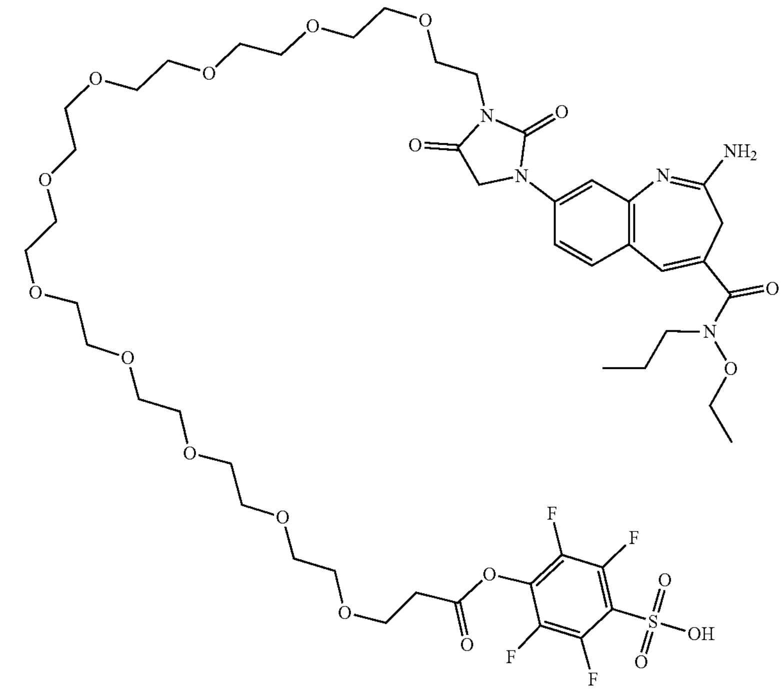 [SMILES: CCCN(OCC)C(=O)C1=Cc2ccc(N3CC(=O)N(CCOCCOCCOCCOCCOCCOCCOCCOCCOCCOCCC(=O)Oc4c(F)c(F)c(S(=O)(=O)O)c(F)c4F)C3=O)cc2N=C(N)C1] | 1126.1 |
| HxBzL-111 | 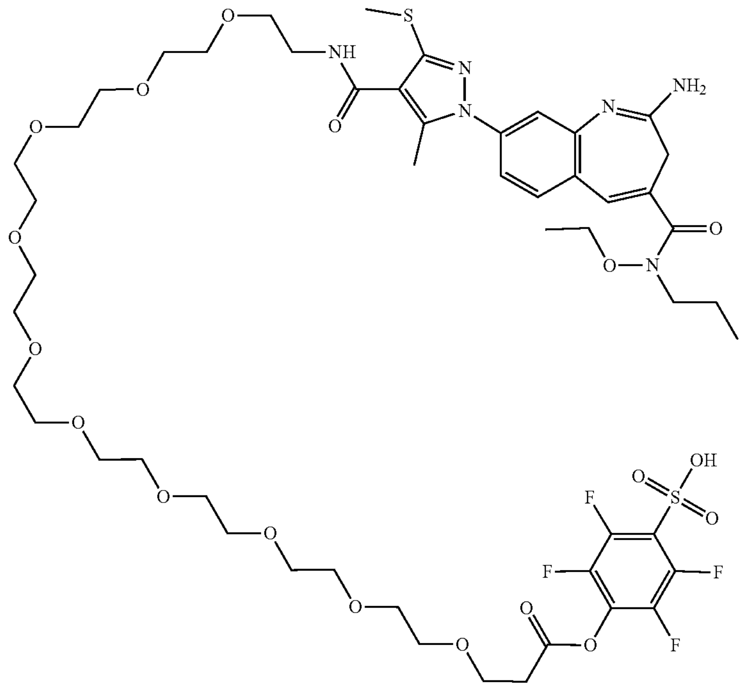 [SMILES: CCCN(OCC)C(=O)C1=Cc2ccc(-n3nc(SC)c(C(=O)NCCOCCOCCOCCOCCOCCOCCOCCOCCOCCOCCC(=O)Oc4c(F)c(F)c(S(=O)(=O)O)c(F)c4F)c3C)cc2N=C(N)C1] | 1197.3 |

TABLE 2b-continued
| 8-Het-2-aminobenzazepine-linker intermediate, Formula II compounds (HxBzL) | | |
|---|---|---|
| HxBzL No. | Structure | MW |
| HxBzL-112 | 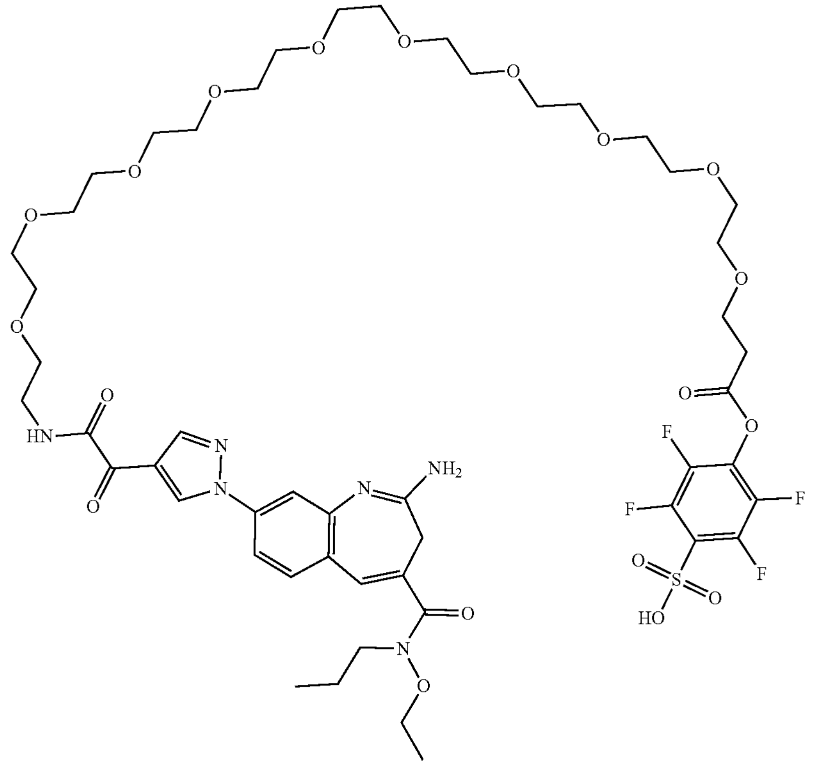 [SMILES: CCCN(OCC)C(=O)C1=Cc2ccc(-n3cc(C(=O)C(=O)NCCOCCOCCOCCOCCOCCOCCOCCOCCOCCOCCC(=O)Oc4c(F)c(F)c(S(=O)(=O)O)c(F)c4F)cn3)cc2N=C(N)C1] | 1165.2 |
| HxBzL-113 | 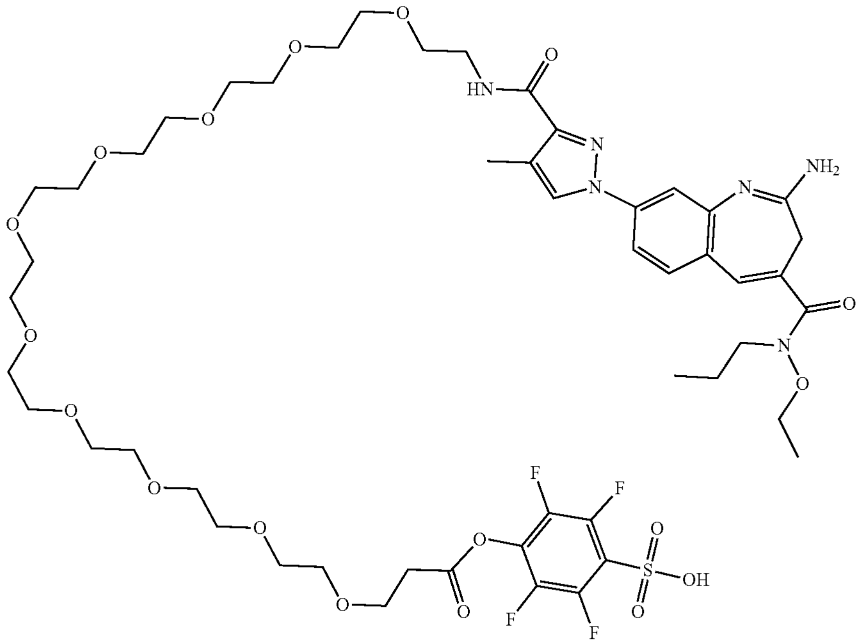 [SMILES: CCCN(OCC)C(=O)C1=Cc2ccc(-n3cc(C)c(C(=O)NCCOCCOCCOCCOCCOCCOCCOCCOCCOCCOCCC(=O)Oc4c(F)c(F)c(S(=O)(=O)O)c(F)c4F)n3)cc2N=C(N)C1] | 1151.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-114 | 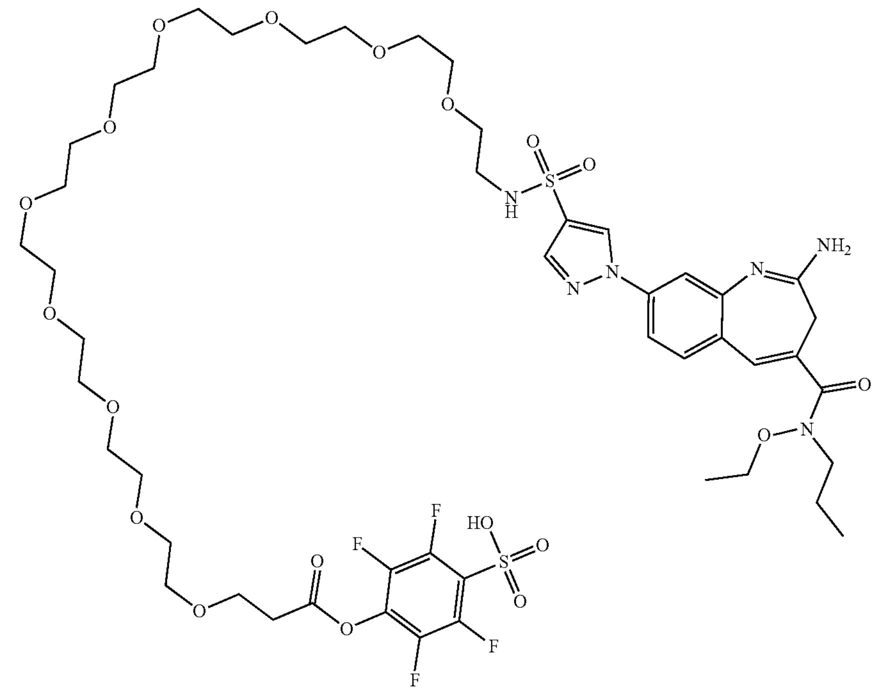 [SMILES: CCCN(OCC)C(=O)C1=Cc2ccc(-n3cc(S(=O)(=O)NCCOCCOCCOCCOCCOCCOCCOCCOCCOCCOCCC(=O)Oc4c(F)c(F)c(S(=O)(=O)O)c(F)c4F)cn3)cc2N=C(N)C1] | 1173.2 |
| HxBzL-115 | 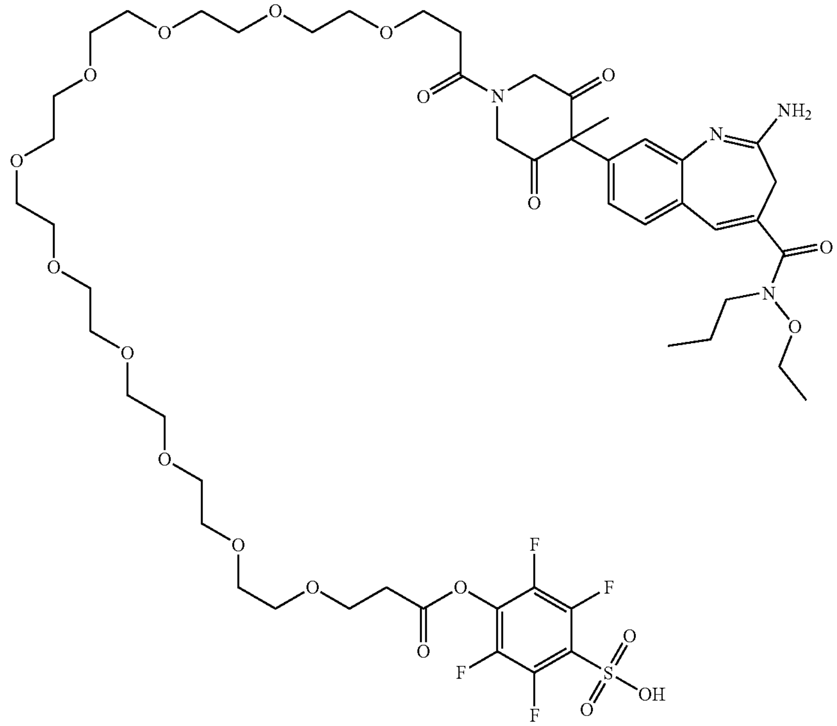 [SMILES: CCCN(OCC)C(=O)C1=Cc2ccc(C3(C)C(=O)CN(C(=O)CCOCCOCCOCCOCCOCCOCCOCCOCCOCCOCCC(=O)Oc4c(F)c(F)c(S(=O)(=O)O)c(F)c4F)CC3=O)cc2N=C(N)C1] | 1181.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-116 | 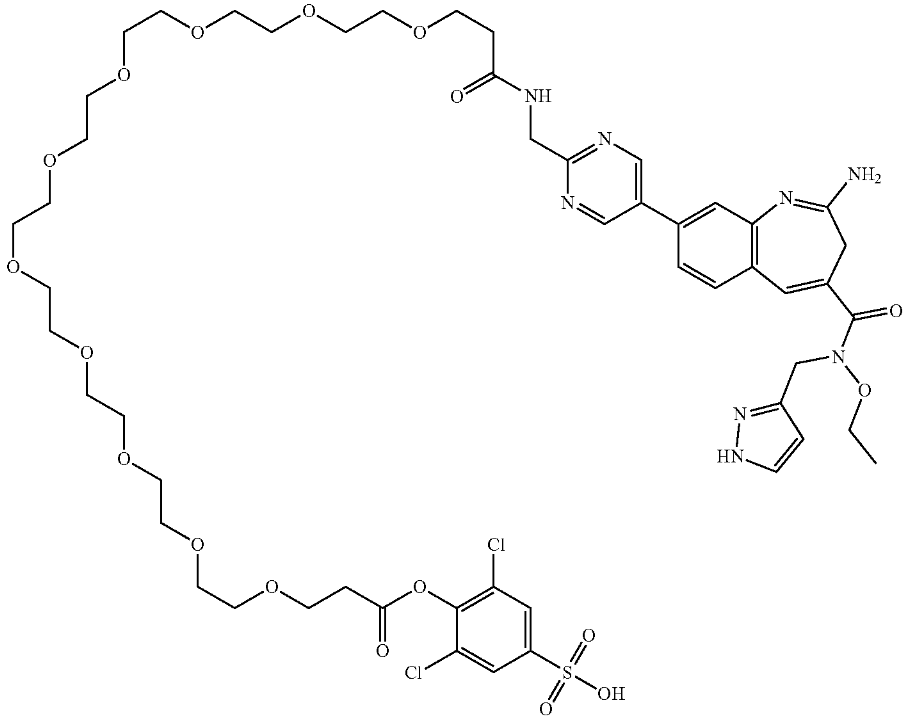 [SMILES: CCON(Cc1cc[nH]n1)C(=O)C1=Cc2ccc(-c3cnc(CNC(=O)CCOCCOCCOCCOCCOCCOCCOCCOCCOCCOCCC(=O)Oc4c(Cl)cc(S(=O)(=O)O)cc4Cl)nc3)cc2N=C(N)C1] | 1198.1 |
| HxBzL-117 | 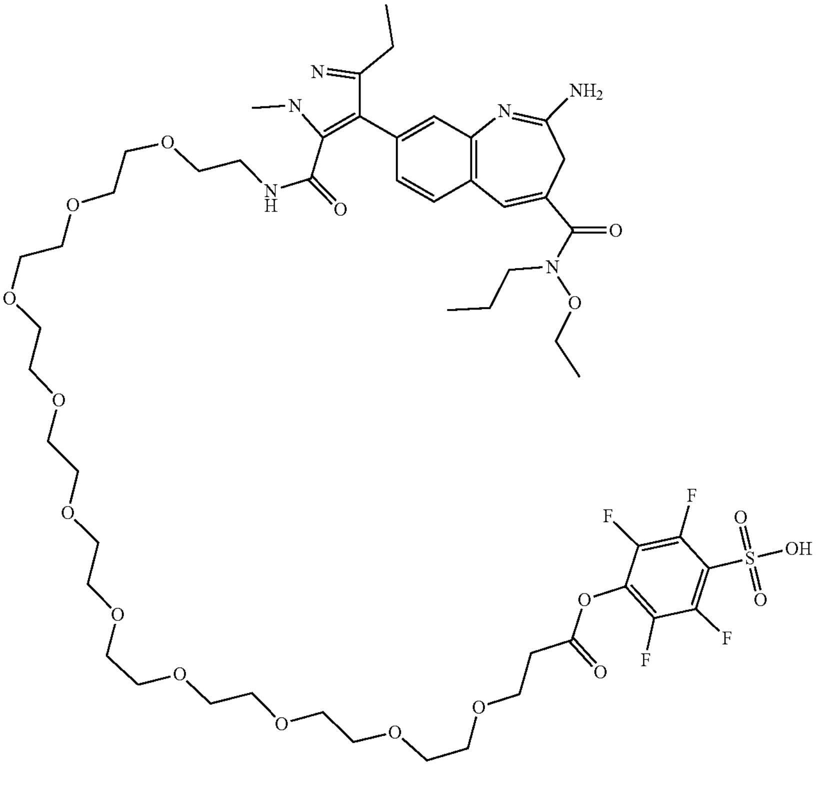 | 1179.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-118 | 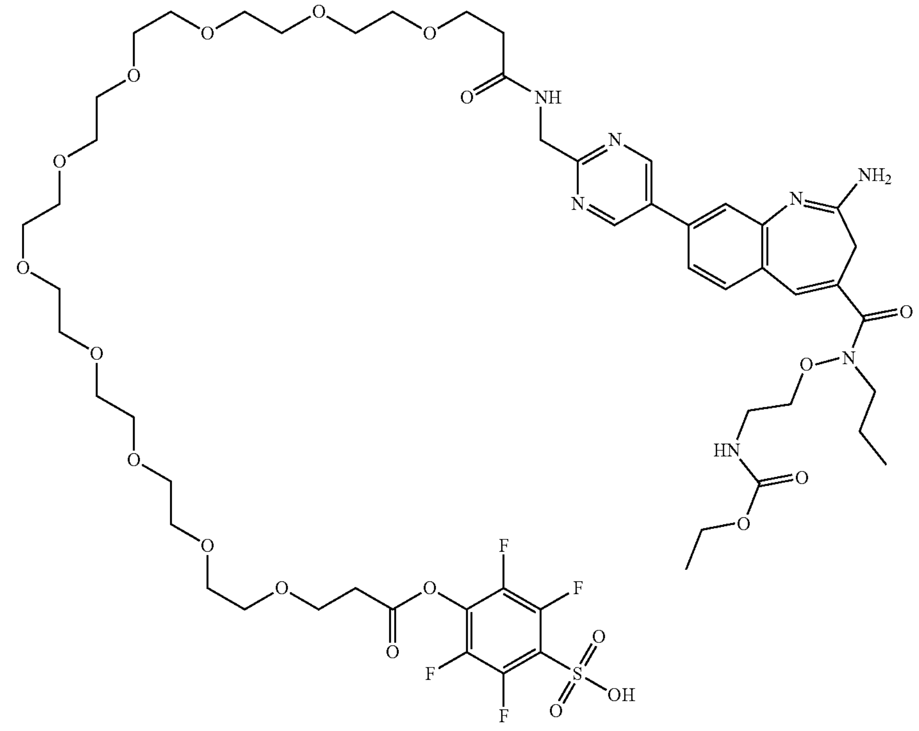 [SMILES: CCCN(OCCNC(=O)OCC)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1250.3 |
| HxBzL-119 | 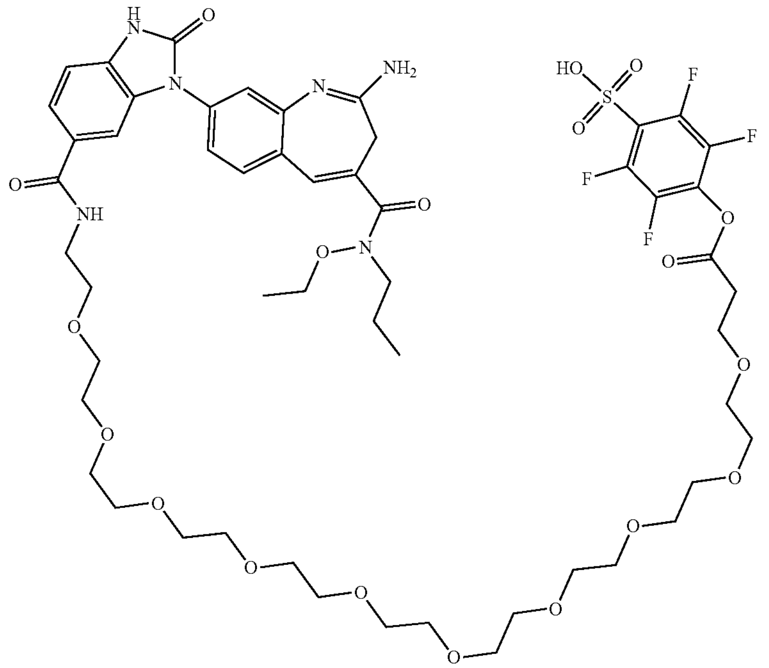 [SMILES: CCCN(OCC)C(=O)C1=Cc2ccc(-n3c(=O)[nH]c4ccc(C(=O)NCCOCCOCCOCCOCCOCCOCCOCCOCCOCCOCCC(=O)Oc5c(F)c(F)c(S(=O)(=O)O)c(F)c5F)cc43)cc2N=C(N)C1] | 1203.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-120 | 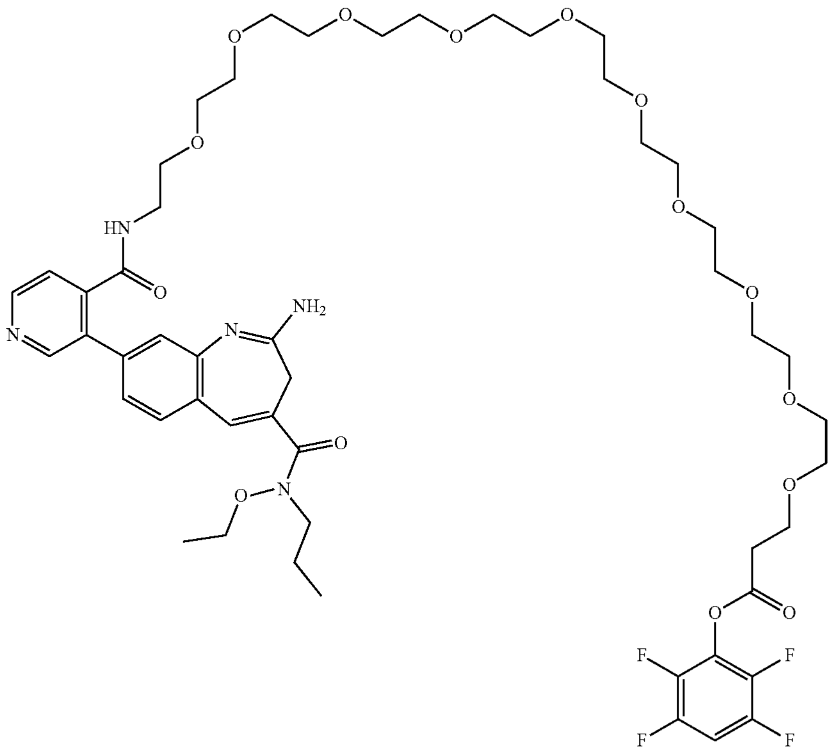 [SMILES: CCCN(OCC)C(=O)C1=Cc2ccc(-c3cnccc3C(=O)NCCOCCOCCOCCOCCOCCOCCOCCOCCOCCOCCC(=O)Oc3c(F)c(F)cc(F)c3F)cc2N=C(N)C1] | 1068.1 |

TABLE 2b-continued
| 8-Het-2-aminobenzazepine-linker intermediate, Formula II compounds (HxBzL) | | |
|---|---|---|
| HxBzL No. | Structure | MW |
| HxBzL-121 | 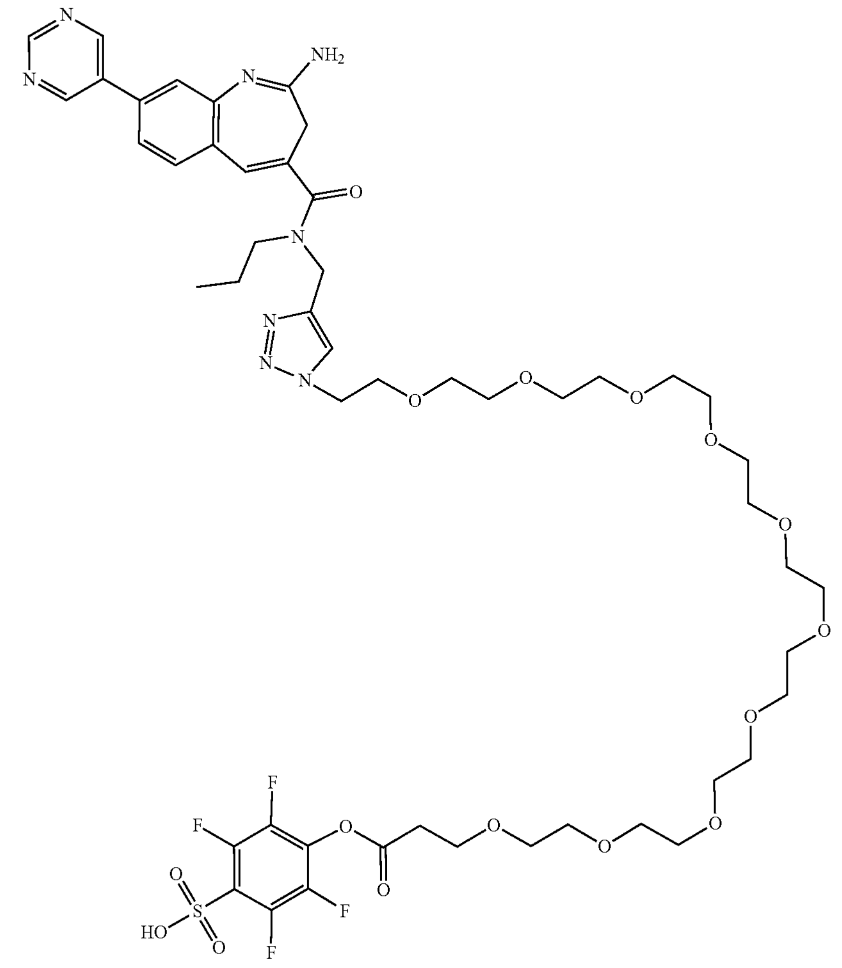 [SMILES: CCCN(Cc1cn(CCOCCOCCOCCOCCOCCOCCOCCOCCOCCOCCC(=O)Oc2c(F)c(F)c(S(=O)(=O)O)c(F)c2F)nn1)C(=O)C1=Cc2ccc(-c3cncnc3)cc2N=C(N)C1] | 1143.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-122 | 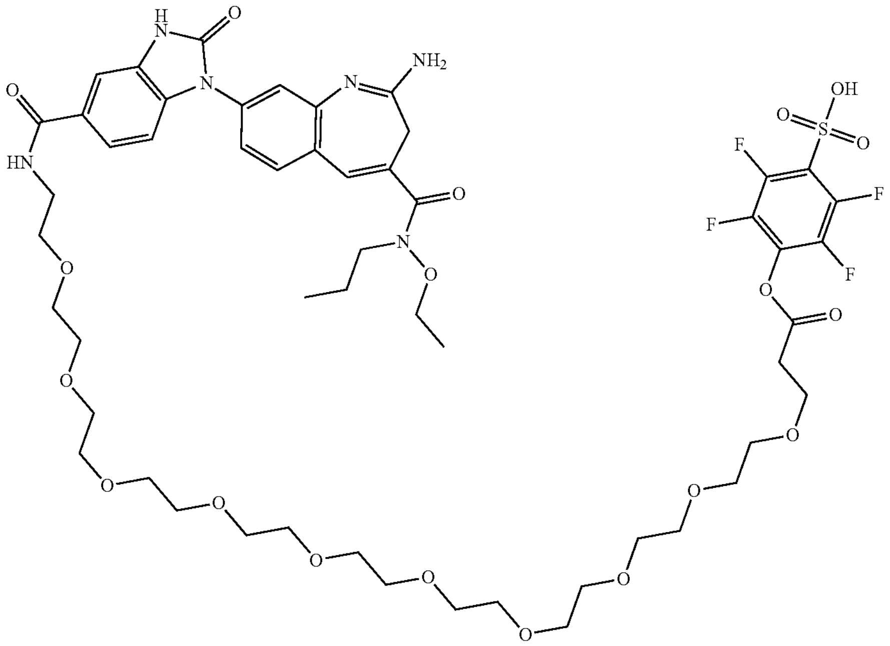 [SMILES: CCCN(OCC)C(=O)C1=Cc2ccc(-n3c(=O)[nH]c4cc(C(=O)NCCOCCOCCOCCOCCOCCOCCOCCOCCOCCOCCC(=O)Oc5c(F)c(F)c(S(=O)(=O)O)c(F)c5F)ccc43)cc2N=C(N)C1] | 1203.2 |
| HxBzL-123 | 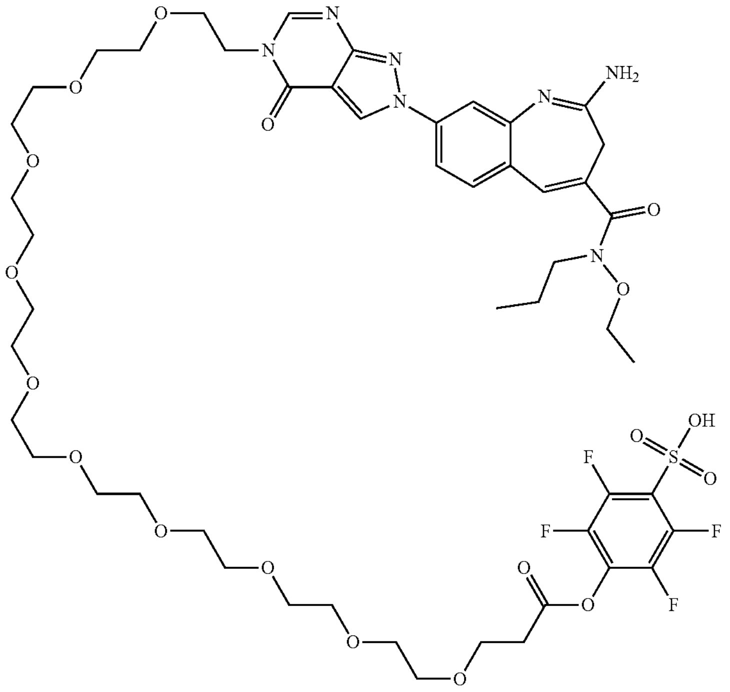 [SMILES: CCCN(OCC)C(=O)C1=Cc2ccc(-n3cc4c(=O)n(CCOCCOCCOCCOCCOCCOCCOCCOCCOCCOCCC(=O)Oc5c(F)c(F)c(S(=O)(=O)O)c(F)c5F)cnc4n3)cc2N=C(N)C1] | 1162.2 |

TABLE 2b-continued
| 8-Het-2-aminobenzazepine-linker intermediate, Formula II compounds (HxBzL) | | |
|---|---|---|
| HxBzL No. | Structure | MW |
| HxBzL-124 | 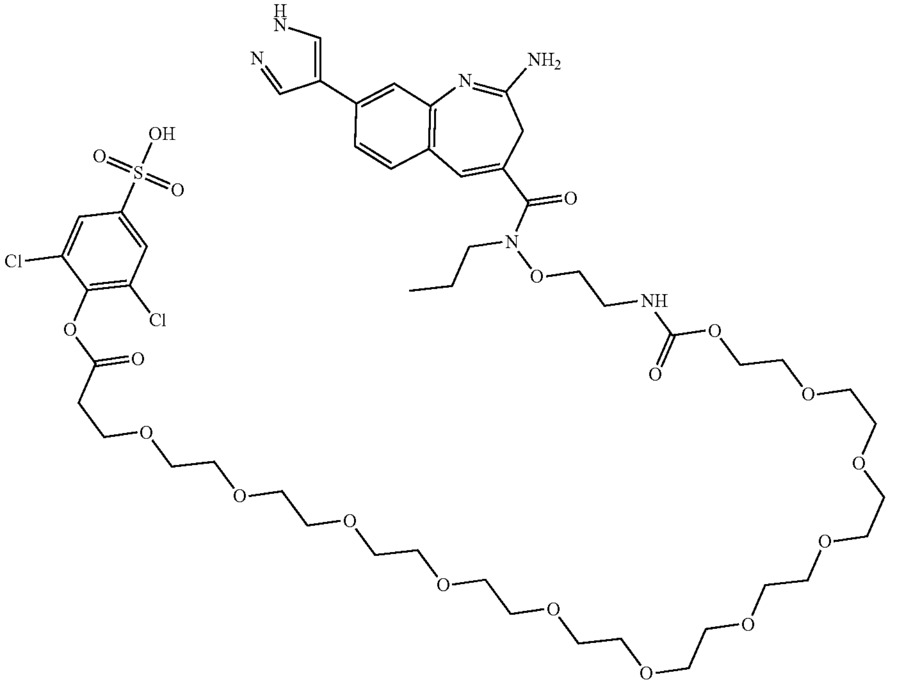 | 1150.1 |
| HxBzL-125 | 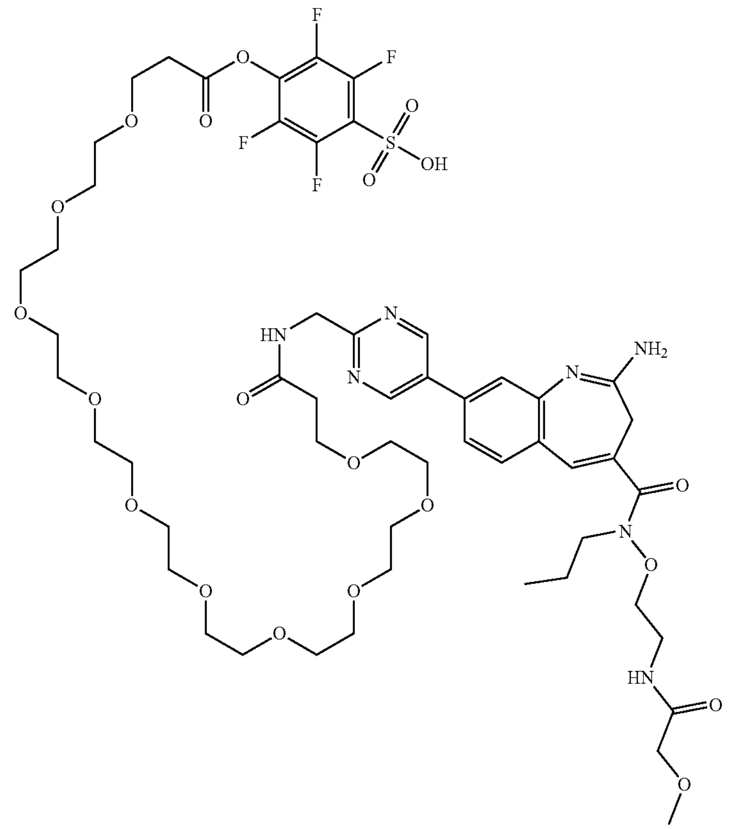 [SMILES: CCCN(OCCNC(=O)COC)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1] | 1250.3 |

TABLE 2b-continued

| 8-Het-2-aminobenzazepine-linker intermediate, Formula II compounds (HxBzL) | | |
|---|---|---|
| HxBzL No. | Structure | MW |
| HxBzL-126 | 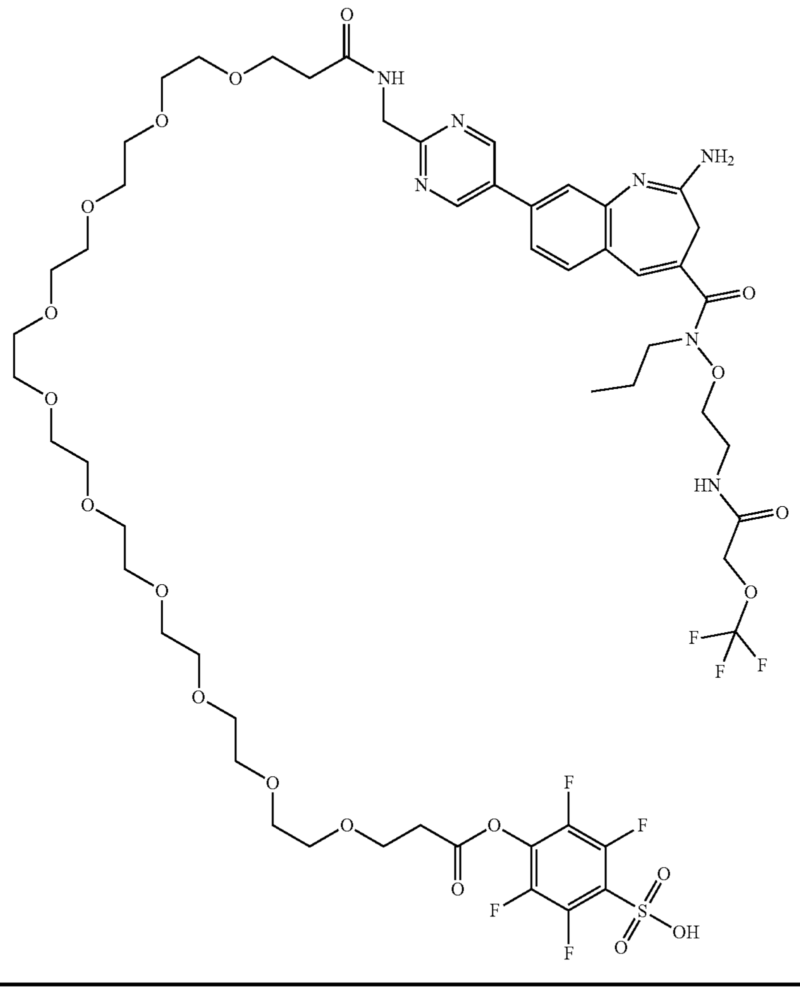 | 1304.3 |

Immunoconjugates

Exemplary embodiments of immunoconjugates comprise an anti-HER2 antibody covalently attached to one or more 8-Het-2-aminobenzazepine (Hx) moieties by a linker, and having Formula I:

Ab-[L-Hx]$_p$ I or a pharmaceutically acceptable salt thereof, wherein:

Ab is an antibody construct that has an antigen binding domain that binds HER2;

p is an integer from 1 to 8;

Hx is the 8-Het-2-aminobenzazepine moiety having the formula:

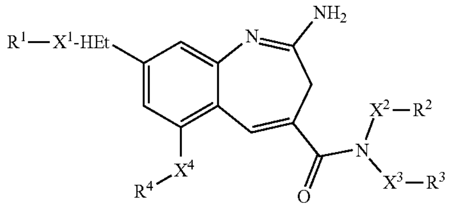

Het is selected from heterocyclyldiyl and heteroaryldiyl;

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:

—($C_1$-$C_{12}$ alkyldiyl)-N($R^5$)—*;

—($C_1$-$C_{12}$ alkyldiyl)-N($R^5$)$_2$;

—($C_1$-$C_{12}$ alkyldiyl)-O$R^5$;

—($C_3$-$C_{12}$ carbocyclyl);

—($C_3$-$C_{12}$ carbocyclyl)-*;

—($C_3$-$C_{12}$ carbocyclyl)-($C_1$-$C_{12}$ alkyldiyl)-N$R^5$—*;

—($C_3$-$C_{12}$ carbocyclyl)-($C_1$-$C_{12}$ alkyldiyl)-N($R^5$)$_2$;

—($C_3$-$C_{12}$ carbocyclyl)-N$R^5$—C(═N$R^5$)N$R^5$—*;

—($C_6$-$C_{20}$ aryl);

—($C_6$-$C_{20}$ aryl)-*;

—($C_6$-$C_{20}$ aryldiyl)-N($R^5$)—*;

—($C_6$-$C_{20}$ aryldiyl)-($C_1$-$C_{12}$ alkyldiyl)-N($R^5$)—*;

—($C_6$-$C_{20}$ aryldiyl)-($C_1$-$C_{12}$ alkyldiyl)-($C_2$-$C_{20}$ heterocyclyldiyl)-*;

—($C_6$-$C_{20}$ aryldiyl)-($C_1$-$C_{12}$ alkyldiyl)-N($R^5$)$_2$;

—($C_6$-$C_{20}$ aryldiyl)-($C_1$-$C_{12}$ alkyldiyl)-N$R^5$—C(═N$R^{5a}$)N($R^5$)—*;

—($C_2$-$C_{20}$ heterocyclyl);

—($C_2$-$C_{20}$ heterocyclyl)-*;

—($C_2$-$C_9$ heterocyclyl)-($C_1$-$C_{12}$ alkyldiyl)-N$R^5$—*;

—($C_2$-$C_9$ heterocyclyl)-($C_1$-$C_{12}$ alkyldiyl)-N($R^5$)$_2$;

—($C_2$-$C_9$ heterocyclyl)-C(═O)—($C_1$-$C_{12}$ alkyldiyl)-N($R^5$)—*;

—($C_2$-$C_9$ heterocyclyl)-N$R^5$—C(═N$R^{5a}$)N$R^5$—*;

—($C_2$-$C_9$ heterocyclyl)-N$R^5$—($C_6$-$C_{20}$ aryldiyl)-($C_1$-$C_{12}$ alkyldiyl)-N($R^5$)—*;

—($C_2$-$C_9$ heterocyclyl)-($C_6$-$C_{20}$ aryldiyl)-*;

—($C_1$-$C_{20}$ heteroaryl);

—($C_1$-$C_{20}$ heteroaryl)-*;

—($C_1$-$C_{20}$ heteroaryl)-($C_1$-$C_{12}$ alkyldiyl)-N($R^5$)—*;

—($C_1$-$C_{20}$ heteroaryl)-($C_1$-$C_{12}$ alkyldiyl)-N($R^5$)$_2$;

—($C_1$-$C_{20}$ heteroaryl)-N$R^5$—C(═N$R^{5a}$)N($R^5$)—*;

—($C_1$-$C_{20}$ heteroaryl)-N($R^5$)C(═O)—($C_1$-$C_{12}$ alkyldiyl)-N($R^5$)—*;

—C(═O)—*;

—C(═O)—($C_1$-$C_{12}$ alkyldiyl)-N($R^5$)—*;

—C(═O)—($C_2$-$C_{20}$ heterocyclyldiyl)-*;

—C(═O)N($R^5$)$_2$;

—C(═O)N($R^5$)—*;

—C(═O)N($R^5$)—($C_1$-$C_{12}$ alkyldiyl)-N($R^5$)C(═O)$R^5$;

—C(═O)N($R^5$)—($C_1$-$C_{12}$ alkyldiyl)-N($R^5$)C(═O)N($R^5$)$_2$;

—C(═O)N$R^5$—($C_1$-$C_{12}$ alkyldiyl)-N($R^5$)$CO_2R^5$;

—C(═O)N$R^5$—($C_1$-$C_{12}$ alkyldiyl)-N($R^5$)C(═N$R^{5a}$)N($R^5$)$_2$;

—C(═O)N$R^5$—($C_1$-$C_{12}$ alkyldiyl)-N$R^5$C(═N$R^{5a}$)$R^5$;

—C(═O)N$R^5$—($C_1$-$C_8$ alkyldiyl)-N$R^5$($C_2$-$C_5$ heteroaryl);

—C(═O)N$R^5$—($C_1$-$C_{20}$ heteroaryldiyl)-N($R^5$)—*;

—C(═O)N$R^5$—($C_1$-$C_{20}$ heteroaryldiyl)-*;

—C(═O)N$R^5$—($C_1$-$C_{20}$ heteroaryldiyl)-($C_1$-$C_{12}$ alkyldiyl)-N($R^5$)$_2$;

—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-NR 5-*;

—N($R^5$)$_2$;

—N($R^5$)—*;

—N($R^5$)C(═O)$R^5$;

—N($R^5$)C(═O)—*;

—N($R^5$)C(═O)N($R^5$)$_2$;

—N($R^5$)C(═O)N($R^5$)—*;

—N($R^5$)$CO_2R^5$;

—N$R^5$C(═N$R^{5a}$)N($R^5$)$_2$;

—N$R^5$C(═N$R^{5a}$)N($R^5$)—*;

—N$R^5$C(═N$R^{5a}$)$R^5$;

—N($R^5$)C(═O)—($C_1$-$C_{12}$ alkyldiyl)-N($R^5$)—*;

—N($R^5$)—($C_2$-$C_5$ heteroaryl);

—N($R^5$)—S(═O)$_2$—($C_1$-$C_{12}$ alkyl);

—O—($C_1$-$C_{12}$ alkyl);

—O—($C_1$-$C_{12}$ alkyldiyl)-N($R^5$)$_2$;

—O—($C_1$-$C_{12}$ alkyldiyl)-N($R^5$)—*;

—O—C(═O)N($R^5$)$_2$;

—O—C(═O)N($R^5$)—*;

—S(═O)$_2$—($C_2$-$C_{20}$ heterocyclyldiyl)-*;

—S(═O)$_2$—($C_2$-$C_{20}$ heterocyclyldiyl)-($C_1$-$C_{12}$ alkyldiyl)-N($R^5$)$_2$;

—S(═O)$_2$—($C_2$-$C_{20}$ heterocyclyldiyl)-($C_1$-$C_{12}$ alkyldiyl)-N$R^5$—*; and —S(═O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(═O), C(═O)N($R^5$), O, N($R^5$), S, S(O)$_2$, and S(O)$_2$N($R^5$);

$R^5$ is independently selected from the group consisting of H, $C_6$-$C_{20}$ aryl, $C_3$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:

—C(═O)—PEG-;

—C(═O)—PEG-C(═O)N($R^6$)—($C_1$-$C_{12}$ alkyldiyl)-C(═O)-Gluc-;

—C(═O)—PEG-O—;

—C(═O)—PEG-O—C(═O)—;

—C(═O)—PEG-C(═O)—;

—C(═O)—PEG-C(═O)—PEP-;

—C(═O)—PEG-N($R^6$)—;

—C(═O)—PEG-N($R^6$)—C(═O)—;

—C(═O)—PEG-N($R^6$)—PEG-C(═O)—PEP-;

—C(═O)—PEG-$N^+$($R^6$)$_2$-PEG-C(═O)—PEP-;

—C(═O)—PEG-C(═O)—PEP-N($R^6$)—($C_1$-$C_{12}$ alkyldiyl)-;

—C(═O)—PEG-C(═O)—PEP-N($R^6$)—($C_1$-$C_{12}$ alkyldiyl)N($R^6$)C(═O)—($C_2$-$C_5$ monoheterocyclyldiyl)-;

—C(═O)—PEG-SS—($C_1$-$C_{12}$ alkyldiyl)-OC(═O)—;

—C(═O)—PEG-SS—($C_1$-$C_{12}$ alkyldiyl)-C(═O)—;

—C(═O)—($C_1$-$C_{12}$ alkyldiyl)-C(═O)—PEP-;

—C(═O)—($C_1$-$C_{12}$ alkyldiyl)-C(═O)—PEP-N($R^6$)—($C_1$-$C_{12}$ alkyldiyl)-;

—C(═O)—($C_1$-$C_{12}$ alkyldiyl)-C(═O)—PEP-N($R^6$)—($C_1$-$C_{12}$ alkyldiyl)-N($R^5$)—C(═O);

—C(═O)—($C_1$-$C_{12}$ alkyldiyl)-C(═O)—PEP-N($R^6$)—($C_1$-$C_{12}$ alkyldiyl)-N($R^6$)C(═O)—($C_2$-$C_5$ monoheterocyclyldiyl)-;

-succinimidyl-($CH_2$)$_m$—C(═O)N($R^6$)—PEG-;

-succinimidyl-($CH_2$)$_m$—C(═O)N($R^6$)—PEG-C(═O)N($R^6$)—($C_1$-$C_{12}$ alkyldiyl)-C(═O)-Gluc-;

-succinimidyl-($CH_2$)$_m$—C(═O)N($R^6$)—PEG-O—;

-succinimidyl-($CH_2$)$_m$—C(═O)N($R^6$)—PEG-O—C(═O)—;

-succinimidyl-($CH_2$)$_m$—C(═O)N($R^6$)—PEG-C(═O)—;

-succinimidyl-($CH_2$)$_m$—C(═O)N($R^6$)—PEG-N($R^5$)—;

-succinimidyl-($CH_2$)$_m$—C(═O)N($R^6$)—PEG-N($R^5$)—C(═O)—;

-succinimidyl-($CH_2$)$_m$—C(═O)N($R^6$)—PEG-C(═O)—PEP-;

-succinimidyl-$(CH_2)_m$—C(═O)N($R^6$)—PEG-SS—($C_1$-$C_{12}$ alkyldiyl)-OC(═O)—;

-succinimidyl-$(CH_2)_m$—C(═O)—PEP-N($R^6$)—($C_1$-$C_{12}$ alkyldiyl)-;

-succinimidyl-$(CH_2)_m$—C(═O)—PEP-N($R^6$)—($C_1$-$C_{12}$ alkyldiyl)N($R^6$)C(═O)—; and -succinimidyl-$(CH_2)_m$—C(═O)—PEP-N($R^6$)—($C_1$-$C_{12}$ alkyldiyl)N($R^6$)C(═O)—($C_2$-$C_5$ monoheterocyclyldiyl)-;

$R^6$ is independently H or $C_1$-$C_6$ alkyl;

PEG has the formula: —$(CH_2CH_2O)_n$—$(CH_2)_m$—; m is an integer from 1 to 5, and n is an integer from 2 to 50;

Glue has the formula:

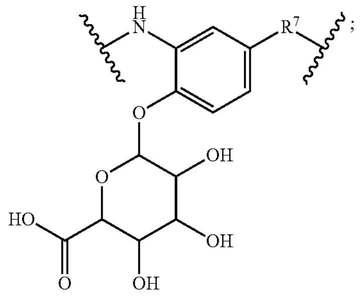

PEP has the formula:

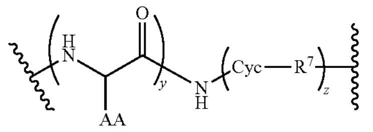

where AA is independently selected from a natural or unnatural amino acid side chain, or one or more of AA, and an adjacent nitrogen atom form a 5-membered ring proline amino acid, and the wavy line indicates a point of attachment;

Cyc is selected from $C_6$-$C_{20}$ aryldiyl and $C_1$-$C_{20}$ heteroaryldiyl, optionally substituted with one or more groups selected from F, Cl, $NO_2$, —OH, —$OCH_3$, and a glucuronic acid having the structure:

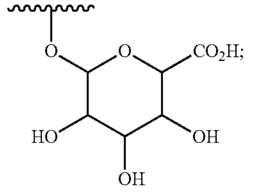 [SMILES: *OC1OC(C(=O)O)C(O)C(O)C1O]

$R^7$ is selected from the group consisting of —CH($R^8$)O—, —$CH_2$—, —$CH_2$N($R^8$)—, and —CH($R^8$)O—C(═O)—, where $R^8$ is selected from H, $C_1$-$C_6$ alkyl, C(═O)—$C_1$-$C_6$ alkyl, and —C(═O)N$(R^9)_2$, where $R^9$ is independently selected from the group consisting of H, $C_1$-$C_{12}$ alkyl, and —$(CH_2CH_2O)_n$—$(CH_2)_m$—OH, where m is an integer from 1 to 5, and n is an integer from 2 to 50, or two $R^9$ groups together form a 5- or 6-membered heterocyclyl ring;

y is an integer from 2 to 12;

z is 0 or 1; and alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH═$CH_2$, —C≡CH, —C≡$CCH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —CH(OH)$CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH($CH_3$)CN, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —COCH(OH)$CH_3$, —$CONH_2$, —$CONHCH_3$, —CON$(CH_3)_2$, —$C(CH_3)_2CONH_2$, —$NH_2$, —$NHCH_3$, —$N(CH_3)_2$, —$NHCOCH_3$, —N($CH_3$)$COCH_3$, —NHS$(O)_2CH_3$, —N($CH_3$)$C(CH_3)_2CONH_2$, —N($CH_3$)$CH_2CH_2S(O)_2CH_3$, —NHC(═NH)H, —NHC(═NH)$CH_3$, —NHC(═NH)$NH_2$, —NHC(═O)$NH_2$, —$NO_2$, ═O, —OH, —$OCH_3$, —$OCH_2CH_3$, —$OCH_2CH_2OCH_3$, —$OCH_2CH_2OH$, —$OCH_2CH_2N(CH_3)_2$, —O$(CH_2CH_2O)_n$—$(CH_2)_m CO_2H$, —O$(CH_2CH_2O)_n$H, —$OCH_2F$, —$OCHF_2$, —$OCF_3$, —$OP(O)(OH)_2$, —$S(O)_2N(CH_3)_2$, —$SCH_3$, —$S(O)_2CH_3$, and —$S(O)_3H$.

An exemplary embodiment of the immunoconjugate of Formula I includes wherein the antibody is selected from trastuzumab and pertuzumab, or a biosimilar or a biobetter thereof.

An exemplary embodiment of the immunoconjugate of Formula I includes wherein Het is selected from the group consisting of pyridyldiyl, pyrimidyldiyl, pyrazolyldiyl, piperazinyldiyl, piperidinyldiyl, and pyrazinyldiyl.

An exemplary embodiment of the immunoconjugate of Formula I includes wherein $X^1$ is a bond, and $R^1$ is H.

An exemplary embodiment of the immunoconjugate of Formula I includes wherein $X^2$ is a bond, and $R^2$ is $C_1$-$C_8$ alkyl.

An exemplary embodiment of the immunoconjugate of Formula I includes wherein $X^2$ and $X^3$ are each a bond, and $R^2$ and $R^3$ are independently selected from $C_1$-$C_8$ alkyl, —O—($C_1$-$C_{12}$ alkyl), —($C_1$-$C_{12}$ alkyldiyl)-$OR^5$, —($C_1$-$C_8$ alkyldiyl)-N($R^5$)$CO_2R^5$, —($C_1$-$C_{12}$ alkyl)-OC(O)N$(R^5)_2$, —O—($C_1$-$C_{12}$ alkyl)-N($R^5$)$CO_2R^5$, and —O—($C_1$-$C_{12}$ alkyl)-OC(O)N$(R^5)_2$.

An exemplary embodiment of the immunoconjugate of Formula I includes wherein $R^2$ is $C_1$-$C_8$ alkyl and $R^3$ is —($C_1$-$C_8$ alkyldiyl)-N($R^5$)$CO_2R^5$.

An exemplary embodiment of the immunoconjugate of Formula I includes wherein $R^2$ is —$CH_2CH_2CH_3$ and $R^3$ is selected from —$CH_2CH_2CH_2NHCO_2$(t-Bu), —$OCH_2CH_2NHCO_2$(cyclobutyl), and —$CH_2CH_2CH_2NHCO_2$(cyclobutyl).

An exemplary embodiment of the immunoconjugate of Formula I includes wherein $R^2$ and $R^3$ are each independently selected from —$CH_2CH_2CH_3$, —$OCH_2CH_3$, —$OCH_2CF_3$, —$CH_2CH_2CF_3$, —$OCH_2CH_2OH$, and —$CH_2CH_2CH_2OH$.

An exemplary embodiment of the immunoconjugate of Formula I includes wherein $R^2$ and $R^3$ are each —$CH_2CH_2CH_3$.

An exemplary embodiment of the immunoconjugate of Formula I includes wherein $R^2$ is —$CH_2CH_2CH_3$ and $R^3$ is —$OCH_2CH_3$.

An exemplary embodiment of the immunoconjugate of Formula I includes wherein $X^3—R^3$ is selected from the group consisting of:
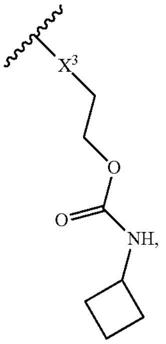
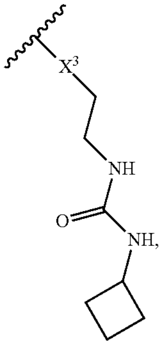
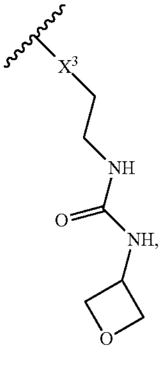
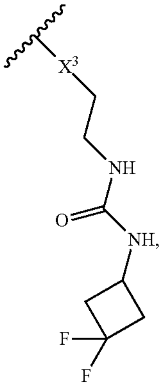
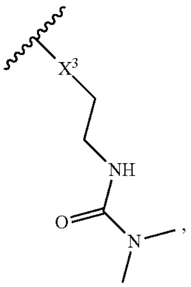
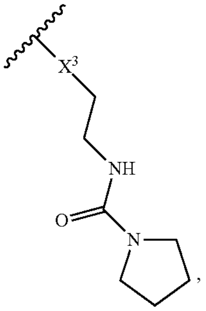
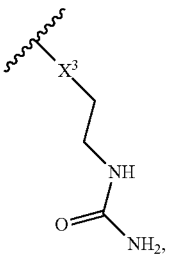
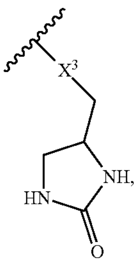
-continued
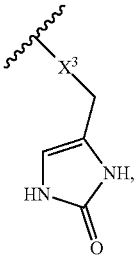
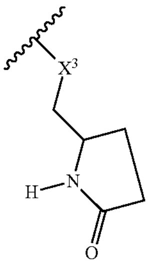
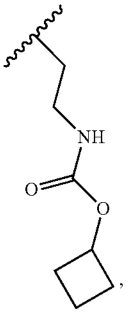
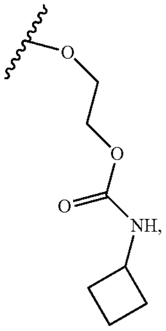
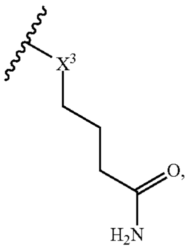
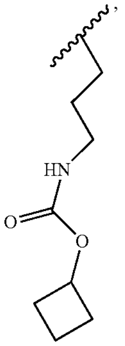
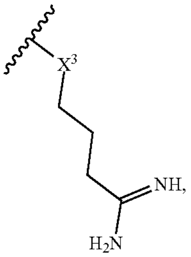
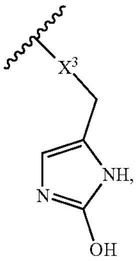
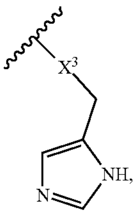
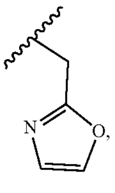
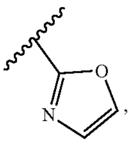
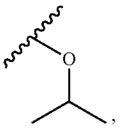

-continued

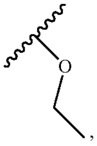,
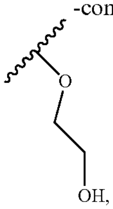, and
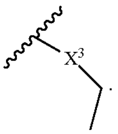.

An exemplary embodiment of the immunoconjugate of Formula I includes wherein $X^4$ is a bond, and $R^4$ is H.

An exemplary embodiment of the immunoconjugate of Formula I includes wherein $R^1$ is attached to L.

An exemplary embodiment of the immunoconjugate of Formula I includes wherein $R^2$ or $R^3$ is attached to L.

An exemplary embodiment of the immunoconjugate of Formula I includes wherein $X^3$—$R^3$-L is selected from the group consisting of:

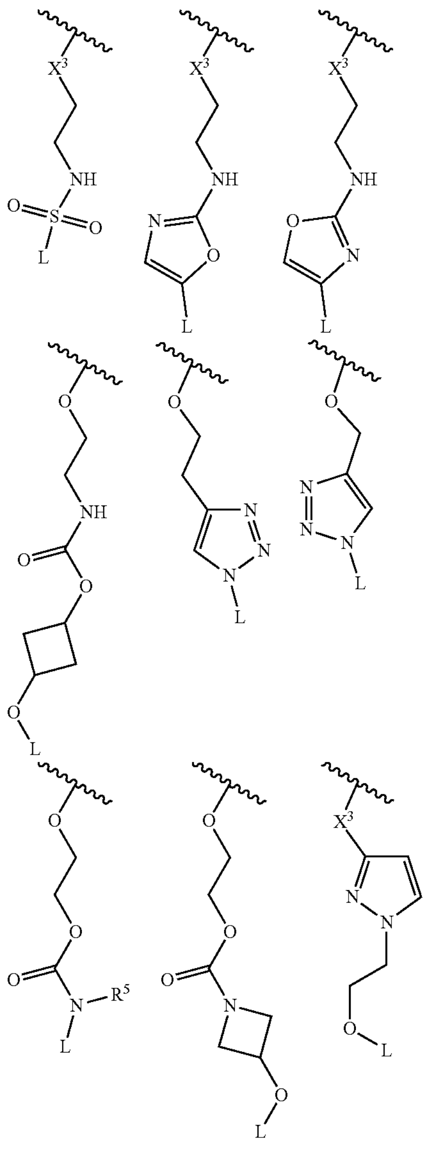

-continued

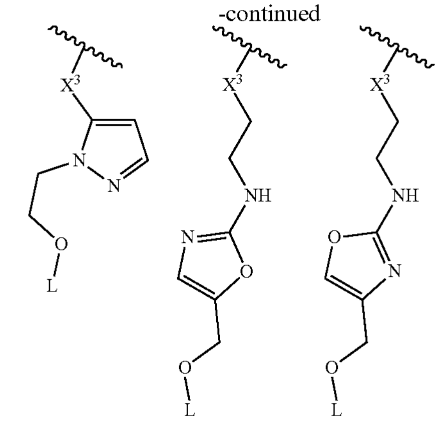

where the wavy line indicates the point of attachment to N.

An exemplary embodiment of the immunoconjugate of Formula I includes wherein $R^4$ is $C_1$-$C_{12}$ alkyl.

An exemplary embodiment of the immunoconjugate of Formula I includes wherein $R^4$ is —($C_1$-$C_{12}$ alkyldiyl)-N($R^5$)—*; where the asterisk * indicates the attachment site of L.

An exemplary embodiment of the immunoconjugate of Formula I includes wherein L is —C(=O)—PEG- or —C(=O)—PEG-C(=O)—.

An exemplary embodiment of the immunoconjugate of Formula I includes wherein L is attached to a cysteine thiol of the antibody.

An exemplary embodiment of the immunoconjugate of Formula I includes wherein for the PEG, m is 1 or 2, and n is an integer from 2 to 10.

An exemplary embodiment of the immunoconjugate of Formula I includes wherein for the PEG, n is 10.

An exemplary embodiment of the immunoconjugate of Formula I includes wherein L comprises PEP and PEP is a dipeptide and has the formula:

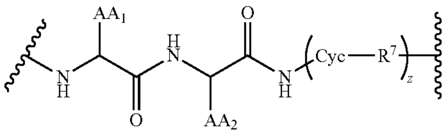.

An exemplary embodiment of the immunoconjugate of Formula I includes wherein $AA_1$ and $AA_2$ are independently selected from H, —$CH_3$, —$CH(CH_3)_2$, —$CH_2(C_6H5)$, —$CH_2CH_2CH_2CH_2NH_2$, —$CH_2CH_2CH_2NHC(NH)NH_2$, —$CHCH(CH_3)CH_3$, —$CH_2SO_3H$, and —$CH_2CH_2CH_2NHC(O)NH_2$; or $AA_1$ and $AA_2$ form a 5-membered ring proline amino acid.

An exemplary embodiment of the immunoconjugate of Formula I includes wherein $AA_1$ is —$CH(CH_3)_2$, and $AA_2$ is —$CH_2CH_2CH_2NHC(O)NH_2$.

An exemplary embodiment of the immunoconjugate of Formula I includes wherein $AA_1$ and $AA_2$ are independently selected from GlcNAc aspartic acid, —$CH_2SO_3H$, and —$CH_2OPO_3H$.

An exemplary embodiment of the immunoconjugate of Formula I includes wherein PEP has the formula:

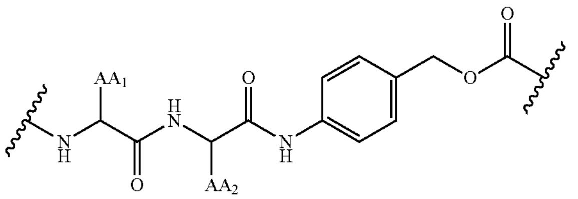

wherein $AA_1$ and $AA_2$ are independently selected from a side chain of a naturally-occurring amino acid.

An exemplary embodiment of the immunoconjugate of Formula I includes wherein L comprises PEP and PEP is a tripeptide and has the formula:

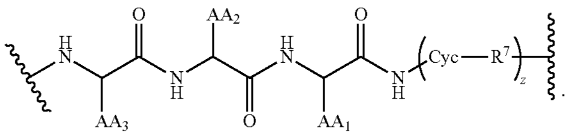

An exemplary embodiment of the immunoconjugate of Formula I includes wherein L comprises PEP and PEP is a tetrapeptide and has the formula:

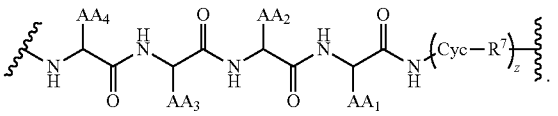

An exemplary embodiment of the immunoconjugate of Formula I includes wherein:

$AA_1$ is selected from the group consisting of Abu, Ala, and Val;

$AA_2$ is selected from the group consisting of Nle(O-Bzl), Oic and Pro;

$AA_3$ is selected from the group consisting of Ala and Met(O)$_2$; and $AA_4$ is selected from the group consisting of Oic, Arg (NO$_2$), Bpa, and Nle(O-Bzl).

An exemplary embodiment of the immunoconjugate of Formula I includes wherein L comprises PEP and PEP is selected from the group consisting of Ala-Pro-Val, Asn-Pro-Val, Ala-Ala-Val, Ala-Ala-Pro-Ala, Ala-Ala-Pro-Val, and Ala-Ala-Pro-Nva.

An exemplary embodiment of the immunoconjugate of Formula I includes wherein L comprises PEP and PEP is selected from the structures:

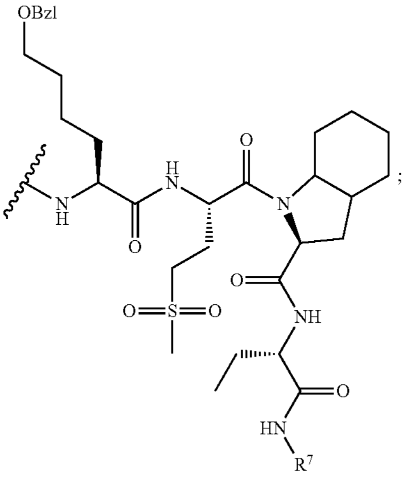

;

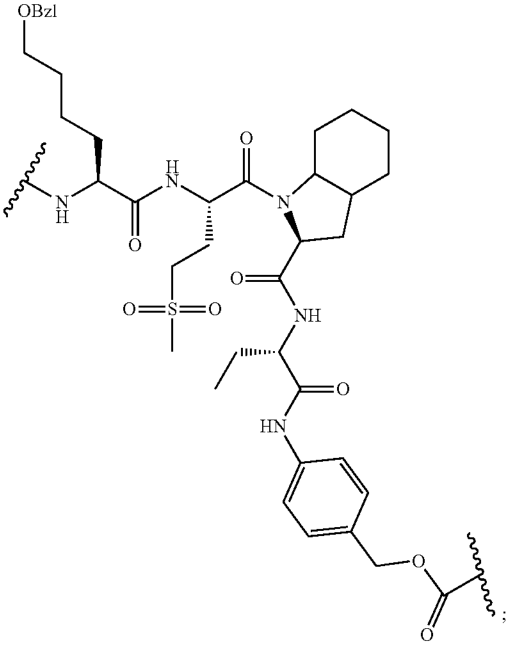

;

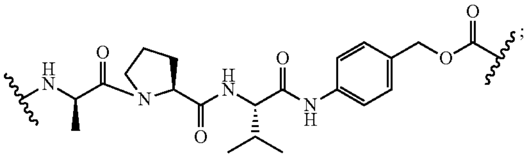

; and

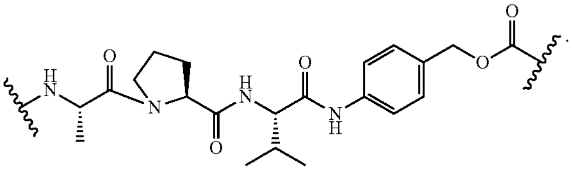

.

An exemplary embodiment of the immunoconjugate of Formula I includes wherein L is selected from the structures:

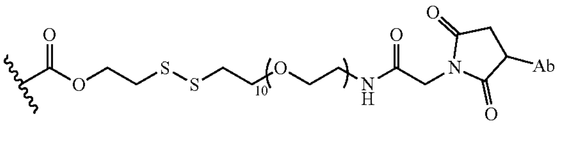

-continued

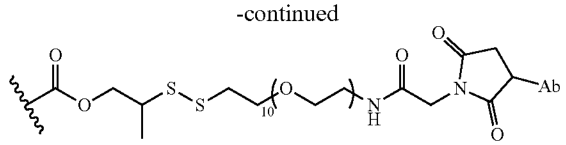

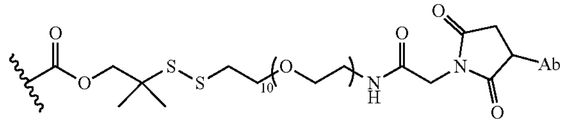

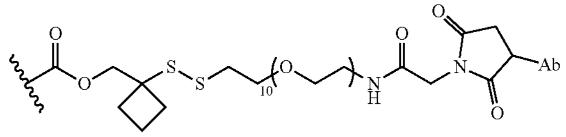

where the wavy line indicates the attachment to $R^5$.

An exemplary embodiment of the immunoconjugate of Formula I having Formula Ia:

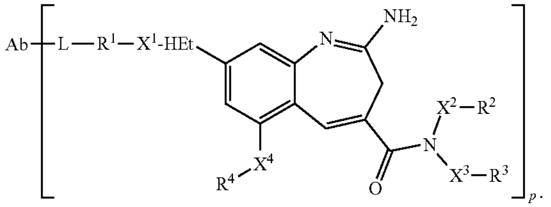

An exemplary embodiment of the immunoconjugate of Formula Ia includes wherein $X^4$ is a bond and $R^4$ is H.

An exemplary embodiment of the immunoconjugate of Formula Ia includes wherein Het is selected from the group consisting of pyridyldiyl, pyrimidyldiyl, pyrazolyldiyl, piperazinyldiyl, piperidinyldiyl, and pyrazinyldiyl.

An exemplary embodiment of the immunoconjugate of Formula Ia includes wherein $X^2$ and $X^3$ are each a bond, and $R^2$ and $R^3$ are independently selected from $C_1$-$C_8$ alkyl, —O—($C_1$-$C_{12}$ alkyl), —($C_1$-$C_{12}$ alkyldiyl)-$OR^5$, —($C_1$-$C_8$ alkyldiyl)-N($R^5$)$CO_2R^5$, and —O—($C_1$-$C_{12}$ alkyl)-N($R^5$)$CO_2R^5$.

An exemplary embodiment of the immunoconjugate of Formula Ia selected from Formulae Ib-Ii:

Ib

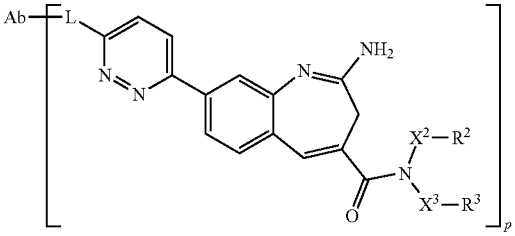

;

Ic

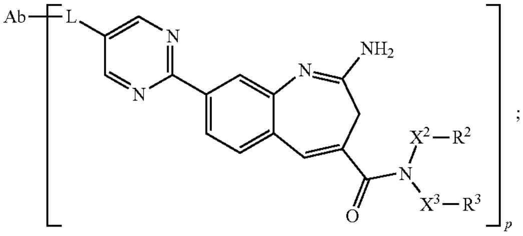

;

Id

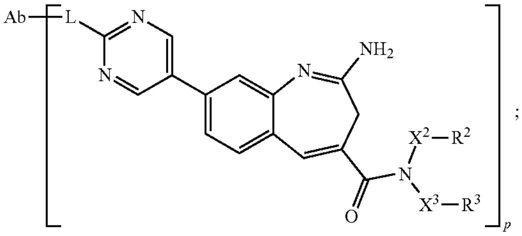

;

Ie

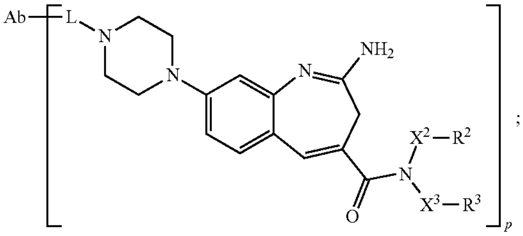

;

If

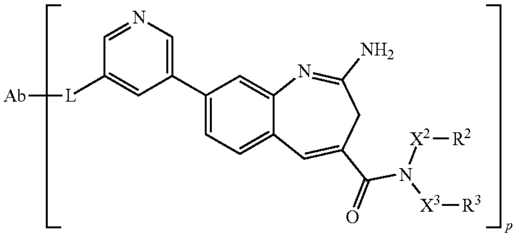

;

Ig

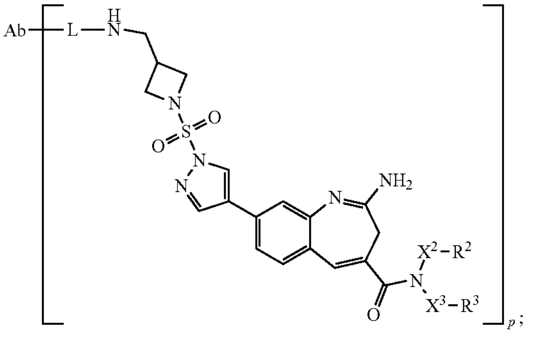

-continued

Ih

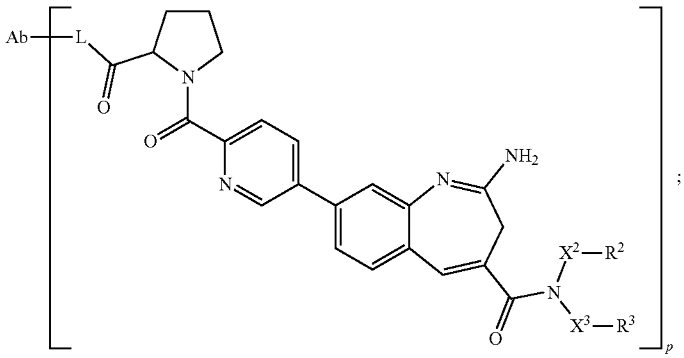

; and

Ii

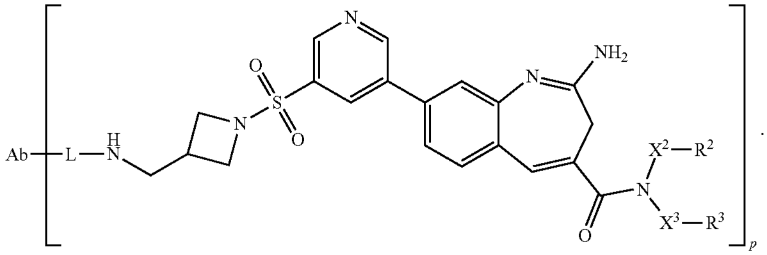

.

An exemplary embodiment of the immunoconjugate of Formula Ia includes wherein $X^2$ and $X^3$ are each a bond, and $R^2$ and $R^3$ are independently selected from $C_1$-$C_8$ alkyl, —O—($C_1$-$C_{12}$ alkyl), —($C_1$-$C_{12}$ alkyldiyl)-$OR^5$, —($C_1$-$C_8$ alkyldiyl)-$N(R^5)CO_2R^5$, and —O—($C_1$-$C_{12}$ alkyl)-$N(R^5)CO_2R^5$.

An exemplary embodiment of the immunoconjugate of Formula Ia includes wherein $X^2$ and $X^3$ are each a bond, $R^2$ is $C_1$-$C_8$ alkyl, and $R^3$ is selected from —O—($C_1$-$C_{12}$ alkyl) and —O—($C_1$-$C_{12}$ alkyl)-$N(R^5)CO_2R^5$.

The invention includes all reasonable combinations, and permutations of the features, of the Formula I embodiments.

In certain embodiments, the immunoconjugate compounds of the invention include those with immunostimulatory activity. The antibody-drug conjugates of the invention selectively deliver an effective dose of a 8-Het-2-aminobenzazepine drug to tumor tissue, whereby greater selectivity (i.e., a lower efficacious dose) may be achieved while increasing the therapeutic index ("therapeutic window") relative to unconjugated 8-Het-2-aminobenzazepine.

Drug loading is represented by p, the number of Hx moieties per antibody in an immunoconjugate of Formula I. Drug (Hx) loading may range from 1 to about 8 drug moieties (D) per antibody. Immunoconjugates of Formula I include mixtures or collections of antibodies conjugated with a range of drug moieties, from 1 to about 8. In some embodiments, the number of drug moieties that can be conjugated to an antibody is limited by the number of reactive or available amino acid side chain residues such as lysine and cysteine. In some embodiments, free cysteine residues are introduced into the antibody amino acid sequence by the methods described herein. In such aspects, p may be 1, 2, 3, 4, 5, 6, 7, or 8, and ranges thereof, such as from 1 to 8 or from 2 to 5. In any such aspect, p and n are equal (i.e., p=n=1, 2, 3, 4, 5, 6, 7, or 8, or some range there between). Exemplary immunoconjugates of Formula I include, but are not limited to, antibodies that have 1, 2, 3, or 4 engineered cysteine amino acids (Lyon, R. et al. (2012) *Methods in Enzym.* 502:123-138). In some embodiments, one or more free cysteine residues are already present in an antibody forming intrachain disulfide bonds, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

For some immunoconjugates, p may be limited by the number of attachment sites on the antibody. For example, where the attachment is a cysteine thiol, as in certain exemplary embodiments described herein, an antibody may have only one or a limited number of cysteine thiol groups, or may have only one or a limited number of sufficiently reactive thiol groups, to which the drug may be attached. In other embodiments, one or more lysine amino groups in the antibody may be available and reactive for conjugation with an Hx-linker compound of Formula II. In certain embodiments, higher drug loading, e.g. p>5, may cause aggregation, insolubility, toxicity, or loss of cellular permeability of certain antibody-drug conjugates. In certain embodiments, the average drug loading for an immunoconjugate ranges from 1 to about 8; from about 2 to about 6; or from about 3 to about 5. In certain embodiments, an antibody is subjected to denaturing conditions to reveal reactive nucleophilic groups such as lysine or cysteine.

The loading (drug/antibody ratio) of an immunoconjugate may be controlled in different ways, and for example, by: (i) limiting the molar excess of the Hx-linker intermediate compound relative to antibody, (ii) limiting the conjugation reaction time or temperature, and (iii) partial or limiting reductive denaturing conditions for optimized antibody reactivity.

It is to be understood that where more than one nucleophilic group of the antibody reacts with a drug, then the resulting product is a mixture of immunoconjugate compounds with a distribution of one or more drug moieties attached to an antibody. The average number of drugs per antibody may be calculated from the mixture by a dual ELISA antibody assay, which is specific for antibody and specific for the drug. Individual immunoconjugate molecules may be identified in the mixture by mass spectroscopy and separated by HPLC, e.g. hydrophobic interaction chromatography (see, e.g., McDonagh et al. (2006) *Prot. Engr. Design & Selection* 19(7):299-307; Hamblett et al. (2004) *Clin. Cancer Res.* 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous immunoconjugate with a single loading value may be isolated from the conjugation mixture by electrophoresis or chromatography.

An exemplary embodiment of the immunoconjugate of Formula I is selected from the Table 3 Immunoconjugates. Assessment of Immunoconjugate Activity In Vitro was conducted according to the methods of Example 203.

TABLE 3a

Anti-HER2, HxBz Immunoconjugates (IC)

| Immuno-conjugate No. | HxBzL Tables 2a and 2b | Antibody | DAR | PBMC Assay TNFα Secretion EC50 [nM] | cDC Assay IL-12p70 Secretion EC50 [nM] |
|---|---|---|---|---|---|
| IC-1 | HxBzL-1 | trastuzumab | 2.5 | | |
| IC-2 | HxBzL-2 | trastuzumab | 2.4 | | |
| IC-3 | HxBzL-3 | trastuzumab | 2.2 | | |
| IC-4 | HxBzL-4 | trastuzumab | 2.2 | | |
| IC-5 | HxBzL-5 | trastuzumab | 2.3 | | |
| IC-6 | HxBzL-6 | trastuzumab | 2.5 | | |
| IC-7 | HxBzL-7 | trastuzumab | 2.1 | | 0.6 |
| IC-8 | HxBzL-9 | trastuzumab | 2.7 | | |
| IC-9 | HxBzL-8 | trastuzumab | 2.5, 2.8 | 1.6 | 1.6 |
| IC-10 | HxBzL-10 | trastuzumab | 3.0 | | 8.4 |
| IC-11 | HxBzL-11 | trastuzumab | 3.1 | | |
| IC-12 | HxBzL-12 | trastuzumab | 2.0 | | 15.1 |
| IC-13 | HxBzL-15 | trastuzumab | 2.5 | | 0.5 |
| IC-14 | HxBzL-16 | trastuzumab | 2.4 | | 1.5 |
| IC-15 | HxBzL-17 | trastuzumab | 2.3 | | 1.8 |
| IC-16 | HxBzL-22 | trastuzumab | 2.7 | | |
| IC-17 | HxBzL-19 | trastuzumab | 2.9 | | 2.0 |
| IC-18 | HxBzL-18 | trastuzumab | 3.0 | | 1.7 |
| IC-19 | HxBzL-23 | trastuzumab | 2.5 | | |
| IC-20 | HxBzL-24 | trastuzumab | 2.7 | | 3.2 |
| IC-21 | HxBzL-20 | trastuzumab | 2.2 | | |
| IC-22 | HxBzL-25 | trastuzumab | 2.1 | | |
| IC-23 | HxBzL-26 | trastuzumab | 2.4 | | 1.6 |
| IC-24 | HxBzL-21 | trastuzumab | 2.2 | | |
| IC-25 | HxBzL-14 | trastuzumab | 2.6 | | |
| IC-26 | HxBzL-27 | trastuzumab | 2.3 | | |
| IC-27 | HxBzL-13 | trastuzumab | 3.4 | | |
| IC-28 | HxBzL-25 | trastuzumab | 2.5 | | |
| IC-29 | HxBzL-28 | trastuzumab | 2.2 | | |
| IC-30 | HxBzL-29 | trastuzumab | 2.7 | | 2.0 |
| IC-31 | HxBzL-30 | trastuzumab | 2.3, 2.8 | | 0.7 |
| IC-32 | HxBzL-31 | trastuzumab | 3.0 | | 1.3 |
| IC-33 | HxBzL-32 | trastuzumab | 2.5, 3.0 | | 1.6 |
| IC-34 | HxBzL-35 | trastuzumab | 2.4, 2.8 | | 2.1 |
| IC-35 | HxBzL-40 | Tras-K107C | 2.0 | | 1.5 |
| IC-36 | HxBzL-37 | trastuzumab | 3.1, 7.7 | | 0.1 |
| IC-37 | HxBzL-40 | trastuzumab | 3.2, 7.7 | | 0.1 |
| IC-38 | HxBzL-38 | trastuzumab | 2.4 | | |
| IC-39 | HxBzL-39 | trastuzumab | 2.1 | | 1.8 |
| IC-40 | HxBzL-44 | trastuzumab | 4.6 | | 0.4 |
| IC-41 | HxBzL-17 | anti-h/rHER2 | 2.2 | | |

TABLE 3a-continued

Anti-HER2, HxBz Immunoconjugates (IC)

| Immuno-conjugate No. | HxBzL Tables 2a and 2b | Antibody | DAR | PBMC Assay TNFα Secretion EC50 [nM] | cDC Assay IL-12p70 Secretion EC50 [nM] |
|---|---|---|---|---|---|
| IC-42 | HxBzL-24 | anti-h/rHER2 | 2.2 | | |
| IC-43 | HxBzL-8 | anti-h/rHER2 | 1.8 | | |
| IC-44 | HxBzL-25 | anti-h/rHER2 | 2.0 | | |
| IC-45 | HxBzL-16 | anti-h/rHER2 | 2.0 | | |
| IC-46 | HxBzL-36 | anti-h/rHER2 | 2.1 | | |
| IC-47 | HxBzL-40 | Tras-K414C | 2.0 | | |
| IC-48 | HxBzL-47 | trastuzumab | 4.6 | | 0.4 |
| IC-49 | HxBzL-48 | trastuzumab | 3.6 | | 0.8 |
| IC-50 | HxBzL-34 | trastuzumab | 2.5 | | |
| IC-51 | HxBzL-41 | trastuzumab | 2.5 | | |
| IC-52 | HxBzL-42 | trastuzumab | 2.5 | | |
| IC-53 | HxBzL-43 | trastuzumab | 2.3 | | |
| IC-54 | HxBzL-45 | trastuzumab | 2.4 | | |
| IC-55 | HxBzL-46 | trastuzumab | 2.2 | | |
| IC-56 | HxBzL-49 | trastuzumab | 2.1 | | 0.5 |
| IC-57 | HxBzL-50 | trastuzumab | 2.7 | | |
| IC-58 | HxBzL-52 | trastuzumab | 2.2 | | |
| IC-59 | HxBzL-53 | trastuzumab | 2.4 | | |
| IC-60 | HxBzL-54 | trastuzumab | 2.7 | | 0.9 |
| IC-61 | HxBzL-51 | trastuzumab | 2.6 | | |
| IC-62 | HxBzL-33 | trastuzumab | 2.2 | | 1.4 |
| IC-63 | HxBzL-55 | trastuzumab | 2.1 | | |

TABLE 3b

Anti-HER2, HxBz Immunoconjugates (IC)

| Immunoconjugate No. | HxBzL Tables 2a and 2b | Antibody | DAR | cDC Assay IL-12p70 Secretion EC50 [nM] |
|---|---|---|---|---|
| IC-64 | HxBzL-67 | trastuzumab | 2.3 | 1.2 |
| IC-65 | HxBzL-66 | trastuzumab | 2.5 | |
| IC-66 | HxBzL-65 | trastuzumab | 2.4 | |
| IC-67 | HxBzL-64 | trastuzumab | 2.5 | |
| IC-68 | HxBzL-63 | trastuzumab | 2.6 | |
| IC-69 | HxBzL-62 | trastuzumab | 2.5 | |
| IC-70 | HxBzL-57 | trastuzumab | 2.6 | |
| IC-71 | HxBzL-61 | trastuzumab | 2.5 | |
| IC-72 | HxBzL-60 | trastuzumab | 2.6 | |
| IC-73 | HxBzL-59 | trastuzumab | 2.4 | |
| IC-74 | HxBzL-58 | trastuzumab | 2.4 | |
| IC-75 | HxBzL-56 | trastuzumab | 2.3 | |
| IC-76 | HxBzL-68 | trastuzumab | 2.6 | |
| IC-77 | HxBzL-71 | trastuzumab | 2.4 | |
| IC-78 | HxBzL-70 | trastuzumab | 2.6 | |
| IC-79 | HxBzL-69 | trastuzumab | 2.7 | |
| IC-80 | HxBzL-8 | Tras-G1fN297A | 2.4 | |
| IC-81 | HxBzL-72 | trastuzumab | 2.3 | 0.6 |
| IC-82 | HxBzL-73 | trastuzumab | 2.6 | 0.8 |
| IC-83 | HxBzL-74 | trastuzumab | 2.5 | 0.8 |
| IC-84 | HxBzL-75 | trastuzumab | 2.3 | 0.9 |
| IC-85 | HxBzL-76 | trastuzumab | 2.6 | 0.8 |
| IC-86 | HxBzL-77 | trastuzumab | 2.5 | |
| IC-87 | HxBzL-86 | trastuzumab | 2.9 | |
| IC-88 | HxBzL-84 | trastuzumab | 2.5 | |
| IC-89 | HxBzL-83 | trastuzumab | 2.5 | |
| IC-90 | HxBzL-82 | trastuzumab | 3.1 | |
| IC-91 | HxBzL-81 | trastuzumab | 2.7 | |
| IC-92 | HxBzL-80 | trastuzumab | 2.4 | |
| IC-93 | HxBzL-78 | trastuzumab | 3.2 | 0.7 |
| IC-94 | HxBzL-92 | trastuzumab | 2.4 | |
| IC-95 | HxBzL-93 | trastuzumab | 2.7 | 1.2 |
| IC-96 | HxBzL-88 | trastuzumab | 2.5 | |
| IC-97 | HxBzL-89 | trastuzumab | 2.3 | 2.3 |
| IC-98 | HxBzL-90 | trastuzumab | 2.5 | |

TABLE 3b-continued

| Anti-HER2, HxBz Immunoconjugates (IC) | | | | |
|---|---|---|---|---|
| Immunoconjugate No. | HxBzL Tables 2a and 2b | Antibody | DAR | cDC Assay IL-12p70 Secretion EC50 [nM] |
| IC-99 | HxBzL-94 | trastuzumab | 2.6 | |
| IC-100 | HxBzL-95 | trastuzumab | 2.4 | |
| IC-101 | HxBzL-91 | trastuzumab | 2.1 | |
| IC-102 | HxBzL-87 | trastuzumab | 2.3 | |
| IC-103 | HxBzL-85 | trastuzumab | 2.8 | 2.0 |
| IC-104 | HxBzL-17 | Tras-G1fN297A | 2.9 | |
| IC-105 | HxBzL-97 | trastuzumab | 3.3 | 0.8 |
| IC-106 | HxBzL-98 | trastuzumab | 3.5 | 0.9 |
| IC-107 | HxBzL-96 | trastuzumab | 3.6 | 0.7 |
| IC-108 | HxBzL-30 | Tras-G1f-N297A | 2.4 | |
| IC-109 | HxBzL-35 | anti-h/rHER2 | 2.4 | |
| IC-110 | HxBzL-105 | trastuzumab | 3.4 | |
| IC-111 | HxBzL-106 | trastuzumab | 3.6 | |
| IC-112 | HxBzL-113 | trastuzumab | 2.4 | |
| IC-113 | HxBzL-111 | trastuzumab | 2.2 | |
| IC-114 | HxBzL-112 | trastuzumab | 5.6 | |
| IC-115 | HxBzL-102 | trastuzumab | 2.7 | |
| IC-116 | HxBzL-103 | trastuzumab | 2.4 | |
| IC-117 | HxBzL-108 | trastuzumab | 2.3 | |
| IC-118 | HxBzL-109 | trastuzumab | 2.4 | |
| IC-119 | HxBzL-110 | trastuzumab | 2.4 | |
| IC-120 | HxBzL-105 | anti-h/rHER2 | 3.3 | |
| IC-121 | HxBzL-106 | anti-h/rHER2 | 3.3 | |
| IC-122 | HxBzL-30 | anti-h/rHER2 | 2.6 | |
| IC-123 | HxBzL-32 | anti-h/rHER2 | 2.7 | |
| IC-124 | HxBzL-123 | trastuzumab | 2.4 | |
| IC-125 | HxBzL-115 | trastuzumab | 2.5 | |
| IC-126 | HxBzL-114 | trastuzumab | 2.4 | |
| IC-127 | HxBzL-118 | trastuzumab | 2.5 | |
| IC-128 | HxBzL-122 | trastuzumab | 2.4 | |
| IC-129 | HxBzL-119 | trastuzumab | 2.5 | |
| IC-130 | HxBzL-117 | trastuzumab | 2.6 | |
| IC-131 | HxBzL-100 | trastuzumab | 2.6 | |
| IC-132 | HxBzL-116 | trastuzumab | 1.8 | |
| IC-133 | HxBzL-101 | trastuzumab | 2.5 | |
| IC-134 | HxBzL-99 | trastuzumab | 2.4 | |
| IC-135 | HxBzL-107 | trastuzumab | 3.7 | 0.01 |
| IC-136 | HxBzL-104 | trastuzumab | 4.1 | 1.1 |
| IC-137 | HxBzL-121 | trastuzumab | 1.9 | |
| IC-138 | HxBzL-125 | trastuzumab | 2.3 | |
| IC-139 | HxBzL-126 | trastuzumab | 2.3 | |
| IC-140 | HxBzL-124 | trastuzumab | 1.9 | 1.9 |
| IC-141 | HxBzL-120 | trastuzumab | 2.1 | |

Compositions of Immunoconjugates

The invention provides a composition, e.g., a pharmaceutically or pharmacologically acceptable composition or formulation, comprising a plurality of immunoconjugates as described herein and optionally a carrier therefor, e.g., a pharmaceutically or pharmacologically acceptable carrier. The immunoconjugates can be the same or different in the composition, i.e., the composition can comprise immunoconjugates that have the same number of adjuvants linked to the same positions on the antibody construct and/or immunoconjugates that have the same number of Hx adjuvants linked to different positions on the antibody construct, that have different numbers of adjuvants linked to the same positions on the antibody construct, or that have different numbers of adjuvants linked to different positions on the antibody construct.

In an exemplary embodiment, a composition comprising the immunoconjugate compounds comprises a mixture of the immunoconjugate compounds, wherein the average drug (Hx) loading per antibody in the mixture of immunoconjugate compounds is about 2 to about 5.

A composition of immunoconjugates of the invention can have an average adjuvant to antibody construct ratio (DAR) of about 0.4 to about 10. A skilled artisan will recognize that the number of 8-Het-2-aminobenzazepine adjuvants conjugated to the antibody construct may vary from immunoconjugate to immunoconjugate in a composition comprising multiple immunoconjugates of the invention and thus the adjuvant to antibody construct (e.g., antibody) ratio can be measured as an average which may be referred to as the drug to antibody ratio (DAR). The adjuvant to antibody construct (e.g., antibody) ratio can be assessed by any suitable means, many of which are known in the art.

The average number of adjuvant moieties per antibody (DAR) in preparations of immunoconjugates from conjugation reactions may be characterized by conventional means such as mass spectrometry, ELISA assay, and HPLC. The quantitative distribution of immunoconjugates in a composition in terms of p may also be determined. In some instances, separation, purification, and characterization of homogeneous immunoconjugates where p is a certain value from immunoconjugates with other drug loadings may be achieved by means such as reverse phase HPLC or electrophoresis.

In some embodiments, the composition further comprises one or more pharmaceutically or pharmacologically acceptable excipients. For example, the immunoconjugates of the invention can be formulated for parenteral administration, such as IV administration or administration into a body cavity or lumen of an organ. Alternatively, the immunoconjugates can be injected intra-tumorally. Compositions for injection will commonly comprise a solution of the immunoconjugate dissolved in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic monoglycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the immunoconjugate. The concentration of the immunoconjugate in the composition can vary widely, and will be selected primarily based on fluid volumes, viscosities, body weight, and the like, in accordance with the particular mode of administration selected and the patient's needs. In certain embodiments, the concentration of an immunoconjugate in a solution formulation for injection will range from about 0.1% (w/w) to about 10% (w/w).

Method of Treating Cancer with Immunoconjugates

The invention provides a method for treating cancer. The method includes administering a therapeutically effective amount of an immunoconjugate as described herein (e.g., as a composition as described herein) to a subject in need thereof, e.g., a subject that has cancer and is in need of treatment for the cancer. The method includes administering a therapeutically effective amount of an immunoconjugate (IC) selected from Tables 3a and 3b.

It is contemplated that the immunoconjugate of the present invention may be used to treat various hyperproliferative diseases or disorders, e.g. characterized by the overexpression of a tumor antigen. Exemplary hyperproliferative disorders include benign or malignant solid tumors and hematological disorders such as leukemia and lymphoid malignancies.

In another aspect, an immunoconjugate for use as a medicament is provided. In certain embodiments, the invention provides an immunoconjugate for use in a method of treating an individual comprising administering to the individual an effective amount of the immunoconjugate. In one such embodiment, the method further comprises administering to the individual an effective amount of at least one additional therapeutic agent, e.g., as described herein.

In a further aspect, the invention provides for the use of an immunoconjugate in the manufacture or preparation of a medicament. In one embodiment, the medicament is for treatment of cancer, the method comprising administering to an individual having cancer an effective amount of the medicament. In one such embodiment, the method further comprises administering to the individual an effective amount of at least one additional therapeutic agent, e.g., as described herein.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon) adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, and skin. In some embodiments, methods for treating non-small cell lung carcinoma include administering an immunoconjugate containing an antibody construct that is capable of binding HER2 (e.g., trastuzumab, pertuzumab, biosimilars thereof, or biobetters thereof).

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); infantile fibrosarcoma, gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; Ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); Kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Merkel cell carcinoma is a rare type of skin cancer that usually appears as a flesh-colored or bluish-red nodule on the face, head or neck. Merkel cell carcinoma is also called neuroendocrine carcinoma of the skin. In some embodiments, methods for treating Merkel cell carcinoma include administering an immunoconjugate containing an antibody construct that is capable of binding HER2 (e.g., trastuzumab, pertuzumab, biosimilars thereof, or biobetters thereof). In some embodiments, the Merkel cell carcinoma has metastasized when administration occurs.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Sternberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

Immunoconjugates of the invention can be used either alone or in combination with other agents in a therapy. For instance, an immunoconjugate may be co-administered with at least one additional therapeutic agent, such as a chemotherapeutic agent. Such combination therapies encompass combined administration (where two or more therapeutic agents are included in the same or separate formulations), and separate administration, in which case, administration of the immunoconjugate can occur prior to, simultaneously, and/or following, administration of the additional therapeutic agent and/or adjuvant. Immunoconjugates can also be used in combination with radiation therapy.

The immunoconjugates of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

The immunoconjugate is administered to a subject in need thereof in any therapeutically effective amount using any suitable dosing regimen, such as the dosing regimens utilized for labetuzumab, biosimilars thereof, and biobetters thereof. For example, the methods can include administering the immunoconjugate to provide a dose of from about 100 ng/kg to about 50 mg/kg to the subject. The immunoconjugate dose can range from about 5 mg/kg to about 50 mg/kg, from about 10 μg/kg to about 5 mg/kg, or from about 100 μg/kg to about 1 mg/kg. The immunoconjugate dose can be about 100, 200, 300, 400, or 500 μg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

In another aspect, the invention provides a method for preventing cancer. The method comprises administering a therapeutically effective amount of an immunoconjugate (e.g., as a composition as described above) to a subject. In certain embodiments, the subject is susceptible to a certain cancer to be prevented. For example, the methods can include administering the immunoconjugate to provide a dose of from about 100 ng/kg to about 50 mg/kg to the subject. The immunoconjugate dose can range from about 5 mg/kg to about 50 mg/kg, from about 10 μg/kg to about 5 mg/kg, or from about 100 μg/kg to about 1 mg/kg. The immunoconjugate dose can be about 100, 200, 300, 400, or 500 μg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

Some embodiments of the invention provide methods for treating cancer as described above, wherein the cancer is breast cancer. Breast cancer can originate from different areas in the breast, and a number of different types of breast cancer have been characterized. For example, the immunoconjugates of the invention can be used for treating ductal carcinoma in situ; invasive ductal carcinoma (e.g., tubular carcinoma; medullary carcinoma; mucinous carcinoma; papillary carcinoma; or cribriform carcinoma of the breast); lobular carcinoma in situ; invasive lobular carcinoma; inflammatory breast cancer; and other forms of breast cancer such as triple negative (test negative for estrogen receptors, progesterone receptors, and excess HER2 protein) breast cancer. In some embodiments, methods for treating breast cancer include administering an immunoconjugate containing an antibody construct that is capable of binding HER2, or tumors over-expressing HER2 (e.g. trastuzumab, pertuzumab, biosimilars, or biobetters thereof).

In some embodiments, the cancer is susceptible to a pro-inflammatory response induced by TLR7 and/or TLR8.

EXAMPLES
Example L-5 Synthesis of 4-[3-[2-[2-[2-[2-[2-[2-[2-[2-[2-[2-[4-[2-amino-4-[ethoxy(propyl)carbamoyl]-3H-1-benzazepin-8-yl]pyrazol-1-yl]ethoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-5
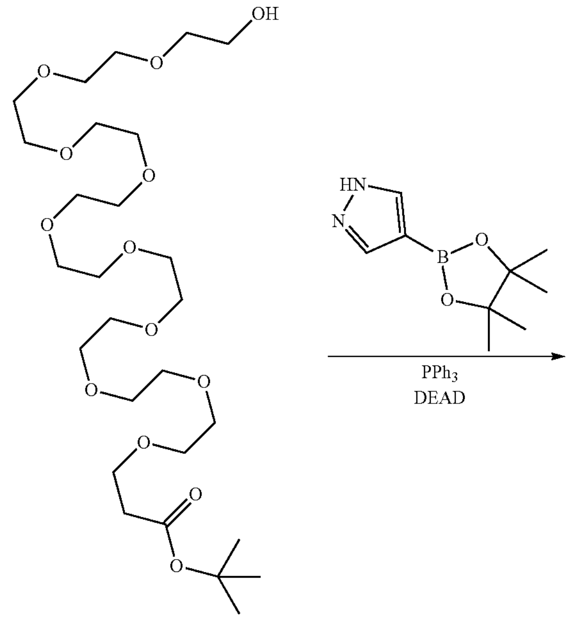
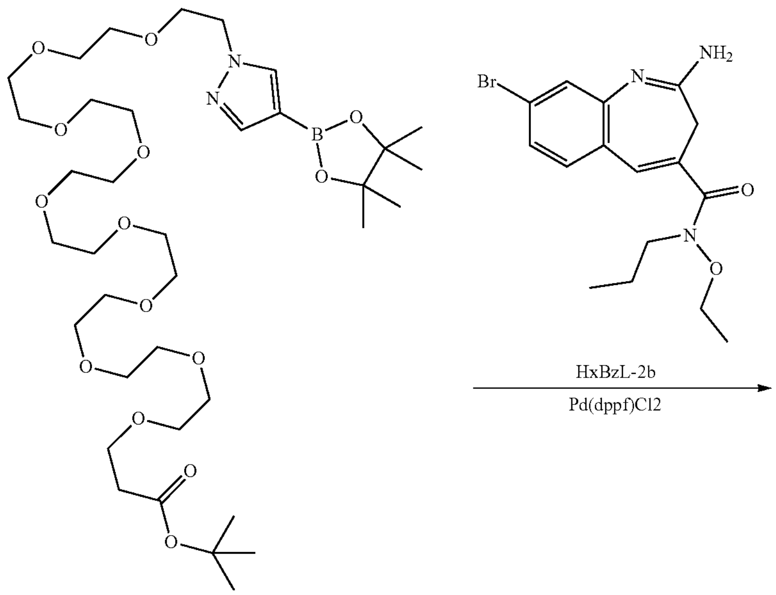
HxBzL-5a -continued
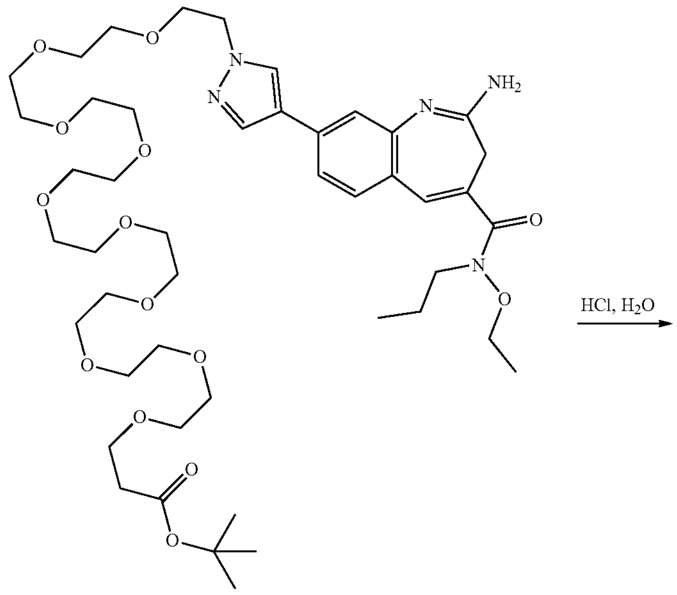
HxBzL-5c
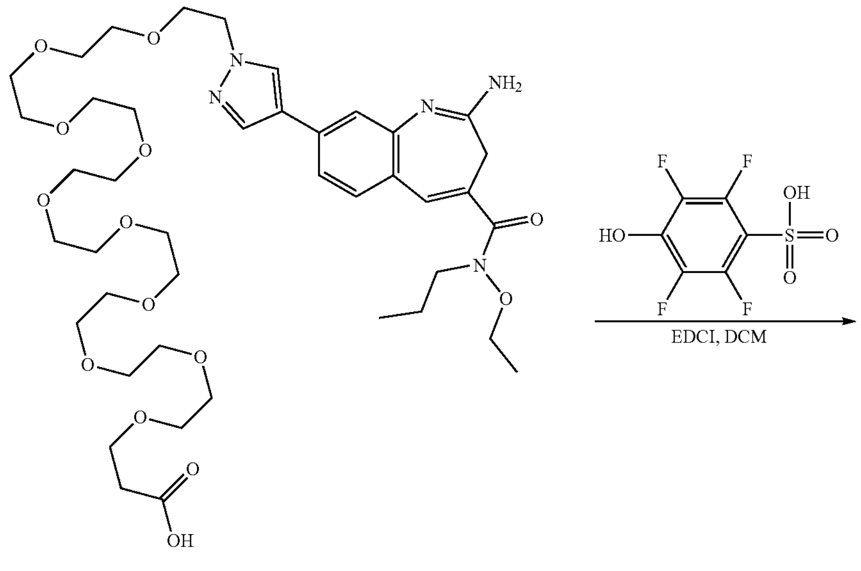
HxBzL-5d -continued

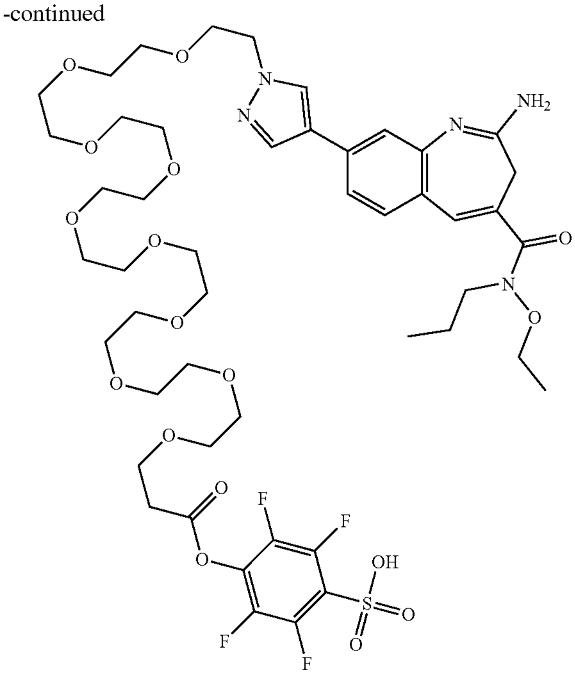

HxBzL-5

Preparation of tert-butyl 3-[2-[2-[2-[2-[2-[2-[2-[2-[2-[2-[4-(4,4,5,5-tetramethyl-1,3,2-dioxaborolan-2-yl)pyrazol-1-yl]ethoxy]ethoxy]ethoxy]ethoxy]ethoxy]ethoxy]ethoxy]ethoxy]ethoxy]ethoxy]propanoate, HxBzL-5a To a solution of 4-(4,4,5,5-tetramethyl-1,3,2-dioxaborolan-2-yl)-1H-pyrazole (1 g, 5.15 mmol, 1 eq) in THF (15 mL) was added $PPh_3$ (1.35 g, 5.15 mmol, 1 eq) and DEAD (0.89 g, 5.15 mmol, 0.94 mL, 1 eq) at 0° C. and stirred at 25° C. for 0.5 hr, then tert-butyl 3-[2-[2-[2-[2-[2-[2-[2-[2-[2-(2-hydroxyethoxy)ethoxy]ethoxy]ethoxy]ethoxy]ethoxy]ethoxy]ethoxy]ethoxy]ethoxy]propanoate (3.02 g, 5.15 mmol, 1 eq) was added and then stirred at 25° C. for 16 hr. The reaction mixture was diluted with water 20 mL and extracted with EtOAc (50 mL*3). The combined organic layers were washed with brine (20 mL*3), dried over $Na_2SO_4$, filtered and concentrated under reduced pressure to give a residue. The residue was purified by column chromatography ($SiO_2$, Petroleum ether/Ethyl acetate=50/1 to Ethyl acetate:MeOH=10:1) to afford HxBzL-5a (3.5 g, 4.59 mmol, 89.04% yield) as yellow oil.

Preparation of tert-butyl 3-[2-[2-[2-[2-[2-[2-[2-[2-[2-[2-[4-[2-amino-4-[ethoxy (propyl)carbamoyl]-3H-1-benzazepin-8-yl]pyrazol-1-yl]ethoxy]ethoxy]ethoxy]ethoxy]ethoxy]ethoxy]ethoxy]ethoxy]ethoxy]ethoxy]propanoate, HxBzL-5c A mixture of HxBzL-2a (625 mg, 819 umol, 2.5 eq), 2-amino-8-bromo-N-ethoxy-N-propyl-3H-1-benzazepine-4-carboxamide, HxBzL-2b (120 mg, 328 umol, 1 eq), a solution of $Na_2CO_3$ (69.5 mg, 655 umol, 2 eq) in Water (0.3 mL) and [LI bis(diphenylphosphino)ferrocene]palladium(II) dichloride, Pd(dppf)$Cl_2$ (23.9 mg, 32.8 umol, 0.1 eq) in DMF (3 mL) was de-gassed and then heated to 120° C. for 5 hr under $N_2$. The mixture was filtered and concentrated under reduced pressure, and the residue was purified by prep-HPLC (TFA condition; column: Phenomenex luna C18 250*50 mm*10 um; mobile phase: [water (0.1% TFA)-ACN]; B %: 35%-65%, 10 min) to afford HxBzL-5c (300 mg, 290 umol, 88.4% yield, TFA) as a yellow solid.

Preparation of 3-[2-[2-[2-[2-[2-[2-[2-[2-[2-[2-[4-[2-amino-4-[ethoxy(propyl) carbamoyl]-3H-1-benzazepin-8-yl]pyrazol-1-yl]ethoxy]ethoxy]ethoxy]ethoxy]ethoxy]ethoxy]ethoxy]ethoxy]ethoxy]ethoxy]propanoic acid, HxBzL-5d To a solution of HxBzL-5c (300 mg, 325 umol, 1 eq) in Water (3 mL) and MeCN (0.5 mL) was added HCl (12 M, 407 uL, 15 eq), and then stirred at 80° C. for 0.5 hr. The mixture was concentrated under reduced pressure to afford HxBzL-5d (200 mg, 222 umol, 68.1% yield, HCl) as a colorless oil.

Preparation of HxBzL-5

To a solution of HxBzL-5d (80.0 mg, 88.7 umol, 1 eq, HCl) and sodium; 2,3,5,6-tetrafluoro-4-hydroxy-benzenesulfonate (119 mg, 443 umol, 5 eq) in DCM (1 mL) and DMA (1 mL) was added 1-ethyl-3-(3-dimethylaminopropyl) carbodiimide hydrochloride, EDCI (84.9 mg, 443 umol, 5 eq), and then stirred at 25° C. for 0.5 hr. The mixture was filtered and concentrated under reduced pressure, the residue was purified by prep-HPLC (TFA condition; column: Phenomenex Synergi C18 150*25*10 um; mobile phase: [water (0.1% TFA)-ACN]; B %: 25%-50%, 8 min) to afford HxBzL-5 (30 mg, 24.8 umol, 28.01% yield, TFA) as a yellow oil. $^1H$ NMR (400 MHz, MeOD) δ 8.20 (s, 1H), 7.93 (s, 1H), 7.65-7.61 (m, 1H), 7.59 (s, 1H), 7.55-7.52 (m, 1H), 7.40 (s, 1H), 4.36 (t, J=4.8 Hz, 2H), 3.96 (q, J=7.2 Hz, 2H), 3.89-3.82 (m, 4H), 3.74 (t, J=7.2 Hz, 2H), 3.63-3.52 (m, 36H), 3.42 (s, 2H), 2.95 (t, J=5.6 Hz, 2H), 1.76 (sxt, J=7.2

Hz, 2H), 1.20 (t, J=7.2 Hz, 3H), 0.99 (t, J=7.6 Hz, 3H). LC/MS [M+H] 1094.4 (calculated); LC/MS [M+H] 1094.3 (observed).
Example L-7 Synthesis of 4-[3-[2-[2-[2-[2-[2-[2-[2-[2-[2-[3-[4-[5-[2-amino-4-[ethoxy(propyl)carbamoyl]-3H-1-benzazepin-8-yl]pyrimidin-2-yl]piperazin-1-yl]-3-oxo-propoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-7
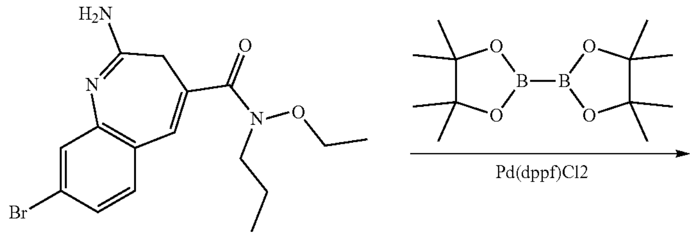
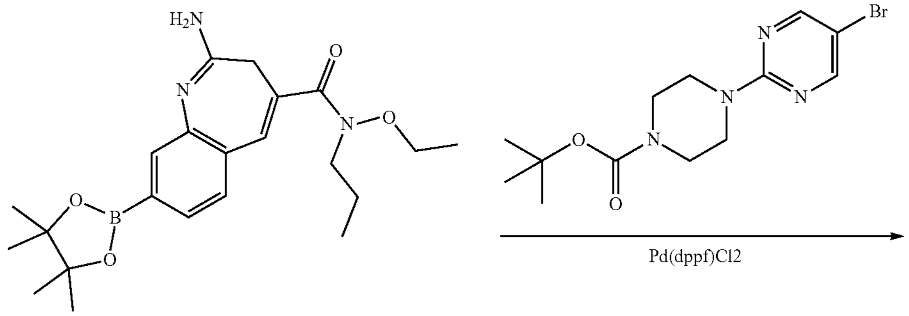
HxBz-4b
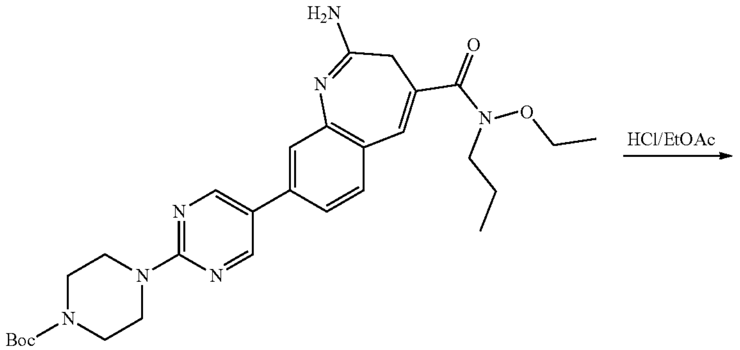
HxBz-4
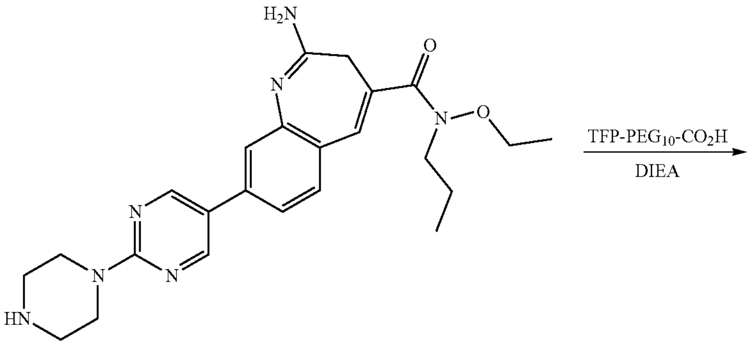
HxBz-3

-continued
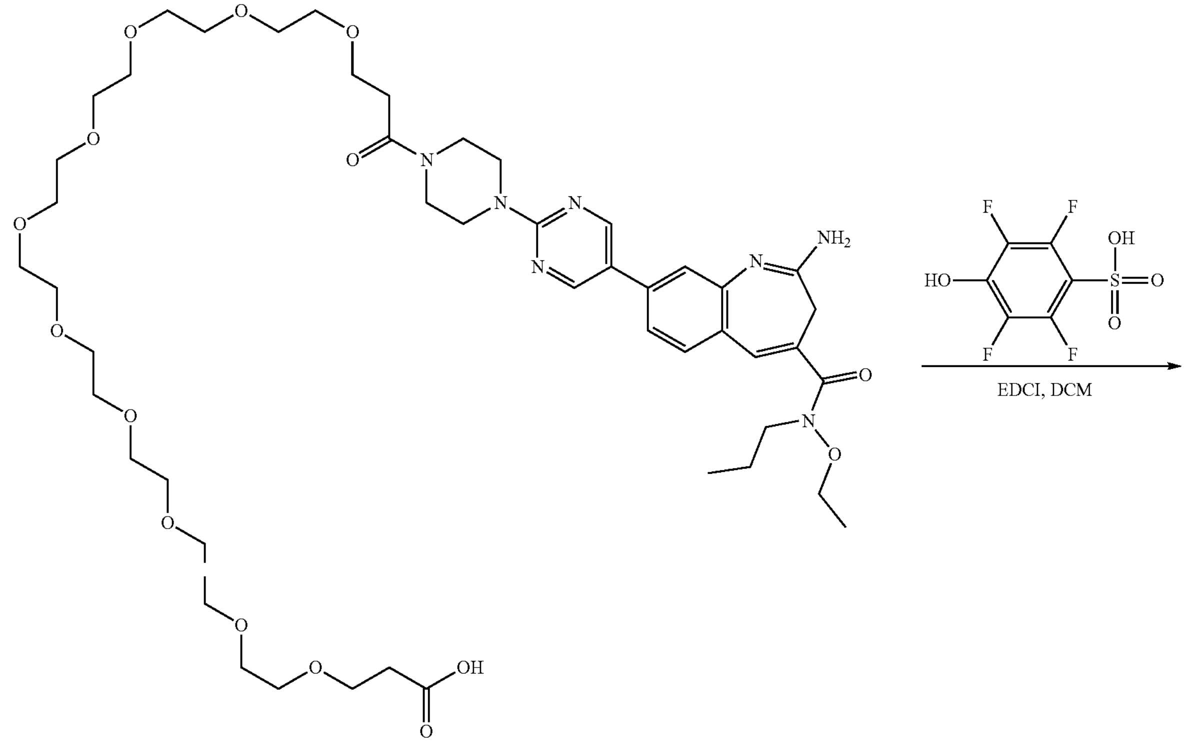
HxBzL-7a
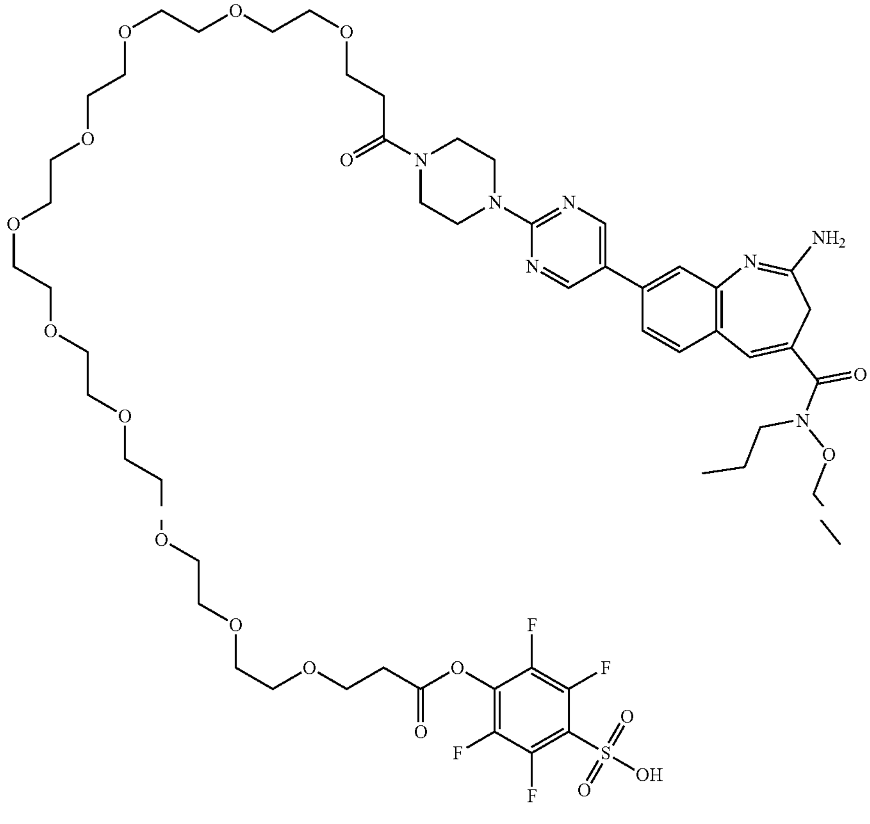
HxBzL-7

Preparation of 2-amino-N-ethoxy-N-propyl-8-(4,4,5,5-tetramethyl-1,3,2-dioxaborolan-2-yl)-3H-1-benzazepine-4-carboxamide, HxBz-4b A mixture of 2-amino-8-bromo-N-ethoxy-N-propyl-3H-1-benzazepine-4-carboxamide, HxBz-4a (0.5 g, 1.37 mmol, 1 eq), 4,4,5,5-tetramethyl-2-(4,4,5,5-tetramethyl-1,3,2-dioxaborolan-2-yl)-1,3,2-dioxaborolane (520 mg, 2.05 mmol, 1.5 eq), Pd(dppf)$Cl_2$ (99.9 mg, 137 umol, 0.1 eq), KOAc (335 mg, 3.41 mmol, 2.5 eq) in dioxane (10 mL) was stirred at 100° C. for 1 hr under $N_2$. Crude HxBz-4b was used for next step without purification (564 mg, 1.36 mmol, 99.96% yield) was obtained as black liquid.

Preparation of tert-butyl 4-[5-[2-amino-4-[ethoxy(propyl)carbamoyl]-3H-1-benzazepin-8-yl]pyrimidin-2-yl]piperazine-1-carboxylate, HxBz-4

A mixture of HxBz-4b (0.45 g, 1.09 mmol, 1 eq), Pd(dppf)$Cl_2$ (39.8 mg, 54.4 umol, 0.05 eq), $K_2CO_3$ (376 mg, 2.72 mmol, 2.5 eq), tert-butyl 4-(5-bromopyrimidin-2-yl)piperazine-1-carboxylate (374 mg, 1.09 mmol, 1 eq) in dioxane (4 mL) and Water (0.5 mL) was stirred at 100° C. for 1 hr under $N_2$. The mixture was concentrated to remove the dioxane, the residue was diluted with EtOAc (10 mL) and water (5 mL). The organic layer was dried over $Na_2SO_4$, concentrated to give a residue. The residue was purified by column chromatography ($SiO_2$, Petroleum ether/Ethyl acetate=1/0 to 0/1, then EA:MeOH=1.5:1), then further purified by Prep-HPLC, column: Phenomenex Synergi C18 150*25*10 um; mobile phase: [water (0.1% TFA)-ACN]; B %: 30%-55%, 8 min) to give HxBz-4 (0.35 g, 637 umol, 58.5% yield) as brown oil. $^1$H NMR (400 MHz, MeOD) δ8.74 (s, 2H), 7.72-7.63 (m, 2H), 7.60 (d, J=1.6 Hz, 1H), 7.45 (s, 1H), 3.99 (q, J=7.2 Hz, 2H), 3.93-3.88 (m, 4H), 3.77 (t, J=7.2 Hz, 2H), 3.60-3.51 (m, 4H), 3.43 (s, 2H), 1.80-1.75 (m, 2H), 1.51 (s, 9H), 1.22 (t, J=7.2 Hz, 3H), 1.02 (t, J=7.2 Hz, 3H). LC/MS [M+H] 550.3 (calculated); LC/MS [M+H] 550.2 (observed).

Preparation of 2-amino-N-ethoxy-8-(2-piperazin-1-ylpyrimidin-5-yl)-N-propyl-3H-1-benzazepine-4-carboxamide, HxBz-3

To a mixture of HxBz-4 (20 mg, 36.4 umol, 1 eq) in DCM (5 mL) was added HCl/EtOAc (4 M, 5 mL, 550 eq), and it was stirred at 25° C. for 0.5 hr. The mixture was concentrated to give HxBz-3 (10.5 mg, 21.4 umol, 58.9% yield, 99.233% purity, HCl) as white solid. $^1$H NMR (400 MHz, MeOD) δ8.70 (s, 2H), 7.65-7.47 (m, 3H), 7.32 (s, 1H), 4.14-3.96 (m, 4H), 3.86 (q, J=7.2 Hz, 2H), 3.64 (t, J=7.2 Hz, 2H), 3.31 (s, 2H), 3.25-3.21 (m, 4H), 1.71-1.62 (m, 2H), 1.08 (t, J=7.2 Hz, 3H), 0.89 (t, J=7.2 Hz, 3H). LC/MS [M+H] 450.3 (calculated); LC/MS [M+H] 450.1 (observed).

Preparation of 3-[2-[2-[2-[2-[2-[2-[2-[2-[2-[3-[[1-[3-[2-amino-4-[3-(tert- butoxycarbonylamino)propyl-ethoxy-carbamoyl]-3H-1-benzazepin-8-yl]phenyl] sulfonyl azetidin-3-yl]methylamino]-3-oxo-propoxy] ethoxy]ethoxy]ethoxy]ethoxy]ethoxy]ethoxy] ethoxy]ethoxy]ethoxy]propanoic acid, HxBzL-7a To a mixture of HxBz-3 (110 mg, 176 umol, 1 eq) in DMF (3 mL) was added DIEA (63.5 mg, 491 umol, 2.8 eq) and 3-[2-[2-[2-[2-[2-[2-[2-[2-[2-[3-oxo-3-(2,3,5,6-tetrafluoro-phenoxy)propoxy]ethoxy]ethoxy]ethoxy]ethoxy]ethoxy] ethoxy]ethoxy]ethoxy]ethoxy]propanoic acid (99.2 mg, 140 umol, 0.8 eq), and then stirred at 25° C. for 0.5 hr. The mixture was purified by Prep-HPLC (column: Waters Xbridge Prep OBD C18 150*40 mm*10 um; mobile phase: [water (10 mM $NH_4HCO_3$)-ACN]; B %: 20%-55%, 8 min) to give HxBzL-7a (28 mg, 24 umol, 13.7% yield) as yellow oil.

Preparation of HxBzL-7

To a mixture of HxBzL-7a (78 mg, 78.8 umol, 1 eq) and sodium; 2,3,5,6-tetrafluoro-4-hydroxy-benzenesulfonate (106 mg, 394 umol, 5 eq) in DCM (3 mL) and DMA (0.3 mL) was added EDCI (75.5 mg, 394 umol, 5 eq), and then it was stirred at 20° C. for 0.5 hr. The mixture was concentrated to give a residue. The residue was purified by prep-HPLC (column: Phenomenex Synergi C18 150*25*10 um; mobile phase: [water (0.1% TFA)-ACN]; B %: 20%-40%, 10 min) to give HxBzL-7 (39.8 mg, 26.4 umol, 33.5% yield, 95.944% purity, 2TFA) as colourless oil. $^1$H NMR (400 MHz, MeOD) δ8.75 (s, 2H), 7.76-7.55 (m, 3H), 7.45 (s, 1H), 4.02-3.73 (m, 16H), 3.68-3.58 (m, 36H), 3.37 (s, 2H), 2.99 (t, J=6.0 Hz, 2H), 2.76 (t, J=6.0 Hz, 2H), 1.85-1.74 (m, 2H), 1.25-1.20 (m, 3H), 1.02 (t, J=7.2 Hz, 3H). LC/MS [M+H] 1218.5 (calculated); LC/MS [M+H] 1218.3 (observed).

Example L-8 Synthesis of 4-[3-[2-[2-[2-[2-[2-[2-[2-[2-[2-[3-[[5-[2-amino-4-[ethoxy(propyl) carbamoyl]-3H-1-benzazepin-8-yl]pyrimidin-2-yl]methylamino]-3-oxo-propoxy]ethoxy]ethoxy]ethoxy] ethoxy]ethoxy]ethoxy]ethoxy]ethoxy]ethoxy] propanoyloxy]-2,3,5,6-tetrafluoro-benzenesulfonic acid, HxBzL-8

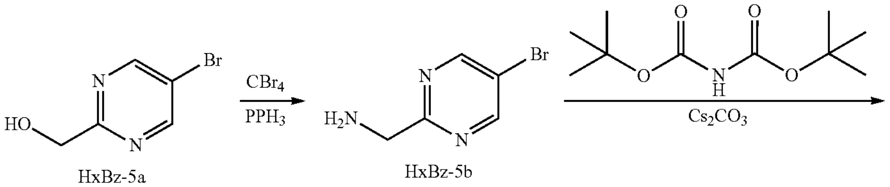

HxBz-5a HxBz-5b

-continued
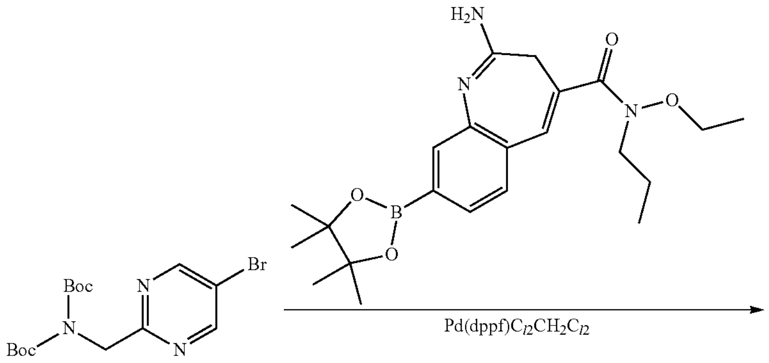
HxBz-5c
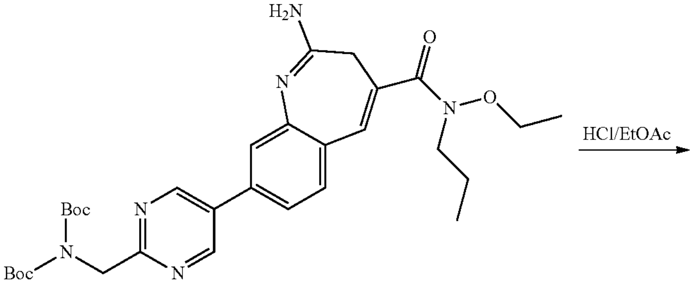
HxBz-5d
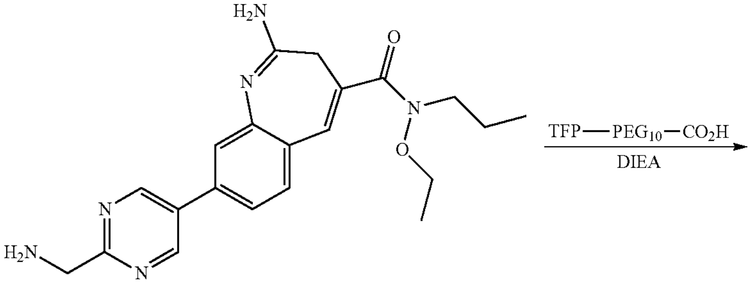
HxBz-5
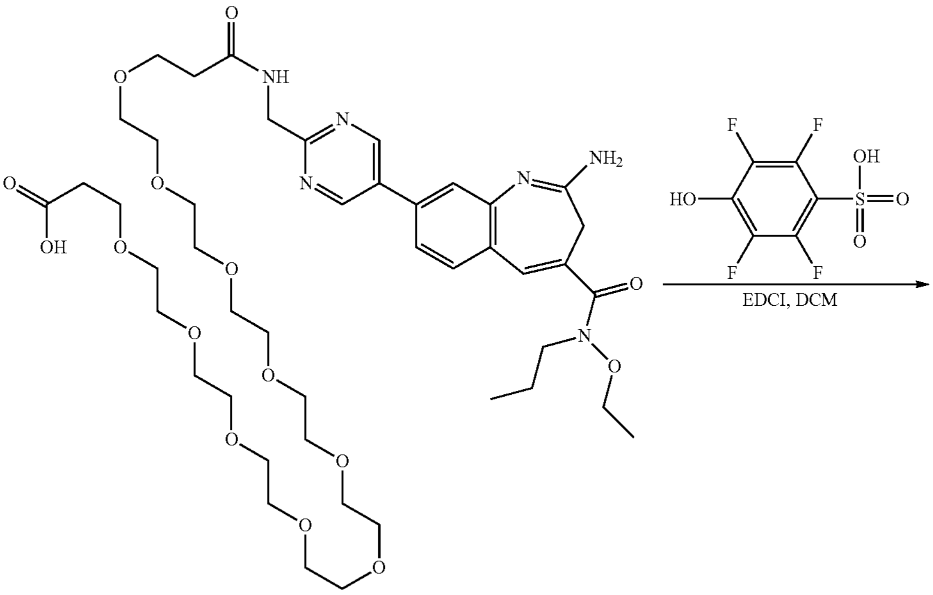
HxBzL-8a -continued

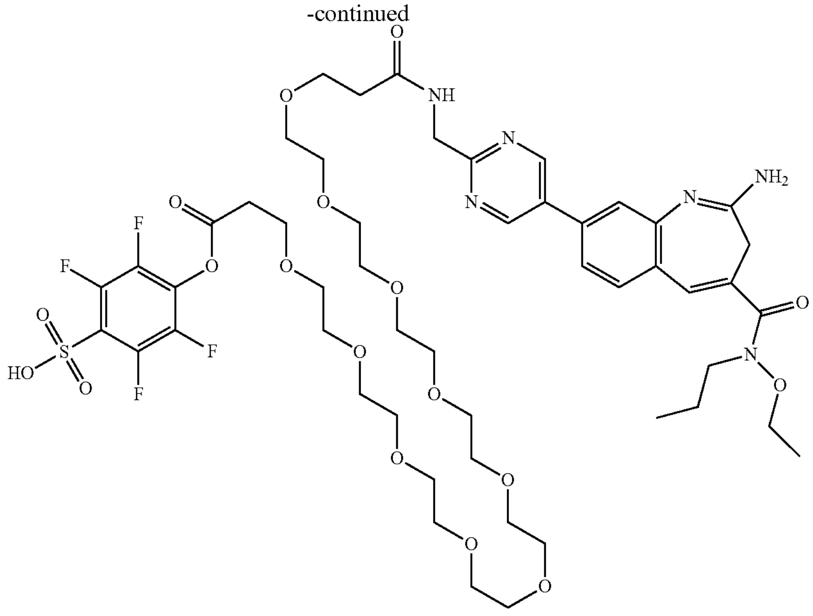

HxBzL-8

Preparation of 5-bromo-2-(bromomethyl)pyrimidine, HxBz-5b

To a solution of (5-bromopyrimidin-2-yl)methanol, HxBz-5a (300 mg, 1.59 mmol, 1.0 eq) in THE (10 mL) was added $PPh_3$ (499 mg, 1.90 mmol, 1.2 eq) and $CBr_4$ (631 mg, 1.90 mmol, 1.2 eq) in one portion at 0° C. under $N_2$. The mixture was stirred at 20° C. for 10 hours. Water (10 mL) was added and the aqueous phase was extracted with ethyl acetate (10 mL*3), the combined organic phase was washed with brine (10 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 8/1) to afford HxBz-5b (290 mg, 1.15 mmol, 72.4% yield) as white solid. $^1H$ NMR (400 MHz, $CDCl_3$) δ 8.81 (s, 2H), 4.59 (s, 2H).

Preparation of tert-butyl N-[(5-bromopyrimidin-2-yl) methyl]-N-tert-butoxycarbonyl-carbamate, HxBz-5c To a mixture of HxBz-5b (290 mg, 1.15 mmol, 1.0 eq) and tert-butyl N-tert-butoxycarbonyl-carbamate (250 mg, 1.15 mmol, 1.0 eq) in DMF (3 mL) was added $Cs_2CO_3$ (562 mg, 1.73 mmol, 1.5 eq) in portions at 20° C. under $N_2$, the mixture was stirred at 20° C. for 2.5 hours. Water (5 mL) was added and the aqueous phase was extracted with ethyl acetate (5 mL*3), the combined organic phase was washed with brine (5 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 5/1) to afford HxBz-5c (350 mg, 901 umol, 78.3% yield) as white solid. $^1H$ NMR (400 MHz, $CDCl_3$) δ 8.74 (s, 2H), 5.01 (s, 2H), 1.48 (s, 18H).

Preparation of tert-butyl N-[[5-[2-amino-4-[ethoxy (propyl)carbamoyl]-3H-1-benzaze-pin-8-yl]pyrimidin-2-yl]methyl]-N-tert-butoxycarbonyl-carbamate, HxBz-5d To a mixture of HxBz-5c (184 mg, 473 umol, 1.0 eq) and 2-amino-N-ethoxy-N-propyl-8-(4,4,5,5-tetramethyl-1,3,2-dioxaborolan-2-yl)-3H-1-benzazepine-4-carboxamide (195 mg, 474 umol, 1.0 eq) in dioxane (10 mL) and $H_2O$ (2 mL) was added $Pd(dppf)Cl_2{\cdot}CH_2Cl_2$ (19.3 mg, 23.7 umol, 0.05 eq) and $K_2CO_3$ (163 mg, 1.18 mmol, 2.5 eq) in one portion under $N_2$, the mixture was de-gassed and heated to 90° C. for 2 hours under $N_2$. Dioxane (10 mL) was removed in vacuum and water (20 mL) was added and the aqueous phase was extracted with ethyl acetate (10 mL*3), the combined organic phase was washed with brine (10 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 0/1 to Ethyl acetate/Methanol=10/1) to afford HxBz-5d (280 mg, 470.83 umol, 99.35% yield) as gray solid. $^1H$ NMR (400 MHz, MeOD) δ9.08 (s, 2H), 7.61 (s, 1H), 7.59 (d, J=2.8 Hz, 2H), 7.38 (s, 1H), 5.08 (s, 2H), 3.98 (q, J=7.2 Hz, 2H), 3.76 (t, J=7.2 Hz, 2H), 1.83-1.75 (m, 2H), 1.47 (s, 18H), 1.20 (t, J=7.2 Hz, 3H), 1.02 (t, J=7.2 Hz, 3H).

Preparation of 2-amino-8-[2-(aminomethyl)pyrimidin-5-yl]-N-ethoxy-N-propyl-3H-1-benzazepine-4-carboxamide, HxBz-5

To a solution of HxBz-5d (20.0 mg, 33.6 umol, 1.0 eq) in EtOAc (5 mL) was added HCl/EtOAc (4 M, 8.41 uL, 1.0 eq) in one portion at 20° C. under $N_2$, the mixture was stirred at 20° C. for 1 hour. The reaction mixture was concentrated in vacuum. The residue was purified by prep-HPLC (column: Phenomenex Synergi C18 150*25*10 um; mobile phase: [water (0.1% TFA)-ACN]; B %: 1%-30%, 8 min) to afford HxBz-5 (6.2 mg, 9.84 umol, 29.2% yield, 98.8% purity, 2TFA) as white solid. $^1H$ NMR (400 MHz, MeOD) δ9.22 (s, 2H), 7.82 (d, J=2.0 Hz, 1H), 7.79-7.75 (m, 2H), 7.47 (s, 1H), 4.49 (s, 2H), 4.00 (q, J=7.2 Hz, 2H), 3.78 (t, J=7.2 Hz, 2H), 3.46 (s, 2H), 1.85-1.77 (m, 2H), 1.22 (t, J=7.2 Hz, 3H), 1.03 (t, J=7.2 Hz, 3H). LC/MS [M+H] 395.2 (calculated); LC/MS [M+H] 395.1 (observed).

Preparation of 3-[2-[2-[2-[2-[2-[2-[2-[2-[2-[3-[[5-[2-amino-4-[ethoxy(propyl)carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-8a To a mixture of HxBz-5 (70 mg, 149 umol, 1.0 eq, 2HCl) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (127 mg, 179 umol, 1.2 eq) in DMF (0.5 mL) was added DIEA (77.4 mg, 599 umol, 104 uL, 4.0 eq) in one portion at 25° C. under $N_2$, the mixture was stirred at 25° C. for 0.5 hour. The reaction mixture was filtered and filtrate was purified by prep-HPLC (column: Phenomenex luna C18 80*40 mm*3 um; mobile phase: [water (0.04% HCl)-ACN]; B %: 12%-39%, 5.5 min) to afford HxBzL-8a (50.0 mg, 53.4 umol, 35.7% yield) as yellow oil. $^1$H NMR (400 MHz, MeOD) δ9.14 (s, 2H), 7.86-7.81 (m, 1H), 7.78-7.74 (m, 2H), 7.48 (s, 1H), 4.72 (s, 2H), 4.00 (q, J=7.2 Hz, 2H), 3.85-3.71 (m, 8H), 3.69-3.58 (m, 38H), 3.47 (s, 2H), 2.62 (t, J=6.0 Hz, 2H), 2.55 (t, J=6.4 Hz, 2H), 1.85-1.76 (m, 2H), 1.23 (t, J=7.2 Hz, 3H), 1.03 (t, J=7.2 Hz, 3H).

Preparation of HxBzL-8

To a mixture of HxBzL-8a (60 mg, 61.7 umol, 1.0 eq, HCl) and (2,3,5,6-tetrafluoro-4-hydroxy-phenyl)sulfonyloxysodium (99.3 mg, 370 umol, 6.0 eq) in DCM (2 mL) and DMA (0.5 mL) was added EDCI (71.0 mg, 370 umol, 6.0 eq) in one portion at 25° C. under $N_2$, the mixture was stirred at 25° C. for 1 hours. The reaction mixture was filtered and the filtrate was purified by prep-HPLC (column: Phenomenex Synergi C18 150*25*10 um; mobile phase: [water (0.1% TFA)-ACN]; B %: 20%-45%, 8 min) to afford HxBzL-8 (38.0 mg, 30.5 umol, 49.3% yield, 93.3% purity) as yellow oil. $^1$H NMR (400 MHz, MeOD) δ9.11 (s, 2H), 7.83-7.79 (m, 1H), 7.77 (s, 1H), 7.76-7.71 (m, 1H), 7.47 (s, 1H), 4.71 (s, 2H), 4.00 (q, J=7.2 Hz, 2H), 3.88 (t, J=5.6 Hz, 2H), 3.85-3.75 (m, 5H), 3.70-3.57 (m, 38H), 3.47 (s, 2H), 2.99 (t, J=6.0 Hz, 2H), 2.62 (t, J=4 Hz, 2H), 1.85-1.75 (m, 2H), 1.23 (t, J=7.2 Hz, 3H), 1.02 (t, J=7.2 Hz, 3H). LC/MS [M+H] 1163.3 (calculated); LC/MS [M+H] 1163.3 (observed).

Example L-10 Synthesis of 4-[3-[2-[2-[2-[2-[2-[2-[2-[2-[2-[3-[[1-[[5-[2-amino-4-[ethoxy(propyl)carbamoyl]-3H-1-benzazepin-8-yl]-3-pyridyl]sulfonyl]azetidin-3-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-10

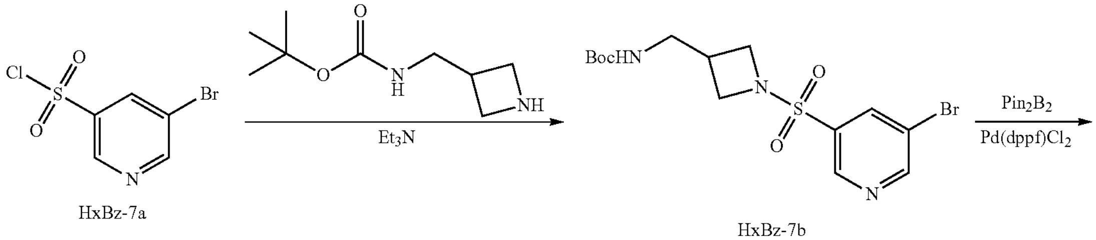

HxBz-7a

HxBz-7b

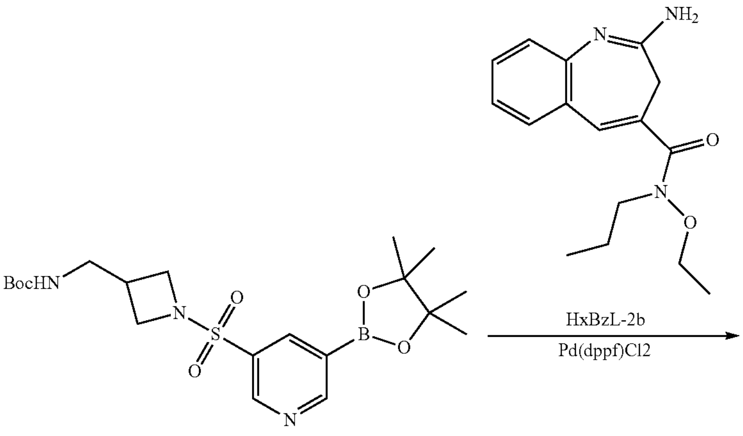

HxBz-7c

-continued
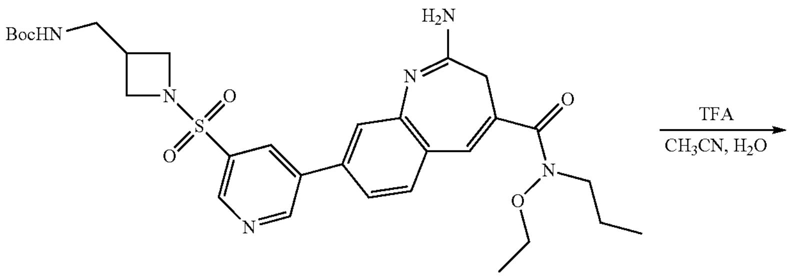
HxBz-7d
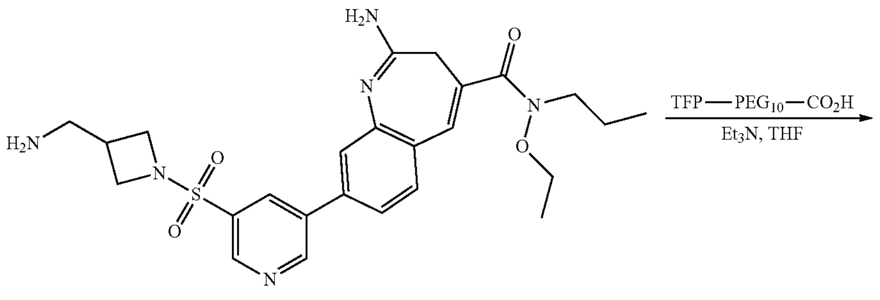
HxBz-7
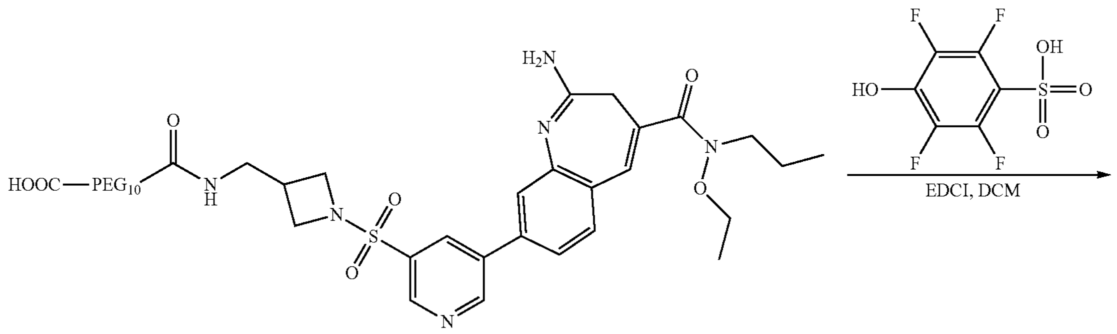
HxBzL-10a
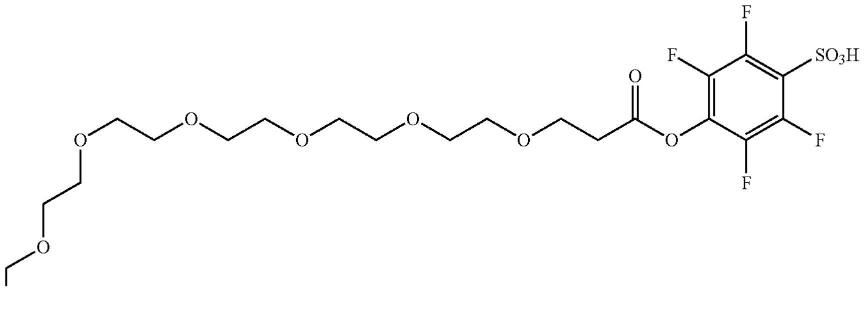

-continued

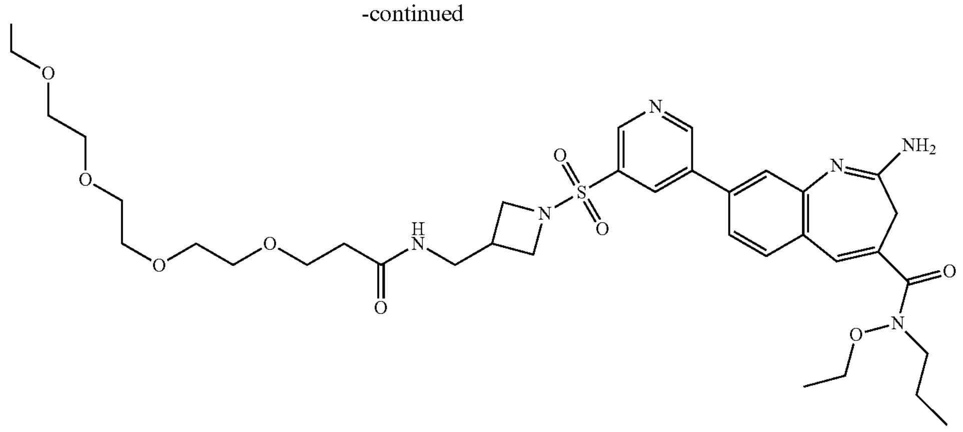

HxBzL-10

Preparation of tert-butyl ((1-((5-bromopyridin-3-yl) sulfonyl)azetidin-3-yl)methyl)carbamate, HxBz-7b To a mixture of tert-butyl N-(azetidin-3-ylmethyl)carbamate (762 mg, 4.09 mmol, 1.05 eq) and 5-bromopyridine-3-sulfonyl chloride, HxBz-7a (1 g, 3.90 mmol, 2.26 mL, 1 eq) in DCM (20 mL) was added $Et_3N$ (789 mg, 7.80 mmol, 1.09 mL, 2 eq) at 25° C. under $N_2$, and then stirred at 25° C. for 1 hours. The mixture was added $H_2O$ (20 mL), then concentrated in vacuum to remove DCM. Desired solid precipitated from the mixture, filtered to get the desired product HxBz-7b (1.1 g, 2.71 mmol, 69.45% yield) as white solid. $^1H$ NMR (DMSO-$d_6$, 400 MHz) δ9.09 (d, J=2.0 Hz, 1H), 8.93 (d, J=2.0 Hz, 1H), 8.40 (t, J=2.0 Hz, 1H), 6.90 (t, J=6.0 Hz, 1H), 3.80 (t, J=8.4 Hz, 2H), 3.52 (dd, J=6.0, 8.0 Hz, 2H), 2.93 (t, J=6.0 Hz, 2H), 2.56-2.52 (m, 1H), 1.34 (s, 9H).

Preparation of tert-butyl ((1-((5-(4,4,5,5-tetramethyl-1,3,2-dioxaborolan-2-yl) pyridin-3-yl)sulfonyl) azetidin-3-yl)methyl)carbamate, HxBz-7c To a mixture of HxBz-7b (0.75 g, 1.85 mmol, 1 eq) 4,4,5,5-tetramethyl-2-(4,4,5,5-tetramethyl-1,3,2-dioxaborolan-2-yl)-1,3,2-dioxaborolane, $Pin_2B_2$, Bis(pinacolato)diboron, CAS Reg. No. 78183~34-3 (703 mg, 2.77 mmol, 1.5 eq) KOAc (362 mg, 3.69 mmol, 2 eq) in dioxane (15 mL) was added Pd(dppf)$Cl_2$ (67.5 mg, 92.3 umol, 0.05 eq) at 25° C. under $N_2$, and then stirred at 100° C. for 1 hours. The mixture was filtered and concentrated in vacuum. Afforded HxBz-7c (0.85 g, crude) as yellow oil.

Preparation of tert-butyl ((1-((5-(2-amino-4-(ethoxy (propyl)carbamoyl)-3H-benzo [b]azepin-8-yl)pyridin-3-yl)sulfonyl)azetidin-3-yl)methyl)carbamate, HxBz-7d To a mixture of HxBz-7c (0.85 g, 1.87 mmol, 1 eq) and 2-amino-8-bromo-N-ethoxy-N-propyl-3H-1-benzazepine-4-carboxamide, HxBzL-2b (755 mg, 2.06 mmol, 1.1 eq) in dioxane (15 mL) was added $K_2CO_3$ (518 mg, 3.75 mmol, 2 eq) in $H_2O$ (3 mL) and Pd(dppf)$Cl_2$ (68.6 mg, 93.7 umol, 0.05 eq) at 25° C. under $N_2$, and it was stirred at 100° C. for 1 hour. The mixture was poured into $H_2O$ (50 mL). The aqueous phase was extracted with ethyl acetate (150 mL*3). The combined organic phase was washed with brine (100 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=5/1, 0/1 to EtOAc/MeOH=10/1). Afforded HxBz-7d (1 g, 1.63 mmol, 87.05% yield) as off-white solid. $^1H$ NMR (DMSO-$d_6$, 400 MHz) δ9.18 (d, J=2.0 Hz, 1H), 8.95 (d, J=2.0 Hz, 1H), 8.42 (t, J=2.0 Hz, 1H), 7.55-7.51 (m, 2H), 7.49-7.45 (m, 1H), 7.30 (s, 1H), 3.96 (q, J=7.6 Hz 2H), 3.90 (t, J=8.0 Hz, 2H), 3.74 (t, J=7.2 Hz, 2H), 3.60 (dd, J=6.0, 8.0 Hz, 2H), 3.35 (s, 2H), 3.06 (d, J=6.0 Hz, 2H), 2.69-2.58 (m, 1H), 1.77 (sxt, J=7.2 Hz, 2H), 1.36 (s, 9H), 1.17 (t, J=7.2 Hz, 3H), 0.99 (t, J=7.2 Hz, 3H).

Preparation of 2-amino-8-[5-[3-(aminomethyl)azetidin-1-yl]sulfonyl-3-pyridyl]-N-ethoxy-N-propyl-3H-1-benzazepine-4-carboxamide, HxBz-7

To a mixture of HxBz-7d (0.8 g, 1.31 mmol, 1 eq) in $CH_3CN$ (10 mL) and $H_2O$ (10 mL) was added TFA (1.49 g, 13.1 mmol, 967 uL, 10 eq) at 25° C. under $N_2$, and then stirred at 80° C. for 1 hours. The mixture was concentrated in vacuum to remove $CH_3CN$, the aqueous was extracted with MTBE (20*3) discarded, then the water phase was freeze-dried directly to afford HxBz-7 (0.9 g, 1.22 mmol, 93.07% yield, 2TFA) as off-white solid. $^1H$ NMR (MeOD, 400 MHz) δ 9.24 (d, J=2.0 Hz, 1H), 9.04 (d, J=2.0 Hz, 1H), 8.50 (t, J=2.0 Hz, 1H), 7.87-7.78 (m, 2H), 7.77-7.72 (m, 1H), 7.46 (s, 1H), 4.06-3.94 (m, 4H), 3.79-3.70 (m, 4H), 3.45 (s, 2H), 3.12 (d, J=7.6 Hz, 2H), 2.83-2.73 (m, 1H), 1.79 (sxt, J=7.2 Hz, 2H), 1.20 (t, J=7.2 Hz, 3H), 1.01 (t, J=7.2 Hz, 3H). LC/MS [M+H] 513.2 (calculated); LC/MS [M+H] 513.2 (observed).

Preparation of 1-(1-((5-(2-amino-4-(ethoxy(propyl) carbamoyl)-3H-benzo [b]azepin-8-yl)pyridin-3-yl) sulfonyl)azetidin-3-yl)-3-oxo-6,9,12,15,18,21,24,27,30,33-decaoxa-2-azahexatriacontan-36-oic acid, HxBzL-10a To a mixture of HxBz-7 (451 mg, 638 umol, 1 eq) in THE (10 mL) was added $Et_3N$ (161 mg, 1.60 mmol, 222 uL, 2.5 eq) at 0° C. under $N_2$, and then stirred at 0° C. for 1 hours. The mixture was poured into $H_2O$ (5 mL), the pH of the mixture was adjusted pH to ~6 with TFA at 0° C., then extracted with MTBE (10 mL) discarded, the aqueous phase was further extracted with DCM/i-PrOH (20 mL*3). The combined organic phase was dried with anhydrous $Na_2SO_4$, filtered and concentrated in vacuum to afford HxBzL-10a (0.6 g, 569.68 umol, 89.25% yield) as light yellow oil.

Preparation of HxBzL-10

To a mixture of HxBzL-10a (0.6 g, 570 umol, 1 eq) and (2,3,5,6-tetrafluoro-4-hydroxy-phenyl)sulfonyloxysodium (611 mg, 2.28 mmol, 4 eq) in DCM (10 mL) and DMA (1.5 mL) was added EDCI (437 mg, 2.28 mmol, 4 eq) at 25° C. under $N_2$, and then stirred at 25° C. for 0.5 hours. The mixture was concentrated in vacuum. The residue was filtered and purified by prep-HPLC column: Phenomenex luna C18 250*50 mm*10 um; mobile phase: [water (0.1% TFA)-ACN]; B %: 30%-50%, 10 min to give HxBzL-10 (370 mg, 288.76 umol, 50.69% yield) as white solid. $^1H$ NMR (MeOD, 400 MHz) δ9.24 (d, J=2.0 Hz, 1H), 9.03 (d, J=2.0 Hz, 1H), 8.51 (t, J=2.0 Hz, 1H), 7.91-7.84 (m, 2H), 7.74 (d, J=8.8 Hz, 1H), 7.47 (s, 1H), 4.03-3.91 (m, 4H), 3.86 (t, J=6.0 Hz, 2H), 3.76 (t, J=7.2 Hz, 2H), 3.66-3.49 (m, 40H), 3.47 (s, 2H), 3.21 (d, J=6.4 Hz, 2H), 3.01-2.92 (m, 2H), 2.79-2.68 (m, 1H), 2.29 (t, J=6.0 Hz, 2H), 1.78 (sxt, J=7.2 Hz, 2H), 1.21 (t, J=7.2 Hz, 3H), 1.01 (t, J=7.2 Hz, 3H). LC/MS [M+H] 1281.5 (calculated); LC/MS [M+H]1281.6 (observed).

Example L-15 Synthesis of 4-[3-[2-[2-[2-[2-[2-[2-[2-[2-[2-[3-[[5-[2-amino-4-[2-(cyclobutoxy-carbonylamino)ethoxy-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-15

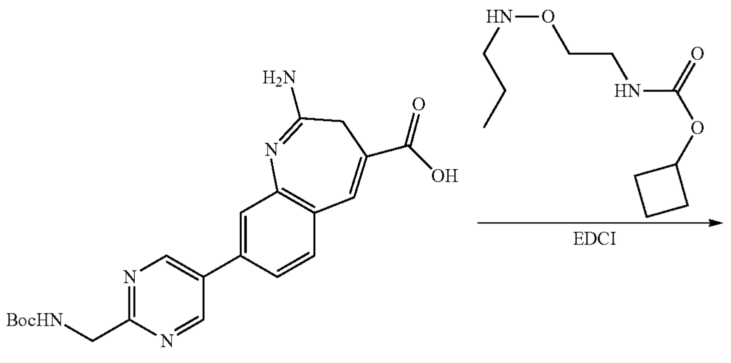

HxBz-15a

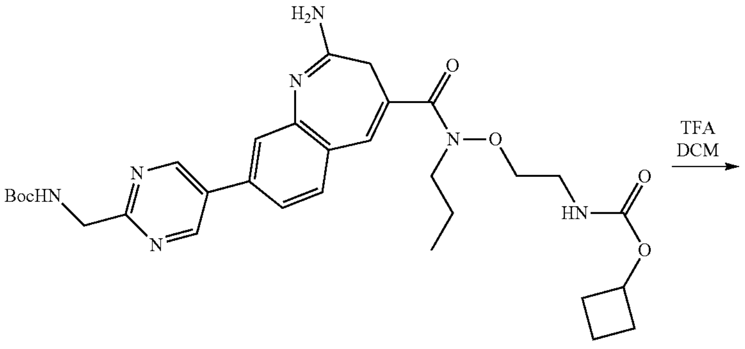

HxBz-15b

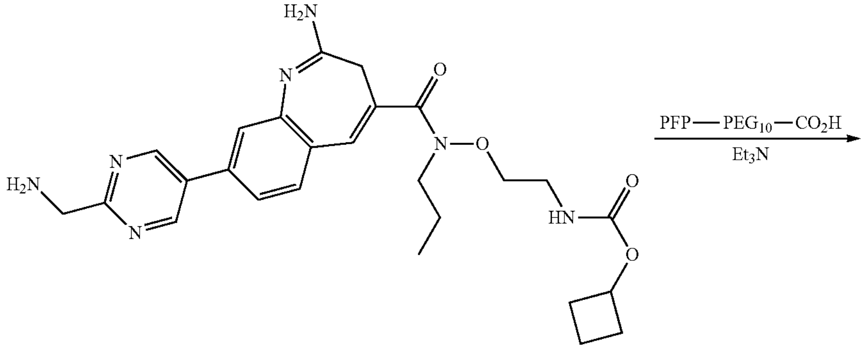

HxBz-15

-continued

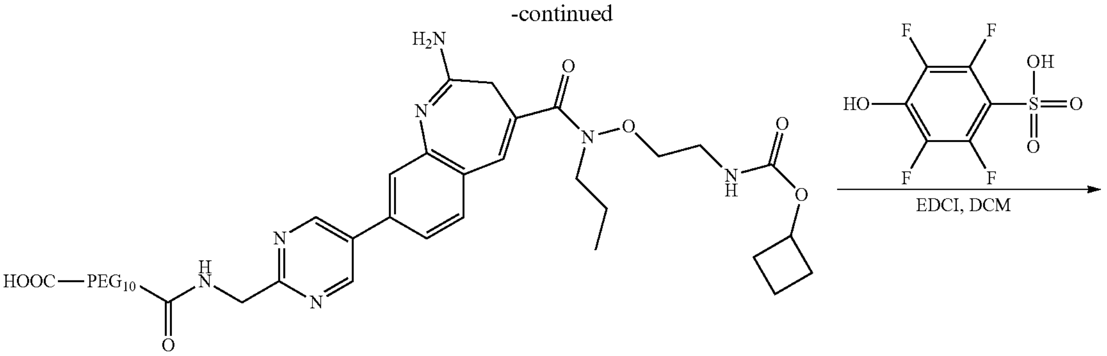

HxBzL-15a

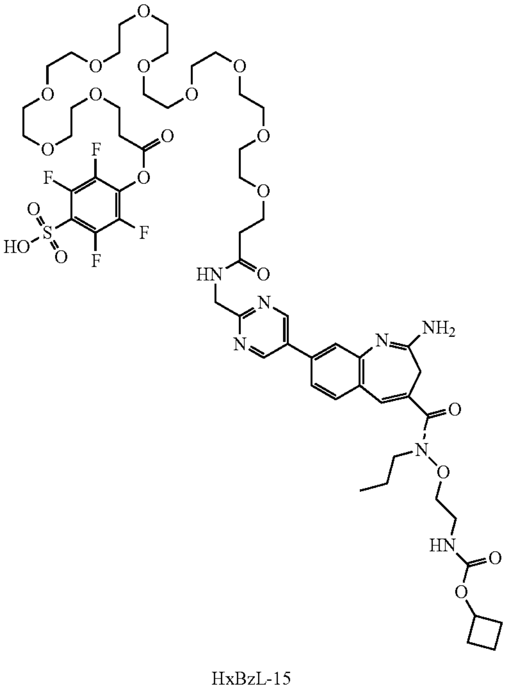 [SMILES: CCCN(OCCNC(=O)OC1CCC1)C(=O)C1=Cc2ccc(-c3cnc(CNC(=O)CCOCCOCCOCCOCCOCCOCCOCCOCCOCCOCCC(=O)Oc4c(F)c(F)c(S(=O)(=O)O)c(F)c4F)nc3)cc2N=C(N)C1]

HxBzL-15

Preparation of cyclobutyl N-[2-[[2-amino-8-[2-[(tert-butoxycarbonylamino)methyl] pyrimidin-5-yl]-3H-1-benzazepine-4-carbonyl]-propyl-amino] oxyethyl]carbamate, HxBz-15b To a mixture of 2-amino-8-[2-[(tert-butoxycarbonylamino)methyl]pyrimidin-5-yl]-3H-1-benzazepine-4-carboxylic acid, HxBz-15a (250 mg, 611 umol, 1.0 eq) and cyclobutyl N-[2-(propylamino-oxy)ethyl]carbamate (201 mg, 794 umol, 1.3 eq, HCl) in DCM (4 mL) and DMA (2 mL) was added EDCI (468 mg, 2.44 mmol, 4.0 eq) in one portion at 25° C. under $N_2$, and it was stirred at 25° C. for 2 hours. DCM (4 mL) was removed in vacuum, water (10 mL) was added and the aqueous phase was extracted with ethyl acetate (10 mL*3), the combined organic phase was washed with brine (5 mL*2), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 0/1 to Ethyl acetate/Methanol=10/1) to afford HxBz-15b (190 mg, 313 umol, 51.2% yield) as brown oil. $^1$H NMR (400 MHz, MeOD) δ9.08 (s, 2H), 7.63 (d, J=8.0 Hz, 1H), 7.58-7.52 (m, 2H), 7.37 (s, 1H), 4.74-4.67 (m, 2H), 4.54 (s, 2H), 3.96 (t, J=4.8 Hz, 2H), 3.76 (t, J=7.2 Hz, 2H), 3.33 (s, 2H), 2.20 (dd, J=2.8, 5.2 Hz, 2H), 1.94-1.86 (m, 2H), 1.82-1.75 (m, 2H), 1.50 (s, 9H), 1.38 (d, J=1.6 Hz, 2H), 1.01 (t, J=7.2 Hz, 3H).

Preparation of cyclobutyl N-[2-[[2-amino-8-[2-(aminomethyl)pyrimidin-5-yl]-3H-1-benzazepine-4-carbonyl]-propyl-amino]oxyethyl]carbamate, HxBz-15

To a solution of HxBz-15b (190 mg, 313 umol, 1.0 eq) in DCM (5 mL) was added $CF_3COOH$ (535 mg, 4.69 mmol, 347 uL, 15 eq) in one portion at 25° C. under $N_2$, and then stirred at 25° C. for 1.5 hours. DCM (5 mL) was removed in vacuum and the residue was diluted with water (10 mL), the aqueous phase was extracted with MTBE (5 mL*4) to remove excess TFA, then the aqueous phase was freeze-dried to afford HxBz-15 (130 mg, 169 umol, 54.1% yield, 95.7% purity, 2TFA) as brown solid. $^1$H NMR (400 MHz, MeOD) δ=9.21 (s, 2H), 7.85-7.76 (m, 3H), 7.49 (s, 1H), 4.66 (t, J=7.2 Hz, 1H), 4.48 (s, 2H), 3.96 (t, J=5.2 Hz, 2H), 3.76 (t, J=7.2 Hz, 2H), 3.43 (s, 2H), 3.31 (s, 2H), 2.20-2.10 (m, 2H), 1.91-1.83 (m, 2H), 1.81-1.74 (m, 2H), 1.70-1.60 (m, 1H), 1.57-1.47 (m, 1H), 1.00 (t, J=7.2 Hz, 3H). LC/MS [M+H] 508.3 (calculated); LC/MS [M+H] 508.1 (observed).

Preparation of 3-[2-[2-[2-[2-[2-[2-[2-[2-[2-[3-[[5-[2-amino-4-[2-(cyclobutoxycarbonyl amino)ethoxy-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-15a To a mixture of HxBz-15 (105 mg, 181 umol, 1.0 eq, 2HCl) and $Et_3N$ (73.2 mg, 723 umol, 100 uL, 4.0 eq) in DMF (1.5 mL) was added 3-[2-[2-[2-[2-[2-[2-[2-[2-[2-[3-oxo-3-(2,3,4,5,6-pentafluorophenoxy)propoxy]ethoxy]ethoxy]ethoxy]ethoxy]ethoxy]ethoxy]ethoxy]ethoxy]ethoxy]propanoic acid, PFP-PEG10-CO2H (131 mg, 181 umol, 1.0 eq) at 0° C. under $N_2$, and it was stirred at 0° C. for 0.5 hour and then was heated 25° C. for another 0.5 hour. The reaction mixture was concentrated, the residue was diluted with water (5 mL) and the aqueous phase was extracted with ethyl acetate (3 mL*2)-discarded, then the aqueous phase was further extracted with DCM/iPrOH=3/1 (5 mL*3), the combined organic phase was dried with anhydrous $Na_2SO_4$, filtered and concentrated in vacuum to afford HxBzL-15a (100 mg, 95.4 umol, 52.7% yield) as yellow oil.

Preparation of HxBzL-15

To a mixture of HxBzL-15a (100 mg, 95.4 umol, 1.0 eq) and (2,3,5,6-tetrafluoro-4-hydroxy-phenyl)sulfonyloxy sodium (128 mg, 477 umol, 5.0 eq) in DCM (1 mL) and DMA (0.5 mL) was added EDCI (91.4 mg, 477 umol, 5.0 eq) in one portion at 25° C. under $N_2$, and then stirred at 25° C. for 1 hour. The reaction mixture was filtered and the filtrate was purified by prep-HPLC (column: Phenomenex Synergi C18 150*25*10 um; mobile phase: [water (0.1% TFA)-ACN]; B %: 15%-35%, 8 min) to afford HxBzL-15 (35.1 mg, 25.6 umol, 26.9% yield, 93.3% purity) as light yellow oil. $^1H$ NMR (400 MHz, MeOD) δ9.12 (s, 2H), 7.84-7.77 (m, 3H), 7.52 (s, 1H), 4.75-4.67 (m, 3H), 3.99 (t, J=5.2 Hz, 2H), 3.88 (t, J=6.0 Hz, 2H), 3.82 (t, J=6.0 Hz, 2H), 3.78 (t, J=7.2 Hz, 2H), 3.70-3.57 (m, 38H), 3.45 (s, 2H), 3.01-2.97 (m, 2H), 2.62 (t, J=6.0 Hz, 2H), 2.24-2.14 (m, 2H), 1.96-1.86 (m, 2H), 1.84-1.75 (m, 2H), 1.73-1.61 (m, 1H), 1.59-1.49 (m, 1H), 1.01 (t, J=7.2 Hz, 3H). LC/MS [M+H] 1276.5 (calculated); LC/MS [M+H] 1276.6 (observed).

Example L-16 Synthesis of 4-[3-[2-[2-[2-[2-[2-[2-[2-[2-[2-[3-[[5-[2-amino-4-[2-(cyclobutylcarbamoylamino)ethoxy-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-16

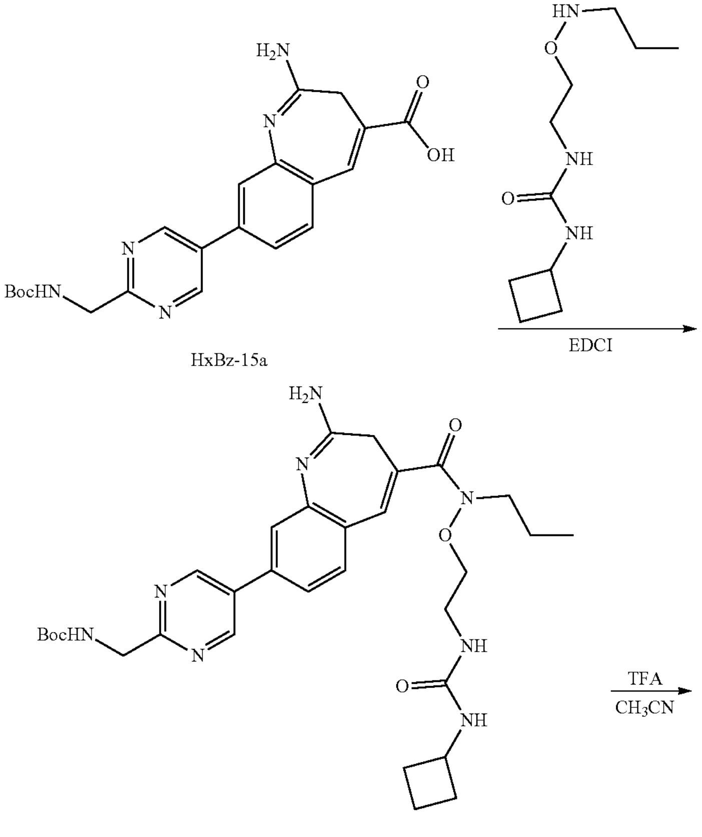

HxBz-15a

HxBz-16a

-continued
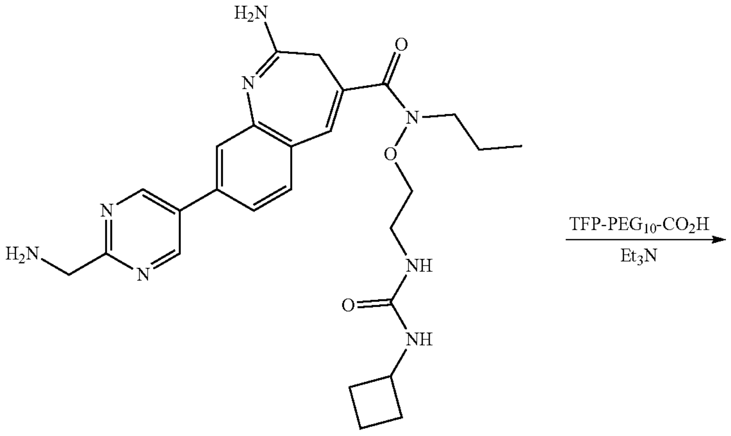
HxBz-16
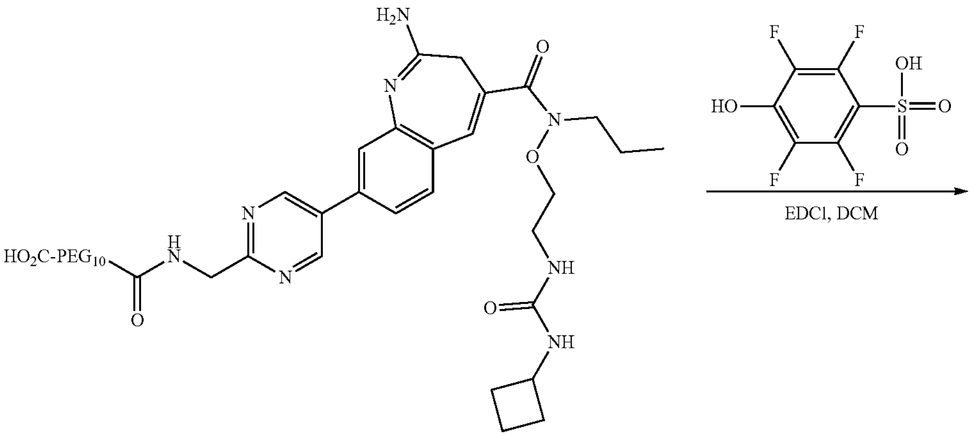
HxBzL-16a

-continued

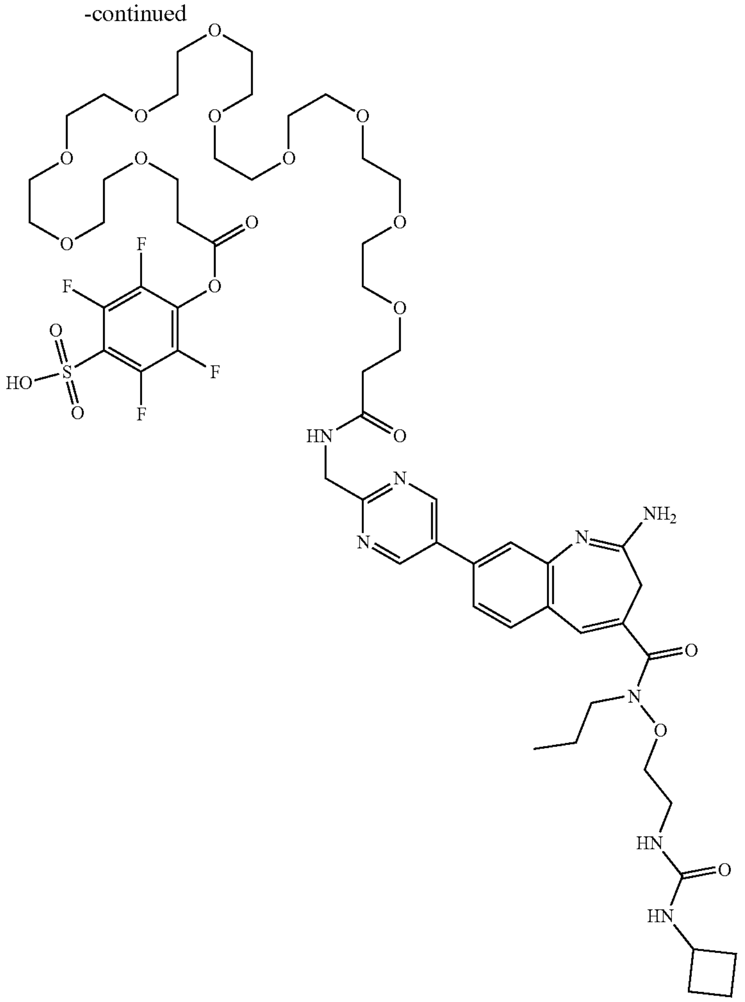

HxBzL-16

Preparation of tert-butyl ((5-(2-amino-4-((2-(3-cyclobutylureido)ethoxy)(propyl) carbamoyl)-3H-benzo[b]azepin-8-yl)pyrimidin-2-yl)methyl)carbamate, HxBz-16a To a solution of 2-amino-8-[2-[(tert-butoxycarbonylamino)methyl] pyrimidin-5-yl]-3H-1-benzazepine-4-carboxylic acid, HxBz-15a (250 mg, 611 umol, 1 eq) 1-cyclobutyl-3-[2-(propylaminooxy)ethyl]urea (231 mg, 916 umol, 1.5 eq, HCl) in DCM (2 mL) and DMA (2 mL) was added EDCI (351 mg, 1.83 mmol, 3 eq), and it was stirred at 25° C. for 0.5 hr. The reaction mixture was concentrated under reduced pressure to remove DCM. The residue was diluted with water (10 mL) and extracted with EtOAc (20 mL*3). The combined organic layers were washed with brine (20 mL*2), dried over $Na_2SO_4$, filtered and concentrated under reduced pressure to give a residue. The residue was purified by column chromatography ($SiO_2$, Petroleum ether/Ethyl acetate=50/1 to Ethyl acetate:MeOH=5:1) to afford HxBz-16a (230 mg, 380 umol, 62.1% yield) as a brown solid.

Preparation of 2-amino-8-[2-(aminomethyl)pyrimidin-5-yl]-N-[2-(cyclobutylcarbamoylamino)ethoxy]-N-propyl-3H-1-benzazepine-4-carboxamide, HxBz-16

To a solution of HxBz-16a (230 mg, 0.38 mmol, 1 eq) in Water (2 mL) and MeCN (2 mL) was added TFA (432 mg, 3.79 mmol, 0.28 mL, 10 eq), and then stirred at 80° C. for 0.5 hr.

The mixture was concentrated under reduced pressure, the residue was diluted with water (2 mL) and extracted with MTBE (3 mL*3)-discarded, the aqueous phase was concentrated under reduced pressure to afford HxBz-16 (230 mg, 371 umol, 97.8% yield, TFA) as a brown solid. $^1H$ NMR (400 MHz, MeOD) δ 9.21 (s, 2H), 7.84-7.73 (m, 3H), 7.47 (s, 1H), 4.48 (s, 2H), 4.01-3.89 (m, 3H), 3.75 (t, J=7.2 Hz, 2H), 3.44 (s, 2H), 3.33 (br s, 2H), 2.19-2.10 (m, 2H), 1.81-1.68 (m, 4H), 1.64-1.55 (m, 2H), 1.00 (t, J=7.2 Hz, 3H). LC/MS [M+H] 507.3 (calculated); LC/MS [M+H] 507.2 (observed).

Preparation of 3-[2-[2-[2-[2-[2-[2-[2-[2-[2-[3-[[5-[2-amino-4-[2-(cyclobutyl carbamoylamino)ethoxy-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-16a To a solution of HxBz-16 (100 mg, 136 umol, 1 eq, 2TFA) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (96.2 mg, 0.14 mmol, 1 eq) in THF (1 mL) was added $Et_3N$ (41.3 mg, 0.41 mmol, 56.8 uL, 3 eq), and then stirred at 25° C. for 0.5 hr. The pH of the mixture was adjusted to about 6 with TFA at 0° C., extracted with EtOAc (5 mL three times)-discarded, and the aqueous was further extracted with DCM/i-PrOH (10 mL*3, 3/1). The organic layers were dried over $Na_2SO_4$ filtered and concentrated under reduced pressure. The crude product HxBzL-16a (120 mg, 115 umol, 84.2% yield) was obtained as yellow oil and used in the next step without further purification.

Preparation of HxBzL-16

To a solution of HxBzL-16a (70 mg, 66.9 umol, 1 eq) and sodium; 2,3,5,6-tetrafluoro-4-hydroxy-benzenesulfonate (71.7 mg, 267 umol, 4 eq) in DMA (0.5 mL) and DCM (1.5 mL) was added EDCI (51.3 mg, 267 umol, 4 eq), and it was stirred at 25° C. for 0.5 hr. The mixture was filtered and concentrated under reduced pressure. The residue was purified by prep-HPLC (TFA condition; column: Phenomenex Synergi C18 150*25*10 um; mobile phase: [water (0.1% TFA)-ACN]; B %: 15%-35%, 8 min). Then the residue was purified by prep-HPLC (TFA condition; column: Phenomenex Synergi C18 150*25*10 um; mobile phase: [water (0.1% TFA)-ACN]; B %: 15%-35%, 8 min) to afford HxBzL-13 (20 mg, 13.3 umol, 19.9% yield, 2TFA) as a colorless oil. $^1H$ NMR (400 MHz, MeOD) δ 9.09 (s, 2H), 7.80-7.71 (m, 3H), 7.47 (s, 1H), 4.69 (s, 2H), 3.95 (br t, J=5.2 Hz, 2H), 3.86 (t, J=6.0 Hz, 2H), 3.80 (t, J=6.0 Hz, 2H), 3.75 (br t, J=7.2 Hz, 2H), 3.68-3.57 (m, 38H), 3.45 (s, 2H), 2.97 (t, J=6.0 Hz, 2H), 2.60 (t, J=6.0 Hz, 2H), 2.15 (br d, J=7.2 Hz, 2H), 1.83-1.68 (m, 4H), 1.64-1.52 (m, 2H), 0.99 (t, J=7.2 Hz, 3H). LC/MS [M+H] 1275.5 (calculated); LC/MS [M+H] 1275.2 (observed).

Example L-17 Synthesis of 4-[3-[2-[2-[2-[2-[2-[2-[2-[2-[2-[3-[[5-[2-amino-4-[3-(cyclobutoxycarbonylamino)propyl-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy] propanoyloxy]-2,3,5,6-tetrafluoro-benzenesulfonic acid, HxBzL-17

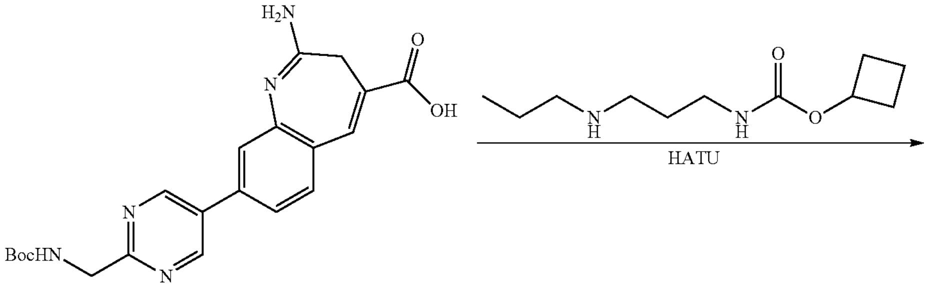

HxBz-14a

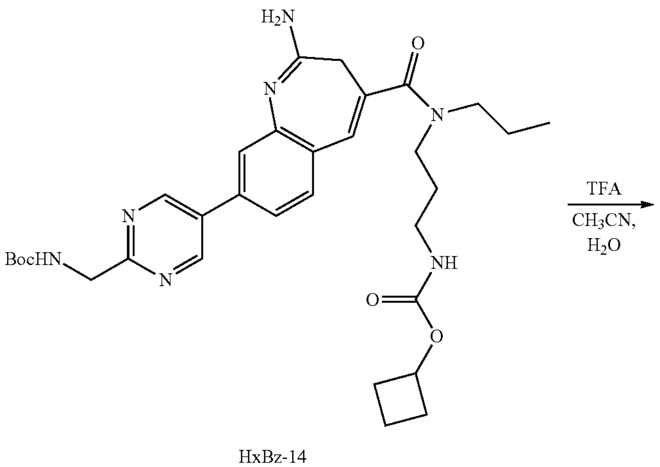

HxBz-14

-continued
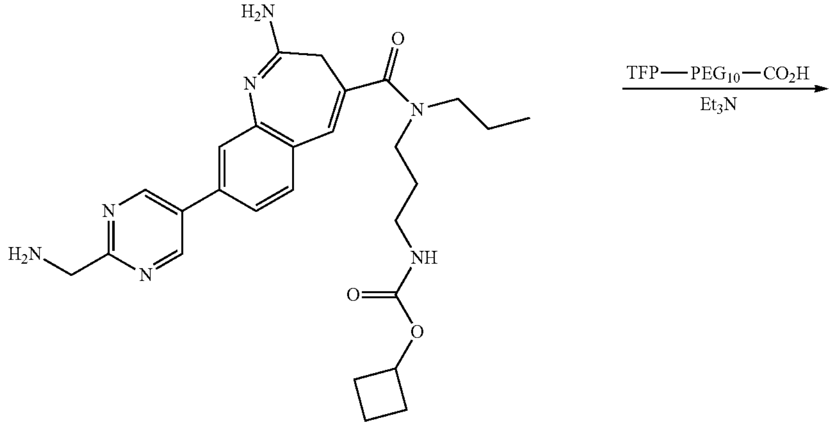
HxBz-13
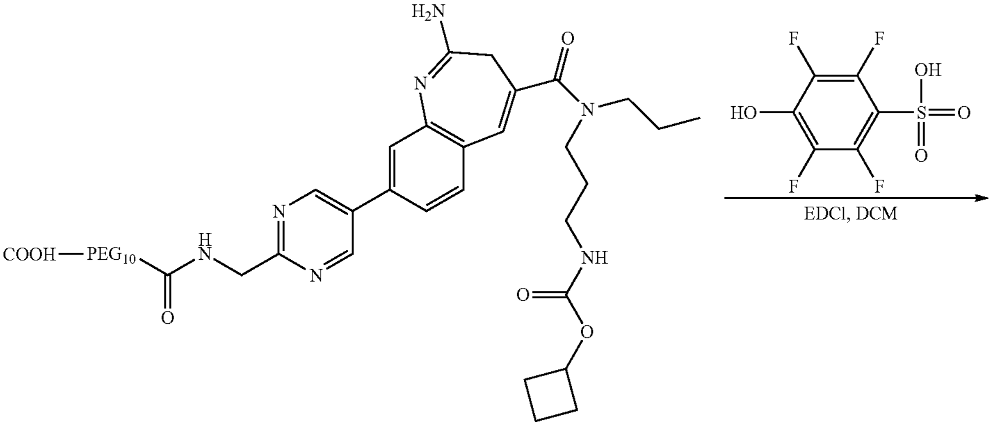
HxBz-17a
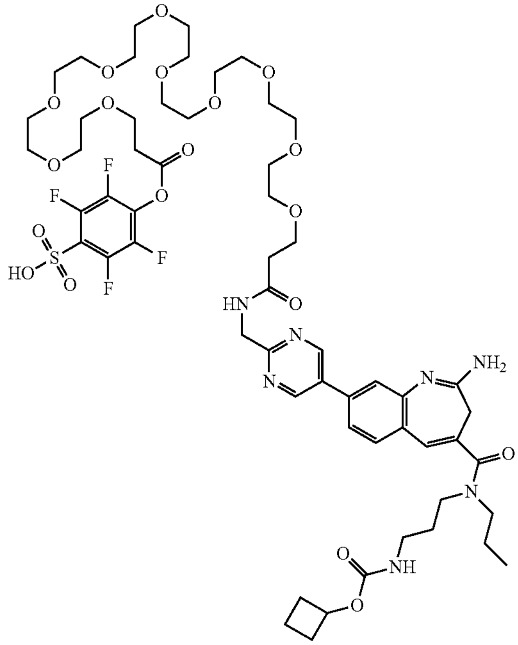
HxBzL-17

Preparation of cyclobutyl N-[3-[[2-amino-8-[2-[(tert-butoxycarbonylamino)methyl]pyrimidin-5-yl]-3H-1-benzazepine-4-carbonyl]-propyl-amino]propyl], HxBz-14

To a mixture of 2-amino-8-[2-[(tert-butoxycarbonylamino)methyl]pyrimidin-5-yl]-3H-1-benzazepine-4-carboxylic acid, HxBz-14a (0.25 g, 611 umol, 1.0 eq) in DMF (4 mL) was added $Et_3N$ (185 mg, 1.83 mmol, 255 uL, 3.0 eq), cyclobutyl N-[3-(propylamino)propyl]carbamate (170 mg, 678 umol, 1.11 eq, HCl) and Hexafluorophosphate Azabenzotriazole Tetramethyl Uronium, HATU (232 mg, 611 umol, 1.0 eq) in one portion at 0° C., and it was stirred at 0° C. for 0.5 h. Then the mixture was diluted with water and extracted with EtOAc (20 mL×3). The organic layer was washed with brine, dried over $Na_2SO_4$, filtered and concentrated. The residue was purified by silica gel chromatography (column height: 250 mm, diameter: 100 mm, 100-200 mesh silica gel, Petroleum ether/Ethyl acetate=1/0, 3/1) to afford HxBz-14 (0.28 g, 462 umol, 75.71% yield) as yellow solid. $^1H$ NMR (MeOD, 400 MHz) δ 9.04 (s, 2H), 7.52 (d, J=8.4 Hz, 1H), 7.48 (d, J=1.6 Hz, 1H), 7.45-7.40 (m, 1H), 6.93 (s, 1H), 4.84-4.84 (m, 1H), 4.64 (s, 4H), 3.54-3.47 (m, 2H), 3.46-3.39 (m, 2H), 3.30 (m, 2H), 3.22-3.07 (m, 2H), 2.32-2.28 (m, 2H), 2.10-2.00 (m, 2H), 1.88-1.79 (m, 3H), 1.75-1.60 (m, 3H), 1.48 (s, 9H), 0.90 (s, 3H). LC/MS [M+H]606.3 (calculated); LC/MS [M+H] 606.2 (observed).

Preparation of cyclobutyl N-[3-[[2-amino-8-[2-(aminomethyl)pyrimidin-5-yl]-3H-1-benzazepine-4-carbonyl]-propyl-amino]propyl]carbamate, HxBz-13

To a mixture of HxBz-14 (0.26 g, 429 umol, 1.0 eq) in $CH_3CN$ (3 mL) and $H_2O$ (1 mL) was added TFA (489 mg, 4.29 mmol, 318 uL, 10.0 eq) in one portion at 25° C. and then stirred at 80° C. for 0.5 h. Then the mixture was concentrated and the residue was diluted with water (10 mL) and the mixture was extracted with MTBE (10 mL×2) to remove excess TFA. The water layer was freeze-dried to give HxBz-13 (0.2 g, 323 umol, 75.20% yield, TFA) as a yellow solid. $^1H$ NMR (MeOD, 400 MHz) δ 9.21 (s, 2H), 7.84-7.71 (m, 3H), 7.12 (s, 1H), 4.85-4.85 (m, 1H), 4.47 (s, 2H), 3.54 (t, J=7.2 Hz, 2H), 3.48 (s, 2H), 3.37 (s, 2H), 3.15 (d, J=15.6 Hz, 2H), 2.30-2.25 (m, 2H), 2.08-2.00 (m, 2H), 1.89-1.66 (m, 6H), 1.01-0.88 (m, 3H). LC/MS [M+H]506.3 (calculated); LC/MS [M+H] 506.2 (observed).

Preparation of 3-[2-[2-[2-[2-[2-[2-[2-[2-[2-[3-[[5-[2-amino-4-[3-(cyclobutoxycarbonylamino)propyl-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-17a To a mixture of HxBz-13 (0.1 g, 161 umol, 1.0 eq, TFA) in THE (3 mL) was added $Et_3N$ (48.9 mg, 484 umol, 67.4 uL, 3.0 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid, TFP-PEG10-CO2H (114 mg, 161 umol, 1.0 eq) in one portion at 0° C. and then stirred at 0° C. for 0.5 h. The pH of the mixture was adjusted 5-6 with TFA at 0° C. Then the mixture was diluted with water (5 mL) and washed with MTBE (10 mL×3). Then the water layer was further extracted with DCM:i-PrOH=3:1 (20 mL×3). The organic layer was dried over $Na_2SO_4$, filtered and concentrated to give HxBzL-17a (0.15 g, 129 umol, 80.11% yield, TFA) as yellow oil.

Preparation of HxBzL-17

To a mixture of HxBzL-17a (0.15 g, 129 umol, 1.0 eq, TFA) in DCM (3 mL) and DMA (0.5 mL) was added sodium; 2,3,5,6-tetrafluoro-4-hydroxy-benzenesulfonate (139 mg, 517 umol, 4.0 eq) and EDCI (149 mg, 776 umol, 6.0 eq) in one portion at 25° C. and then stirred at 25° C. for 0.5 h. The mixture was concentrated and filtered. Then the residue was purified by prep-HPLC (column: Phenomenex Synergi C18 150*25*10 um; mobile phase: [water (0.1% TFA)-ACN]; B %: 15%-40%, 8 min) to give HxBzL-17 (75.3 mg, 59.1 umol, 45.71% yield) as yellow oil. $^1H$ NMR (MeOD, 400 MHz) δ9.09 (s, 2H), 7.82-7.67 (m, 3H), 7.11 (s, 1H), 4.86-4.82 (m, 1H), 4.69 (s, 2H), 3.86 (t, J=6.0 Hz, 2H), 3.80 (t, J=6.0 Hz, 2H), 3.66-3.48 (m, 40H), 3.38 (s, 2H), 3.22-3.06 (m, 2H), 2.97 (t, J=6.0 Hz, 2H), 2.64-2.58 (m, 2H), 2.32-2.25 (m, 2H), 2.09-1.95 (m, 2H), 1.91-1.80 (m, 3H), 1.75-1.61 (m, 3H), 0.93 (s, 3H). LC/MS [M+H] 1274.5 (calculated); LC/MS [M+H] 1274.3 (observed).

Example L-18 Synthesis of 4-[3-[2-[2-[2-[2-[2-[2-[2-[2-[2-[2-[[5-[2-amino-4-[ethoxy(propyl)carbamoyl]-3H-1-benzazepin-8-yl]pyrimidine-2-carbonyl]amino]ethoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-18

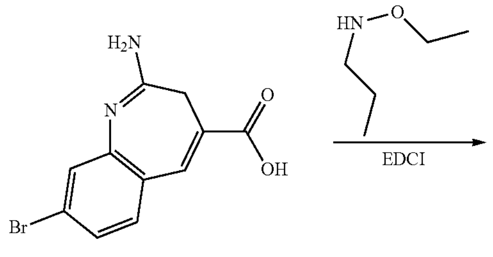

HxBz-11a

-continued
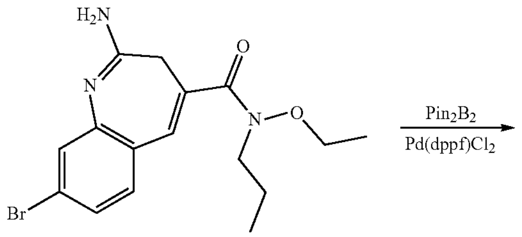
HxBz-11b
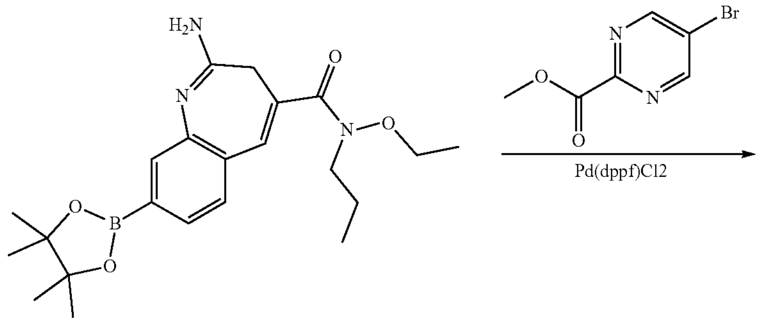
HxBz-11c
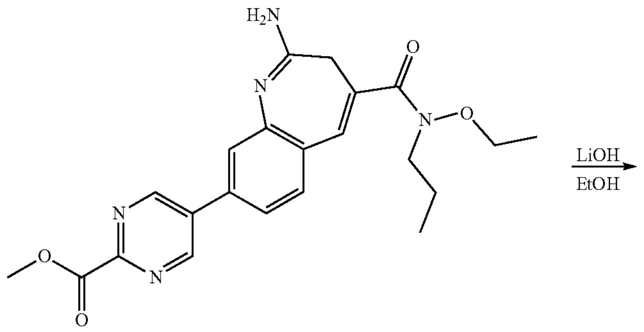
HxBz-11
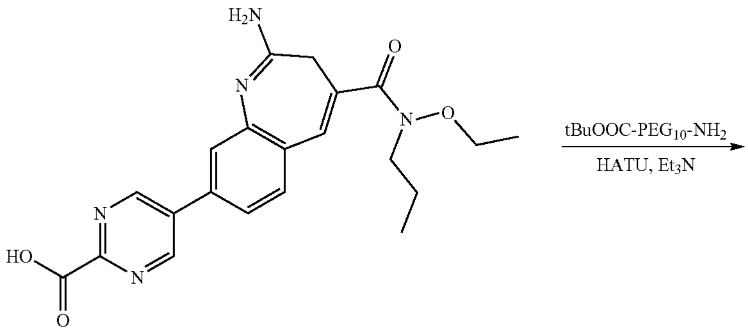
HxBzL-18a -continued
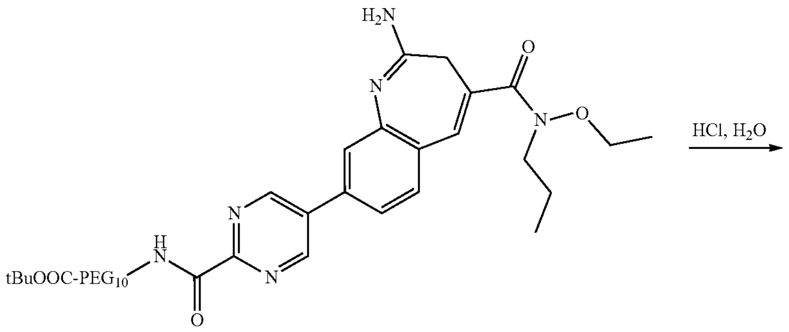
HxBzL-18b
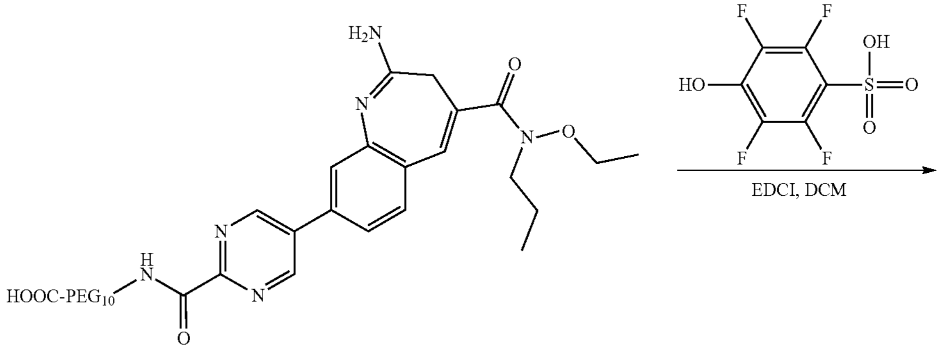
HxBzL-18c
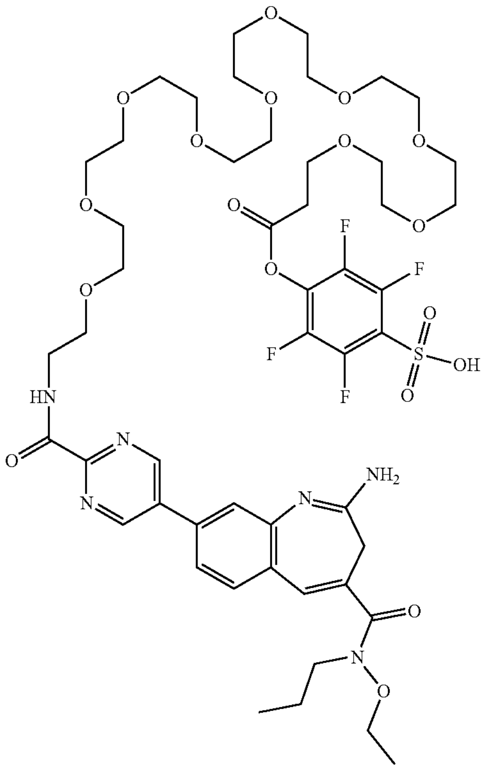
HxBzL-18

Preparation of 2-amino-8-bromo-N-ethoxy-N-propyl-3H-1-benzazepine-4-carboxamide, HxBz-11b To a mixture of N-ethoxypropan-1-amine (9.6 g, 68.8 mmol, 1.3 eq, HCl) and 2-amino-8-bromo-3H-1-benzazepine-4-carboxylic acid, HxBz-11a (14.8 g, 52.9 mmol, 1.0 eq) in DMA (150 mL) and DCM (150 mL) was added EDCI (40.6 g, 211 mmol, 4.0 eq) at 25° C. under $N_2$. The mixture was stirred at 25° C. for 2 hours. The pH of the mixture was adjusted to ~9 with $NaHCO_3$ and concentrated in reduced pressure to remove DCM at 45° C. The aqueous phase was extracted with ethyl acetate (100 mL×3). The combined organic phase was washed with brine (1000 mL×2), dried with anhydrous $Na_2SO_4$, filtered and concentrated in vacuum. The residue was triturated with MTBE/PE=1/1 at 25° C. to afford HxBz-11b (12.5 g, 34.1 mmol, 64.5% yield) as white solid. $^1$H NMR (MeOD, 400 MHz) δ 7.31 (d, J=2.0 Hz, 1H), 7.26-7.22 (m, 1H), 7.18 (s, 1H), 7.17-7.14 (m, 1H), 3.92 (q, J=6.8 Hz, 2H), 3.71 (t, J=7.2 Hz, 2H), 3.31 (s, 2H), 1.79-1.70 (m, 2H), 1.15 (t, J=7.2 Hz, 3H), 0.97 (t, J=7.6 Hz, 3H).

Preparation of 2-amino-N-ethoxy-N-propyl-8-(4,4,5,5-tetramethyl-1,3,2-dioxaborolan-2-yl)-3H-1-benzazepine-4-carboxamide, HxBz-11c A mixture of HxBz-11b (500 mg, 1.37 mmol, 1.0 eq), $Pin_2B_2$ (416 mg, 1.64 mmol, 1.2 eq), KOAc (335 mg, 3.41 mmol, 2.5 eq) and Pd(dppf)$Cl_2$ (99.9 mg, 136 umol, 0.1 eq) in dioxane (10 mL) was degassed and purged with $N_2$ for 3 times, and then the mixture was stirred at 95° C. for 1 hr under $N_2$ atmosphere. The mixture was concentrated in vacuum. The residue was poured into ice-water (w/w=1/1) (10 mL) and stirred for 5 min. The aqueous phase was extracted with MTBE (10 mL×1), then the aqueous phase was further extracted with DCM/i-PrOH=3/1 (10 mL×3). The combined organic phase (DCM/i-PrOH) was dried with anhydrous $Na_2SO_4$, filtered and concentrated in vacuum to give HxBz-11c (490 mg, crude), used in the next step without further purification as black solid.

Preparation of methyl 5-(2-amino-4-(ethoxy(propyl)carbamoyl)-3H-benzo[b]azepin-8-yl)pyrimidine-2-carboxylate, HxBz-11

A mixture of HxBz-11c (390 mg, 944 umol, 1.0 eq), methyl 5-bromopyrimidine-2-carboxylate (266 mg, 1.23 mmol, 1.3 eq), Pd(dppf)$Cl_2$ (69.0 mg, 94.3 umol, 0.1 eq), $K_3PO_4$ (401 mg, 1.89 mmol, 2.0 eq) in dioxane (15 mL) and $H_2O$ (2 mL) was degassed and purged with $N_2$ for 3 times, and then stirred at 80° C. for 1 hr under $N_2$ atmosphere. The mixture was filtered and filtrate was concentrated in vacuum. The residue was purified by prep-HPLC (column: Phenomenex Synergi C18 150*25*10 um; mobile phase: [water (0.1% TFA)-ACN]; B %: 5%-30%, 8 min) to afford HxBz-11 (105 mg, 161 umol, 17.1% yield, TFA) as white solid. $^1$H NMR (MeOD, 400 MHz) δ 9.30 (s, 2H), 7.89 (dd, J=2.0, 2.0 Hz, 1H), 7.83-7.74 (m, 2H), 7.47 (s, 1H), 4.06 (s, 3H), 4.00 (t, J=6.8 Hz, 2H), 3.76 (t, J=7.2 Hz, 2H), 3.45 (s, 2H), 1.83-1.74 (m, 2H), 1.21 (t, J=6.8 Hz, 3H), 1.01 (t, J=7.2 Hz, 3H). LC/MS [M+H] 424.1 (calculated); LC/MS [M+H] 424.1 (observed).

Preparation of 5-[2-amino-4-[ethoxy(propyl)carbamoyl]-3H-1-benzazepin-8-yl]pyrimidine-2-carboxylic acid, HxBzL-18a To a solution of HxBz-11 (330 mg, 779 umol, 1.0 eq) in EtOH (5 mL) and $H_2O$ (0.5 mL) was added LiOH·$H_2O$ (131 mg, 3.12 mmol, 4.0 eq). The mixture was stirred at 25° C. for 2 hrs. The pH of the mixture was adjusted to ~6 with HCl (4M) and concentrated in vacuum to remove EtOH. The residue was diluted with water (10 mL). The aqueous phase was extracted with DCM/i-PrOH=3/1 (10 mL×3). The combined organic phase was dried with anhydrous $Na_2SO_4$, filtered and concentrated in vacuum to afford HxBzL-18a (200 mg, 488 umol, 62.7% yield) as yellow solid.

Preparation of tert-butyl 3-[2-[2-[2-[2-[2-[2-[2-[2-[2-[2-[[1-[[5-[2-amino-4-[3-(3,3-dimethylbutanoylamino)propyl-propyl-carbamoyl]-3H-1-benzazepin-8-yl]-3-pyridyl]sulfonyl]azetidin-3-yl]methyl-methylamino]ethoxy]ethoxy]ethoxy]ethoxy]ethoxy]ethoxy]ethoxy]ethoxy]ethoxy]ethoxy]propanoate, HxBzL-18b To mixture of HxBzL-18a (195 mg, 332 umol, 0.8 eq) and tert-butyl 3-[2-[2-[2-[2-[2-[2-[2-[2-[2-(2-aminoethoxy)ethoxy]ethoxy]ethoxy]ethoxy]ethoxy]ethoxy]ethoxy]ethoxy]ethoxy]propanoate, tBuOOC-$PEG_{10}$-$NH_2$ (390 mg, 666 umol, 1.0 eq) in DMF (5 mL) was added $Et_3N$ (126 mg, 1.25 mmol, 173 uL, 3.0 eq) and HATU (158 mg, 415 umol, 1.0 eq) at 0° C. The mixture was stirred at 0° C. for 1 hr. The mixture was purified by prep-HPLC (column: Phenomenex luna C18 80*40 mm*3 um; mobile phase: [water (0.1% TFA)-ACN]; B %: 25%-50%, 7 min) to afford HxBzL-18b (80 mg, 66.4 umol, 16.0% yield, TFA) as yellow oil.

Preparation of 3-[2-[2-[2-[2-[2-[2-[2-[2-[2-[2-[[5-[2-amino-4-[ethoxy(propyl) carbamoyl]-3H-1-benzazepin-8-yl]pyrimidine-2-carbonyl]amino]ethoxy]ethoxy]ethoxy]ethoxy]ethoxy]ethoxy]ethoxy]ethoxy]ethoxy]ethoxy]propanoic acid, HxBzL-18c To a solution of HxBzL-18b (80 mg, 66.4 umol, 1.0 eq, TFA) in MeCN (2 mL) and H2O (1 mL) was added HCl (12 M, 83.0 uL, 15.0 eq), and it was stirred at 80° C. for 1 hr. The mixture was concentrated in vacuum to give a residue, the residue was freeze-dried to afford HxBzL-18c (60 mg, 62.7 umol, 94.4% yield, HCl) as colorless oil.

Preparation of HxBzL-18

To a solution of HxBzL-18c (60 mg, 60.4 umol, 1.0 eq, 2HCl) and (2,3,5,6-tetrafluoro-4-hydroxy-phenyl)sulfonyloxysodium (64.7 mg, 241 umol, 4.0 eq) in DCM (2 mL) and DMA (0.5 mL) was added EDCI (46.3 mg, 241 umol, 4.0 eq), and then stirred at 25° C. for 1 hr. The mixture was concentrated in vacuum and filtered. The residue was purified by prep-HPLC (column: Phenomenex Synergi C18 150*25*10 um; mobile phase: [water (0.1% TFA)-ACN]; B %: 15%-35%, 8 min) to afford HxBzL-18 (36 mg, 31.3 umol, 51.9% yield) as yellow oil. $^1$H NMR (MeOD, 400 MHz) δ 9.27 (s, 2H), 7.90-7.81 (m, 2H), 7.75 (d, J=8.4 Hz, 1H), 7.46 (s, 1H), 3.98 (q, J=6.8 Hz, 2H), 3.85 (t, J=6.0 Hz, 2H), 3.78-3.75 (m, 2H), 3.73-3.72 (m, 2H), 3.70-3.56 (m, 36H), 3.46 (s, 2H), 2.96 (t, J=6.0 Hz, 2H), 1.84-1.71 (m, 2H), 1.21 (t, J=6.8 Hz, 3H), 1.00 (t, J=7.6 Hz, 3H). LC/MS [M+H] 1149.4 (calculated); LC/MS [M+H] 1149.5 (observed).

Example L-19 Synthesis of 4-[3-[2-[2-[2-[2-[2-[2-[2-[2-[2-[2-[[(2S)-1-[5-[2-amino-4-[ethoxy(propyl)carbamoyl]-3H-1-benzazepin-8-yl]pyrimidine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-19
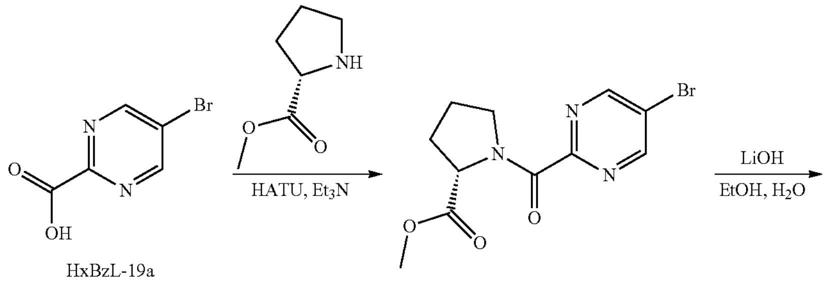
HxBzL-19a HxBzL-19b
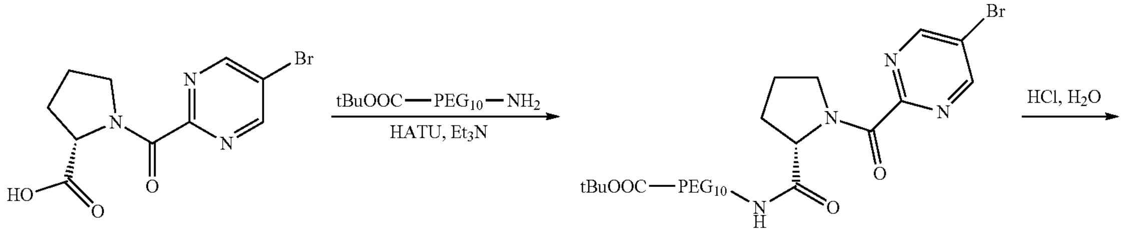
HxBzL-19c HxBzL-19d
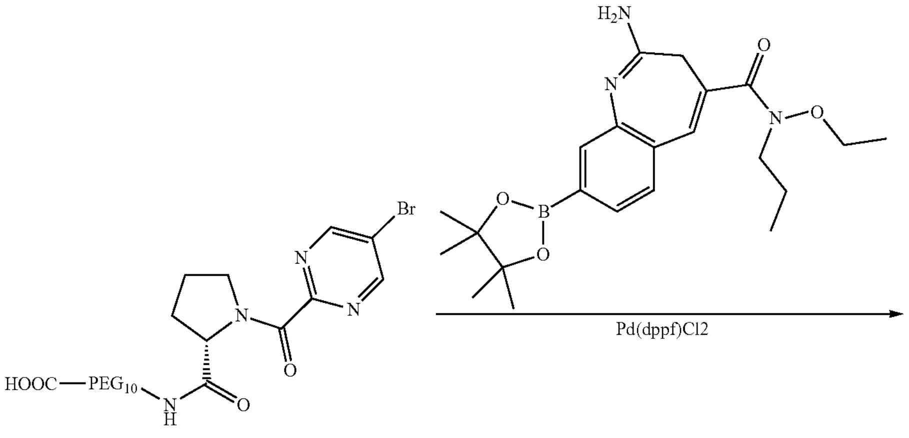
HxBzL-19e -continued

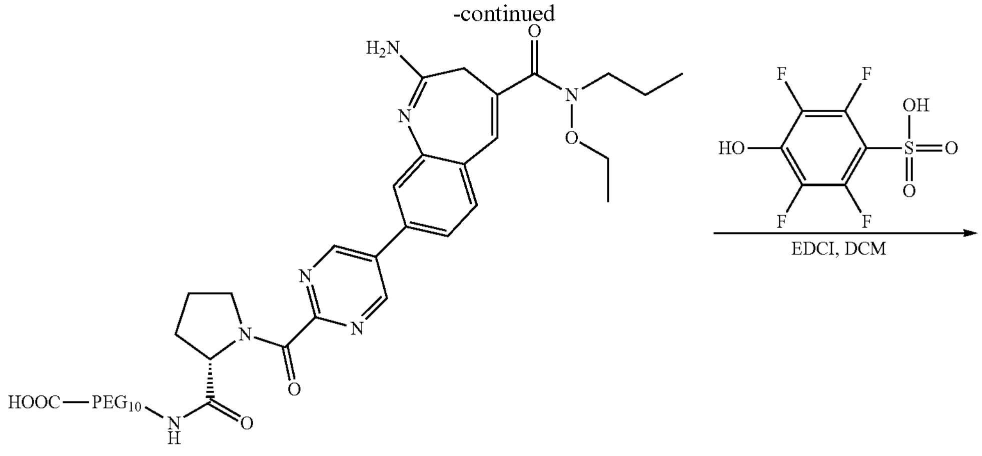

HxBzL-19f

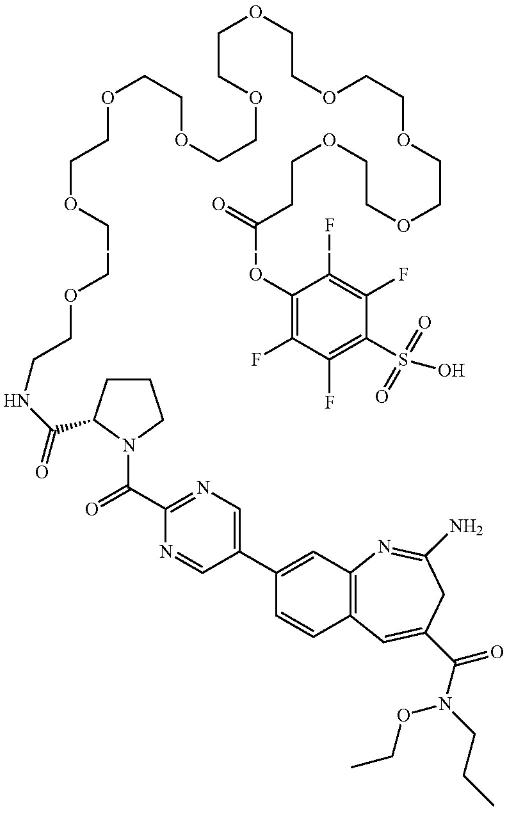

HxBzL-19

Preparation of methyl (2S)-1-(5-bromopyrimidine-2-carbonyl) pyrrolidine-2-carboxylate, HxBzL-19b To a mixture of 5-bromopyrimidine-2-carboxylic acid, HxBzL-19a (400 mg, 1.97 mmol, 1.0 eq), $Et_3N$ (598 mg, 5.91 mmol, 822 uL, 3.0 eq) and methyl (2S)-pyrrolidine-2-carboxylate (342 mg, 2.07 mmol, 1.05 eq, HCl) in DMF (8 mL) was added HATU (749 mg, 1.97 mmol, 1.0 eq) in one portion at 0° C. under $N_2$, and then stirred at 0° C. for 30 min, then heated to 25° C. and stirred for another 0.5 hour. Water (20 mL) was added and the aqueous phase was extracted with ethyl acetate (20 mL*4), the combined organic phase was washed with brine (10 mL*1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 4/1) to afford HxBzL-19b (320 mg, 1.02 mmol, 51.7% yield) as yellow oil.

Preparation of (2S)-1-(5-bromopyrimidine-2-carbonyl) pyrrolidine-2-carboxylic acid, HxBzL-19c To a solution of HxBzL-19b (320 mg, 1.02 mmol, 1.0 eq) in MeOH (5 mL) and $H_2O$ (5 mL) was added $LiOH·H_2O$ (171 mg, 4.07 mmol, 4.0 eq) in one portion at 25° C. under $N_2$, and it was stirred at 25° C. for 2 hours. The reaction mixture was quenched with HCl (4 M) until pH=7, MeOH (5 mL) was removed in vacuum, the desired solid precipitated from the aqueous phase, filtered and dried to afford HxBzL-19c (300 mg, crude) as light yellow solid.

Preparation of tert-butyl 3-[2-[2-[2-[2-[2-[2-[2-[2-[2-[2-[[(2S)-1-(5-bromopyrimidine-2-carbonyl)pyrrolidine-2-carbonyl]amino]ethoxy]ethoxy]ethoxy]ethoxy]ethoxy]ethoxy]ethoxy]ethoxy]ethoxy]ethoxy]propanoate, HxBzL-19d To a mixture of HxBzL-19c (200 mg, 666 umol, 1.0 eq), $Et_3N$ (168 mg, 1.67 mmol, 232 uL, 2.5 eq) and tert-butyl 3-[2-[2-[2-[2-[2-[2-[2-[2-[2-(2-aminoethoxy)ethoxy]ethoxy]ethoxy]ethoxy]ethoxy] ethoxy]ethoxy]ethoxy]ethoxy]propanoate (390 mg, 666 umol, 1.0 eq) in DMF (1 mL) was added HATU (253 mg, 666 umol, 1.0 eq) in one portion at 0° C. under $N_2$, and it was stirred at 0° C. for 30 min, then heated to 25° C. and stirred for another 0.5 hour. The reaction mixture was filtered and the filtrate was purified by prep-HPLC (column: Phenomenex luna C18 250*50 mm*10 um; mobile phase: [water (0.1% TFA)-ACN]; B %: 20%-60%, 10 min) to afford HxBzL-19d (300 mg, 346 umol, 51.8% yield) as colorless oil.

Preparation of 3-[2-[2-[2-[2-[2-[2-[2-[2-[2-[2-[[(2S)-1-(5-bromopyrimidine-2-carbonyl) pyrrolidine-2-carbonyl]amino]ethoxy]ethoxy]ethoxy]ethoxy]ethoxy]ethoxy]ethoxy]ethoxy]ethoxy]ethoxy]propanoic acid, HxBzL-19e To a solution of HxBzL-19d (300 mg, 345 umol, 1.0 eq) in MeCN (1 mL) and $H_2O$ (3 mL) was added HCl (12 M, 864 uL, 30 eq) in one portion at 25° C. under $N_2$, and then stirred at 80° C. for 1 hour. The reaction mixture was concentrated in vacuum to afford HxBzL-19e (250 mg, 307.99 umol, 89.09% yield) as yellow oil.

Preparation of 3-[2-[2-[2-[2-[2-[2-[2-[2-[2-[2-[[(2S)-1-[5-[2-amino-4-[ethoxy(propyl) carbamoyl]-3H-1-benzazepin-8-yl]pyrimidine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoic acid, HxBzL-19f A solution of HxBzL-19e (150 mg, 185 umol, 1.0 eq), 2-amino-N-ethoxy-N-propyl-8-(4,4,5,5-tetramethyl-1,3,2-dioxaborolan-2-yl)-3H-1-benzazepine-4-carboxamide (91.6 mg, 222 umol, 1.2 eq), Pd(dppf)$Cl_2$ (13.5 mg, 18.5 umol, 0.1 eq) and $K_2CO_3$ (63.8 mg, 462 umol, 2.5 eq) in dioxane (3 mL) and $H_2O$ (0.3 mL) was de-gassed and then heated to 95° C. for 2 hours under $N_2$. The reaction mixture was filtered and the filtrate was concentrated in vacuum, the residue was purified by prep-HPLC (column: Phenomenex luna C18 80*40 mm*3 um; mobile phase: [water (0.04% HCl)-ACN]; B %: 5%-45%, 7 min) to afford HxBzL-19f (110 mg, 108 umol, 58.4% yield) as yellow oil.

Preparation of HxBzL-19

To a mixture of HxBzL-19f (110 mg, 108 umol, 1.0 eq) and (2,3,5,6-tetrafluoro-4-hydroxy-phenyl)sulfonyloxysodium (145 mg, 540 umol, 5.0 eq) in DCM (2 mL) and DMA (0.5 mL) was added EDCI (103 mg, 540 umol, 5.0 eq) in one portion at 25° C. under $N_2$, and it was stirred at 25° C. for 1 hour. The reaction mixture was filtered and the filtrate was purified by prep-HPLC (column: Phenomenex Synergi C18 150*25*10 um; mobile phase: [water (0.1% TFA)-ACN]; B %: 10%-40%, 8 min) to afford HxBzL-19 (66.5 mg, 50.9 umol, 47.1% yield, 95.3% purity) as light yellow oil. $^1H$ NMR (400 MHz, MeOD) δ9.28-9.24 (m, 2H), 7.91-7.81 (m, 2H), 7.80-7.74 (m, 1H), 7.50-7.47 (m, 1H), 4.00 (q, J=7.2 Hz, 2H), 3.88 (dt, J=3.2, 5.6 Hz, 4H), 3.81-3.74 (m, 4H), 3.70-3.53 (m, 37H), 3.50-3.32 (m, 5H), 3.02-2.96 (m, 2H), 2.16-1.97 (m, 4H), 1.84-1.76 (m, 2H), 1.23 (t, 7.2 Hz, 3H), 1.03 (t, 7.2 Hz, 3H). LC/MS [M+H]1246.5 (calculated); LC/MS [M+H] 1246.7 (observed).

Example L-24 Synthesis of 4-[3-[2-[2-[2-[2-[2-[2-[2-[2-[2-[3-[[5-[2-amino-4-[2-(dimethylcarbamoylamino)ethoxy-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-24

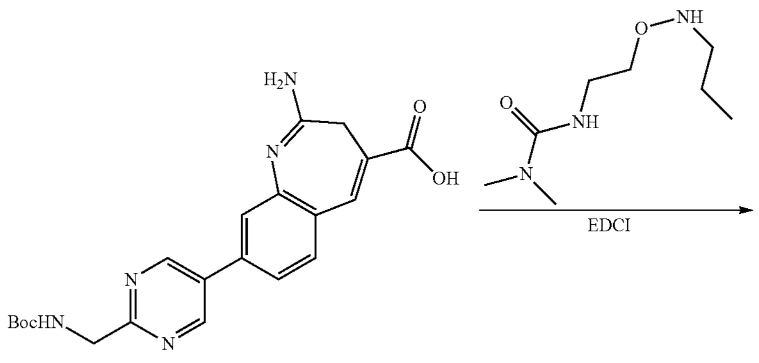

HxBz-14a

-continued
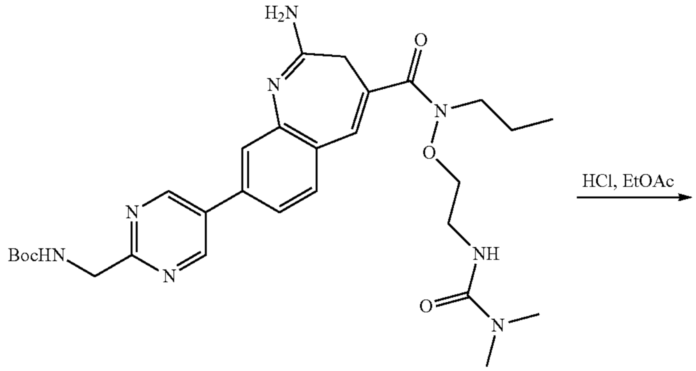
HxBz-20a
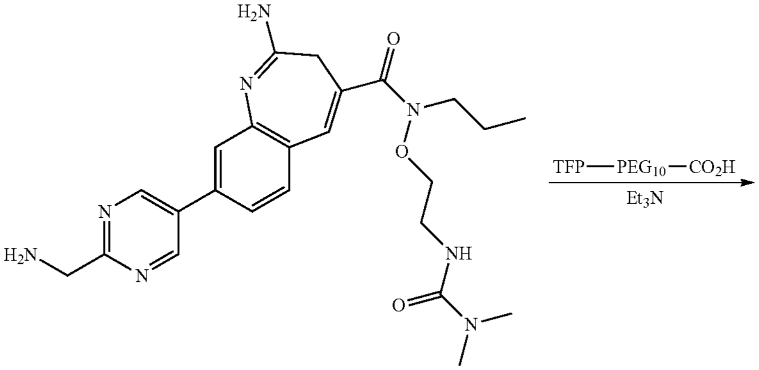
HxBz-20
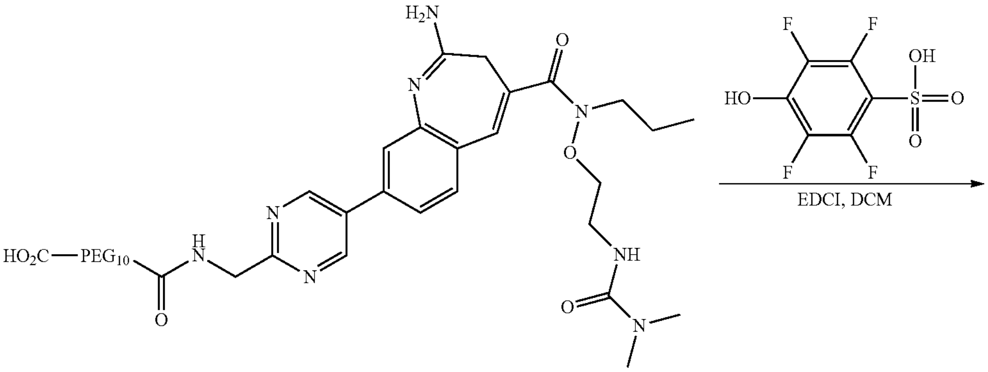
HxBzL-24a
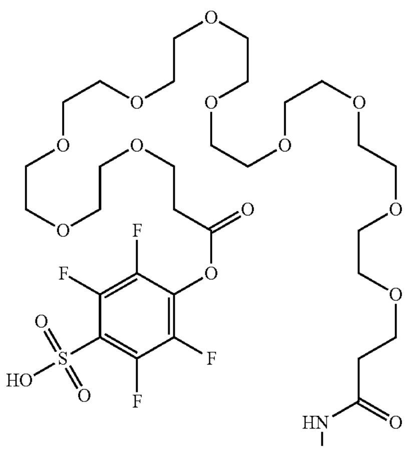

-continued

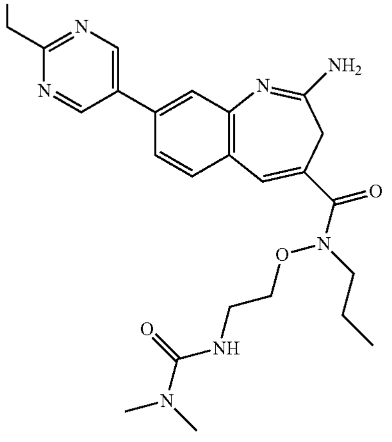

HxBzL-24

Preparation of tert-butyl ((5-(2-amino-4-((2-(3,3-dimethylureido)ethoxy)(propyl) carbamoyl)-3H-benzo[b]azepin-8-yl)pyrimidin-2-yl)methyl)carbamate, HxBz-20a To a mixture of 2-amino-8-[2-[(tert-butoxycarbonylamino)methyl]pyrimidin-5-yl]-3H-1-benzazepine-4-carboxylic acid, HxBz-14a (250 mg, 611 umol, 1 eq) and 1,1-dimethyl-3-[2-(propylaminooxy)ethyl]urea (165 mg, 733 umol, 1.2 eq, HCl) in DCM (3 mL) and DMA (1 mL) was added EDCI (468 mg, 2.44 mmol, 4 eq), and it was stirred at 25° C. for 1 hr. The mixture was concentrated in vacuum to remove DCM, the residue was diluted with water (10 mL), the pH of mixture was adjusted to ~8 with aq $Na_2CO_3$. The aqueous phase was extracted with ethyl acetate (10 mL*4). The combined organic phase was washed with brine (20 mL*1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 0/1, Ethyl acetate/Methanol=1/0, 3/1) to afford HxBz-20a (260 mg, 447.75 umol, 73.33% yield) as yellow solid.

Preparation of HxBz-20

To a solution of HxBz-20a (130 mg, 224 umol, 1 eq) in EtOAc (3.00 mL) was added HCl/EtOAc (4 M, 3.00 mL, 53.60 eq), and then stirred at 25° C. for 1 h. The mixture was concentrated to give HxBz-20 (115 mg, 207.77 umol, 92.81% yield, 2HCl) as light red solid. $^1$H NMR (MeOD, 400 MHz) δ 9.22 (s, 2H), 7.86-7.80 (m, 2H), 7.80-7.74 (m, 1H), 7.50 (s, 1H), 4.48 (s, 2H), 3.97 (t, J=5.2 Hz, 2H), 3.76 (t, J=7.2 Hz, 2H), 3.45 (s, 2H), 3.38-3.34 (m, 2H), 2.74 (s, 6H), 1.83-1.73 (m, 2H), 1.00 (t, J=7.6 Hz, 3H). LC/MS [M+H] 481.3 (calculated); LC/MS [M+H] 481.1 (observed).

Preparation of 3-[2-[2-[2-[2-[2-[2-[2-[2-[2-[3-[[5-[2-amino-4-[2-(dimethylcarbamoyl amino)ethoxy-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-24a To a solution of HxBz-20 (65.0 mg, 117 umol, 1 eq, 2HCl) in DMF (1.00 mL) was added $Et_3N$ (48.0 mg, 470 umol, 4 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid, HxBzL-21a (83.0 mg, 117 umol, 1 eq), and then stirred at 0° C. for 1 h. The mixture was diluted with water (10 mL) and the pH of the mixture was adjusted to about 6 by progressively adding TFA and extracted with MTBE (10 mL)-discarded, the aqueous was further extracted with DCM:i-PrOH=3:1 (20 mLx3). The organic layer was dried over $Na_2SO_4$, filtered and concentrated to give HxBzL-24a (95 mg, 93.03 umol, 79.22% yield) as light yellow oil.

Preparation of HxBzL-24

To a solution of HxBzL-24a (90.0 mg, 88.1 umol, 1 eq) and (2,3,5,6-tetrafluoro-4-hydroxy-phenyl)sulfonyloxysodium (95.0 mg, 353 umol, 4 eq) in DCM (2.00 mL) and DMA (0.10 mL) was added EDCI (68.0 mg, 353 umol, 4 eq), and it was stirred at 25° C. for 1 h. The mixture was concentrated and filtered. The residue was purified by prep-HPLC (column: Phenomenex Synergi C18 150*25*10 um; mobile phase: [water (0.1% TFA)-ACN]; B %: 5%-35%, 8 min) to give HxBzL-24 (51 mg, 37.41 umol, 42.45% yield, TFA) as light yellow oil. $^1$H NMR (MeOD, 400 MHz) δ 9.10 (s, 2H), 7.83-7.70 (m, 3H), 7.48 (s, 1H), 4.69 (s, 2H), 3.97 (t, J=5.2 Hz, 2H), 3.86 (t, J=5.6 Hz, 2H), 3.80 (t, J=6.0 Hz, 2H), 3.78-3.74 (m, 2H), 3.65-3.55 (m, 36H), 3.45 (s, 2H), 3.37-3.34 (m, 2H), 2.97 (t, J=5.6 Hz, 2H), 2.74 (s, 6H), 2.60 (t, J=6.0 Hz, 2H), 1.83-1.72 (m, 1H), 1.00 (t, J=7.2 Hz, 3H). LC/MS [M+H] 1249.5 (calculated); LC/MS [M+H] 1249.6 (observed).

Example L-26 Synthesis of 4-[3-[2-[2-[2-[2-[2-[2-[2-[2-[2-[3-[[5-[2-amino-4-[2-hydroxyethoxy(propyl)carbamoyl]-3H-1-benzazepin-8-yl]pyrimidin-2-yl]methylamino]-3-oxo-propoxy]ethoxy]ethoxy]ethoxy]ethoxy] ethoxy]ethoxy]ethoxy]ethoxy]ethoxy]propanoyloxy]-2,3,5,6-tetrafluoro-benzenesulfonic acid, HxBzL-26
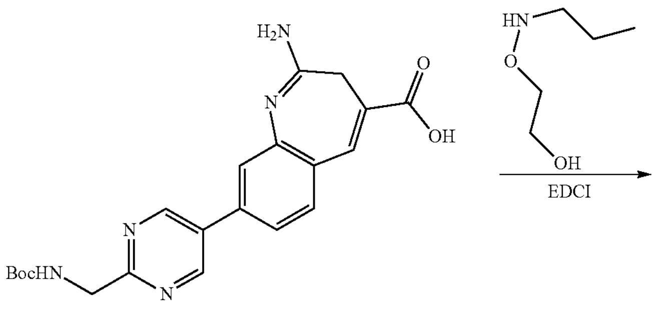
HxBz-14a
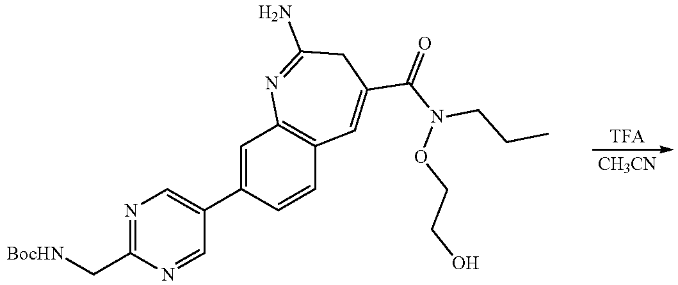
HxBz-22a
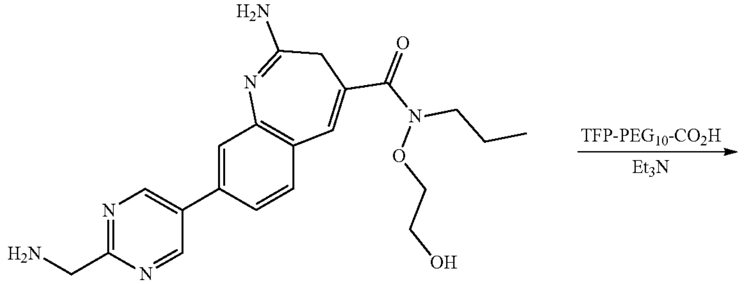
HxBz-22
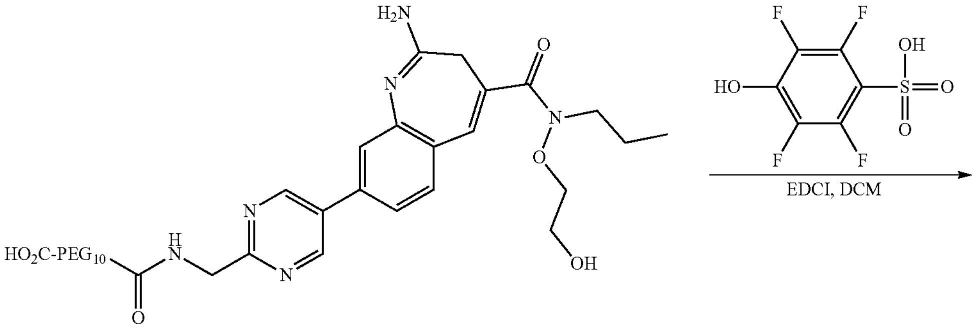
HxBzL-26a -continued

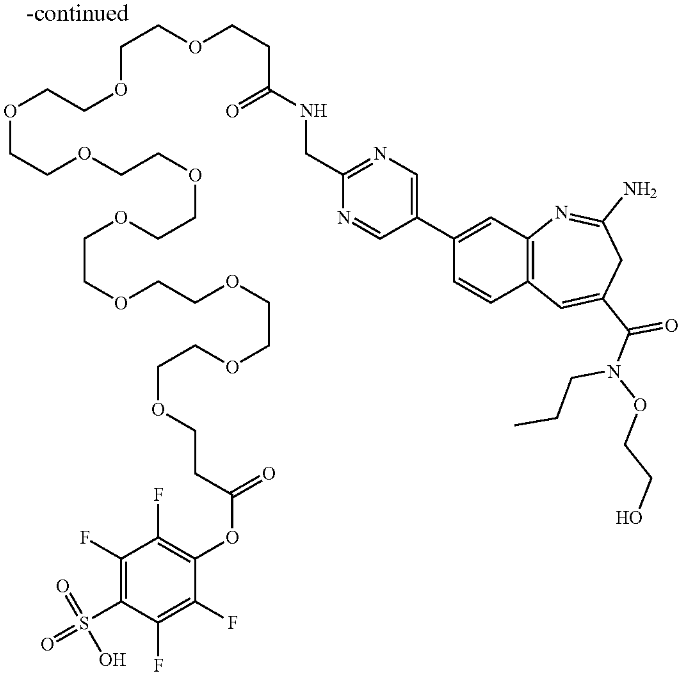

HxBzL-26

Preparation of tert-butyl N-[[5-[2-amino-4-[2-hydroxyethoxy(propyl)carbamoyl]-3H-1-benzazepin-8-yl]pyrimidin-2-yl]methyl]carbamate, HxBz-22a To a mixture of 2-amino-8-[2-[(tert-butoxycarbonylamino)methyl]pyrimidin-5-yl]-3H-1-benzazepine-4-carboxylic acid, HxBz-14a (0.35 g, 855 umol, 1.0 eq) and 2-(propylaminooxy)ethanol (200 mg, 1.28 mmol, 1.5 eq, HCl) in DCM (6 mL) and DMA (0.5 mL) was added EDCI (492 mg, 2.56 mmol, 3.0 eq) in one portion at 25° C. and then stirred at 25° C. for 0.5 h. The mixture was concentrated to remove DCM and the residue was diluted with $H_2O$ (10 mL). The pH of the mixture was adjusted to about 8 with aq·$NaHCO_3$. Then the aqueous phase was extracted with EtOAc (20 mL×3). The organic layer was brine, dried over $Na_2SO_4$, filtered and concentrated. The residue was purified by silica gel chromatography (column height: 250 mm, diameter: 100 mm, 100-200 mesh silica gel, Ethyl acetate/MeOH=1/0, 10/1) to afford HxBz-22a (0.37 g, 725 umol, 84.77% yield) as yellow oil. $^1$H NMR (MeOD, 400 MHz) δ9.08-9.01 (m, 2H), 7.59 (d, J=8.0 Hz, 1H), 7.54-7.46 (m, 2H), 7.40 (s, 1H), 4.56-4.49 (m, 2H), 4.02-3.95 (m, 2H), 3.81-3.74 (m, 2H), 3.73-3.66 (m, 2H), 1.88-1.72 (m, 2H), 1.48 (s, 9H), 0.99 (t, J=7.6 Hz, 3H).

Preparation of 2-amino-8-[2-(aminomethyl)pyrimidin-5-yl]-N-(2-hydroxyethoxy)-N-propyl-3H-1-benzazepine-4-carboxamide, HxBz-22

To a mixture of HxBz-22a (0.35 g, 685 umol, 1.0 eq) in $H_2O$ (4 mL) and $CH_3CN$ (0.5 mL) was added TFA (1.17 g, 10.3 mmol, 761 uL, 15.0 eq) in one portion at 25° C. and then stirred at 80° C. for 0.5 h. The mixture was extracted with MTBE (10 mL×2) to remove excess TFA. Then the water layer was freeze-dried. The residue was further purified by prep-HPLC (column: Phenomenex Luna 80*30 mm*3 um; mobile phase: [water (0.1% TFA)-ACN]; B %: 1%-20%, 8 min) to give HxBz-22 (0.32 g, 501 umol, 73.11% yield, 2TFA) as white solid. $^1$H NMR (MeOD, 400 MHz) δ9.20 (s, 2H), 7.84-7.72 (m, 3H), 7.56 (s, 1H), 4.47 (s, 2H), 4.03-3.96 (m, 2H), 3.79 (t, J=7.2 Hz, 2H), 3.74-3.66 (m, 2H), 3.53-3.36 (m, 2H), 1.88-1.72 (m, 2H), 1.00 (t, J=7.6 Hz, 3H). LC/MS [M+H] 411.2 (calculated); LC/MS [M+H] 411.1 (observed).

Preparation of 3-[2-[2-[2-[2-[2-[2-[2-[2-[2-[2-[3-[[5-[2-amino-4-[2-hydroxyethoxy(propyl) carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-26a To a mixture of HxBz-22 (0.23 g, 560 umol, 1.0 eq, 2TFA) in THF (6 mL) was added $Et_3N$ (170 mg, 1.68 mmol, 234 uL, 3.0 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (396 mg, 560 umol, 1.0 eq) in one portion at 0° C. and then stirred at 0° C. for 0.5 h. The mixture was diluted with water (5 ml) and the pH of the mixture was adjusted to ~6 with TFA at 0° C. The aqueous phase was extracted with EtOAc (10 mL)-discarded. The water layer was further extracted with DCM:i-PrOH=3:1 (20 mL×2). The organic layer was dried over $Na_2SO_4$, filtered and concentrated to give HxBzL-26a (0.53 g, crude, TFA) was obtained as yellow oil.

Preparation of HxBzL-26

To a mixture of HxBzL-26a (0.35 g, 329 umol, 1.0 eq, TFA) and sodium; 2,3,5,6-tetrafluoro-4-hydroxy-benzenesulfonate (352 mg, 1.31 mmol, 4.0 eq) in DCM (4 mL) and DMA (0.5 mL) was added EDCI (378 mg, 1.97 mmol, 6.0 eq) in one portion at 25° C. and then stirred at 25° C. for 0.5 h. The mixture was concentrated and filtered. Then the residue was purified by prep-HPLC (column: Phenomenex luna C18 250*50 mm*10 um; mobile phase: [water (0.1% TFA)-ACN]; B %: 20%-50%, 10 min) to give HxBzL-26 (80.4 mg, 68.2 umol, 20.75% yield) as light yellow oil. $^{1}H$ NMR (MeOD, 400 MHz) δ9.08 (s, 2H), 7.82-7.70 (m, 3H), 7.56 (s, 1H), 4.69 (s, 2H), 4.06-3.97 (m, 2H), 3.86 (t, J=6.0 Hz, 2H), 3.83-3.76 (m, 4H), 3.74-3.69 (m, 2H), 3.65-3.57 (m, 36H), 3.46 (s, 2H), 3.02-2.92 (m, 2H), 2.60 (t, J=6.0 Hz, 2H), 1.87-1.72 (m, 2H), 1.00 (t, J=7.2 Hz, 3H). LC/MS [M+H] 1179.4 (calculated); LC/MS [M+H]1179.3 (observed).

Example L-30 Synthesis of 4-[3-[2-[2-[2-[2-[2-[2-[2-[2-[2-[3-[[5-[2-amino-4-[2-(isopropoxycarbonylamino)ethoxy-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-30

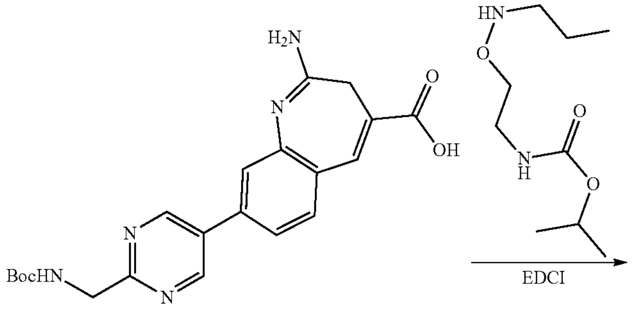

HxBz-14a

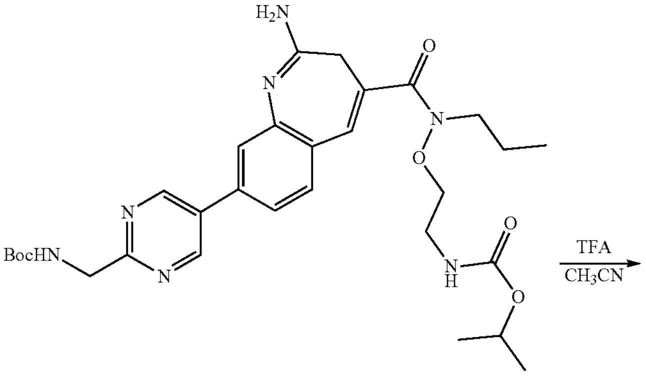

HxBz-27a

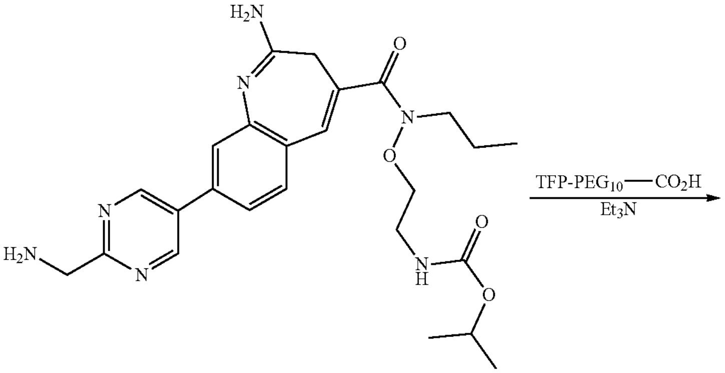

HxBz-27

-continued

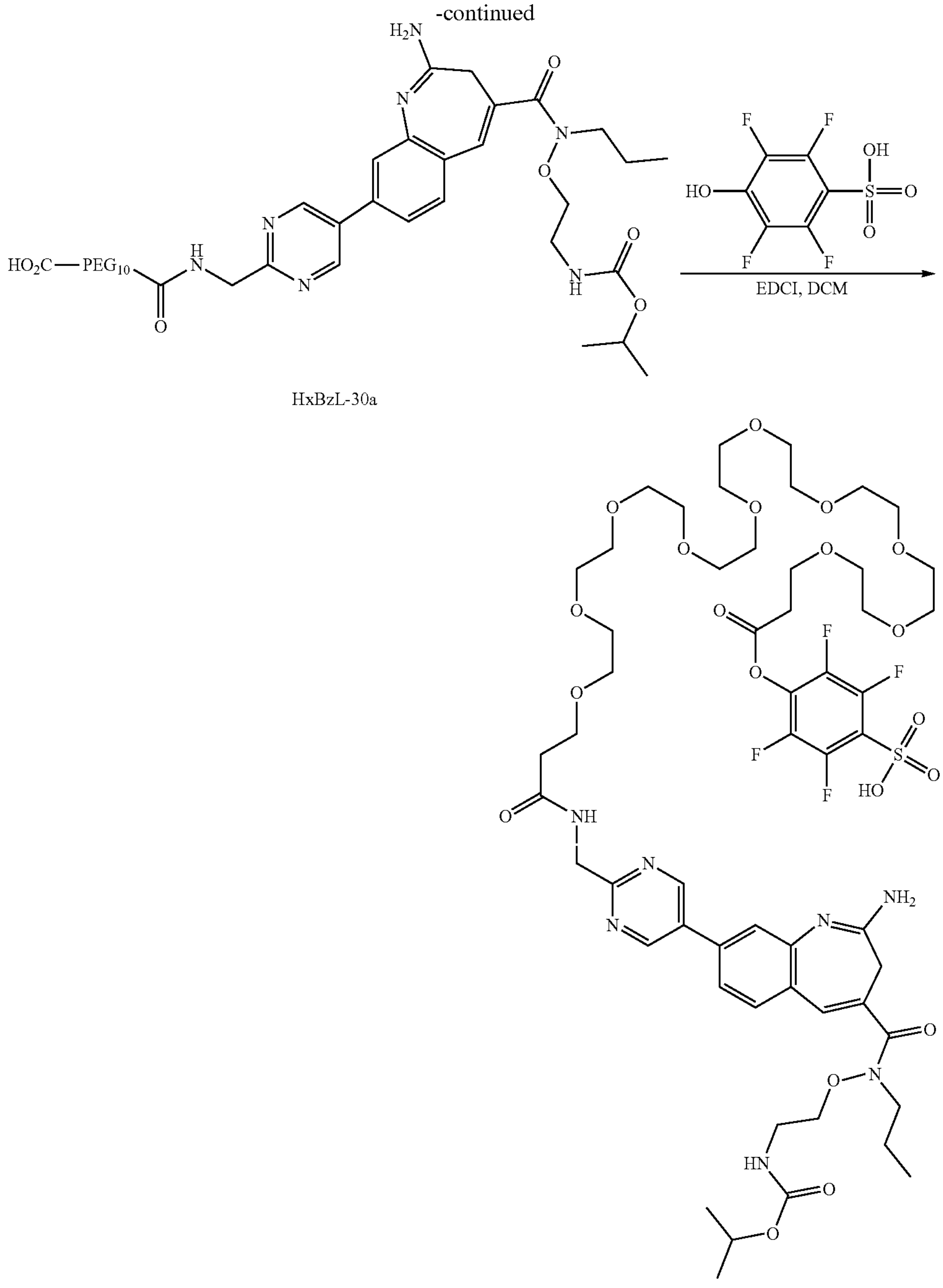

HxBzL-30a

HxBzL-30

Preparation of isopropyl N-[2-[[2-amino-8-[2-[(tert-butoxycarbonylamino)methyl]pyrimidin-5-yl]-3H-1-benzazepine-4-carbonyl]-propyl-amino]oxyethyl] carbamate, HxBz-27a To mixture of 2-amino-8-[2-[(tert-butoxycarbonylamino) methyl]pyrimidin-5-yl]-3H-1-benzazepine-4-carboxylic acid, HxBz-14a (350 mg, 855 umol, 1.0 eq) and isopropyl N-[2-(propylaminooxy)ethyl]carbamate (268 mg, 1.11 mmol, 1.3 eq, HCl) in DCM (5 mL) and DMA (3 mL) was added EDCI (656 mg, 3.42 mmol, 4.0 eq), and it was stirred at 25° C. for 1 hr. The mixture was concentrated under reduced pressure at 30° C. The residue was poured into ice-water (w/w=1/1) (10 mL) and stirred for 5 min. The pH of the mixture was adjusted to ~8 with aq $NaHCO_3$. The aqueous phase was extracted with ethyl acetate (20 mL×3). The combined organic phase was washed with brine (10 mL×3), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 1/1, Ethyl acetate/Methanol=1/0, 10/1) to afford HxBz-27a (460 mg, 772 umol, 90.3% yield) as yellow solid. $^1H$ NMR (MeOD, 400 MHz) δ 9.04 (s, 2H), 7.57 (d, J=8.0 Hz, 1H), 7.51-7.44 (m, 2H), 7.32 (s, 1H), 4.74-4.68 (m, 1H), 4.52 (s, 2H), 3.94 (t, J=5.2 Hz, 2H), 3.73 (t, J=7.2 Hz, 2H), 3.30-3.26 (m, 2H), 1.76 (sxt, J=7.2 Hz, 2H), 1.47 (s, 9H), 1.12 (d, J=6.0 Hz, 6H), 0.98 (t, J=7.4 Hz, 3H).

Preparation of isopropyl N-[2-[[2-amino-8-[2-(aminomethyl)pyrimidin-5-yl]-3H-1-benzazepine-4-carbonyl]-propyl-amino]oxyethyl]carbamate, HxBz-27

To a solution of HxBz-27a (410 mg, 688 umol, 1.0 eq) in MeCN (0.5 mL) and $H_2O$ (5 mL) was added TFA (1.18 g, 10.3 mmol, 764 uL, 15.0 eq), and then stirred at 80° C. for 1 hr. The mixture was concentrated in vacuum to remove $CH_3CN$, The aqueous phase was extracted with MTBE (5 mL×3) to remove excess TFA. The water phase was freeze-dried to afford HxBz-27 (400 mg, 553 umol, 80.3% yield, 2TFA) as white solid. $^1H$ NMR (MeOD, 400 MHz) δ 9.21 (s, 2H), 7.86-7.74 (m, 3H), 7.51 (s, 1H), 4.76-4.63 (m, 1H), 4.48 (s, 2H), 3.98 (t, J=5.2 Hz, 2H), 3.77 (t, J=7.2 Hz, 2H), 3.43 (s, 2H), 1.78 (sxt, J=7.2 Hz, 2H), 1.12 (d, J=6.4 Hz, 6H), 1.00 (t, J=7.2 Hz, 3H). LC/MS [M+H] 496.2 (calculated); LC/MS [M+H] 496.1 (observed).

Preparation of 3-[2-[2-[2-[2-[2-[2-[2-[2-[2-[3-[[5-[2-amino-4-[2-(isopropoxycarbonylamino)ethoxy-propyl- carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-30a To a solution of HxBz-27 (130 mg, 180 umol, 1.0 eq, 2TFA) in THE (2 mL) was added $Et_3N$ (54.5 mg, 539 umol, 75.0 uL, 3.0 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (127 mg, 180 umol, 1.0 eq) at 0° C. and then stirred at 0° C. for 0.5 hr. The mixture was concentrated in vacuum. The residue was diluted with water (10 mL), the pH of the mixture was adjusted to ~6 with TFA. The aqueous phase was extracted with MTBE (5 mL×3)-discarded. The water phase was further extracted with DCM/i-PrOH=3/1 (10 mL×3). The organic phase was concentrated in vacuum to afford HxBzL-30a (180 mg, 174 umol, 96.7% yield) as yellow oil.

Preparation of HxBzL-30

To mixture of HxBzL-30a (180 mg, 174 umol, 1.0 eq) and (2,3,5,6-tetrafluoro-4-hydroxy-phenyl)sulfonyloxysodium (186 mg, 695 umol, 4.0 eq) in DCM (2 mL) and DMA (0.5 mL) was added EDCI (266 mg, 1.39 mmol, 8.0 eq), and then stirred at 25° C. for 0.5 hr. The mixture was concentrated in vacuum and filtered. The residue was purified by prep-HPLC (column: Phenomenex Synergi C18 150*25*10 um; mobile phase: [water (0.1% TFA)-ACN]; B %: 15%-35%, 8 min) to afford HxBzL-30 (91 mg, 66.0 umol, 38.0% yield, TFA) as yellow solid. $^1H$ NMR (MeOD, 400 MHz) δ 9.08 (s, 2H), 7.82-7.73 (m, 3H), 7.50 (s, 1H), 4.75-4.66 (m, 3H), 3.97 (t, J=5.2 Hz, 2H), 3.86 (t, J=6.0 Hz, 2H), 3.80 (t, J=6.0 Hz, 2H), 3.75 (br t, J=7.2 Hz, 2H), 3.66-3.56 (m, 36H), 3.45-3.42 (m, 2H), 2.96 (t, J=6.0 Hz, 2H), 2.60 (t, J=6.4 Hz, 2H), 1.84-1.70 (m, 2H), 1.12 (d, J=6.0 Hz, 6H), 0.99 (t, J=7.6 Hz, 3H). LC/MS [M+H] 1264.4 (calculated); LC/MS [M+H] 1264.7 (observed).

Example L-35 Synthesis of 4-[3-[2-[2-[2-[2-[2-[2-[2-[2-[2-[3-[[5-[2-amino-4-[propyl-[2-(pyrrolidine-1-carbonylamino)ethoxy]carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy] propanoyloxy]-2,3,5,6-tetrafluoro-benzenesulfonic acid, HxBzL-35

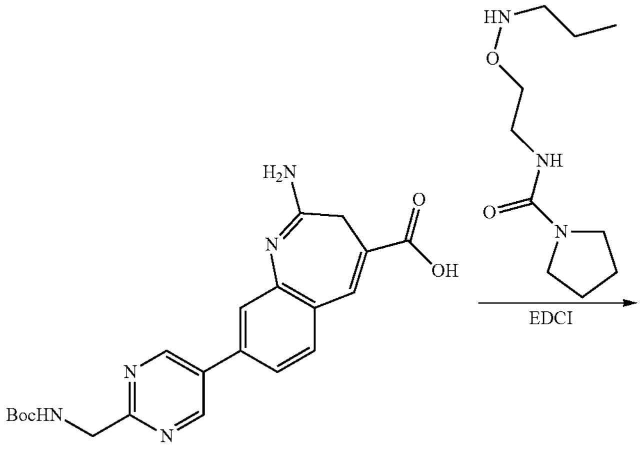

HxBz-14a

-continued
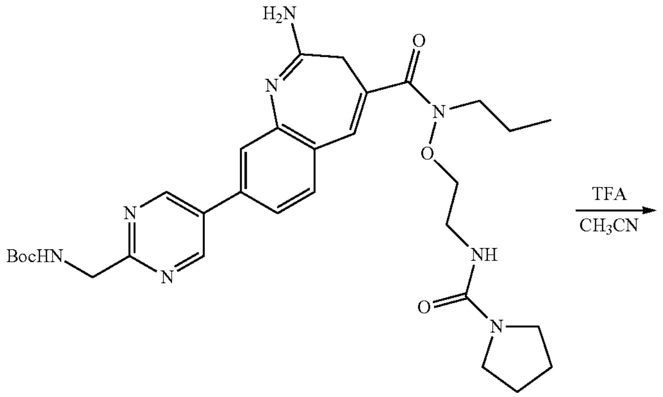
HxBzL-35a
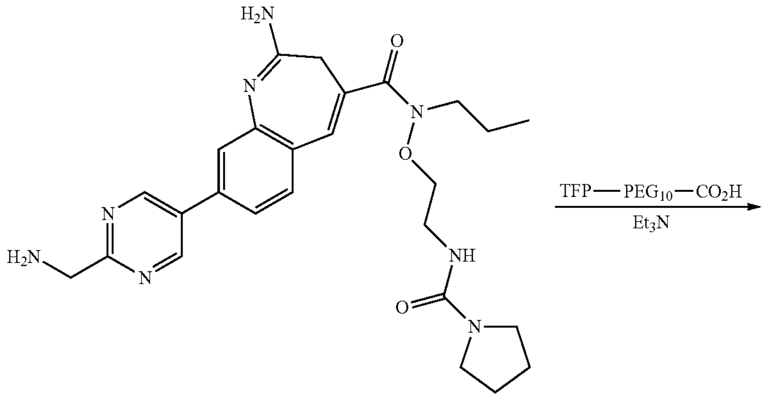
HxBzL-35b
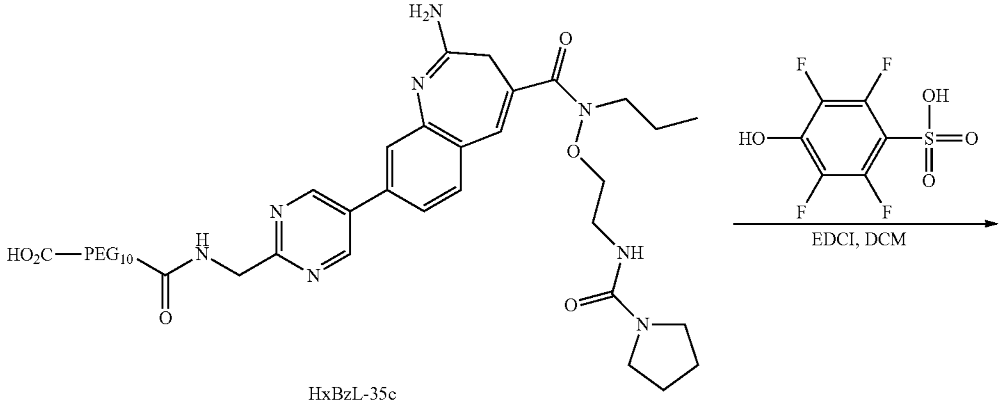
HxBzL-35c

-continued

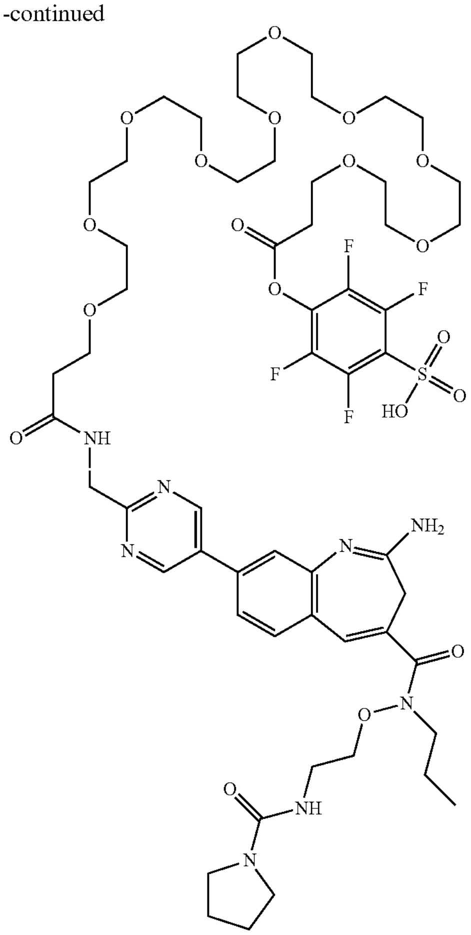

HxBzL-35

Preparation of tert-butyl N-[[5-[2-amino-4-[propyl-[2-(pyrrolidine-1-carbonylamino) ethoxy]carbamoyl]-3H-1-benzazepin-8-yl]pyrimidin-2-yl]methyl] carbamate, HxBzL-35a To a mixture of 2-amino-8-[2-[(tert-butoxycarbonylamino)methyl]pyrimidin-5-yl]-3H-1-benzazepine-4-carboxylic acid, HxBz-14a (0.25 g, 611 umol, 1.3 eq) in DCM (4 mL) and DMA (0.5 mL) was added N-[2-(propylaminooxy)ethyl]pyrrolidine-1-carboxamide (118 mg, 469 umol, 1.0 eq, HCl) and EDCI (270.12 mg, 1.41 mmol, 3.0 eq) in one portion at 25° C. and then stirred at 25° C. for 0.5 h. Then the mixture was concentrated and filtered. The mixture was purified by prep-HPLC (column: Phenomenex luna C18 100*40 mm*5 um; mobile phase: [water (0.1% TFA)-ACN]; B %: 7%-38%, 8 min) to give HxBzL-35a (0.1 g, 165 umol, 35.09% yield) as yellow solid. $^1$H NMR (MeOD, 400 MHz) δ9.08 (s, 2H), 7.88-7.68 (m, 3H), 7.50 (s, 1H), 4.54 (s, 2H), 4.02-3.89 (m, 2H), 3.76 (t, J=7.2 Hz, 2H), 3.44 (s, 2H), 3.36 (t, J=5.6 Hz, 2H), 3.19-3.07 (m, 4H), 1.86-1.68 (m, 6H), 1.47 (s, 9H), 1.00 (t, J=7.6 Hz, 3H).

Preparation of 2-amino-8-[2-(aminomethyl)pyrimidin-5-yl]-N-propyl-N-[2-(pyrrolidine-1-carbonylamino)ethoxy]-3H-1-benzazepine-4-carboxamide, HxBzL-35b To a mixture of HxBzL-35a (0.09 g, 148 umol, 1.0 eq) in $H_2O$ (4 mL) and $CH_3CN$ (0.5 mL) was added TFA (254 mg, 2.23 mmol, 165 uL, 15.0 eq) in one portion at 25° C. and then stirred at 80° C. for 0.5 h. Then the mixture was extracted with MTBE (10 mL×3)-discarded. The water layer was freeze-dried to give HxBzL-35b (0.1 g, 136 umol, 91.76% yield, 2TFA) was obtained as a yellow solid. $^1$H NMR (MeOD, 400 MHz) δ9.21 (s, 2H), 7.86-7.70 (m, 3H), 7.49 (s, 1H), 4.48 (s, 2H), 3.97 (t, J=5.6 Hz, 2H), 3.76 (t, J=7.2 Hz, 2H), 3.48-3.43 (m, 2H), 3.37 (t, J=5.2 Hz, 2H), 3.13 (s, 4H), 1.81-1.71 (m, 6H), 1.00 (t, J=7.6 Hz, 3H).

Preparation of 3-[2-[2-[2-[2-[2-[2-[2-[2-[2-[3-[[5-[2-amino-4-[propyl-[2-(pyrrolidine-1-carbonylamino) ethoxy]carbamoyl]-3H-1-benzazepin-8-yl]pyrimidin-2-yl]methylamino]-3-oxo-propoxy]ethoxy] ethoxy]ethoxy]ethoxy]ethoxy]ethoxy]ethoxy] ethoxy]ethoxy]propanoic acid, HxBzL-35c To a mixture of HxBzL-35b (70 mg, 82.5 umol, 1.0 eq, 3TFA) in THE (2 mL) was added $Et_3N$ (25.0 mg, 247 umol, 34.4 uL, 3.0 eq) and 3-[2-[2-[2-[2-[2-[2-[2-[2-[2-[3-oxo-3-(2,3,5,6-tetrafluorophenoxy)propoxy]ethoxy]ethoxy] ethoxy]ethoxy]ethoxy]ethoxy]ethoxy]ethoxy]ethoxy]propanoic acid (69.9 mg, 98.9 umol, 1.2 eq) in one portion at 0° C. and then stirred at 0° C. for 0.5 h. The mixture was diluted with water (5 mL) and the pH was adjusted to ~6 with TFA at 0° C. Then the mixture was extracted with EtOAc (10 mL)-discarded. The water layer was further extracted with DCM:i-PrOH=3:1 (10 mL×2). The organic layer was dried over $Na_2SO_4$, filtered and concentrated to give HxBzL-35c (0.1 g, crude, TFA) was obtained as yellow oil.

Preparation of HxBzL-35

To a mixture of HxBzL-35c (0.1 g, 86.1 umol, 1.0 eq, TFA) in DCM (2 mL) and DMA (0.5 mL) was added sodium; 2,3,5,6-tetrafluoro-4-hydroxy-benzenesulfonate (115 mg, 431 umol, 5.0 eq) and EDCI (116 mg, 603 umol, 7.0 eq) in one portion at 25° C. and then stirred at 25° C. for 0.5 h. The mixture was concentrated. Then the residue was purified by prep-HPLC (column: Phenomenex Synergi C18 150*25*10 um; mobile phase: [water (0.1% TFA)-ACN]; B %: 10%-35%, 8 min) to give HxBzL-35 (46.4 mg, 33.4 umol, 38.78% yield, TFA) as yellow oil. $^1$H NMR (MeOD, 400 MHz) δ9.09 (s, 2H), 7.85-7.66 (m, 3H), 7.49 (s, 1H), 4.70 (s, 2H), 3.97 (t, J=5.6 Hz, 2H), 3.90-3.84 (m, 2H), 3.80 (t, J=6.0 Hz, 2H), 3.66-3.58 (m, 38H), 3.45 (s, 2H), 3.37 (t, J=5.2 Hz, 2H), 3.13 (s, 4H), 3.01-2.93 (m, 2H), 2.60 (t, J=6.0 Hz, 2H), 1.86-1.68 (m, 6H), 1.00 (t, J=7.6 Hz, 3H). LC/MS [M+H] 1275.5 (calculated); LC/MS [M+H] 1275.6 (observed).

Example L-36 Synthesis of 4-[3-[2-[2-[2-[2-[2-[2-[2-[2-[2-[3-[[1-[[5-[2-amino-4-[3-(cyclobutoxycarbonylamino)propyl-propyl-carbamoyl]-3H-1-benzazepin-8-yl]-3-pyridyl]sulfonyl]azetidin-3-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid HxBzL-36

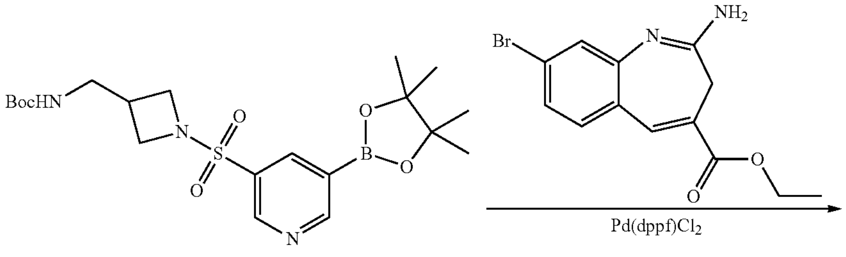

HxBz-32a

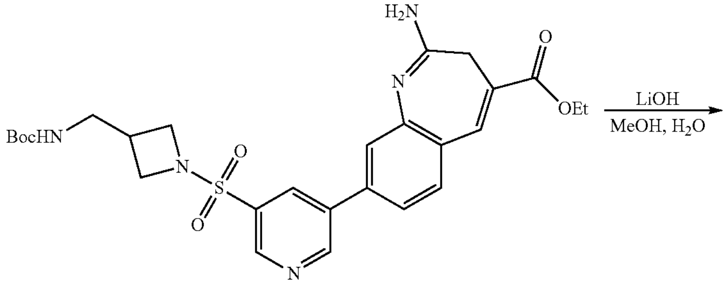

HxBz-32b

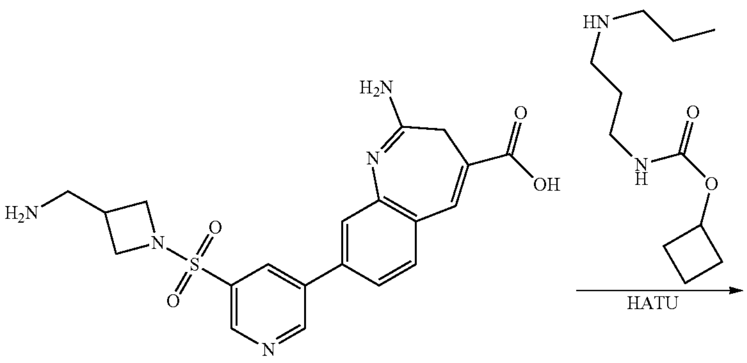

HxBz-32c

-continued
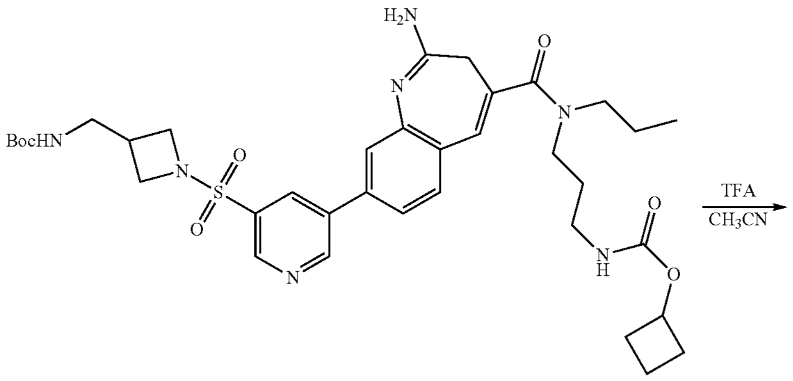
HxBz-32d
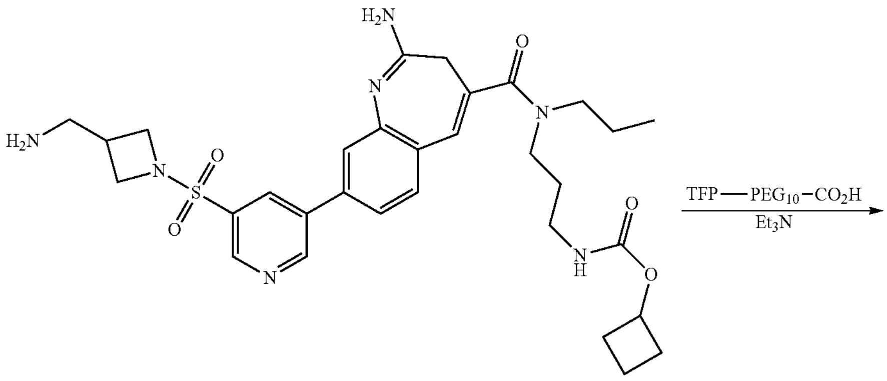
HxBz-32
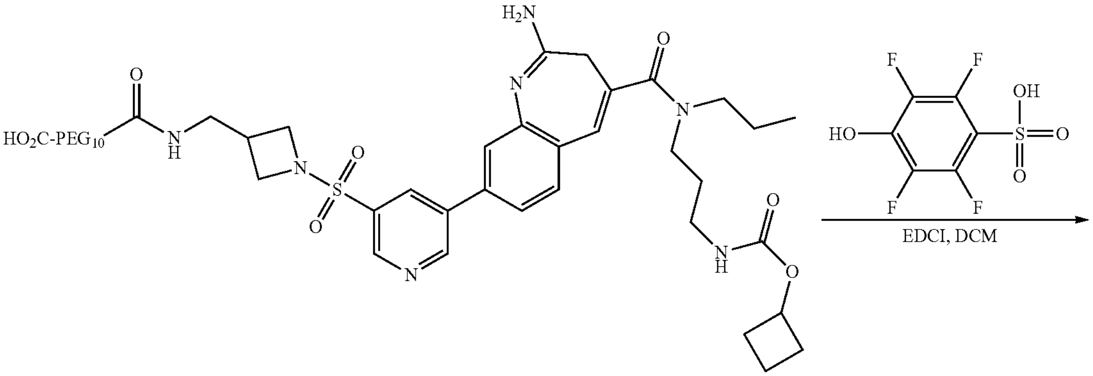
HxBzL-36a

-continued

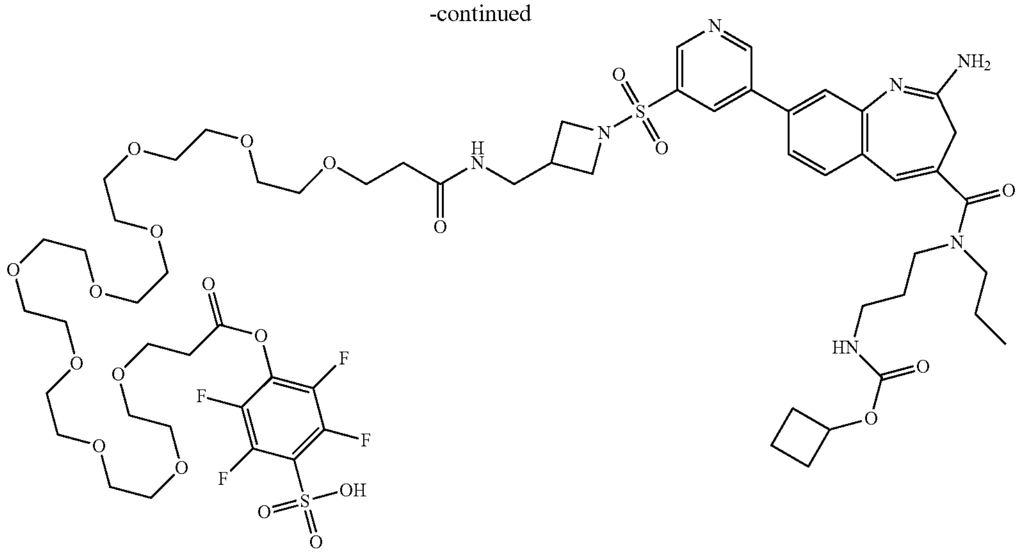

HxBzL-36

Preparation of ethyl 2-amino-8-(5-((3-(((tert-butoxycarbonyl)amino)methyl) azetidin-1-yl)sulfonyl) pyridin-3-yl)-3H-benzo[b]azepine-4-carboxylate, HxBz-32b To a solution of tert-butyl N-[[1-[[5-(4,4,5,5-tetramethyl-1,3,2-dioxaborolan-2-yl)-3-pyridyl] sulfonyl]azetidin-3-yl] methyl]carbamate, HxBz-32a (5 g, 11.0 mmol, 1 eq) and ethyl 2-amino-8-bromo-3H-1-benzazepine-4-carboxylate (3.41 g, 11.0 mmol, 1 eq) in dioxane (50 mL) and $H_2O$ (5 mL) was added $K_2CO_3$ (3.05 g, 22.1 mmol, 2 eq) and $Pd(dppf)Cl_2$ (403 mg, 551 umol, 0.05 eq) at 25° C. under $N_2$, and then stirred at 90° C. for 2 hr. The mixture was filtered and concentrated to give a residue. The residue was diluted with water (100 mL) and extracted with EtOAc (50 mL×3). The organic layer was washed with brine (50 mL), dried over $Na_2SO_4$, filtered and concentrated to give HxBz-32a which was triturated with $CH_3CN$ at 25° C. for 15 min to give HxBz-32b (5.5 g, 9.90 mmol, 89.75% yield) was obtained as grayness solid. $^1H$ NMR (DMSO-$d_6$, 400 MHz) δ9.29 (s, 1H), 8.94 (s, 1H), 8.32 (s, 1H), 7.80 (s, 1H), 7.60 (d, J=8.0 Hz, 1H), 7.50-7.41 (m, 2H), 7.04-6.85 (m, 3H), 4.25 (q, J=7.2 Hz, 2H), 3.82 (t, J=8.0 Hz, 2H), 3.58-3.52 (m, 2H), 2.99-2.85 (m, 4H), 2.56-2.51 (m, 1H), 1.35-1.30 (m, 12H).

Preparation of 2-amino-8-(5-((3-(((tert-butoxycarbonyl)amino)methyl)azetidin-1-yl)sulfonyl)pyridin-3-yl)-3H-benzo[b]azepine-4-carboxylic acid, HxBz-32c To a solution of HxBz-32b (3.2 g, 5.76 mmol, 1 eq) in MeOH (40 mL) and $H_2O$ (5 mL) was added $LiOH \cdot H_2O$ (725 mg, 17.3 mmol, 3 eq), and then stirred at 60° C. for 4 hr. The reaction mixture was concentrated under reduced pressure to remove EtOH. The pH of the mixture was adjusted to about 5 with HCl (12 M) at 0° C. and then filtered, the filter cake was dried under reduced pressure to give the crude product. The crude product was triturated with $CH_3CN$ at 25° C. for 20 min. to give HxBz-32c (2.7 g, 5.12 mmol, 88.86% yield) was obtained as a grayness solid. $^1H$ NMR (DMSO-$d_6$, 400 MHz) δ9.34 (s, 1H), 9.02 (s, 1H), 8.42 (s, 1H), 7.98-7.92 (m, 2H), 7.89-7.83 (m, 2H), 3.83 (t, J=8.0 Hz, 2H), 3.59-3.49 (m, 4H), 2.90 (d, J=6.0 Hz, 2H), 2.56-2.54 (m, 1H), 1.30 (s, 9H).

Preparation of cyclobutyl N-[3-[[2-amino-8-[5-[3-[(tert-butoxycarbonylamino) methyl]azetidin-1-yl] sulfonyl-3-pyridyl]-3H-1-benzazepine-4-carbonyl]-propyl-amino]propyl]carbamate, HxBz-32d To a solution of HxBz-32c (400 mg, 758 umol, 1 eq) in DMF (10.0 mL) was added HATU (317 mg, 834 umol, 1.1 eq), DIEA (490 mg, 3.79 mmol, 660 uL, 5 eq) and cyclobutyl N-[3-(propylamino)propyl]carbamate (380 mg, 1.52 mmol, 2 eq, HCl), and it was stirred at 25° C. for 1 h. The mixture was diluted with water (50 mL) and extracted with EtOAc (30 mL×3). The organic layer was washed with brine (20 mL×3), dried over $Na_2SO_4$, filtered and concentrate. The residue was purified by flash silica gel chromatography (ISCO®; 1 g SepaFlash® Silica Flash Column, Eluent of 0~30% Ethyl acetate/MeOH @ 35 mL/min) to give HxBz-32d (340 mg, 469.69 umol, 61.95% yield) as light yellow solid. $^1H$ NMR (MeOD, 400 MHz) δ9.18 (d, J=2.0 Hz, 1H), 8.95 (d, J=2.0 Hz, 1H), 8.42 (t, J=2.0 Hz, 1H), 7.58-7.50 (m, 2H), 7.49-7.43 (m, 1H), 6.93 (s, 1H), 4.85-4.76 (m, 1H), 3.90 (t, J=8.4 Hz, 2H), 3.64-3.56 (m, 2H), 3.54-3.48 (m, 2H), 3.47-3.39 (m, 2H), 3.32 (br s, 2H), 3.22-3.02 (m, 4H), 2.70-2.57 (m, 1H), 2.35-2.01 (m, 4H), 1.90-1.80 (m, 2H), 1.77-1.47 (m, 4H), 1.37 (s, 9H), 1.05-0.76 (m, 3H).

Preparation of cyclobutyl N-[3-[[2-amino-8-[5-[3-(aminomethyl)azetidin-1-yl]sulfonyl-3-pyridyl]-3H-1-benzazepine-4-carbonyl]-propyl-amino]propyl] carbamate, HxBz-32

To a solution of HxBz-32d (340 mg, 470 umol, 1 eq) in $CH_3CN$ (2.00 mL) and $H_2O$ (1.00 mL) was added TFA (428 mg, 3.76 mmol, 278 uL, 8 eq), and then stirred at 80° C. for 1 h. The mixture was concentrated and filtered. The residue was purified by prep-HPLC (column: Phenomenex luna C18 100*40 mm*5 um; mobile phase: [water (0.1% TFA)-ACN]; B %: 5%-35%, 8 min) to give HxBz-32 (400 mg, 470 umol, 99.98% yield, 2TFA) as light yellow solid. $^1$H NMR (MeOD, 400 MHz) δ9.24 (d, J=1.6 Hz, 1H), 9.04 (d, J=1.6 Hz, 1H), 8.49 (s, 1H), 7.88-7.71 (m, 3H), 7.13 (br s, 1H), 4.85-4.80 (m, 1H), 4.03 (t, J=8.4 Hz, 2H), 3.73 (dd, J=5.6, 8.4 Hz, 2H), 3.59-3.43 (m, 4H), 3.38 (br s, 2H), 3.12 (br d, J=7.6 Hz, 4H), 2.83-2.73 (m, 1H), 2.37-2.12 (m, 2H), 2.00-2.10 (m, 4H), 1.78-1.43 (m, 4H), 1.05-0.83 (m, 3H). LC/MS [M+H] 624.3 (calculated); LC/MS [M+H] 624.2 (observed).

Preparation of 3-[2-[2-[2-[2-[2-[2-[2-[2-[2-[3-[[1-[[5-[2-amino-4-[3-(cyclobutoxycarbonylamino)propyl-propyl-carbamoyl]-3H-1-benzazepin-8-yl]-3-pyridyl]sulfonyl]azetidin-3-yl]methylamino]-3-oxo-propoxy]ethoxy]ethoxy]ethoxy]ethoxy]ethoxy]ethoxy]ethoxy]ethoxy]ethoxy]propanoic acid, HxBzL-36a To a solution of HxBz-32 (200 mg, 235 umol, 1 eq, 2TFA) in THE (2.00 mL) was added $Et_3N$ (71.0 mg, 704 umol, 98.0 uL, 3 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (166 mg, 235 umol, 1 eq), and then stirred at 0° C. for 1 h. The mixture was concentrated and diluted with water (10 mL) and the pH of the mixture was adjusted ~6 by progressively adding TFA and extracted with MTBE (10 mL)-discarded, the aqueous phase was further extracted with DCM:i-PrOH=3:1 (20 mL×3). The organic layer was dried over $Na_2SO_4$, filtered and concentrated to give HxBzL-36a (210 mg, 180.36 umol, 76.81% yield) as light yellow oil.

Preparation of HxBzL-36

To a solution of HxBzL-33a (210 mg, 180 umol, 1 eq) and 2,3,5,6-tetrafluoro-4-hydroxy-benzenesulfonic acid (178 mg, 721 umol, 4 eq) in DCM (4.00 mL) and DMA (0.20 mL) was added EDCI (138 mg, 721 umol, 4 eq), and then stirred at 25° C. for 1 h. The mixture was concentrated and filtered. The residue was purified by prep-HPLC (column: Phenomenex Luna 80*30 mm*3 um; mobile phase: [water (0.2% FA)-ACN]; B %: 15%-40%, 8 min) to give HxBzL-36 (98 mg, 68.13 umol, 37.77% yield, FA) as white solid. $^1$H NMR (MeOD, 400 MHz) δ9.23 (d, J=2.0 Hz, 1H), 9.02 (d, J=2.0 Hz, 1H), 8.48 (t, J=2.0 Hz, 1H), 7.91-7.67 (m, 3H), 7.13 (s, 1H), 4.85-4.80 (m, 1H), 3.93 (t, J=8.4 Hz, 2H), 3.86 (t, J=5.6 Hz, 2H), 3.66-3.55 (m, 40H), 3.54-3.48 (m, 4H), 3.40 (br s, 2H), 3.25-3.08 (m, 4H), 2.97 (t, J=5.6 Hz, 2H), 2.79-2.68 (m, 1H), 2.29 (br t, J=6.0 Hz, 3H), 1.93-1.80 (m, 3H), 1.77-1.52 (m, 4H), 1.01-0.88 (m, 3H). LC/MS [M+H] 1392.5 (calculated); LC/MS [M+H] 1392.3 (observed).

Example L-37 Synthesis of cyclobutyl (2-((2-amino-8-(2-(39-(2,5-dioxo-2,5-dihydro-1H-pyrrol-1-yl)-3,37-dioxo-6,9,12,15,18,21,24,27,30,33-decaoxa-2,36-diazanonatriacontyl)pyrimidin-5-yl)-N-propyl-3H-benzo[b]azepine-4-carboxamido)oxy)ethyl) carbamate, HxBzL-37

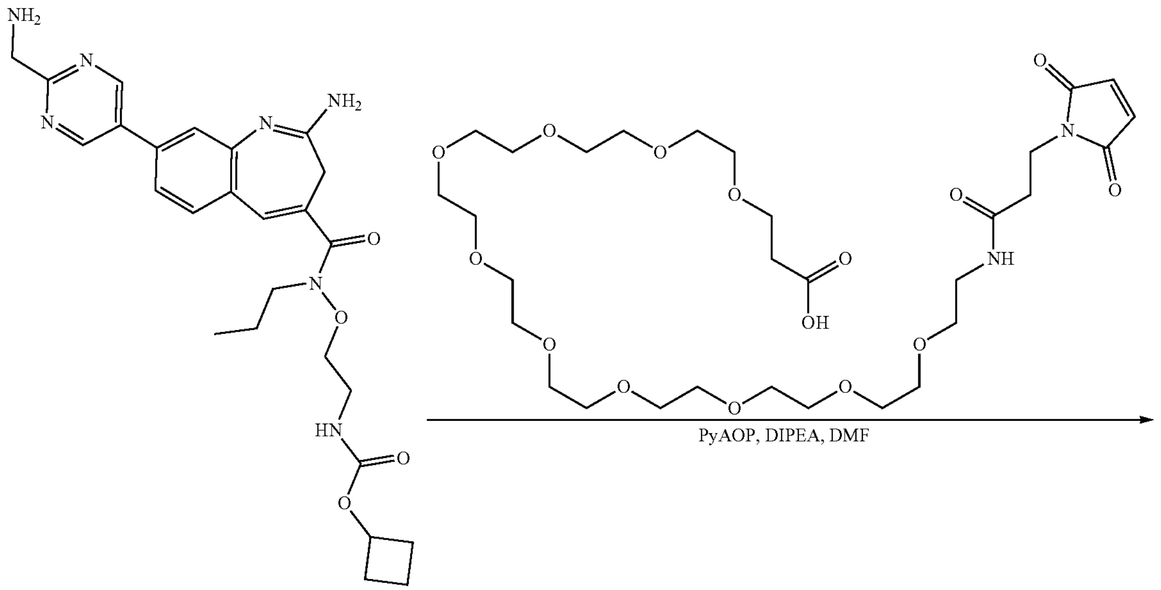

HxBzL-37a

-continued

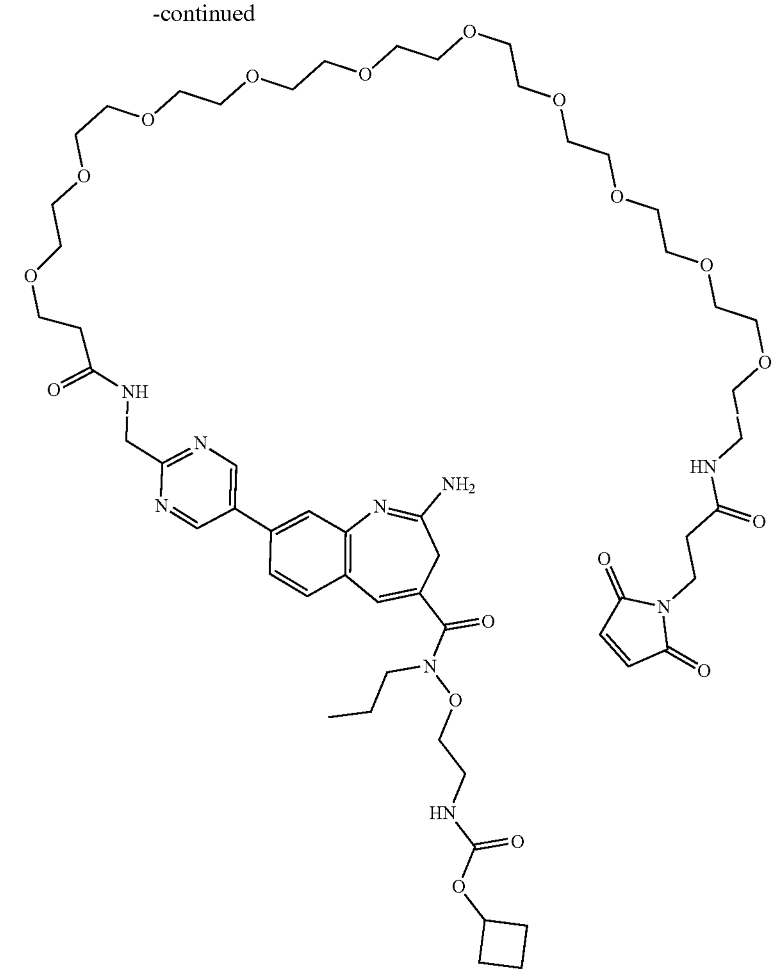

HxBzL-37

To a solution of cyclobutyl (2-((2-amino-8-(2-(aminomethyl)pyrimidin-5-yl)-N-propyl-3H-benzo[b]azepine-4-carboxamido)oxy)ethyl)carbamate, HxBzL-37a (23.6 mg, 0.046 mmol, 1 eq) and 1-(2,5-dioxo-2,5-dihydro-1H-pyrrol-1-yl)-3-oxo-7,10,13,16,19,22,25,28,31,34-decaoxa-4-aza-heptatriacontan-37-oic acid (31.7 mg, 0.046 mmol, 1 eq) in DMF (1 ml) was added DIPEA (49 μl, 0.28 mmol, 6 eq), followed by ((7-azabenzotriazol-1-yloxy)tripyrrolidinophosphonium hexafluorophosphate), PyAOP, CAS Reg. No. 156311-83-0 (59 mg, 0.113 mmol, 2.4 eq). The reaction was stirred at room temperature for 2 hours, then concentrated and purified by prep-HPLC to give HxBzL-37 (4.9 mg, 0.0042 mmol, 9%). LC/MS [M+H] 1170.6 (calculated); LC/MS [M+H] 1170.9 (observed).

Example L-41 Synthesis of 4-[3-[2-[2-[2-[2-[2-[2-[2-[2-[2-[3-[[5-[2-amino-4-[ethoxy(propyl)carbamoyl]-3H-1-benzazepin-8-yl]-2-pyridyl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-41

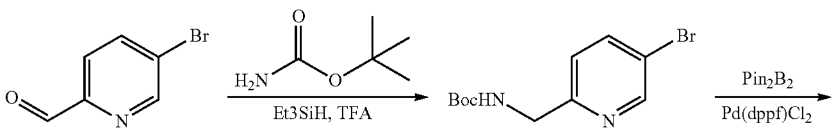

HxBz-36a HxBz-36b

-continued
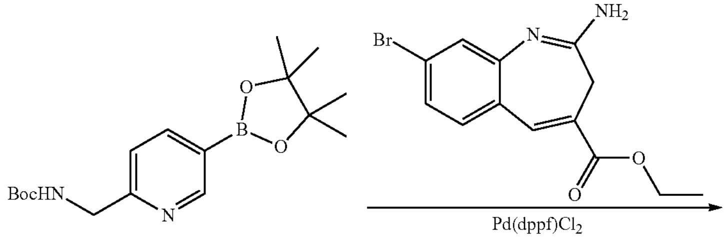
HxBz-36c
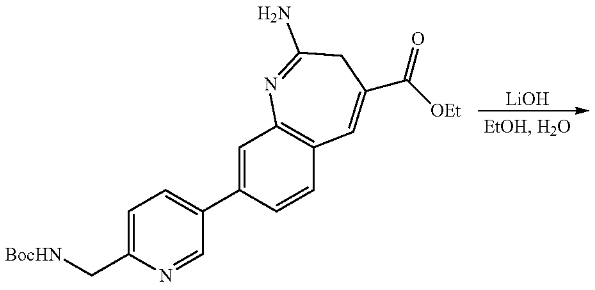
HxBz-36d
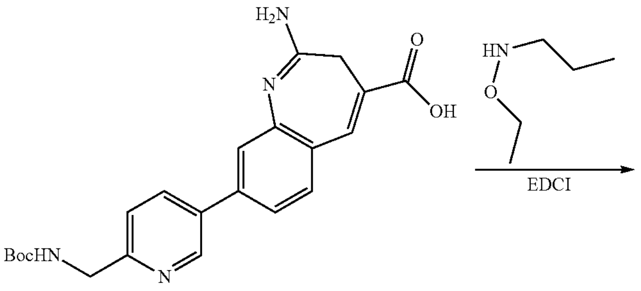
HxBz-36e
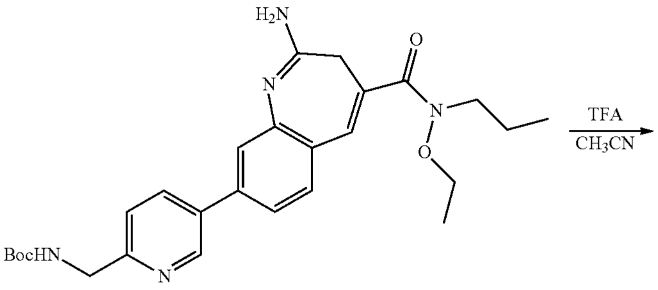
HxBz-36f
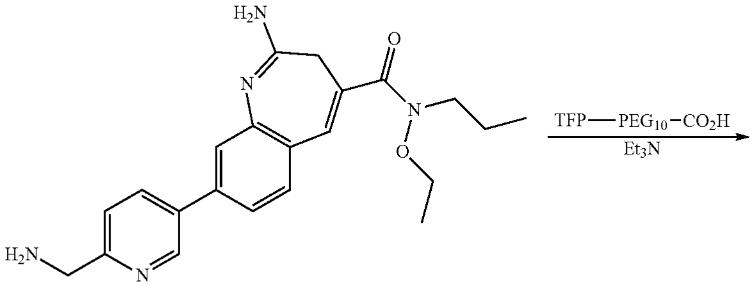
HxBz-36

-continued

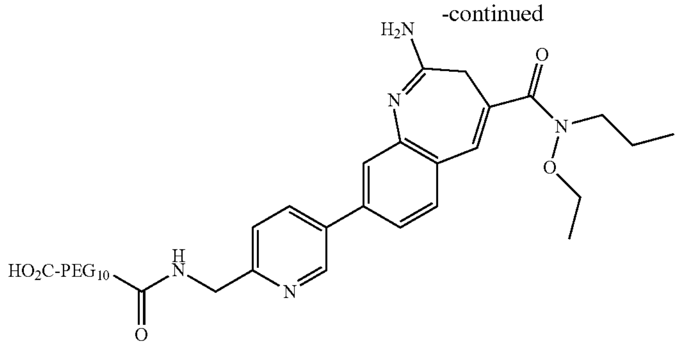

HxBzL-41a

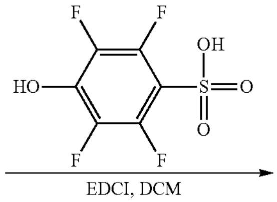

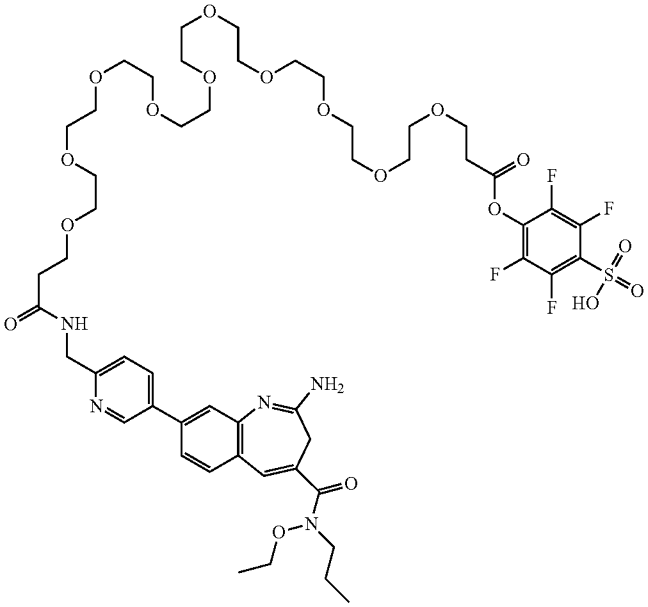

HxBzL-41

Preparation of tert-butyl N-[(5-bromo-2-pyridyl)methyl]carbamate, HxBz-36b

To a solution of 5-bromopyridine-2-carbaldehyde, HxBz-36a (5.00 g, 26.9 mmol, 1 eq) and tert-butyl carbamate (6.30 g, 53.8 mmol, 2 eq) in $CH_3CN$ (250 mL) was added TFA (9.19 g, 80.6 mmol, 5.97 mL, 3 eq) and $Et_3SiH$ (31.3 g, 268.8 mmol, 42.9 mL, 10 eq) at 0° C. and it was stirred at 25° C. for 3 h. The reaction mixture was quenched by addition of aq. $Na_2CO_3$ (200 mL) at 0° C., concentrated under reduced pressure. The residue was diluted with (200 mL) and extracted with EtOAc (100 mL×3). The combined organic layers were washed with brine (50 mL), dried over $Na_2SO_4$, filtered and concentrated under reduced pressure. The residue was purified by column chromatography ($SiO_2$, Petroleum ether:Ethyl acetate=1:0 to 1:1). HxBz-36b (9 g, crude) was obtained as a light yellow solid. $^1H$ NMR ($CDCl_3$, 400 MHz) δ8.59 (d, J=2.4 Hz, 1H), 7.78 (dd, J=2.4, 8.4 Hz, 1H), 7.20 (d, J=8.4 Hz, 1H), 5.50 (br s, 1H), 4.58-4.29 (m, 2H), 1.45 (s, 9H)

Preparation of tert-butyl N-[[5-(4,4,5,5-tetramethyl-1,3,2-dioxaborolan-2-yl)-2-pyridyl]methyl]carbamate, HxBz-36c A mixture of HxBz-36b (8.00 g, 27.9 mmol, 1 eq), $Pin_2B_2$ (8.49 g, 33.4 mmol, 1.2 eq), $Pd(dppf)Cl_2$ (1.02 g, 1.39 mmol, 0.05 eq) and KOAc (5.47 g, 55.7 mmol, 2 eq) in dioxane (80 mL) was degassed and purged with $N_2$ for 3 times. The mixture was stirred at 90° C. for 2 h under $N_2$ atmosphere and then without workup, directly used for next step, HxBz-36c (9.4 g, crude) was obtained as a black brown oil.

Preparation of ethyl 2-amino-8-[6-[(tert-butoxycarbonylamino)methyl]-3-pyridyl]-3H-1-benzazepine-4-carboxylate, HxBz-36d A mixture of HxBz-36c (9.30 g, 27.82 mmol, 2 eq), ethyl 2-amino-8-bromo-3H-1-benzazepine-4-carboxylate (4.30 g, 13.9 mmol, 1 eq), $Pd(dppf)Cl_2$ (509 mg, 695 umol, 0.05 eq) and $K_2CO_3$ (3.84 g, 27.8 mmol, 2 eq) in dioxane (80 mL) and $H_2O$ (8 mL) was degassed and purged with $N_2$ for 3 times, and then it was stirred at 90° C. for 3 h under $N_2$ atmosphere. The reaction mixture was filtered and concentrated under reduced pressure. The residue was diluted with $H_2O$ (50 mL) and extracted with EtOAc (50 mL×3). The combined organic layers were washed with brine (30 mL×3), dried over $Na_2SO_4$, filtered and concentrated under reduced pressure. The residue was purified by column chromatography ($SiO_2$, Petroleum ether:Ethyl acetate=1:0 to 0:1) and then ($SiO_2$, EtOAc:MeOH=1:0 to 5:1) to give HxBz-36d (2.40 g, 5.50 mmol, 39.5% yield) was obtained as a light yellow solid. $^1$H NMR (MeOD, 400 MHz) δ8.76 (s, 1H), 8.10 (br d, J=8.0 Hz, 1H), 7.85 (s, 1H), 7.58-7.33 (m, 4H), 4.40 (s, 2H), 4.32 (q, J=7.2 Hz, 2H), 3.05 (s, 2H), 1.48 (s, 9H), 1.38 (t, J=7.2 Hz, 3H).

Preparation of 2-amino-8-[6-[(tert-butoxycarbonylamino)methyl]-3-pyridyl]-3H-1-benzazepine-4-carboxylic acid, HxBz-36e To a solution of HxBz-36d (2.40 g, 5.50 mmol, 1 eq) in EtOH (30 mL) was added a solution of LiOH·$H_2O$ (923 mg, 22.0 mmol, 4 eq) in $H_2O$ (6 mL) and then it was stirred at 40° C. for 2 h. The pH of the reaction mixture was adjusted to 5-6 by addition of 1 M HCl at 0° C., and then concentrated under reduced pressure to remove EtOH. The residue was diluted with $H_2O$ (10 mL) and filtered and the filter cake was dried under reduced pressure to give HxBz-36e (1.88 g, 4.60 mmol, 83.7% yield) was obtained as a gray solid. $^1$H NMR (DMSO, 400 MHz) δ9.01 (s, 1H), 8.50 (br d, J=8.4 Hz, 1H), 7.93 (s, 1H), 7.83 (s, 2H), 7.75 (s, 1H), 7.73-7.66 (m, 1H), 4.41 (br s, 2H), 3.51 (s, 2H), 1.40 (s, 9H).

Preparation of tert-butyl N-[[5-[2-amino-4-[ethoxy(propyl)carbamoyl]-3H-1-benzazepin-8-yl]-2-pyridyl]methyl]carbamate, HxBz-36f To a solution of HxBz-36e (0.35 g, 857 umol, 1 eq) and N-ethoxypropan-1-amine (144 mg, 1.03 mmol, 1.2 eq, HCl) in DCM (3 mL) and DMA (3 mL) was added EDCI (493 mg, 2.57 mmol, 3 eq) and then it was stirred at 25° C. for 1 h. The reaction mixture was concentrated under reduced pressure to remove DCM. The residue was diluted with $H_2O$ (10 mL) and the pH of the mixture was adjusted to ~9 by addition of aq. $Na_2CO_3$ at 0° C., extracted with EtOAc (10 mL×3). The combined organic layers were washed with brine (5 mL×3), dried over $Na_2SO_4$, filtered and concentrated under reduced pressure. The residue was purified by column chromatography ($SiO_2$, Petroleum ether:Ethyl acetate=1:0 to 0:1) and then ($SiO_2$, EtOAc:MeOH=1:0 to 3:1) to give HxBz-36f (0.33 g, 669 umol, 78.0% yield) as a light yellow solid. $^1$H NMR (MeOD, 400 MHz) δ8.76 (d, J=2.0 Hz, 1H), 8.11 (br d, J=8.4 Hz, 1H), 7.47 (d, J=8.4 Hz, 2H), 7.43 (d, J=2.0 Hz, 1H), 7.40-7.34 (m, 1H), 7.29 (s, 1H), 4.40 (s, 2H), 3.95 (q, J=7.2 Hz, 2H), 3.73 (t, J=7.2 Hz, 2H), 3.31 (s, 2H), 1.82-1.70 (m, 2H), 1.48 (s, 9H), 1.17 (t, J=7.2 Hz, 3H), 0.99 (t, J=7.2 Hz, 3H).

Preparation of 2-amino-8-[6-(aminomethyl)-3-pyridyl]-N-ethoxy-N-propyl-3H-1-benzazepine-4-carboxamide, HxBz-36

To a solution of HxBz-36f (0.33 g, 669 umol, 1 eq) in $CH_3CN$ (3 mL) and $H_2O$ (3 mL) was added TFA (610 mg, 5.35 mmol, 396 uL, 8 eq), and then stirred at 80° C. for 0.5 h. The reaction mixture was concentrated under reduced pressure to remove solvent. The residue was diluted with $H_2O$ (5 mL) and extracted with MTBE (5 mL×3) and discarded. The water phase was concentrated under reduced pressure to give HxBz-36 (0.33 g, 530.95 umol, 79.42% yield, 2TFA) as a light yellow solid. $^1$H NMR (MeOD, 400 MHz) δ8.99 (d, J=2.0 Hz, 1H), 8.20 (dd, J=2.4, 8.4 Hz, 1H), 7.79-7.67 (m, 3H), 7.59 (d, J=8.4 Hz, 1H), 7.45 (s, 1H), 4.36 (s, 2H), 3.98 (q, J=7.2 Hz, 2H), 3.76 (t, J=7.2 Hz, 2H), 3.43 (s, 2H), 1.83-1.72 (m, 2H), 1.26-1.16 (m, 3H), 1.01 (t, J=7.2 Hz, 3H). LC/MS [M+H] 394.2 (calculated); LC/MS [M+H] 394.2 (observed).

Example L-40 Synthesis of cyclobutyl (2-((2-amino-8-(2-(38-(2,5-dioxo-2,5-dihydro-1H-pyrrol-1-yl)-3,37-dioxo-6,9,12,15,18,21,24,27,30,33-decaoxa-2,36-diazaoctatriacontyl)pyrimidin-5-yl)-N-propyl-3H-benzo[b]azepine-4-carboxamido)oxy)ethyl) carbamate, HxBzL-40

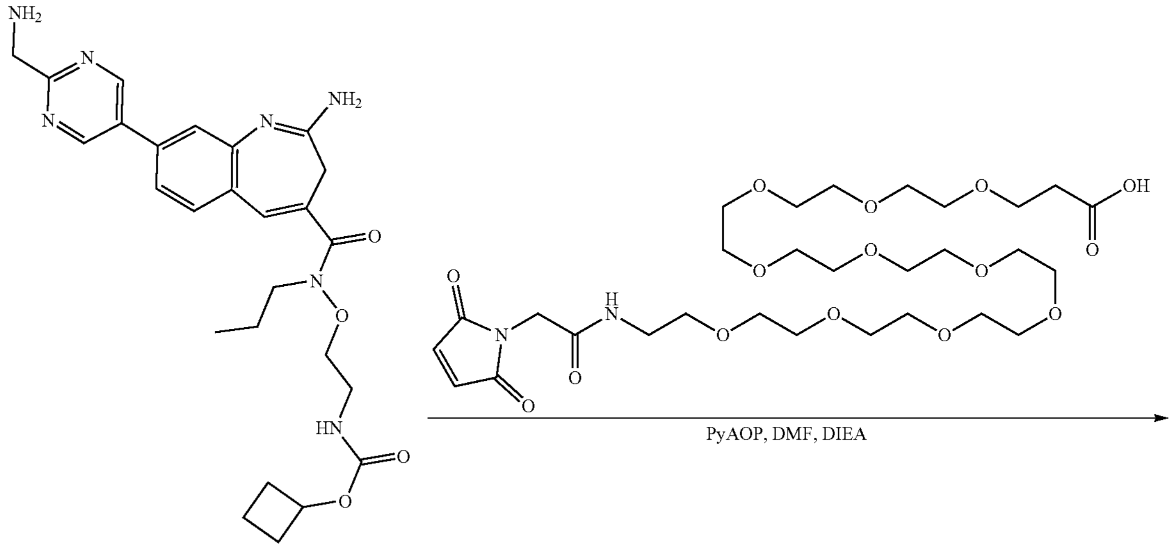

HxBzL-40a

-continued

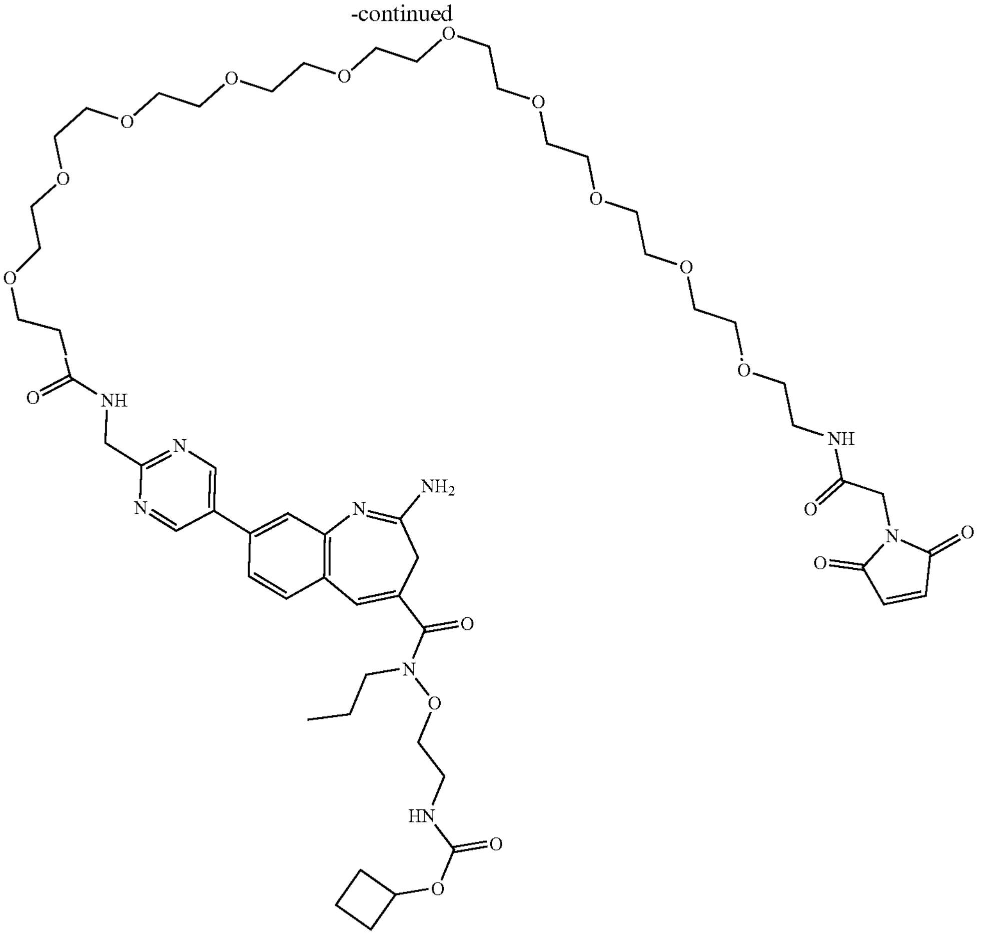

HxBzL-40

To a stirred solution of cyclobutyl (2-((2-amino-8-(2-(aminomethyl)pyrimidin-5-yl)-N-propyl-3H-benzo[b]azepine-4-carboxamido)oxy)ethyl)carbamate, HxBzL-40a (12.4 mg, 0.024 mmol, 1 eq) and 1-(2,5-dioxo-2,5-dihydro-1H-pyrrol-1-yl)-2-oxo-6,9,12,15,18,21,24,27,30,33-decaoxa-3-azahexatriacontan-36-oic acid (16.3 mg, 0.024 mmol, 1 eq) in DMF (0.5 ml) was added DIPEA (25.5 μl, 0.15 mmol, 6 eq), followed by PyAOP (31.0 mg, 0.059 mmol, 2.4 eq). The reaction was stirred at room temperature and monitored by LC/MS, then concentrated and purified by prep-HPLC to give HxBzL-40 (6.7 mg, 0.0058 mmol, 24%). LC/MS [M+H] 1156.6 (calculated); LC/MS [M+H] 1156.9 (observed).

Preparation of 3-[2-[2-[2-[2-[2-[2-[2-[2-[2-[3-[[5-[2-amino-4-[ethoxy(propyl) carbamoyl]-3H-1-benzazepin-8-yl]-2-pyridyl]methylamino]-3-oxo-propoxy]ethoxy]ethoxy]ethoxy]ethoxy]ethoxy]ethoxy]ethoxy]ethoxy]ethoxy]propanoic acid, HxBzL-41a To a solution of HxBz-36 (0.15 g, 241 umol, 1 eq, 2TFA) in THF (3 mL) was added TEA (73.3 mg, 724 umol, 3 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (171 mg, 241 umol, 1 eq) at 0° C. and it was stirred at 20° C. for 0.5 h. The pH of the reaction mixture was adjusted to 5-6 with TFA at 0° C., and then diluted with $H_2O$ (10 mL) and extracted with EtOAc (5 mL×3) and discarded. The water phase was further extracted with DCM:i-PrOH=3:1 (5 mL×3). The combined organic layers were dried over $Na_2SO_4$, filtered and concentrated under reduced pressure to give HxBzL-41a (0.23 g, 219 umol, 90.9% yield, TFA) as a colorless oil. $^1H$ NMR (MeOD, 400 MHz) δ8.91 (d, J=2.0 Hz, 1H), 8.33 (dd, J=2.0, 8.0 Hz, 1H), 7.83-7.77 (m, 1H), 7.75-7.69 (m, 3H), 7.47 (s, 1H), 4.64 (s, 2H), 3.98 (q, J=7.2 Hz, 2H), 3.83-3.74 (m, 4H), 3.71 (t, J=6.4 Hz, 2H), 3.66-3.50 (m, 36H), 3.45 (s, 2H), 2.58 (t, J=6.0 Hz, 2H), 2.53 (t, J=6.0 Hz, 2H), 1.83-1.73 (m, 2H), 1.21 (t, J=7.2 Hz, 3H), 1.01 (t, J=7.2 Hz, 3H)

Preparation of HxBzL-41

To a solution of HxBzL-41a (0.18 g, 172 umol, 1 eq, TFA) in DCM (3 mL) and DMA (0.3 mL) was added (2,3,5,6-tetrafluoro-4-hydroxy-phenyl)sulfonyloxysodium (184 mg, 687 umol, 4 eq) and EDCI (132 mg, 687 umol, 4 eq) and it was stirred at 20° C. for 0.5 h. The reaction mixture was concentrated under reduced pressure to remove DCM, and filtered. The residue was purified by prep-HPLC (TFA condition; column: Phenomenex Luna 80*30 mm*3 um; mobile phase: [water (0.1% TFA)-ACN]; B %: 10%-35%, 8 min) to give HxBzL-41 (116.7 mg, 91.4 umol, 53.2% yield, TFA) as a white solid. $^1H$ NMR (MeOD, 400 MHz) δ9.01 (d, J=2.0 Hz, 1H), 8.57 (dd, J=2.0, 8.4 Hz, 1H), 7.92 (d, J=8.4 Hz, 1H), 7.84-7.79 (m, 2H), 7.75-7.68 (m, 1H), 7.45 (s, 1H), 4.72 (s, 2H), 3.98 (q, J=7.2 Hz, 2H), 3.85 (t, J=6.0

Hz, 2H), 3.82-3.72 (m, 4H), 3.67-3.51 (m, 36H), 3.45 (s, 2H), 2.96 (t, J=6.0 Hz, 2H), 2.59 (t, J=6.0 Hz, 2H), 1.83-1.73 (m, 2H), 1.21 (t, J=7.2 Hz, 3H), 1.01 (t, J=7.2 Hz, 3H). LC/MS [M+H]1162.5 (calculated); LC/MS [M+H] 1162.5 (observed).
Example L-42 Synthesis of 4-[3-[2-[2-[2-[2-[2-[2-[2-[2-[2-[3-[[5-[2-amino-4-[3-(cyclobutoxycarbonylamino)propyl-propyl-carbamoyl]-3H-1-benzazepin-8-yl]-2-pyridyl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-42
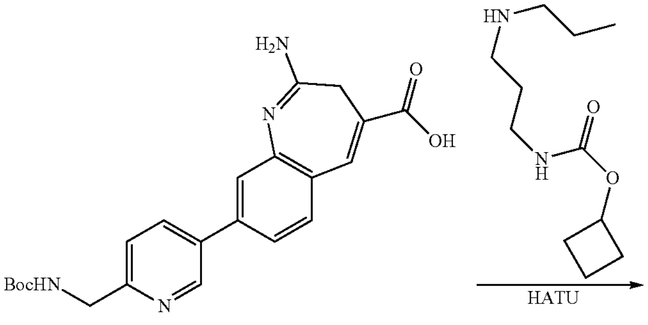
HxBz-38a
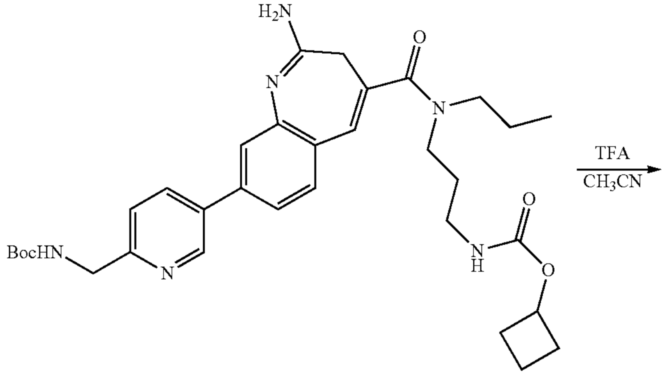
HxBz-38b
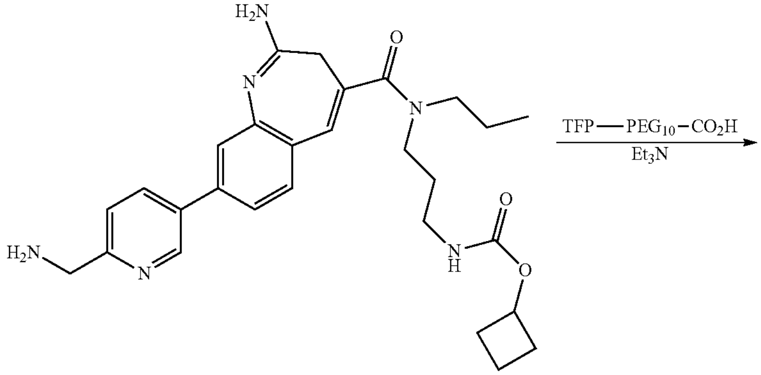
HxBz-38

-continued

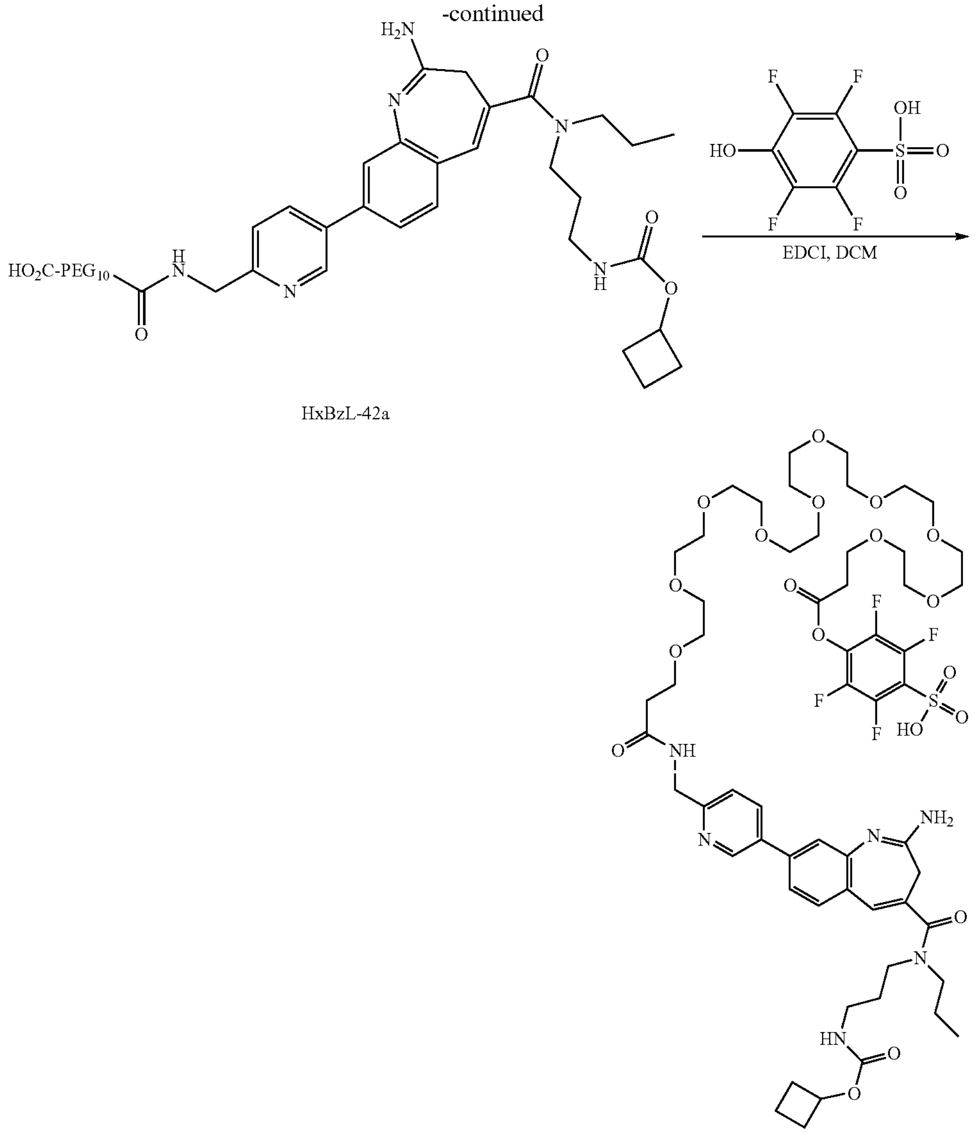

HxBzL-42a

HxBzL-42

Preparation of cyclobutyl N-[3-[[2-amino-8-[6-[(tert-butoxycarbonylamino) methyl]-3-pyridyl]-3H-1-benzazepine-4-carbonyl]-propyl-amino]propyl] carbamate, HxBz-38b To a solution of 2-amino-8-[6-[(tert-butoxycarbonylamino)methyl]-3-pyridyl]-3H-1-benzazepine-4-carboxylic acid, HxBz-38a (0.35 g, 857 umol, 1 eq) and cyclobutyl N-[3-(propylamino)propyl]carbamate (258 mg, 1.03 mmol, 1.2 eq, HCl) in DMF (5 mL) was added HATU (326 mg, 857 umol, 1 eq) and DIEA (332 mg, 2.57 mmol, 448 uL, 3 eq), and then stirred at 20° C. for 2 hr. The reaction mixture was quenched by addition $H_2O$ (20 mL) at 0° C., and extracted with EtOAc (20 mL×3). The combined organic layers were washed with brine (50 mL), dried over $Na_2SO_4$, filtered and concentrated under reduced pressure to give a residue. The residue was purified by column chromatography (SiO2, MeOH/Ethyl acetate=1/5) to give HxBz-38b (0.45 g, 744.12 umol, 86.84% yield) as a yellow solid.

Preparation of cyclobutyl N-[3-[[2-amino-8-[6-[(tert-butoxycarbonylamino)methyl]-3-pyridyl]-3H-1-benzazepine-4-carbonyl]-propyl-amino]propyl] carbamate, HxBz-38

To a solution of HxBz-38b (0.45 g, 744 umol, 1 eq) in MeCN (5 mL) and $H_2O$ (5 mL) was added TFA (679 mg, 5.95 mmol, 441 uL, 8 eq), and it was stirred at 80° C. for 0.5 hr. The reaction mixture was concentrated under reduced pressure to remove MeCN, and then extracted with MTBE (5 mL) to remove excess TFA. The aqueous layers was concentrated to give a residue, the residue was purified by prep-HPLC (column: Phenomenex Luna 80*30 mm*3 um; mobile phase: [water (0.10% TFA)-ACN]; B %: 10%-40%, 8 min) to give HxBz-38 (0.4 g, 646 umol, 86.89% yield, TFA) as a yellow solid. $^1$H NMR (MeOD, 400 MHz) δ 8.99 (d, J=1.8 Hz, 1H), 8.20 (dd, J=2.4, 8.2 Hz, 1H), 7.80-7.66 (m, 3H), 7.59 (d, J=8.4 Hz, 1H), 7.10 (br s, 1H), 4.85-4.80 (m, 1H), 4.36 (s, 2H), 3.54 (br t, J=7.2 Hz, 2H), 3.47 (br s, 2H), 3.36 (br s, 2H), 3.13 (br s, 2H), 2.42-1.96 (m, 2H), 1.92-1.79 (m, 3H), 1.77-1.59 (m, 3H), 0.94 (br s, 3H). LC/MS [M+H] 505.3 (calculated); LC/MS [M+H] 505.3 (observed).

Preparation of 3-[2-[2-[2-[2-[2-[2-[2-[2-[2-[3-[[5-[2-amino-4-[3-(cyclobutoxycarbonylamino)propyl-propyl-carbamoyl]-3H-1-benzazepin-8-yl]-2-pyridyl]methylamino]-3-oxo-propoxy]ethoxy]ethoxy]ethoxy]ethoxy]ethoxy]ethoxy]ethoxy]ethoxy]ethoxy]propanoic acid, HxBzL-42a To a solution of HxBz-38 (0.15 g, 204 umol, 1 eq, 2TFA) in THF (5 mL) was added $Et_3N$ (62.1 mg, 614 umol, 85.49 uL, 3 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (145 mg, 205 umol, 1 eq), and then stirred at 0° C. for 2 hr. The reaction mixture was quenched by addition $H_2O$ (5 mL), and the pH of the mixture was adjusted to about 6 with TFA, and then extracted with EtOAc (10 ml)-discarded, the aqueous phase was further extracted with DCM/PrOH=3/1 (20 mL×3), dried over $Na_2SO_4$, filtered and concentrated under reduced pressure to give a residue, HxBzL-42a (0.2 g, 191 umol, 93.46% yield) as a yellow oil.

Preparation of HxBzL-42

To a solution of HxBzL-42a (0.2 g, 191 umol, 1 eq) and sodium; 2,3,5,6-tetrafluoro-4-hydroxy-benzenesulfonate (154 mg, 574 umol, 3 eq) in DCM (2 mL) and DMA (1 mL) was added EDCI (110 mg, 574 umol, 3 eq), and then stirred at 20° C. for 1 hr. The reaction mixture was concentrated under reduced pressure to remove DCM and filtered. The residue was purified by prep-HPLC (column: Phenomenex Luna 80*30 mm*3 um; mobile phase: [water (0.1% TFA)-ACN]; B %: 20%-40%, 8 min) to give HxBzL-42 (0.08 g, 62.83 umol, 32.83% yield) as a yellow solid. $^1$H NMR (MeOD, 400 MHz) δ 9.03 (d, J=1.8 Hz, 1H), 8.61 (br d, J=8.4 Hz, 1H), 7.95 (d, J=8.4 Hz, 1H), 7.87-7.78 (m, 2H), 7.73 (br s, 1H), 7.11 (s, 1H), 4.73 (s, 3H), 3.85 (t, J=5.6 Hz, 2H), 3.80 (t, J=5.6 Hz, 2H), 3.67-3.50 (m, 38H), 3.64 (br s, 1H), 3.38 (br s, 2H), 3.13 (br s, 2H), 2.95 (t, J=5.6 Hz, 2H), 2.59 (t, J=5.6 Hz, 2H), 2.35-1.96 (m, 2H), 1.94-1.81 (m, 3H), 1.77-1.64 (m, 4H), 0.93 (br s, 3H). LC/MS [M+H] 1273.5 (calculated); LC/MS [M+H] 1273.7 (observed).

Example L-43 Synthesis of 4-[3-[2-[2-[2-[2-[2-[2-[2-[2-[2-[2-[[(2S)-1-[5-[2-amino-4-[ethoxy(propyl)carbamoyl]-3H-1-benzazepin-8-yl]pyridine-2-carbonyl]pyrrolidine-2-carbonyl]amino]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-43

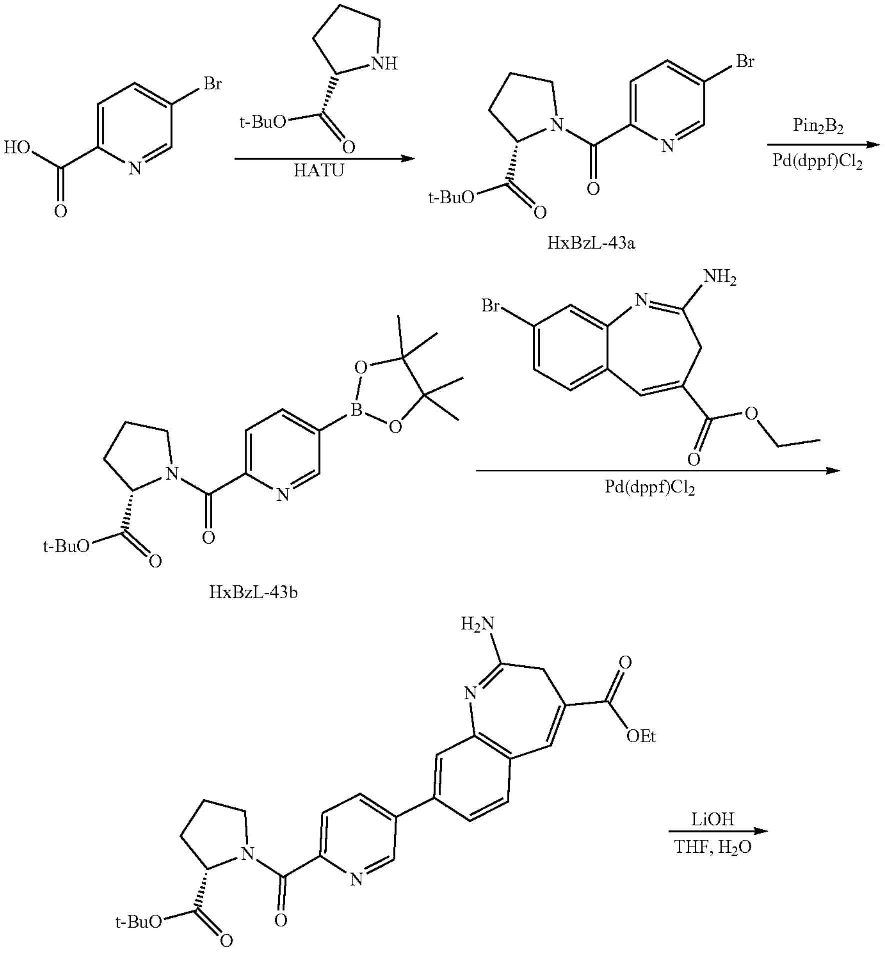

HxBzL-43a

HxBzL-43b

HxBzL-43c

-continued
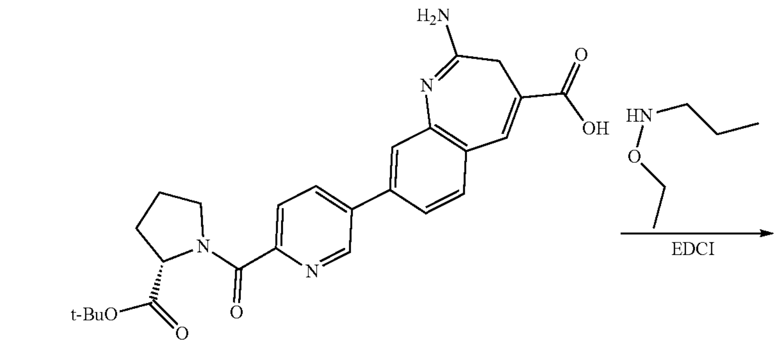
HxBzL-43d
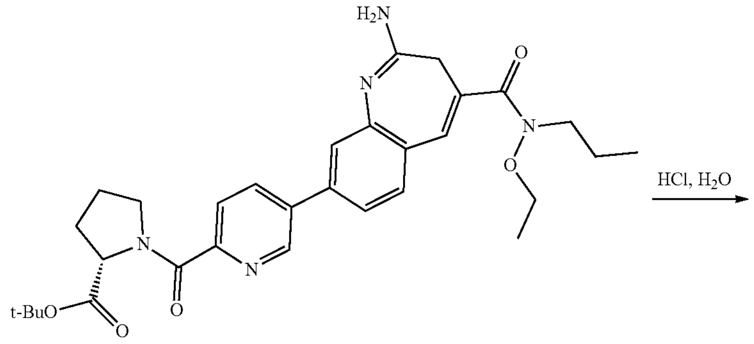
HxBzL-43e
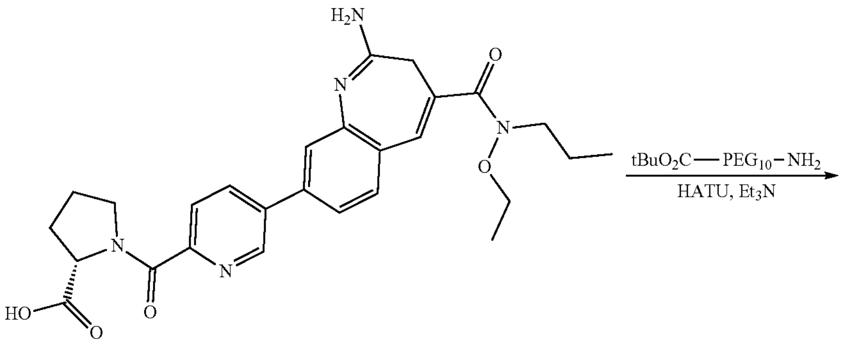
HxBzL-43f
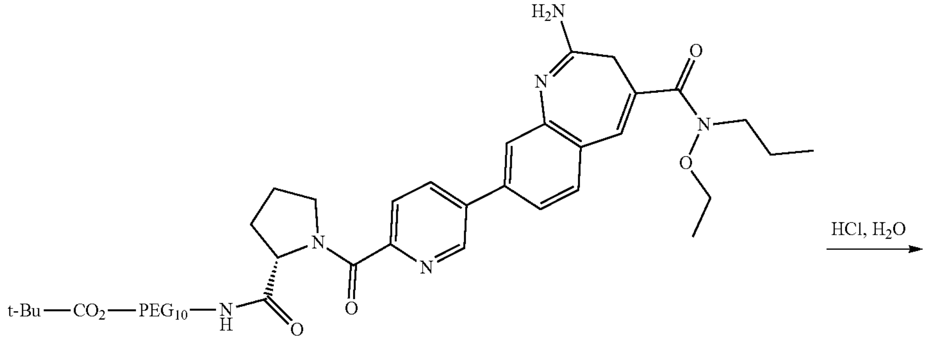
HxBzL-43g -continued
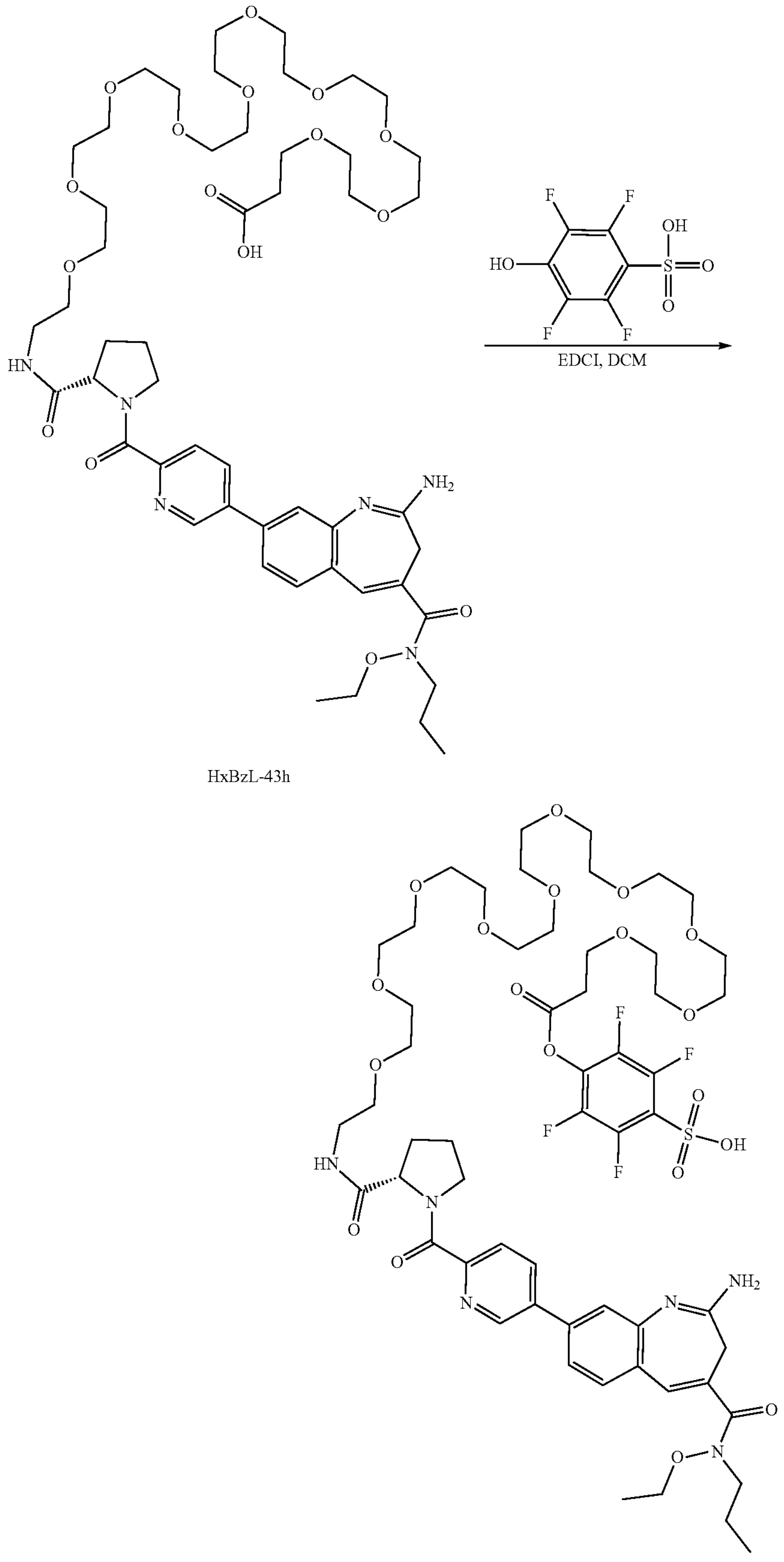
HxBzL-43h
HxBzL-43

Preparation of tert-butyl (2S)-1-(5-bromopyridine-2-carbonyl)pyrrolidine-2-carboxylate, HxBzL-43a To a mixture of 5-bromopyridine-2-carboxylic acid (2.00 g, 9.90 mmol, 1.0 eq), $Et_3N$ (2.50 g, 24.7 mmol, 3.45 mL, 2.5 eq) and tert-butyl (2S)-pyrrolidine-2-carboxylate (2.06 g, 9.90 mmol, 1.0 eq, HCl) in DMF (10 mL) was added HATU (3.76 g, 9.90 mmol, 1.0 eq) in one portion at 0° C. under $N_2$, the mixture was stirred at 0° C. for 30 min, then heated to 25° C. and stirred for another 0.5 hour. Water (30 mL) was added and the aqueous phase was extracted with ethyl acetate (30 mL*3), the combined organic phase was washed with brine (30 mL*1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=20/1, 2/1) to afford HxBzL-43a (3.40 g, 9.57 mmol, 96.6% yield) as yellow oil. $^1H$ NMR (400 MHz, $CDCl_3$) δ 8.65 (d, J=1.6 Hz, 1H), 7.96-7.92 (m, 2H), 5.03 (dd, J=3.2, 8.4 Hz, 1H), 3.91-3.85 (m, 2H), 2.33-2.28 (m, 2H), 2.18-2.12 (m, 2H), 1.55-1.48 (m, 9H).

Preparation of tert-butyl (2S)-1-[5-(4,4,5,5-tetramethyl-1,3,2-dioxaborolan-2-yl) pyridine-2-carbonyl] pyrrolidine-2-carboxylate, HxBzL-43b A solution of HxBzL-43a (3.40 g, 9.57 mmol, 1.0 eq), 4,4,5,5-tetramethyl-2-(4,4,5,5-tetramethyl-1,3,2-dioxaborolan-2-yl)-1,3,2-dioxaborolane (2.92 g, 11.5 mmol, 1.2 eq), $Pd(dppf)Cl_2$ (700 mg, 957 umol, 0.1 eq) and AcOK (2.35 g, 23.9 mmol, 2.5 eq) in dioxane (30 mL) was de-gassed and then heated to 100° C. for 3 hours under $N_2$. The reaction mixture was concentrated in vacuum to afford HxBzL-43b (3.60 g, crude) as black oil, it was used directly to next step without purification.

Preparation of ethyl 2-amino-8-[6-[(2S)-2-tert-butoxycarbonylpyrrolidine-1-carbonyl]-3-pyridyl]-3H-1-benzazepine-4-carboxylate, HxBzL-43c A solution of HxBzL-43b (3.60 g, 8.95 mmol, 1.0 eq), ethyl 2-amino-8-bromo-3H-1-benzazepine-4-carboxylate (2.77 g, 8.95 mmol, 1.0 eq), $Pd(dppf)Cl_2$ (655 mg, 895 umol, 0.1 eq) and $K_3PO_4$ (3.80 g, 17.9 mmol, 2.0 eq) in dioxane (45 mL) and $H_2O$ (5 mL) was de-gassed and then heated to 95° C. for 2 hours under $N_2$. Dioxane (45 mL) was removed and the aqueous phase was extracted with ethyl acetate (30 mL*3), the combined organic phase was washed with brine (30 mL*1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 0/1) to afford HxBzL-43c (1.60 g, 3.17 mmol, 35.4% yield) as light yellow solid.

Preparation of 2-amino-8-[6-[(2S)-2-tert-butoxycarbonylpyrrolidine-1-carbonyl]-3-pyridyl]-3H-1-benzazepine-4-carboxylic acid, HxBzL-43d To a solution of HxBzL-43c (1.60 g, 3.17 mmol, 1.0 eq) in MeOH (10 mL) and $H_2O$ (5 mL) was added $LiOH \cdot H_2O$ (399 mg, 9.51 mmol, 3.0 eq) in one portion at 25° C. under $N_2$, and it was stirred at 25° C. for 10 hours. The reaction mixture was quenched with HCl (4 M) until pH=7, then MeOH (10 mL) was removed and the precipitation was filtered, dried to afford HxBzL-43d (1.10 g, 2.31 mmol, 72.8% yield) as white solid. $^1H$ NMR (400 MHz, DMSO-$d_6$) δ8.86 (d, J=2.0 Hz, 1H), 8.32-8.26 (m, 1H), 8.01 (d, J=8.4 Hz, 1H), 7.95-7.65 (m, 5H), 5.04-5.01 (m, 1H), 3.79-3.82 (m, 2H), 3.52 (s, 2H), 2.36-2.27 (m, 1H), 2.03-1.94 (m, 1H), 1.89-1.77 (m, 2H), 1.45-1.23 (m, 9H).

Preparation of tert-butyl (2S)-1-[5-[2-amino-4-[ethoxy(propyl)carbamoyl]-3H-1-benzazepin-8-yl] pyridine-2-carbonyl]pyrrolidine-2-carboxylate, HxBzL-43e To a mixture of HxBzL-43d (200 mg, 420 umol, 1.0 eq) and N-ethoxypropan-1-amine (64.5 mg, 462 umol, 1.1 eq, HCl) in DCM (4 mL) and DMA (2 mL) was added EDCI (322 mg, 1.68 mmol, 4.0 eq) in one portion at 25° C. under $N_2$, and then stirred at 25° C. for 1 hour. DCM (4 mL) was removed and water (8 mL) was added, then the pH of aqueous phase was adjusted to ~8 with saturated $NaHCO_3$, extracted with ethyl acetate (5 mL*3), the combined organic phase was washed with brine (5 mL*1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 0/1 to Ethyl acetate/Methanol=10/1) to afford HxBzL-43e (200 mg, 356 umol, 84.8% yield) as brown oil.

Preparation of (2S)-1-[5-[2-amino-4-[ethoxy(propyl) carbamoyl]-3H-1-benzazepin-8-yl]pyridine-2-carbonyl]pyrrolidine-2-carboxylic acid, HxBzL-43f To a solution of HxBzL-43e (200 mg, 356 umol, 1.0 eq) in MeCN (1 mL) and $H_2O$ (2 mL) was added HCl (12 M, 890 uL, 30 eq) in one portion at 25° C. under $N_2$, The mixture was stirred at 80° C. for 1 hour, the reaction mixture was concentrated in vacuum to afford HxBzL-43f (175 mg, 346 umol, 97.2% yield) as yellow oil.

Preparation of tert-butyl 3-[2-[2-[2-[2-[2-[2-[2-[2-[2-[2-[[(2S)-1-[5-[2-amino-4-[ethoxy (propyl)carbamoyl]-3H-1-benzazepin-8-yl]pyridine-2-carbonyl] pyrrolidine-2-carbonyl]amino]ethoxy]ethoxy] ethoxy]ethoxy]ethoxy]ethoxy]ethoxy]ethoxy] ethoxy]ethoxy]propanoate, HxBzL-43g To a mixture of HxBzL-43f (175 mg, 346 umol, 1.0 eq), tert-butyl 3-[2-[2-[2-[2-[2-[2-[2-[2-[2-(2-aminoethoxy) ethoxy]ethoxy]ethoxy]ethoxy]ethoxy]ethoxy]ethoxy] ethoxy]ethoxy]propanoate (203 mg, 346 umol, 1.0 eq) and $Et_3N$ (105 mg, 1.04 mmol, 145 uL, 3.0 eq) in DMF (2 mL) was added HATU (132 mg, 346 umol, 1.0 eq) in one portion at 0° C. under $N_2$, and it was stirred at 0° C. for 30 min, then heated to 25° C. and stirred for another 0.5 hour. The reaction mixture was filtered and the filtrate was purified by prep-HPLC (column: Phenomenex luna C18 250*50 mm*10 um; mobile phase: [water (0.1% TFA)-ACN]; B %: 20%-50%, 10 min) to afford HxBzL-43g (150 mg, 126 umol, 36.5% yield, TFA) as light yellow oil.

Preparation of 3-[2-[2-[2-[2-[2-[2-[2-[2-[2-[2-[[(2S)-1-[5-[2-amino-4-[ethoxy(propyl) carbamoyl]-3H-1-benzazepin-8-yl]pyridine-2-carbonyl]pyrrolidine-2-carbonyl]amino]ethoxy]ethoxy]ethoxy]ethoxy] ethoxy]ethoxy]ethoxy]ethoxy]ethoxy]ethoxy] propanoic acid, HxBzL-43h To a solution of HxBzL-43g (150 mg, 140 umol, 1.0 eq) in MeCN (0.2 mL) and $H_2O$ (2 mL) was added HCl (12 M, 349 uL, 30 eq) in one portion at 25° C. under $N_2$, and then stirred at 80° C. for 1 hour. The reaction mixture was concentrated in vacuum to remove $CH_3CN$ and the aqueous phase was freeze-dried to afford HxBzL-43h (140 mg, 137.64 umol, 98.48% yield) as brown oil.

Preparation of HxBzL-43

To a mixture of HxBzL-43h (140 mg, 138 umol, 1.0 eq) and (2,3,5,6-tetrafluoro-4-hydroxy-phenyl)sulfonyloxysodium (185 mg, 688 umol, 5.0 eq) in DCM (1.5 mL) and DMA (0.5 mL) was added EDCI (132 mg, 688 umol, 5.0 eq) in one portion at 20° C. under $N_2$, and then stirred at 20° C. for 1 hours. The reaction mixture was filtered and the filtrate was purified by prep-HPLC (column: Phenomenex Luna 80*30 mm*3 um; mobile phase: [water (0.1% TFA)-ACN]; B %: 10%-40%, 8 min) to afford HxBzL-43 (46.3 mg, 35.5 umol, 25.8% yield, 95.5% purity) as light yellow oil. $^1H$ NMR (400 MHz, MeOD) δ8.96 (d, J=2.0 Hz, 1H), 8.28 (dd, J=2.4, 8.4 Hz, 1H), 8.01 (d, J=8.4 Hz, 1H), 7.84 (s, 2H), 7.82 (d, J=1.6 Hz, 1H), 7.48 (s, 1H), 5.16 (dd, J=4.4, 8.0 Hz, 1H), 4.00 (q, J=7.2 Hz, 2H), 3.90-3.84 (m, 3H), 3.77 (t, J=7.2 Hz, 2H), 3.68-3.56 (m, 36H), 3.53-3.43 (m, 6H), 3.22-3.14 (m, 2H), 3.01-2.96 (m, 2H), 2.42-2.35 (m, 1H), 2.13-1.96 (m, 3H), 1.85-1.75 (m, 2H), 1.23 (t, J=7.2 Hz, 3H), 1.03 (t, J=7.2 Hz, 3H). LC/MS [M+H] 1245.5 (calculated); LC/MS [M+H] 1245.4 (observed).

Example L-45 Synthesis of 4-[3-[2-[2-[2-[2-[2-[2-[2-[2-[2-[2-[[(2R)-1-[5-[2-amino-4-[ethoxy(propyl)carbamoyl]-3H-1-benzazepin-8-yl]pyrimidine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-45

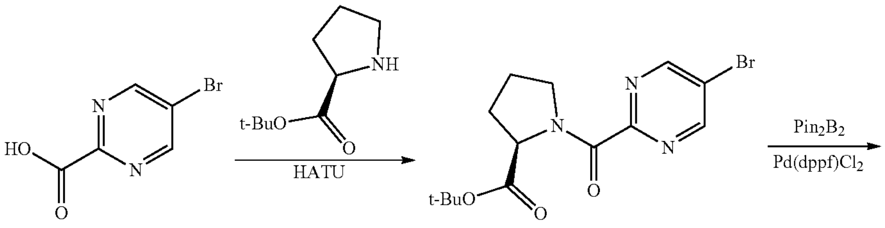

HxBzL-45a HxBzL-45b

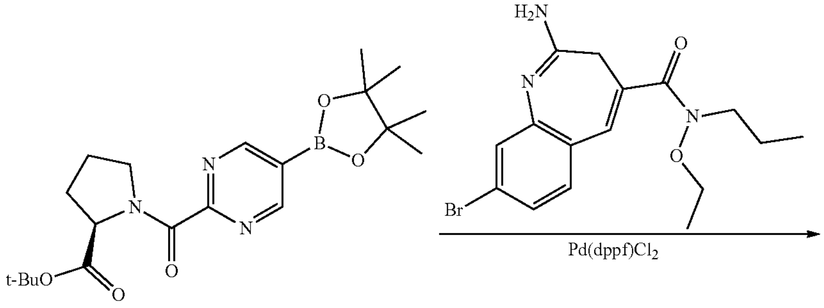

HxBzL-45c

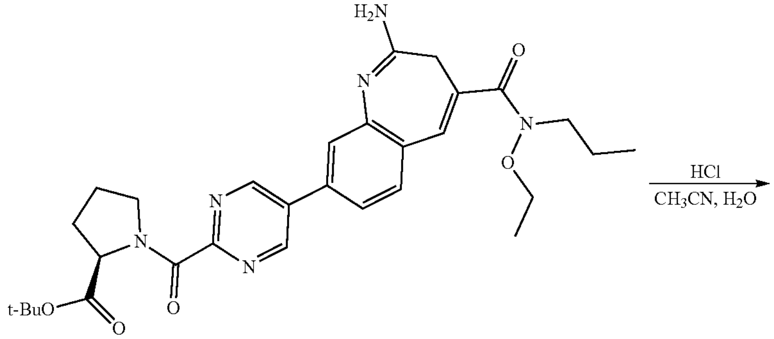

HxBzL-45d

-continued
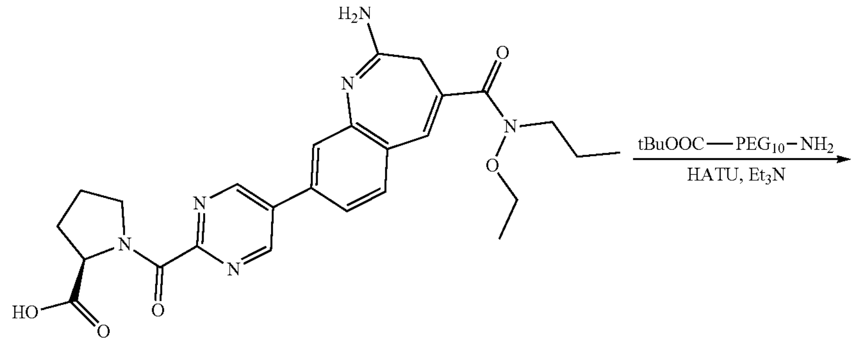
HxBzL-45e
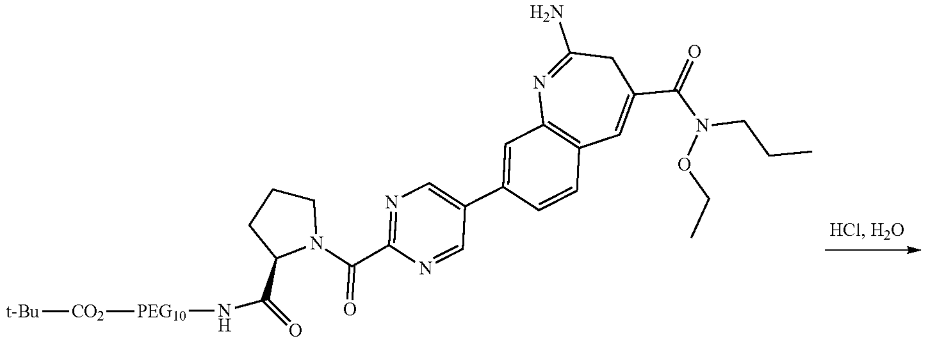
HxBzL-45f
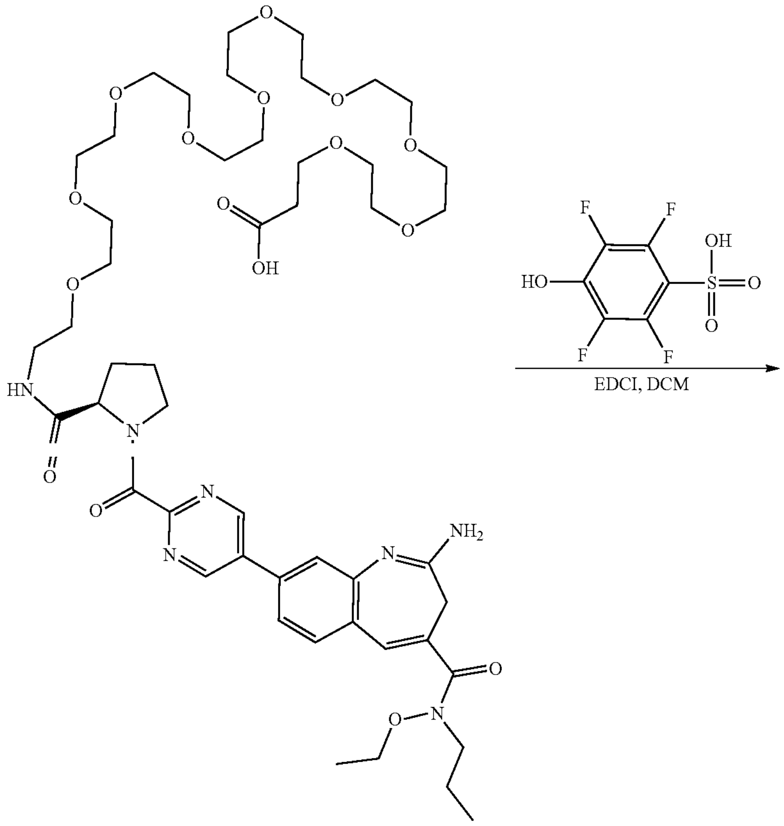
HxBzL-45g

-continued

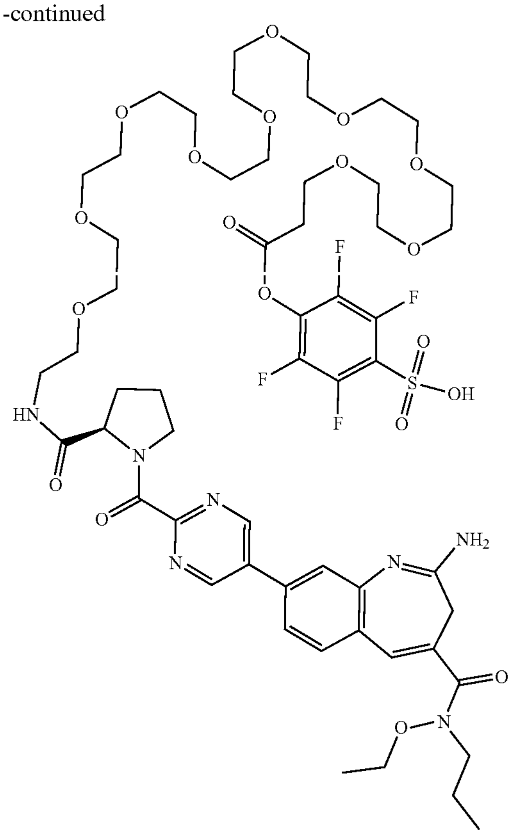

HxBzL-45

Preparation of (R)-tert-butyl 1-(5-bromopyrimidine-2-carbonyl)pyrrolidine-2-carboxylate, HxBzL-45b To a solution of 5-bromopyrimidine-2-carboxylic acid, HxBzL-45a (200 mg, 985 umol, 1 eq) in DMF (3 mL) was added DIEA (509 mg, 3.94 mmol, 686 uL, 4 eq) and HATU (412 mg, 1.08 mmol, 1.1 eq) at 0° C. and then stirred for 10 mins, tert-butyl (2S)-pyrrolidine-2-carboxylate (186 mg, 1.08 mmol, 1.1 eq) was added to the mixture and it was stirred at 25° C. for another 3 h. The reaction mixture was diluted with water 20 mL and extracted with EtOAc (20 mL×3). The combined organic layers were washed with brine (20 mL×2), dried over $Na_2SO_4$, filtered and concentrated under reduced pressure to give a residue. The residue was purified by column chromatography ($SiO_2$, Petroleum ether/Ethyl acetate=50/1 to 1/1) to afford HxBzL-45b (200 mg, 561 umol, 56.99% yield) as a white solid. $^1H$ NMR (400 MHz, DMSO-$d_6$) δ 9.18-9.10 (m, 2H), 4.70-4.41 (m, 1H), 3.75-3.48 (m, 2H), 2.42-1.87 (m, 4H), 1.56-1.30 (m, 9H)

Preparation of (R)-tert-butyl 1-(5-(4,4,5,5-tetramethyl-1,3,2-dioxaborolan-2-yl) pyrimidine-2-carbonyl)pyrrolidine-2-carboxylate, HxBzL-45c To a solution of HxBzL-45b (200 mg, 561 umol, 1 eq) and $Pin_2B_2$ (214 mg, 842 umol, 1.5 eq) in dioxane (5 mL) was added KOAc (110 mg, 1.12 mmol, 2 eq) and Pd(dppf)$Cl_2$ (41.1 mg, 56.2 umol, 0.1 eq) under $N_2$ protected, and then stirred at 90° C. for 2 h. The mixture was filtered and concentrated under reduced pressure. The crude product HxBzL-45c (230 mg, crude) obtained as brown solid was used into the next step without further purification.

Preparation of (R)-tert-butyl 1-(5-(2-amino-4-(ethoxy(propyl)carbamoyl)-3H-benzo [b]azepin-8-yl)pyrimidine-2-carbonyl)pyrrolidine-2-carboxylate, HxBzL-45d To a solution of HxBzL-45c (230 mg, 570 umol, 1 eq) and 2-amino-8-bromo-N-ethoxy-N-propyl-3H-1-benzazepine-4-carboxamide (209 mg, 570 umol, 1 eq) in dioxane (5 mL) was added a solution of $K_2CO_3$ (158 mg, 1.14 mmol, 2 eq) in Water (0.2 mL) and Pd(dppf)$Cl_2$ (41.7 mg, 57 umol, 0.1 eq) under $N_2$ protected, and then stirred at 90° C. for 16 h. The mixture was filtered and concentrated under reduced pressure. The residue was purified by column chromatography ($SiO_2$, Petroleum ether/Ethyl acetate=50/1 to Ethyl acetate:MeOH=5:1) to afford HxBzL-45d (240 mg, 427 umol, 74.8% yield) as yellow oil.

Preparation of (R)-1-(5-(2-amino-4-(ethoxy(propyl) carbamoyl)-3H-benzo[b] azepin-8-yl)pyrimidine-2-carbonyl)pyrrolidine-2-carboxylic acid, HxBzL-45e To a solution of HxBzL-45d (240 mg, 427 umol, 1 eq) in $H_2O$ (5 mL) and MeCN (2 mL) was added HCl (12 M, 355 uL, 10 eq), and then stirred at 80° C. for 1 h. The mixture was filtered and concentrated under reduced pressure to afford HxBzL-45e (170 mg, 336 umol, 78.7% yield) was obtained as yellow oil.

Preparation of tert-butyl 3-[2-[2-[2-[2-[2-[2-[2-[2-[2-[2-[[(2R)-1-[5-[2-amino-4-[ethoxy(propyl)carbamoyl]-3H-1-benzazepin-8-yl]pyrimidine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoate, HxBzL-45f To a solution of tert-butyl 3-[2-[2-[2-[2-[2-[2-[2-[2-[2-(2-
To a solution of tert-butyl 3-[2-[2-[2-[2-[2-[2-[2-[2-[2-(2-
aminoethoxy)ethoxy]ethoxy]ethoxy]ethoxy]ethoxy]ethoxy]ethoxy]ethoxy]ethoxy]propanoate (167 mg, 284 umol, 1.2 eq) and HxBzL-45e (120 mg, 237 umol, 1 eq) and DIEA (91.9 mg, 711 umol, 124 uL, 3 eq) in DMF (2 mL) was added HATU (90.1 mg, 237 umol, 1 eq) at 0° C., and it was stirred at 0° C. for 2 h. the mixture was filtered and concentrated under reduced pressure to give a residue. The residue was purified by prep-HPLC (column: Phenomenex Luna 80*30 mm*3 um; mobile phase: [water (0.1% TFA)-ACN]; B %: 20%-45%, 8 min) to give HxBzL-45f (120 mg, 112 umol, 47.2% yield) as a light yellow oil.

Preparation of 3-[2-[2-[2-[2-[2-[2-[2-[2-[2-[2-[[(2R)-1-[5-[2-amino-4-[ethoxy (propyl)carbamoyl]-3H-1-benzazepin-8-yl]pyrimidine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoic acid, HxBzL-45g To a mixture of HxBzL-45f (115 mg, 107 umol, 1 eq) in $H_2O$ (3 mL) was added HCl (12 M, 89.2 uL, 10 eq), and then stirred at 80° C. for 1 h. The mixture was filtered and concentrated under reduced pressure to give HxBzL-45g (105 mg, 103 umol, 96.3% yield) as a colorless oil. $^1$H NMR (MeOD, 400 MHz) δ9.39-9.04 (m, 2H), 7.88-7.80 (m, 2H), 7.78-7.74 (m, 1H), 7.48 (d, J=3.0 Hz, 1H), 4.90-4.62 (m, 1H), 4.03-3.95 (m, 2H), 3.92-3.80 (m, 2H), 3.76 (t, J=7.2 Hz, 2H), 3.72-3.67 (m, 2H), 3.66-3.57 (m, 38H), 3.48-3.38 (m, 4H), 3.29-3.11 (m, 2H), 2.47 (dt, J=2.8, 6.2 Hz, 2H), 2.15-1.98 (m, 4H), 1.84-1.73 (m, 2H), 1.44 (s, 9H), 1.22 (t, J=7.2 Hz, 3H), 1.01 (t, J=7.4 Hz, 3H)

Preparation of HxBzL-45

To a solution of HxBzL-45g (105 mg, 103 umol, 1 eq) and sodium; 2,3,5,6-tetrafluoro-4-hydroxy-benzenesulfonate (111 mg, 413 umol, 4 eq) in DCM (2 mL) and DMA (0.5 mL) was added EDCI (79.1 mg, 413 umol, 4 eq), and then stirred at 20° C. for 1 h. the mixture was filtered and concentrated under residue pressure. The residue was purified by prep-HPLC (column: Phenomenex Luna 80*30 mm*3 um; mobile phase: [water (0.1% TFA)-ACN]; B %: 10%-40%, 8 min) to give HxBzL-45 (60.0 mg, 44.1 umol, 42.8% yield, TFA) as a light yellow oil. $^1$H NMR (MeOD, 400 MHz) δ9.27-9.21 (m, 2H), 7.89-7.81 (m, 2H), 7.77-7.72 (m, 1H), 7.48-7.44 (m, 1H), 5.05-4.62 (m, 1H), 3.99 (q, J=7.0 Hz, 2H), 3.89-3.83 (m, 4H), 3.76 (br t, J=7.0 Hz, 2H), 3.66-3.53 (m, 36H), 3.50-3.42 (m, 4H), 3.28-3.20 (m, 2H), 3.16-3.05 (m, 1H), 2.99-2.94 (m, 2H), 2.46-2.26 (m, 1H), 2.12-1.97 (m, 3H), 1.82-1.74 (m, 2H), 1.21 (dt, J=1.8, 7.2 Hz, 3H), 1.04-0.98 (m, 3H). LC/MS [M+H] 1246.5 (calculated); LC/MS [M+H] 1246.4 (observed).

Example L-46 Synthesis of 4-[3-[2-[2-[2-[2-[2-[2-[2-[2-[2-[2-[[(2R)-1-[5-[2-amino-4-[ethoxy(propyl)carbamoyl]-3H-1-benzazepin-8-yl]pyridine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-46

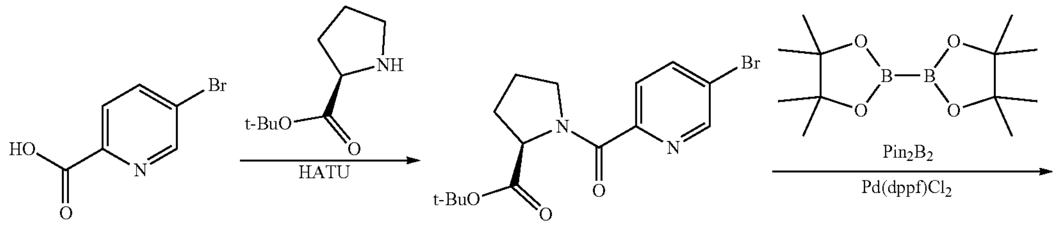

HxBzL-46a HxBzL-46b

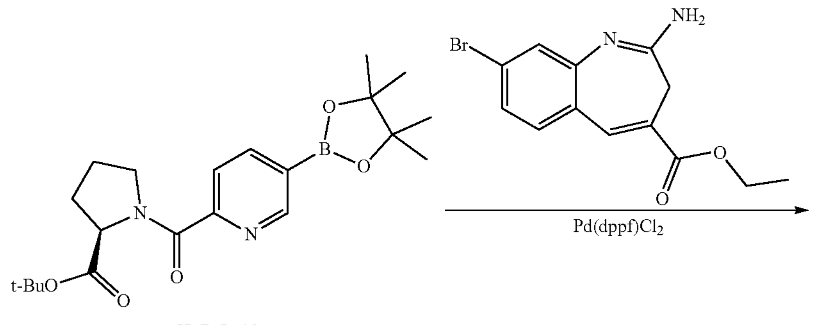

HxBzL-46c

-continued
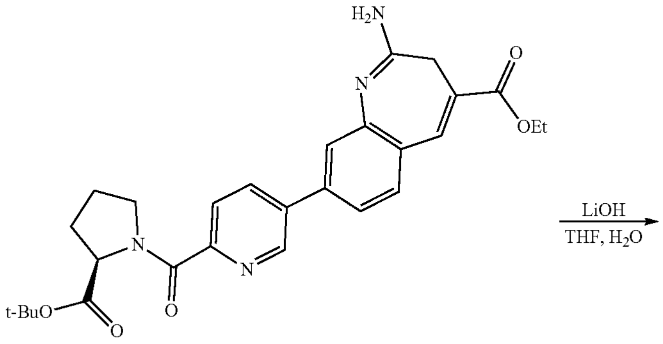
HxBzL-46d
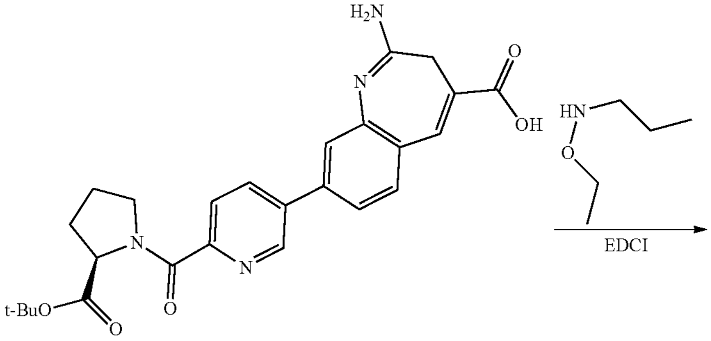
HxBzL-46e
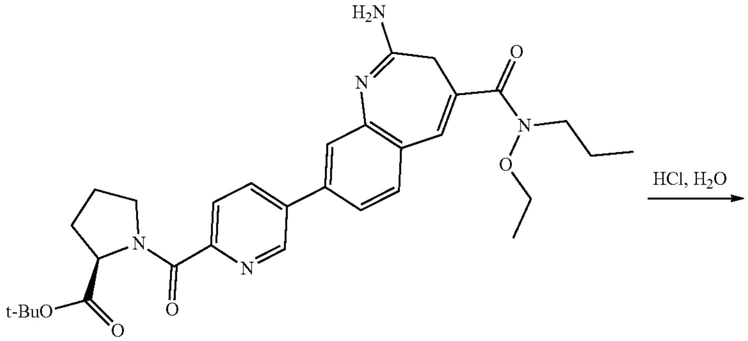
HxBzL-46f
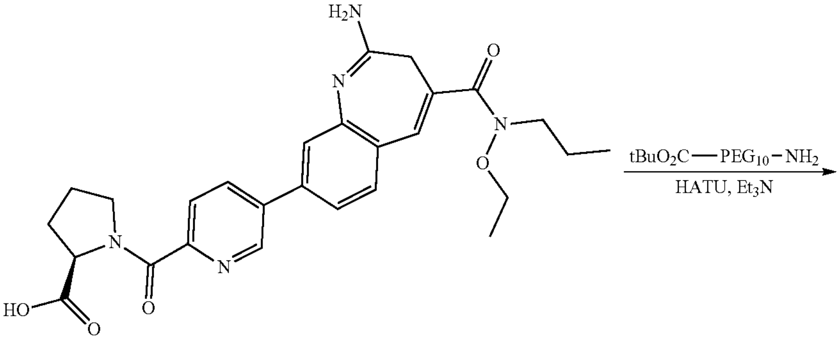
HxBzL-46g -continued
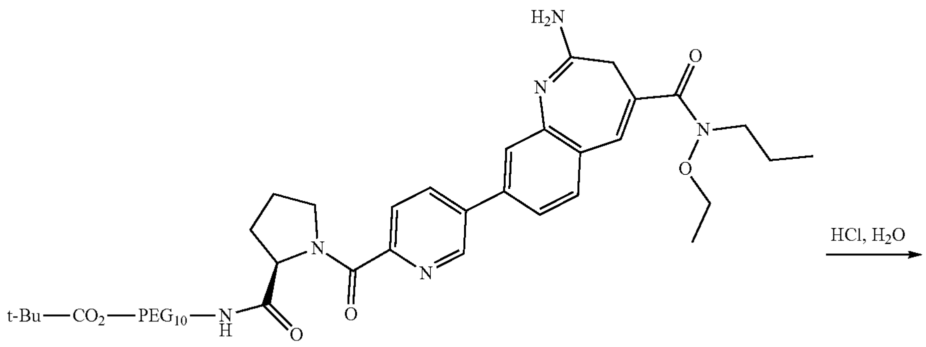
HxBzL-46h
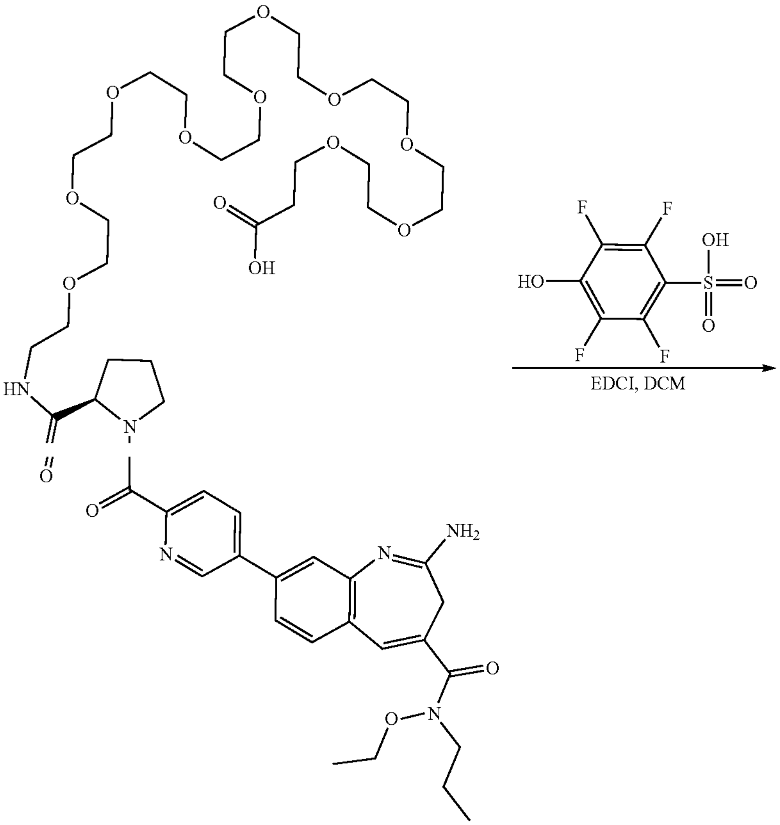
HxBzL-46i
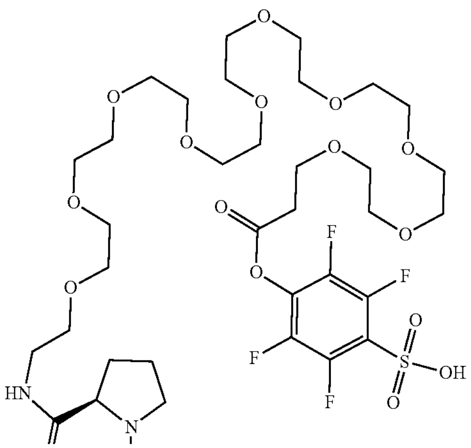

-continued

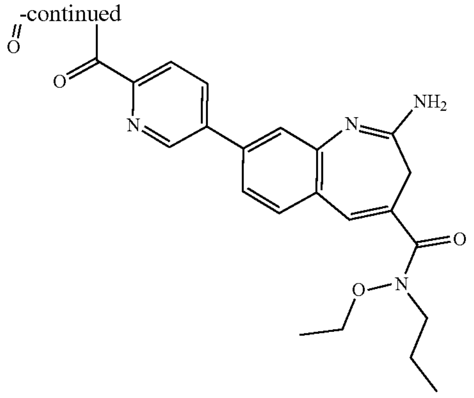

HxBzL-46

Preparation of tert-butyl (2R)-1-(5-bromopyridine-2-carbonyl) pyrrolidine-2-carboxylate, HxBzL-46b To a mixture of 5-bromopyridine-2-carboxylic acid, HxBzL-46a (2.19 g, 10.8 mmol, 1 eq) in DMF (50 mL) was added HATU (4.53 g, 11.9 mmol, 1.1 eq) and $Et_3N$ (3.29 g, 32.5 mmol, 4.52 mL, 3 eq), then tert-butyl (2R)-pyrrolidine-2-carboxylate (2.25 g, 10.8 mmol, 1 eq, HCl) was added. The mixture was stirred at 20° C. for 0.5 hr. The reaction mixture was partitioned between EtOAc (150 mL) and water (100 mL). The organic phase was separated, dried over $Na_2SO_4$, concentrated to give a residue. The residue was purified by column chromatography ($SiO_2$, Petroleum ether/Ethyl acetate=1/0 to 2/1) to give HxBzL-46b (3.8 g, 10.7 mmol, 98.8% yield) as yellow oil. $^1$H NMR (400 MHz, MeOD) δ8.76-8.61 (m, 1H), 8.17-8.13 (m, 1H), 7.91-7.74 (m, 1H), 5.07-4.51 (m, 1H), 3.96-3.67 (m, 2H), 2.43-2.27 (m, 1H), 2.18-1.90 (m, 3H), 1.51 (s, 3H), 1.37 (s, 6H).

Preparation of tert-butyl (2R)-1-[5-(4,4,5,5-tetramethyl-1,3,2-dioxaborolan-2-yl)pyridine-2-carbonyl] pyrrolidine-2-carboxylate, HxBzL-46c To a mixture of tert HxBzL-46b (3.5 g, 9.85 mmol, 1 eq), 4,4,5,5-tetramethyl-2-(4,4,5,5-tetramethyl-1,3,2-dioxaborolan-2-yl)-1,3,2-dioxaborolane, $Pin_2B_2$, Bis(pinacolato)diboron, CAS Reg. No. 78183-34-3 (3.75 g, 14.8 mmol, 1.5 eq), KOAc (2.42 g, 24.6 mmol, 2.5 eq) in dioxane (80 mL) was added Pd(dppf)$Cl_2$ (721 mg, 985 umol, 0.1 eq), and then stirred at 100° C. for 2 hr. The mixture was used for next step without work up and purification. HxBzL-46c (3.96 g, 9.84 mmol, 100.00% yield) was obtained as black liquid.

Preparation of ethyl 2-amino-8-[6-[(2R)-2-tert-butoxycarbonylpyrrolidine-1-carbonyl]-3-pyridyl]-3H-1-benzazepine-4-carboxylate, HxBzL-46d A mixture of HxBzL-46c (3.96 g, 9.84 mmol, 1 eq), ethyl 2-amino-8-bromo-3H-1-benzazepine-4-carboxylate (3.04 g, 9.84 mmol, 1 eq), Pd(dppf)$Cl_2$ (360 mg, 492 umol, 0.05 eq) and $K_2CO_3$ (3.40 g, 24.6 mmol, 2.5 eq) in dioxane (100 mL) and $H_2O$ (8 mL) was stirred at 100° C. for 2 hr. The reaction mixture was concentrated to give a residue. The residue was dissolved in EtOAc (100 mL) and was washed by water (50 mL). The organic phase was separated, dried over $Na_2SO_4$, filtered and concentrated under reduced pressure to give a residue. The crude was purified by column chromatography ($SiO_2$, Petroleum ether/Ethyl acetate=1/0 to 0/1, EA:MeOH=5:1) to give HxBzL-46d (4 g, 7.93 mmol, 80.5% yield) as yellow solid. $^1$H NMR (400 MHz, MeOD) δ9.07-8.72 (m, 1H), 8.29-8.16 (m, 1H), 8.12-7.78 (m, 2H), 7.62-7.40 (m, 3H), 5.17-4.47 (m, 1H), 4.34 (q, J=7.2 Hz, 2H), 4.04-3.75 (m, 2H), 3.67-2.94 (m, 2H), 2.49-2.27 (m, 1H), 2.22-1.88 (m, 3H), 1.53 (s, 3H), 1.43-1.34 (m, 9H).

Preparation of 2-amino-8-[6-[(2R)-2-tert-butoxycarbonyl pyrrolidine-1-carbonyl]-3-pyridyl]-3H-1-benzazepine-4-carboxylic acid, HxBzL-46e To a mixture of HxBzL-46d (3.5 g, 6.94 mmol, 1 eq) in THF (20 mL) and $H_2O$ (40 mL) was added LiOH·$H_2O$ (582 mg, 13.9 mmol, 2 eq), and then stirred at 20° C. for 3 hr. The mixture was concentrated to remove THF, then the pH of the mixture was adjusted to ~5 with HCl (4M), and the solid formed form the mixture. The mixture was filtered, and the filtered cake was dried in vacuum, HxBzL-46e (3.3 g, 6.93 mmol, 99.8% yield) was obtained as white solid.

Preparation of tert-butyl (2R)-1-[5-[2-amino-4-[ethoxy(propyl) carbamoyl]-3H-1-benzazepin-8-yl] pyridine-2-carbonyl]pyrrolidine-2-carboxylate, HxBzL-46f To a mixture of HxBzL-46e (0.4 g, 839 umol, 1 eq) and N-ethoxypropan-1-amine (117 mg, 839 umol, 1 eq, HCl) in DCM (5 mL) and DMA (5 mL) was added EDCI (483 mg, 2.52 mmol, 3 eq), and then stirred at 20° C. for 1 hr. The reaction mixture was concentrated to remove DCM, the residue was partitioned between EtOAc (20 mL) and water (20 mL). The organic phase was separated, dried over $Na_2SO_4$, filtered and concentrated under reduced pressure to give a residue. The residue was purified by column chromatography ($SiO_2$, Petroleum ether/Ethyl acetate=1/0 to 0/1, EA:MeOH=5:1) to give HxBzL-46f (0.32 g, 570 umol, 67.9% yield) as yellow solid. $^1$H NMR (400 MHz, MeOD) δ9.06-8.77 (m, 1H), 8.26-8.17 (m, 1H), 8.07-7.87 (m, 1H), 7.53-7.36 (m, 3H), 7.30 (s, 1H), 5.17-4.50 (m, 1H), 4.01-3.69 (m, 6H), 3.01-2.88 (m, 2H), 2.45-2.30 (m, 1H), 2.18-2.03 (m, 2H), 2.02-1.94 (m, 1H), 1.82-1.73 (m, 2H), 1.52 (s, 3H), 1.36 (s, 6H), 1.18 (t, J=7.2 Hz, 3H), 1.00 (t, J=7.2 Hz, 3H).

Preparation of (2R)-1-[5-[2-amino-4-[ethoxy (propyl) carbamoyl]-3H-1-benzazepin-8-yl]pyridine-2-carbonyl]pyrrolidine-2-carboxylic acid, HxBzL-46g To a mixture of HxBzL-46f (260 mg, 463 umol, 1 eq) in $H_2O$ (5 mL) was added HCl (12 M, 579 uL, 15 eq), and then stirred at 80° C. for 1 hr. The mixture was concentrated to give HxBzL-46g (0.25 g, 461 umol, 99.6% yield, HCl) as yellow oil.

Preparation of tert-butyl 3-[2-[2-[2-[2-[2-[2-[2-[2-[2-[2-[[(2R)-1-[5-[2-amino-4-[ethoxy (propyl)carbamoyl]-3H-1-benzazepin-8-yl]pyridine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoate, HxBzL-46h To a mixture of HxBzL-46g (200 mg, 369 umol, 1 eq, HCl) and tert-butyl 3-[2-[2-[2-[2-[2-[2-[2-[2-[2-(2-aminoethoxy)ethoxy]ethoxy]ethoxy]ethoxy]ethoxy]ethoxy]ethoxy]ethoxy]ethoxy]propanoate (216 mg, 369 umol, 1 eq) in DMF (5 mL) was added HATU (154 mg, 406 umol, 1.1 eq) and DIEA (143 mg, 1.11 mmol, 193 uL, 3 eq) at 0° C., and it was stirred at 0° C. for 1 hr. The mixture was concentrated to give a residue. The residue was purified by prep-HPLC (column: Phenomenex Luna 80*30 mm*3 um; mobile phase: [water (0.1% TFA)-ACN]; B %: 25%-51%, 8 min) to give HxBzL-46h (340 mg, 286 umol, 77.6% yield, TFA) as yellow oil.

Preparation of 3-[2-[2-[2-[2-[2-[2-[2-[2-[2-[2-[[(2R)-1-[5-[2-amino-4-[ethoxy(propyl)carbamoyl]-3H-1-benzazepin-8-yl]pyridine-2-carbonyl]pyrrolidine-2-carbonyl]amino]ethoxy]ethoxy]ethoxy]ethoxy]ethoxy]ethoxy]ethoxy]ethoxy]ethoxy]ethoxy]propanoic acid, HxBzL-46i To a mixture of HxBzL-46h (340 mg, 286 umol, 1 eq, TFA) in $H_2O$ (20 mL) was added HCl (12 M, 358 uL, 15 eq), and then stirred at 80° C. for 0.5 hr. The mixture was concentrated to residue. The crude was purified by prep-HPLC (column: Phenomenex Luna 80*30 mm*3 um; mobile phase: [water (0.1% TFA)-ACN]; B %: 10%-40%, 8 min) to give HxBzL-46i (220 mg, 209 umol, 72.9% yield, HCl) as yellow oil.

Preparation of HxBzL-46

To a mixture of HxBzL-46i (180 mg, 171 umol, 1 eq, HCl) and sodium; 2,3,5,6-tetrafluoro-4-hydroxy-benzenesulfonate (183 mg, 683 umol, 4 eq) in DMA (0.3 mL) and DCM (3 mL) was added EDCI (164 mg, 854 umol, 5 eq), and it was stirred at 15° C. for 0.5 hr. The mixture was concentrated to residue. The residue was purified by prep-HPLC (column: Phenomenex Luna 80*30 mm*3 um; mobile phase: [water (0.1% TFA)-ACN]; B %: 15%-45%, 8 min) to give HxBzL-46 (94 mg, 72.6 umol, 42.5% yield, 96.2% purity) as colorless oil. $^1H$ NMR (400 MHz, MeOD) δ9.10-8.85 (m, 1H), 8.43-8.16 (m, 1H), 8.11-7.94 (m, 1H), 7.91-7.71 (m, 3H), 7.48 (s, 1H), 5.18-4.65 (m, 1H), 4.07-3.72 (m, 8H), 3.69-3.39 (m, 40H), 3.30-3.13 (m, 2H), 3.00-2.97 (m, 2H), 2.59-2.23 (m, 1H), 2.19-1.66 (m, 5H), 1.25-1.21 (m, 3H), 1.05-1.00 (m, 3H). LC/MS [M+H] 1245.5 (calculated); LC/MS [M+H] 1245.4 (observed).

Example L-50 Synthesis of (2,3,5,6-tetrafluorophenyl) 3-[2-[2-[2-[2-[2-[2-[2-[2-[2-[3-[[5-[2-amino-4-[propyl(1H-pyrazol-5-ylmethoxy)carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoate, HxBzL-50

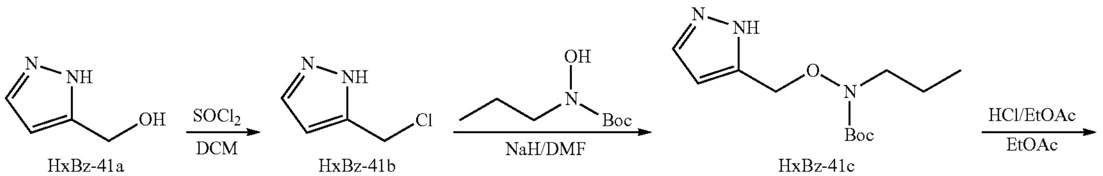

HxBz-41a HxBz-41b HxBz-41c

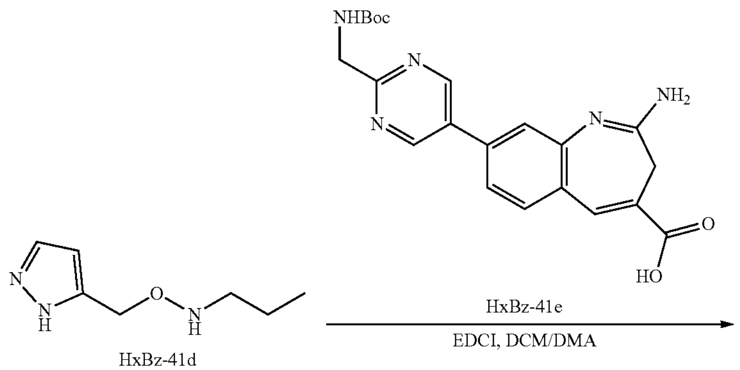

HxBz-41d HxBz-41e

-continued
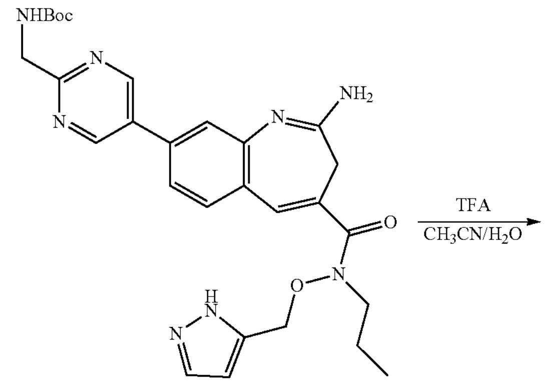
HxBz-41f
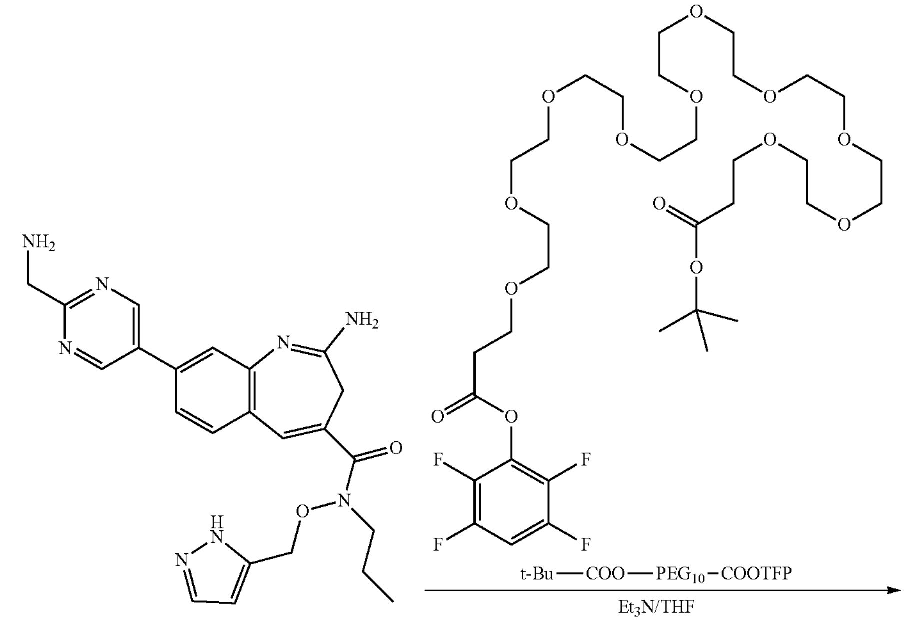
HxBz-41
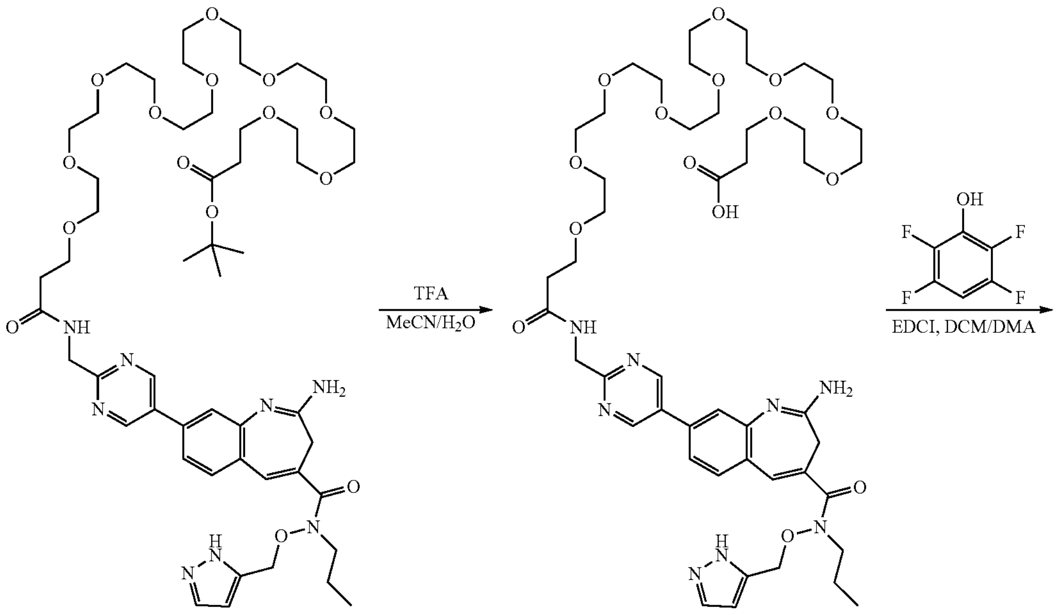
HxBzL-50a
HxBzL-50b -continued

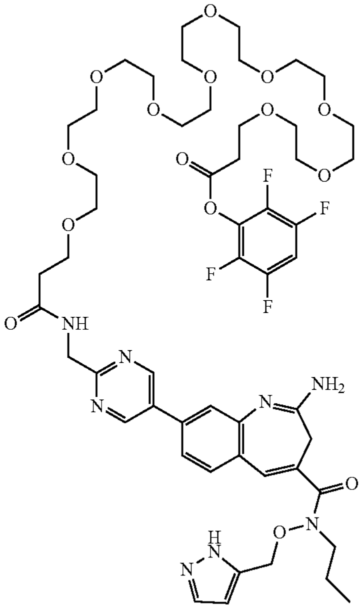

HxBzL-50

Preparation of 5-(chloromethyl)-1H-pyrazole, HxBz-41b

To a solution of 1H-pyrazol-5-ylmethanol, HxBz-41a (4 g, 40.8 mmol, 1 eq) in DCM (10 mL) was added thionyl chloride, $SOCl_2$ (9.70 g, 81.55 mmol, 5.92 mL, 2 eq) and then stirred at 0° C. to 20° C. for 2 hr. The reaction mixture was concentrated under reduced pressure to get HxBz-41b (4.5 g, 38.6 mmol, 94.70% yield) as a white solid. LC/MS [M+H] 117.0 (calculated); LC/MS [M+H] 117.0 (observed).

Preparation of tert-butyl N-propyl-N-(1H-pyrazol-5-ylmethoxy)carbamate, HxBz-41c To a solution of HxBz-41b (3.01 g, 17.2 mmol, 1 eq) in DMF (20 mL) was added NaH (1.03 g, 25.7 mmol, 60% purity, 1.5 eq) at 0° C., the mixture was stirred 0.5 hr at this temperature, then KI (285 mg, 1.72 mmol, 0.1 eq) and 5-(chloromethyl)-1H-pyrazole (2 g, 17.16 mmol, 1 eq) was added. The result mixture was stirred at 20° C. for 12 hr. The reaction mixture was quenched by addition $NH_4Cl$ 20 mL at 0° C., and extracted with EtOAc (20 mL×3). The combined organic layers were washed with brine (50 mL), dried over $Na_2SO_4$, filtered and concentrated under reduced pressure to give a residue. The residue was purified by prep-HPLC (column: Phenomenex luna C18 (250*70 mm, 15 um); mobile phase: [water (0.1% TFA)-ACN]; B %: 20%-45%, 20 min) to give HxBz-41c (0.6 g, 2.35 mmol, 13.69% yield) as a yellow oil. LC/MS [M+H] 256.1 (calculated); LC/MS [M+H] 256.1 (observed).

Preparation of N-(1H-pyrazol-5-ylmethoxy)propan-1-amine, HxBz-41d

To a solution of HxBz-41c (0.5 g, 1.96 mmol, 1 eq) in MeCN (2 mL) and $H_2O$ (2 mL) was added TFA (2.23 g, 19.58 mmol, 1.45 mL, 10 eq), and then stirred at 80° C. for 1 hr. The reaction mixture was concentrated under reduced pressure to remove MeCN. The aqueous phase was extracted with MTBE 20 mL to remove excess TFA. The water layer was lyophilized to give HxBz-41d (0.25 g, crude, TFA) as a yellow oil. $^1H$ NMR (MeOH, 400 MHz) δ 7.10 (d, J=2.4 Hz, 1H), 6.47 (d, J=2.4 Hz, 1H), 5.13 (s, 2H), 3.30-3.20 (m, 2H), 1.78-1.71 (m, 2H), 1.02 (t, J=7.2 Hz, 2H). LC/MS [M+H] 156.1 (calculated); LC/MS [M+H] 156.1 (observed).

Preparation of tert-butyl N-[[5-[2-amino-4-[propyl (1H-pyrazol-5-ylmethoxy)carbamoyl]-3H-1-benzazepin-8-yl]pyrimidin-2-yl]methyl]carbamate, HxBz-41f To a solution of HxBz-41d (0.2 g, 743 umol, 1 eq, TFA salt) and 2-amino-8-[2-[(tert-butoxycarbonylamino)methyl] pyrimidin-5-yl]-3H-1-benzazepine-4-carboxylic acid, HxBz-41e (304 mg, 743 umol, 1 eq) in DCM (2 mL) and DMA (1 mL) was added EDCI (854 mg, 4.46 mmol, 6 eq), and then stirred at 20° C. for 2 hr. The mixture was quenched with $NaHCO_3$ to adjusted pH=~8, and then extracted with EtOAc (30 mL×4). The combined organic layers were washed with brine (30 mL), dried over $Na_2SO_4$, filtered and concentrated under reduced pressure to give a residue. The residue was purified by column chromatography ($SiO_2$, MeOH/Ethyl acetate=1/5) to give HxBz-41f (0.35 g, 640.30 umol, 86.19% yield) as a yellow solid. LC/MS [M+H] 547.3 (calculated); LC/MS [M+H] 547.3 (observed).

Preparation of 2-amino-8-[2-(aminomethyl)pyrimidin-5-yl]-N-propyl-N-(1H-pyrazol-5-ylmethoxy)-3H-1-benzazepine-4-carboxamide, HxBz-41

To a solution of HxBz-41f (0.35 g, 640 umol, 1 eq) in MeCN (2 mL) and $H_2O$ (2 mL) was added TFA (584 mg, 5.12 mmol, 379 uL, 8 eq), and then stirred at 80° C. for 1 hr. The reaction mixture was concentrated under reduced pressure to give a residue. The residue was purified by prep-HPLC (column: Phenomenex Luna 80*30 mm*3 um;

mobile phase: [water (0.1% TFA)-ACN]; B %: 1%-25%, 8 min) to give HxBz-41 (0.25 g, 371 umol, 57.88% yield, 2TFA) as a yellow solid. $^1$H NMR (MeOH, 400 MHz) δ 9.20 (s, 2H), 7.82-7.78 (m, 1H), 7.74 (d, J=2.0 Hz, 1H), 7.69 (d, J=8.4 Hz, 1H), 7.55 (d, J=2.0 Hz, 1H), 7.26 (s, 1H), 6.31 (d, J=2.0 Hz, 1H), 4.96 (s, 2H), 4.48 (s, 2H), 3.80 (t, J=7.4 Hz, 2H), 3.26 (s, 2H), 1.88-1.73 (m, 2H), 1.01 (t, J=7.4 Hz, 3H). LC/MS [M+H] 447.2 (calculated); LC/MS [M+H] 447.2 (observed).

Preparation of tert-butyl 3-[2-[2-[2-[2-[2-[2-[2-[2-[2-[3-[[5-[2-amino-4-[propyl(1H-pyrazol-5-yl-methoxy)carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoate, HxBzL-50a To a solution HxBz-41 (0.2 g, 296 umol, 1 eq, 2TFA) in THF (10 mL) was added $Et_3N$ (90.0 mg, 889 umol, 124 uL, 3 eq) and (2,3,5,6-tetrafluorophenyl)$_3$-[2-[2-[2-[2-[2-[2-[2-[2-[2-(3-tert-butoxy-3-oxo-propoxy)ethoxy]ethoxy]ethoxy]ethoxy]ethoxy]ethoxy]ethoxy]ethoxy]ethoxy]propanoate, t-Bu-COO-PEG10-COOTFP (226 mg, 296 umol, 1 eq), and then stirred at 0° C. for 2 hr. The reaction mixture was quenched by addition $H_2O$ 5 mL, and the pH of the mixture was adjusted to ~6 with TFA at 0° C., the aqueous phase was extracted with EtOAc (10 ml*2) to remove byproduct, and the water phase was further extracted with DCM/PrOH=10/1 (20 mL×3), the combined organic phase was dried over $Na_2SO_4$, filtered and concentrated under reduced pressure to give compound HxBzL-50a as a yellow oil. LC/MS [M+H] 1043.56 (calculated); LC/MS [M+H] 1043.6 (observed).

Preparation of 3-[2-[2-[2-[2-[2-[2-[2-[2-[2-[3-[[5-[2-amino-4-[propyl (1H-pyrazol-5-ylmethoxy)carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-50b To a solution of HxBzL-50a (0.2 g, 192 umol, 1 eq) in MeCN (2 mL) and $H_2O$ (2 mL) was added HCl (12 M, 320 uL, 20 eq), and then stirred at 80° C. for 2 hr. The reaction mixture was concentrated under reduced pressure to give a residue. The residue was purified by prep-HPLC (column: Phenomenex Luna 80*30 mm*3 um; mobile phase: [water (0.1% TFA)-ACN]; B %: 5%-35%, 8 min) to give HxBzL-50b (0.13 g, 132 umol, 68.69% yield) as a yellow oil. LC/MS [M+H] 987.5 (calculated); LC/MS [M+H] 987.6 (observed).

Preparation of HxBzL-50

To a solution of HxBzL-50b (0.1 g, 101 umol, 1 eq) and 2,3,5,6-tetrafluorophenol (67.3 mg, 405 umol, 4 eq) in DCM (1 mL) and DMA (1 mL) was added EDCI (77.7 mg, 405 umol, 4 eq), and then stirred at 20° C. for 1 hr. The reaction mixture was filtered. The residue was purified by prep-HPLC (column: Phenomenex Luna 80*30 mm*3 um; mobile phase: [water (0.1% TFA)-ACN]; B %: 20%-40%, 8 min) to give HxBzL-50 (0.0216 g, 19.0 umol, 18.78% yield) as a yellow solid. $^1$H NMR (MeOH, 400 MHz) δ 9.10 (s, 2H), 7.78 (dd, J=1.6, 8.0 Hz, 1H), 7.71-7.66 (m, 2H), 7.57 (d, J=2.4 Hz, 1H), 7.48-7.37 (m, 1H), 7.26 (s, 1H), 7.28-7.24 (m, 1H), 6.31 (d, J=2.4 Hz, 1H), 4.96 (s, 2H), 4.69 (s, 2H), 3.86 (t, J=6.0 Hz, 2H), 3.83-3.76 (m, 4H), 3.68-3.55 (m, 36H), 3.26 (s, 2H), 3.02-2.91 (m, 2H), 2.60 (t, J=6.0 Hz, 2H), 1.80 (t, J=7.2 Hz, 2H), 1.01 (t, J=7.2 Hz, 3H). LC/MS [M+H] 1135.5 (calculated); LC/MS [M+H]1135.6 (observed).

Example L-64 Synthesis of 4-[3-[2-[2-[2-[2-[2-[2-[2-[2-[2-[3-[[5-[2-amino-4-[2-(1-ethyl-2-oxo-imidazolidin-4-yl)ethyl-propyl-carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-64

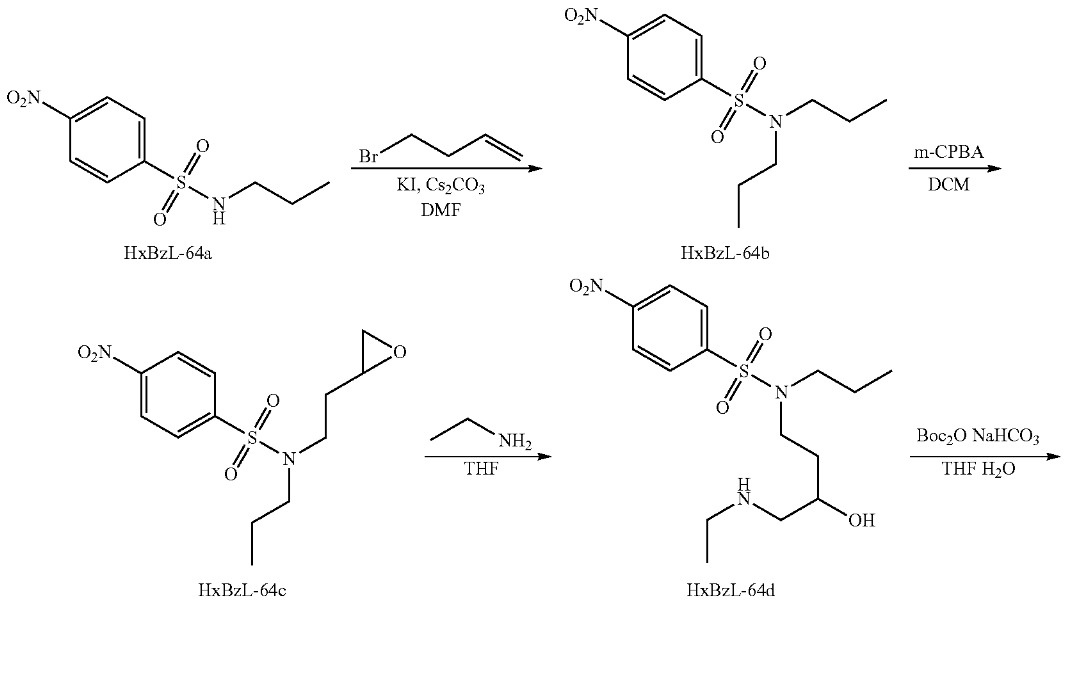

HxBzL-64a
HxBzL-64b
HxBzL-64c
HxBzL-64d

-continued
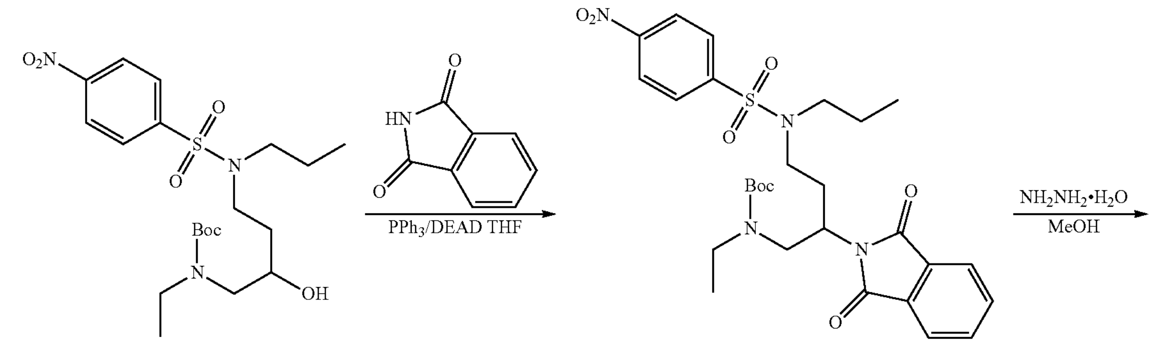
HxBzL-64e HxBzL-64f
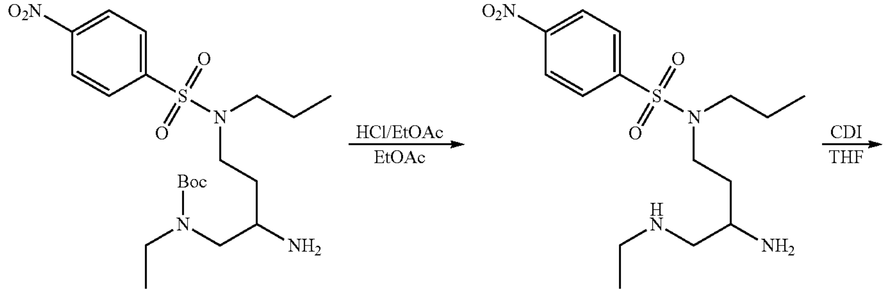
HxBzL-64g HxBzL-64h
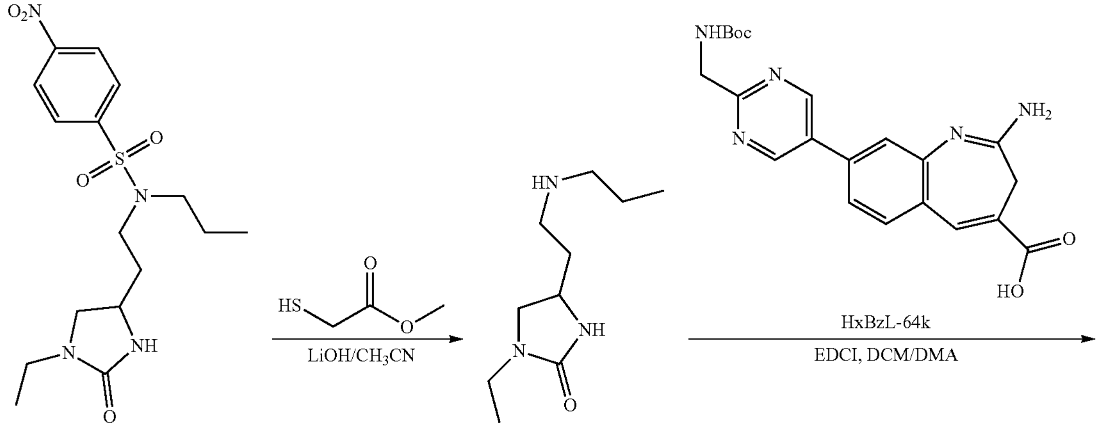
HxBzL-64g HxBzL-64j
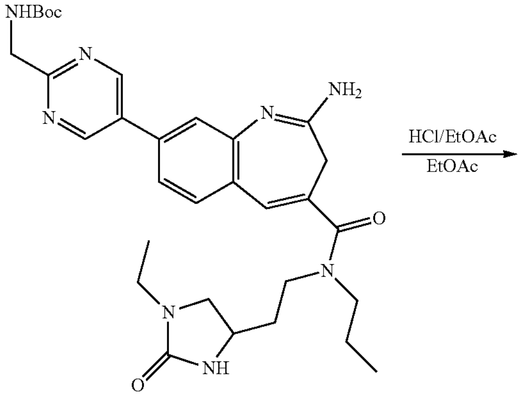
HxBzL-64l -continued
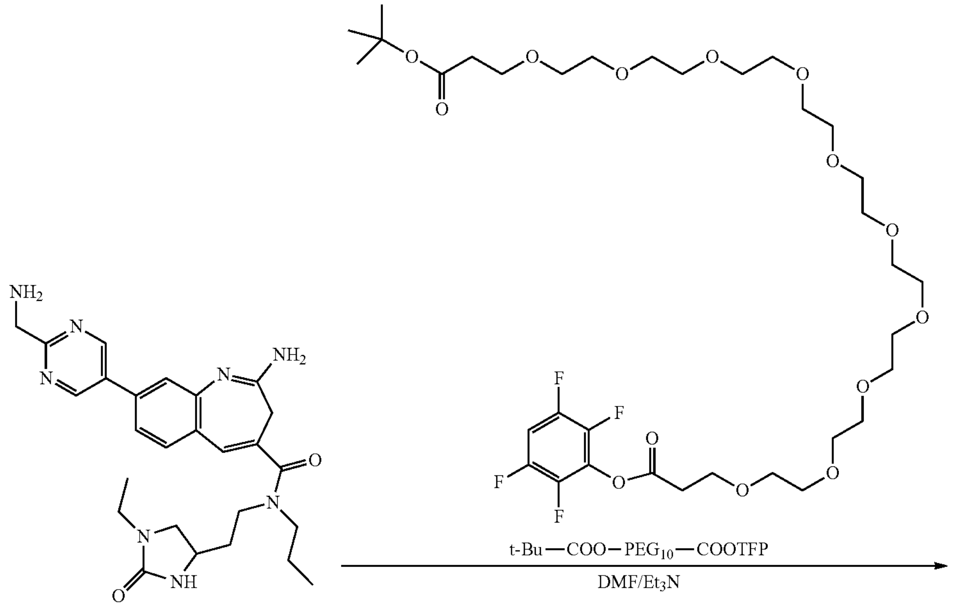
HxBzL-64m
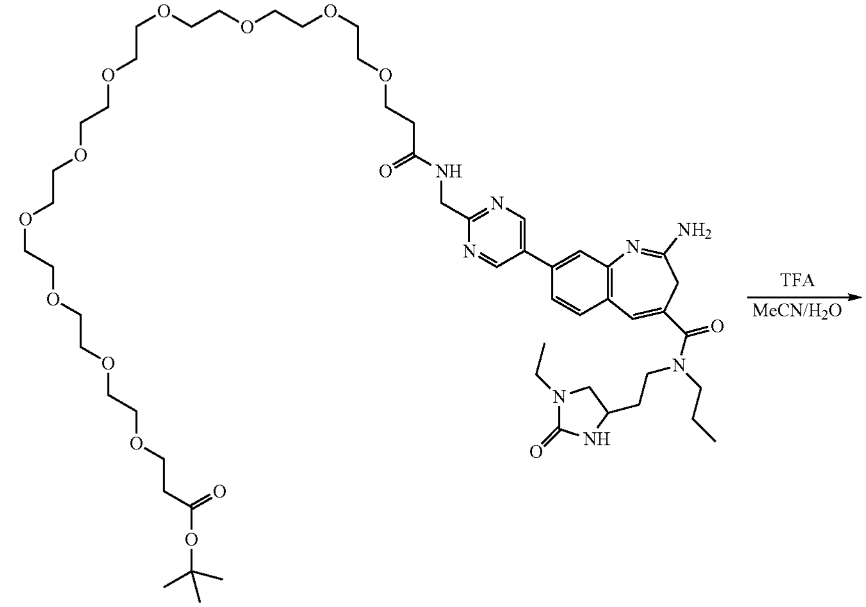
HxBzL-64n -continued

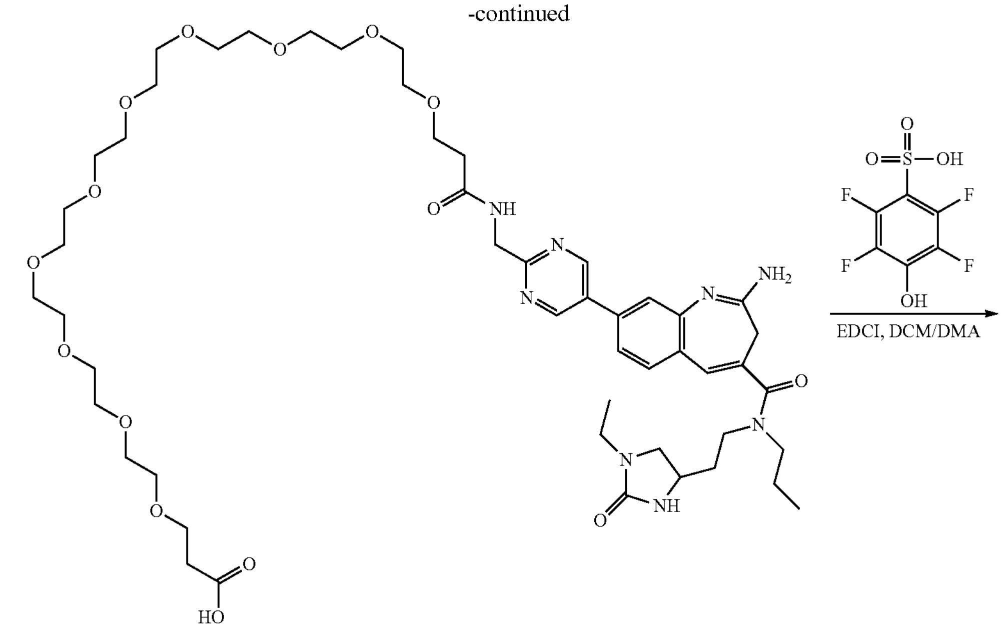

HxBzL-64o

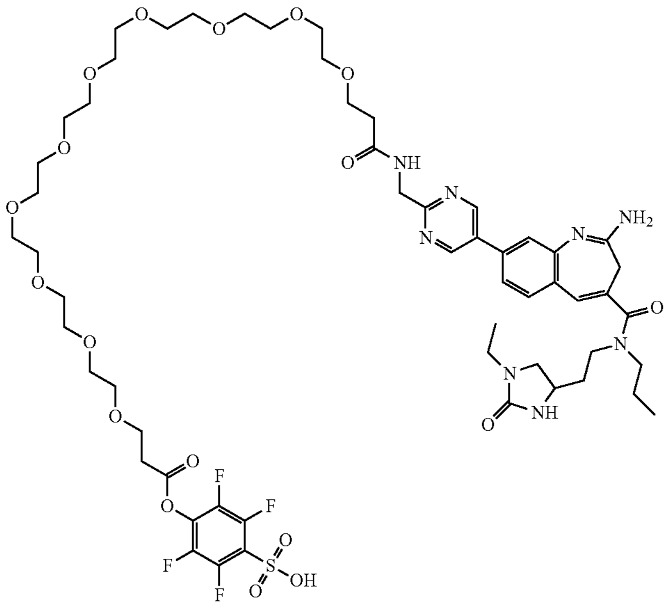

HxBzL-64

Preparation of N-but-3-enyl-4-nitro-N-propyl-benzenesulfonamide, HxBzL-64b

To a solution of 4-nitro-N-propyl-benzenesulfonamide, HxBzL-64a (12 g, 49.1 mmol, 1.0 eq) in DMF (150 mL) was added $Cs_2CO_3$ (40.0 g, 123 mmol, 2.5 eq), KI (8.16 g, 49.1 mmol, 1.0 eq) and 4-bromobut-1-ene (19.9 g, 147 mmol, 15.0 mL, 3.0 eq) and then stirred at 40° C. for 12 hrs under N2. The reaction mixture was poured into ice-water (w/w=1/1) (150 mL) and stirred for 10 min. The aqueous phase was extracted with ethyl acetate (100 mL×3). The combined organic phase was washed with brine (100 mL×2), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 10/1) to afford HxBzL-64b (11 g, 36.9 mmol, 75.1% yield) as yellow solid. $^1H$ NMR (MeOD, 400 MHz) δ 8.51-8.36 (m, 2H), 8.14-7.94 (m, 2H), 5.77-5.70 (m, 1H), 5.10-4.96 (m, 2H), 3.25 (t, J=7.2 Hz, 2H), 3.15 (t, J=7.2 Hz, 2H), 2.31 (q, J=7.2 Hz, 2H), 1.67-1.44 (m, 2H), 0.88 (t, J=7.2 Hz, 3H). LC/MS [M+H] 299.1 (calculated); LC/MS [M+H] 299.0 (observed).

Preparation of 4-nitro-N-[2-(oxiran-2-yl)ethyl]-N-propyl-benzenesulfonamide, HxBzL-64c To a solution of HxBzL-64b (13.5 g, 45.3 mmol, 1.0 eq) in DCM (200 mL) was added meta-chloroperbenzoic acid, m-CPBA (18.4 g, 90.5 mmol, 85% purity, 2.0 eq) at 0° C., and then stirred at 20° C. for 12 hrs. The mixture was filtered and filtrate was washed with sat. $NaHSO_3$ (30 mL×1) and brine (100 mL). The organic phase was dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 3/1) to afford HxBzL-64c (12 g, 38.2 mmol, 84.4% yield) as white solid. LC/MS [M+H] 315.1 (calculated); LC/MS [M+H] 315.0 (observed).

Preparation of N-[4-(ethylamino)-3-hydroxy-butyl]-4-nitro-N-propyl-benzenesulfonamide, HxBzL-64d To a solution of HxBzL-64c (7 g, 22 mmol, 1.0 eq) in THE (100 mL) was added ethanamine (33.5 g, 445 mmol, 48.6 mL, 60% purity, 20 eq) at 0° C., and then stirred at 30° C. for 2 hrs. The mixture was concentrated in vacuum at 45° C. The crude product HxBzL-64d (8 g, 22.3 mmol, 99.95% yield) was used into the next step without further purification as yellow solid. LC/MS [M+H] 360.1 (calculated); LC/MS [M+H] 360.2 (observed).

Preparation of tert-butyl N-ethyl-N-[2-hydroxy-4-[(4-nitrophenyl)sulfonyl-propyl-amino]butyl]carbamate, HxBzL-64e To a solution of HxBzL-64d (7.6 g, 21.1 mmol, 1.0 eq) in THE (70 mL) and $H_2O$ (10 mL) was added $NaHCO_3$ (3.55 g, 42.3 mmol, 1.64 mL, 2.0 eq) and $Boc_2O$ (9.23 g, 42.3 mmol, 9.71 mL, 2.0 eq). The mixture was stirred at 25° C. for 1 hr. The resulting mixture was poured into ice-water (w/w=1/1) (50 mL) and stirred for 10 min. The aqueous phase was extracted with ethyl acetate (50 mL×3). The combined organic phase was washed with brine (50 mL×1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 2/1) to afford HxBzL-64e (8.6 g, 18.7 mmol, 88.5% yield) as yellow oil. $^1H$ NMR (MeOD, 400 MHz) δ 8.46-8.39 (m, 2H), 8.13-8.04 (m, 2H), 3.78-3.70 (m, 1H), 3.39-3.2 (m, 3H), 3.29-3.22 (m, 2H), 3.20-3.14 (m, 2H), 3.10-3.00 (m, 1H), 1.79-1.69 (m, 1H), 1.65-1.53 (m, 3H), 1.45 (s, 9H), 1.09 (t, J=7.2 Hz, 3H), 0.90 (t, J=7.2 Hz, 3H).

Preparation of tert-butyl N-[2-(1,3-dioxoisoindolin-2-yl)-4-[(4-nitrophenyl) sulfonyl-propyl-amino] butyl]-N-ethyl-carbamate, HxBzL-64f To mixture of HxBzL-64e (5 g, 10.9 mmol, 1.0 eq) and isoindoline-1,3-dione (1.76 g, 12.0 mmol, 1.1 eq) in THE (50 mL) was added triphenylphosphine, $PPh_3$ (4.28 g, 16.3 mmol, 1.5 eq) and diethylazodicarboxylate, DEAD (2.84 g, 16.3 mmol, 2.97 mL, 1.5 eq) at 0° C., and then stirred at 20° C. for 1 hr. The mixture was poured into ice-water (w/w=1/1) (50 mL) and stirred for 10 min. The aqueous phase was extracted with ethyl acetate (30 mL×3). The combined organic phase was washed with brine (30 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 1/1) to afford HxBzL-64f (8.8 g, crude) as yellow solid. LC/MS [M+H] 589.2 (calculated); LC/MS [M+H] 589.2 (observed).

Preparation of tert-butyl N-[2-amino-4-[(4-nitrophenyl)sulfonyl-propyl-amino]butyl]-N-ethyl-carbamate, HxBzL-64g To a solution of HxBzL-64f (4.4 g, 7.47 mmol, 1.0 eq) in MeOH (50 mL) was added $NH_2NH_2 \cdot H_2O$ (2.25 g, 44.9 mmol, 2.18 mL, 6.0 eq) at 20° C., and then stirred at 80° C. for 12 hrs. The mixture was filtered and filtrate was concentrated in vacuum to afford HxBzL-64g (3.4 g, 7.41 mmol, 99.2% yield) as yellow oil. LC/MS [M+H] 459.2 (calculated); LC/MS [M+H] 459.2 (observed).

Preparation of N-[3-amino-4-(ethylamino)butyl]-4-nitro-N-propyl-benzenesulfonamide, HxBzL-64h To a solution of HxBzL-64g (2.9 g, 6.32 mmol, 1.0 eq) in EtOAc (30 mL) was added HCl/EtOAc (4 M, 29.0 mL, 18.3 eq), and then stirred at 20° C. for 1 hr. The mixture was concentrated in vacuum to give HxBzL-64h (2.7 g, crude, 2HCl) as yellow solid. $^1H$ NMR (MeOD, 400 MHz) δ 8.35 (d, J=8.8 Hz, 2H), 8.09 (d, J=8.8 Hz, 2H), 3.78-3.69 (m, 1H), 3.45-3.31 (m, 4H), 3.17-3.05 (m, 4H), 2.12-1.99 (m, 2H), 1.57-1.43 (m, 2H), 1.32 (t, J=7.2 Hz, 3H), 0.80 (t, J=7.2 Hz, 3H). LC/MS [M+H] 359.17 (calculated); LC/MS [M+H] 359.1 (observed).

Preparation of N-[2-(1-ethyl-2-oxo-imidazolidin-4-yl)ethyl]-4-nitro-N-propyl-benzenesulfonamide, HxBzL-64i To mixture of HxBzL-64h (2.7 g, 7.53 mmol, 1.0 eq) and $Et_3N$ (1.91 g, 18.8 mmol, 2.62 mL, 2.5 eq) in THE (30 mL) was added carbonyldiimidazole, CDI (2.44 g, 15.1 mmol, 2.0 eq) at 0° C. The mixture was stirred at 25° C. for 12 hrs. The result mixture was poured into ice-water (w/w=1/1) (50 mL) and stirred for 10 min. The aqueous phase was extracted with ethyl acetate (30 mL×3). The combined organic phase was washed with brine (50 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 0/1) to give HxBzL-64i (300 mg, 780 umol, 10.4% yield) as yellow oil. $^1H$ NMR (MeOD, 400 MHz) δ 8.39 (d, J=8.8 Hz, 2H), 8.02 (d, J=8.8 Hz, 2H), 3.99-3.95 (m, 1H), 3.77-3.63 (t, J=8.8 Hz, 1H), 3.48-3.38 (m, 1H), 3.35-3.23 (m, 2H), 3.22-3.04 (m, 4H), 1.98-1.74 (m, 2H), 1.66-1.45 (m, 2H), 1.15 (t, J=7.2 Hz, 3H), 0.87 (t, J=7.2 Hz, 3H)

Preparation of 1-ethyl-4-[2-(propylamino)ethyl] imidazolidin-2-one, HxBzL-64j

To a solution of HxBzL-64i (300 mg, 780 umol, 1.0 eq) in MeCN (10 mL) was added $LiOH \cdot H_2O$ (196 mg, 4.68 mmol, 6.0 eq) and methyl 2-sulfanylacetate (0.45 g, 4.24 mmol, 384 uL, 5.43 eq), and then stirred at 25° C. for 2 hrs. The mixture was filtered and filtrate was concentrated in vacuum. The residue was diluted with $H_2O$ (20 mL), then the pH of water phase was adjusted to 3-4 with HCl (1M), and then extracted with EtOAc (20 mL×3) to remove the byproduct, then the water phase was freeze-drying to afford HxBzL-64j (180 mg, 763 umol, 97.8% yield, HCl) as colorless oil. $^1H$ NMR (MeOD, 400 MHz) δ 3.83-3.73 (m, 1H), 3.65 (t, J=8.8 Hz, 1H), 3.28-3.13 (m, 3H), 3.12-3.03 (m, 2H), 3.02-2.93 (m, 2H), 2.01-1.84 (m, 2H), 1.79-1.67 (m, 2H), 1.11 (t, J=7.2 Hz, 3H), 1.03 (t, J=7.2 Hz, 3H).

Preparation of tert-butyl N-[[5-[2-amino-4-[2-(1-ethyl-2-oxo-imidazolidin-4-yl) ethyl-propyl-carbamoyl]-3H-1-benzazepin-8-yl]pyrimidin-2-yl]methyl] carbamate, HxBzL-641

To a solution of 2-amino-8-[2-[(tert-butoxycarbonylamino)methyl]pyrimidin-5-yl]-3H-1-benzazepine-4-carboxylic acid, HxBzL-64k (210 mg, 513 umol, 1.0 eq) in DMF (6 mL) was added HATU (205 mg, 539 umol, 1.05 eq), DIEA (331 mg, 2.56 mmol, 447 uL, 5.0 eq) and HxBzL-61j (145 mg, 615 umol, 1.2 eq, HCl), and then stirred at 25° C. for 1 hr. The result mixture was poured into ice-water (w/w=1/1) (10 mL) and stirred for 5 min. The aqueous phase was extracted with ethyl acetate (10 mL×3). The combined organic phase was washed with brine (10 mL×2), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=1/0, 1/0, Ethyl acetate/Methanol=1/0, 3/1) to afford HxBzL-641 (300 mg, 508 umol, 99.0% yield) as a yellow solid. LC/MS [M+H] 591.3 (calculated); LC/MS [M+H] 591.3 (observed).

Preparation of 2-amino-8-[2-(aminomethyl)pyrimidin-5-yl]-N-[2-(1-ethyl-2-oxo-imidazolidin-4-yl) ethyl]-N-propyl-3H-1-benzazepine-4-carboxamide, HxBzL-64m To a solution of HxBzL-641 (300 mg, 508 umol, 1.0 eq) in EtOAc (5 mL) was added HCl/EtOAc (4 M, 6.00 mL, 47.3 eq), and then stirred at 25° C. for 1 hr. The mixture was concentrated in vacuum. The residue was purified by prep-HPLC (column: Phenomenex Luna 80*30 mm*3 um; mobile phase: [water (0.1% TFA)-ACN]; B %: 1%-30%, 8 min) to afford HxBzL-64m (142 mg, 198 umol, 38.91% yield, 2TFA) as yellow solid. $^1H$ NMR (MeOD, 400 MHz) δ 9.22 (s, 2H), 7.88-7.71 (m, 3H), 7.15 (s, 1H), 4.49 (s, 2H), 3.75-3.60 (m, 2H), 3.57-3.50 (m, 4H), 3.39 (s, 2H), 3.28-3.18 (m, 3H), 2.02-1.97 (s, 1H), 1.88-1.83 (m, 1H), 1.81-1.65 (m, 2H), 1.15-1.10 (m, 3H), 1.01-0.95 (m, 3H). LC/MS [M+H] 491.28 (calculated); LC/MS [M+H] 491.3 (observed).

Preparation of tert-butyl 3-[2-[2-[2-[2-[2-[2-[2-[2-[2-[3-[[5-[2-amino-4-[2-(1-ethyl-2-oxo-imidazolidin-4-yl)ethyl-propyl-carbamoyl]-3H-1-benzazepin-8-yl]pyrimidin-2-yl]methylamino]-3-oxo-propoxy] ethoxy]ethoxy]ethoxy]ethoxy]ethoxy]ethoxy] ethoxy]ethoxy]ethoxy]propanoate, HxBzL-64n To a solution of HxBzL-64m (90 mg, 125 umol, 1.0 eq, 2TFA) and $Et_3N$ (38.02 mg, 376 umol, 52.3 uL, 3.0 eq) in DMF (1 mL) was added (2,3,5,6-tetrafluorophenyl) 3-[2-[2-[2-[2-[2-[2-[2-[2-[2-(3-tert-butoxy-3-oxo-propoxy)ethoxy] ethoxy]ethoxy]ethoxy]ethoxy]ethoxy]ethoxy]ethoxy] ethoxy]propanoate, t-Bu-COO-PEG10-COOTFP (95.5 mg, 125 umol, 1.0 eq) at 0° C., and then stirred at 25° C. for 1 hr. Water (10 mL) was added, then the pH of the mixture was adjusted to about 6 with TFA. The aqueous phase was extracted with MTBE (5 mL×3) to remove the byproduct. The water phase was further extracted with DCM/i-PrOH=3/1 (10 mL×3). The organic phase (DCM/i-PrOH) was concentrated in vacuum to afford HxBzL-64n (130 mg, 120 umol, 95.5% yield) as yellow oil.

Preparation of 3-[2-[2-[2-[2-[2-[2-[2-[2-[2-[3-[[5-[2-amino-4-[2-(1-ethyl-2-oxo-imidazolidin-4-yl)ethyl-propyl-carbamoyl]-3H-1-benzazepin-8-yl]pyrimidin-2-yl]methylamino]-3-oxo-propoxy]ethoxy]ethoxy] ethoxy]ethoxy]ethoxy]ethoxy]ethoxy]ethoxy] ethoxy]propanoic acid, HxBzL-64o To a solution of HxBzL-64n (100 mg, 92.0 umol, 1.0 eq) in MeCN (0.5 mL) and $H_2O$ (1 mL) was added TFA (83.9 mg, 735 umol, 54.5 uL, 8.0 eq), and then stirred at 80° C. for 1 hr. The mixture was concentrated in vacuum to give a residue, the residue was diluted with water (10 mL) and the aqueous phase was extracted with MTBE (10 mL) to remove excess TFA, and the water phase was lyophilized to HxBzL-64o (100 mg, 87.3 umol, 94.9% yield, TFA) as yellow oil.

Preparation of HxBzL-64

To a solution of HxBzL-64o (100 mg, 87.3 umol, 1.0 eq, TFA) and sodium 2,3,5,6-tetrafluoro-4-hydroxy-benzenesulfonate (70.2 mg, 262 umol, 3.0 eq) in DCM (1 mL) and DMA (0.5 mL) was added EDCI (67.0 mg, 349 umol, 4.0 eq), and then stirred at 20° C. for 1 hr. The mixture was concentrated in vacuum. The residue was purified by prep-HPLC (column: Phenomenex Luna 80*30 mm*3 um; mobile phase: [water (0.1% TFA)-ACN]; B %: 10%-35%, 8 min) to afford HxBzL-64 (30 mg, 23.8 umol, 27.3% yield) as yellow oil. $^1H$ NMR (MeOD, 400 MHz) δ 9.10 (s, 2H), 7.81-7.68 (m, 3H), 7.14 (s, 1H), 4.71 (s, 2H), 3.88 (t, J=6.0 Hz, 2H), 3.80 (t, J=6.0 Hz, 2H), 3.68-3.59 (m, 37H), 3.55-3.50 (m, 3H), 3.40 (s, 2H), 3.26-3.20 (m, 3H), 2.98 (t, J=6.0 Hz, 2H), 2.62 (t, J=6.0 Hz, 2H), 2.06-1.82 (m, 2H), 1.80-1.67 (m, 2H), 1.15-1.10 (m, 3H), 1.01-0.93 (m, 3H). LC/MS [M+H] 1259.5 (calculated); LC/MS [M+H]1259.6 (observed).

Example L-68 Synthesis of 4-[3-[2-[2-[2-[2-[2-[2-[2-[2-[2-[3-[[(1S)-1-[[(1S)-1-[[4-[[5-[2-amino-4-[ethoxy(propyl)carbamoyl]-3H-1-benzazepin-8-yl]pyrimidin-2-yl]methylcarbamoyloxymethyl]phenyl]carbamoyl]-4-ureido-butyl]carbamoyl]-2-methyl-propyl]amino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-68
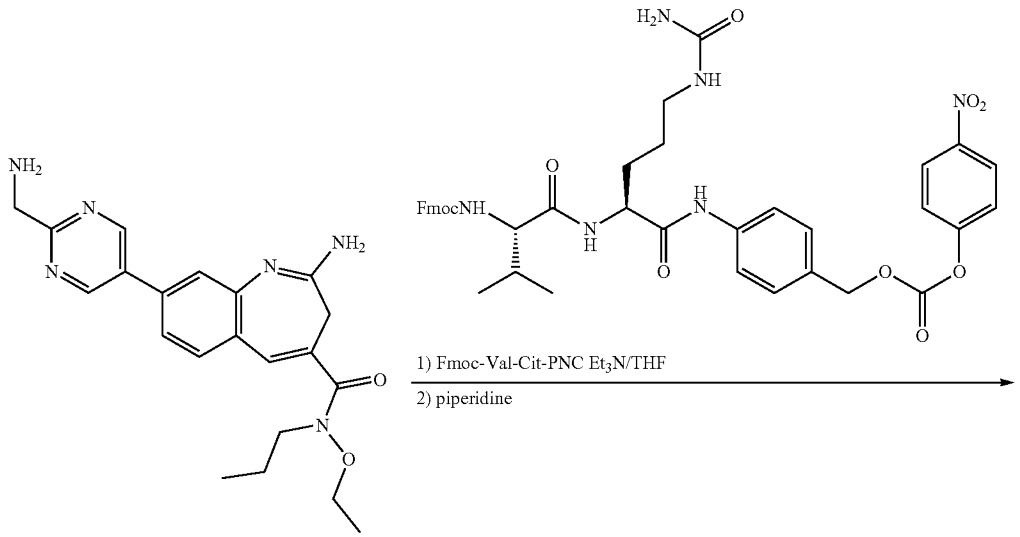
HxBz-5
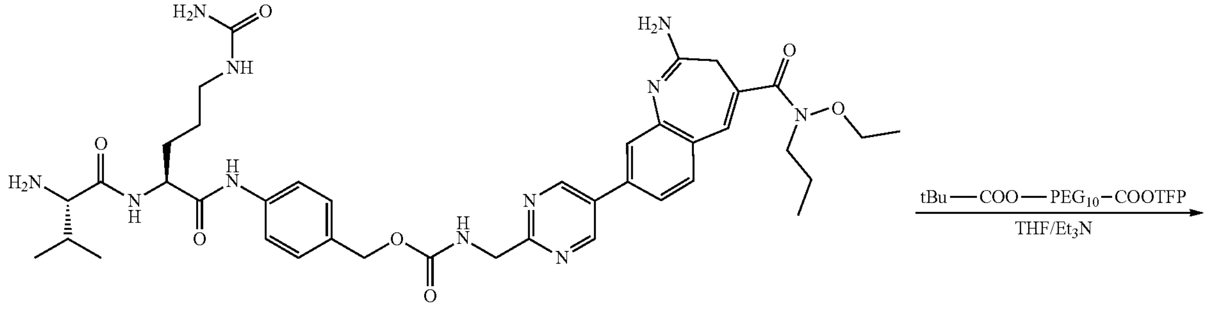
HxBzL-68a
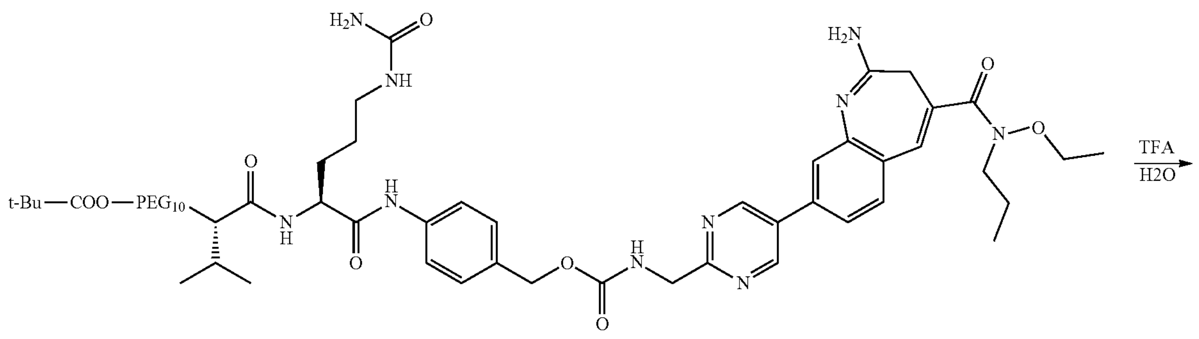
HxBzL-68b -continued

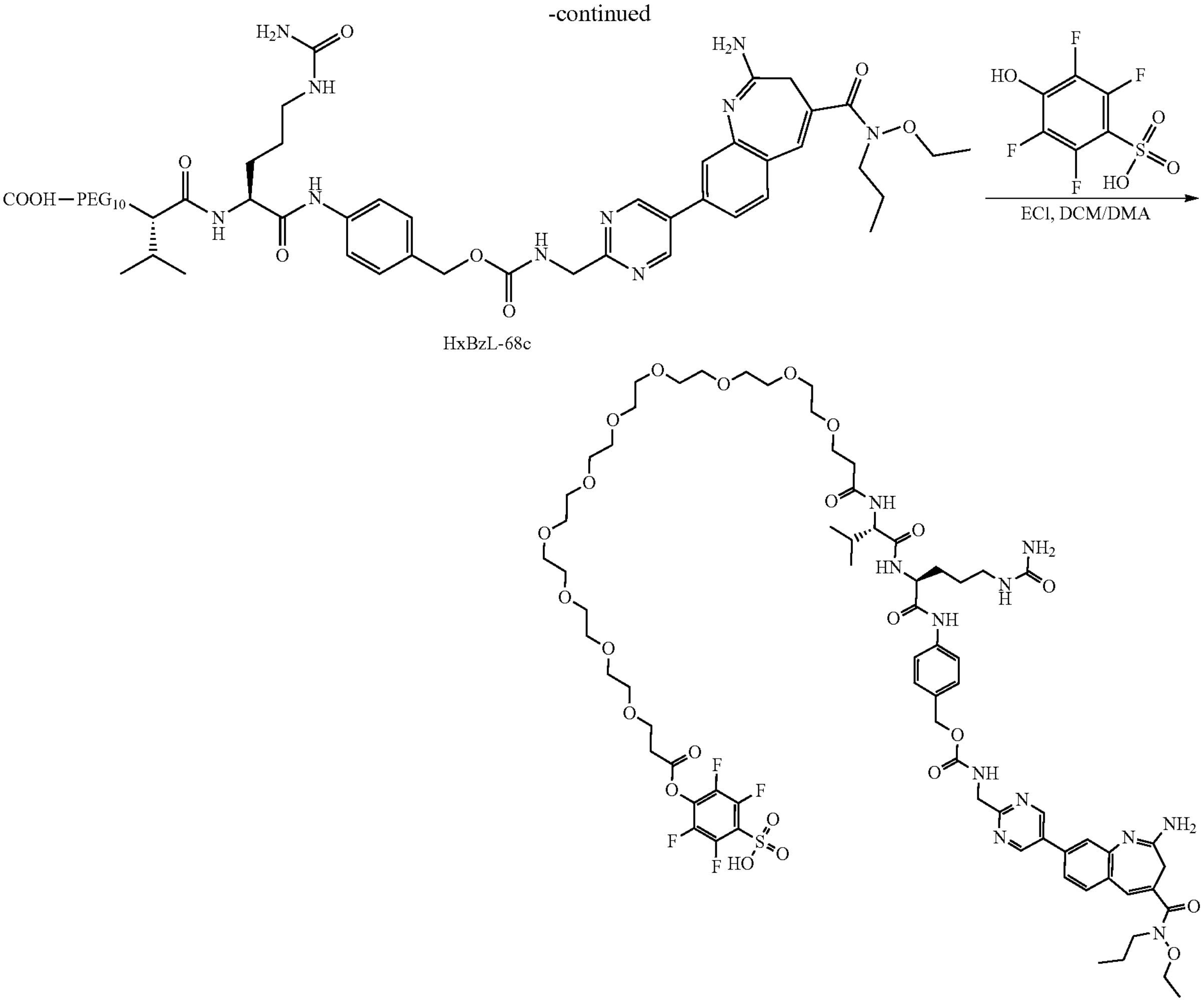

HxBzL-68c

HxBzL-68

Preparation of 4-((S)-2-((S)-2-((((9H-fluoren-9-yl) methoxy)carbonyl)amino)-3-methylbutanamido)-5-ureidopentanamido)benzyl ((5-(2-amino-4-(ethoxy (propyl)carbamoyl)-3H-benzo[b]azepin-8-yl) pyrimidin-2-yl)methyl)carbamate, HxBzL-68a To a solution of 2-amino-8-[2-(aminomethyl)pyrimidin-5-yl]-N-ethoxy-N-propyl-3H-1-benzazepine-4-carboxamide, HxBz-5 (41.2 mg, 96 umol, 1 eq, HCl) and $Et_3N$ (29.0 mg, 287 umol, 39.9 uL, 3 eq) in DMF (0.5 mL) was added (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate, Fmoc-Val-Cit-PNC (110 mg, 143 umol, 1.5 eq) at 0° C., and then stirred at 25° C. for 1 hr. Piperidine (24.4 mg, 287 umol, 28.3 uL, 3 eq) was added to the mixture and stirred at 25° C. for another 1 hr. The mixture was filtered and concentrated under reduced pressure. The residue was purified by prep-HPLC (TFA condition; column: Phenomenex Luna 80*30 mm*3 um; mobile phase: [water (0.1% TFA)-ACN]; B %: 5%-30%, 8 min) to afford HxBzL-68a (60 mg, 75.0 umol, 78.4% yield) as yellow oil. LC/MS [M+H] 800.4 (calculated); LC/MS [M+H] 800.6 (observed).

Preparation of tert-butyl 3-[2-[2-[2-[2-[2-[2-[2-[2-[2-[3-[[(1S)-1-[[(1S)-1-[[4-[[5-[2-amino-4-[ethoxy (propyl)carbamoyl]-3H-1-benzazepin-8-yl]pyrimidin-2-yl]methylcarbamoyloxymethyl]phenyl] carbamoyl]-4-ureido-butyl]carbamoyl]-2-methyl-propyl]amino]-3-oxo-propoxy]ethoxy]ethoxy] ethoxy]ethoxy]ethoxy]ethoxy]ethoxy]ethoxy] ethoxy]propanoate, HxBzL-68b To a solution of HxBzL-68a (60 mg, 65.7 umol, 1 eq, TFA) in THE (2 mL) was added $Et_3N$ (19.9 mg, 197 umol, 27.4 uL, 3 eq) and (2,3,5,6-tetrafluorophenyl) 3-[2-[2-[2-[2-[2-[2-[2-[2-[2-(3-tert-butoxy-3-oxo-propoxy)ethoxy] ethoxy]ethoxy]ethoxy]ethoxy]ethoxy]ethoxy]ethoxy]ethoxy] ethoxy]propanoate, t-Bu-COO-PEG10-COOTFP (50.1 mg, 66 umol, 1 eq), and then stirred at 25° C. for 1 hr. The reaction mixture was diluted with water 2 mL, then the pH of the aqueous phase was adjusted to 5~6 with TFA, and extracted with DCM/i-prOH (5 mL×3, 3/1), the combined organic phase was dried over $Na_2SO_4$, filtered and concentrated under reduced pressure to give HxBzL-68b (90 mg, 64.4 umol, 98.2% yield) as yellow oil which was used into the next step without further purification. LC/MS [M+H] 1396.8 (calculated); LC/MS [M+H] 1396.7 (observed).

Preparation of 3-[2-[2-[2-[2-[2-[2-[2-[2-[2-[3-[[(1 S)-1-[[(1S)-1-[[4-[[5-[2-amino-4-[ethoxy(propyl) carbamoyl]-3H-1-benzazepin-8-yl]pyrimidin-2-yl] methylcarbamoyloxymethyl]phenyl]carbamoyl]-4-ureido-butyl]carbamoyl]-2-methyl-propyl]amino]-3-oxo-propoxy]ethoxy]ethoxy]ethoxy]ethoxy]ethoxy] ethoxy]ethoxy]ethoxy]ethoxy]propanoic acid, HxBzL-68c To a solution of HxBzL-68b (90 mg, 64 umol, 1 eq) in water (3 mL) and MeCN (1 mL) was added TFA (73.5 mg, 644 umol, 47.7 uL, 10 eq), and then stirred at 80° C. for 2 hr. The reaction mixture was diluted with water 2 mL, then the pH of the aqueous phase was adjusted to 5~6 with TFA, and extracted with DCM/i-prOH (5 mL×3, 3/1), the combined organic phase was dried over $Na_2SO_4$, filtered and concentrated under reduced pressure to give HxBzL-68c (100 mg, crude) was obtained as yellow oil. LC/MS [M+H] 1340.7 (calculated); LC/MS [M+H]1340.6 (observed).

Preparation of HxBzL-68

To a solution of HxBzL-68c (100 mg, 74.6 umol, 1 eq) and sodium 2,3,5,6-tetrafluoro-4-hydroxy-benzenesulfonate (80.0 mg, 298 umol, 4 eq) in DCM (1 mL) and DMA (0.5 mL) was added EDCI (57.2 mg, 298 umol, 4 eq), and then stirred at 25° C. for 1 hr. The mixture was filtered and concentrated under reduced pressure. The residue was purified by prep-HPLC (TFA condition; column: Phenomenex Luna 80*30 mm*3 um; mobile phase: [water (0.1% TFA)-ACN]; B %: 15%-40%, 8 min) to afford HxBzL-68 (20 mg, 12.75 umol, 17.09% yield) as a white solid. $^1$H NMR (400 MHz, MeOD) δ 9.08 (s, 2H), 7.83-7.78 (m, 1H), 7.77-7.71 (m, 2H), 7.65 (br d, J=7.6 Hz, 2H), 7.47 (s, 1H), 7.42-7.34 (m, 2H), 5.12 (s, 2H), 4.62 (s, 2H), 4.54-4.48 (m, 1H), 4.23-4.18 (m, 1H), 4.02-3.98 (m, 2H), 3.87 (t, J=6.0 Hz, 2H), 3.80-3.75 (m, 2H), 3.65-3.60 (m, 36H), 3.52-3.49 (m, 2H), 3.47 (s, 2H), 3.21-3.14 (m, 2H), 2.98 (t, J=6.0 Hz, 2H), 2.61-2.53 (m, 2H), 2.20-2.10 (m, 1H), 2.02-1.88 (m, 1H), 1.85-1.71 (m, 3H), 1.70-1.52 (m, 2H), 1.23 (t, J=7.2 Hz, 3H), 1.05-0.99 (m, 9H). LC/MS [M+H] 1568.6 (calculated); LC/MS [M+H]1568.6 (observed).

Example L-77 Synthesis of 4-((1-(5-(2-amino-4-(ethoxy(propyl)carbamoyl)-3H-benzo[b]azepin-8-yl) pyrimidin-2-yl)-3-oxo-6,9,12-trioxa-2-azapentadecan-15-oyl)oxy)-2,3,5,6-tetrafluorobenzenesulfonic acid, HxBzL-77

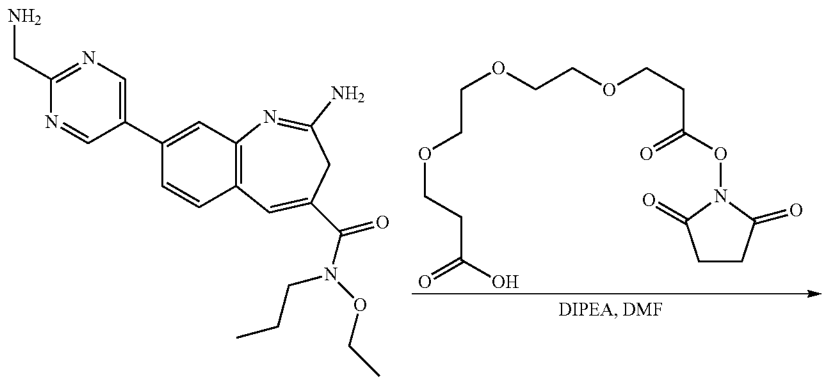

HxBzL-77a

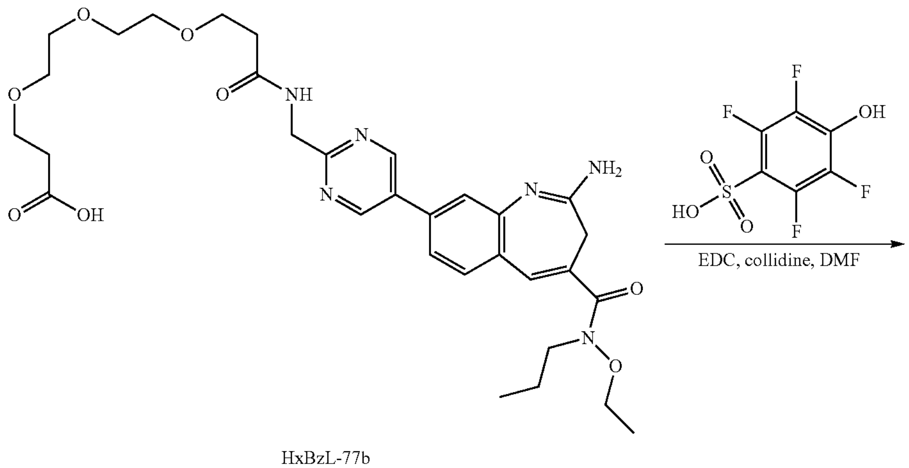

HxBzL-77b

-continued

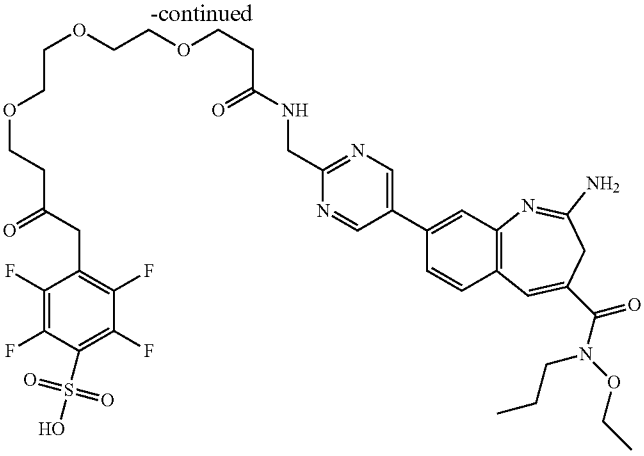

HxBzL-77

Preparation of 1-(5-(2-amino-4-(ethoxy(propyl)carbamoyl)-3H-benzo[b]azepin-8-yl)pyrimidin-2-yl)-3-oxo-6,9,12-trioxa-2-azapentadecan-15-oic acid, HxBzL-77b To a stirring solution of 2-amino-8-(2-(aminomethyl)pyrimidin-5-yl)-N-ethoxy-N-propyl-3H-benzo[b]azepine-4-carboxamide, HxBzL-77a (25.2 mg, 0.064 mmol, 1 eq) and 3-(2-(2-(3-((2,5-dioxopyrrolidin-1-yl)oxy)-3-oxopropoxy)ethoxy)ethoxy)propanoic acid (22.2 mg, 0.064 mmol, 1 eq) in DMF (0.5 ml) was added diisopropylethylamine, DIPEA (56 μl, 0.32 mmol, 5 eq). The reaction was stirred at room temperature and monitored by LC/MS, then purified by prep-HPLC to give HxBzL-77b (28.8 mg, 0.046 mmol, 72%). LC/MS [M+H] 627.3 (calculated); LC/MS [M+H] 627.6 (observed).

Preparation of HxBzL-77

To a stirring solution of HxBzL-77b (28.8 mg, 0.046 mmol, 1 eq) and sodium 2,3,5,6-tetrafluoro-4-hydroxy-benzenesulfonate (61.6 mg, 0.23 mmol, 5 eq) in DMF (0.5 ml) was added 2,4,6-collidine (61 μl, 0.46 mmol, 10 eq), followed by EDC (13.2 mg, 0.069, 1.5 eq). The reaction was stirred at room temperature and monitored by LC/MS, and then concentrated and purified by prep-HPLC to give HxBzL-77 (8.1 mg, 0.0095 mmol, 21%). LC/MS [M+H] 855.3 (calculated); LC/MS [M+H] 855.6 (observed).

Example L-78 Synthesis of 4-((1-(5-(4-(((1H-pyrazol-4-yl)methyl)(propyl)carbamoyl)-2-amino-3H-benzo[b]azepin-8-yl)pyrimidin-2-yl)-3-oxo-6,9,12,15,18,21,24,27,30,33-decaoxa-2-azahexatriacontan-36-oyl)oxy)-3,5-dichlorobenzenesulfonic acid, HxBzL-78

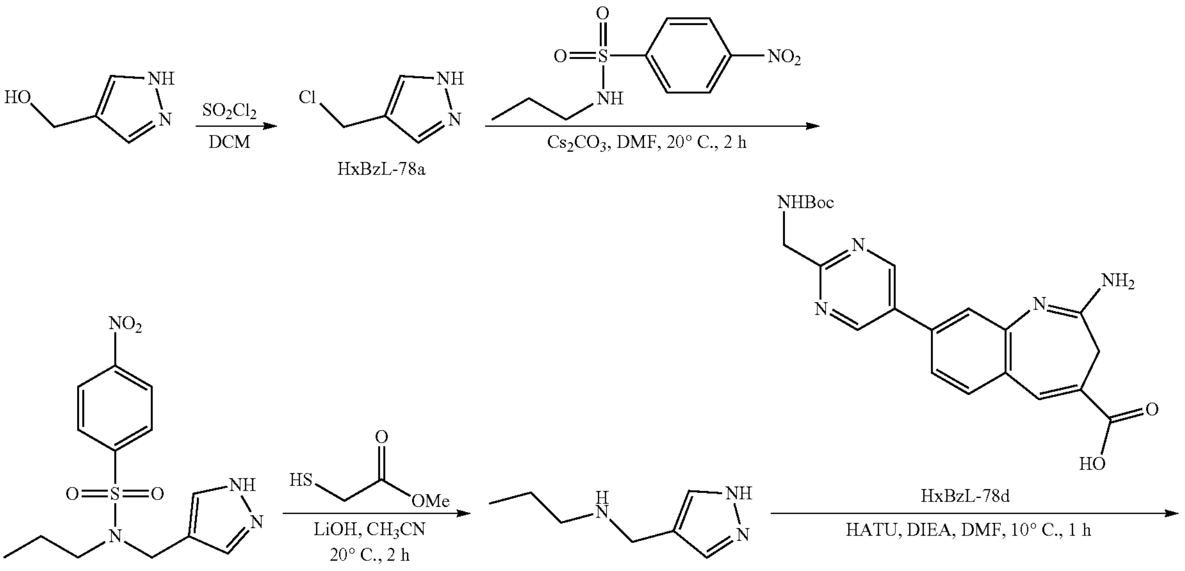

-continued
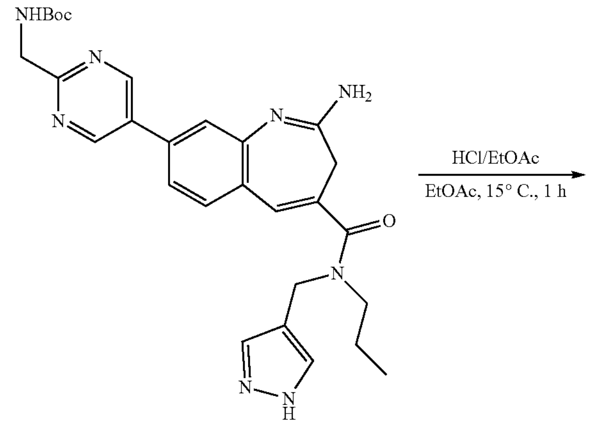
HxBzL-78e
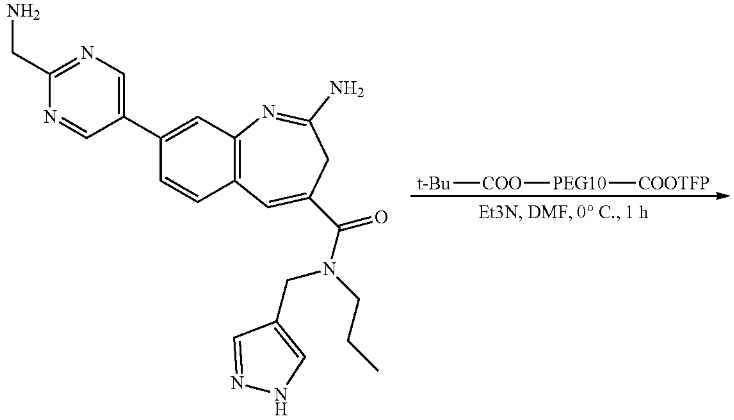
HxBzL-78f
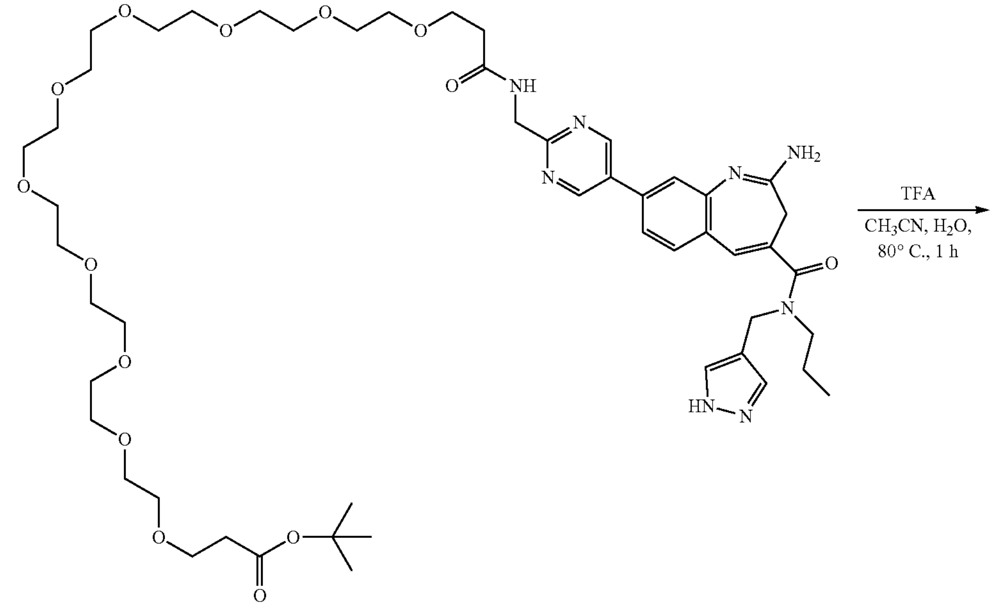
HxBzL-78g

-continued

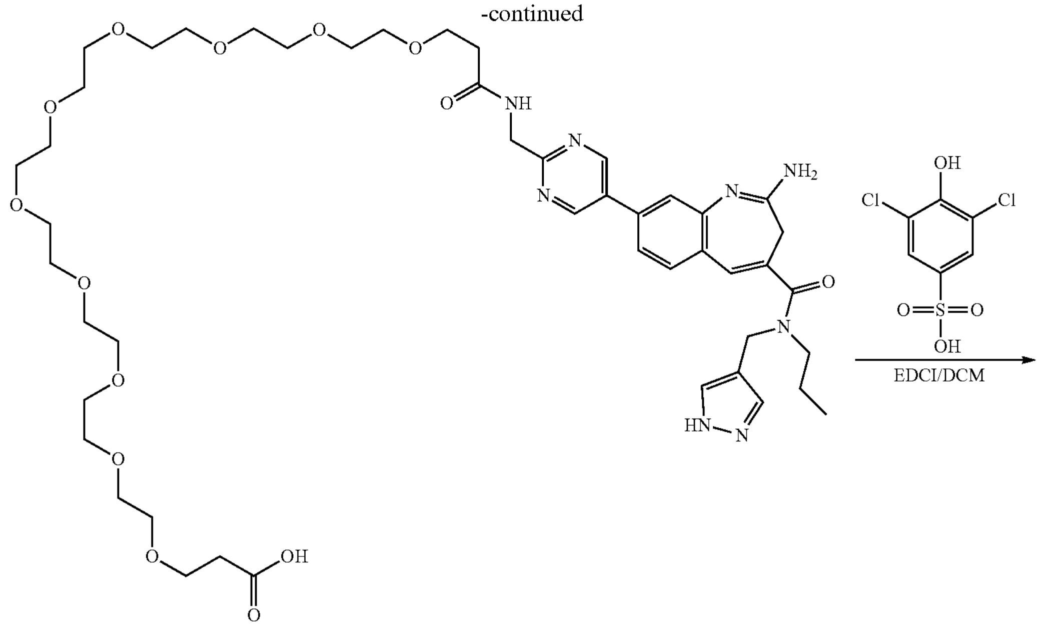

HxBzL-78h

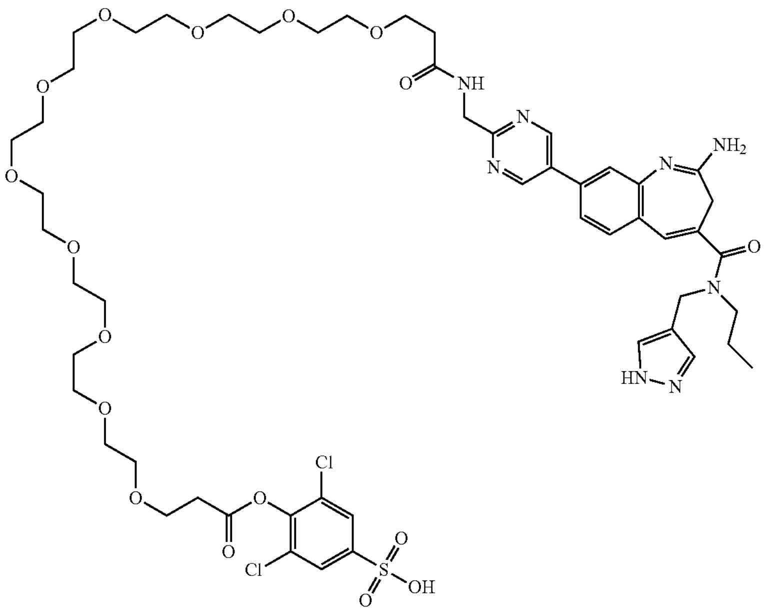

HxBzL-78

Preparation of 4-(chloromethyl)-1H-pyrazole, HxBzL-78a

To a solution of 1H-pyrazol-4-ylmethanol (2.50 g, 25.5 mmol, 1 eq) in DCM (40.0 mL) was added $SOCl_2$ (6.06 g, 50.9 mmol, 3.70 mL, 2 eq) at 0° C., and then stirred at 20° C. for 2 h. The mixture was concentrated to give HxBzL-78a (4 g, crude) as white solid.

Preparation of 4-nitro-N-propyl-N-(1H-pyrazol-4-ylmethyl)benzenesulfonamide, HxBzL-78b To a solution of 4-nitro-N-propyl-benzenesulfonamide (5.76 g, 23.60 mmol, 1.1 eq) in DMF (20.0 mL) was added $Cs_2CO_3$ (21.0 g, 64.35 mmol, 3 eq) and HxBzL-78a (2.5 g, 21.45 mmol, 1 eq), and then stirred at 20° C. for 2 h. The mixture was diluted with water (50 mL) and extracted with EtOAc (30 mL×3). The organic layer was washed with brine (20 mL×3), dried over $Na_2SO_4$, filtered and concentrate. The residue was purified by flash silica gel chromatography (ISCO®; 8 g SepaFlash® Silica Flash Column, Eluent of 0~70% Ethyl acetate/Petroleum ether gradient at 45 mL/min) to give HxBzL-78b (2.7 g, 8.32 mmol, 38.81% yield) was obtained as white solid. $^1$H NMR ($CDCl_3$, 400 MHz) δ9.05-8.79 (m, 1H), 8.34 (d, J=8.8 Hz, 2H), 7.97 (d, J=8.8 Hz, 2H), 7.46 (s, 2H), 4.37 (s, 2H), 3.22-3.10 (m, 2H), 1.52 (sxt, J=7.2 Hz, 2H), 0.82 (t, J=7.2 Hz, 3H)

Preparation of N-(1H-pyrazol-4-ylmethyl)propan-1-amine, HxBzL-78c

To a solution of HxBzL-78b (2.40 g, 7.40 mmol, 1 eq) in $CH_3CN$ (20.0 mL) was added $LiOH{\cdot}H_2O$ (1.86 g, 44.40 mmol, 6 eq) and methyl 2-sulfanylacetate (2.66 g, 25.06 mmol, 2.27 mL, 3.39 eq) at 0° C., and then stirred at 20° C. for 2 h. The mixture was filtered and concentrated, the residue was diluted with water (40 mL) and the pH of the water phase was adjusted to ~1 by progressively adding HCl (12 M) at 0° C. and extracted with EtOAc (40 mL) to remove the byproduct. Water phase was lyophilized to give HxBzL-78c (1.2 g, 6.83 mmol, 92.33% yield, HCl) as white solid. $^1$H NMR (MeOD, 400 MHz) δ8.28 (s, 2H), 4.26 (s, 2H), 3.04 (br d, J=7.6 Hz, 2H), 1.77 (qd, J=7.6, 15.2 Hz, 2H), 1.03 (t, J=7.6 Hz, 3H).

Preparation of tert-butyl ((5-(4-(((1H-pyrazol-4-yl)methyl)(propyl)carbamoyl)-2-amino-3H-benzo[b]azepin-8-yl)pyrimidin-2-yl)methyl)carbamate, HxBzL-78e To a solution of 2-amino-8-[2-[(tert-butoxycarbonylamino)methyl]pyrimidin-5-yl]-3H-1-benzazepine-4-carboxylic acid, HxBzL-78d (300 mg, 732.71 umol, 1 eq) in DMF (8.00 mL) was added HATU (293 mg, 769.35 umol, 1.05 eq) and DIEA (474 mg, 3.66 mmol, 638 uL, 5 eq) and HxBzL-78c (193 mg, 1.10 mmol, 1.5 eq, HCl), and then stirred at 10° C. for 1 h. The mixture was diluted with water (30 mL) and extracted with EtOAc (30 mL×3). The organic layer was washed with brine (20 mL×3), dried over $Na_2SO_4$, filtered and concentrate. The residue was purified by flash silica gel chromatography (ISCO®; 1 g SepaFlash® Silica Flash Column, Eluent of 0~40% Ethyl acetate/MeOH@ 35 mL/min) to give tert-butyl ((5-(4-(((1H-pyrazol-4-yl)methyl)(propyl)carbamoyl)-2-amino-3H-benzo[b]azepin-8-yl)pyrimidin-2-yl)methyl)carbamate (230 mg, 433.46 umol, 59.16% yield) as light yellow solid. LC/MS [M+H]531.28 (calculated); LC/MS [M+H] 531.2 (observed).

Preparation of N-((1H-pyrazol-4-yl)methyl)-2-amino-8-(2-(aminomethyl)pyrimidin-5-yl)-N-propyl-3H-benzo[b]azepine-4-carboxamide, HxBzL-78f To a solution of HxBzL-78e (230 mg, 433.46 umol, 1 eq) in EtOAc (5.00 mL) was added HCl/EtOAc (4 M, 5.00 mL, 46.14 eq), and then stirred at 15° C. for 1 h. The mixture was concentrated to give a residue. The residue was purified by prep-HPLC (column: Phenomenex Luna 80*30 mm*3 um; mobile phase: [water (0.1% TFA)-ACN]; B %: 1%-25%, 8 min) to give HxBzL-78f (210 mg, 385.66 umol, 88.97% yield, TFA) as white solid. $^1$H NMR (MeOD, 400 MHz) δ9.20 (s, 2H), 7.83-7.73 (m, 2H), 7.73-7.60 (m, 3H), 7.13 (s, 1H), 4.72-4.58 (m, 2H), 4.47 (s, 2H), 3.52-3.44 (m, 2H), 3.37 (br s, 2H), 1.78-1.64 (m, 2H), 0.98-0.89 (m, 3H). LC/MS [M+H] 431.2 (calculated); LC/MS [M+H] 431.3 (observed).

Preparation of tert-butyl 1-(5-(4-(((1H-pyrazol-4-yl)methyl)(propyl)carbamoyl)-2-amino-3H-benzo[b]azepin-8-yl)pyrimidin-2-yl)-3-oxo-6,9,12,15,18,21,24,27,30,33-decaoxa-2-azahexatriacontan-36-oate, HxBzL-78g To a solution of HxBzL-78f (110 mg, 236 umol, 1 eq, HCl) in DMF (2.00 mL) was added $Et_3N$ (72.0 mg, 707 umol, 98.0 uL, 3 eq) and (2,3,5,6-tetrafluorophenyl) 3-[2-[2-[2-[2-[2-[2-[2-[2-[2-(3-tert-butoxy-3-oxo-propoxy)ethoxy]ethoxy]ethoxy]ethoxy]ethoxy]ethoxy]ethoxy]ethoxy]ethoxy]propanoate, t-Bu-COO-PEG10-COOTFP (198 mg, 259 umol, 1.1 eq), and then stirred at 0° C. for 1 h. The mixture was filtered and purified by prep-HPLC (column: Phenomenex Luna 80*30 mm*3 um; mobile phase: [water (0.1% TFA)-ACN]; B %: 30%-50%, 8 min) to give HxBzL-78g (110 mg, 96.39 umol, 40.92% yield, TFA) as colorless oil. LC/MS [M+H] 1027.56 (calculated); LC/MS [M+H]1027.5 (observed).

Preparation of 1-(5-(4-(((1H-pyrazol-4-yl)methyl)(propyl)carbamoyl)-2-amino-3H-benzo[b]azepin-8-yl)pyrimidin-2-yl)-3-oxo-6,9,12,15,18,21,24,27,30,33-decaoxa-2-azahexatriacontan-36-oic acid, HxBzL-78h To a solution of HxBzL-78g (110 mg, 96.39 umol, 1 eq, TFA) in $CH_3CN$ (2.00 mL) and $H_2O$ (1.00 mL) was added TFA (88.0 mg, 771.10 umol, 57.0 uL, 8 eq), and then stirred at 80° C. for 1 h. The mixture was concentrated to give a residue. The residue was purified by prep-HPLC (column: Phenomenex Luna 80*30 mm*3 um; mobile phase: [water (0.1% TFA)-ACN]; B %: 5%-35%, 8 min) to give HxBzL-78h (100 mg, 92.16 umol, 95.61% yield, TFA) as colorless oil. $^1$H NMR (MeOD, 400 MHz) δ9.09 (s, 2H), 7.85-7.63 (m, 5H), 7.13 (s, 1H), 4.69 (s, 2H), 4.62 (s, 2H), 3.80 (t, J=6.0 Hz, 2H), 3.71 (t, J=6.4 Hz, 2H), 3.67-3.58 (m, 36H), 3.50-3.44 (m, 2H), 3.36 (s, 2H), 2.60 (t, J=6.0 Hz, 2H), 2.53 (t, J=6.4 Hz, 2H), 1.77-1.66 (m, 2H), 0.93 (br s, 3H). LC/MS [M+H] 971.5 (calculated); LC/MS [M+H] 971.6 (observed).

Preparation of HxBzL-78

To a mixture of HxBzL-78h (110 mg, 113.27 umol, 1 eq) and 3,5-dichloro-4-hydroxy-benzenesulfonic acid (138 mg, 566 umol, 5 eq) in DCM (3 mL) and DMA (0.5 mL) was added DIEA (29.8 mg, 226 umol, 2 eq) and EDCI (108 mg, 566 umol, 5 eq) at 25° C. under $N_2$, and then stirred at 25° C. for 1 hours. The mixture was filtered and concentrated in vacuum. The residue was purified by prep-HPLC column: Phenomenex Luna 80*30 mm*3 um; mobile phase: [water (0.1% TFA)-ACN]; B %: 10%-30%, 8 min. to give HxBzL-78 (20 mg, 16.72 umol, 14.76% yield) as light yellow oil. $^1$H NMR (MeOD, 400 MHz) δ9.07 (s, 2H), 7.80-7.61 (m, 7H), 7.11 (s, 1H), 4.76-4.58 (m, 4H), 3.86 (t, J=6.0 Hz, 2H), 3.79 (t, J=6.0 Hz, 2H), 3.67-3.54 (m, 36H), 3.47 (br t, J=7.2 Hz, 2H), 3.36 (s, 2H), 2.92 (t, J=6.0 Hz, 2H), 2.60 (t, J=6.0 Hz, 2H), 1.71 (br d, J=7.2 Hz, 2H), 0.91 (br s, 3H). LC/MS [M+H] 1195.4 (calculated); LC/MS [M+H] 1195.4 (observed).

Example L-82 Synthesis of 4-[3-[2-[2-[2-[2-[2-[2-[2-[2-[2-[3-[[5-[2-amino-4-[propyl-[2-(trifluoromethoxy)ethoxy]carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-82
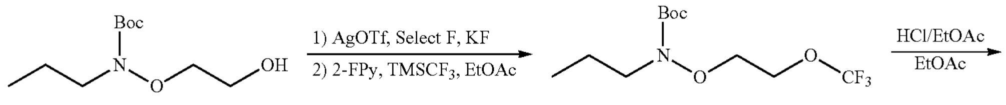
HxBzL-82a HxBzL-82b
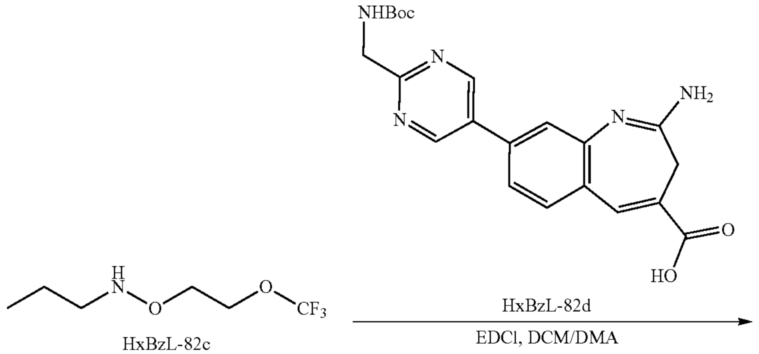
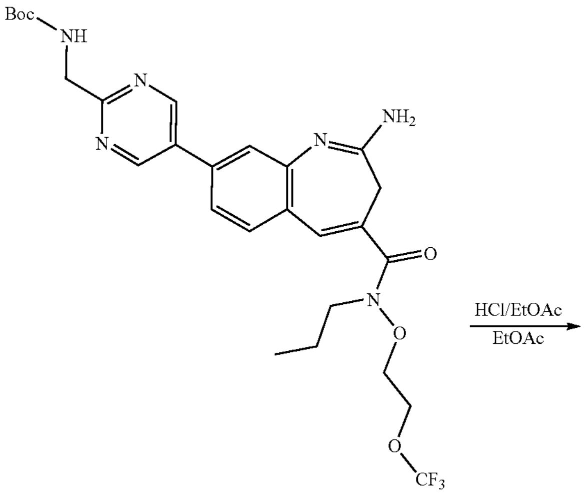
HxBzL-82e -continued
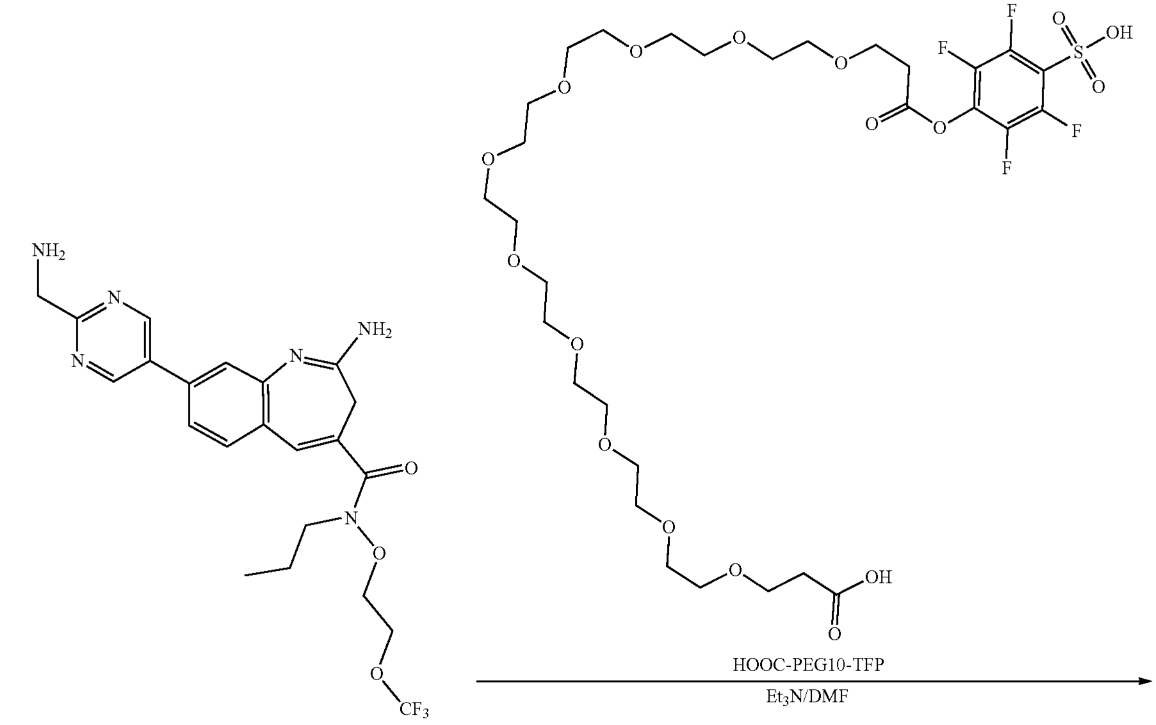
HxBzL-82f
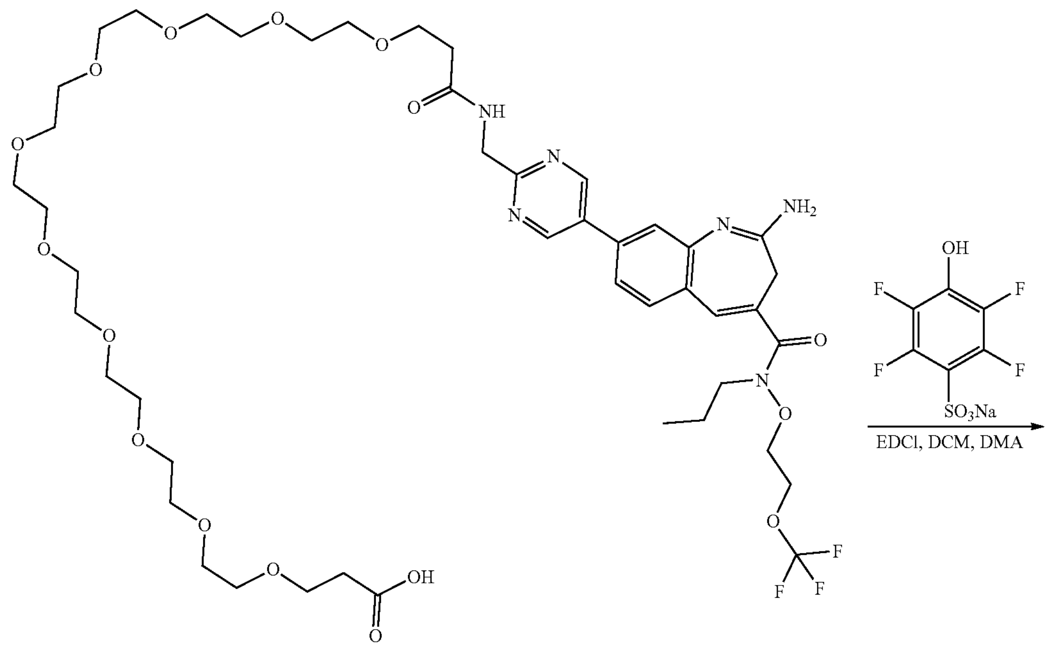
HxBzL-82g -continued

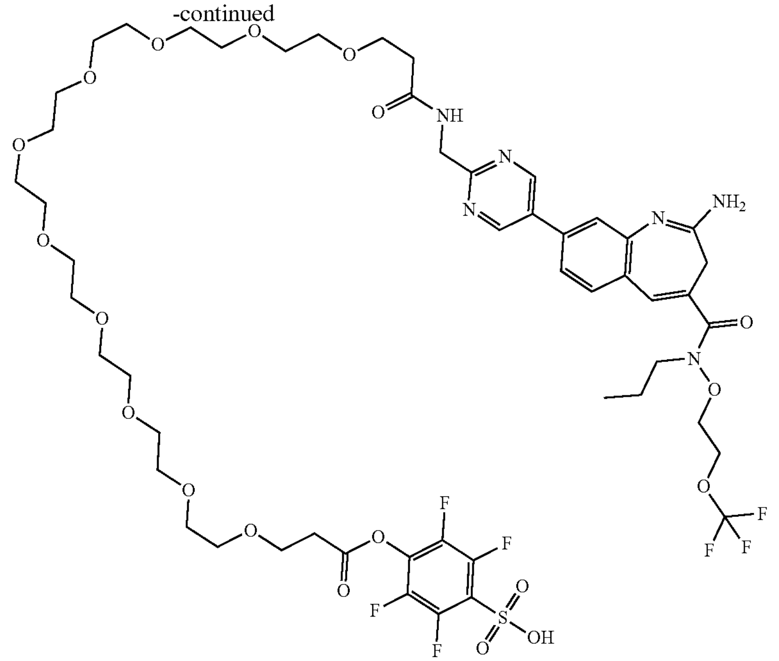

HxBzL-82

Preparation of tert-butyl N-propyl-N-[2-(trifluoromethoxy)ethoxy]carbamate, HxBzL-82b To a mixture of silver triflate, AgOTf (1.76 g, 6.84 mmol, 3 eq), 1-chloromethyl-4-fluoro-1,4-diazoniabicyclo[2.2.2] octane bis(tetrafluoroborate), Select F, CAS Reg. No. 140681-55-6 (1.21 g, 3.42 mmol, 1.5 eq), KF (530 mg, 9.12 mmol, 214 uL, 4 eq) and tert-butyl N-(2-hydroxyethoxy)-N-propyl-carbamate, HxBzL-82a (0.5 g, 2.28 mmol, 1 eq) were added successively under nitrogen gas, $N_2$. Ethylacetate EtOAc (15 mL), 2-fluoropyridine, 2-FPy (664 mg, 6.84 mmol, 588 uL, 3 eq) and trifluoromethyltrimethylsilane, $TMSCF_3$ (973 mg, 6.84 mmol, 3 eq) were then added successively under $N_2$ at 15° C. The resulting mixture was stirred at 25° C. for 12 h. The reaction mixture was filtered and concentrated under reduced pressure. The residue was purified by column chromatography ($SiO_2$, Petroleum ether: MTBE=1:0 to 10:1) to give HxBzL-82b (0.26 g, 905 umol, 39.7% yield) as a colorless oil. $^1H$ NMR ($CDCl_3$, 400 MHz) δ4.21-4.01 (m, 4H), 3.48-3.34 (m, 2H), 1.76-1.59 (m, 2H), 1.50 (s, 9H), 0.92 (t, J=7.2 Hz, 3H)

Preparation of N-[2-(trifluoromethoxy)ethoxy]propan-1-amine, HxBzL-82c

To a solution of HxBzL-82b (260 mg, 905 umol, 1 eq) in EtOAc (1 mL) was added HCl/EtOAc (4 M, 10 mL, 44.2 eq). The mixture was stirred at 15° C. for 0.5 h. The reaction mixture was concentrated under reduced pressure to give HxBzL-82c (0.26 g, crude, HCl) as a yellow oil. $^1H$ NMR (MeOD, 400 MHz) δ4.42-4.36 (m, 2H), 4.35-4.29 (m, 2H), 3.34-3.28 (m, 2H), 1.83-1.72 (m, 2H), 1.06 (t, J=7.2 Hz, 3H)

Preparation of tert-butyl N-[[5-[2-amino-4-[propyl-[2-(trifluoromethoxy)ethoxy]carbamoyl]-3H-1-benzazepin-8-yl]pyrimidin-2-yl]methyl]carbamate, HxBzL-82e To a solution of 2-amino-8-[2-[(tert-butoxycarbonylamino)methyl] pyrimidin-5-yl]-3H-1-benzazepine-4-carboxylic acid, HxBzL-82d (330 mg, 805.98 umol, 1 eq) in DCM (5 mL) and DMA (5 mL) was added HxBzL-82c (252 mg, 1.13 mmol, 1.4 eq, HCl) and EDCI (464 mg, 2.42 mmol, 3 eq) at 0° C. and the mixture was stirred at 15° C. for 1 h. The reaction mixture was concentrated under reduced pressure to remove DCM. The residue was diluted with $H_2O$ (20 mL) and adjusted to pH=8-9 with aq. $NaHCO_3$ and extracted with EtOAc (20 mL×3). The combined organic layers were washed with brine (10 mL×3), dried over $Na_2SO_4$, filtered and concentrated under reduced pressure to give a residue. The residue was purified by column chromatography ($SiO_2$, Petroleum ether:Ethyl acetate=1:0 to 0:1) and then (SiO2, EtOAc:MeOH=1:0 to 5:1) to give crude product. The residue was purified further by prep-HPLC (TFA condition: column: Phenomenex Luna C18 150*30 mm*5 um; mobile phase: [water (0.1% TFA)-ACN]; B %: 20%-50%, 9 min.) to give HxBzL-82e (0.15 g, 217 umol, 26.9% yield, TFA) as a light yellow solid. $^1H$ NMR (MeOD-$d_4$, 400 MHz) δ9.08 (s, 2H), 7.82-7.76 (m, 1H), 7.74-7.70 (m, 2H), 7.49 (s, 1H), 4.53 (s, 2H), 4.26-4.14 (m, 4H), 3.79 (t, J=7.2 Hz, 2H), 3.43 (s, 2H), 1.85-1.75 (m, 2H), 1.48 (s, 9H), 1.01 (t, J=7.2 Hz, 3H). LC/MS [M+H] 579.25 (calculated); LC/MS [M+H] 579.3 (observed).

Preparation of 2-amino-8-[2-(aminomethyl)pyrimidin-5-yl]-N-propyl-N-[2-(trifluoromethoxy)ethoxy]-3H-1-benzazepine-4-carboxamide, HxBzL-82f To a solution of HxBzL-82e (0.26 g, 449 umol, 1 eq) in EtOAc (1 mL) was added HCl/EtOAc (4 M, 10 mL, 89.0 eq) and then stirred at 15° C. for 1 h. The reaction mixture was filtered and the solid was dried under reduced pressure to give HxBzL-82f (185 mg, 336 umol, 74.7% yield, 2HCl) as a light yellow solid. $^1H$ NMR (MeOD-$d_4$, 400 MHz) δ9.21 (s, 2H), 7.86-7.79 (m, 2H), 7.78-7.71 (m, 1H), 7.50 (s, 1H), 4.48 (s, 2H), 4.26-4.17 (m, 4H), 3.79 (t, J=7.2 Hz, 2H), 3.44 (s, 2H), 1.85-1.75 (m, 2H), 1.01 (t, J=7.2 Hz, 3H). LC/MS [M+H] 479.2 (calculated); LC/MS [M+H] 479.2 (observed).

Preparation of 3-[2-[2-[2-[2-[2-[2-[2-[2-[2-[2-[3-[[5-[2-amino-4-[propyl-[2-(trifluoromethoxy)ethoxy]carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoic acid, HxBzL-82g To a solution of HxBzL-82f (80 mg, 145 umol, 1 eq, 2HCl) in DMF (2 mL) was added TEA (29.4 mg, 290 umol, 40.4 uL, 2 eq) and 3-[2-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid, HOOC-PEG10-TFP (103 mg, 145 umol, 1 eq) at 0° C. The mixture was stirred at 15° C. for 1 h. The pH of the reaction mixture was adjusted to 5-6 with TFA at 0° C., and then filtered and concentrated under reduced pressure. The residue was purified by prep-HPLC (TFA condition: column: Phenomenex Luna 80*30 mm*3 um; mobile phase: [water (0.1% TFA)-ACN]; B %: 15%-50%, 8 min) to give HxBzL-82g (85 mg, 75.0 umol, 51.7% yield, TFA) as a light yellow oil. $^1$H NMR (MeOD-$d_4$, 400 MHz) δ9.10 (s, 2H), 7.84-7.78 (m, 1H), 7.76-7.70 (m, 2H), 7.50 (s, 1H), 4.69 (s, 2H), 4.27-4.16 (m, 4H), 3.85-3.76 (m, 4H), 3.72 (t, J=6.4 Hz, 2H), 3.65 (s, 4H), 3.64-3.58 (m, 32H), 3.44 (s, 2H), 2.60 (t, J=6.0 Hz, 2H), 2.53 (t, J=6.4 Hz, 2H), 1.86-1.74 (m, 2H), 1.01 (t, J=7.2 Hz, 3H). LC/MS [M+H] 1019.47 (calculated); LC/MS [M+H] 1019.5 (observed).

Preparation of HxBzL-82

To a solution of HxBzL-82g (80 mg, 70.6 umol, 1 eq, TFA) in DCM (3 mL) and DMA (0.5 mL) was added (2,3,5,6-tetrafluoro-4-hydroxy-phenyl)sulfonyloxysodium (75.7 mg, 282 umol, 4 eq) and EDCI (54.1 mg, 282 umol, 4 eq). The mixture was stirred at 15° C. for 0.5 h. The reaction mixture was concentrated under reduced pressure to remove DCM and filtered. The residue was purified by prep-HPLC (TFA condition: column: Phenomenex Luna 80*30 mm*3 um; mobile phase: [water (0.1% TFA)-ACN]; B %: 15%-40%, 8 min) to give HxBzL-82 (41.1 mg, 30.2 umol, 42.8% yield, TFA) as a light yellow solid. $^1$H NMR (MeOD, 400 MHz) δ9.09 (br s, 2H), 7.85-7.62 (m, 3H), 7.48 (br s, 1H), 4.68 (br s, 2H), 4.24-4.20 (m, 4H), 3.91-3.74 (m, 5H), 3.71-3.39 (m, 40H), 2.99-2.93 (m, 2H), 2.64-2.56 (m, 2H), 1.82-1.75 (m, 2H), 1.03-0.96 (m, 3H). LC/MS [M+H] 1247.4 (calculated); LC/MS [M+H] 1247.4 (observed).

Example L-85 Synthesis of 4-[3-[2-[2-[2-[2-[2-[2-[2-[2-[2-[3-[[5-[2-amino-4-[propyl-[2-(2,2,2-trifluoroethoxy)ethoxy]carbamoyl]-3H-1-benzazepin-8-yl]pyrimidin-2-yl]methylamino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-85

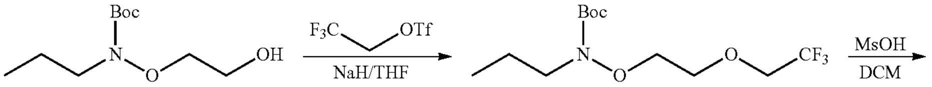

HxBzL-85a

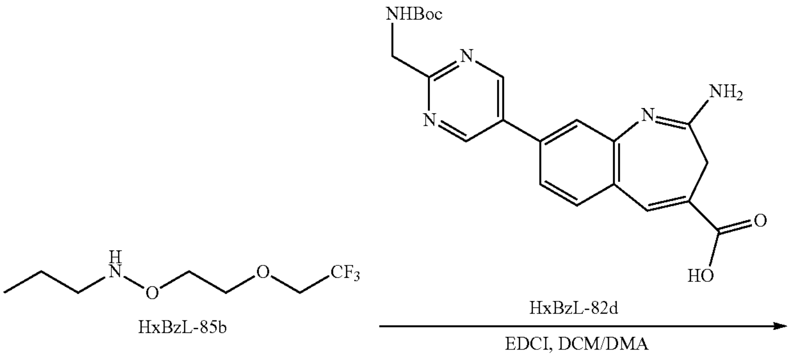

HxBzL-85b

HxBzL-82d

-continued
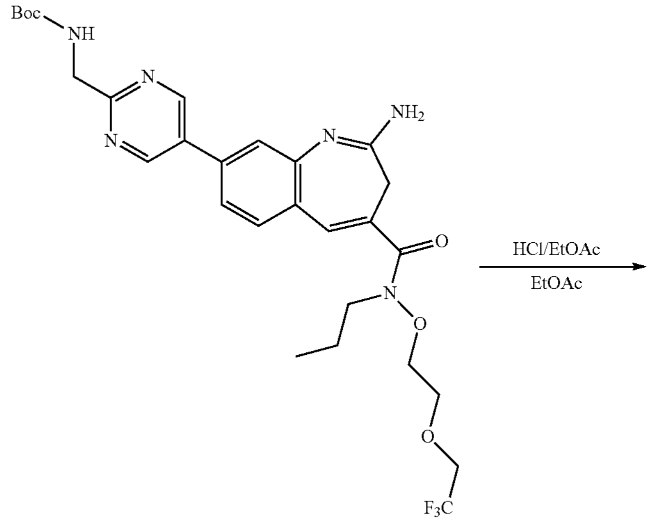
HxBzL-85c
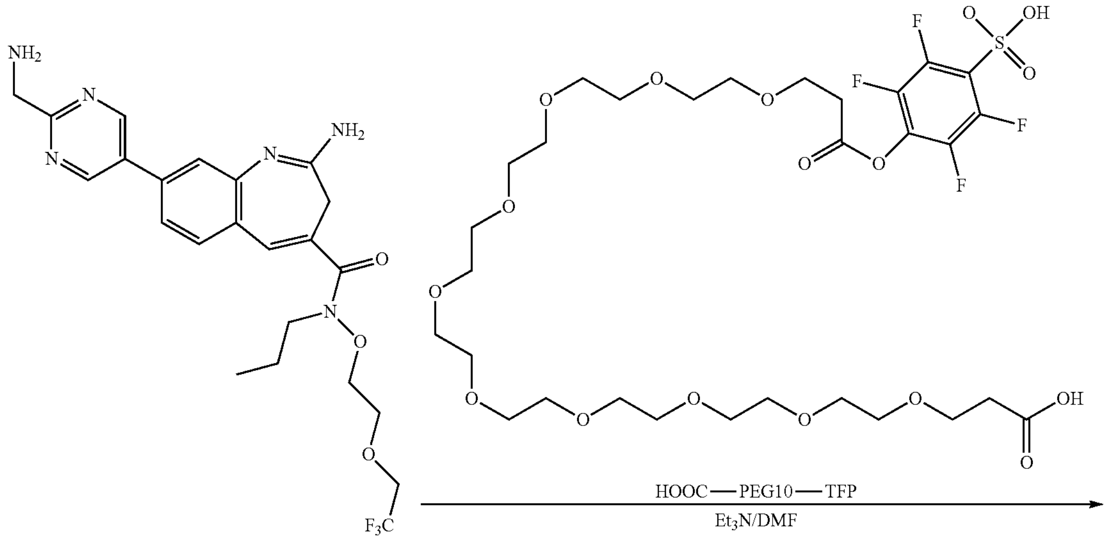
HxBzL-85d

-continued
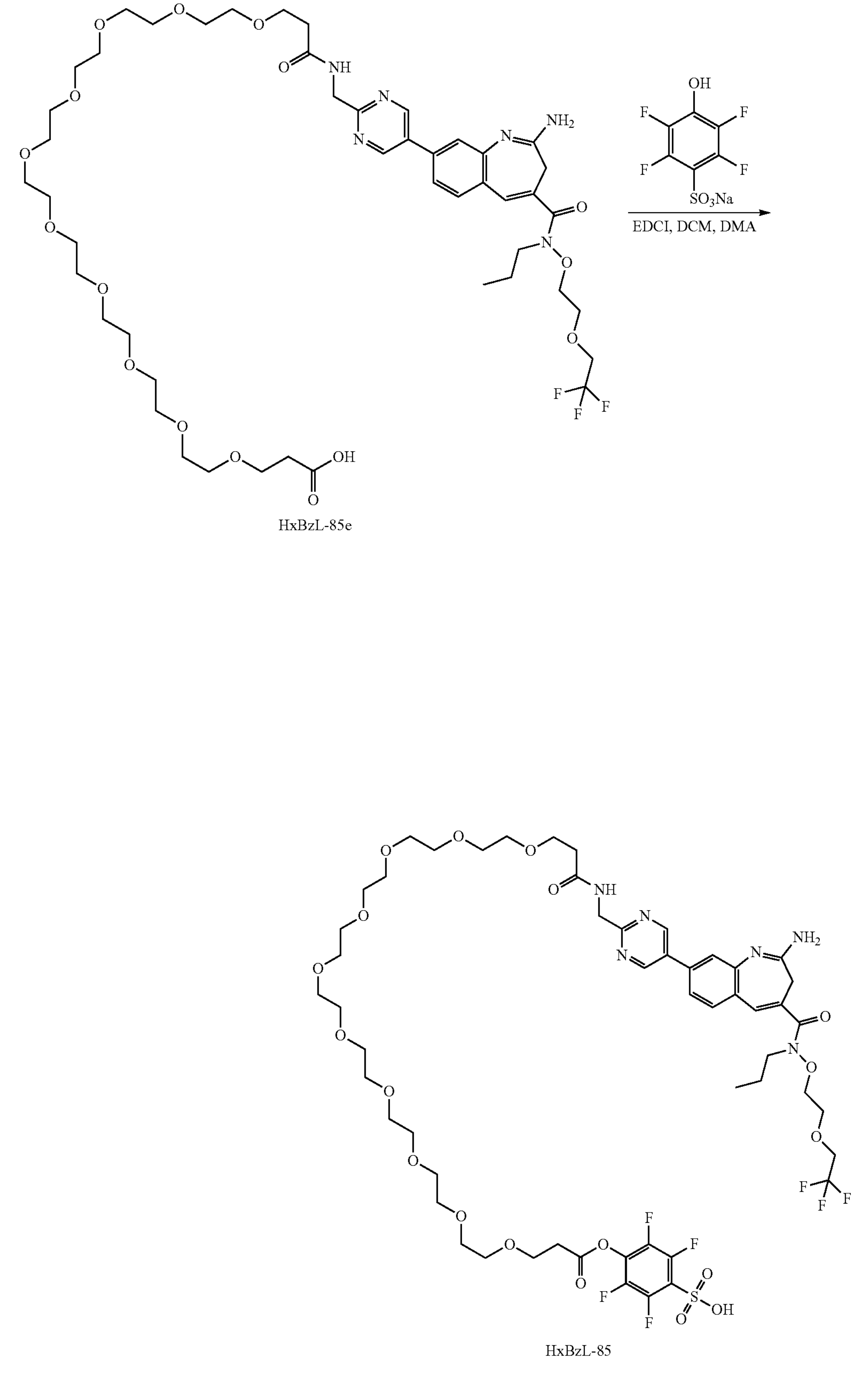
HxBzL-85e
HxBzL-85

Preparation of tert-butyl N-propyl-N-[2-(2,2,2-trifluoroethoxy)ethoxy]carbamate, HxBzL-85a To a solution of tert-butyl N-(2-hydroxyethoxy)-N-propyl-carbamate (750 mg, 3.42 mmol, 1 eq) in THE (20 mL) was added sodium hydride, NaH (205 mg, 5.13 mmol, 60% purity, 1.5 eq) at 0° C. After 30 min, 2,2,2-trifluoroethyl trifluoromethanesulfonate (1.19 g, 5.13 mmol, 1.5 eq) was added at 0° C. and the mixture was stirred at 15° C. for 1 h. The reaction mixture was quenched by addition of aq. $NH_4Cl$ (30 mL) at 0° C., and then extracted with EtOAc (20 mL×3). The combined organic layers were washed with brine (10 mL), dried over $Na_2SO_4$, filtered and concentrated under reduced pressure to give a residue. The residue was purified by column chromatography ($SiO_2$, Petroleum ether: MTBE=1:0 to 5:1) to give HxBzL-85a (0.4 g, 1.33 mmol, 38.8% yield) as a light yellow oil. $^1H$ NMR ($CDCl_3$, 400 MHz) δ4.07-4.01 (m, 2H), 3.92 (q, J=8.8 Hz, 2H), 3.86-3.79 (m, 2H), 3.46-3.37 (m, 2H), 1.70-1.62 (m, 2H), 1.50 (s, 9H), 0.92 (t, J=7.2 Hz, 3H)

Preparation of N-[2-(2,2,2-trifluoroethoxy)ethoxy]propan-1-amine, HxBzL-85b

To a solution of HxBzL-85a (150 mg, 498 umol, 1 eq) in DCM (5 mL) was added methanesulfonic acid, MsOH (144 mg, 1.49 mmol, 106 uL, 3 eq). The mixture was stirred at 15° C. for 0.5 h. The reaction mixture was concentrated under reduced pressure to give HxBzL-85b (0.15 g, crude, MsOH salt) as a light yellow oil. $^1H$ NMR (MeOD-$d_4$, 400 MHz) δ4.32-4.26 (m, 2H), 4.02 (q, J=8.8 Hz, 2H), 3.94-3.88 (m, 2H), 3.30-3.28 (m, 2H), 1.85-1.68 (m, 2H), 1.04 (t, J=7.2 Hz, 3H)

Preparation of tert-butyl N-[[5-[2-amino-4-[propyl-[2-(2,2,2-trifluoroethoxy) ethoxy]carbamoyl]-3H-1-benzazepin-8-yl]pyrimidin-2-yl]methyl]carbamate, HxBzL-85c To a solution of 2-amino-8-[2-[(tert-butoxycarbonylamino)methyl] pyrimidin-5-yl]-3H-1-benzazepine-4-carboxylic acid, HxBzL-82d (185 mg, 452 umol, 1 eq) and HxBzL-85b (175 mg, 587 umol, 1.3 eq, MsOH) in DMA (4 mL) and DCM (4 mL) was added EDCI (260 mg, 1.36 mmol, 3 eq) at 0° C. The mixture was stirred at 15° C. for 1 h. The reaction mixture was concentrated under reduced pressure to remove DCM. The residue was diluted with $H_2O$ (15 mL) and adjusted pH to ~9 with aq. $Na_2CO_3$ at 0° C. and extracted with EtOAc (10 mL×3). The combined organic layers were washed with brine (5 mL×3), dried over $Na_2SO_4$, filtered and concentrated under reduced pressure to give a residue. The residue was purified by prep-HPLC (TFA condition: column: Phenomenex Luna 80*30 mm*3 um; mobile phase: [water (0.1% TFA)-ACN]; B %: 15%-50%, 8 min) to give HxBzL-85c (150 mg, 212 umol, 47.0% yield, TFA) was obtained as a light yellow solid. $^1H$ NMR (MeOD-$d_4$, 400 MHz) δ9.07 (s, 2H), 7.81-7.76 (m, 1H), 7.75-7.69 (m, 2H), 7.50 (s, 1H), 4.53 (s, 2H), 4.15-4.06 (m, 2H), 3.88 (q, J=8.8 Hz, 2H), 3.82-3.74 (m, 4H), 3.45 (s, 2H), 1.84-1.74 (m, 2H), 1.48 (s, 9H), 1.00 (t, J=7.2 Hz, 3H). LC/MS [M+H] 593.3 (calculated); LC/MS [M+H] 593.3 (observed).

Preparation of 2-amino-8-[2-(aminomethyl)pyrimidin-5-yl]-N-propyl-N-[2-(2,2,2-trifluoroethoxy) ethoxy]-3H-1-benzazepine-4-carboxamide, HxBzL-85d To a solution of HxBzL-85c (130 mg, 184 umol, 1 eq, TFA) in EtOAc (1 mL) was added HCl/EtOAc (4 M, 13.0 mL, 283 eq). The mixture was stirred at 15° C. for 0.5 h. The reaction mixture was concentrated under reduced pressure to give HxBzL-85d (110 mg, crude, 2HCl) as a light yellow solid. $^1H$ NMR (MeOD-$d_4$, 400 MHz) δ9.21 (s, 2H), 7.85-7.78 (m, 2H), 7.77-7.72 (m, 1H), 7.50 (s, 1H), 4.48 (s, 2H), 4.15-4.08 (m, 2H), 3.89 (q, J=8.8 Hz, 2H), 3.82-3.74 (m, 4H), 3.46 (s, 2H), 1.84-1.74 (m, 2H), 1.01 (t, J=7.2 Hz, 3H). LC/MS [M+H] 493.2 (calculated); LC/MS [M+H] 493.2 (observed).

Preparation of 3-[2-[2-[2-[2-[2-[2-[2-[2-[2-[3-[[5-[2-amino-4-[propyl-[2-(2,2,2-trifluoroethoxy)ethoxy] carbamoyl]-3H-1-benzazepin-8-yl]pyrimidin-2-yl] methylamino]-3-oxo-propoxy]ethoxy]ethoxy] ethoxy]ethoxy]ethoxy]ethoxy]ethoxy]ethoxy] ethoxy]propanoic acid, HxBzL-85e To a solution of HxBzL-85d (65 mg, 115 umol, 1 eq, 2HCl) in DMF (2 mL) was added TEA (34.9 mg, 345 umol, 48.0 uL, 3 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid, HOOC-PEG10-TFP (106 mg, 149 umol, 1.3 eq) at 0° C., and then stirred at 15° C. for 0.5 h. The pH of the reaction mixture was adjusted to ~6 with TFA at 0° C. and filtered. The residue was purified by prep-HPLC (TFA condition: column: Phenomenex Luna 80*30 mm*3 um; mobile phase: [water (0.1% TFA)-ACN]; B %: 10%-40%, 8 min) to give HxBzL-85e (80 mg, 69.7 umol, 60.7% yield, TFA) was obtained as a light yellow oil. $^1H$ NMR (MeOD-$d_4$, 400 MHz) δ9.09 (s, 2H), 7.83-7.78 (m, 1H), 7.74 (d, J=8.8 Hz, 2H), 7.51 (s, 1H), 4.69 (s, 2H), 4.16-4.08 (m, 2H), 3.89 (q, J=8.8 Hz, 2H), 3.83-3.75 (m, 6H), 3.72 (t, J=6.0 Hz, 2H), 3.67-3.56 (m, 36H), 3.46 (s, 2H), 2.60 (t, J=6.0 Hz, 2H), 2.53 (t, J=6.0 Hz, 2H), 1.84-1.74 (m, 2H), 1.00 (t, J=7.2 Hz, 3H). LC/MS [M+H] 1033.5 (calculated); LC/MS [M+H] 1033.6 (observed).

Preparation of HxBzL-85

To a solution of HxBzL-85e (75 mg, 65.4 umol, 1 eq, TFA) in DMA (0.5 mL) and DCM (3 mL) was added (2,3,5,6-tetrafluoro-4-hydroxy-phenyl)sulfonyloxysodium (70.1 mg, 262 umol, 4 eq) and EDCI (62.7 mg, 327 umol, 5 eq) and then stirred at 15° C. for 0.5 h. The reaction mixture was concentrated under reduced pressure to remove DCM, filtered and concentrated under reduced pressure. The residue was purified by prep-HPLC (TFA condition: column: Phenomenex Luna 80*30 mm*3 um; mobile phase: [water (0.1% TFA)-ACN]; B %: 15%-40%, 8 min) to give HxBzL-85 (79.8 mg, 58.0 umol, 88.7% yield, TFA) as a light yellow oil. $^1H$ NMR (MeOD-$d_4$, 400 MHz) δ9.09 (s, 2H), 7.82-7.68 (m, 3H), 7.49 (s, 1H), 4.69 (s, 2H), 4.14-4.08 (m, 2H), 3.94-3.84 (m, 4H), 3.83-3.74 (m, 6H), 3.69-3.55 (m, 36H), 3.46 (s, 2H), 2.97 (t, J=6.0 Hz, 2H), 2.60 (t, J=6.0 Hz, 2H), 1.85-1.73 (m, 2H), 1.00 (t, J=7.2 Hz, 3H). LC/MS [M+H] 1261.4 (calculated); LC/MS [M+H] 1261.6 (observed).

Synthesis of 4-[3-[2-[2-[2-[2-[2-[2-[2-[2-[2-[2-[3-[[(1S)-2-[(2S)-2-[[(1S)-1-[[4-[[5-[2-amino-4-[ethoxy(propyl)carbamoyl]-3H-1-benzazepin-8-yl]pyrimidin-2-yl]methylcarbamoyloxymethyl]phenyl]carbamoyl]-2-methyl-propyl]carbamoyl]pyrrolidin-1-yl]-1-methyl-2-oxo-ethyl]amino]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-91
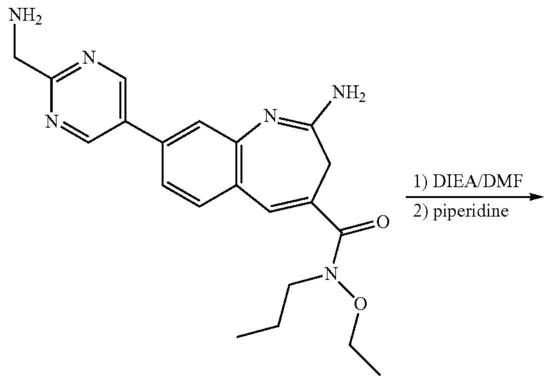
HxBz-5
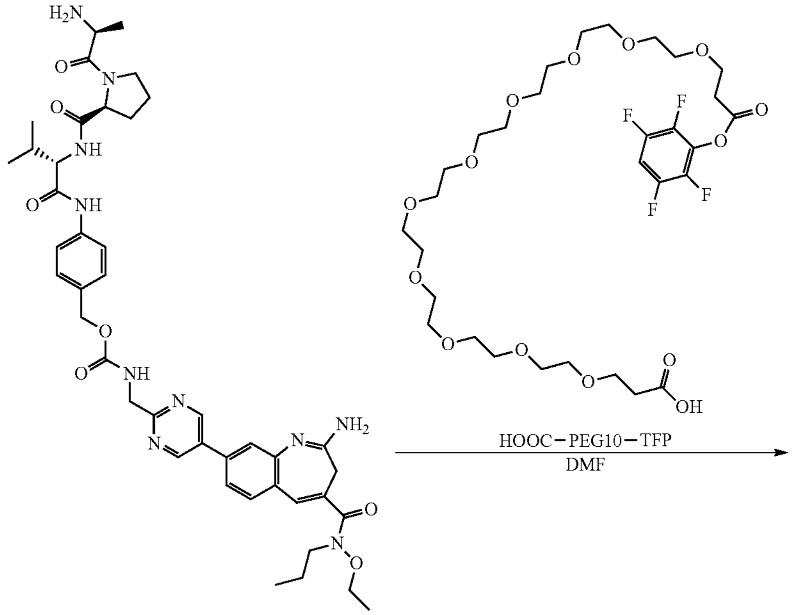
HxBzL-91a -continued

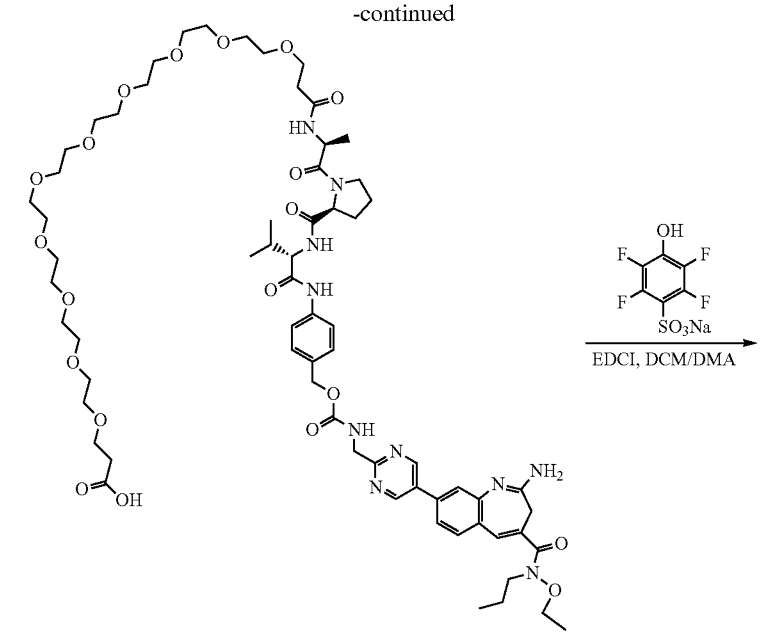

HxBzL-91b

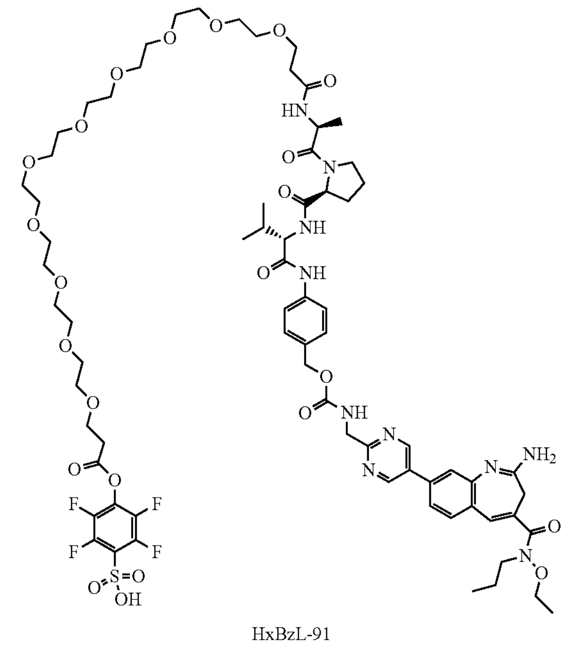

HxBzL-91

Preparation of [4-[[(2S)-2-[[(2S)-1-[(2S)-2-(9H-fluoren-9-ylmethoxycarbonylamino) propanoyl]pyrrolidine-2-carbonyl]amino]-3-methyl-butanoyl] amino]phenyl]methylN-[[5-[2-amino-4-[ethoxy (propyl)carbamoyl]-3H-1-benzazepin-8-yl] pyrimidin-2-yl]methyl]carbamate, HxBzL-91a To a solution of 2-amino-8-[2-(aminomethyl)pyrimidin-5-yl]-N-ethoxy-N-propyl-3H-1-benzazepine-4-carboxamide, HxBz-5 (0.15 g, 348.08 umol, 1 eq, HCl) and [4-[[(2S)-2-[[(2S)-1-[(2S)-2-(9H-fluoren-9-ylmethoxycarbonylamino)propanoyl]pyrrolidine-2-carbonyl]amino]-3-methyl-butanoyl]amino]phenyl]methyl (4-nitrophenyl) carbonate (270.75 mg, 348.08 umol, 1 eq) in DMF (5 mL) was added $Et_3N$ (106 mg, 1.04 mmol, 145 uL, 3 eq). The mixture was stirred at 20° C. for 2 hr. Then piperidine (74.2 mg, 871 umol, 86.0 uL, 3 eq) in DMF (1 mL) was added. The mixture was stirred at 20° C. for another 1 hr. The reaction mixture was filtered. The residue was purified by prep-HPLC (column: Phenomenex Luna 80*30 mm*3 um; mobile phase: [water (0.1% TFA)-ACN]; B %: 15%-45%, 8 min) to give HxBzL-91a (0.12 g, 148 umol, 50.96% yield) as a white solid. LC/MS [M+H] 811.4 (calculated); LC/MS [M+H] 811.6 (observed).

Preparation of 3-[2-[2-[2-[2-[2-[2-[2-[2-[2-[3-[[(1 S)-2-[(2S)-2-[[(1S)-1-[[4-[[5-[2-amino-4-[ethoxy (propyl)carbamoyl]-3H-1-benzazepin-8-yl]pyrimidin-2-yl]methylcarbamoyloxymethyl]phenyl]carbamoyl]-2-methyl-propyl]carbamoyl]pyrrolidin-1-yl]-1-methyl-2-oxo-ethyl]amino]-3-oxo-propoxy] ethoxy]ethoxy]ethoxy]ethoxy]ethoxy]ethoxy] ethoxy]ethoxy]ethoxy]propanoic acid, HxBzL-91b To a solution of HxBzL-91a (0.12 g, 148 umol, 1 eq) in DMF (5 mL) was added $Et_3N$ (44.9 mg, 444 umol, 61.8 uL, 3 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy] ethoxy]ethoxy]ethoxy]ethoxy]ethoxy]propanoic acid, HOOC-PEG10-TFP (105 mg, 148 umol, 1 eq), and then stirred at 20° C. for 1 hr. The reaction mixture was filtered and purified by prep-HPLC (column: Phenomenex Luna 80*30 mm*3 um; mobile phase: [water (0.1% TFA)-ACN]; B %: 20%-50%, 8 min) to give HxBzL-91b (0.15 g, 111 umol, 75.00% yield) as a white solid. LC/MS [M+H] 1351.7 (calculated); LC/MS [M+H] 1351.8 (observed).

Preparation of HxBzL-91

To a solution of HxBzL-91b (0.15 g, 111 umol, 1 eq) and (2,3,5,6-tetrafluoro-4-hydroxy-phenyl)sulfonyloxy sodium (89.3 mg, 333 umol, 3 eq) in DCM (5 mL) and DMA (1 mL) was added EDCI (63.8 mg, 333 umol, 3 eq). The mixture was stirred at 20° C. for 2 hr. The reaction mixture was filtered and purified by prep-HPLC (column: Phenomenex Luna 80*30 mm*3 um; mobile phase: [water (0.1% TFA)-ACN]; B %: 20%-45%, 8 min) to give HxBzL-91 (0.11 g, 69.6 umol, 62.74% yield) as a yellow solid. $^1H$ NMR (MeOH, 400 MHz) δ 9.06 (s, 2H), 7.83-7.69 (m, 3H), 7.59 (d, J=8.4 Hz, 1H), 7.45 (s, 1H), 7.36 (d, J=8.4 Hz, 1H), 5.09 (s, 2H), 4.66-4.57 (m, 4H), 4.35-4.18 (m, 1H), 3.98 (q, J=6.8 Hz, 2H), 3.85 (br t, J=6.0 Hz, 2H), 3.81-3.68 (m, 5H), 3.67-3.54 (m, 37H), 3.45 (s, 2H), 2.96 (t, J=5.6 Hz, 2H), 2.56-2.44 (m, 2H), 2.22-2.15 (m, 2H), 2.05-2.00 (m, 2H), 1.87-1.71 (m, 2H), 1.44-1.28 (m, 3H), 1.21 (br t, J=7.2 Hz, 3H), 1.09-0.85 (m, 9H). LC/MS [M+H] 1579.65 (calculated); LC/MS [M+H] 1579.6 (observed).

Example L-96 Synthesis of 2-amino-8-(2-((1-(2,5-dioxo-2,5-dihydro-1H-pyrrol-1-yl)-2-oxo-6,9,12,15,18,21,24,27,30-nonaoxa-3-azadotriacontan-32-yl)carbamoyl)pyrimidin-5-yl)-N-ethoxy-N-propyl-3H-benzo[b]azepine-4-carboxamide, HxBzL-96

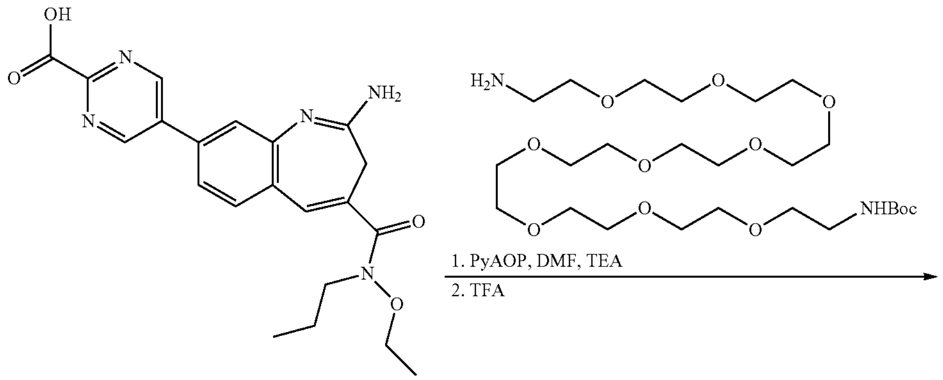

HxBzL-96a

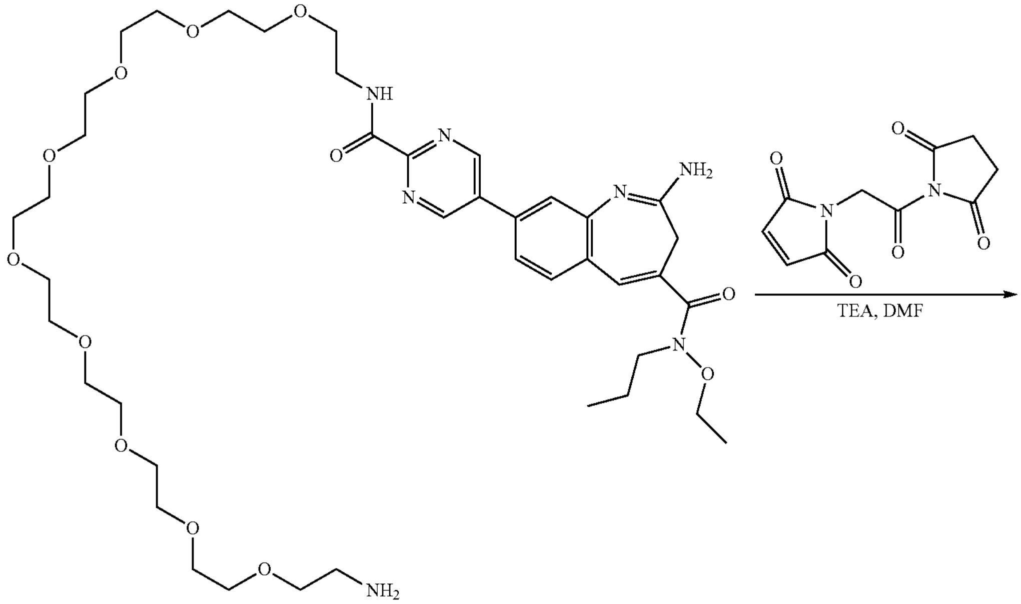

HxBzL-96b

-continued

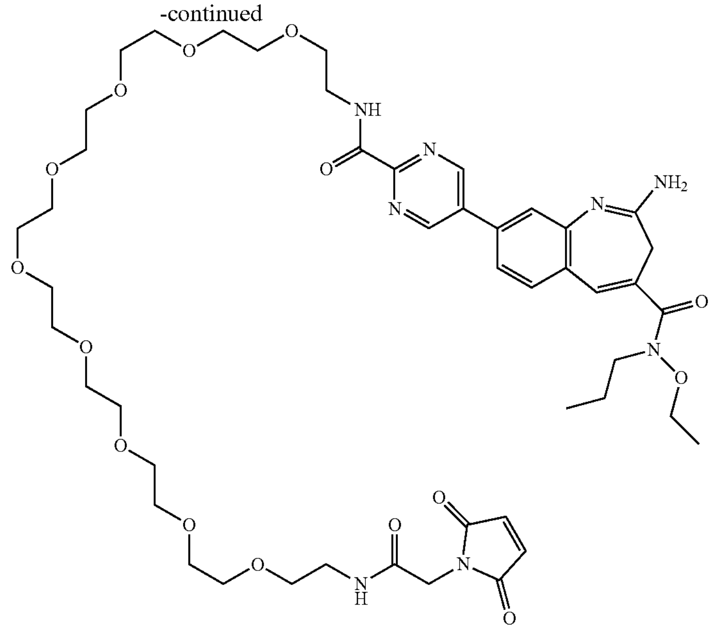

HxBzL-96

Preparation of 2-amino-8-(2-((29-amino-3,6,9,12,15,18,21,24,27-nonaoxanonacosyl)carbamoyl)pyrimidin-5-yl)-N-ethoxy-N-propyl-3H-benzo[b]azepine-4-carboxamide, HxBzL-96b To a solution of 5-(2-amino-4-(ethoxy(propyl)carbamoyl)-3H-benzo[b]azepin-8-yl)pyrimidine-2-carboxylic acid, HxBzL-96a (0.0106 g, 0.026 mmol, 1 eq) and tert-butyl (29-amino-3,6,9,12,15,18,21,24,27-nonaoxanonacosyl)carbamate (0.014 g, 0.026 mmol, 1 eq) in DMF (0.5 ml) was added triethylamine, TEA (36 μl, 0.26 mmol, 10 eq), followed by (7-Azabenzotriazol-1-yloxy)tripyrrolidinophosphonium hexafluorophosphate, PyAOP, CAS Reg. No. 156311-83-0 (0.013 g, 0.026 mmol, 1 eq). The reaction was stirred at room temperature and monitored by LC/MS. The reaction was concentrated and purified by prep-HPLC to give tert-butyl (1-(5-(2-amino-4-(ethoxy(propyl)carbamoyl)-3H-benzo[b]azepin-8-yl)pyrimidin-2-yl)-1-oxo-5,8,11,14,17,20,23,26,29-nonaoxa-2-azahentriacontan-31-yl)carbamate, which was then dissolved in TFA and concentrated to give HxBzL-96b (17.1 mg, 0.020 mmol, 77%). LC/MS [M+H] 848.5 (calculated); LC/MS [M+H] 848.8 (observed).

Preparation of HxBzL-96

To a solution of HxBzL-96b (17.1 mg, 0.020 mmol, 1.33 eq) in DMF (0.5 ml) was added TEA (28 μl, 0.20 mmol, 13.3 eq) followed by N-(α-maleimidoacetoxy) succinimide ester (3.8 mg, 0.015 mmol, 1 eq). The reaction was stirred at room temperature and monitored by LC/MS, then concentrated and purified by prep-HPLC to give HxBzL-96 (8.5 mg, 0.0086 mmol, 57%). LC/MS [M+H] 985.5 (calculated); LC/MS [M+H] 985.6 (observed).

Example L-104 Synthesis of 1-(2,5-dioxo-2,5-dihydro-1H-pyrrol-1-yl)-2-oxo-6,9,12,15,18,21,24,27,30,33-decaoxa-3-azapentatriacontan-35-yl (2-((2-amino-N-propyl-8-(pyrimidin-5-yl)-3H-benzo[b]azepine-4-carboxamido)oxy)ethyl)carbamate, HxBzL-104

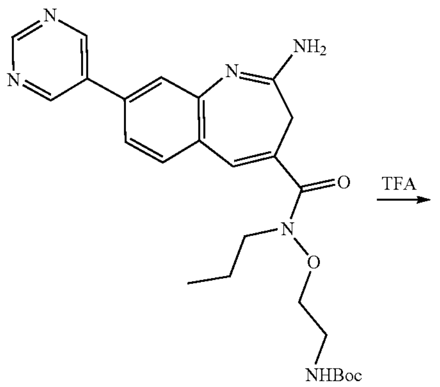

HxBzL-104a

-continued
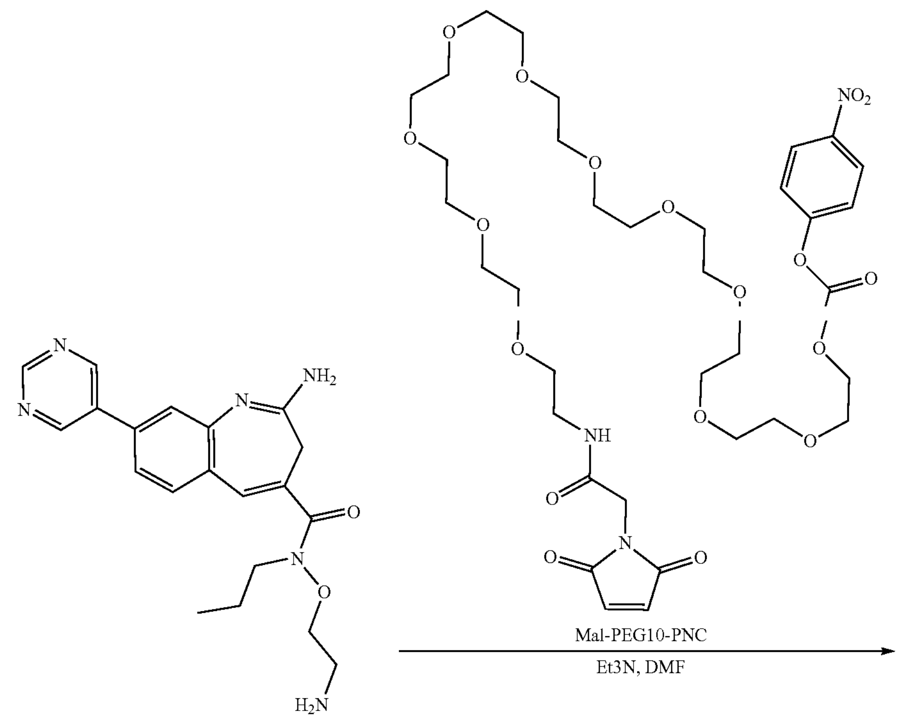
HxBzL-104b
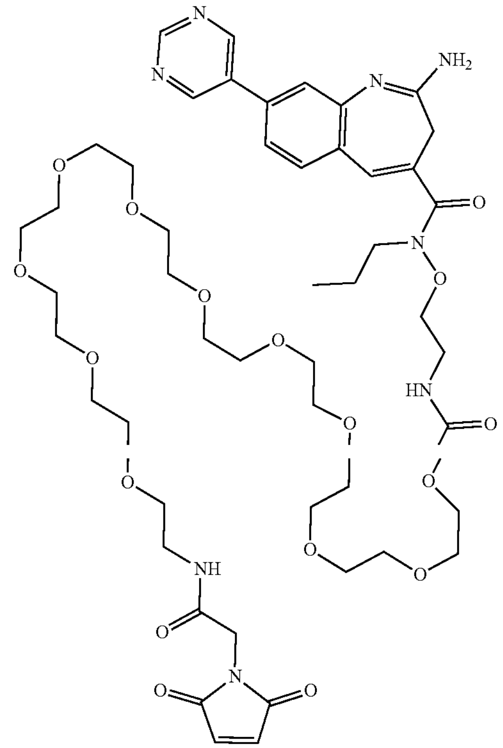
HxBzL-104

Preparation of 2-amino-N-(2-aminoethoxy)-N-propyl-8-(pyrimidin-5-yl)-3H-benzo[b]azepine-4-carboxamide, HxBzL-104b tert-Butyl (2-((2-amino-N-propyl-8-(pyrimidin-5-yl)-3H-benzo[b]azepine-4-carboxamido)oxy)ethyl)carbamate, HxBzL-104a (5.1 mg, 0.011 mmol, 1 eq) was suspended in 100 μl TFA. After 30 minutes, the solution was concentrated to give HxBzL-104b as a TFA salt (7.4 mg, 0.012 mmol, 100%). LC/MS [M+H] 381.2 (calculated); LC/MS [M+H] 381.3 (observed).

Preparation of HxBzL-104

To a solution of HxBzL-104b (7.4 mg, 0.012 mmol, 1 eq) in DMF (0.5 ml) was added triethylamine (13.5 μl, 0.097 mmol, 8 eq) and 1-(2,5-dioxo-2,5-dihydro-1H-pyrrol-1-yl)-2-oxo-6,9,12,15,18,21,24,27,30,33-decaoxa-3-azapentatriacontan-35-yl (4-nitrophenyl) carbonate, Mal-PEG10-PNC (15.6 mg, 0.019 mmol, 1.6 eq). The solution was stirred at room temperature and monitored by LC/MS. Upon consumption of amine starting material, the reaction was concentrated and purified by prep-HPLC to obtain HxBzL-104. LC/MS [M+H] 1045.5 (calculated); LC/MS [M+H] 1045.8 (observed).

Example L-107 Synthesis of 1-(2,5-dioxo-2,5-dihydro-1H-pyrrol-1-yl)-2-oxo-6,9,12,15,18,21,24,27,30,33-decaoxa-3-azapentatriacontan-35-yl (2-((2-amino-8-(4-methylpyridin-3-yl)-N-propyl-3H-benzo[b]azepine-4-carboxamido)oxy)ethyl)carbamate, HxBzL-107

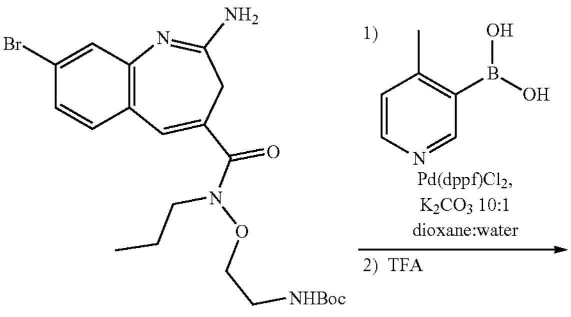

HxBzL-107a

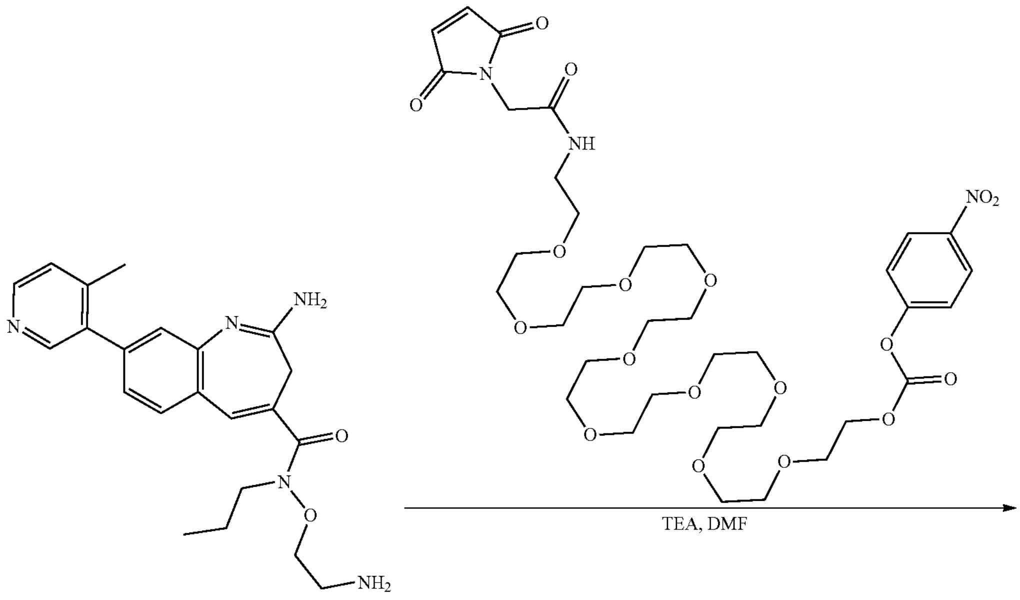

HxBzL-107b

-continued

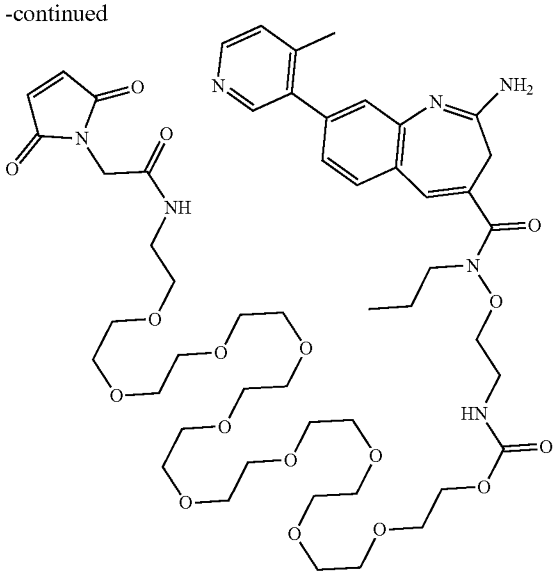

HxBzL-107

Preparation of 2-amino-N-(2-aminoethoxy)-8-(4-methylpyridin-3-yl)-N-propyl-3H-benzo[b]azepine-4-carboxamide, HxBzL-107b A suspension of tert-butyl (2-((2-amino-8-bromo-N-propyl-3H-benzo[b]azepine-4-carboxamido)oxy)ethyl)carbamate, HxBzL-107a (30 mg, 0.062 mmol, 1 eq), (4-methylpyridin-3-yl)boronic acid (17 mg, 0.125 mmol, 2 eq), potassium carbonate (54 mg, 0.39 mmol, 6.3 eq), and [1,1'-Bis(diphenylphosphino)ferrocene]dichloropalladium(II) (2.3 mg, 0.0032 mmol, 0.05 eq) in 10:1 dioxane:water was stirred at 80° C. and monitored by LC/MS. The reaction mixture was concentrated and purified by reverse-phase column chromatography to give tert-butyl (2-((2-amino-8-(4-methylpyridin-3-yl)-N-propyl-3H-benzo[b]azepine-4-carboxamido)oxy)ethyl)carbamate, which was dissolved in minimal TFA and then concentrated to give HxBzL-107b (12.4 mg, 0.032 mmol, 52%). LC/MS [M+2H] 197.6 (calculated); LC/MS [M+2H] 197.9 (observed).

Preparation of HxBzL-107

To a solution of HxBzL-107b (12.4 mg, 0.32 mmol, 1 eq) and 1-(2,5-dioxo-2,5-dihydro-1H-pyrrol-1-yl)-2-oxo-6,9,12,15,18,21,24,27,30,33-decaoxa-3-azapentatriacontan-35-yl (4-nitrophenyl) carbonate (25.3 mg, 0.32 mmol, 1 eq) in DMF (0.5 ml) was added TEA (22 μl, 0.16 mmol, 5 eq). The reaction was stirred at room temperature and monitored by LC/MS, then concentrated and purified by prep-HPLC to give HxBzL-107 (6.1 mg, 0.0058 mmol, 18%). LC/MS [M+H] 1058.5 (calculated); LC/MS [M+H] 1058.7 (observed).

Example L-114 Synthesis of 4-[3-[2-[2-[2-[2-[2-[2-[2-[2-[2-[2-[[1-[2-amino-4-[ethoxy (propyl)carbamoyl]-3H-1-benzazepin-8-yl]pyrazol-4-yl]sulfonylamino]ethoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, HxBzL-114

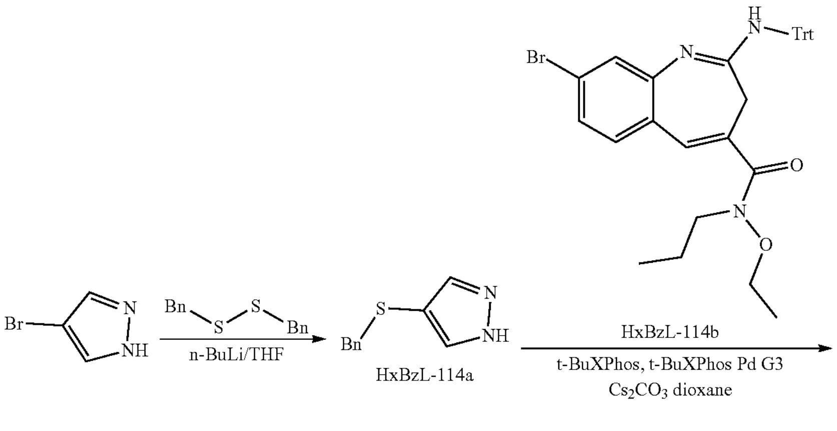

-continued
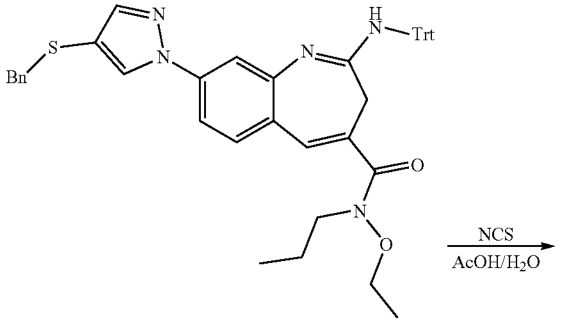
HxBzL-114c
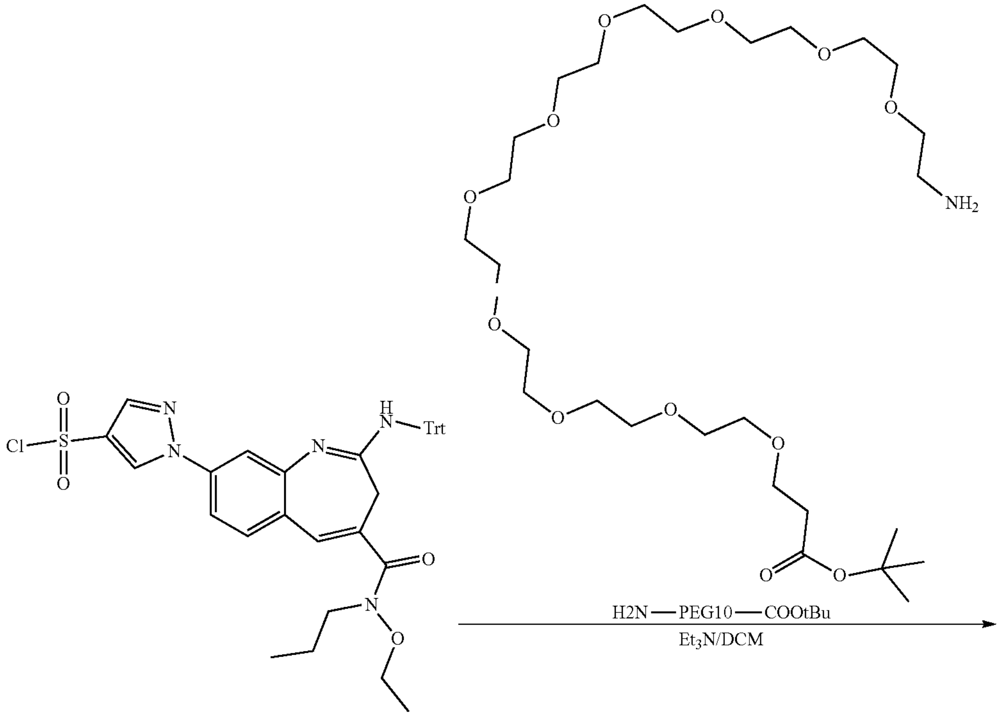
HxBzL-114d
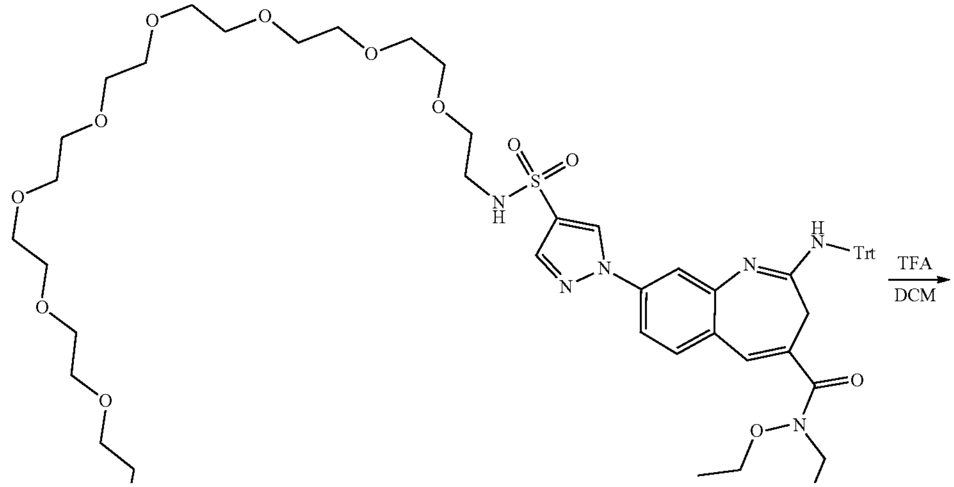

-continued
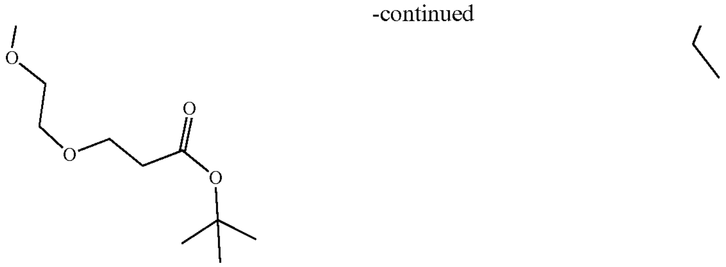
HxBzL-114e
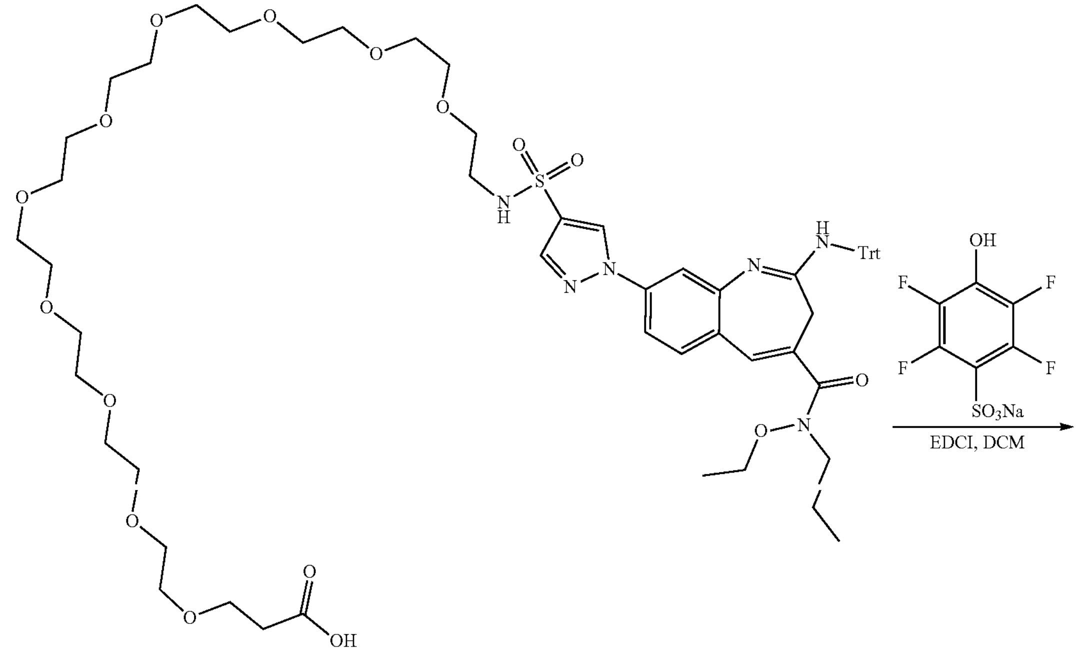
HxBzL-114f
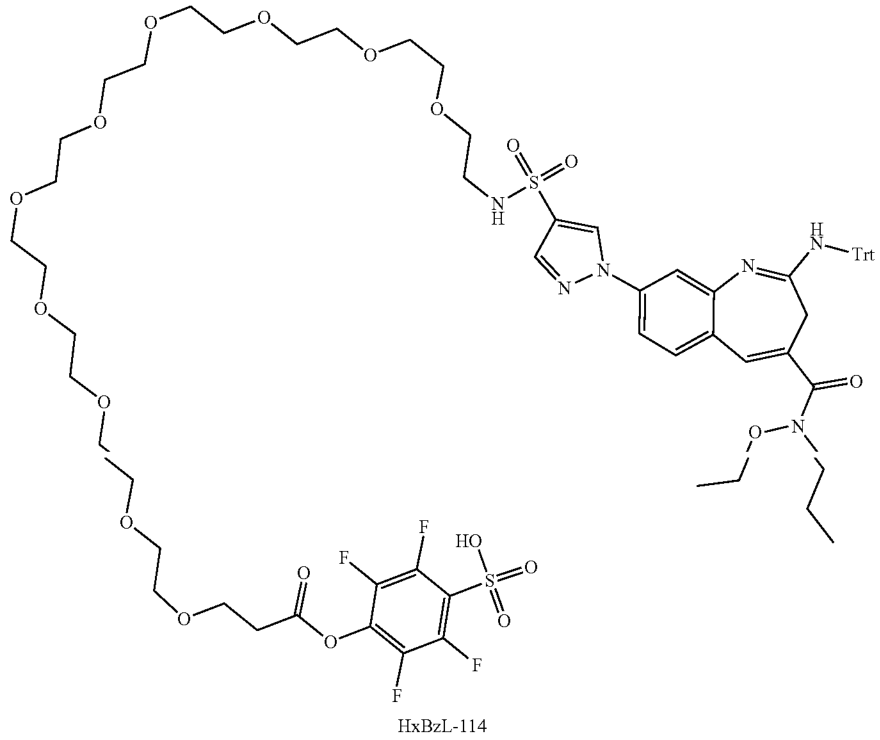
HxBzL-114

Preparation of 4-benzylsulfanyl-1H-pyrazole, HxBzL-114a

To a solution of 4-bromo-1H-pyrazole (2.00 g, 13.6 mmol, 1.0 eq) in THE (20 mL) was added n-BuLi (2.50 M, 17.9 mL, 3.3 eq) dropwise at 0° C. After the mixture was stirred at 20° C. for 1 h, (benzyldisulfanyl)methylbenzene (3.35 g, 13.6 mmol, 1.0 eq) was added and the mixture was stirred at 0° C. for another 2 hours. The reaction was quenched by ice/$H_2O$ (10 mL) slowly and adjusted pH to about 6 with 2N HCl. Then the mixture was extracted with EtOAc (20 mL*3). The combined organic phase was washed with brine (50 mL), dried over anhydrous $Na_2SO_4$, filtered and concentrated in vacuum. The residue was purified by flash silica gel chromatography (ISCO®; 40 g SepaFlash Silica Flash Column, El gradient of 0 to 30% Ethyl acetate/Petroleum ether gradient 50 mL/min) to afford HxBzL-114a (1.70 g, 8.93 mmol, 65.6% yield) as yellow solid. $^1H$ NMR ($CDCl_3$, 400 MHz) δ7.31 (s, 2H), 7.21-7.17 (m, 3H), 7.07-7.06 (m, 2H), 3.73 (s, 2H)

Preparation of 8-(4-benzylsulfanylpyrazol-1-yl)-N-ethoxy-N-propyl-2-(tritylamino)-3H-1-benzazepine-4-carboxamide, HxBzL-114c To a mixture of 8-bromo-N-ethoxy-N-propyl-2-(tritylamino)-3H-1-benzazepine-4-carboxamide, HxBzL-114b (300 mg, 492 umol, 1.0 eq) and HxBzL-114a (187 mg, 985 umol, 2.0 eq) in dioxane (6 mL) was added $Cs_2CO_3$ (321 mg, 985 umol, 2.0 eq), [(2-Di-tert-butylphosphino-2',4',6'-triisopropyl-1,1'-biphenyl)-2-(2'-amino-1,1'-biphenyl)] palladium(II) methanesulfonate, tBuXPhos Pd G3, CAS Reg. No. 1447963-75-8 (117 mg, 147 umol, 0.3 eq) and di-tert-butyl-[2-(2,4,6-triisopropylphenyl)phenyl]phosphane, tBuXPhos, CAS Reg. No. 564483-19-8 (62.8 mg, 147 umol, 0.3 eq) in one portion at 20° C. under $N_2$, and then stirred at 120° C. for 15 hours. The mixture was poured into water (10 mL). The aqueous phase was extracted with ethyl acetate (5 mL*3). The combined organic phase was washed with brine (10 mL), dried with anhydrous $Na_2SO_4$, filtered and concentrated in vacuum. The residue was purified by flash silica gel chromatography (ISCO®; 20 g SepaFlash Silica Flash Column, Eluent of 0~50% Ethyl acetate/Petroleum ether gradient 40 mL/min) to afford HxBzL-114c (0.300 g, 417 umol, 84.7% yield) as yellow solid. LC/MS [M+H] 718.3 (calculated); LC/MS [M+H] 718.4 (observed).

Preparation of 1-[4-[ethoxy(propyl)carbamoyl]-2-(tritylamino)-3H-1-benzazepin-8-yl]pyrazole-4-sulfonyl chloride, HxBzL-114d To a mixture of HxBzL-114c (300 mg, 417 umol, 1.0 eq) in $H_2O$ (0.7 mL), AcOH (2 mL) was added N-chlorosuccinimide, NCS (223 mg, 1.67 mmol, 4.0 eq) at 20° C., and then stirred at 20° C. for 1 hour. The mixture was poured into ice-water (w/w=1/1) (10 mL) and adjusted pH to about 7 with $NaHCO_3$·aq. The aqueous phase was extracted with ethyl acetate (10 mL*3). The combined organic phase was washed with brine (15 mL), dried with anhydrous $Na_2SO_4$, filtered and concentrated in vacuum to give HxBzL-114d (0.300 g, crude) as yellow oil. LC/MS [M+H] 694.2 (calculated); LC/MS [M+H] 694.2 (observed).

Preparation of tert-butyl 3-[2-[2-[2-[2-[2-[2-[2-[2-[2-[2-[[1-[4-[ethoxy (propyl)carbamoyl]-2-(tritylamino)-3H-1-benzazepin-8-yl]pyrazol-4-yl]sulfonylamino]ethoxy]ethoxy]ethoxy]ethoxy]ethoxy]ethoxy]ethoxy]ethoxy]ethoxy]ethoxy]propanoate, HxBzL-114e To a mixture of HxBzL-114d (0.30 g, 432 umol, 1.0 eq) and tert-butyl 3-[2-[2-[2-[2-[2-[2-[2-[2-[2-(2-aminoethoxy) ethoxy]ethoxy]ethoxy]ethoxy]ethoxy]ethoxy]ethoxy] ethoxy]ethoxy]propanoate, H2N-PEG10-COOtBu (253 mg, 432 umol, 1.0 eq) in DCM (5 mL) was added $Et_3N$ (65.5 mg, 648 umol, 90.2 uL, 1.5 eq) at 0° C., and then stirred at 20° C. for 1 hour. The mixture was poured into ice-water (w/w=1/1) (10 mL). The aqueous phase was extracted with DCM (5 mL*3). The combined organic phase was washed with brine (15 mL), dried with anhydrous $Na_2SO_4$, filtered and concentrated in vacuum to give HxBzL-114e (570 mg, crude) as yellow oil. LC/MS [M+H]1243.6 (calculated); LC/MS [M+H] 1243.6 (observed).

Preparation of 3-[2-[2-[2-[2-[2-[2-[2-[2-[2-[2-[[1-[2-amino-4-[ethoxy(propyl) carbamoyl]-3H-1-benzazepin-8-yl]pyrazol-4-yl]sulfonylamino]ethoxy]ethoxy]ethoxy]ethoxy]ethoxy]ethoxy]ethoxy]ethoxy]ethoxy]ethoxy]propanoic acid, HxBzL-114f To a mixture of HxBzL-114e (280 mg, 225 umol, 1.0 eq) in DCM (3 mL) was added TFA (770 mg, 6.76 mmol, 500 uL, 30 eq) at 20° C., and then stirred at 50° C. for 15 hours. The mixture was concentrated in vacuum to give a residue. The residue was purified by prep-HPLC (column: Phenomenex Luna 80*30 mm*3 um; mobile phase: [water (0.1% TFA)-ACN]; B %: 10%-35%, 8 min) to afford HxBzL-114f (50.0 mg, 52.9 umol, 23.5% yield) as white solid. $^1H$ NMR (MeOD, 400 MHz) δ8.90 (s, 1H), 8.07 (s, 1H), 7.97 (d, J=2.0 Hz, 1H), 7.93 (dd, J=2.0, 8.8 Hz, 1H), 7.73 (d, J=8.8 Hz, 1H), 7.45 (s, 1H), 3.98 (q, J=7.2 Hz, 2H), 3.80-3.67 (m, 4H), 3.65-3.51 (m, 38H), 3.43 (s, 2H), 3.19 (t, J=5.2 Hz, 2H), 2.53 (t, J=6.4 Hz, 2H), 1.84-1.72 (m, 2H), 1.21 (t, J=7.2 Hz, 3H), 1.00 (t, J=7.2 Hz, 3H). LC/MS [M+H] 945.4 (calculated); LC/MS [M+H] 945.5 (observed).

Preparation of HxBzL-114

To a mixture of HxBzL-114f (50.0 mg, 52.9 umol, 1.0 eq) in DCM (2 mL) and DMA (0.4 mL) was added sodium 2,3,5,6-tetrafluoro-4-hydroxy-benzenesulfonate (56.7 mg, 211 umol, 4.0 eq) and EDCI (50.7 mg, 264 umol, 5.0 eq) in one portion at 25° C., and then stirred at 25° C. for 0.5 h. The mixture was concentrated in reduced pressure to give a residue. The residue was purified by prep-HPLC (column: Phenomenex Luna 80*30 mm*3 um; mobile phase: [water (0.10% TFA)-ACN]; B %: 15%-50%, 8 min) to afford HxBzL-114 (27.8 mg, 23.7 umol, 44.7% yield) as white solid. $^1H$ NMR (MeOD, 400 MHz) δ8.89 (s, 1H), 8.05 (s, 1H), 7.96 (d, J=2.0 Hz, 1H), 7.92 (dd, J=2.0, 8.4 Hz, 1H), 7.71 (d, J=8.4 Hz, 1H), 7.44 (s, 1H), 3.97 (q, J=7.2 Hz, 2H), 3.85 (t, J=5.6 Hz, 2H), 3.75 (t, J=7.2 Hz, 2H), 3.68-3.50 (m, 38H), 3.45 (s, 2H), 3.19 (t, J=5.6 Hz, 2H), 2.96 (t, J=6.0 Hz, 2H), 1.77 (t, J=7.2 Hz, 2H), 1.20 (t, J=7.2 Hz, 3H), 1.00 (t, J=7.2 Hz, 3H). LC/MS [M+H] 1173.4 (calculated); LC/MS [M+H] 1173.5 (observed).

Example L-115 Synthesis of 4-[3-[2-[2-[2-[2-[2-[2-[2-[2-[2-[3-[4-[2-amino-4-[ethoxy(propyl) carbamoyl]-3H-1-benzazepin-8-yl]-4-methyl-3,5-dioxo-1-piperidyl]-3-oxo-propoxy]ethoxy] ethoxy]ethoxy] ethoxy]ethoxy]ethoxy]ethoxy]ethoxy]ethoxy] propanoyloxy]-2,3,5,6-tetrafluoro-benzenesulfonic acid, HxBzL-115
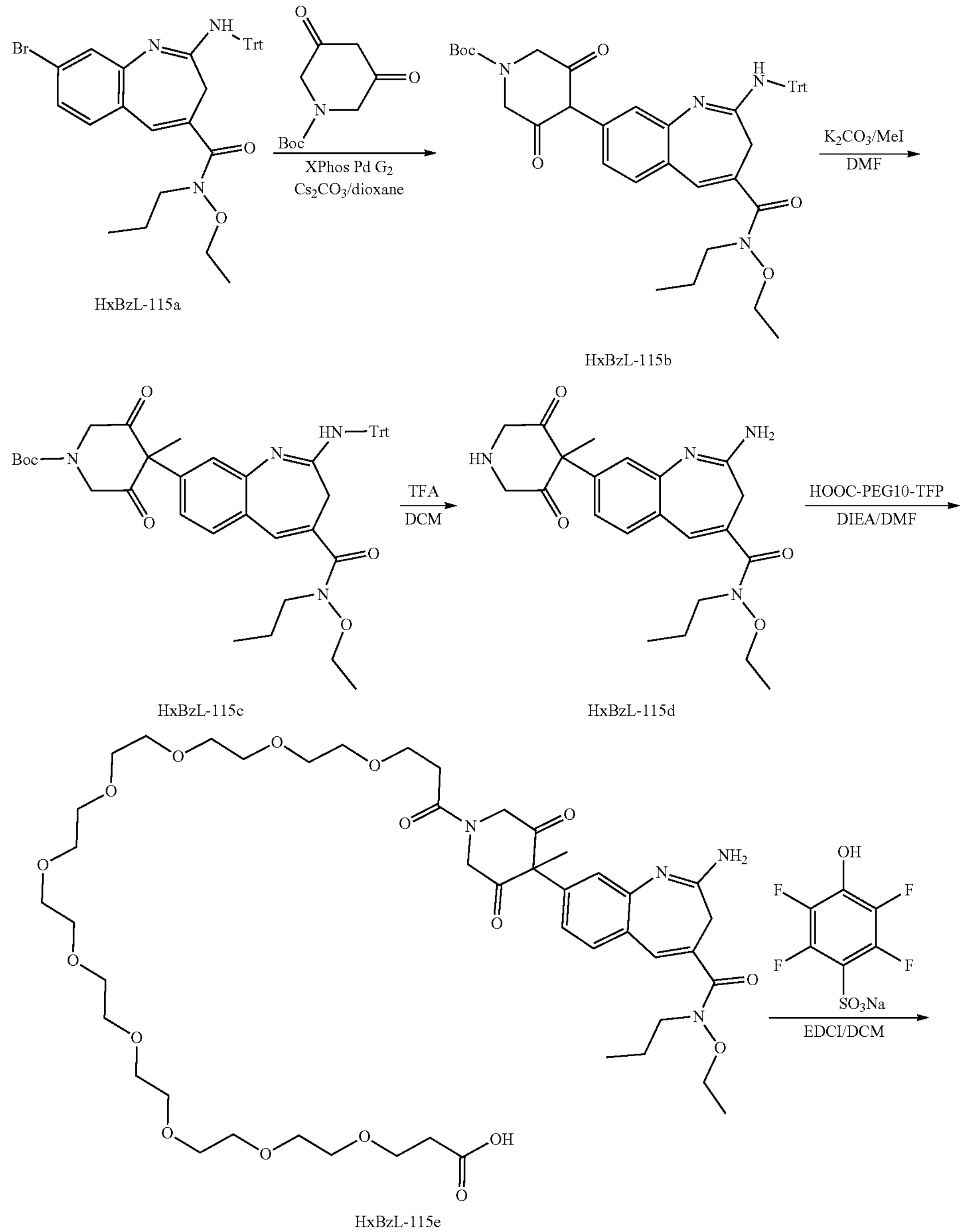
HxBzL-115a
HxBzL-115b
HxBzL-115c
HxBzL-115d
HxBzL-115e -continued

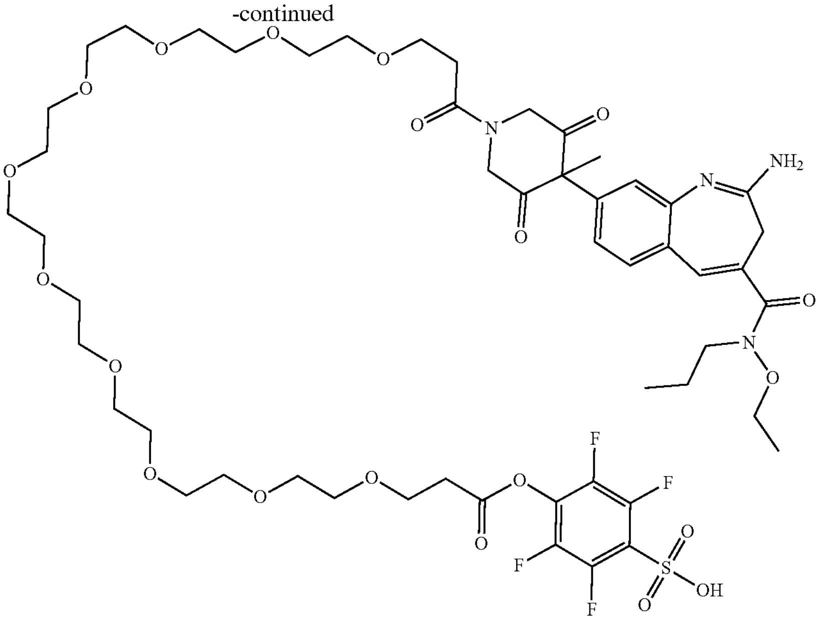

HxBzL-115

Preparation of tert-butyl 4-[4-[ethoxy(propyl)carbamoyl]-2-(tritylamino)-3H-1-benzazepin-8-yl]-3,5-dioxo-piperidine-1-carboxylate HxBzL-115b To a mixture of 8-bromo-N-ethoxy-N-propyl-2-(tritylamino)-3H-1-benzazepine-4-carboxamide, HxBzL-115a (1 g, 1.64 mmol, 1.0 eq) and tert-butyl 3,5-dioxopiperidine-1-carboxylate (420 mg, 1.97 mmol, 1.2 eq) in dioxane (20 mL) was added $Cs_2CO_3$ (1.07 g, 3.29 mmol, 2.0 eq) and [2-(2-aminophenyl)phenyl]-chloro-palladium; dicyclohexyl-[3-(2,4,6-triisopropylphenyl)phenyl] phosphane, XPhos Pd G2, CAS Reg. No. 1310584-14-5 (129 mg, 164 umol, 0.1 eq) in one portion at 25° C. under $N_2$, and then stirred at 100° C. for 12 hours. The mixture was diluted with water and extracted with EtOAc (30 mL×3). The organic layer was washed with brine, dried over $Na_2SO_4$, filtered and concentrated. The residue was purified by silica gel chromatography (column height: 250 mm, diameter: 100 mm, 100-200 mesh silica gel, Ethyl acetate/MeOH=1/0, 10/1) to afford HxBzL-115b (0.35 g, 472.41 umol, 28.75% yield) as yellow solid. LC/MS [M+H] 741.36 (calculated); LC/MS [M+H] 741.4 (observed).

Preparation of tert-butyl 4-[4-[ethoxy(propyl)carbamoyl]-2-(tritylamino)-3H-1-benzazepin-8-yl]-4-methyl-3,5-dioxo-piperidine-1-carboxylate, HxBzL-115c To a mixture of HxBzL-115b (0.2 g, 269 umol, 1.0 eq) in DMF (1 mL) was added $K_2CO_3$ (74.6 mg, 539 umol, 2.0 eq) and MeI (11.5 mg, 80.9 umol, 5.04 uL, 0.3 eq) in one portion at 25° C., and then stirred at 25° C. for 12 h. The mixture was diluted with water and extracted with EtOAc (20 mL×3). The organic layer was washed with brine, dried over $Na_2SO_4$, filtered and concentrated. The residue was purified by silica gel chromatography (column height: 250 mm, diameter: 100 mm, 100-200 mesh silica gel, Petroleum ether/Ethyl acetate=1/0, 1/1) to afford HxBzL-115c (0.12 g, 158.96 umol, 58.89% yield) as yellow oil. LC/MS [M+H] 755.37 (calculated); LC/MS [M+H] 755.4 (observed).

Preparation of 2-amino-N-ethoxy-8-(4-methyl-3,5-dioxo-4-piperidyl)-N-propyl-3H-1-benzazepine-4-carboxamide, HxBzL-115d To a mixture of HxBzL-115c (0.12 g, 159 umol, 1.0 eq) in DCM (4 mL) was added TFA (362 mg, 3.18 mmol, 235 uL, 20.0 eq) in one portion at 25° C., and then stirred at 50° C. for 12 h. The mixture was concentrated in vacuum to give HxBzL-115d (0.07 g, crude, TFA) as yellow oil. LC/MS [M+H] 413.2 (calculated); LC/MS [M+H] 413.2 (observed).

Preparation of 3-[2-[2-[2-[2-[2-[2-[2-[2-[2-[3-[4-[2-amino-4-[ethoxy(propyl)carbamoyl]-3H-1-benzazepin-8-yl]-4-methyl-3,5-dioxo-1-piperidyl]-3-oxo-propoxy]ethoxy]ethoxy]ethoxy]ethoxy]ethoxy]ethoxy]ethoxy]ethoxy]ethoxy]propanoic acid, HxBzL-115e To a mixture of HxBzL-115d (30 mg, 56.9 umol, 1.0 eq, TFA) in DMF (1 mL) was added Et3N (17.3 mg, 171 umol, 23.8 uL, 3.0 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid, HOOC-PEG10-TFP (48.3 mg, 68.4 umol, 1.2 eq) in one portion at 25° C., and then stirred at 25° C. for 0.5 h. The mixture was filtered and purified by prep-HPLC (column: Phenomenex Luna 80*30 mm*3 um; mobile phase: [water (0.1% TFA)-ACN]; B %: 5%-35%, 8 min) to give HxBzL-115e (7 mg, 7.34 umol, 12.89% yield) as yellow oil. LC/MS [M+H] 953.5 (calculated); LC/MS [M+H] 953.5 (observed).

Preparation of HxBzL-115

To a mixture of 3-[2-[2-[2-[2-[2-[2-[2-[2-[2-[3-[4-[2-amino-4-[ethoxy(propyl)carbamoyl]-3H-1-benzazepin-8-yl]-4-methyl-3,5-dioxo-1-piperidyl]-3-oxo-propoxy]ethoxy]ethoxy]ethoxy] ethoxy]ethoxy]ethoxy]ethoxy]ethoxy]ethoxy]propanoic acid (7 mg, 7.34 umol, 1.0 eq) in DCM (0.5 mL) and DMF (0.05 mL) was added sodium;

2,3,5,6-tetrafluoro-4-hydroxy-benzenesulfonate (7.88 mg, 29.4 umol, 4.0 eq) and EDCI (7.04 mg, 36.72 umol, 5.0 eq) in one portion at 25° C., and then stirred at 25° C. for 0.5 h. The mixture was filtered and purified by prep-HPLC (column: Phenomenex Luna 80*30 mm*3 um; mobile phase: [water (0.1% TFA)-ACN]; B %: 15%-45%, 8 mincolumn: Phenomenex Luna 80*30 mm*3 um; mobile phase: [water (0.1% TFA)-ACN]; B %: 15%-45%, 8 min) to give HxBzL-115 (3 mg, 2.54 umol, 34.58% yield) as yellow solid. $^1$H NMR (MeOD, 400 MHz) δ 7.59 (d, J=8.0 Hz, 1H), 7.36 (s, 1H), 7.06-6.98 (m, 2H), 5.25 (dd, J=2.0, 19.6 Hz, 1H), 4.14 (d, J=19.6 Hz, 1H), 3.95 (q, J=7.2 Hz, 2H), 3.87 (t, J=6.0 Hz, 2H), 3.76-3.69 (m, 2H), 3.67-3.56 (m, 36H), 3.55-3.50 (m, 2H), 3.45-3.35 (m, 4H), 2.98 (t, J=6.0 Hz, 2H), 2.55-2.41 (m, 1H), 2.06-1.91 (m, 1H), 1.83-1.67 (m, 2H), 1.44 (s, 3H), 1.18 (t, J=7.2 Hz, 3H), 0.98 (t, J=7.2 Hz, 3H). LC/MS [M+H]1181.4 (calculated); LC/MS [M+H] 1181.5 (observed).

Example 201 Preparation of Immunoconjugates (IC)

To prepare a lysine-conjugated Immunoconjugate, an antibody is buffer exchanged into a conjugation buffer containing 100 mM boric acid, 50 mM sodium chloride, 1 mM ethylenediaminetetraacetic acid at pH 8.3, using G-25 SEPHADEX™ desalting columns (Sigma-Aldrich, St. Louis, MO) or Zeba™ Spin Desalting Columns (Thermo Fisher Scientific). The eluates are then each adjusted to a concentration of about 1-10 mg/ml using the buffer and then sterile filtered. The antibody is pre-warmed to 20-30° C. and rapidly mixed with 2-20 (e.g., 7-10) molar equivalents of a tetrafluorophenyl (TFP) or sulfonic tetrafluorophenyl (sulfo-TFP) ester, 8-Het-2-aminobenzazepine-linker (HxBzL) compound of Formula II dissolved in dimethylsulfoxide (DMSO) or dimethylacetamide (DMA) to a concentration of 5 to 20 mM. The reaction is allowed to proceed for about 16 hours at 30° C. and the immunoconjugate (IC) is separated from reactants by running over two successive G-25 desalting columns or Zeba™ Spin Desalting Columns equilibrated in phosphate buffered saline (PBS) at pH 7.2 to provide the Immunoconjugate (IC) of Tables 3a and 3b. Adjuvant-antibody ratio (DA R) is determined by liquid chromatography mass spectrometry analysis using a C4 reverse phase column on an ACQUITY™ UPLC H-class (Waters Corporation, Milford, MA) connected to a XEVO™ G2-XS TOF mass spectrometer (Waters Corporation).

To prepare a cysteine-conjugated Immunoconjugate, an antibody is buffer exchanged into a conjugation buffer containing PBS, pH 7.2 with 2 mM EDTA using Zeba™ Spin Desalting Columns (Thermo Fisher Scientific). The interchain disulfides are reduced using 2-4 molar excess of Tris (2-carboxyethyl) phosphine (TCEP) or dithiothreitol (DTT) at 37° C. for 30 min-2 hours. Excess TCEP or DTT was removed using a Zeba™ Spin Desalting column pre-equilibrated with the conjugation buffer. The concentration of the buffer-exchanged antibody was adjusted to approximately 5 to 20 mg/ml using the conjugation buffer and sterile-filtered. The maleimide-HxBzL compound is either dissolved in dimethylsulfoxide (DMSO) or dimethylacetamide (DMA) to a concentration of 5 to 20 mM. For conjugation, the antibody is mixed with 10 to 20 molar equivalents of maleimide-HxBzL. In some instances, additional DMA or DMSO up to 20% (v/v), was added to improve the solubility of the maleimide-HxBzL in the conjugation buffer. The reaction is allowed to proceed for approximately 30 min to 4 hours at 20° C. The resulting conjugate is purified away from the unreacted maleimide-HxBzL using two successive Zeba™ Spin Desalting Columns. The columns are pre-equilibrated with phosphate-buffered saline (PBS), pH 7.2. Adjuvant to antibody ratio (DAR) is estimated by liquid chromatography mass spectrometry analysis using a C4 reverse phase column on an ACQUITY™ UPLC H-class (Waters Corporation, Milford, MA) connected to a XEVO™ G2-XS TOF mass spectrometer (Waters Corporation).

For conjugation, the antibody may be dissolved in an aqueous buffer system known in the art that will not adversely impact the stability or antigen-binding specificity of the antibody. Phosphate buffered saline may be used. The HxBzL compound is dissolved in a solvent system comprising at least one polar aprotic solvent as described elsewhere herein. In some such aspects, HxBzL is dissolved to a concentration of about 5 mM, about 10 mM, about 20 mM, about 30 mM, about 40 mM or about 50 mM, and ranges thereof such as from about 5 mM to about 50 mM or from about 10 mM to about 30 mM in pH 8 Tris buffer (e.g., 50 mM Tris). In some aspects, the 8-Het-2-aminobenzazepine-linker intermediate is dissolved in DMSO (dimethylsulfoxide), DMA (dimethylacetamide), acetonitrile, or another suitable dipolar aprotic solvent.

Alternatively in the conjugation reaction, an equivalent excess of HxBzL solution may be diluted and combined with antibody solution. The HxBzL solution may suitably be diluted with at least one polar aprotic solvent and at least one polar protic solvent, examples of which include water, methanol, ethanol, n-propanol, and acetic acid. The molar equivalents of 8-Het-2-aminobenzazepine-linker intermediate to antibody may be about 1.5:1, about 3:1, about 5:1, about 10:1, about 15:1, or about 20:1, and ranges thereof, such as from about 1.5:1 to about 20:1 from about 1.5:1 to about 15:1, from about 1.5:1 to about 10:1, from about 3:1 to about 15:1, from about 3:1 to about 10:1, from about 5:1 to about 15:1 or from about 5:1 to about 10:1. The reaction may suitably be monitored for completion by methods known in the art, such as LC-MS. The conjugation reaction is typically complete in a range from about 1 hour to about 16 hours. After the reaction is complete, a reagent may be added to the reaction mixture to quench the reaction. If antibody thiol groups are reacting with a thiol-reactive group such as maleimide of the 8-Het-2-aminobenzazepine-linker intermediate, unreacted antibody thiol groups may be reacted with a capping reagent. An example of a suitable capping reagent is ethylmaleimide.

Following conjugation, the immunoconjugates may be purified and separated from unconjugated reactants and/or conjugate aggregates by purification methods known in the art such as, for example and not limited to, size exclusion chromatography, hydrophobic interaction chromatography, ion exchange chromatography, chromatofocusing, ultrafiltration, centrifugal ultrafiltration, tangential flow filtration, and combinations thereof. For instance, purification may be preceded by diluting the immunoconjugate, such in 20 mM sodium succinate, pH 5. The diluted solution is applied to a cation exchange column followed by washing with, e.g., at least 10 column volumes of 20 mM sodium succinate, pH 5. The conjugate may be suitably eluted with a buffer such as PBS.

Example 202 HEK Reporter Assay

HEK293 reporter cells expressing human TLR7 or human TLR8 were purchased from Invivogen and vendor protocols were followed for cellular propagation and experimentation.

Briefly, cells were grown to 80-85% confluence at 5% $CO_2$ in DMEM supplemented with 10% FBS, Zeocin, and Blasticidin. Cells were then seeded in 96-well flat plates at $4\times10^4$ cells/well with substrate containing HEK detection medium and immunostimulatory molecules. Activity was measured using a plate reader at 620-655 nm wavelength.

Example 203 Assessment of Immunoconjugate Activity In Vitro

This example shows that Immunoconjugates of the invention are effective at eliciting immune activation, and therefore are useful for the treatment of cancer.

a) Isolation of Human Antigen Presenting Cells: Human myeloid antigen presenting cells (APCs) were negatively selected from human peripheral blood obtained from healthy blood donors (Stanford Blood Center, Palo Alto, California) by density gradient centrifugation using a method to isolate monocytes from whole blood by negative selection, ROSETTESEP™ Human Monocyte Enrichment Cocktail (Stem Cell Technologies, Vancouver, Canada) containing monoclonal antibodies against CD14, CD16, CD40, CD86, CD123, and HLA-DR. Immature APCs were subsequently purified to >90% purity via negative selection using a cell separation method, EASYSEP™ Human Monocyte Enrichment Kit (Stem Cell Technologies) without CD16 depletion containing monoclonal antibodies against CD14, CD16, CD40, CD86, CD123, and HLA-DR.

b) Myeloid APC Activation Assay: $2\times10^5$ APCs are incubated in 96-well plates (Corning, Corning, NY) containing iscove's modified dulbecco's medium, IMDM (Lonza) supplemented with 10% FBS, 100 U/mL penicillin, 100 µg/mL (micrograms per milliliter) streptomycin, 2 mM L-glutamine, sodium pyruvate, non-essential amino acids, and where indicated, various concentrations of unconjugated (naked) antibodies and immunoconjugates of the invention (as prepared according to the Example above). Cell-free supernatants are analyzed after 18 hours via ELISA to measure TNFα secretion as a readout of a proinflammatory response.

c) PBMC Activation Assay: Human peripheral blood mononuclear cells were isolated from human peripheral blood obtained from healthy blood donors (Stanford Blood Center, Palo Alto, California) by density gradient centrifugation. PBMCs were incubated in 96-well plates (Corning, Corning, NY) in a co-culture with CEA-expressing tumor cells (e.g. MKN-45, HPAF-II) at a 10:1 effector to target cell ratio. Cells were stimulated with various concentrations of unconjugated (naked) antibodies and immunoconjugates of the invention (as prepared according to the Example above). Cell-free supernatants were analyzed by cytokine bead array using a LegendPlex™ kit according to manufacturer's guidelines (BioLegend®, San Diego, CA).

d) Isolation of Human Conventional Dendritic Cells: Human conventional dendritic cells (cDCs) were negatively selected from human peripheral blood obtained from healthy blood donors (Stanford Blood Center, Palo Alto, California) by density gradient centrifugation. Briefly, cells are first enriched by using a ROSETTESEP™ Human CD3 Depletion Cocktail (Stem Cell Technologies, Vancouver, Canada) to remove T cells from the cell preparation. cDCs are then further enriched via negative selection using an EASYSEP™ Human Myeloid DC Enrichment Kit (Stem Cell Technologies).

e) CDC Activation Assay: $8\times10^4$ APCs were co-cultured with tumor cells expressing the ISAC target antigen at a 10:1 effector (CDC) to target (tumor cell) ratio. Cells were incubated in 96-well plates (Corning, Corning, NY) containing RPMI-1640 medium supplemented with 10% FBS, and where indicated, various concentrations of the indicated immunoconjugate of the invention (as prepared according to the example above). Following overnight incubation of about 18 hours, cell-free supernatants were collected and analyzed for cytokine secretion (including TNFα) using a flow cytometry-based multiplex immunoassay cytokine bead array, LEGENDplex™ (BioLegend, Inc.)

Activation of myeloid cell types can be measured using various screen assays in addition to the assay described in which different myeloid populations are utilized. These may include the following: monocytes isolated from healthy donor blood, M-CSF differentiated Macrophages, GM-CSF differentiated Macrophages, GM-CSF+IL-4 monocyte-derived Dendritic Cells, conventional Dendritic Cells (cDCs) isolated from healthy donor blood, and myeloid cells polarized to an immunosuppressive state (also referred to as myeloid derived suppressor cells or MDSCs). Examples of MDSC polarized cells include monocytes differentiated toward immunosuppressive state such as M2a MΦ (IL4/IL13), M2c MΦ (IL10/TGFb), GM-CSF/IL6 MDSCs and tumor-educated monocytes (TEM). TEM differentiation can be performed using tumor-conditioned media (e.g. 786.0, MDA-MB-231, HCC1954). Primary tumor-associated myeloid cells may also include primary cells present in dissociated tumor cell suspensions (Discovery Life Sciences).

Assessment of activation of the described populations of myeloid cells may be performed as a mono-culture or as a co-culture with cells expressing the antigen of interest which the immunoconjugate may bind to via the CDR region of the antibody. Following incubation for 18-48 hours, activation may be assessed by upregulation of cell surface co-stimulatory molecules using flow cytometry or by measurement of secreted proinflammatory cytokines. For cytokine measurement, cell-free supernatant is harvested and analyzed by flow cytometry-based multiplex immunoassay cytokine bead array, LEGENDplex™ (BioLegend, Inc.) using flow cytometry.

All references, including publications, patent applications, and patents, cited herein are hereby incorporated by reference to the same extent as if each reference were individually and specifically indicated to be incorporated by reference and were set forth in its entirety herein.

The invention claimed is:

1. An 8-Het-2-aminobenzazepine-linker compound of formula:

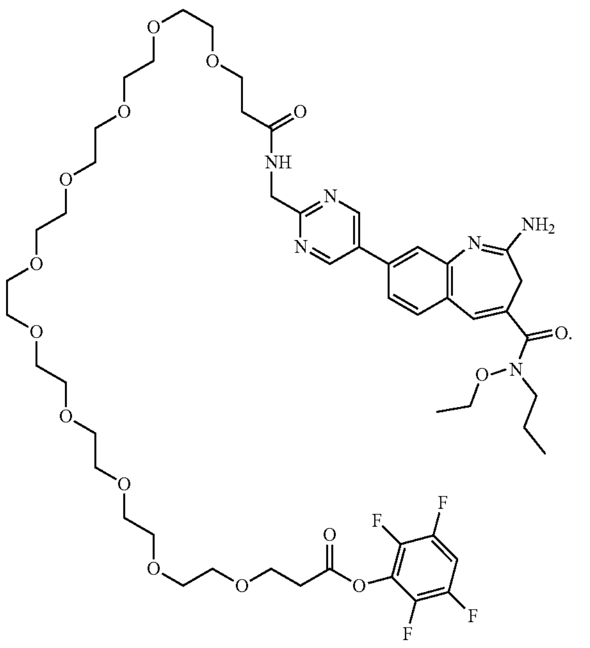 [SMILES: CCCN(OCC)C(=O)C1=Cc2ccc(-c3cnc(CNC(=O)CCOCCOCCOCCOCCOCCOCCOCCOCCOCCOCCC(=O)Oc4c(F)c(F)cc(F)c4F)nc3)cc2N=C(N)C1]

2. An immunoconjugate comprising an antibody covalently attached to one or more 8-Het-2-aminobenzazepine moieties by a linker, and having formula:

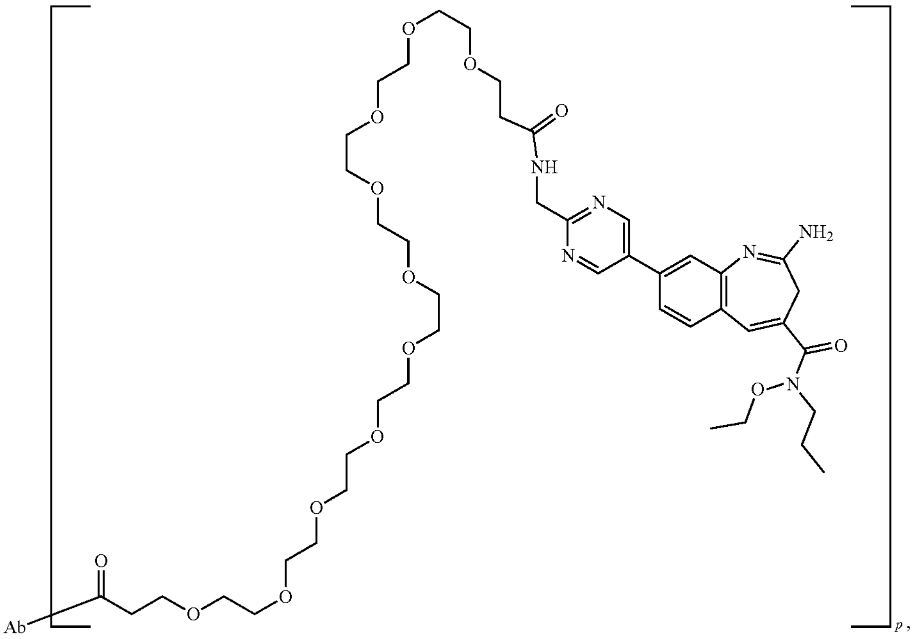

or a pharmaceutically acceptable salt thereof, wherein Ab is an antibody and p is an integer from 1 to 8.

3. A pharmaceutical composition comprising a therapeutically effective amount of an immunoconjugate according to claim 2 or a pharmaceutically acceptable salt thereof, and one or more pharmaceutically acceptable diluents, vehicles, carriers, excipients, or a combination thereof.

4. A method for treating cancer in a subject comprising administering to the subject a therapeutically effective amount of an immunoconjugate according to claim 2 or a pharmaceutically acceptable salt thereof.

* * * * *